US012503491B2

(12) United States Patent
Bierer et al.

(10) Patent No.: US 12,503,491 B2
(45) Date of Patent: Dec. 23, 2025

(54) MASP INHIBITORY COMPOUNDS AND USES THEREOF

(71) Applicants: Bayer Aktiengesellschaft, Leverkusen (DE); Bayer Pharma Aktiengesellschaft, Berlin (DE)

(72) Inventors: Donald Bierer, Haan (DE); Ingo Flamme, Reichshof (DE); Dmitry Zubov, Remscheid (DE); Thomas Neubauer, Wuppertal (DE); Adrian Tersteegen, Wuppertal (DE); Cathleen Juhl, Hamburg (DE); Marie Glatz, Wuppertal (DE); Jan Dreher, Wuppertal (DE); Simon Holton, Berlin (DE); Carsten Terjung, Bochum (DE); Lars Baumann, Wülfrath (DE); Thorsten Poethko, Schwelm (DE); Jiancheng Xiong, Wuhan (CN); Yibo Qiu, Ann Arbor, MI (US)

(73) Assignees: Bayer Aktiengesellschaft, Leverkusen (DE); Bayer Pharma Aktiengesellschaft, Berlin (DE)

( * ) Notice: Subject to any disclaimer, the term of this patent is extended or adjusted under 35 U.S.C. 154(b) by 0 days.

(21) Appl. No.: 18/299,600

(22) Filed: Apr. 12, 2023

(65) Prior Publication Data

US 2024/0124522 A1 Apr. 18, 2024

Related U.S. Application Data

(60) Division of application No. 17/138,447, filed on Dec. 30, 2020, now Pat. No. 11,667,675, which is a continuation of application No. PCT/EP2020/062040, filed on Apr. 30, 2020.

(30) Foreign Application Priority Data

May 7, 2019 (WO) ................ PCT/CN2019/085791

(51) Int. Cl.

| | |
|---|---|
| ***C07K 7/08*** | (2006.01) |
| ***A61K 38/10*** | (2006.01) |
| ***A61K 45/06*** | (2006.01) |
| ***A61P 13/12*** | (2006.01) |

(52) U.S. Cl.

CPC ................ *C07K 7/08* (2013.01); *A61K 38/10* (2013.01); *A61K 45/06* (2013.01); *A61P 13/12* (2018.01)

(58) Field of Classification Search

None

See application file for complete search history.

(56) References Cited

FOREIGN PATENT DOCUMENTS

| | | | |
|---|---|---|---|
| EP | 1343516 | A2 | 9/2003 |
| EP | 2435059 | A1 | 4/2012 |
| WO | 0006568 | A1 | 2/2000 |
| WO | 0006569 | A1 | 2/2000 |
| WO | 0119780 | A2 | 3/2001 |
| WO | 0242301 | A1 | 5/2002 |
| WO | 03095451 | A1 | 11/2003 |
| WO | 2004075837 | A2 | 9/2004 |
| WO | 2005123128 | A2 | 12/2005 |
| WO | 2007117996 | A2 | 10/2007 |
| WO | 2010136831 | A1 | 12/2010 |
| WO | 2011147809 | A1 | 12/2011 |
| WO | 2012004258 | A1 | 1/2012 |
| WO | 2012028647 | A1 | 3/2012 |
| WO | 2012059549 | A1 | 5/2012 |
| WO | 2012139888 | A1 | 10/2012 |
| WO | 2013192240 | A2 | 12/2013 |
| WO | 2014012934 | A1 | 1/2014 |
| WO | 2014144542 | A2 | 9/2014 |
| WO | 2015054298 | A1 | 4/2015 |
| WO | 2015200916 | A2 | 12/2015 |

OTHER PUBLICATIONS

Leslie, Science Now, May 2012) (Year: 2012).*
Panos et al., Am J Med. Apr. 1990;88(4):396-404 (Year: 1990).*
Farmer et al., Current Atherosclerosis Reports 2002, 4:92-98 (Year: 2002).*
Héja, D. et al. (Jun. 8, 2012) "Monospecific Inhibitors Show That Both Mannan-binding lectin-associated Serine Protease-1 (MASP-1) and -2 are Essential for Lectin Pathway Activation and Reveal Structural Plasticity of MASP-2," Journal of Biological Chemistry, 287(24):20290-20300.
International Search Report, dated Jul. 3, 2020 for International Application No. PCT/EP2020/062040, filed Apr. 30, 2020, 5 pages.
Kocsis, A. et al. (2010) "Selective Inhibition of the Lectin Pathway of Complement with Phage Display Selected Peptides againstMannose-Binding Lectin-Associated Serine Protease (MASP)-1 and -2: Significant Contribution of MASP-1 to Lectin Pathway Activation," Journal of Immunology , 185:4169-4178.

(Continued)

*Primary Examiner* — Sergio Coffa

(57) ABSTRACT

The present invention relates to novel Mannose-binding lectin (MBL)-associated serine protease (MASP) inhibitory compounds, as well as analogues and derivatives thereof, to processes for the preparation thereof, to the use thereof alone or in combinations for treatment and/or prevention of diseases and to the use thereof for production of medicaments for treatment and/or prevention of diseases, especially for treatment and/or prevention of renal and cardiovascular disorders and of ischemia reperfusion injuries.

8 Claims, No Drawings

Specification includes a Sequence Listing.

(56) References Cited

OTHER PUBLICATIONS

Mahatmanto, T. (Sep. 19, 2015) "Seed Biopharmaceutical Cyclic Peptides: From Discovery to Applications," Biopolymers, 104(6):804-814.
Zheng, Y. et al. (2015) "Orthogonal Cysteine—Penicillamine Disulfide Pairing for Directing the Oxidative Folding of Peptides," J. Am. Chem. Soc. 137: 15094-15097.
Caliceti, Paolo et al., "Pharmacokinetic and biodistribution properties of poly(ethylene glycol)-protein conjugates," Advanced Drug Delivery Reviews, 2003, 55, pp. 1261-1277, Elsevier B.V.
Corrigan, Owen I., "Salt Forms: Pharmaceutical Aspects," Encyclopedia of Pharmaceutical Technology, 2007, vol. 1, 3rd Edition, 3177-3187.
Cui, Hong-Kui et al., "Diaminodiacid-Based Solid-Phase Synthesis of Peptide Disulfide Bond Mimics," Angew. Chem. Int. Ed. 2013, 52, 9558-9562.
Darmon, Michael et al., "Diagnostic accuracy of Doppler renal resistive index for reversibility of acute kidney injury in critically ill patients," Intensive Care Med (2011) 37:68-76.
Dunkelberger, Jason R. et al., "Complement and its role in innate and adaptive immune responses," Cell Research (2010) 20:34-50.
Ellinghaus, Peter et al., "Comparing the global mRNA expression profile of human atrial and ventricular myocardium with high-density oligonucleotide arrays," The Journal of Thoracic and Cardiovascular Surgery, Jun. 2005, vol. 129, No. 6, 1383-1390.
Farmer, John A. et al., "Atherosclerosis and Inflammation," Current Atherosclerosis Reports 2002, 4:92-98.
Farrar, Conrad A. et al., "Collectin-11 detects stress-induced L-fucose pattern to trigger renal epithelial injury," J Clin Invest. 2016;126(5):1911-1925.
Fischer, Jan-Patrick et al., "Adrenomedullin disulfide bond mimetics uncover structural requirements for AM1 receptor activation," Wiley Journal of Peptide Science, 2019, pp. 1-13, European Peptide Society and John Wiley Sons, Ltd.
Garred, Peter et al., "A journey through the lectin pathway of complement—MBL and beyond," Immunological Reviews 2016; 274: 74-97.
Gennaro, Alfonso, "Remington's Pharmaceutical Sciences, 17th ed.," Journal of Pharmaceutical Sciences, vol. 74, No. 10, Oct. 1985.
Guo, Ye et al., "Diaminodiacid Bridges to Improve Folding and Tune the Bioactivity of Disulfide-Rich Peptides," Angew. Chem. Int. Ed. 2015, 54, 14276-14281.
Halfbrodt, Dr. Wolfgang, "Citation of NMR Peaklist Data within Patent Applications," Research Disclosure database No. 605005, 2014.
Heja, David et al., "Revised mechanism of complement lectin-pathway activation revealing the role of serine protease MASP-1 as the exclusive activator of MASP-2," PNAS, Jun. 26, 2012, vol. 109, No. 26, 10498-10503.
Huang, Dong-Liang et al., "Non-reducible disulfide bond replacement implies that disulfide exchange is not required for hepcidin-ferroportin interaction," Chem. Commun., 2019, 55, 2821.
Kourra, C.M.B.K. et al., "Converting disulfide bridges in native peptides to stable methylene thioacetals," Chem. Sci., 2016, 7, pp. 7007-7012, Royal Society of Chemistry.
Leslie, MD, Kevin O., "Idiopathic Pulmonary Fibrosis May be a Disease of Recurrent, Tractional Injury to the Periphery of the Aging Lung," Arch Pathol Lab Med—vol. 136, Jun. 2012.
Matejkova, Sarka et al., "Carbamylated erythropoietin-FC fusion protein and recombinant human erythropoietin during porcine kidney ischemia/reperfusion injury," Intensive Care Med (2013) 39:497-510.
Moller-Kristensen, M. et al., "Mannan-Binding Lectin Recognizes Structures on Ischaemic Reperfused Mouse Kidneys and is Implicated in Tissue Injury," Blackwell Publishing Ltd., 2005, Scandinavian Journal of Immunology 61, 426-434.
Nomenclature of α-Amino Acids, Biochemistry, vol. 14, No. 2, 1975, 449-462.
Peleg-Shulman, Tal et al., "Reversible PEGylation: A Novel Technology to Release Native Interferon a2 over a Prolonged Time Period," J. Med. Chem. 2004, 47, 4897-4904.
Schwaeble, Wilhelm J. et al., "Targeting of mannan-binding lectin-associated serine protease-2 confers protection from myocardial and gastrointestinal ischemia/reperfusion injury," PNAS, May 3, 2011, vol. 108, No. 18, 7523-7528.
Sebesta, Radovan et al., Preparation of (S,S)-Fmoc-ß2hlle-OH, (S)-Fmoc-ß2hMet-OH, and (S)-Fmoc-ß2hTyr(tBu)-OH for Solid-Phase Syntheses of ß2- and ß2/ß3-Peptides1) Helvetica Chimica Acta—vol. 86, 2003.
Sieve, Irina et al., "Regulation and function of endothelial glycocalyx layer in vascular diseases," Vascular Pharmacology 100, 2018, 26-33.
Simon, Florian et al., "Effects of Intravenous Sulfide During Porcine Aortic Occlusionyinduced Kidney Ischemia/Reperfusion Injury," Shock, vol. 35, No. 2, pp. 156-163, 2011.
Stahl, P. Heinrich et al., "Handbook of Pharmaceutical Salts: Properties, Selection, and Use," Journal of Medicinal Chemistry, 2003, vol. 46, No. 7, 1277-1278.
Sun, Shuai-Shuai et al., "Efficient synthesis of a side-chain extended diaminodiacid for solid-phase synthesis of peptide disulfide bond mimics," Tetrahedron Letters 60, 2019, 1197-1201.
Vippila, Mohana Rao et al., "Synthesis and Antiproliferative Activity Evaluation of the Disulfide-Containing Cyclic Peptide Thiochondrilline C and Derivatives," J. Nat. Prod. 2015, 78, 2398-2404.
Wang, Tao et al., "Efficient synthesis of hydrocarbon-bridged diaminodiacids through nickel-catalyzed reductive cross-coupling," Tetrahedron Letters 58, 2017, 3970-3973.
Wang, Tao et al., "Synthesis of Peptide Disulfide-Bond Mimics by Using Fully Orthogonally Protected Diaminodiacids," Org. Lett. 2018, 20, 6074-6078.
Xu, Yang et al., "Dmab/ivDde protected diaminodiacids for solid-phase synthesis of peptide disulfide-bond mimics," Tetrahedron Letters 58, 2017, 1677-1680.

* cited by examiner

MASP INHIBITORY COMPOUNDS AND USES THEREOF

CROSS REFERENCE TO RELATED APPLICATIONS

This application is a divisional application of U.S. patent application Ser. No. 17/138,447, filed Dec. 30, 2020, now U.S. Pat. No. 11,667,675, which is a continuation application of International Application No. PCT/EP2020/062040, filed internationally on Apr. 30, 2020, which claims the benefit of International Application No. PCT/CN2019/085791, filed internationally on May 7, 2019.

REFERENCE TO AN ELECTRONIC SEQUENCE LISTING

The contents of the electronic sequence listing (777052046210subseqlist.xml; Size: 1,591,054 bytes; and Date of Creation: Jul. 13, 2023) are herein incorporated by reference in their entirety.

The present invention relates to novel Mannose-binding lectin (MBL)-associated serine protease (MASP) inhibitory compounds, as well as analogues and derivatives thereof, to processes for the preparation thereof, to the use thereof alone or in combinations for treatment and/or prevention of diseases and to the use thereof for production of medicaments for treatment and/or prevention of diseases, especially for treatment and/or prevention of renal and cardiovascular disorders and of ischemia reperfusion injuries.

The complement system consists of a complex cascading network of proteins, receptors and enzymes of which many are circulating in the blood stream. The complement system is an important constituent of innate immunity and essential for the defense against invading pathogens and clearance of dead and virus infected cells. It forms a bridge between innate and adaptive immune responses. Activation of the complement system is also involved in the pathologies of sepsis and ischemia reperfusion injuries, e.g. after myocardial infarction, ischemic kidney injury or organ transplantation. Three branches of the complement system have been identified: the lectin pathway, the classical and the alternative pathway (Dunkelberger and Song, Complement and its role in innate and adaptive immune responses. *Cell Res.* 2010; 20(1): 34-50). The lectin pathway is activated by deposition of lectins which are circulating in the blood stream and under normal conditions have a sentinel function against invading pathogens and dead cells by recognizing foreign and altered carbohydrate surface patterns, respectively, and decorating their surfaces. Mannose-binding lectin (MBL), ficolins and collectins are the major representatives of these lectins which are produced in liver, kidney and other organs (Garred et al., *A journey through the lectin pathway of complement-MBL and beyond. Immunol Rev.* 2016; 274 (1):74-97). Their deposition is followed by further recruitment of zymogens of essentially two closely related serine proteases from the blood stream, mannose-binding lectin-associated serine protease 1 and 2 (MASP-1 and MASP-2) forming a complex in which the zymogens come into close proximity to each other. The current concept is that under in vivo conditions MASP-1 zymogen after recruitment is self-activating and then activates the MASP-2 zymogen by cleavage. Activated MASP-1 furthermore cleaves complement factor C2 into C2a and C2b. Activated MASP2 also cleaves C2 and complement factor C4 into C4a and C4b which together with C2a forms the C4bC2a complex which serves as complement factor C3 convertase. Constitution of C3 convertase activity and consecutive C3 deposition to target cell surfaces represents the point of convergence of all three complement pathways activating the common downstream cascade that results in generation of inflammatory mediators and target cell lysis. In intact human serum activities of both MASP-enzymes are indispensable for C3 convertase formation (Héja et al, Revised mechanism of complement lectin-pathway activation revealing the role of serine protease MASP-1 as the exclusive activator of MASP-2. *Proc Natl Acad Sci USA.* 2012; 109(26): 10498-503).

The microvascular system plays a crucial role during inflammatory and ischemic organ disorders. Barrier function, leukocyte trafficking and coagulation control are closely dependent on the integrity of the luminal endothelial cell surface in small blood vessels. The luminal endothelial surface is lined by a dense coat of glycosylation extensions from membrane integrated glycoproteins, proteoglycans, and glycolipids which in their entirety are called glycokalyx. Electron microscopic analyses of samples from animal experiments and human pathologies have shown that in particular the endothelial glycokalyx is rapidly and fundamentally being degraded upon ischemic challenge as well as under inflammatory conditions such as in sepsis. These changes lead to exposure of carbohydrate residues to the blood stream that under normal conditions are not detectable (for review see: Sieve et al., Regulation and function of endothelial glycocalyx layer in vascular diseases. *Vascul Pharmacol.* 2018; 100: 26-33). Beside other changes of the cell surface in particular the altered carbohydrate pattern is thought to activate the lectin pathway causing deposition of the pattern recognizing lectins, subsequent C3 deposition and initiation of cell lysis. MBL and C3 deposition was shown to occur after ischemia and acute kidney injury across species including man. The lectin pathway activation was of particular relevance for reperfusion damage as targeted deletion of MBL and MASP-2 protected mice from ischemia reperfusion damages in kidney heart and intestine (Mϕller-Kristensen et al., Mannan-binding lectin recognizes structures on ischaemic reperfused mouse kidneys and is implicated in tissue injury. *Scand J Immunol.* 2005; 61(5): 426-34; Schwaeble et al., Targeting of mannan-binding lectin-associated serine protease-2 confers protection from myocardial and gastrointestinal ischemia/reperfusion injury. *Proc Natl Acad Sci USA.* 2011; 108(18): 7523-8). Moreover, deletion of collectin 11, another MASP activating lectin which is predominantly expressed in the kidney, made mice resistant against ischemic acute kidney injury (Farrar et al., Collectin-11 detects stress-induced L-fucose pattern to trigger renal epithelial injury. *J Clin Invest.* 2016; 126(5): 1911-1925). Selective peptide inhibitors of MASP-1 and MASP-2 have been identified from phage display libraries employing natural trypsin inhibitors from sun flower or grass hoppers as a starting point. These peptides have been shown to inhibit the lectin pathway dependent C3 convertase formation in vitro (Kocsis et al., Selective inhibition of the lectin pathway of complement with phage display selected peptides against mannose-binding lectin-associated serine protease (MASP)-1 and -2: significant contribution of MASP-1 to lectin pathway activation. *J Immunol.* 2010; 185(7): 4169-78; Héja et al., Monospecific inhibitors show that both mannan-binding lectin-associated serine protease-1 (MASP-1) and are essential for lectin pathway activation and reveal structural plasticity of MASP-2. *J Biol Chem.* 2012; 287(24): 20290-300). However, no evidence for pharmaceutical utility and in vivo efficacy of those peptide inhibitors is available, yet. Similarly, antibodies directed against MASP-2 which interfere with MASP zymogen interaction have been identified and brought to clinical development for atypical hemolytic uremic syndrome and other inflammatory kidney disorders (ClinicalTrials.gov Identifier: NCT03205995; NCT02682407; NCT03608033). However, clinical proof for utility in the prevention or treatment of acute, in particular ischemic organ damage is still missing.

WO 2004/075837 discloses anti-MASP antibodies, functionally equivalent fragments thereof and MASP binding peptides for decreasing the morbidity and mortality caused by tissue damage associated with ischemia-reperfusion injury or TAAA repair by inhibition of the complement system. Small peptides such as the sunflower MASP inhibitor-1 (SFMI-1) and sunflower MASP inhibitor-2 (SFMI-2) as well as derivatives thereof for the treatment of diseases related to the complement system, primarily the lectin pathway were first described in WO 2010/136831.

WO 2015/054298 discloses methods for preserving vision or reducing vision loss in a subject and for inhibiting or reducing photoreceptor cell death in a subject by reducing the activity of MASP-1, MASP-2 or MASP-3. WO 2004/106384, WO 2005/123128, WO 2007/117996 and WO 2014/144542 disclose anti-MASP-2 antibodies for the therapy of diseases associated with MASP-2-dependent complement activation.

It was the object of the present invention to provide novel peptides, having inhibitory effects on MASP-1 and/or MASP-2 enzymes and other beneficial properties making them suitable as efficient and safe alternatives for the prophylaxis and/or treatment of MASP-1 and/or MASP-2-associated disorders as defined below. It was a further object to provide novel peptides, having an improved inhibitory effect on human MASP-1 and/or MASP-2 enzyme and/or rat MASP-1 and/or MASP-2 enzyme.

The present invention generally relates to peptides acting as inhibitors of MASP-1 and/or MASP-2 enzymes and methods of making and using the same.

In particular, the invention provides compounds containing a peptide, which may be isolated and/or purified, comprising, essentially consisting of, or consisting of, the following structural formula (I):

$$(X^0)_p(X^1)_q(X^2)_rX^3X^4X^5X^6X^7X^8X^9X^{10}X^{11}X^{12}(X^{13})_s(X^{14})_t(X^{15})_u \quad \text{(I)},$$

or a derivative, prodrug, analogue, pharmaceutically acceptable salt, solvate or solvate of the salt, wherein $X^0$ represents a group of the formula (IIa)

(IIa)

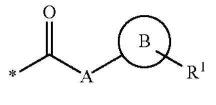

wherein

* marks the bond to a terminal amino group of the adjoining amino acid,

A is a bond or $C_1$-$C_6$-alkylene, wherein one $CH_2$ group in $C_1$-$C_6$-alkylene may be exchanged for —O— or —S—, and wherein $C_1$-$C_6$-alkylene is up to trisubstituted identically or differently by a radical selected from the group consisting of hydroxyl, methoxy, ethoxy, carboxy, amino and halogen, B is absent, aryl, heteroaryl, $C_3$-$C_8$-cycloalkyl or $C_3$-$C_7$-heterocycloalkyl, wherein aryl, heteroaryl, $C_3$-$C_8$-cycloalkyl and $C_3$-$C_7$-heterocycloalkyl can be up to trisubstituted identically or differently by a radical selected from the group of $C_1$-$C_4$-alkyl, hydroxyl, methoxy, ethoxy, carbonyl, carboxy, amino and halogen, and $R^1$ is hydrogen, halogen, amino, hydroxyl or $C_1$-$C_2$O-alkyl, wherein $C_1$-$C_2$O-alkyl is up to trisubstituted identically or differently by a radical selected from the group consisting of hydroxyl, carboxy, amino and halogen, p represents the integer 0 or 1, $X^1$ represents any natural amino acid or an unnatural amino acid, whereas any natural amino acid and/or unnatural amino acid can be in D- or L-stereoconfiguration, and in case p is 0 and q is different from 0, the terminal amino group of $X^1$ is unsubstituted, acetylated or mono- or disubstituted with $C_1$-$C_{20}$-alkyl, q represents an integer of from 0 to 5, $X^2$ represents a natural amino acid selected from a list consisting of I, L, M, V and A, or an unnatural amino acid selected from a list consisting of L-N-Methylisoleucine ((N-Me)I), allo-L-Isoleucine (allo-J), L-Cyclobutylalanine (Cba), L-Norvaline (Nva), L-2-Aminobutyric acid (Abu), (2S,3S)-2-[(3R)-3-Amino-2-oxopyrrolidin-1-yl]-3-methylpentanoic acid, (2S,3S)-2-[2-Oxopiperazin-1-yl]-3-methylpentanoic acid, (2S,3S)-2-[(3S)-2-oxopiperazin-1-yl]-3-methylpentanoic acid, L-Methionine-L-sulfoxide, L-Methionine-sulfone and L-tert-butylglycine, whereas each natural amino acid and/or unnatural amino acid in L-stereoconfiguration can be replaced by the stereoisomer in D-stereoconfiguration, and in case p and q are both 0 and r is 1, the terminal amino group of $X^2$ is unsubstituted, acetylated or mono- or disubstituted with $C_1$-$C_{20}$-alkyl, r represents the integer 0 or 1, $X^3$ represents the natural amino acid C, or an unnatural amino acid selected from a list consisting of L-Penicillamine (Pen) and L-N-Methylcysteine ((N-Me)C), and in case p and q and r are all 0, the terminal amino group of $X^3$ is unsubstituted, acetylated or mono- or disubstituted with $C_1$-$C_{20}$-alkyl, $X^4$ represents a natural amino acid selected from a list consisting of S, C, T, R or K, or an unnatural amino acid selected from a list consisting of allo-L-Threonine (allo-T), L-Homoserine (hSer) and L-Ornithine (Orn), $X^5$ represents the natural amino acid R or N(5)-methyl-L-arginine ((Me)R), $X^6$ represents a natural amino acid selected from a list consisting of S, C or T, or an unnatural amino acid selected from a list consisting of allo-L-Threonine (allo-T) and L-2,3-diaminopropionic acid (Dap), $X^7$ represents a natural amino acid selected from a list consisting of L, F or N or an unnatural amino acid selected from a list consisting of 2,3,3a,4,5,6,7,7a-Octahydroindole-2-carboxylic acid (Oic), L-4-Bromophenylalanine ((4-Bromo)F), 2,5-Difluoro-L-phenylalanine ((2,5-Difluoro)F), L-tert-Butylalanine ((tBu)A), 2-Chloro-L-phenylalanine ((2-Chloro)F), L-2-Bromophenylalanine ((2-Bromo)F), (S)-2-(Amino)-1,6-hexanedioic acid (AAD), (2S)-2-amino-4,4,4-trifluorobutanoic acid, L-2-amino-4-cyanobutyric acid (Cnba), 4-Fluoro-Leucine ((4-Fluoro)L), (S)-(trifluoromethyl)-L-cysteine, (2S)-2-amino-3-(1-methylcyclopropyl)propanoic acid, L-tert-Butylglycine ((tBu)G), 3-(Trimethylsilyl)-L-alanine, 2,5-difluoro-L-phenylalanine, 2-Amino-7-(tert-butoxy)-7-oxoheptanoic acid, 5,5,5-Trifluoro-L-leucine ((Trifluoro)L), 2-Methyl-L-phenylalanine ((2-Me)F), L-Cyclobutylalanine (Cba), L-Cyclopentylalanine (Cpa), L-cyclopropylmethylalanine, L-trifluoromethylalanine, L-difluoromethylalanine, 2-Fluoro-L-phenylalanine ((2-Fluoro)F), (2S)-3-(2,3-difluorophenyl)-2-aminopropanoic acid, (2S)-3-(3-Cyanophenyl)-2-aminopropanoic acid, and (2S)-3-(indol-4-yl)-2-(amino)propanoic acid, $X^8$ represents the natural amino acid P, or an unnatural amino acid selected from a list consisting of (1S,2S,5R)-3-azabicyclo[3.1.0]hexane-2-carboxylic acid, L-Hydroxyproline (Hyp), (3S)-Morpholine-3-carboxylic acid (Morpholine-3-carboxylic), L-Pipecolic acid (Pip), (4aR,6aR,9S,11aS)-11-oxo-2,3,4,4a,6a,7,8,9,11,11a-decahydro-1H-pyrido[3,2-e]pyrrolo[1,2-a]azepine-9-carboxylic acid, trans-4-fluoroproline ((trans-4-Fluoro)P) and (1R,2S,5S)-3-azabicyclo[3.1.0]hexane-2-carboxylic acid, $X^9$ represents the natural amino acid P, or an unnatural amino acid selected from a list consisting of 2,3,3a,4,5,6,7,7a-Octahydroindole-2-carboxylic acid (Oic), L-Hydroxyproline (Hyp), (2S,4S)-4-Trifluoromethyl-pyrrolidine-2-carboxylic acid ((4-CF3)P), (2S,4S)-4-fluoroproline ((cis-4-Fluoro)P), trans-4-fluoroproline ((trans-4-Fluoro)P), (2S)-2-amino-4,4,4-trifluorobutanoic acid, L-trans-3-hydroxyproline ((3S-OH)P, (1R,3S,5R)-2-azabicyclo[3.1.0]hexane-3-carboxylic acid, (6S)-5-Azaspiro-[2.4]heptane-6-carboxylic acid, rel-(1R,3R,5R,6R)-6-(trifluoromethyl)-2-azabicyclo[3.1.0]hexane-3-carboxylic acid, (2S)-2-Amino-4,4,4-trifluorobutanoic acid, (2S,3aS,6aS)-octahydrocyclopenta[b]-pyrrole-2-carboxylic acid, trans-4-fluoroproline ((trans-4-Fluoro)P), (2S,4S)-4-fluoroproline ((cis-4-Fluoro)P), L-4,4-difluoroproline ((Difluoro)P), rel-(3R,6R)-1,1-difluoro-5-azaspiro[2.4]heptane-6-carboxylic acid (enantiomer 1) and rel-(3R,6R)-1,1-difluoro-5-azaspiro[2.4]heptane-6-carboxylic acid (enantiomer 2), $X^{10}$ represents the natural amino acid I, or an unnatural amino acid selected from a list consisting of L-Cyclopentylglycine (Cpg), L-Cyclohexylglycine (Chg), (S)-2-amino-3-ethyl-pentanoic acid, 3-Chlorophenylglycine ((3-Chloro-Ph)G), L-tert-butylglycine, allo-L-Isoleucine (allo-I), L-Cyclobutylglycine, L-Norvaline (Nva) and (2S)-2-(Amino)-2-[(1S,3R)-3-hydroxycyclohexyl]acetic acid, $X^{11}$ represents the natural amino acid C, or an unnatural amino acid selected from a list consisting of L-N-Methylcysteine ((N-Me)C) and L-Penicillamine (Pen), $X^{12}$ represents the natural amino acid I, or an unnatural amino acid selected from a list consisting of allo-L-Isoleucine (allo-I), (S)-2-Amino-2-cyclobutylacetic acid (Cbg), (2S,3S)-2-((amino)methyl)-3-methylpentanoic acid, L-Phenylglycine (Phg), 2-[(1S,2S)-1-(amino)-2-methylbutyl]-1,3-oxazole-4-carboxylic acid, 2-methyl-D-alloisoleucine, L-Norvaline (Nva), L-2-Aminobutyric acid (Abu), L-tert-butylglycine and Aminoisobutyric acid (Aib), and in case u and t and s are all 0, the terminal carboxyl group of $X^{12}$ is unsubstituted or amidated, $X^{13}$ represents a natural amino acid selected from a list consisting of P, A, S, T, G, D, E, Q or N or an unnatural amino acid selected from a list consisting of N-Methyl-Glycine ((N-Me)G), 5-azaspiro-[2.4]heptane-6-carboxylic acid, L-2-Aminobutyric acid (Abu), 2-Aminoisobutyric acid (Aib), 2-Methyl-L-Proline (2-Me)P, Hydroxyproline (Hyp), 2,3,3a,4,5,6,7,7a-Octahydroindole-2-carboxylic acid (Oic), trans-4-fluoroproline ((trans-4-Fluoro)P), (2S,4S)-4-fluoroproline ((cis-4-Fluoro)P), L-4,4-difluoroproline ((Difluoro)P), L-Cyclopentylglycine (Cpg), (S)-2-Amino-2-cyclobutylacetic acid (Cbg) and (2S)-Pyrrolidin-2-ylacetic acid (beta-homo-P), whereas each natural amino acid and/or unnatural amino acid in L-stereoconfiguration can be replaced by the stereoisomer in D-stereoconfiguration, and in case u and t are both 0 and s is different from 0, the terminal carboxyl group of $X^{13}$ is unsubstituted or amidated, s represents an integer of from 0 to 3, $X^{14}$ represents any natural amino acid or an unnatural amino acid, whereas any natural amino acid and/or unnatural amino acid can be in D- or L-stereoconfiguration, and in case u is 0 and t is different from 0, the terminal carboxyl group of $X^{14}$ is unsubstituted or amidated, t represents an integer of from 0 to 4, $X^{15}$ represents a group of the formula (IIb)

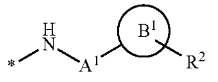

(IIb)

wherein

* marks the bond to a terminal carboxyl group of the adjoining amino acid, $A^1$ is a bond or $C_1$-$C_6$-alkylene, wherein one $CH_2$ group in $C_1$-$C_6$-alkylene may be exchanged for —O— or —S—, and wherein $C_1$-$C_6$-alkylene is up to trisubstituted identically or differently by a radical selected from the group consisting of hydroxyl, methoxy, ethoxy, carboxy, amino and halogen, $B^1$ is absent, aryl, heteroaryl, $C_3$-$C_8$-cycloalkyl or $C_3$-$C_7$-heterocycloalkyl, wherein aryl, heteroaryl, $C_3$-$C_8$-cycloalkyl and $C_3$-$C_7$-heterocycloalkyl can be up to trisubstituted identically or differently by a radical selected from the group of $C_1$-$C_4$-alkyl, hydroxyl, methoxy, ethoxy, carbonyl, carboxy, amino and halogen, and $R^2$ is hydrogen, halogen, amino, hydroxyl or $C_1$-$C_2$O-alkyl, wherein $C_1$-$C_2$O-alkyl is up to trisubstituted identically or differently by a radical selected from the group consisting of hydroxyl, carboxy, amino and halogen, u represents the integer 0 or 1, with the proviso that at least one of $X^1$ to $X^{14}$ is an unnatural amino acid.

The invention further provides compounds containing a peptide of the following formula (II), $$(X^1)_q(X^2)_rX^3X^4X^5X^6X^7X^8X^9X^{10}X^{11}X^{12}(X^{13})_s(X^{14})_t \quad \text{(II)},$$

or a derivative, prodrug, analogue, pharmaceutically acceptable salt, solvate or solvate of the salt, wherein $X^1$ represents a natural amino acid or an unnatural amino acid, q represents the integer 0 or 1, $X^2$ represents the natural amino acid I, r represents the integer 0 or 1, $X^3$ represents the natural amino acid C or the unnatural amino acid L-Penicillamine (Pen), $X^4$ represents the natural amino acid S, $X^5$ represents the natural amino acid R or the unnatural amino acid N(5)-Methyl-L-arginine ((Me)R), $X^6$ represents the natural amino acid S, $X^7$ represents the natural amino acid L or the unnatural amino acid L-tert-Butylalanine ((tBu)A), $X^8$ represents the natural amino acid P or the unnatural amino acid L-Proline (3,4-$_2$H), $X^9$ represents the natural amino acid P or the unnatural amino acid 2,3,3a,4,5,6,7,7a-Octahydroindole-2-carboxylic acid (Oic), $X^{10}$ represents the natural amino acid I, $X^{11}$ represents an unnatural amino acid selected from a list consisting of L-N-Methylcysteine ((NMe)C) and L-Penicillamine (Pen)

$X^{12}$ represents the natural amino acid I, $X^{13}$ represents the natural amino acid P, s represents the integer 0 or 1, $X^{14}$ represents a natural amino acid selected from a list consisting of D, Q and E, t represents the integer 0 or 1, wherein the N-terminus of the peptide is unsubstituted, acetylated or mono- or disubstituted with $C_1$-$C_{20}$-alkyl, wherein the C-terminus of the peptide is unsubstituted or amidated, and wherein the peptide is cyclized, preferably via a linkage connecting $X^3$ and $X^{11}$.

Unless otherwise defined herein, scientific and technical terms used in this application shall have the meanings that are commonly understood by those of ordinary skill in the art. Generally, nomenclature used in connection with, and techniques of, chemistry, molecular biology, cell and cancer biology, immunology, microbiology, pharmacology, and protein and nucleic acid chemistry, described herein, are those well-known and commonly used in the art.

Throughout this specification, the word "comprise" or variations thereof such as "comprises" or "comprising" will be understood to imply the inclusion of a stated integer (or components) or group of integers (or components), but not the exclusion of any other integer (or components) or group of integers (or components). The singular forms "a", "an" and "the" include the plurals unless the context clearly dictates otherwise. The term "including" and "containing" is used to mean "including but not limited to", which expressions can be used interchangeably. In particular, the expression "compound containing a peptide" means a compound which contains a defined peptide sequence and which can optionally contain further chemical groups or substituents covalently bound to the peptide, e.g. amino acids, fatty acids, chemical groups to enhance pharmacodynamic or pharmacokinetic properties of the peptide or any other chemical groups. It is also to be understood that the expression "compound containing a peptide" explicitly includes the defined peptide sequence without any further chemical groups or substituents covalently bound to that peptide.

As used herein, the following terms have the meanings ascribed to them unless specified otherwise. "Essentially consisting of" is understood as a peptide being at least 80%, at least 85%, at least 90%, at least 95%, at least 96%, at least 97%, at least 98%, or at least 99% identical to the peptide it is compared to.

The terms "protein", "polypeptide" and "peptide" are used interchangeably to refer broadly to a sequence of two or more amino acids linked together, preferable by peptide (amide) bonds. Peptide (amide) bonds are formed when the carboxyl group of one amino acid reacts with the amino group of another. It should be further understood that the terms "protein", "polypeptide" and "peptide" do not indicate a specific length of a polymer of amino acids, nor is it intended to imply or distinguish whether the polypeptide is produced using recombinant techniques, chemical or enzymatic synthesis, or is naturally occurring. It should be further understood, that a peptide can contain one or more parts which are no amino acids under the definition of the present application. These parts are preferably present at the N- and C-terminal ends of the peptide.

The term "amino acid" or "any amino acid" as used herein refers to organic compounds containing amine (—$NH_2$) and carboxyl (—COOH) functional groups, along with a side chain and refers to any and all amino acids, including naturally occurring amino acids (e.g., α-L-amino acids), unnatural amino acids, modified amino acids, and non-natural amino acids. "Natural amino acids" include those found in nature, such as, e.g., the 23 amino acids that combine into peptide chains to form the building-blocks of a vast array of proteins. These are primarily L stereoisomers, although a few D-amino acids occur in bacterial envelopes and some antibiotics. The 20 proteinogenic, natural amino acids in the standard genetic code are listed in Table 2. The "non-standard" natural amino acids are pyrrolysine (found in methanogenic organisms and other eukaryotes), selenocysteine (present in many non-eukaryotes as well as most eukaryotes), and N-formylmethionine (encoded by the start codon AUG in bacteria, mitochondria and chloroplasts).

"Unnatural" or "non-natural" amino acids are non-proteinogenic amino acids (i.e., those not naturally encoded or found in the genetic code) that either occur naturally or are chemically synthesized. Over 140 natural amino acids are known and thousands of more combinations are possible. Examples of "unnatural" amino acids include β-amino acids ($β^3$ and $β^2$), homo-amino acids, proline and pyruvic acid derivatives, 3-substituted alanine derivatives, glycine derivatives, ring-substituted phenylalanine and tyrosine derivatives, linear core amino acids, diamino acids, D-amino acids, and N-methyl amino acids. Unnatural or non-natural amino acids also include modified amino acids. "Modified" amino acids include amino acids (e.g., natural amino acids) that have been chemically modified to include a group, groups, or chemical moiety not naturally present in the amino acid. According to the present invention preferred unnatural amino acids are listed in Table 1. Table 1 displays unnatural amino acids as D- and/or L-stereoisomers, however preferred unnatural amino acids according to the invention are both D- and L-stereoisomers of unnatural amino acids listed in Table 1.

TABLE 1

| Preferred unnatural amino acids |
|---|
| (1R,2R)-2-Amino-1-cyclopentanecarboxylic acid (R,R-ACPC) |
| (1R,3S)-3-(Amino)cyclopentanecarboxylic acid |
| (1R,3S,5R)-2-azabicyclo[3.1.0]hexane-3-carboxylic acid |
| (1S,2S)-2-Amino-1-cyclopentanecarboxylic acid (S,S-ACPC) |
| (1S,2S,5R)-3-azabicyclo[3.1.0]hexane-2-carboxylic acid |
| (1R,2S,5S)-3-Azabicyclo[3.1.0]hexane-2-carboxylic acid |
| (1S,3R)-3-(Amino)cyclopentanecarboxylic acid |
| (1S,3R)-3-(Amino)cyclopentanecarboxylic acid |
| (1S,3R,4R)-2-Azabicyclo[2.2.1]heptane-3-carboxylic acid |
| (2S)-2-(Amino)-2-[(1S,3R)-3-hydroxycyclohexyl]acetic acid |
| (2S)-2-(Amino)-2-[(1S,3S)-3-hydroxycyclohexyl]acetic acid |
| (2R)-Amino-(1-methyl-1H-indazol-5-yl)acetic acid |
| (2S)-2-Amino-5-methyl-hexanoic acid |
| (2S)-2-[(3R)-3-Amino-2-oxopyrrolidin-1-yl]-4-methylpentanoic acid |
| (2S)-2[(amino)-2-(tetrahydro-2H-pyran-4-yl)]acetic acid |
| (2S)-2-amino-3-(1-methylcyclopropyl)propanoic acid |
| (2S)-2-amino-3-(2,3,4,5,6-pentafluorophenyl)propanoic acid |

TABLE 1-continued

| Preferred unnatural amino acids |
|---|
| (2S)-2-amino-3-(4-tert-butylphenyl)propanoic acid |
| (2S)-2-Amino-4-(benzylamino)-4-oxobutanecarboxylic acid |
| (2S)-2-amino-4,4,4-trifluorobutanoic acid |
| (2S)-2-Amino-5-methyl-hexanoic acid |
| (2S)-3-(2,3-difluorophenyl)-2-aminopropanoic acid |
| (2S)-3-(3-Cyanophenyl)-2-aminopropanoic acid |
| (2S)-3-(4-carboxyphenyl)-2-aminopropanoic acid |
| (2S)-3-(indol-4-yl)-2-(amino)propanoic acid |
| (2S)-3-(Triazol-1-yl)-2-(amino)propanoic acid |
| (2S)-Amino-(1-methyl-1H-indazol-5-yl)acetic acid |
| (2S)-Amino-2-[3-(Trifluoromethyl)bicyclo[1.1.1]pent-1-yl]acetic acid |
| (2S)-Pyrrolidin-2-ylacetic acid (beta-homo-P) |
| (2S,3aS,6aS)-octahydrocyclopenta[b]pyrrole-2-carboxylic acid |
| (2S,3S)-2-((Amino)methyl)-3-methylpentanoic acid |
| (2S,3S)-2-[(3R)-3-Amino-2-oxopyrrolidin-1-yl]-3-methylpentanoic acid |
| (2S,3S)-2-[(3S)-2-oxopiperazin-1-yl]-3-methylpentanoic acid |
| (2S,4S)-4-fluoroproline ((cis-4-Fluoro)P) |
| (2S,4S)-4-Trifluoromethyl-pyrrolidine-2-carboxylic acid ((4-CF3)P) |
| (3R,6R)-1,1-Difluoro-5-azaspiro[2.4]heptane-6-carboxylic acid (enantiomer 1) |
| (3R,6R)-1,1-Difluoro-5-azaspiro[2.4]heptane-6-carboxylic acid (enantiomer 2) |
| (4aR,6aR,9S,11aS)-11-oxo-2,3,4,4a,6a,7,8,9,11,11a-decahydro-1H-pyrido[3,2-e]pyrrolo[1,2-a]azepine-9-carboxylic acid |
| (6S)-5-Azaspiro[2.4]heptane-6-carboxylic acid |
| (R)-3-Aminoadipic acid |
| (R)-4-Amino-6-methylheptanoic acid |
| (R)-Piperidine-3-Carboxylic Acid |
| (R)-Pyrrolidine-3-Carboxylic Acid |
| (S)-(1-Piperidin-3-yl)-acetic acid |
| (S)-(trifluoromethyl)-L-cysteine |
| (S)-2-(Amino)-1,6-hexanedioic acid (AAD) |
| (S)-2-Amino-2-cyclobutylacetic acid (Cbg) |
| (S)-2-Amino-3-ethyl-pentanoic acid |
| (S)-3-(1-Pyrrolidine-2-yl)-propionic acid |
| (S)-4-Piperazine-2-carboxylic acid |
| (S)-Piperidine-3-carboxylic acid |
| (S)-Pyrrolidine-2-carboxylic acid (beta-P) |
| [(2R)-4,4-Difluoropyrrolidin-2-yl]acetic acid |
| 1-(Aminomethyl)-cyclopropyl-1-carboxylic acid |
| 1,13-Diamino-4,7,10-trioxatridecan-succinamic acid |
| 12-Amino-4,7,10-trioxadodecanoic acid |
| 14-Amino-3,6,9,12-tetraoxatetradecanoic acid |
| 15-Amino-4,7,10,13-tetraoxa(Pen)tadecanoic acid |
| 17-Amino-3,6,9,12,15-(Pen)taoxaheptadecanoic acid |
| 18-Amino-4,7,10,13,16-(Pen)taoxaoctadecanoic acid |
| 1-Amino-3,6,9,12,15,18,21,24,27-nonaoxatriacontan-30-oic acid |
| 1-Amino-3,6,9,12,15,18,21,24-octaoxaheptacosan-27-oic acid |
| 1-Amino-3,6,9,12,15,18,21-heptaoxatetracosan-24-oic acid |
| 1-Amino-3,6,9,12,15,18-hexaoxahenicosan-21-oic acid |
| 1-Aminocyclobutane-1-carboxylic acid (ACBA) |
| 1-Benzyl-L-histidine (H(1-Bn)) |
| 1-Methyl-L-histidine (H(1-Me)) |
| 2-(Cyclohexylamino)acetic acid |
| 2,3,3a,4,5,6,7,7a-Octahydroindole-2-carboxylic acid (Oic) |
| 2,5-difluoro-L-phenylalanine |
| 2-[(1S,2S)-1-(amino)-2-methylbutyl]-1,3-oxazole-4-carboxylic acid |
| 2-Amino-1,7-heptanedioic acid |
| 2-Amino-5,5,5-trifluoro-4-methyl-pentanoic acid |
| 2-Amino-7-(tert-butoxy)-7-oxoheptanoic acid |
| 2-Aminoisobutyric acid (Aib) |
| 2-Chloro-L-phenylalanine ((2-Chloro)F) |
| 2-Fluoro-L-phenylalanine ((2-Fluoro)F) |
| 2-Methyl-D-alloisoleucine |
| 2-Methyl-L-phenylalanine ((2-Me)F) |
| 2-Methyl-L-Proline (2-Me)P, |
| 3-(1,3-Benzothiazol-2-yl)-L-alanine ((Bth)A) |
| 3-(Aminomethyl)benzoic acid |
| 3-(Trimethylsilyl)-L-alanine |
| 3-Amino-2,2-dimethylpropionic acid |
| 3-Aminomethylphenylacetic acid |
| 3-Azido-L-Alanine |
| 3-Carboxyphenylalanine |
| 3-Chloro-L-Phenylalanine |
| 3-Chlorophenylglycine ((3-Chloro-Ph)G) |
| 3-Cyano-L-phenylalanine |
| 3-Ethyl-L-Norvaline |
| 3-Fluoro-L-phenylalanine |

TABLE 1-continued

| Preferred unnatural amino acids |
|---|
| 3-Methyl-L-phenylalanine |
| 4-(3,5-Dimethyl-1,2-oxazol-4-yl)-L-phenylalanine |
| 4-(Aminomethyl)benzoic acid |
| 4-Aminomethylphenylacetic acid |
| 4-Ethyl-L-norleucine |
| 4-Fluoro-Leucine ((4-Fluoro)L) |
| 4-Fluoro-L-phenylalanine((4-Fluoro)F) |
| 5,5,5-Trifluoro-L-leucine ((Trifluoro)L) |
| 5-azaspiro[2.4]heptane-6-carboxylic acid |
| 6-Aminohexanoic acid (Ahx) |
| 8-Aminocubane-1-carboxylic acid |
| 9-Amino-4,7-dioxanonanoic acid |
| allo-L-Isoleucine (allo-I) |
| allo-L-Threonine (allo-T) |
| Aminocyclobutanecarboxylic acid (ACBC) |
| Aminoisobutyric acid (Aib) |
| beta-Alanine (beta-A) |
| Cyclohexylalanine (Cha) |
| D-2-Chlorophenylalanine |
| D-beta-Proline |
| D-cyclohexylalanine |
| D-Hydroxyproline |
| D-N-Methylalanine |
| Gamma-Aminobutyric acid (Gamma-Abu) |
| Hydroxyproline (Hyp) |
| Iminodiacetic acid |
| L-Homoserine (hSer) |
| L-1-Napthylalanine (1-Nal) |
| L-2,3-Diaminopropionic acid (Dap) |
| L-2,4-Diaminobutyric acid (Dab) |
| L-2,6-Difluorophenylalanine |
| L-2-Amino-4-cyanobutyric acid |
| L-2-Aminobutyric acid (Abu) |
| L-2-Bromophenylalanine ((2-Bromo)F) |
| L-2-Napthylalanine (2-Nal) |
| L-2-Pyridylalanine (2-Pal) |
| L-2-Thienylalanine |
| L-3-Bromophenylalanine ((3-Bromo)F) |
| L-3-Methylhistidine (H(3-Me)) |
| L-3-Pyridylalanine (3-Pal) |
| L-4,4-difluoroproline ((Difluoro)P) |
| L-4-Aminophenylalanine ((4-Amino)F) |
| L-4-Bromophenylalanine |
| L-4-Pyridylalanine |
| L-Citrulline (Cit) |
| L-Cyclobutylalanine (Cba) |
| L-Cyclobutylglycind |
| L-Cyclohexylalanine |
| L-Cyclohexylglycine |
| L-Cyclohexylglycine (Chg) |
| L-Cyclopentylalanine |
| L-cyclopentylalanine (Cpa) |
| L-Cyclopentylglycine (Cpg) |
| L-Cyclopropylmethylalanine |
| L-Difluoromethylalanine |
| L-Dihydroorotic acid (Hoo) |
| L-Homocysteine |
| L-Hydroxyproline (Hyp) |
| L-Methionine-L-sulfoxide |
| L-Methionine-sulfone |
| L-N,N-Dimethylalanine ((N,N-diMe)A) |
| L-N-Methylalanine |
| L-N-Methylcysteine ((N-Me)C) |
| L-N-Methylisoleucine ((N-Me)I) |
| L-N-Methylphenylalanine ((N-Me)F) |
| L-Norleucine (Nle) |
| L-Norvaline (Nva) |
| L-Ornithine (Orn) |
| L-Penicillamine (Pen) |
| L-Phenylglycine (Phg) |
| L-Pipecolic acid (Pip) |
| L-Propargylglycine |
| L-Pyroglutamic acid (Pyr) |
| L-tert-Butylalanine ((tBu)A) |
| L-tert-Butylglycine ((tBu)G) |
| L-trans-3-Hydroxyproline ((3S-OH)P) |
| L-Trifluoromethylalanine |
| Morpholine-3-carboxylic |

TABLE 1-continued

| Preferred unnatural amino acids |
| --- |
| N(5)-methyl-L-arginine ((Me)R) |
| N-e-Isopropyl-L-lysine |
| N-Methyl-Alanine (N-Me)A |
| N-Methyl-Glycine ((N-Me)G) |
| N-Phenylglycine ((N-Ph)G) |
| Palmitic acid (Palm) |
| rel-(1R,2S)-2-Amino-1-cyclopentanecarboxylic acid (ACPC) |
| rel-(1R,3R,5R,6R)-6-(Trifluoromethyl)-2-azabicyclo[3.1.0]hexane-3-carboxylic acid |
| rel-(1R,3S)-3-[(Amino)methyl]cyclohexanecarboxylic acid |
| rel-(3R,6R)-1,1-difluoro-5-azaspiro[2.4]heptane-6-carboxylic acid (enantiomer 1) |
| rel-(3R,6R)-1,1-difluoro-5-azaspiro[2.4]heptane-6-carboxylic acid (enantiomer 2) |
| S-2-amino-3-ethyl-pentanoic acid |
| S-3-1-Pyrrolidin-2-yl-propionic acid |
| Tranexamic acid (Tranexamic) |
| trans-2-(3-(Amino)cyclohexyl)acetic acid |
| trans-4-Fluoroproline ((trans-4-Fluoro)P) |
| 3-Amino-3-methylbutyric acid |

More preferred unnatural amino acid are selected from a list consisting of N-Methyl-Alanine (N-Me)A, N-Methyl-Glycine ((N-Me)G), (1R,3S,4S)-2-azabicyclo[2.2.1]heptane-3-carboxylic acid, L-3-Bromophenylalanine ((3-Bromo)F), L-N,N-Dimethylalanine ((N,N-diMe)A), N,N-Dimethylglycine ((N,N-diMe)G), N-Phenylglycine ((N-Ph)G), (R)-Piperidine-3-carboxylic acid, (S)-Piperidine-3-carboxylic acid, L-tert-Butylalanine ((tBu)A), L-2-Pyridylalanine (2-Pal), L-3-Pyridylalanine (3-Pal), L-4-Pyridylalanine (4-Pal), 3-(Aminomethyl)benzoic acid, 3-Amino-2,2-dimethylpropionic acid, 3-Amino-3-methylbutyric acid, 4-(Aminomethyl)benzoic acid, L-2-Aminobutyric acid (Abu), 1-Aminocyclobutane-1-carboxylic acid (ACBA), 6-Aminohexanoic acid (Ahx), 2-Aminoisobutyric acid (Aib), L-2-Thienylalanine (beta-2-thienylalanine), beta-Alanine (beta-A), beta-Proline (beta-P), L-Citrulline (Cit), L-2,4-Diaminobutyric acid (Dab), L-2,3-Diaminopropionic acid (Dap), Gamma-Aminobutyric acid (Gamma-Abu), L-3-Methylhistidine (3-Me)H), L-Dihydroorotic acid (Hoo), L-Norleucine (Nle), N-Methyl-L-proline ((N-Me)P), L-Norvaline (Nva), L-Ornithine (Orn), L-Pipecolic acid (Pip), (2S)-2[(Amino)-2-(tetrahydro-2H-pyran-4-yl)]acetic acid; 2,3,3a,4,5,6,7,7a-Octahydroindole-2-carboxylic acid (Oic), L-N-Methylcysteine ((N-Me)C), N(5)-methyl-L-arginine ((Me)R), L-Penicillamine (Pen) and Tranexamic acid (Tranexamic).

Most preferred unnatural amino acid are selected from a list consisting of N-Methyl-L-Alanine (N-Me)A, N-Methyl-Glycine ((N-Me)G), L-Norleucine (Nle), L-Norvaline (Nva), L-Ornithine (Orn), N(5)-methyl-L-arginine ((Me)R), L-tert-Butylalanine ((tBu)A), 2,3,3a,4,5,6,7,7a-Octahydroindole-2-carboxylic acid (Oic), L-N-Methylcysteine ((N-Me)C) and L-Penicillamine (Pen).

It should be further understood, that a peptide according to the invention can contain one or more chemical groups which are no amino acid under the definition of the present invention. These chemical groups can be present at the N- and/or C-terminal ends of a peptid and are represented by formula $X^0$ and $X^{15}$. It should be understood that all amino acids and chemical groups of the peptids of the present invention are connected via peptide (amide) bonds. Generally peptides are formed by linking α-amino and carboxy groups of α-amino acids, which are then linked by a-peptide bonds. According to the present invention a peptide bond can be formed by any carboxyl- and amino group being present in a respective natural or unnatural amino acid. For example, α-amino acids which contain a second amino group in addition to the α-amino group (e.g. L-lysine) or α-amino acids which, in addition to the a-carboxy group, contain a second carboxy group, (eg. L-aspartic acid and L-glutamic acid) can be connected via the additional amino- or carboxy group.

In accordance with the understanding of a person skilled in the art, the peptide sequences disclosed herein represent sequences of amino acids, which are connected via a-peptide bonds. An amino acid linked via a peptide bond, which is not an a-peptide bond, are marked by a "*". The "*" is either on the left or the right side of the amino acid, to illustrate whether the additional amino group or the additional carboxy group of that amino acid is used for the peptide bond to the adjoining amino acid (e.g. (*L), (E*), (*Dap) etc.).

In accordance with the understanding of a person skilled in the art, the peptide sequences disclosed herein are shown proceeding from left to right, with the left end of the sequence being the "N-terminus" ("amino terminus", "N-terminal end") of the peptide and the right end of the sequence being the "C-terminus" ("carboxy terminus", "C-terminal end") of the peptide. This terminology N-terminus (amino terminus, N-terminal end)" applies irrespective of whether the peptide actually contains an amino group at the N-terminus. This terminology C-terminus (carboxy terminus, C-terminal end) applies irrespective of whether the peptide actually contains a carboxy group at the C-terminus. The term "terminal amino group" refers to any amino group present at the N-terminus. The term "terminal carboxyl group" refers to any carboxyl group present at the C-terminus.

According to the present invention the N-terminus can be formed by $X^0$, in case p represents 1. Alternatively the N-terminus can be formed by $X^1$, in case q represents at least 1 and p represents 0. Alternatively the N-terminus can be formed by $X^2$, in case r represents 1 and p and q both represent 0. In case p, q and r all represent 0, the N-terminus is formed by $X^3$ in case of a linear peptide. In case the peptide of the present invention is cyclized via a linkage connecting $X^3$ and $X^{11}$ and p, q and r all represent 0, the peptid does not comprise an N-terminus.

According to the present invention the C-terminus can be formed by $X^{15}$, in case u represents 1. Alternatively the C-terminus can be formed by $X^{14}$, in case t represents an integer of at least 1 and u represents 0. Alternatively the C-terminus can be formed by $X^{13}$ in case s represents 1 and t and u both represent 0. In case s, t and u all represent 0, the C-terminus is formed by $X^{12}$.

In the present invention the names of naturally occurring and non-naturally occurring aminoacyl residues used herein are preferably following the naming conventions suggested by the IUPAC Commission on the Nomenclature of Organic Chemistry and the IUPAC-IUB Commission on Biochemical Nomenclature as set out in *Nomenclature of α-Amino Acids* (*Recommendations,* 1974), *Biochemistry,* 14(2), (1975).

In the present specification naturally occurring proteinogenic amino acids are usually designated by their conventional single-letter abbreviations. Alternatively, they can also be referred to by their three-letter abbreviations (e.g. in particular in the sequence listings) or by their full name as shown in Table 2 below:

TABLE 2

| Standard Abbreviations for Natural Amino Acids | | |
|---|---|---|
| 3-Letter | 1-Letter | Amino Acid |
| Ala | A | Alanine |
| Arg | R | Arginine |
| Asn | N | Asparagine |
| Asp | D | Aspartic acid |
| Cys | C | Cysteine |
| Glu | E | Glutamic acid |
| Gln | Q | Glutamine |
| Gly | G | Glycine |
| His | H | Histidine |
| Ile | I | Isoleucine |
| Leu | L | Leucine |
| Lys | K | Lysine |
| Met | M | Methionine |
| Phe | F | Phenylalanine |
| Pro | P | Proline |
| Ser | S | Serine |
| Thr | T | Threonine |
| Trp | W | Tryptophan |
| Tyr | Y | Tyrosine |
| Val | V | Valine |

In the case of non-proteinogenic or non-naturally occurring amino acids, unless they are referred to by their full name (e.g. ornithine, etc.), frequently employed three- to six-character codes are employed for residues thereof, including those abbreviations as indicated in the abbreviation list below (Table 3).

The term "L-amino acid" as used herein refers to the "L" isomeric form of an amino acid, and conversely the term "D-amino acid" refers to the "D" isomeric form of an amino acid. It is further a conventional manner to indicate the L-amino acid with capital letters such as Ala/A, Arg/R, etc. and the D-amino acid with small letters such as ala/a, arg/r, etc.

The three-letter code in the form as indicated in Table 2 above, i.e. Ala, Arg, Asn etc. and as generally used in the present specification, shall generally comprise the D- and L-form as well as homo- and nor-forms, unless explicitly indicated otherwise. The prefix "nor" refers to a structural analog that can be derived from a parent compound by the removal of one carbon atom along with the accompanying hydrogen atoms. The prefix "homo" indicates the next higher member in a homologous series. A reference to a specific isomeric form will be indicated by the capital prefix L- or D- as described above (e.g. D-Arg, L-Arg etc.). A specific reference to homo- or nor-forms will accordingly be explicitly indicated by a respective prefix (e.g. homo-Arg, homo-R, nor-Arg, nor-R, homo-Cys, homo-C etc.).

The term "$C_1$-$C_6$-alkyl" means a linear or branched, saturated, monovalent hydrocarbon group having 1, 2, 3, 4, 5 or 6 carbon atoms, e.g. a methyl, ethyl, propyl, isopropyl, butyl, sec-butyl, isobutyl, tert-butyl, pentyl, isopentyl, 2-methylbutyl, 1-methylbutyl, 1-ethylpropyl, 1,2-dimethylpropyl, neo-pentyl, 1,1-dimethylpropyl, hexyl, 1-methylpentyl, 2-methylpentyl, 3-methylpentyl, 4-methylpentyl, 1-ethylbutyl, 2-ethylbutyl, 1,1-dimethylbutyl, 2,2-dimethylbutyl, 3,3-dimethylbutyl, 2,3-dimethylbutyl, 1,2-dimethylbutyl or 1,3-dimethylbutyl group, or an isomer thereof. Particularly, said group has 1, 2, 3 or 4 carbon atoms ("$C_1$-$C_4$-alkyl"), e.g. a methyl, ethyl, propyl, isopropyl, butyl, sec-butyl isobutyl, or tert-butyl group, more particularly 1, 2 or 3 carbon atoms ("$C_1$-$C_3$-alkyl"), e.g. a methyl, ethyl, n-propyl or isopropyl group. Particularly preferred is methyl, ethyl, n-propyl. Most preferred is methyl.

The term "$C_1$-$C_{20}$-alkyl" means a linear or branched, saturated, monovalent hydrocarbon group having 1, to 20 carbon atoms, e.g. a methyl, ethyl, propyl, isopropyl, butyl, sec-butyl isobutyl, tert-butyl or pentyl, isopentyl, hexyl, isohexyl, heptyl, isoheptyl, octyl and isooctyl, nonyl, decyl, dodecyl or eicosyl.

The term "$C_1$-$C_4$-alkylene" means a straight-chain or branched hydrocarbon bridge having 1 to 4 carbon atoms, e.g. methylene, ethylene, propylene, (α-methylethylene, β-methylethylene, α-ethylethylene, β-ethylethylene, butylene, α-methylpropylene, β-methylpropylene and γ-methylpropylene.

The term "$C_1$-$C_6$-alkylene" means a straight-chain or branched hydrocarbon bridge having 1 to 6 carbon atoms, e.g. methylene, ethylene, propylene, (α-methylethylene, β-methylethylene, α-ethylethylene, β-ethylethylene, butylene, α-methylpropylene, β-methylpropylene, γ-methylpropylene, α-ethylpropylene, β-ethylpropylene, y-ethylpropylene, pentylene and hexylene.

The term "$C_3$-$C_8$-cycloalkyl" means a saturated hydrocarbon ring which contains 3, 4, 5, 6, 7 or 8 carbon atoms. Said $C_3$-$C_8$-cycloalkyl group is for example, a monocyclic hydrocarbon ring, e.g. a cyclopropyl, cyclobutyl, cyclopentyl, cyclohexyl, cycloheptyl or cyclooctyl group, a bicyclic hydrocarbon ring, e.g. a bicyclo[4.2.0]octyl or octahydropentalenyl, or a bridged or caged saturated ring groups such as norborane or adamantane, and cubane.

The term "$C_3$-$C_7$-heterocycloalkyl" means a saturated heterocycle with 4, 5, 6 or 7 which contains one or two identical or different ring heteroatoms from the series N, O and S, it being possible for said heterocycloalkyl group to be attached to the rest of the molecule via any one of the carbon atoms or, if present, a nitrogen atom. Said $C_3$-$C_7$-heterocycloalkyl group, without being limited thereto, can be a 4-membered ring, such as azetidinyl, oxetanyl or thietanyl, for example; or a 5-membered ring, such as tetrahydrofuranyl, 1,3-dioxolanyl, thiolanyl, pyrrolidinyl, imidazolidinyl, pyrazolidinyl, 1,1-dioxidothiolanyl, 1,2-oxazolidinyl, 1,3-oxazolidinyl or 1,3-thiazolidinyl, for example; or a 6 membered ring, such as tetrahydropyranyl, tetrahydrothiopyranyl, piperidinyl, morpholinyl, dithianyl, thiomorpholinyl, piperazinyl, hexahydropyrimidinyl, 1,3-dioxanyl, 1,4-dioxanyl or 1,2-oxazinanyl, for example, or a 7 membered ring, such as azepanyl, 1,4-diazepanyl or 1,4-oxazepanyl, for example.

The term "aryl" means an unsaturated or partially unsaturated cycle having 6 to 10 carbon atoms. Preferred aryl radicals are phenyl and naphthyl.

The term "heteroaryl" means a monovalent, monocyclic, bicyclic or tricyclic aromatic ring having 5, 6, 8, 9, 10, 11, 12, 13 or 14 ring atoms (a "5 to 14 membered heteroaryl" group), particularly 5, 6, 9 or 10 ring atoms, which contains at least one ring heteroatom and optionally one, two or three further ring heteroatoms from the series: N, O and/or S, and which is bound via a ring carbon atom or optionally via a ring nitrogen atom (if allowed by valency). Said heteroaryl group can be a 5-membered heteroaryl group, such as, for example, thienyl, furanyl, pyrrolyl, oxazolyl, thiazolyl, imidazolyl, pyrazolyl, isoxazolyl, isothiazolyl, oxadiazolyl, triazolyl, thiadiazolyl or tetrazolyl; or a 6-membered heteroaryl group, such as, for example, pyridinyl, pyridazinyl, pyrimidinyl, pyrazinyl or triazinyl; or a tricyclic heteroaryl group, such as, for example, carbazolyl, acridinyl or phenazinyl; or a 9-membered heteroaryl group, such as, for example, benzofuranyl, benzothienyl, benzoxazolyl, benzisoxazolyl, benzimidazolyl, benzothiazolyl, benzotriazolyl, indazolyl, indolyl, isoindolyl, indolizinyl or purinyl; or a 10-membered heteroaryl group, such as, for example, quinolinyl, quinazolinyl, isoquinolinyl, cinnolinyl, phthalazinyl, quinoxalinyl or pteridinyl.

In general, and unless otherwise mentioned, the heteroaryl or heteroarylene groups include all possible isomeric forms thereof, e.g.: tautomers and positional isomers with respect to the point of linkage to the rest of the molecule. Thus, for some illustrative non-restricting examples, the term pyridinyl includes pyridine-2-yl, pyridine-3-yl and pyridine-4-yl; or the term thienyl includes thien-2 yl- and thien-3-yl.

Among sequences disclosed herein are sequences incorporating either an "—OH" moiety or an "—$NH_2$" moiety at the carboxy terminus (C-terminus) of the sequence. An "—OH" or an "—$NH_2$" moiety at the C-terminus of the sequence indicates a hydroxy group or an amino group, corresponding to the presence of a carboxy group or an amido (—(C═O)—$NH_2$) group at the C-terminus, respectively. In each sequence of the invention, a C-terminal "—OH" moiety may be substituted for a C-terminal "—$NH_2$" moiety, which is also referred to as "amidated C-terminus" in the present invention, and vice-versa. However, among said alternatives a C-terminal "—OH" moiety is preferred.

The term "acetylated" (also abbreviated "Ac") refers to an acetyl protection of the N-terminal moiety through acetylation of the N-terminus of a peptide (N-terminus of the peptide is acetylated).

According to a further embodiment, the invention provides compounds containing a peptide, which may be isolated and/or purified, comprising, essentially consisting of, or consisting of, formula (I) or a derivative, prodrug, analogue, pharmaceutically acceptable salt, solvate or solvate of the salt, wherein $X^0$ is a chemical group selected from the list consisting of, (1S,2S,4S)-Bicyclo[2.2.1]hept-5-en-2-ylacetic acid, (2,4-Dioxoimidazolidin-1-yl)acetic acid, 2-(Thiomorpholine)acetic acid ((2-Thiomorpholine)acetyl), 2-(N-Isopropyl-N-methylamino)acetic acid, (S)-3-Methylvaleric acid ((S)-3-Methylpentanoic acid), 2-(3-Pyridyl)acetic acid, 2-(Cyclohexylamino)acetic acid (2-(Cyclohexylamino)acetyl), 2-(Diethylamino)acetic acid (2-(Diethylamino)acetyl), 2-(Morpholine)acetic acid (2-(Morpholine)acetyl), 2-(N-Methyl-N-cyclopropylamino)acetic acid (2-(N-Methyl-N-cyclopropylamino)acetyl), 2-(Piperidin)acetic acid (2-(Piperidin) acetyl), 2-(Pyrrolidine)acetic acid (2-(Pyrrolidine) acetyl), 2-Hydroxyacetic acid (2-Hydroxyacetyl), 2-Hydroxyisobutyric acid (2-Hydroxyisobutyric), 3-(Aminomethyl)benzoic acid, 3-Methoxypropionic acid, 4-(Aminomethyl)benzoic acid, 4-Methylpentanoic acid (4-Methylvaleric), 5-Chorothiophene-carboxylic acid, 1-(Aminomethyl)-cyclopropyl-1-carboxylic acid (ACMP), Adipic acid, (S)-Azetidine-2-carboxylic acid, Benzoic acid (Benzoic), 4-(3,5-Dimethyl-1,2-oxazol-4-yl)-L-phenylalanine, Cyclobutanecarboxylic acid (Cyclobutanecarboxylic), 2-(Cyclobutyl)acetic acid (Cyclobutylacetic), Cyclobutylacetic acid (Cyclobutylacetic), Cyclohexylacetic acid (Cyclohexylacetic), Cyclohexanecarboxylic acid (Cyclohexylcarboxylic), Cyclopentanecarboxylic acid, Cyclopentylacetic acid (Cyclopentylacetic), Cyclopropanecarboxylic acid (Cyclopropanecarboxylic), Cyclopropylacetic acid, D-(+)Biotin, Fumaric acid, 3-Phenylpropanoic acid (Hydrocinnamic), Isobutyric acid, Isovaleric acid (Isovaleric), L-(+)-Lactic acid (Lactic), Phenylacetic acid, Piperidin-4-ylacetic acid, Pivalic acid (Pivalic), Suberic acid, tert-Butylacetic acid, Tetrahydropyranyl-4-acetic acid, Tetrahydro-2H-pyran-3-ylacetic acid and trans-2-(3-((t-butoxy)carbonylamino)cyclohexyl)acetic acid), p represents the integer 0 or 1, $X^1$ represents a natural amino acid selected from the list consisting of A, F, G, H, I, K, L, P, R, S, T, V, W and Y or an unnatural amino acid selected from a list consisting of N-Methyl-Alanine (N-Me)A, N-Methyl-Glycine ((N-Me)G), (1R,3S,4S)-2-azabicyclo[2.2.1] heptane-3-carboxylic acid, L-3-Bromophenylalanine ((3-Bromo)F), L-N,N-Dimethylalanine ((N,N-diMe) A), N,N-Dimethylglycine ((N,N-diMe)G), N-Phenylglycine ((N-Ph)G), (R)-Piperidine-3-carboxylic acid, (S)-Piperidine-3-carboxylic acid, L-tert-Butylalanine ((tBu)A), L-2-Pyridylalanine (2-Pal), L-3-Pyridylalanine (3-Pal), L-4-Pyridylalanine (4-Pal), 3-(Aminomethyl)benzoic acid, 3-Amino-2,2-dimethylpropionic acid, 3-Amino-3-methylbutyric acid, 4-(Aminomethyl)benzoic acid, L-2-Aminobutyric acid (Abu), 1-Aminocyclobutane-1-carboxylic acid (ACBA), 6-Aminohexanoic acid (Ahx), 2-Aminoisobutyric acid (Aib), L-2-Thienylalanine (beta-2-thienylalanine), beta-Alanine (beta-A), beta-Proline (beta-P), L-Citrulline (Cit), L-2,4-Diaminobutyric acid (Dab), L-2,3-Diaminopropionic acid (Dap), Gamma-Aminobutyric acid (Gamma-Abu), L-3-Methylhistidine (3-Me)H), L-Dihydroorotic acid (Hoo), L-Norleucine (Nle), N-Methyl-L-proline ((N-Me)P), L-Norvaline (Nva), L-Ornithine (Orn), L-Pipecolic acid (Pip), (2S)-2[(Amino)-2-(tetrahydro-2H-pyran-4-yl)]acetic acid and Tranexamic acid (Tranexamic), whereas each natural amino acid and/or unnatural amino acid in L-stereoconfiguration can be replaced by the stereoisomer in D-stereoconfiguration, q represents an integer of from 0 to 5, $X^2$ represents the natural amino acid I or an unnatural amino acid selected from a list consisting of L-N-Methylisoleucine ((N-Me)I), allo-L-Isoleucine (allo-I), L-Cyclobutylalanine (Cba), L-Norvaline (Nva), L-2-Aminobutyric acid (Abu), (2S,3S)-2-[(3R)-3-Amino-2-oxopyrrolidin-1-yl]-3-methylpentanoic acid, (2S,3S)-2-[2-Oxopiperazin-1-yl]-3-methylpentanoic acid and (2S,3S)-2-[(3S)-2-oxopiperazin-1-yl]-3-methylpentanoic acid, whereas each natural amino acid and/or unnatural amino acid in L-stereoconfiguration can be replaced by the stereoisomer in D-stereoconfiguration, r represents the integer 0 or 1, $X^3$ represents the natural amino acid C or the unnatural amino acid L-Penicillamine (Pen), $X^4$ represents a natural amino acid selected from a list consisting of S, C, T, R and K, $X^5$ represents the natural amino acid R or the unnatural amino acid N(5)-methyl-L-arginine ((Me)R), $X^6$ represents the natural amino acid S, or an unnatural amino acid selected from a list consisting of allo-L-Threonine (allo-T) and L-2,3-diaminopropionic acid (Dap), $X^7$ represents a natural amino acid selected from a list consisting of L and N, or an unnatural amino acid selected from a list consisting of 2,5-Difluoro-L-phenylalanine ((2,5-Difluoro)F), L-2-Bromophenylalanine ((2-Bromo)F), 2-Chloro-L-phenylalanine ((2-Chloro) F), L-4-Bromophenylalanine ((4-Bromo)F), 4-Fluoro-L-Leucine ((4-Fluoro)L), L-tert-Butylalanine ((tBu)A), L-tert-Butylglycine ((tBu)G), 5,5,5-Trifluoro-L-leucine ((Trifluoro)L), (S)-2-(Amino)-1,6-hexanedioic acid (AAD), (2S)-2-amino-4,4,4-trifluorobutanoic acid, L-2-amino-4-cyanobutyric acid (Cnba), (S)-(trifluoromethyl)-L-cysteine, (2S)-2-amino-3-(1-methylcyclopropyl)propanoic acid, (2S)-3-(2,3-difluorophenyl)-2-aminopropanoic acid, 2,3,3a,4,5,6,7,7a-Octahydroindole-2-carboxylic acid (Oic), 3-(Trimethylsilyl)-L-alanine and 2-Amino-7-(tert-butoxy)-7-oxoheptanoic acid, $X^8$ represents the natural amino acid P, or an unnatural amino acid selected from a list consisting of (1S,2S,5R)-3-azabicyclo[3.1.0]hexane-2-carboxylic acid, (1R,2S,5S)-3-azabicyclo[3.1.0]hexane-2-carboxylic acid, trans-4-fluoroproline ((trans-4-Fluoro)P), L-Hydroxyproline (Hyp), (3S)-Morpholine-3-carboxylic acid (Morpholine-3-carboxylic), L-Pipecolic acid (Pip) and (4aR,6aR,9S,11aS)-11-Oxo-2,3,4,4a,6a,7,8,9,11,11a-decahydro-1H-pyrido[3,2-e]pyrrolo[1,2-a]azepine-9-carboxylic acid, $X^9$ represents the natural amino acid P, or an unnatural amino acid selected from a list consisting of 2,3,3a,4,5,6,7,7a-Octahydroindole-2-carboxylic acid (Oic), (6S)-5-Azaspiro[2.4]heptane-6-carboxylic acid, rel-(1R,3R,5R,6R)-6-(trifluoromethyl)-2-azabicyclo [3.1.0]hexane-3-carboxylic acid, (2S,4S)-4-Trifluoromethyl-pyrrolidine-2-carboxylic acid ((4-CF3)P), (2S,3aS,6aS)-octahydrocyclopenta[b]pyrrole-2-carboxylic acid, (1R,3S,5R)-2-azabicyclo[3.1.0]hexane-3-carboxylic acid, (2S)-2-Amino-4,4,4-trifluorobutanoic acid, L-trans-3-hydroxyproline ((3S—OH)P, trans-4-fluoroproline ((trans-4-Fluoro)P), L-Hydroxyproline (Hyp), (2S,4S)-4-Fluoroproline ((cis-4-Fluoro)P), (3R,6R)-1,1-Difluoro-5-azaspiro[2.4]heptane-6-carboxylic acid (enantiomer 1) and (3R,6R)-1,1-Difluoro-5-azaspiro[2.4]heptane-6-carboxylic acid (enantiomer 2), $X^{10}$ represents the natural amino acid I, or an unnatural amino acid selected from a list consisting of (2S)-2-(Amino)-2-[(1S,3R)-3-hydroxycyclohexyl]acetic acid, 3-Chlorophenylglycine ((3-Chloro-Ph)G), (S)-2-amino-3-ethyl-pentanoic acid, allo-L-Isoleucine (allo-I), L-Cyclohexylglycine (Chg), L-Cyclopentylglycine (Cpg), L-Cyclobutylglycine and L-Norvaline (Nva), $X^{11}$ represents the natural amino acid C, or an unnatural amino acid selected from a list consisting of LN-Methylcysteine ((N-Me)C) and L-Penicillamine (Pen), $X^{12}$ represents the natural amino acid I, or an unnatural amino acid selected from a list consisting of 2-[(1S,2S)-1-(amino)-2-methylbutyl]-1,3-oxazole-4-carboxylic acid, (S)-2-Amino-2-cyclobutylacetic acid (Cbg), allo-L-Isoleucine (allo-J), L-Phenylglycine (Phg), 2-methyl-D-alloisoleucine and (2S,3S)-2-((amino)methyl)-3-methylpentanoic acid, and in case u and t and s are all 0, the terminal carboxyl group of $X^{12}$ is unsubstituted or amidated, $X^{13}$ represents a natural amino acid selected from a list consisting of P, A and D or an unnatural amino acid selected from a list consisting of 2-Methyl-L-Proline (2-Me)P, N-Methyl-Glycine ((N-Me)G), trans-4-fluoroproline ((trans-4-Fluoro)P), L-2-Aminobutyric acid (Abu), 2-Aminoisobutyric acid (Aib), Hydroxyproline (Hyp) and 2,3,3a,4,5,6,7,7a-Octahydroindole-2-carboxylic acid (Oic), whereas each natural amino acid and/or unnatural amino acid in L-stereoconfiguration can be replaced by the stereoisomer in D-stereoconfiguration, and in case u and t are both 0 and s is different from 0, the terminal carboxyl group of $X^{13}$ is unsubstituted or amidated, s represents an integer of from 0 to 3, $X^{14}$ represents a natural amino acid selected from a list consisting of D, E, G, K, N, P and Q or an unnatural amino acid selected from a list consisting of 3-Carboxyphenylalanine ((3-Carboxy)F), (2S)-2-Amino-4-(benzylamino)-4-oxobutanecarboxylic acid ((N-Benzyl)D), N-Methyl-Glycine ((N-Me)G), 6-Aminohexanoic acid (Ahx), (2S)-Pyrrolidin-2-ylacetic acid (beta-homo-P), L-2,3-Diaminopropionic acid (Dap), L-Ornithine (Orn) and Tranexamic acid (Tranexamic), and in case u is 0 and t is different from 0, the terminal carboxyl group of $X^{14}$ is unsubstituted or amidated, whereas each natural amino acid and/or unnatural amino acid in L-stereoconfiguration can be replaced by the stereoisomer in D-stereoconfiguration, t represents an integer of from 0 to 4, $X^{15}$ is a chemical group selected from the list consisting of (1R,3S)-3-(Amino)cyclopentanecarboxylic acid, (1S,3R)-3-(Amino)cyclopentanecarboxylic acid, (R)-4-Amino-6-methylheptanoic acid, (S)(1-Piperidin-3-yl)-acetic acid, (S)-3-(1-Pyrrolidine-2-yl)-propionic acid, (S)-3-(2H-tetrazol-5-yl)propanoic acid, (S)-Pyrrolidine-3-carboxylic acid, 5-Azaspiro[2.4]heptane-1-carboxylic acid and (2S)-3-(Triazol-1-yl)-2-(amino) propanoic acid, u represents the integer 0 or 1, with the proviso that the peptide contains at least one unnatural amino acid.

According to a further embodiment, the invention provides compounds containing a peptide, which may be isolated and/or purified, comprising, essentially consisting of, or consisting of, formula (I) or a derivative, prodrug, analogue, pharmaceutically acceptable salt, solvate or solvate of the salt, wherein $X^0$ is a chemical group selected from the list consisting of (1R,3S,4S)-2-azabicyclo[2.2.1]heptane-3-carboxylic acid, (2-Thiomorpholine)acetic acid, (N-Isopropyl-N-methylamino)acetic acid, 2-(3-Pyridyl)acetic acid, 2-(Cyclohexylamino)acetic acid, 2-(Diethylamino)acetic acid, 2-(Morpholine)acetic acid, 2-(Piperidin)acetic acid, 2-(Pyrrolidine)acetic acid, 3-(Aminomethyl)benzoic acid, 4-(Aminomethyl)benzoic acid, 1-(Aminomethyl)-cyclopropyl-1-carboxylic acid (ACMP), Azetidine-2-carboxylic acid, Benzoic acid, Cyclobutylacetic acid, Cyclopropylacetic acid, Phenylacetic acid, Piperidin-4-ylacetic acid, Tetrahydro-2H-pyran-3-ylacetic acid, Tranexamic acid and trans-2-(3-((t-butoxy)carbonylamino)cyclohexyl)acetic acid, p represents the integer 0 or 1, $X^1$ represents a natural amino acid selected from a list consisting of A, F, G, H, I, K, L, P, R, S, T, V, W and Y or an unnatural amino acid selected from a list consisting of L-N,N-Dimethylalanine ((N,N-diMe)A), N-Methyl-Alanine (N-Me)A, N-Methyl-Glycine ((N-Me)G), L-2-Pyridylalanine (2-Pal), L-3-Pyridylalanine (3-Pal), L-4-Pyridylalanine (4-Pal), L-2-Aminobutyric acid (Abu), 6-Aminohexanoic acid (Ahx), 2-Aminoisobutyric acid (Aib), 3-(Aminomethyl)benzoic acid, 3-Amino-2,2-dimethylpropionic acid, 3-Amino-3-methylbutyric acid, 4-(Aminomethyl)benzoic acid, beta-2-thienylalanine, (S)-Pyrrolidine-2-carboxylic acid (beta-P), L-Citrulline (Cit), L-2,4-diaminobutyric acid (Dab), L-2,3-diaminopropionic acid (Dap), Gamma-Aminobutyric acid (Gamma-Abu), L-3-Methylhistidine (H(3-Me)), L-Dihydroorotic acid (Hoo), L-Norleucine (Nle), L-Norvaline (Nva), L-Ornithine (Orn), L-Pipecolic acid (Pip), N-Methyl-L-proline ((N-Me)P), Tranexamic acid (Tranexamic), (1R,3S,4S)-2-azabicyclo[2.2.1]heptane-3-carboxylic acid and (2S)-2 [(amino)-2-(tetrahydro-2H-pyran-4-yl)]acetic acid, whereas each natural amino acid and/or unnatural amino acid in L-stereoconfiguration can be replaced by the stereoisomer in D-stereoconfiguration, q represents an integer of from 0 to 5, $X^2$ represents the natural amino acid I or an unnatural amino acid selected from a list consisting of L-N-Methylisoleucine ((N-Me)I), L-Cyclobutylalanine (Cba), L-Norvaline (Nva) and L-2-Aminobutyric acid (Abu), whereas each natural amino acid and/or unnatural amino acid in L-stereoconfiguration can be replaced by the stereoisomer in D-stereoconfiguration, r represents the integer 0 or 1, $X^3$ represents the natural amino acid C or the unnatural amino acid L-Penicillamine (Pen), $X^4$ represents a natural amino acid selected from a list consisting of S and T, $X^5$ represents the natural amino acid R, $X^6$ represents the natural amino acid S or the unnatural amino acid allo-L-Threonine (allo-T), $X^7$ represents a natural amino acid selected from a list consisting of N and L, or an unnatural amino acid selected from a list consisting of 2,5-Difluoro-L-phenylalanine ((2,5-Difluoro)F), L-2-Bromophenylalanine ((2-Bromo)F), 2-Chloro-L-phenylalanine ((2-Chloro) F), 4-Fluoro-L-Leucine ((4-Fluoro)L), L-tert-Butylalanine ((tBu)A), (S)-(trifluoromethyl)-L-cysteine, (2S)-2-amino-3-(1-methylcyclopropyl)propanoic acid and 2,3,3a,4,5,6,7,7a-Octahydroindole-2-carboxylic acid (Oic), 3-(Trimethylsilyl)-L-alanine, $X^8$ represents the natural amino acid P, or an unnatural amino acid selected from a list consisting of (1S,2S, 5R)-3-azabicyclo[3.1.0]hexane-2-carboxylic acid and (4aR,6aR,9S,11aS)-11-oxo-2,3,4,4a,6a,7,8,9,11,11a-decahydro-1H-pyrido[3,2-e]pyrrolo[1,2-a]azepine-9-carboxylic acid, $X^9$ represents the natural amino acid P, or an unnatural amino acid selected from a list consisting of 2,3,3a,4, 5,6,7,7a-Octahydroindole-2-carboxylic acid (Oic), (2S, 4S)-4-Trifluoromethyl-pyrrolidine-2-carboxylic acid ((4-CF3)P), (6S)-5-Azaspiro[2.4]heptane-6-carboxylic acid, rel-(1R,3R,5R,6R)-6-(trifluoromethyl)-2-azabicyclo[3.1.0]hexane-3-carboxylic acid, (2S,3aS,6aS)-octahydrocyclopenta[b]pyrrole-2-carboxylic acid, rel-(3R,6R)-1,1-difluoro-5-azaspiro[2.4]heptane-6-carboxylic acid (enantiomer 1) and rel-(3R,6R)-1,1-difluoro-5-azaspiro[2.4]heptane-6-carboxylic acid (enantiomer 2), $X^{10}$ represents the natural amino acid I, or an unnatural amino acid selected from a list consisting of (2S)-2-(Amino)-2-[(1S,3R)-3-hydroxycyclohexyl]acetic acid, (S)-2-amino-3-ethyl-pentanoic acid, L-Cyclohexylglycine (Chg) and L-Cyclopentylglycine (Cpg), $X^{11}$ represents the natural amino acid C, or an unnatural amino acid selected from a list consisting of LN-Methylcysteine ((N-Me)C) and L-Penicillamine (Pen), $X^{12}$ represents the natural amino acid I, or an unnatural amino acid selected from a list consisting of allo-L-Isoleucine (allo-I), (S)-2-Amino-2-cyclobutylacetic acid (Cbg) and 2-[(1S,2S)-1-(amino)-2-methylbutyl]-1,3-oxazole-4-carboxylic acid, and in case u and t and s are all 0, the terminal carboxyl group of $X^{12}$ is unsubstituted or amidated, $X^{13}$ represents a natural amino acid selected from a list consisting of P and D or an unnatural amino acid selected from a list consisting of 2-Aminoisobutyric acid (Aib), 2-Methyl-L-Proline (2-Me)P and trans-4-fluoroproline ((trans-4-Fluoro)P), whereas each natural amino acid and/or unnatural amino acid in L-stereoconfiguration can be replaced by the stereoisomer in D-stereoconfiguration, and in case u and t are both 0 and s is different from 0, the terminal carboxyl group of $X^{13}$ unsubstituted or amidated, s represents an integer of from 0 to 3, $X^{14}$ represents a natural amino acid selected from a list consisting of D, Q, N, E and P or an unnatural amino acid selected from a list consisting of 3-Carboxyphenylalanine ((3-Carboxy)F), N-Methyl-Glycine ((N-Me)G), (2S)-Pyrrolidin-2-ylacetic acid (beta-homo-P), L-2,3-Diaminopropionic acid (Dap), L-Ornithine (Orn) and Tranexamic acid (Tranexamic), whereas each natural amino acid and/or unnatural amino acid in L-stereoconfiguration can be replaced by the stereoisomer in D-stereoconfiguration, and in case u is 0 and t is different from 0, the terminal carboxyl group of $X^{14}$ is unsubstituted or amidated, t represents an integer of from 0 to 4, $X^{15}$ is a chemical group selected from the list consisting of (1R,3S)-3-(Amino)cyclopentanecarboxylic acid, (1S,3R)-3-(Amino)cyclopentanecarboxylic acid, (R)-4-Amino-6-methylheptanoic acid, (S)(1-Piperidin-3-yl)-acetic acid, (S)-3-(1-Pyrrolidine-2-yl)-propionic acid, (S)-3-(2H-tetrazol-5-yl)propanoic acid, (S)-Pyrrolidine-3-carboxylic acid, 5-Azaspiro[2.4]heptane-1-carboxylic acid and (2S)-3-(Triazol-1-yl)-2-(amino) propanoic acid, u represents the integer 0 or 1, with the proviso that the peptide contains at least one unnatural amino acid.

According to a further embodiment, the invention provides compounds containing a peptide, which may be isolated and/or purified, comprising, essentially consisting of, or consisting of, formula (I) or a derivative, prodrug, analogue, pharmaceutically acceptable salt, solvate or solvate of the salt, wherein p represents an integer of 0, $X^1$ represents a natural amino acid selected from the list consisting of A and G or an unnatural amino acid selected from a list consisting of N-Methyl-L-Alanine (N-Me)A, N-Methyl-Glycine ((NMe)G), L-Norleucine (Nle), L-Norvaline (Nva) and L-Ornithine (Orn), q represents the integer 0 or 1, $X^2$ represents the natural amino acid I, r represents the integer 0 or 1, $X^3$ represents the natural amino acid C or the unnatural amino acid L-Penicillamine (Pen), $X^4$ represents the natural amino acid S, $X^5$ represents the natural amino acid R or the unnatural amino acid N(5)-methyl-L-arginine ((Me)R), $X^6$ represents the natural amino acid S, $X^7$ represents the natural amino acid L or the unnatural amino acid L-tert-Butylalanine ((tBu)A), $X^8$ represents the natural amino acid P, $X^9$ represents the natural amino acid P or the unnatural amino acid 2,3,3a,4,5,6,7,7a-Octahydroindole-2-carboxylic acid (Oic), $X^{10}$ represents the natural amino acid I, $X^{11}$ represents the natural amino acid C, or an unnatural amino acid selected from a list consisting of L-N-Methylcysteine ((N-Me)C) and L-Penicillamine (Pen), $X^{12}$ represents the natural amino acid I, and in case u and t and s are all 0, the terminal carboxyl group of $X^{12}$ is unsubstituted or amidated, $X^{13}$ represents the natural amino acid P, and in case u and t are both 0 and s is different from 0, the terminal carboxyl group of $X^{13}$ is unsubstituted or amidated, s represents the integer 0 or 1, $X^{14}$ represents a natural amino acid selected from a list consisting of D, Q and E, and in case u is 0 and t is different from 0, the terminal carboxyl group of $X^{14}$ is unsubstituted or amidated, t represents the integer 0 or 1, u represents an integer of 0, with the proviso that the peptide contains at least one unnatural amino acid.

According to a further embodiment, the invention provides a compound containing a peptide of the following formula (II), $$(X^1)_q(X^2)_rX^3X^4X^5X^6X^7X^8X^9X^{10}X^{11}X^{12}(X^{13})_s(X^{14})_t \quad (II),$$

or a derivative, prodrug, analogue, pharmaceutically acceptable salt, solvate or solvate of the salt, wherein $X^1$ represents a natural amino acid selected from a list consisting of A and G, or an unnatural amino acid selected from a list consisting of N-Methyl-L-Alanine (N-Me)A, N-Methyl-Glycine ((NMe)G), L-Norleucine (Nle), L-Norvaline (Nva) and L-Ornithine (Orn), q represents the integer 0 or 1, $X^2$ represents the natural amino acid I, r represents the integer 0 or 1, $X^3$ represents the natural amino acid C or the unnatural amino acid L-Penicillamine (Pen), $X^4$ represents the natural amino acid S, $X^5$ represents the natural amino acid R or the unnatural amino acid N(5)-Methyl-L-arginine ((Me)R), $X^6$ represents the natural amino acid S, $X^7$ represents the natural amino acid L or the unnatural amino acid L-tert-Butylalanine ((tBu)A), $X^8$ represents the natural amino acid P or the unnatural amino acid L-Proline (3,4-$_2$H), $X^9$ represents the natural amino acid P or the unnatural amino acid 2,3,3a,4,5,6,7,7a-Octahydroindole-2-carboxylic acid (Oic), $X^{10}$ represents the natural amino acid I, $X^{11}$ represents an unnatural amino acid selected from a list consisting of L-N-Methylcysteine ((N-Me)C) and L-Penicillamine (Pen), $X^{12}$ represents the natural amino acid I, $X^{13}$ represents the natural amino acid P, s represents the integer 0 or 1, $X^{14}$ represents a natural amino acid selected from a list consisting of D, Q and E, t represents the integer 0 or 1, wherein the N-terminus of the peptide is unsubstituted, acetylated or mono- or disubstituted with $C_1$-$C_{20}$-alkyl, wherein the C-terminus of the peptide is unsubstituted or amidated, and wherein the peptide is cyclized via a linkage connecting $X^3$ and $X^{11}$.

According to a further embodiment, the invention provides a compound containing a peptide of formula (II) or a derivative, prodrug, analogue, pharmaceutically acceptable salt, solvate or solvate of the salt, wherein $X^1$ represents a natural amino acid or an unnatural amino acid, q represents the integer 0 or 1, $X^2$ represents the natural amino acid I, r represents the integer 0 or 1, $X^3$ represents the natural amino acid C or the unnatural amino acid L-Penicillamine (Pen), $X^4$ represents the natural amino acid S, $X^5$ represents the natural amino acid R or the unnatural amino acid N(5)-Methyl-L-arginine ((Me)R), $X^6$ represents the natural amino acid S, $X^7$ represents the natural amino acid L or the unnatural amino acid L-tert-Butylalanine ((tBu)A), $X^8$ represents the natural amino acid P or the unnatural amino acid L-Proline (3,4-$_2$H), $X^9$ represents the unnatural amino acid 2,3,3a,4,5,6,7,7a-Octahydroindole-2-carboxylic acid (Oic), $X^{10}$ represents the natural amino acid I, $X^{11}$ represents the natural amino acid C, or an unnatural amino acid selected from a list consisting of L-N-Methylcysteine ((N-Me)C) and L-Penicillamine (Pen), $X^{12}$ represents the natural amino acid I, $X^{13}$ represents the natural amino acid P, s represents the integer 0 or 1, $X^{14}$ represents a natural amino acid selected from a list consisting of D, Q and E, t represents the integer 0 or 1, wherein the N-terminus of the peptide is unsubstituted, acetylated or mono- or disubstituted with $C_1$-$C_{20}$-alkyl, wherein the C-terminus of the peptide is unsubstituted or amidated, and wherein the peptide is cyclized via a linkage connecting $X^3$ and $X^{11}$.

According to a further embodiment, the invention provides a compound containing a peptide of formula (II) or a derivative, prodrug, analogue, pharmaceutically acceptable salt, solvate or solvate of the salt, wherein $X^1$ represents a natural amino acid selected from a list consisting of A and G, or an unnatural amino acid selected from a list consisting of N-Methyl-L-Alanine (N-Me)A, N-Methyl-Glycine ((NMe)G), L-Norleucine (Nle), L-Norvaline (Nva) and L-Ornithine (Orn), q represents the integer 0 or 1, $X^2$ represents the natural amino acid I, r represents the integer 0 or 1, $X^3$ represents the natural amino acid C or the unnatural amino acid L-Penicillamine (Pen), $X^4$ represents the natural amino acid S, $X^5$ represents the natural amino acid R or the unnatural amino acid N(5)-Methyl-L-arginine ((Me)R), $X^6$ represents the natural amino acid S, $X^7$ represents the natural amino acid L or the unnatural amino acid L-tert-Butylalanine ((tBu)A), $X^8$ represents the natural amino acid P or the unnatural amino acid L-Proline (3,4-$_2$H), $X^9$ represents the unnatural amino acid 2,3,3a,4,5,6,7,7a-Octahydroindole-2-carboxylic acid (Oic), $X^{10}$ represents the natural amino acid I, $X^{11}$ represents the natural amino acid C, or an unnatural amino acid selected from a list consisting of L-N-Methylcysteine ((N-Me)C) and L-Penicillamine (Pen), $X^{12}$ represents the natural amino acid I, $X^{13}$ represents the natural amino acid P, s represents the integer 0 or 1, $X^{14}$ represents a natural amino acid selected from a list consisting of D, Q and E, t represents the integer 0 or 1, wherein the N-terminus of the peptide is unsubstituted or acetylated, wherein the C-terminus of the peptide is unsubstituted or amidated, and wherein the peptide is cyclized via a linkage connecting $X^3$ and $X^{11}$.

In particular, the invention provides compounds containing a peptide of the formula (I) or compounds containing a peptide of the formula (II).

According to the present invention, the following definitions of $X^1$ to $X^{14}$ apply to peptides of formula (I) and peptides of formula (II), definitions of positions $X^0$ and $X^{15}$ apply to peptides of formula (I).

According to the present invention $X^0$, if present, can be a chemical group which is not an amino acid, according to the definition herein.

According to a further embodiment of the invention, $X^0$ represents a chemical group selected from the list consisting of 2-cyanobenzoic acid, (1S,2S,4S)-Bicyclo[2.2.1]hept-5-en-2-ylacetic acid, (2,4-Dioxoimidazolidin-1-yl)acetic acid, 2-(Thiomorpholine)acetic acid ((2-Thiomorpholine)acetyl), 2-(N-Isopropyl-N-methylamino)acetic acid, (S)-3-Methylvaleric Acid ((S)-3-Methylpentanoic acid), 2-(3-Pyridyl) acetic acid, 2-(Cyclohexylamino)acetic acid (2-(Cyclohexylamino)acetyl), 2-(Diethylamino)acetic acid (2-(Diethylamino)acetyl), 2-(Morpholine)acetic acid (2-(Morpholine)acetyl), 2-(N-Methyl-N-cyclopropylamino) acetic acid (2-(N-Methyl-N-cyclopropylamino)acetyl), 2-(Piperidin)acetic acid (2-(Piperidin)acetyl), 2-(Pyrrolidine)acetic acid (2-(Pyrrolidine)acetyl), 2-Hydroxyacetic acid (2-Hydroxyacetyl), 2-Hydroxyisobutyric acid (2-Hydroxyisobutyric), 3-(Aminomethyl)benzoic acid, 3-Methoxypropionic acid, 4-(Aminomethyl)benzoic acid, 4-Methylpentanoic acid (4-Methylvaleric), 5-Chorothiophene-carboxylic acid, 1-(Aminomethyl)-cyclopropyl-1-carboxylic acid (ACMP), Adipic acid, (S)-Azetidine-2-carboxylic acid, Benzoic acid (Benzoic), 4-(3,5-Dimethyl-1,2-oxazol-4-yl)-L-phenylalanine, Cyclobutanecarboxylic acid (Cyclobutanecarboxylic), 2-(Cyclobutyl)acetic acid (Cyclobutylacetic), Cyclobutylacetic acid (Cyclobutylacetic), Cyclohexylacetic acid (Cyclohexylacetic), Cyclohexanecarboxylic acid (Cyclohexylcarboxylic), Cyclopentanecarboxylic acid, Cyclopentylacetic acid (Cyclopentylacetic), Cyclopropanecarboxylic acid (Cyclopropanecarboxylic), Cyclopropylacetic acid, D-(+)Biotin, Fumaric acid, 3-Phenylpropanoic acid (Hydrocinnamic), Isobutyric acid, Isovaleric acid (Isovaleric), L-(+)-Lactic acid (Lactic), Phenylacetic acid, Piperidin-4-ylacetic acid, Pivalic acid (Pivalic), Suberic acid, tert-Butylacetic acid, Tetrahydropyranyl-4-acetic acid, Tetrahydro-2H-pyran-3-ylacetic acid and trans-2-(3-((t-butoxy)carbonylamino)cyclohexyl)acetic acid).

According to a further embodiment of the invention, $X^0$ represents a chemical group selected from the list consisting of 2-cyanobenzoic acid, (1R,3S,4S)-2-azabicyclo[2.2.1] heptane-3-carboxylic acid, (2-Thiomorpholine)acetic acid, (N-Isopropyl-N-methylamino)acetic acid, 2-(3-Pyridyl)acetic acid, 2-(Cyclohexylamino)acetic acid, 2-(Diethylamino) acetic acid, 2-(Morpholine)acetic acid, 2-(Piperidin)acetic acid, 2-(Pyrrolidine)acetic acid, 3-(Aminomethyl)benzoic acid, 4-(Aminomethyl)benzoic acid, 1-(Aminomethyl)-cyclopropyl-1-carboxylic acid (ACMP), Azetidine-2-carboxylic acid, Benzoic acid, Cyclobutylacetic acid, Cyclopropylacetic acid, Phenylacetic acid, Piperidin-4-ylacetic acid, Tetrahydro-2H-pyran-3-ylacetic acid, Tranexamic acid and trans-2-(3-((t-butoxy)carbonylamino)cyclohexyl)acetic acid.

According to a further embodiment of the invention, $X^0$ is a chemical group selected from an unnatural amino acid as defined above, 2-cyanobenzoic acid, a substituted benzoic acid or phenyl acetic acids.

According to a further embodiment of the invention, $X^0$ is Hoo, ODD or Ahx.

According to a further embodiment of the invention, p represents an integer of 1.

According to a further embodiment of the invention, p represents an integer of 0.

According to a further embodiment, the invention provides compounds containing a peptide, which may be isolated and/or purified, comprising, essentially consisting of, or consisting of, formula (I) or formula (II) or a derivative, prodrug, analogue, pharmaceutically acceptable salt, solvate or solvate of the salt, wherein $X^1$ represents any natural amino acid, or an unnatural amino acid, preferably selected from a list consisting of unnatural amino acids listed in table 1, whereas each natural amino acid and/or unnatural amino acid in L-stereoconfiguration can be replaced by the stereoisomer in D-stereoconfiguration.

According to a further embodiment of the invention, $X^1$ represents a natural amino acid selected from a list consisting of A, F, G, H, I, K, L, P, R, S, T, V, W and Y, or an unnatural amino acid selected from a list consisting of N-Methyl-Alanine (N-Me)A, N-Methyl-Glycine ((N-Me) G), (1R,3S,4S)-2-azabicyclo[2.2.1]heptane-3-carboxylic acid, L-3-Bromophenylalanine ((3-Bromo)F), L-N,N-Dimethylalanine ((N,N-diMe)A), N,N-Dimethylglycine ((N,N-diMe)G), N-Phenylglycine ((N-Ph)G), (R)-Piperidine-3-carboxylic acid, (S)-Piperidine-3-carboxylic acid, L-tert-Butylalanine ((tBu)A), L-2-Pyridylalanine (2-Pal), L-3-Pyridylalanine (3-Pal), L-4-Pyridylalanine (4-Pal), 3-(Aminomethyl)benzoic acid, 3-Amino-2,2-dimethylpropionic acid, 3-Amino-3-methylbutyric acid, 4-(Aminomethyl) benzoic acid, L-2-Aminobutyric acid (Abu), 1-Aminocyclobutane-1-carboxylic acid (ACBA), 6-Aminohexanoic acid (Ahx), 2-Aminoisobutyric acid (Aib), L-2-Thienylalanine (beta-2-thienylalanine), beta-Alanine (beta-A), beta-Proline (beta-P), L-Citrulline (Cit), L-2,4-Diaminobutyric acid (Dab), L-2,3-Diaminopropionic acid (Dap), Gamma-Aminobutyric acid (Gamma-Abu), L-3-Methylhistidine (3-Me)H), L-Dihydroorotic acid (Hoo), L-Norleucine (Nle), N-Methyl-L-proline ((N-Me)P), L-Norvaline (Nva), L-Ornithine (Orn), L-Pipecolic acid (Pip), (2S)-2[(Amino)-2-(tetrahydro-2H-pyran-4-yl)]acetic acid and Tranexamic acid (Tranexamic), whereas each natural amino acid and/or unnatural amino acid in L-stereoconfiguration can be replaced by the stereoisomer in D-stereoconfiguration.

According to a further embodiment of the invention, $X^1$ represents a natural amino acid selected from a list consisting of A and G, or an unnatural amino acid selected from a list consisting of N-Methyl-L-Alanine (N-Me)A, N-Methyl-Glycine ((N-Me)G), L-Norleucine (Nle), L-Norvaline (Nva) and L-Ornithine (Orn), whereas each natural amino acid and/or unnatural amino acid in L-stereoconfiguration can be replaced by the stereoisomer in D-stereoconfiguration.

According to a further embodiment of the invention, $X^1$ represents a natural amino acid selected from a list consisting of A and G, or an unnatural amino acid selected from a list consisting of N-Methyl-L-Alanine (N-Me)A, N-Methyl-Glycine ((N-Me)G), L-Norleucine (Nle), L-Norvaline (Nva) and L-Ornithine (Orn).

According to a further embodiment of the invention, $X^1$ represents the natural amino acid A or the unnatural amino acid N-Methyl-Glycine ((N-Me)G).

According to a further embodiment of the invention, in case p is 0 and q is different from 0, the terminal amino group of $X^1$ is unsubstituted, acetylated or mono- or disubstituted with $C_1$-$C_4$-alkyl, preferably monosubstituted, with $C_1$-$C_{20}$-alkyl.

According to a further embodiment of the invention, $X^1$ is methylated.

According to a further embodiment of the invention, $X^1$ is acetylated.

According to a further embodiment of the invention, q represents an integer of 0.

According to a further embodiment of the invention, q represents an integer of 1.

According to a further embodiment, the invention provides compounds containing a peptide, which may be isolated and/or purified, comprising, essentially consisting of, or consisting of, formula (I) or formula (II) or a derivative, prodrug, analogue, pharmaceutically acceptable salt, solvate or solvate of the salt, wherein $X^2$ represents a natural amino acid selected from a list consisting of I, L, M, V and A, or an unnatural amino acid selected from a list consisting of L-N-Methylisoleucine ((N-Me)I), allo-L-Isoleucine (allo-I), L-Cyclobutylalanine (Cba), L-Norvaline (Nva), L-2-Aminobutyric acid (Abu), (2S,3S)-2-[(3R)-3-Amino-2-oxopyrrolidin-1-yl]-3-methylpentanoic acid, (2S,3S)-2-[2-Oxopiperazin-1-yl]-3-methylpentanoic acid, (2S,3S)-2-[(3S)-2-oxopiperazin-1-yl]-3-methylpentanoic acid, L-Methionine-L-sulfoxide, L-Methionine-sulfone and L-tert-butylglycine, whereas each natural amino acid and/or unnatural amino acid in L-stereoconfiguration can be replaced by the stereoisomer in D-stereoconfiguration.

According to a further embodiment of the invention, $X^2$ represents the natural amino acid I or an unnatural amino acid selected from a list consisting of L-N-Methylisoleucine ((N-Me)I), allo-L-Isoleucine (allo-I), L-Cyclobutylalanine (Cba), L-Norvaline (Nva), L-2-Aminobutyric acid (Abu), (2S,3S)-2-[(3R)-3-Amino-2-oxopyrrolidin-1-yl]-3-methylpentanoic acid, (2S,3S)-2-[2-Oxopiperazin-1-yl]-3-methylpentanoic acid and (2S,3S)-2-[(3S)-2-oxopiperazin-1-yl]-3-methylpentanoic acid, whereas each natural amino acid and/or unnatural amino acid in L-stereoconfiguration can be replaced by the stereoisomer in D-stereoconfiguration.

According to a further embodiment of the invention, $X^2$ represents the natural amino acid I or an unnatural amino acid selected from a list consisting of L-N-Methylisoleucine ((N-Me)I), L-Cyclobutylalanine (Cba), L-Norvaline (Nva) and L-2-Aminobutyric acid (Abu), whereas each natural amino acid and/or unnatural amino acid in L-stereoconfiguration can be replaced by the stereoisomer in D-stereoconfiguration.

According to a further embodiment of the invention, $X^2$ represents the natural amino acid I.

According to a further embodiment of the invention, in case p and q are both 0 and r is 1, the terminal amino group of $X^2$ is unsubstituted, acetylated or mono- or disubstituted with $C_1$-$C_{20}$-alkyl, preferably monosubstituted, with $C_1$-$C_4$-alkyl.

According to a further embodiment of the invention, r represents an integer of 0.

According to a further embodiment of the invention, r represents an integer of 1.

According to a further embodiment, the invention provides compounds containing a peptide, which may be isolated and/or purified, comprising, essentially consisting of, or consisting of, formula (I) or formula (II) or a derivative, prodrug, analogue, pharmaceutically acceptable salt, solvate or solvate of the salt, wherein $X^3$ represents the natural amino acid C, or an unnatural amino acid selected from a list consisting of L-Penicillamine (Pen) and L-N-Methylcysteine ((N-Me)C).

According to a further embodiment of the invention, $X^3$ represents the natural amino acid C or the unnatural amino acid L-Penicillamine (Pen).

According to a further embodiment of the invention, $X^3$ represents the natural amino acid C.

According to a further embodiment of the invention, in case p and q and r are all 0, the terminal amino group of $X^3$ is unsubstituted, acetylated or mono- or disubstituted with $C_1$-$C_4$-alkyl, preferably monosubstituted, with $C_1$-$C_{20}$-alkyl.

According to a further embodiment, the invention provides compounds containing a peptide, which may be isolated and/or purified, comprising, essentially consisting of, or consisting of, formula (I) or formula (II) or a derivative, prodrug, analogue, pharmaceutically acceptable salt, solvate or solvate of the salt, wherein $X^4$ represents a natural amino acid selected from a list consisting of S, C, T, R or K, or an unnatural amino acid selected from a list consisting of allo-L-Threonine (allo-T), L-Homoserine (hSer) and L-Ornithine (Orn).

According to a further embodiment of the invention, $X^4$ represents a natural amino acid selected from a list consisting of S, C, T, R and K.

According to a further embodiment of the invention, $X^4$ represents a natural amino acid selected from a list consisting of S or T.

According to a further embodiment of the invention, $X^4$ represents the natural amino acid S.

According to a further embodiment, the invention provides compounds containing a peptide, which may be isolated and/or purified, comprising, essentially consisting of, or consisting of, formula (I) or formula (II) or a derivative, prodrug, analogue, pharmaceutically acceptable salt, solvate or solvate of the salt, wherein $X^5$ represents the natural amino acid R or the unnatural amino acid N(5)-methyl-L-arginine ((Me)R).

According to a further embodiment of the invention, $X^5$ represents the natural amino acid R or the unnatural amino acid N(5)-methyl-L-arginine ((Me)R).

According to a further embodiment of the invention, $X^5$ represents the natural amino acid R.

According to a further embodiment, the invention provides compounds containing a peptide, which may be isolated and/or purified, comprising, essentially consisting of, or consisting of, formula (I) or formula (II) or a derivative, prodrug, analogue, pharmaceutically acceptable salt, solvate or solvate of the salt, wherein $X^6$ represents a natural amino acid selected from a list consisting of S, C or T, or an unnatural amino acid selected from a list consisting of allo-L-Threonine (allo-T) and L-2,3-diaminopropionic acid (Dap).

According to a further embodiment of the invention, $X^6$ represents the natural amino acid S or an unnatural amino acid selected from a list consisting of allo-L-Threonine (allo-T) and L-2,3-diaminopropionic acid (Dap).

According to a further embodiment of the invention, $X^6$ represents the natural amino acid S or the unnatural amino acid allo-L-Threonine (allo-T).

According to a further embodiment of the invention, $X^6$ represents the natural amino acid S.

According to a further embodiment, the invention provides compounds containing a peptide, which may be isolated and/or purified, comprising, essentially consisting of, or consisting of, formula (I) or formula (II) or a derivative, prodrug, analogue, pharmaceutically acceptable salt, solvate or solvate of the salt, wherein $X^7$ represents a natural amino acid selected from a list consisting of L, F or N or an unnatural amino acid selected from a list consisting of 2,3,3a,4,5,6,7,7a-Octahydroindole-2-carboxylic acid (Oic), L-4-Bromophenylalanine ((4-Bromo)F), 2,5-Difluoro-L-phenylalanine ((2,5-Difluoro)F), L-tert-Butylalanine ((tBu)A), 2-Chloro-L-phenylalanine ((2-Chloro)F), L-2-Bromophenylalanine ((2-Bromo)F), (S)-2-(Amino)-1,6-hexanedioic acid (AAD), (2S)-2-amino-4,4,4-trifluorobutanoic acid, L-2-amino-4-cyanobutyric acid (Cnba), 4-Fluoro-Leucine ((4-Fluoro)L), (S)-(trifluoromethyl)-L-cysteine, (2S)-2-amino-3-(1-methylcyclopropyl) propanoic acid, L-tert-Butylglycine ((tBu)G), 3-(Trimethylsilyl)-L-alanine, 2,5-difluoro-L-phenylalanine, 2-Amino-7-(tert-butoxy)-7-oxoheptanoic acid, 5,5,5-Trifluoro-L-leucine ((Trifluoro)L), 2-Methyl-L-phenylalanine ((2-Me) F), L-Cyclobutylalanine (Cba), L-Cyclopentylalanine (Cpa), L-cyclopropylmethylalanine, L-trifluoromethylalanine, L-difluoromethylalanine, 2-Fluoro-L-phenylalanine ((2-Fluoro)F), (2S)-3-(2,3-difluorophenyl)-2-aminopropanoic acid, (2S)-3-(3-Cyanophenyl)-2-aminopropanoic acid, 2-Amino-5,5,5-trifluoro-4-methyl-pentanoic acid, (2S)-2-Amino-5-methyl-hexanoic acid and (2S)-3-(indol-4-yl)-2-(amino)propanoic acid.

According to a further embodiment of the invention, $X^7$ represents a natural amino acid selected from a list consisting of L and N, or an unnatural amino acid selected from a list consisting of 2,5-Difluoro-L-phenylalanine ((2,5-Difluoro)F), L-2-Bromophenylalanine ((2-Bromo)F), 2-Chloro-L-phenylalanine ((2-Chloro)F), L-4-Bromophenylalanine ((4-Bromo)F), 4-Fluoro-L-Leucine ((4-Fluoro) L), L-tert-Butylalanine ((tBu)A), L-tert-Butylglycine ((tBu) G), 5,5,5-Trifluoro-L-leucine ((Trifluoro)L), (S)-2-(Amino)-1,6-hexanedioic acid (AAD), (2S)-2-amino-4,4,4-trifluorobutanoic acid, L-2-amino-4-cyanobutyric acid (Cnba), (S)-(trifluoromethyl)-L-cysteine, (2S)-2-amino-3-(1-methylcyclopropyl)propanoic acid, (2S)-3-(2,3-difluorophenyl)-2-aminopropanoic acid, 2,3,3a,4,5,6,7,7a-Octahydroindole-2-carboxylic acid (Oic), 3-(Trimethylsilyl)-L-alanine and 2-Amino-7-(tert-butoxy)-7-oxoheptanoic acid.

According to a further embodiment of the invention, $X^7$ represents a natural amino acid selected from a list consisting of N or L, or an unnatural amino acid selected from a list consisting of 2,5-Difluoro-L-phenylalanine ((2,5-Difluoro) F), L-2-Bromophenylalanine ((2-Bromo)F), 2-Chloro-L-phenylalanine ((2-Chloro)F), 4-Fluoro-L-Leucine ((4-Fluoro)L), L-tert-Butylalanine ((tBu)A), (S)-(trifluoromethyl)-L-cysteine, (2S)-2-amino-3-(1-methylcyclopropyl)propanoic acid and 2,3,3a,4,5,6,7,7a-Octahydroindole-2-carboxylic acid (Oic), 3-(Trimethylsilyl)-L-alanine.

According to a further embodiment of the invention, $X^7$ represents the natural amino acid L or the unnatural amino acid L-tert-Butylalanine ((tBu)A).

According to a further embodiment of the invention, $X^7$ represents the unnatural amino acid L-tert-Butylalanine ((tBu)A).

According to a further embodiment of the invention, $X^7$ represents the natural amino acid L.

According to a further embodiment, the invention provides compounds containing a peptide, which may be isolated and/or purified, comprising, essentially consisting of, or consisting of, formula (I) or formula (II) or a derivative, prodrug, analogue, pharmaceutically acceptable salt, solvate or solvate of the salt, wherein $X^8$ represents the natural amino acid P, or an unnatural amino acid selected from a list consisting of L-Proline (3,4-$_2$H), (1S,2S,5R)-3-azabicyclo [3.1.0]hexane-2-carboxylic acid, (1R,2S,5S)-3-azabicyclo [3.1.0]hexane-2-carboxylic acid, L-Hydroxyproline (Hyp), (3S)-Morpholine-3-carboxylic acid (Morpholine-3-carboxylic), L-Pipecolic acid (Pip), (4aR,6aR,9S,11aS)-11-oxo-2,3,4,4a,6a,7,8,9,11,11a-decahydro-1H-pyrido[3,2-e]pyrrolo [1,2-a]azepine-9-carboxylic acid, trans-4-fluoroproline ((trans-4-Fluoro)P) and (1R,2S,5S)-3-azabicyclo[3.1.0] hexane-2-carboxylic acid.

According to a further embodiment of the invention, $X^8$ represents the natural amino acid P, or an unnatural amino acid selected from a list consisting of L-Proline (3,4-$_2$H), (1S,2S,5R)-3-azabicyclo[3.1.0]hexane-2-carboxylic acid, trans-4-fluoroproline ((trans-4-Fluoro)P), L-Hydroxyproline (Hyp), (3S)-Morpholine-3-carboxylic acid (Morpholine-3-carboxylic), L-Pipecolic acid (Pip) and (4aR,6aR,9S,11aS)-11-Oxo-2,3,4,4a,6a,7,8,9,11,11a-decahydro-1H-pyrido[3,2-e]pyrrolo[1,2-a]azepine-9-carboxylic acid.

According to a further embodiment of the invention, $X^8$ represents the natural amino acid P, or an unnatural amino acid selected from a list consisting of L-Proline (3,4-$_2$H), (1S,2S,5R)-3-azabicyclo[3.1.0]hexane-2-carboxylic acid and (4aR,6aR,9S,11aS)-11-oxo-2,3,4,4a,6a,7,8,9,11,11a-decahydro-1H-pyrido[3,2-e]pyrrolo[1,2-a]azepine-9-carboxylic acid.

According to a further embodiment of the invention, $X^8$ represents the natural amino acid P or the unnatural amino acid L-Proline (3,4-$_2$H).

According to a further embodiment of the invention, $X^8$ represents the natural amino acid P.

According to a further embodiment, the invention provides compounds containing a peptide, which may be isolated and/or purified, comprising, essentially consisting of, or consisting of, formula (I) or formula (II) or a derivative, prodrug, analogue, pharmaceutically acceptable salt, solvate or solvate of the salt, wherein $X^9$ represents the natural amino acid P, or an unnatural amino acid selected from a list consisting of 2,3,3a,4,5,6,7,7a-Octahydroindole-2-carboxylic acid (Oic), L-Hydroxyproline (Hyp), (2S,4S)-4-Trifluoromethyl-pyrrolidine-2-carboxylic acid ((4-CF3)P), (2S, 4S)-4-fluoroproline ((cis-4-Fluoro)P), trans-4-fluoroproline ((trans-4-Fluoro)P), (2S)-2-amino-4,4,4-trifluorobutanoic acid, L-trans-3-hydroxyproline ((3S—OH)P, (1R,3S,5R)-2-azabicyclo[3.1.0]hexane-3-carboxylic acid, (6S)-5-Azaspiro [2.4]heptane-6-carboxylic acid, rel-(1R,3R,5R,6R)-6-(trifluoromethyl)-2-azabicyclo[3.1.0]hexane-3-carboxylic acid, (2S)-2-Amino-4,4,4-trifluorobutanoic acid, (2S,3aS,6aS)-octahydrocyclopenta[b]pyrrole-2-carboxylic acid, trans-4-fluoroproline ((trans-4-Fluoro)P), (2S,4S)-4-fluoroproline ((cis-4-Fluoro)P), L-4,4-difluoroproline ((Difluoro)P), rel-(3R,6R)-1,1-difluoro-5-azaspiro[2.4]heptane-6-carboxylic acid (enantiomer 1) and rel-(3R,6R)-1,1-difluoro-5-azaspiro [2.4]heptane-6-carboxylic acid (enantiomer 2).

According to a further embodiment of the invention, $X^9$ represents the natural amino acid P, or an unnatural amino acid selected from a list consisting of 2,3,3a,4,5,6,7,7a-Octahydroindole-2-carboxylic acid (Oic), (6S)-5-Azaspiro [2.4]heptane-6-carboxylic acid, rel-(1R,3R,5R,6R)-6-(trifluoromethyl)-2-azabicyclo[3.1.0]hexane-3-carboxylic acid, (2S,4S)-4-Trifluoromethyl-pyrrolidine-2-carboxylic acid ((4-CF3)P), (2S,3aS,6aS)-octahydrocyclopenta[b]pyrrole-2-carboxylic acid, (1R,3S,5R)-2-azabicyclo[3.1.0]hexane-3-carboxylic acid, (2S)-2-Amino-4,4,4-trifluorobutanoic acid, L-trans-3-hydroxyproline ((3S—OH)P, trans-4-fluoroproline ((trans-4-Fluoro)P), L-Hydroxyproline (Hyp), (2S,4S)-4-Fluoroproline ((cis-4-Fluoro)P), (3R,6R)-1,1-Difluoro-5-azaspiro[2.4]heptane-6-carboxylic acid (enantiomer 1) and (3R,6R)-1,1-Difluoro-5-azaspiro[2.4]heptane-6-carboxylic acid (enantiomer 2).

According to a further embodiment of the invention, $X^9$ represents the natural amino acid P, or an unnatural amino acid selected from a list consisting of 2,3,3a,4,5,6,7,7a-Octahydroindole-2-carboxylic acid (Oic), (2S,4S)-4-Trifluoromethyl-pyrrolidine-2-carboxylic acid ((4-CF3)P), (6S)-5-Azaspiro[2.4]heptane-6-carboxylic acid, rel-(1R,3R,5R,6R)-6-(trifluoromethyl)-2-azabicyclo[3.1.0]hexane-3-carboxylic acid, (2S,3aS,6aS)-octahydrocyclopenta[b]pyrrole-2-carboxylic acid, rel-(3R,6R)-1,1-difluoro-5-azaspiro[2.4]heptane-6-carboxylic acid (enantiomer 1) and rel-(3R,6R)-1,1-difluoro-5-azaspiro[2.4]heptane-6-carboxylic acid (enantiomer 2).

According to a further embodiment of the invention, $X^9$ represents the natural amino acid P or the unnatural amino acid 2,3,3a,4,5,6,7,7a-Octahydroindole-2-carboxylic acid (Oic).

According to a further embodiment of the invention, $X^9$ represents the unnatural amino acid 2,3,3a,4,5,6,7,7a-Octahydroindole-2-carboxylic acid (Oic).

According to a further embodiment, the invention provides compounds containing a peptide, which may be isolated and/or purified, comprising, essentially consisting of, or consisting of, formula (I) or formula (II) or a derivative, prodrug, analogue, pharmaceutically acceptable salt, solvate or solvate of the salt, wherein $X^{10}$ represents the natural amino acid I, or an unnatural amino acid selected from a list consisting of L-Cyclopentylglycine (Cpg), L-Cyclohexylglycine (Chg), (S)-2-amino-3-ethyl-pentanoic acid, 3-Chlorophenylglycine ((3-Chloro-Ph)G), L-tert-butylglycine, allo-L-Isoleucine (allo-I), L-Cyclobutylglycine, L-Norvaline (Nva) and (2S)-2-(Amino)-2-[(1S,3R)-3-hydroxycyclohexyl]acetic acid.

According to a further embodiment of the invention, $X^{10}$ represents the natural amino acid I, or an unnatural amino acid selected from a list consisting of (2S)-2-(Amino)-2-[(1S,3R)-3-hydroxycyclohexyl]acetic acid, 3-Chlorophenylglycine ((3-Chloro-Ph)G), (S)-2-amino-3-ethyl-pentanoic acid, allo-L-Isoleucine (allo-I), L-Cyclohexylglycine (Chg), L-Cyclopentylglycine (Cpg), L-Cyclobutylglycine and L-Norvaline (Nva).

According to a further embodiment of the invention, $X^{10}$ represents the natural amino acid I, or an unnatural amino acid selected from a list consisting of (2S)-2-(Amino)-2-[(1S,3R)-3-hydroxycyclohexyl]acetic acid, (S)-2-amino-3-ethyl-pentanoic acid, L-Cyclohexylglycine (Chg) and L-Cyclopentylglycine (Cpg).

According to a further embodiment of the invention, $X^{10}$ represents the natural amino acid I.

According to a further embodiment, the invention provides compounds containing a peptide, which may be isolated and/or purified, comprising, essentially consisting of, or consisting of, formula (I) or formula (II) or a derivative, prodrug, analogue, pharmaceutically acceptable salt, solvate or solvate of the salt, wherein $X^{11}$ represents the natural amino acid C, or an unnatural amino acid selected from a list consisting of L-N-Methylcysteine ((N-Me)C) and L-Penicillamine (Pen).

According to a further embodiment of the invention, $X^{11}$ represents the natural amino acid C, or an unnatural amino acid selected from a list consisting of L-N-Methylcysteine ((N-Me)C) and L-Penicillamine (Pen).

According to a further embodiment of the invention, $X^{11}$ represents an unnatural amino acid selected from a list consisting of L-N-Methylcysteine ((N-Me)C) and L-Penicillamine (Pen).

According to a further embodiment of the invention, $X^{11}$ represents the unnatural amino acid L-Penicillamine (Pen).

According to a further embodiment, the invention provides compounds containing a peptide, which may be isolated and/or purified, comprising, essentially consisting of, or consisting of, formula (I) or formula (II) or a derivative, prodrug, analogue, pharmaceutically acceptable salt, solvate or solvate of the salt, wherein $X^9$ represents the unnatural amino acid 2,3,3a,4,5,6,7,7a-Octahydroindole-2-carboxylic acid (Oic) and $X^{11}$ represents the unnatural amino acid L-N-Methylcysteine ((N-Me)C) or the unnatural amino acid L-Penicillamine (Pen).

According to a further embodiment of the invention, $X^9$ represents the unnatural amino acid 2,3,3a,4,5,6,7,7a-Octahydroindole-2-carboxylic acid (Oic) and $X^{11}$ represents the unnatural amino acid L-Penicillamine (Pen).

According to a further embodiment of the invention, $X^9$ represents the unnatural amino acid 2,3,3a,4,5,6,7,7a-Octahydroindole-2-carboxylic acid (Oic) and $X^{11}$ represents an unnatural amino acid selected from a list consisting of L-N-Methylcysteine ((N-Me)C) and L-Penicillamine (Pen).

According to a further embodiment, the invention provides compounds containing a peptide, which may be isolated and/or purified, comprising, essentially consisting of, or consisting of, formula (I) or formula (II) or a derivative, prodrug, analogue, pharmaceutically acceptable salt, solvate or solvate of the salt, wherein $X^{12}$ represents the natural amino acid I, or an unnatural amino acid selected from a list consisting of allo-L-Isoleucine (allo-I), (S)-2-Amino-2-cyclobutylacetic acid (Cbg), (2S,3S)-2-((amino)methyl)-3-methylpentanoic acid, L-Phenylglycine (Phg), 2-[(1S,2S)-1-(amino)-2-methylbutyl]-1,3-oxazole-4-carboxylic acid, 2-methyl-D-alloisoleucine, L-Norvaline (Nva), L-2-Aminobutyric acid (Abu), L-tert-butylglycine and Aminoisobutyric acid (Aib).

According to a further embodiment of the invention, $X^{12}$ represents the natural amino acid I, or an unnatural amino acid selected from a list consisting of 2-[(1S,2S)-1-(amino)-2-methylbutyl]-1,3-oxazole-4-carboxylic acid, (S)-2-Amino-2-cyclobutylacetic acid (Cbg), allo-L-Isoleucine (allo-I), L-Phenylglycine (Phg), 2-methyl-D-alloisoleucine and (2S,3S)-2-((amino)methyl)-3-methylpentanoic acid.

According to a further embodiment of the invention, $X^{12}$ represents the natural amino acid I, or an unnatural amino acid selected from a list consisting of allo-L-Isoleucine (allo-I), (S)-2-Amino-2-cyclobutylacetic acid (Cbg) and 2-[(1S,2S)-1-(amino)-2-methylbutyl]-1,3-oxazole-4-carboxylic acid.

According to a further embodiment of the invention, $X^{12}$ represents the natural amino acid I.

According to a further embodiment of the invention, in case u and t and s are all 0, the terminal carboxyl group of $X^{12}$ is unsubstituted or amidated.

According to a further embodiment, the invention provides compounds containing a peptide, which may be isolated and/or purified, comprising, essentially consisting of, or consisting of, formula (I) or formula (II) or a derivative, prodrug, analogue, pharmaceutically acceptable salt, solvate or solvate of the salt, wherein $X^{13}$ represents a natural amino acid selected from a list consisting of P, A, S, T, G, D, E, Q or N or an unnatural amino acid selected from a list consisting of N-Methyl-Glycine ((N-Me)G), 5-azaspiro[2.4] heptane-6-carboxylic acid, L-2-Aminobutyric acid (Abu), 2-Aminoisobutyric acid (Aib), 2-Methyl-L-Proline (2-Me)P, Hydroxyproline (Hyp), 2,3,3a,4,5,6,7,7a-Octahydroindole-2-carboxylic acid (Oic), trans-4-fluoroproline ((trans-4-Fluoro)P), (2S,4S)-4-fluoroproline ((cis-4-Fluoro)P), L-4,4-difluoroproline ((Difluoro)P), L-Cyclopentylglycine (Cpg), (S)-2-Amino-2-cyclobutylacetic acid (Cbg) and (2S)-Pyrrolidin-2-ylacetic acid (beta-homo-P), whereas each natural amino acid and/or unnatural amino acid in L-stereoconfiguration can be replaced by the stereoisomer in D-stereoconfiguration.

According to a further embodiment of the invention, $X^{13}$ represents a natural amino acid selected from a list consisting of P, A and D or an unnatural amino acid selected from a list consisting of 2-Methyl-L-Proline (2-Me)P, N-Methyl-Glycine ((N-Me)G), trans-4-fluoroproline ((trans-4-Fluoro) P), L-2-Aminobutyric acid (Abu), 2-Aminoisobutyric acid (Aib), Hydroxyproline (Hyp) and 2,3,3a,4,5,6,7,7a-Octahydroindole-2-carboxylic acid (Oic), whereas each natural amino acid and/or unnatural amino acid in L-stereoconfiguration can be replaced by the stereoisomer in D-stereoconfiguration.

According to a further embodiment of the invention, $X^{13}$ represents a natural amino acid selected from a list consisting of P or D or an unnatural amino acid selected from a list consisting of 2-Aminoisobutyric acid (Aib), 2-Methyl-L-Proline (2-Me)P and trans-4-fluoroproline ((trans-4-Fluoro) P), whereas each natural amino acid and/or unnatural amino acid in L-stereoconfiguration can be replaced by the stereoisomer in D-stereoconfiguration.

According to a further embodiment of the invention, $X^{13}$ represents the natural amino acid P.

According to a further embodiment of the invention, s represents an integer of 0.

According to a further embodiment of the invention, s represents an integer of 1.

According to a further embodiment of the invention, in case u and t are both 0 and s is different from 0, the terminal carboxyl group of $X^{13}$ is unsubstituted or amidated.

According to a further embodiment of the invention, in case t is 0 and s is 1, the terminal carboxyl group of $X^{13}$ is unsubstituted or amidated.

According to a further embodiment, the invention provides compounds containing a peptide, which may be isolated and/or purified, comprising, essentially consisting of, or consisting of, formula (I) or formula (II) or a derivative, prodrug, analogue, pharmaceutically acceptable salt, solvate or solvate of the salt, wherein $X^{14}$ represents any natural amino acid or an unnatural amino acid, whereas any natural amino acid and/or unnatural amino acid can be in D- or L-stereoconfiguration.

According to a further embodiment of the invention, $X^{14}$ represents a natural amino acid selected from a list consisting of D, E, G, K, N, P and Q or an unnatural amino acid selected from a list consisting of 3-Carboxyphenylalanine ((3-Carboxy)F), (2S)-2-Amino-4-(benzylamino)-4-oxobutanecarboxylic acid ((N-Benzyl)D), N-Methyl-Glycine ((N-Me)G), 6-Aminohexanoic acid (Ahx), (2S)-Pyrrolidin-2-ylacetic acid (beta-homo-P), L-2,3-Diaminopropionic acid (Dap), L-Ornithine (Orn) and Tranexamic acid (Tranexamic), whereas each natural amino acid and/or unnatural amino acid in L-stereoconfiguration can be replaced by the stereoisomer in D-stereoconfiguration.

According to a further embodiment of the invention, $X^{14}$ represents a natural amino acid selected from a list consisting of D, Q, N, E and P or an unnatural amino acid selected from a list consisting of 3-Carboxyphenylalanine ((3-Carboxy)F), N-Methyl-Glycine ((N-Me)G), (2S)-Pyrrolidin-2-ylacetic acid (beta-homo-P), L-2,3-Diaminopropionic acid (Dap), L-Ornithine (Orn) and Tranexamic acid (Tranexamic), whereas each natural amino acid and/or unnatural amino acid in L-stereoconfiguration can be replaced by the stereoisomer in D-stereoconfiguration.

According to a further embodiment of the invention, $X^{14}$ represents a natural amino acid selected from a list consisting of D, Q or I.

According to a further embodiment of the invention, $X^{14}$ represents the natural amino acid D.

According to a further embodiment of the invention, the C-terminal "—OH" moiety at $X^{14}$ is substituted for a C-terminal "—$NH_2$" moiety.

According to a further embodiment of the invention, q represents an integer of 0.

According to a further embodiment of the invention, q represents an integer of 1.

According to a further embodiment of the invention, in case s and t represent the integer 1, the terminal carboxyl group of $X^{14}$ is unsubstituted or amidated.

According to a further embodiment of the invention, in case s and t represent the integer 1, the terminal carboxyl group of $X^{14}$ is unsubstituted.

According to the present invention $X^{15}$, if present, can be a chemical group which is not an amino acid.

According to a further embodiment of the invention, $X^{15}$ is a chemical group selected from the list consisting of —$NH_2$, —NH—$C_1$-$C_6$-alkyl, (1R,3S)-3-(Amino)cyclopentanecarboxylic acid, (1S,3R)-3-(Amino)cyclopentanecarboxylic acid, (R)-4-Amino-6-methylheptanoic acid, (S)-(1-Piperidin-3-yl)-acetic acid, (S)-3-(1-Pyrrolidine-2-yl)-propionic acid, (S)-3-(2H-tetrazol-5-yl)propanoic acid, (S)-Pyrrolidine-3-carboxylic acid, 5-Azaspiro[2.4]heptane-1-carboxylic acid and (2S)-3-(Triazol-1-yl)-2-(amino) propanoic acid.

According to a further embodiment of the invention, $X^{15}$ is a chemical group selected from —$NH_2$ or —NH—$C_1$-$C_6$-alkyl, preferably —$NH_2$.

According to a further embodiment of the invention, q represents an integer of 0.

According to a further embodiment of the invention, q represents an integer of 1.

According to a further embodiment of the invention, the N-terminus of the peptide is unsubstituted, acetylated or mono- or disubstituted with $C_1$-$C_{20}$-alkyl.

According to a further embodiment of the invention, the N-terminus of the peptide is unsubstituted, acetylated or mono- or disubstituted with $C_1$-$C_4$-alkyl.

According to a further embodiment of the invention, the N-terminus of the peptide is unsubstituted or acetylated.

According to a further embodiment of the invention, the C-terminus is unsubstituted or amidated.

According to a further embodiment of the invention, the N-terminus and C-terminus is unsubstituted.

According to a further embodiment, the invention provides compounds containing a peptide, which may be isolated and/or purified, comprising, essentially consisting of, or consisting of, formula (I) or formula (II) or a derivative, prodrug, analogue, pharmaceutically acceptable salt, solvate or solvate of the salt, which are selected from the group consisting of example 29, 44, 45, 67, 75, 109, 166, 185, 443 and 466 or which are selected from the group consisting of example 29, 44, 45, 67, 75, 109, 166, 185, 443, 466 and 499.

The peptide of formulae (I) or (II) can be linear or cyclized. The term "cyclized," as used herein, refers to a reaction in which one part of a polypeptide molecule (e.g. Cys, (N-Me)Cys or Pen) becomes linked to another part of the polypeptide molecule (e.g. another Cys, (N-Me)Cys or Pen) to form a closed ring, such as by forming a disulfide bridge (—S—S—) or other similar bonds such as a carbon-sulphur bond (e.g. (—$CH_2$—S—) or (—$(CH_2)_2$—S—)), a sulphur-carbon bond (e.g. (—S—$CH_2$—) or (—S—$(CH_2)_2$—)), a carbon-sulphur-carbon bond (—$CH_2$—S—$CH_2$—) or a carbon-carbon bond (e.g. (—$CH_2$—$CH_2$—). According to the present invention a linkage between positions $X^3$ and $X^{11}$ of the peptide is preferred. An amino acid followed by a "+" in a sequence of a peptide according to the invention refers to a cyclic peptide, wherein the amino acid is linked to another amino acid followed by a "+" by a disulfide bridge forming a closed ring. Alternatively two linked chemical groups of a polypeptide molecule can be depicted by a connecting line.

According to a further embodiment, the invention provides compounds containing a peptide, which may be isolated and/or purified, comprising, essentially consisting of, or consisting of, formula (I) or formula (II) or a derivative, prodrug, analogue, pharmaceutically acceptable salt, solvate or solvate of the salt, wherein the peptide is cyclized.

According to a further embodiment of the invention, the peptide of formula (I) or formula (II) is cyclized via a linkage connecting $X^3$ and $X^{11}$.

According to a further embodiment of the invention, the peptide of formula (U) or formula (II) is cyclized via a linkage connecting $X^3$ and $X^{11}$ are and wherein $X^3$ and $X^{11}$ are connected via a linker of the formula —S—S—, —$CH_2$—S—, —S—$CH_2$—, —$CH_2$—$CH_2$—, —S—$(CH_2)_2$—, —$(CH_2)_2$—S— or —$CH_2$—S—$CH_2$—.

According to a further embodiment of the invention, the peptide of formula (I) or formula (II) is cyclized via a linkage connecting $X^3$ and $X^{11}$ and wherein $X^3$ and $X^{11}$ are connected via a disulfide bond of the formula —S—S—.

The peptide of the present invention can be substituted with a suitable watersoluble polymer characterized by repeating units. Suitable polymers may be selected from the group consisting of polyalkyloxy polymers, hyaluronic acid and derivatives thereof, polyvinyl alcohols, polyoxazolines, polyanhydrides, poly(ortho esters), polycarbonates, polyurethanes, polyacrylic acids, polyacrylamides, polyacrylates, polymethacrylates, polyorganophosphazenes, polysiloxanes, polyvinylpyrrolidone, polycyanoacrylates, and polyesters.

The petides of the present invention can be substituted with at least one polyethylene group (PEG group). The at least one PEG group is preferably bound to the N-terminal and/or C-terminal end. The PEG group can be bound to any suitable functional group of a chemical group and/or amino acid of the peptide, e.g. hydroxyl group, carboxyl group, amino group, thiol group, preferably an amino or carboxy group. Preferably the peptide according to the invention contains one PEG group bound to the N-terminal end or one PEG group bound to the C-terminal end. More preferably the one PEG group is bound to the N-terminal or C-terminal end via an amide bond.

PEGylation of peptides may enhance their solubility, reduce immunogenicity, improve stability and/or increase half live by reducing renal clearance, which is a well known concept since early 1980s (Caliceti P., Veronese F. M., Adv. Drug Deliv. Rev. 2003, 55, 1261-1277). For several drugs this has been used with success, but with many examples the PEGylation reduces efficacy of drug substance to an extent that this concept is not suitable any more (T. Peleg-Shulman et al., J. Med. Chem., 2004, 47, 4897-4904).

A PEG group according to the invention is any group containing at least two ethylene oxide units to form an oligomer or polymer ethylene oxide. The PEG group is covalently coupled to a peptide of the present invention (PEGylation), which is then referred to as a PEGylated peptide. Generally, this type of modification to a molecule is well known in the art.

PEG group may consist of an interconnecting moiety, a polymer moiety, and an end group. Interconnecting moieties may consist of a $C_1$-$C_{20}$ alkyl, which is optionally interrupted or terminated by hetero atoms or functional groups selected from the group consisting of —O—, —S—, $N(R^X)$, C(O), $C(O)R^X$, $C(O)N(R^X)$, $N(R^X)C(O)$, one or more $C_3$-$C_8$-cycloalkyl, $C_3$-$C_7$-heterocycloalkyl, aryl or heteraryl, wherein $R^X$ is hydrogen or $C_1$-$C_6$-alkyl, which is optionally interrupted or terminated by one or more of the abovementioned atoms or groups, which further have a hydrogen as terminal atom. Polymer moieties consist of at least two ethylene oxide units, optionally interrupted or terminated by one or more hetero atoms or functional groups selected from the group consisting of —O—, —S—, $N(R^X)$, C(O), $C(O)R^X$, $C(O)N(R^X)$, $N(R^X)C(O)$, $C_1$-$C_6$-alkyl, $C_3$-$C_8$-cycloalkyl, $C_3$-$C_7$-heterocycloalkyl, aryl or heteraryl, wherein $R^X$ is hydrogen or $C_1$-$C_6$-alkyl.

The end group may consist of an hetero atoms or functional groups selected from OH, SH, $N(R^X)_2$, $C(O)R^X$; $COR^X$, $COOR^X$, $C(O)N(R^X)$, $N(R^X)C(O)NH_2$ wherein $R^X$ is hydrogen or $C_1$-$C_6$-alkyl. Preferred end groups are COOH and $C(O)NH_2$.

Examples of PEG spacer according to the present invention comprise PEG1 (10 atoms) having 1 ethylene glycol unit (n=1; 10 atoms), PEG2 (13 atoms) having 2 ethylene glycol units (n=2; 13 atoms), PEG3 (16 atoms) having 3 ethylene glycol units (n=3; 16 atoms), PEG4 (19 atoms) having 4 ethylene glycol units (n=4; 19 atoms), PEG5 (22 atoms) having 5 ethylene glycol units (n=5; 22 atoms), PEG6 (25 atoms) having 6 ethylene glycol units (n=6; 25 atoms) etc.

It is noted that the PEG groups as defined herein may be indicated with different names by commercial suppliers, which shall not exclude such identical compounds with different names from the present invention.

According to a further embodiment, the invention provides compounds containing a peptide, which may be isolated and/or purified, comprising, essentially consisting of, or consisting of, formula (I) or formula (II) or a derivative, prodrug, analogue, pharmaceutically acceptable salt, solvate or solvate of the salt, wherein the peptide is substituted by at least one PEG group.

According to a further embodiment of the invention, the peptide is substituted by one PEG group.

According to a further embodiment of the invention, the peptide is substituted by one PEG group, wherein the PEG group is bound to the C-terminal end, preferably via an amide bond.

According to a further embodiment of the invention, the peptide is substituted by at least one PEG group, whereas the at least one or more PEG group is a group of the formula (IIIa)

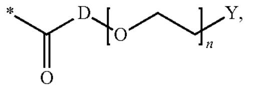

(IIIa)

wherein

* marks the attachment to a nitrogen or oxygen atom,

D is $C_1$-$C_4$-alkylene,

Y is selected from the group consisting of hydroxyl, methoxy, ethoxy, carboxy, carboxamide or amino and n represents an integer of from 2 to 15, or a group of the formula (IIIb)

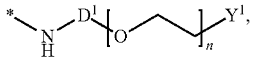

(IIIb)

wherein

* marks the bond to a carbonyl group, $D^1$ is $C_1$-$C_4$-alkylene, $Y^1$ is selected from the group consisting of hydroxyl, methoxy, ethoxy, carboxy, carboxamide or amino and m represents an integer of from 2 to 15, or TTDS.

According to a further embodiment of the invention, the peptide is substituted by at least one PEG group, whereas the at least one or more PEG group selected from a list consisting of PEG1 (10 atoms), PEG2 (13 atoms), PEG3(16 atoms), PEG4 (19 atoms), PEG4-$CH_2CO_2H$ (15 atoms), PEG5 (22 atoms), PEG5-CH $_2CO_2H$ (18 atoms), PEG7 (25 atoms), PEG8 (28 atoms), PEG9 (31 atoms) and TTDS.

The peptide of the present invention can comprise at least one $C_8$-$C_{20}$ fatty acid. Generally, such fatty acid may be branched or cyclic. The at least one $C_8$-$C_{20}$ fatty acid is preferably bound to the N-terminal and/or C-terminal end. The $C_8$-$C_{20}$ fatty acid can be bound to any suitable functional group of a chemical group and/or amino acid of the peptide, e.g. hydroxyl group, carboxyl group, amino group, thiol group, preferably an amino or carboxy group. Preferably the peptide according to the invention contains one $C_8$-$C_{20}$ fatty acid bound to the N-terminal end or one $C_8$-$C_{20}$ fatty acid bound to the C-terminal end. More preferably the one $C_8$-$C_{20}$ fatty acid is bound to the N-terminal or C-terminal end via an amide bond. Preferably the fatty acid side chain formed by $X^0$ or $X^{15}$ is a fatty acid $>C_8$, more preferably a fatty acid $\geq C_{12}$, more preferably a fatty acid $\geq C_{14}$. It is further preferred that the fatty acid side chain formed by $X^0$ or $X^{15}$ is a $C_{12}$-$C_{18}$ fatty acid, preferably a $C_{12}$-$C_{16}$ fatty acid, or a $C_{14}$-$C_{18}$ fatty acid, or a $C_{14}$-$C_{16}$ fatty acid. Most preferred is a $C_{16}$ fatty acid such as palmitic acid (palmitoyl, Palm) and a $C_{18}$ fatty acid such as 1,18-Octadecanedioic acid (ODD).

It is further understood that the moiety at the N-terminus or C-terminus may be a bond, e.g., a covalent bond, particularly in situations where the amino terminus or carboxy terminus is bound to a linker or to another chemical moiety.

Chemical groups, unnatural amino acids or moieties may be abbreviated herein as shown in Table 3.

TABLE 3

Abbreviations/expressions and nomenclature used for chemical groups, unnatural amino acids or further moieties in the sequences

| Abbreviation/Expression | Abbreviation/Expression Definition |
|---|---|
| Cyclohexylcarboxylic | Cyclohexanecarboxylic acid |
| (2S)-Amino-2-[3-(Trifluoromethyl)bicyclo[1.1.1]pent-1-yl]acetic acid | (2S)-Amino-2-[3-(Trifluoromethyl)bicyclo[1.1.1]pent-1-yl]acetic acid |
| (S)-3-(2H-tetrazol-5-yl)propanoic acid | (S)-3-(2H-tetrazol-5-yl)propanoic acid |
| (1R,3S)-3-(Amino)cyclopentanecarboxylic acid | (1R,3S)-3-(Amino)cyclopentanecarboxylic acid |
| (1R,3S,4S)-2-azabicyclo[2.2.1]heptane-3-carboxylic acid | (1R,3S,4S)-2-azabicyclo[2.2.1]heptane-3-carboxylic acid |
| (1R,3S,5R)-2-Azabicyclo[3.1.0]hexane-3-carboxylic acid | (1R,3S,5R)-2-Azabicyclo[3.1.0]hexane-3-carboxylic acid |
| (1S,2S,4S)-Bicyclo[2.2.1]hept-5-en-2-ylacetic acid | (1S,2S,4S)-Bicyclo[2.2.1]hept-5-en-2-ylacetic acid |
| (1R,2S,5S)-3-Azabicyclo[3.1.0]hexane-2-carboxylic acid | (1R,2S,5S)-3-Azabicyclo[3.1.0]hexane-2-carboxylic acid |
| (1S,3R)-3-(Amino)cyclopentanecarboxylic acid | (1S,3R)-3-(Amino)cyclopentanecarboxylic acid |
| (1S,3R,4R)-2-Azabicyclo[2.2.1]heptane-3-carboxylic acid | (1S,3R,4R)-2-Azabicyclo[2.2.1]heptane-3-carboxylic acid |
| (2,4-Dioxoimidazolidin-1-yl)acetic acid | (2,4-Dioxoimidazolidin-1-yl)acetic acid |
| (2-CN)F | 2-Cyano-L-phenylalanine |
| (2-Fluoro)F | 2-Fluoro-L-phenylalanine |
| (2-Me)F | 2-Methyl-L-phenylalanine |
| (4-Pyranoyl)G | (2S)-(tetrahydro-2H-pyran-4-yl)ethanoic acid |
| (4-CF3)P | (2S,4S)-4-Trifluoromethyl-pyrrolidine-2-carboxylic acid |
| (3,3-Difluorocyclobutyl)acetic acid | (3,3-difluorocyclobutyl)acetic acid |
| (3-CN)F | 3-Cyano-L-phenylalanine |
| (3-Fluoro)F | 3-Fluoro-L-phenylalanine |
| (4-Fluoro)F | 4-Fluoro-L-phenylalanine |
| 5-Azaspiro[2.4]heptane-1-carboxylic acid | 5-Azaspiro[2.4]heptane-1-carboxylic acid |
| D-(+)Biotin | D-(+)Biotin |
| (N,N-diMe)A | L-N,N-Dimethylalanine |
| (N,N-diMe)G | N,N-Dimethylglycine |
| (N-Isopropyl-N-methylamino)acetyl | 2-(N-Isopropyl-N-methylamino)acetic acid |
| ((N-Me)A) | L-N-Methylalanine |
| ((N-Me)a) | D-N-Methylalanine |
| ((N-Me)C) | L-N-Methylcysteine |
| (N-Me)F | L-N-Methylphenylalanine |
| (N-Me)G | N-Methyl-Glycine |

TABLE 3-continued

| Abbreviations/expressions and nomenclature used for chemical groups, unnatural amino acids or further moieties in the sequences | |
|---|---|
| Abbreviation/Expression | Abbreviation/Expression Definition |
| (N-Me)I | L-N-Methylisoleucine |
| (N-Ph)G | N-Phenylglycine |
| (R)-3-Aminoadipic acid | (R)-3-Aminoadipic acid |
| (R)-4-Amino-6-methylheptanoic acid | (R)-4-Amino-6-methylheptanoic acid |
| (R)-Piperidine-3-Carboxylic Acid | (R)-Piperidine-3-Carboxylic Acid |
| (R)-Pyrrolidine-3-Carboxylic Acid | (R)-Pyrrolidine-3-Carboxylic Acid |
| (S)-(1-Piperidin-3-yl)-acetic acid | (S)-(1-Piperidin-3-yl)-acetic acid |
| (S)-2-Amino-3-ethyl-pentanoic acid | (S)-2-Amino-3-ethyl-pentanoic acid |
| (S)-3-(1-Pyrrolidine-2-yl)-propionic acid | (S)-3-(1-Pyrrolidine-2-yl)-propionic acid |
| (S)-3-(2H-Tetrazol-5-yl)propionic acid | (S)-3-(2H-Tetrazol-5-yl)propionic acid |
| (S)-3-Methylpentanoic acid | (S)-3-Methylvaleric Acid |
| (S)-4-Piperazine-2-carboxylic acid | (S)-4-Piperazine-2-carboxylic acid |
| (S)-Piperidine-3-carboxylic acid | (S)-Piperidine-3-carboxylic acid |
| (S)-Pyrrolidine-3-carboxylic acid | (S)-Pyrrolidine-3-carboxylic acid |
| [(2R)-4,4-Difluoropyrrolidin-2-yl]acetic acid | [(2R)-4,4-Difluoropyrrolidin-2-yl]acetic acid |
| [(6S)-5-Azaspiro[2.4]hept-6-yl]acetic | [(6S)-5-Azaspiro[2.4]hept-6-yl]acetic acid |
| 1,1-Dioxidotetrahydro-2H-thiopyran-4-yl)acetic acid | 1,1-Dioxidotetrahydro-2H-thiopyran-4-yl)acetic acid |
| 1-Nal | L-1-Napthylalanine |
| 2-(3-Pyridyl)acetic acid | 2-(3-Pyridyl)acetic acid |
| 2-(Aminomethyl)benzoic acid | 2-(Aminomethyl)benzoic acid |
| 2-(Cyclohexylamino)acetyl | 2-(Cyclohexylamino)acetic acid |
| 2-(Diethylamino)acetyl | 2-(Diethylamino)acetic acid |
| 2-(Morpholine)acetyl | 2-(Morpholine)acetic acid |
| 2-(N-Methyl-N-cyclopropylamino)acetyl | 2-(N-Methyl-N-cyclopropylamino)acetic acid |
| 2-(Piperidin)acetyl | 2-(Piperidin)acetic acid |
| 2-(Pyrrolidine)acetyl | 2-(Pyrrolidine)acetic acid |
| 2-(Thian-4-yl)acetic acid | 2-(Thian-4-yl)acetic acid |
| 2-(Thiomorpholine)acetyl | 2-(Thiomorpholine)acetic acid |
| (2,3-Difluoro)F | 2,3-Difluoro-L-phenylalanine |
| 2-aminobenzoic acid | 2-Aminobenzoic acid |
| 2-Azaspiro[3.3]heptane-6-carboxylic acid | 2-Azaspiro[3.3]heptane-6-carboxylic acid |
| (2-Bromo)F | L-2-Bromophenylalanine |
| (2-Chloro)F | 2-Chloro-L-phenylalanine |
| 2-Cyanobenzoic acid | 2-Cyanobenzoic acid |
| 2-Fluorobenzoic acid | 2-Fluorobenzoic acid |
| 2-Hydroxyacetyl | 2-Hydroxyacetic acid |
| 2-Hydroxyisobutyric | 2-Hydroxyisobutyric acid |
| 2-Methylbenzoic acid | 2-Methylbenzoic acid |
| (2-Me)F | 2-Methyl-L-phenylalanine |
| 2-Nal | L-2-Napthylalanine |
| 2-Pal | L-2-Pyridylalanine |
| beta-homo-P | (2S)-Pyrrolidin-2-ylacetic acid |
| 3-(2-Oxoimidazolidin-1-yl)benzoic acid | 3-(2-Oxoimidazolidin-1-yl)benzoic acid |
| 3-(3-Oxo-1,3,4,5,6,7-hexahydro-2H-indazol-2-yl)benzoic acid | 3-(3-Oxo-1,3,4,5,6,7-hexahydro-2H-indazol-2-yl)benzoic acid |
| 3-(Aminomethyl)benzoic acid | 3-(Aminomethyl)benzoic acid |
| 3-(Isobutyrylamino)benzoic acid | 3-(Isobutyrylamino)benzoic acid |
| 3-(Trifluoromethyl)bicyclo[1.1.1]pent-1-yl]acetic acid | 3-(Trifluoromethyl)bicyclo[1.1.1]pent-1-yl]acetic acid |
| 3-[(E)-(2-carboxycyclohexen-1-yl)azo]benzoic acid | 3-[(E)-(2-carboxycyclohexen-1-yl)azo]benzoic acid |
| 3-Acetamidobenzoic acid | 3-Acetamidobenzoic acid |
| 3-Amino-2,2-dimethylpropionic acid | 3-Amino-2,2-dimethylpropionic acid |
| 3-Amino-3-methylbutyric acid | 3-Amino-3-methylbutyric acid |
| 3-Aminobenzoic acid | 3-Aminobenzoic acid |
| 3-Aminomethylphenylacetic acid | 3-Aminomethylphenylacetic acid |
| (3-Bromo)F | L-3-Bromophenylalanine |
| 3-Carboxybenzoic acid | 3-Carboxybenzoic acid |
| (3-Chloro)F | 3-Chloro-L-Phenylalanine |
| (3-Chloro-Ph)G | 3-Chlorophenylglycine |
| 3-Cyanobenzoic acid | 3-Cyanobenzoic acid |
| 3-Fluorobenzoic acid | 3-Fluorobenzoic acid |
| (3-Me)F | 3-Methyl-L-phenylalanine |
| 3-Methoxypropionic acid | 3-Methoxypropionic acid |
| 3-methylbenzoic acid | 3-Methylbenzoic acid |
| 3-Pal | L-3-Pyridylalanine |
| 4-(Aminomethyl)benzoic acid | 4-(Aminomethyl)benzoic acid |
| 4-Aminobenzoic acid | 4-Aminobenzoic acid |
| 4-Aminomethylphenylacetic acid | 4-Aminomethylphenylacetic acid |
| (4-Amino)F | L-4-Aminophenylalanine |
| (4-Bromo)F | L-4-Bromophenylalanine |
| 4-Carboxybenzoic acid | 4-Carboxybenzoic acid |
| 4-Cyanobenzoic acid | 4-Cyanobenzoic acid |
| 4-Fluorobenzoic acid | 4-Fluorobenzoic acid |
| (4-Fluoro)L | 4-Fluoro-L-Leucine |
| 4-Methyl-3-oxo-3,4-dihydro-2H-1,4-benzoxazine- | 4-Methyl-3-oxo-3,4-dihydro-2H-1,4-benzoxazine- |

TABLE 3-continued

Abbreviations/expressions and nomenclature used for chemical groups, unnatural amino acids or further moieties in the sequences

| Abbreviation/Expression | Abbreviation/Expression Definition |
|---|---|
| 8-carboxylic acid | 8-carboxylic acid |
| 4-methylbenzoic acid | 4-Methylbenzoic acid |
| 4-Methylvaleric | 4-Methylpentanoic acid |
| 4-Pal | L-4-Pyridylalanine |
| 4-Piperidinepropanoic acid | 4-Piperidinepropanoic acid |
| 4-Tetrahydropyranoyl | 4-Tetrahydropyranoyl |
| 5-Chlorothiophene-2-carboxylic acid | 5-Chlorothiophene-2-carboxylic acid |
| 8-aminocubane-1-carboxylic acid | 8-Aminocubane-1-carboxylic acid |
| AAD | (S)-2-(Amino)-1,6-hexanedioic acid |
| Abu | L-2-Aminobutyric acid |
| ACBA | 1-Aminocyclobutane-1-carboxylic acid |
| ACBC | Aminocyclobutanecarboxylic acid |
| ACMP | 1-(Aminomethyl)-cyclopropyl-1-carboxylic acid |
| S,S-ACPC | (1S,2S)-2-Amino-1-cyclopentanecarboxylic acid |
| R,R-ACPC | (1R,2R)-2-Amino-1-cyclopentanecarboxylic acid |
| ACPC | rel-(1R,2S)-2-Amino-1-cyclopentanecarboxylic acid |
| Adipic acid | Adipic acid |
| Ahx | 6-Aminohexanoic acid |
| Aib | 2-Aminoisobutyric acid |
| (tBu)A | L-tert-Butylalanine |
| allo-I | allo-L-Isoleucine |
| allo-T | allo-L-Threonine |
| (2-Me)P | 2-Methyl-L-Proline |
| (Me)R | N(5)-methyl-L-arginine |
| Azetidine-2-carboxylic acid | (S)-Azetidine-2-carboxylic acid |
| Benzoic | Benzoic acid |
| beta-2-thienylalanine | L-2-Thienylalanine |
| beta-A | beta-Alanine |
| 4-(3,5-Dimethyl-1,2-oxazol-4-yl)-L-phenylalanine | 4-(3,5-Dimethyl-1,2-oxazol-4-yl)-L-phenylalanine |
| (2S)-2-amino-3-(4-tert-butylphenyl)propanoic acid | (2S)-2-amino-3-(4-tert-butylphenyl)propanoic acid |
| (2S)-2-Amino-5-methyl-hexanoic acid | (2S)-2-Amino-5-methyl-hexanoic acid |
| (2S)-2-Amino-4,4,4-trifluorobutanoic acid | (2S)-2-Amino-4,4,4-trifluorobutanoic acid |
| (2S)-3-(4-carboxyphenyl)-2-aminopropanoic acid | (2S)-3-(4-carboxyphenyl)-2-aminopropanoic acid |
| (2S)-2-amino-3-(4-carbamoylphenyl)propanoic acid | (2S)-2-amino-3-(4-carbamoylphenyl)propanoic acid |
| (2S)-2-Amino-3-(2,3,4,5,6-(pentafluoro-phenyl)propanoic acid | (2S)-2-Amino-3-(2,3,4,5,6-(pentafluoro-phenyl)propanoic acid |
| (2S)-3-(3-Cyanophenyl)-2-aminopropanoic acid | (2S)-3-(3-Cyanophenyl)-2-aminopropanoic acid |
| 3-Azido-L-Alanine | 3-Azido-L-Alanine |
| 2-Amino-5,5,5-trifluoro-4-methyl-pentanoic acid | 2-Amino-5,5,5-trifluoro-4-methyl-pentanoic acid |
| (1S,2S,5R)-3-azabicyclo[3.1.0]hexane-2-carboxylic acid | (1S,2S,5R)-3-azabicyclo[3.1.0]hexane-2-carboxylic acid |
| Cba | L-Cyclobutylalanine |
| Cbg | (S)-2-Amino-2-cyclobutylacetic acid |
| Cha | L-Cyclohexylalanine |
| Cha | D-cyclohexylalanine |
| Chg | L-Cyclohexylglycine |
| (Difluoro)P | L-4,4-Difluoroproline |
| (cis-Fluoro)P | (2S,4S)-4-Fluoroproline |
| Cit | L-Citrulline |
| Cnba | L-2-Amino-4-cyanobutyric acid |
| 3,3-dimethyl-1,3-azasilolidine-5-carboxylic acid | 3,3-dimethyl-1,3-azasilolidine-5-carboxylic acid |
| (S)-(trifluoromethyl)-L-cysteine | (S)-(trifluoromethyl)-L-cysteine |
| (2S)-2-amino-3-(1-methylcyclopropyl)propanoic acid | (2S)-2-amino-3-(1-methylcyclopropyl)propanoic acid |
| (2S)-3-(indol-4-yl)-2-(amino)propanoic acid | (2S)-3-(indol-4-yl)-2-(amino)propanoic acid |
| (2S)-3-(2,3-difluorophenyl)-2-aminopropanoic acid | (2S)-3-(2,3-difluorophenyl)-2-aminopropanoic acid |
| CpA | L-Cyclopentylalanine |
| Cpg | L-Cyclopentylglycine |
| Cyclobutanecarboxylic | Cyclobutanecarboxylic acid |
| Cyclobutylacetic | 2-(Cyclobutyl)acetic acid |
| Cyclobutylglycine | L-Cyclobutylglycine |
| Cyclohexylacetic | Cyclohexylacetic acid |
| Cyclopentanecarboxylic acid | Cyclopentanecarboxylic acid |
| Cyclopentylacetic | Cyclopentylacetic acid |
| Cyclopropanecarboxylic | Cyclopropanecarboxylic acid |
| Cyclopropylacetic acid | Cyclopropylacetic acid |
| (2-Chloro)f | D-2-Chlorophenylalanine |
| Dab | L-2,4-Diaminobutyric acid |
| Dap | L-2,3-Diaminopropionic acid |
| beta-p | D-beta-Proline |
| hyp | D-Hydroxyproline |
| (N-Benzyl)D | (2S)-2-Amino-4-(benzylamino)-4-oxobutanecarboxylic acid |
| Freidinger's Lactam | (2S)-2-[(3R)-3-Amino-2-oxopyrrolidin-1-yl]-4-methylpentanoic acid |
| Fumaric acid | Fumaric acid |
| Gamma-Abu | Gamma-Aminobutyric acid |
| (tBu)G | L-tert-Butylglycine |

TABLE 3-continued

| Abbreviation/Expression | Abbreviation/Expression Definition |
|---|---|
| (1-Bn)H | 1-Benzyl-L-histidine |
| (1-Me)H | 1-Methyl-L-histidine |
| (3-Me)H | L-3-Methylhistidine |
| Homo-C | L-Homocysteine |
| Hoo | L-Dihydroorotic acid |
| Hydrocinnamic | 3-Phenylpropanoic acid |
| Hyp | L-Hydroxyproline |
| Ida | Iminodiacetic acid |
| Isobutyric acid | Isobutyric acid |
| Isonipecotic acid | Isonipecotic acid |
| Isovaleric | Isovaleric acid |
| K(ISP) | N-e-Isopropyl-L-lysine |
| (3-Et)Nva | 3-Ethyl-L-Norvaline |
| Lactic | L-(+)-Lactic acid |
| (Bth)A | 3-(1,3-Benzothiazol-2-yl)-L-alanine |
| beta-P | (S)-Pyrrolidine-2-carboxylic acid |
| L-Propargylglycine | L-Propargylglycine |
| Morpholine-3-carboxylic | (3S)-Morpholine-3-carboxylic acid |
| Nicotinic acid | Nicotinic acid |
| Nle | L-Norleucine |
| (N-Me)P | N-Methyl-L-proline |
| Nva | L-Norvaline |
| ODD | 1,18-Octadecanedioic acid |
| Oic | 2,3,3a,4,5,6,7,7a-Octahydroindole-2-carboxylic acid |
| Orn | L-Ornithine |
| Palm | Palmitic acid |
| PEG1(10 atoms) | 9-Amino-4,7-dioxanonanoic acid |
| PEG2(13 atoms) | 12-Amino-4,7,10-trioxadodecanoic acid |
| PEG3(16 atoms) | 15-Amino-4,7,10,13-tetraoxa(Pen)tadecanoic acid |
| PEG4(19 atoms) | 18-Amino-4,7,10,13,16-(Pen)taoxaoctadecanoic acid |
| PEG4-CH2CO2H (15 atoms) | 14-Amino-3,6,9,12-tetraoxatetradecanoic acid |
| PEG5(22 atoms) | 1-Amino-3,6,9,12,15,18-hexaoxahenicosan-21-oic acid |
| PEG5-CH2CO2H (18 atoms) | 17-Amino-3,6,9,12,15-(Pen)taoxaheptadecanoic acid |
| PEG7(25 atoms) | 1-Amino-3,6,9,12,15,18,21-heptaoxatetracosan-24-oic acid |
| PEG8(28 atoms) | 1-Amino-3,6,9,12,15,18,21,24-octaoxaheptacosan-27-oic acid |
| PEG9(31 atoms) | 1-Amino-3,6,9,12,15,18,21,24,27-nonaoxatriacontan-30-oic acid |
| Pen | L-Penicillamine |
| Phenylacetic acid | Phenylacetic acid |
| Phg | L-Phenylglycine |
| Picolinic acid | Picolinic acid |
| Pip | L-Pipecolic acid |
| Piperidin-4-ylacetic acid | Piperidin-4-ylacetic acid |
| Pivalic | Pivalic acid |
| (3S-OH)P | L-trans-3-Hydroxyproline |
| Pyr | L-Pyroglutamic acid |
| S-2-amino-3-ethyl-pentanoic acid | S-2-amino-3-ethyl-pentanoic acid |
| Pyrrolidineacetyl | 2-(Pyrrolidin-1-yl)acetic acid |
| S-3-1-Pyrrolidin-2-yl-propionic acid | S-3-1-Pyrrolidin-2-yl-propionic acid |
| Suberic acid | Suberic acid |
| tert-Butylacetic acid | tert-Butylacetic acid |
| Tetrahydropyranyl-4-acetic acid | Tetrahydropyranyl-4-acetic acid |
| TFA | Trifluoroacetic acid |
| Thi | L-2-Thienylalanine |
| (2S,3S)-2-[(3R)-3-Amino-2-oxopyrrolidin-1-yl]-3-methylpentanoic acid | (2S,3S)-2-[(3R)-3-Amino-2-oxopyrrolidin-1-yl]-3-methylpentanoic acid |
| (2S,3S)-2-[2-Oxopiperazin-1-yl]-3-methylpentanoic acid | (2S,3S)-2-[2-Oxopiperazin-1-yl]-3-methylpentanoic acid |
| (2S,3S)-2-[(3S)-2-oxopiperazin-1-yl]-3-methylpentanoic acid | (2S,3S)-2-[(3S)-2-oxopiperazin-1-yl]-3-methylpentanoic acid |
| (1R,3S,5R)-2-Azabicyclo[3.1.0]hexane-3-carboxylic acid | (1R,3S,5R)-2-Azabicyclo[3.1.0]hexane-3-carboxylic acid |
| 3-(Trimethylsilyl)-L-alanine | 3-(Trimethylsilyl)-L-alanine |
| (6S)-5-Azaspiro[2.4]heptane-6-carboxylic acid | (6S)-5-Azaspiro[2.4]heptane-6-carboxylic acid |
| rel-(1R,3R,5R,6R)-6-(Trifluoromethyl)-2-azabicyclo[3.1.0]hexane-3-carboxylic acid | rel-(1R,3R,5R,6R)-6-(Trifluoromethyl)-2-azabicyclo[3.1.0]hexane-3-carboxylic acid |
| (4aR,6aR,9S,11aS)-11-Oxo-2,3,4,4a,6a,7,8,9,11,11a-decahydro-1H-pyrido[3,2-e]pyrrolo[1,2-a]azepine-9-carboxylic acid | (4aR,6aR,9S,11aS)-11-Oxo-2,3,4,4a,6a,7,8,9,11,11a-decahydro-1H-pyrido[3,2-e]pyrrolo[1,2-a]azepine-9-carboxylic acid |
| (2S)-2[(Amino)-2-(tetrahydro-2H-pyran-4-yl)]acetic acid | (2S)-2[(Amino)-2-(tetrahydro-2H-pyran-4-yl)]acetic acid |
| (2S,3S)-2-((Amino)methyl)-3-methylpentanoic acid | (2S,3S)-2-((Amino)methyl)-3-methylpentanoic acid |
| 2-[(1S,2S)-1-(Amino)-2-methylbutyl]-1,3-oxazole-4-carboxylic acid | 2-[(1S,2S)-1-(Amino)-2-methylbutyl]-1,3-oxazole-4-carboxylic acid |
| (2S)-Amino-(1-methyl-1H-indazol-5-yl)acetic acid | (2S)-Amino-(1-methyl-1H-indazol-5-yl)acetic acid |
| (2R)-Amino-(1-methyl-1H-indazol-5-yl)acetic acid | (2R)-Amino-(1-methyl-1H-indazol-5-yl)acetic acid |
| (3-Carboxy)F | 3-Carboxyphenylalanine |
| 2-Methyl-D-alloisoleucine | 2-Methyl-D-alloisoleucine |
| 4-Ethyl-L-norleucine | 4-Ethyl-L-norleucine |
| L-2,6-Difluorophenylalanine | L-2,6-Difluorophenylalanine |
| (2,5-Difluoro)F | 2,5-Difluoro-L-phenylalanine |
| (2S,3aS,6aS)-Octahydrocyclopenta[b]pyrrole-2- | (2S,3aS,6aS)-Octahydrocyclopenta[b]pyrrole-2- |

Abbreviations/expressions and nomenclature used for chemical groups, unnatural amino acids or further moieties in the sequences TABLE 3-continued Abbreviations/expressions and nomenclature used for chemical groups, unnatural amino acids or further moieties in the sequences

| Abbreviation/Expression | Abbreviation/Expression Definition |
|---|---|
| carboxylic acid | carboxylic acid |
| (2S)-2-(Amino)-2-[(1S,3R)-3-hydroxycyclohexyl]acetic acid | (2S)-2-(Amino)-2-[(1S,3R)-3-hydroxycyclohexyl]acetic acid |
| (2S)-2-(Amino)-2-[(1S,3S)-3-hydroxycyclohexyl]acetic acid | (2S)-2-(Amino)-2-[(1S,3S)-3-hydroxycyclohexyl]acetic acid |
| 2-Amino-7-(tert-butoxy)-7-oxoheptanoic acid | 2-Amino-7-(tert-butoxy)-7-oxoheptanoic acid |
| (2S)-3-(Triazol-1-yl)-2-(amino)propanoic acid | (2S)-3-(Triazol-1-yl)-2-(amino)propanoic acid |
| Tetrahydro-2H-pyran-3-ylacetic acid | Tetrahydro-2H-pyran-3-ylacetic acid |
| rel-(1R,3S)-3-[(Amino)methyl]cyclohexanecarboxylic acid | rel-(1R,3S)-3-[(Amino)methyl]cyclohexanecarboxylic acid |
| (3R,6R)-1,1-Difluoro-5-azaspiro[2.4]heptane-6-carboxylic acid (enantiomer 1) | (3R,6R)-1,1-Difluoro-5-azaspiro[2.4]heptane-6-carboxylic acid (enantiomer 1) |
| (3R,6R)-1,1-Difluoro-5-azaspiro[2.4]heptane-6-carboxylic acid (enantiomer 2) | (3R,6R)-1,1-Difluoro-5-azaspiro[2.4]heptane-6-carboxylic acid (enantiomer 2) |
| Tranexamic | Tranexamic acid |
| trans-2-(3-(Amino)cyclohexyl)acetic acid | trans-2-(3-(Amino)cyclohexyl)acetic acid |
| (trans-4-Fluoro)P | trans-4-Fluoroproline |
| (Trifluoro)1/L | 5,5,5-Trifluoro-DL-leucine |
| TTDS | 1,13-Diamino-4,7,10-trioxatridecan-succinamic acid |
| (R)-Pyrrolidine-3-acetic acid | (R)-Pyrrolidine-3-acetic acid |
| Pro-D2 | L-Proline (3,4-2H) (deuterated) |
| (2S)-2-(morpholin-4-yl)propanoic acid | (2S)-2-(morpholin-4-yl)propanoic acid |
| L-dehydroproline | 3,4-dehydro-L-proline |
| (3S)-2-azaspiro[4.4]nonane-3-carboxylic acid | (3S)-2-azaspiro[4.4]nonane-3-carboxylic acid |
| (2R)-2-amino-3-(trifluoromethylsulfanyl)propanoic acid | (2R)-2-amino-3-(trifluoromethylsulfanyl)propanoic acid |
| Arg(13C6,15N4) | L-Arginine-N-Fmoc, Pbf-OH (13C6, 15N4) |

The term "mimetic", used in context with some amino acids in the definition of several moieties of the peptide according to formula (I) or formula (II) of the present invention, represents a respective amino acid mimetic, such as e.g. an arginine mimetic, an isoleucine mimetic or a proline mimetic. Generally, a "protein mimetic" indicates a molecule such as a peptide, a modified peptide or any other molecule that biologically mimics the action or activity of some other protein. In context with the use of the term "mimetic" in connection with a certain amino acid said term "mimetic" analogously indicates any other amino acid, amino acid analogue, amino acid derivative, amino acid conjugate or the like, which biologically mimics the action or activity of the respective amino acid.

Proline mimetics according to the present invention comprise in particular (1S,2S,5R)-3-Azabicyclo[3.1.0]hexane-2-carboxylic acid, Hyp, Morpholine-3-carboxylic, Pip, (4aR,6aR,9S,11aS)-11-Oxo-2,3,4,4a,6a,7,8,9,11,11a-decahydro-1H-pyrido[3,2-e]pyrrolo[1,2-a]azepine-9-carboxylic acid or (trans-4-Fluoro)P, (1R,2S,5S)-3-azabicyclo[3.1.0]hexane-2-carboxylic acid, Oic, Hyp, (4-CF3)P, (cis-4-Fluoro)P, 3,3-dimethyl-1,3-azasilolidine-5-carboxylic acid, (3S—OH)P, (1R,3S,5R)-2-Azabicyclo[3.1.0]hexane-3-carboxylic acid, (6S)-5-Azaspiro[2.4]heptane-6-carboxylic acid, rel-(1R,3R,5R,6R)-6-(Trifluoromethyl)-2-azabicyclo[3.1.0]hexane-3-carboxylic acid, (2S,3aS,6aS)-Octahydrocyclopenta[b]pyrrole-2-carboxylic acid or difluoroproline, (3R,6R)-1,1-Difluoro-5-azaspiro[2.4]heptane-6-carboxylic acid (enantiomer 1), (3R,6R)-1,1-Difluoro-5-azaspiro[2.4]heptane-6-carboxylic acid (enantiomer 2) and substituted prolines.

Isoleucine mimetics according to the present invention comprise in particular (N-Methyl)-I, allo-Ile, Cba, Nva, Abu, Leu, Cpg, cyclohexyl-Gly, (S)-2-Amino-3-ethyl-pentanoic acid, 3-Chloro-Phg, allo-Ile, Chg, Cyclobutylglycine, allo-Ile, Cbg, (2S,3S)-2-((Amino)methyl)-3-methylpentanoic acid, Phg, 2-[(1S,2S)-1-(Amino)-2-methylbutyl]-1,3-oxazole-4-carboxylic acid, 2-Methyl-D-alloisoleucine, Nva, Abu or Ala.

Leucine mimetics according to the present invention comprise in particular (tBu)A, (2-Chloro)F, (2-Bromo)F, AAD, (2S)-2-Amino-4,4,4-trifluorobutanoic acid, Cnba, (4-Fluoro)L, (S)-(trifluoromethyl)-L-cysteine, (2S)-2-amino-3-(1-methylcyclopropyl)propanoic acid, Gly(tBu), 3-(Trimethylsilyl)-L-alanine, 2,5-difluoro-L-phenylalanine, 2-Amino-7-(tert-butoxy)-7-oxoheptanoic acid, 5,5,5-Trifluoro-L-leucine ((Trifluoro)L), (2-Me)F, Cba, Cpa, cyclopropylmethylalanine, trifluoromethylalanine or difluoromethylalanine, (2-Fluoro)F, (2S)-3-(2,3-difluorophenyl)-2-aminopropanoic acid, (2S)-3-(3-Cyanophenyl)-2-aminopropanoic acid, 2-Amino-5,5,5-trifluoro-4-methyl-pentanoic acid, (2S)-2-Amino-5-methyl-hexanoic acid or (2S)-3-(indol-4-yl)-2-(amino)propanoic acid.

The invention further comprises analogues and derivatives of the described peptides. The term "analogue" or "derivative" of a peptide or an amino acid sequence according to the present invention comprises in particular any amino acid sequence having a sequence identity of at least 80% or at least 85%, preferably at least 90%, more preferably at least 95%, and even more preferably of at least 99% identity to said sequence, and same or comparable properties or activity. Sequence identity can be determined by common techniques, such as visual comparison or by means of any computer tool generally used in the field. Examples comprise BLAST programs used with default parameters.

An analogue or derivative of a peptide or an amino acid sequence of the invention may result from changes derived from mutation or variation in the sequences of peptides of the invention, including the deletion or insertion of one or more amino acids or the substitution of one or more amino acids, or even to alternative splicing. Several of these modifications may be combined. Preferably, an analogue of an amino acid sequence of the invention comprises conservative substitutions relative to the sequence of amino acids.

The term "conservative substitution" as used herein denotes that one or more amino acids are replaced by another, biologically similar residue. Examples include substitution of amino acid residues with similar characteristics, e.g., small amino acids, acidic amino acids, polar amino acids, basic amino acids, hydrophobic amino acids and aromatic amino acids. See, for example, the scheme in Table 4 below, wherein conservative substitutions of amino acids are grouped by physicochemical properties. I: neutral, hydrophilic; II: acids and amides; III: basic; IV: hydrophobic; V: aromatic, bulky amino acids, VI: neutral or hydrophobic; VII: acidic; VIII: polar.

TABLE 4

| Amino Acids grouped according to their physicochemical properties | | | | | | | |
|---|---|---|---|---|---|---|---|
| I | II | III | IV | V | VI | VII | VIII |
| Ala | Asn | His | Met | Phe | Ala | Glu | Met |
| Ser | Asp | Arg | Leu | Tyr | Leu | Asp | Ser |
| Thr | Glu | Lys | Ile | Trp | Ile | | Thr |
| Pro | Gln | | Val | | Pro | | Cys |
| Gly | | | Cys | | Gly | | Asn |
| | | | | | Val | | Gln |

A peptide analogue or derivative may also comprise one or more additional modifications such as, e.g., conjugation to another compound to form an amino acid conjugate.

Such a modification may, alternatively or additionally, result from conjugation to the side-chains of one or more amino acid residues in a peptide of the present invention for example a chemical group as defined above in context with the chemical group $X^0$ or a polymeric moiety such as a PEG group. Such modification may, for example, increase solubility and/or half-life in vivo (e.g. in plasma) and/or bioavailability of the peptide and are also known to reduce clearance (e.g. renal clearance) of therapeutic proteins and peptides. Suitable modifications are well known to a skilled person and comprise in particular, without being limited thereto, PEGylation of one or more side chains of the peptide of the present invention. Therein, "PEGylation" represents the act of coupling (e.g., covalently) a Polyethylene glycol (PEG) structure to the peptide of the invention. The skilled person knows well possible PEGs for coupling to the amino acid side chains of small peptides for forming a respective conjugate, e.g. from WO 2015/200916 A1, which are herein incorporated by reference.

All peptides of this invention unless otherwise noted are TFA salts. The invention comprises further pharmaceutically acceptable salts of the peptides as defined herein and salt free forms. Therein, pharmaceutically acceptable salts represent salts or zwitterionic forms of the peptides or compounds of the present invention which are water or oil-soluble or dispersible, which are suitable for treatment of diseases without undue toxicity, irritation, and allergic response; which are commensurate with a reasonable benefit/risk ratio, and which are effective for their intended use. The salts can be prepared during the final isolation and purification of the compounds or separately by reacting an amino group with a suitable acid. Representative acid addition salts include acetate, adipate, alginate, citrate, aspartate, benzoate, benzenesulfonate, bisulfate, butyrate, camphorate, camphorsulfonate, carbonate, digluconate, glycerophosphate, hemisulfate, heptanoate, hexanoate, formate, fumarate, hydrochloride, hydrobromide, hydroiodide, 2-hydroxyethansulfonate (isethionate), lactate, maleate, mesitylenesulfonate, methanesulfonate, naphthylenesulfonate, nicotinate, 2-naphthalenesulfonate, oxalate, pamoate, pectinate, persulfate, 3-phenylproprionate, picrate, pivalate, propionate, succinate, sulfate, tartrate, trichloroacetate, trifluoroacetate, phosphate, glutamate, bicarbonate, para-toluenesulfonate, and undecanoate. Preferred acid addition salts include trifluoroacetate, formate, hydrochloride, and acetate.

Also, amino groups in the compounds of the present invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. A pharmaceutically acceptable salt may suitably be a salt chosen, e.g., among acid addition salts and basic salts. Examples of acid addition salts include chloride salts, citrate salts and acetate salts.

Examples of basic salts include salts where the cation is selected from alkali metal cations, such as sodium or potassium ions, alkaline earth metal cations, such as calcium or magnesium ions, as well as substituted ammonium ions, such as ions of the type $N(R^1)(R^2)(R^3)(R^4)^+$, where $R^1$, $R^2$, $R^3$ and $R^4$ independently from each other will typically designate hydrogen, optionally substituted $C_{1-6}$-alkyl or optionally substituted $C_{2-6}$-alkenyl. Examples of relevant $C_{1-6}$-alkyl groups include methyl, ethyl, 1-propyl and 2-propyl groups. Examples of $C_{2-6}$-alkenyl groups of possible relevance include ethenyl, 1-propenyl and 2-propenyl. Therein, salts where the cation is selected among sodium, potassium and calcium are preferred.

Other examples of pharmaceutically acceptable salts are described in "*Remington's Pharmaceutical Sciences*", 17th edition, Alfonso R. Gennaro (Ed.), Mark Publishing Company, Easton, PA, USA, 1985 (and more recent editions thereof), in the "*Encyclopedia of Pharmaceutical Technology*", 3rd edition, James Swarbrick (Ed.), Informa Healthcare USA (Inc.), NY, USA, 2007. Also, for a review on suitable salts, see *Handbook of Pharmaceutical Salts: Properties, Selection, and Use* by Stahl and Wermuth (Wiley-VCH, 2002). Other suitable base salts are formed from bases which form non-toxic salts. Representative examples include the aluminum, arginine, benzathine, calcium, choline, diethylamine, diolamine, glycine, lysine, magnesium, meglumine, olamine, potassium, sodium, tromethamine, and zinc salts, preferably choline. Hemisalts of acids and bases may also be formed, e.g., hemisulphate and hemicalcium salts.

The invention further comprises solvates of the peptides as defined herein. Therein the term "solvate" refers to a complex of defined stoichiometry formed between a solute (e.g., a peptide according to the invention or pharmaceutically acceptable salt thereof) and a solvent. The solvent in this connection may, for example, be water, ethanol or another pharmaceutically acceptable, typically small-molecular organic species, such as, but not limited to, acetic acid or lactic acid. When the solvent in question is water, such a solvate is normally referred to as a hydrate.

The compounds according to the invention have useful pharmacological properties and can be used for prevention and treatment of disorders in humans and animals.

In the context of the present invention, the term "treatment" or "treat" includes the inhibition, delay, arrest, amelioration, attenuation, limitation, reduction, suppression, reversal or cure of a disease, a condition, a disorder, an injury or health impairment, of the development, course or the progression of such states and/or the symptoms of such states. Here, the term "therapy" is understood to be synonymous with the term "treatment".

In the context of the present invention, the terms "prevention", "prophylaxis" or "precaution" are used synonymously and refer to the avoidance or reduction of the risk to get, to contract, to suffer from or to have a disease, a condition, a disorder, an injury or a health impairment, a development or a progression of such states and/or the symptoms of such states.

The treatment or the prevention of a disease, a condition, a disorder, an injury or a health impairment may take place partially or completely.

The compounds according to the invention are particularly suitable for the treatment and/or prevention of cardiovascular, cardiopulmonary, renal, pulmonary, fibrotic, thromboembolic, and inflammatory disorders.

Accordingly, the compounds according to the invention can be used in medicaments for the treatment and/or prevention of cardiovascular and cardiopulmonary disorders and their sequels such as, for example inflammatory heart diseases, myocarditis, endocarditis, pericarditis, rheumatic fever without and with heart involvement, acute rheumatic pericarditis, acute rheumatic endocarditis, acute rheumatic myocarditis, chronic rheumatic heart diseases with and without endocarditis, valvulitis, pericarditis, ischemic heart diseases such as unstable angina pectoris and acute myocardial infarction, atrial and ventricular arrhythmias and impaired conduction such as, for example, grade I-III atrioventricular blocks, supraventricular tachyarrhythmia, atrial fibrillation, atrial flutter, ventricular fibrillation, ventricular flutter, ventricular tachyarrhythmia, Torsade de pointes tachycardia, atrial and ventricular extrasystoles, AV-junctional extrasystoles, sick sinus syndrome, stroke due to occlusion and stenosis of cerebral arteries (Cerebral infarction following e.g. thromboembolic, atherosclerotic, infectious and inflammatory vascular lesions), for the treatment and/or prevention of stroke due to intracerebral or intracranial haemorrhage, peripheral ischemic tissue damage (e.g. atherosclerotic gangrene) due to diseases of arteries, arterioles and capillaries (e.g. thromboembolic, atherosclerotic, infectious and inflammatory vascular lesions, endarteritis deformans or obliterans, and aneurysm dissection), phlebitis and thrombophlebitis, for preventing postprocedural disorders of the circulatory system, e.g. systemic inflammatory response syndrome, vasoplegia after surgery, postcardiotomy syndrome, postprocedural hypotension and heart failure, for preventing and treating ischemia reperfusion injury and organ dysfunction for example after thrombolysis therapies, percutaneous transluminal angioplasties (PTA), percutaneous transluminal coronary angioplasties (PTCA), bypass operations and heart, lung, liver and kidney transplants, and for the prevention and treatment of delayed graft function after kidney transplantation.

The compounds according to the invention are furthermore suited for the treatment of shock such as cardiogenic shock, septic shock and anaphylactic shock by preventing MASP mediated end organ damages.

Moreover, the compounds according to the invention have antiinflammatory action and can therefore be used as antiinflammatories for treatment and/or prevention of sepsis (SIRS), multiple organ failure (MODS, MOF), inflammatory disorders of the kidney, chronic bowel inflammations (IBD, Crohn's Disease, UC), pancreatitis, peritonitis, rheumatoid disorders, inflammatory skin disorders and inflammatory eye disorders.

By virtue of their activity profile, the compounds according to the invention are particularly suitable for the treatment and/or prevention of cardiovascular, pulmonary, cerebral and renal sequels of sepsis and systemic inflammatory response syndrome.

The compounds according to the invention are particularly suitable for the treatment and/or prevention of ischemia and/or reperfusion-related damage to the heart and the kidney and other organs in the context of resuscitation and surgical interventions such as but not restricted to bypass operations, heart valve surgery, and aortic aneurysm surgery, The compounds according to the invention can additionally also be used for preventing ischaemic and/or reperfusion-related damage to organs or tissues and also as additives for perfusion and preservation solutions of organs, organ parts, tissues or tissue parts of human or animal origin, in particular for surgical interventions or in the field of transplantation medicine.

Furthermore, the compounds according to the invention are suitable for the treatment and/or prevention of diseases of the blood and blood-forming organs and the immune system including but not limited to acquired haemolytic anaemia, haemolytic-uraemic syndrome, paroxysmal nocturnal haemoglobinuria [MarchiafavaMicheli], coagulation defects, purpura and other haemorrhagic conditions, disseminated intravascular coagulation [defibrination syndrome], essential (haemorrhagic) thrombocythaemia, purpura fulminans, thrombotic thrombocytopenic purpura, allergic purpura, allergic vasculitis, lymphopenia and lgranulocytosis, and sarcoidosis.

Furthermore, the compounds according to the invention are suitable for the treatment and/or prevention of sequels of diabetes mellitus such as renal complications of diabetes mellitus, diabetic nephropathy, intracapillary glomerulonephrosis, ophthalmic complications of diabetes mellitus, diabetic retinopathy, neurological complications, diabetic polyneuropathy, and circulatory complications such as microangiopathy and gangrene.

Moreover, the compounds according to the invention are suitable for the treatment and/or prevention of inflammatory diseases of the nervous system such as multiple sclerosis, meningitis and encephalitis, bacterial and viral meningitis and encephalitis, postimmunization encephalitis, inflammatory polyneuropathy, and polyneuropathy in infectious and parasitic diseases.

The compounds according to the invention are furthermore suitable for the treatment and/or prevention of diseases of the eye and its adnexa, such as acute and subacute iridocyclitis, choroidal degeneration, chorioretinal inflammation, chorioretinal inflammation in infectious and parasitic diseases, background retinopathy and retinal vascular changes, proliferative retinopathy, degeneration of macula and posterior pole, peripheral retinal degeneration, age-related macular degeneration (AMD) including dry (non-exudative) and wet (exudative, neovascular) AMD, choroidal neovascularization (CNV), choroidal neovascular membranes (CNVM), cystoid macular oedema (CME), epiretinal membranes (ERM) and macular perforations, myopia-associated choroidal neovascularization, angioid and vascular streaks, retinal detachment, diabetic retinopathy, diabetic macular oedema (DME), atrophic and hypertrophic lesions in the retinal pigment epithelium, retinal vein occlusion, choroidal retinal vein occlusion, macular oedema, macular oedema associated with retinal vein occlusion, postprocedural disorders of eye and adnexa, e.g. keratopathy following cataract surgery.

Furthermore, the compounds according to the invention are suitable for the treatment and/or prevention of diseases of the respiratory system including but not restricted to viral, bacterial, and mycotic pneumonia, radiation pneumonitis, pneumoconiosis, allergic alveolitis, airway disease due to specific organic dust, e.g. farmer lung, bronchitis, pneumonitis and pulmonary oedema due to chemicals, gases, fumes and vapours, drug-induced interstitial lung disorders, adult respiratory distress syndrome (ARDS) and acute lung injury (ALI), acute oedema of the lung, interstitial pulmonary diseases with fibrosis, rheumatoid lung disease, respiratory disorders in other diffuse connective tissue disorders, such as associated to systemic lupus erythematosus, sclerodermia and Wegener granulomatosis.

Furthermore, the compounds according to the invention are suitable for treatment and/or prevention of microvascular injury, thrombosis and consecutive thromboembolic events caused by viral infections such as, but not restricted to, Influenza viruses (e.g. caused by strains of serotypes H1N1, H5N1, H7N9), and Corona viruses (e.g. SARS-CoV, the pathogen of severe acute respiratory syndrome (SARS), MERSCoV, the pathogen of Middle East respiratory syndrome (MERS), and SARS-CoV-2 the pathogen of COVID-19 pandemic).

Furthermore, the compounds according to the invention are suitable for the treatment and/or prevention of diseases of the digestive system including but not restricted to noninfective enteritis and colitis such as Crohn disease and ulcerative colitis, pancreatitis (including acute alcohol- and drug induced pancreatitis), cholecystitis, inflammatory liver diseases, hepatorenal syndrome, postprocedural disorders of the liver, e.g. after liver surgery.

By virtue of their activity profile, the compounds according to the invention are particularly suitable for the treatment and/or prevention of diseases of the genitourinary system including but not restricted to acute renal failure, acute kidney injury (AKI), surgery associated AKI, sepsis associated AKI, contrast media and chemotherapy induced AKI, ischaemia and infarction of the kidney, complications such as hypersensitivity in the context of hemodialysis and hemodiafiltration, cystitis, irradiation cystitis, inflammatory diseases of the prostate, and endometriosis.

The compounds according to the invention are furthermore suitable for the treatment and/or prevention of sequels of burns and injuries including but not restricted to early complications of trauma, traumatic anuria, crush syndrome, renal failure following crushing, traumatic ischaemia of muscle, traumatic brain injury, organ damage after exposure to electric current, radiation and extreme ambient air temperature and pressure, after exposure to smoke, fire and flames, after contact with venomous animals and plants.

By virtue of their activity profile, the compounds according to the invention are furthermore suitable for the treatment of inflammatory skin diseases for example dermal lupus erythematosus, bullous disorders and acantholytic skin diseases such as pemphigus subtypes, papulosquamous disorders such as psoriasis, dermatitis and eczema, urticaria and erythema.

According to a further embodiment, the invention provides a compound containing a peptide which may be isolated and/or purified, comprising, essentially consisting of, or consisting of, formula (I) or formula (II) or a derivative, prodrug, analogue or pharmaceutically acceptable salts or solvates thereof for the use in the prophylaxis and/or treatment of diseases.

According to a further embodiment, the invention provides a compound containing a peptide which may be isolated and/or purified, comprising, essentially consisting of, or consisting of, formula (I) or formula (II) or a derivative, prodrug, analogue or pharmaceutically acceptable salts or solvates thereof for the use in the prophylaxis and/or treatment of MASP-associated disorders.

According to a further embodiment, the invention provides a compound containing a peptide which may be isolated and/or purified, comprising, essentially consisting of, or consisting of, formula (I) or formula (II) or a derivative, prodrug, analogue, pharmaceutically acceptable salt, solvate or solvate of the salt, which acts as a MASP-1 and/or MASP-2 inhibitor and/or which inhibits C3 deposition, for the use in the prophylaxis and/or treatment of MASP-associated disorders.

According to a further embodiment, the invention provides a compound containing a peptide which may be isolated and/or purified, comprising, essentially consisting of, or consisting of, formula (I) or formula (II) or a derivative, prodrug, analogue or pharmaceutically acceptable salts or solvates thereof for the use in the prophylaxis and/or treatment of cardiovascular and cardiopulmonary disorders, shock, inflammatory disorders, cardiovascular, pulmonary, cerebral and renal sequels of sepsis, ischemia and/or reperfusion-related damage, acute kidney injury, transplant protection and delayed graft function, diseases of the blood and blood-forming organs and the immune system, sequels of diabetes mellitus, inflammatory diseases of the nervous system, diseases of the eye, diseases of the skin, diseases of the respiratory, digestive or genitourinary system and sequels of burns and injuries.

According to a further embodiment, the invention provides a compound containing a peptide which may be isolated and/or purified, comprising, essentially consisting of, or consisting of, formula (I) or formula (II) or a derivative, prodrug, analogue or pharmaceutically acceptable salts or solvates thereof for the use in the prophylaxis and/or treatment of diseases of the genitourinary system including but not restricted to acute renal failure, acute kidney injury (AKI), surgery associated AKI, sepsis associated AKI, contrast media and chemotherapy induced AKI, ischaemia and infarction of the kidney, complications such as hypersensitivity in the context of hemodialysis and hemodiafiltration, cystitis, irradiation cystitis, inflammatory diseases of the prostate, and endometriosis.

The invention further relates to a method of treating or ameliorating MASP-associated disorders, as defined above, in a subject or patient by administering at least one peptide, derivative or analogue as defined herein or a pharmaceutically acceptable salt or solvate thereof, a complex or a pharmaceutical composition as defined above, to said subject or patient in need thereof.

As used herein, the terms “patient”, “subject” or “individual” may be used interchangeably and refer to either a human or a non-human animal. These terms include mammals such as humans, primates, livestock animals (e.g., bovines, porcines), companion animals (e.g., canines, felines) and rodents (e.g., mice and rats). The term “mammal” refers to any mammalian species such as a human, mouse, rat, dog, cat, hamster, guinea pig, rabbit, livestock, and the like.

According to the invention the at least one peptide, derivative or analogue as defined herein or the pharmaceutically acceptable salt or solvate thereof, or the complex as defined above is administered to a patient or subject in a therapeutically effective amount, wherein a “therapeutically effective amount” of a compound of the present invention is meant to describe a sufficient amount of a compound of the present invention to treat an MASP-associated disorder as defined herein. In particular embodiments, the therapeutically effective amount will achieve a desired benefit/risk ratio applicable to any medical treatment.

The present invention particularly comprises the following embodiments, wherein the substituents or moieties of the peptide according to formula (I) or formula (II) as defined below, may independently have the meanings as described below.

A peptide or a compound containing a peptide, or derivative or analogue thereof as defined herein or the pharmaceutically acceptable salt or solvate thereof or the complex or the pharmaceutical composition (as defined below), are hereinafter commonly also referred to as "MASP inhibitory peptide of the present invention".

In some embodiments, a MASP inhibitory peptide of the present invention binds to MASP-1 and/or MASP-2, e.g. human MASP-1 and/or MASP-2. In certain embodiments, a MASP inhibitory peptide of the present invention specifically binds to human MASP-1 and/or MASP-2. As used herein, "specifically binds" refers to a specific binding agent's preferential interaction with a given ligand over other agents in a sample. For example, a specific binding agent that specifically binds a given ligand binds the given ligand, under suitable conditions, in an amount or a degree that is observable over that of any nonspecific interaction with other components in the sample. Suitable conditions are those that allow interaction between a given specific binding agent and a given ligand. These conditions include pH, temperature, concentration, solvent, time of incubation, and the like, and may differ among given specific binding agent and ligand pairs, but may be readily determined by those skilled in the art. In some embodiments, a MASP inhibitory peptide of the present invention binds MASP1 and/or MASP-2 with greater specificity than a MASP inhibitory peptide reference compound (e.g. any one of the MASP inhibitory peptide reference compounds provided herein).

The invention thus further relates to a complex comprising at least one peptide or compound containing a peptide, derivative or analogue as defined herein bound to MASP-1 or MASP-2.

In some embodiments, a MASP inhibitory peptide of the present invention exhibits specific binding to MASP-1 and/or MASP-2, especially human MASP-1 and/or MASP-2, that is at least about 10%, 20%, 30%, 40%, 50%, 60%, 70%, 80%, 90%, 100%, 200%, 300%, 400%, 500%, 700%, 1000%, or 10000% higher than a selected MASP inhibitory peptide reference compound.

In some embodiments, a MASP inhibitory peptide of the present invention exhibits specific binding to MASP1 and/or MASP-2, especially human MASP-1 and/or MASP-2, that is at least about 1, 2, 3, 4, 5-fold, or at least about 10, 20, 50, or 100-fold higher than a selected MASP inhibitory peptide reference compound.

In some embodiments, a MASP inhibitory peptide of the present invention exhibits a binding affinity to MASP-1 and/or MASP-2 that is at least about 10%, 20%, 30%, 40%, 50%, 60%, 70%, 80%, 90%, 100%, 200%, 300%, 400%, 500%, 700%, 1000%, or 10000% higher than a selected MASP inhibitory peptide reference compound.

In some embodiments, a MASP inhibitory peptide of the present invention exhibits a binding affinity to MASP-1 and/or MASP-2 that is at least about 1, 2, 3, 4, 5-fold, or at least about 10, 20, 50, 100 or 1000-fold higher than a selected MASP inhibitory peptide reference compound.

In some embodiments, a MASP inhibitory peptide of the present invention exhibits an inhibition of MASP-1 and/or MASP-2 (e.g., rat or human MASP-1 and/or MASP-2) activity. In some embodiments, the activity is an in vitro or an in vivo activity, e.g. an in vitro or in vivo activity described herein. In some embodiments, a MASP inhibitory peptide of the present invention inhibits at least about 10%, 20%, 30%, 40%, 50%, 60%, 70%, 80%, 90%, 100%, 200%, 300%, 400%, 500%, 700%, 1000%, or 10000% of the MASP-1 and/or MASP-2 activity inhibited by a selected MASP inhibitory peptide reference compound.

In certain embodiments, the MASP inhibitory peptide of the present invention exhibits 1.5, 2, 3, 4, 5, 6, 7, 8, 9, 10, 11, 12, 13, 14, 15, 16, 17, 18, 19, 20, 30, 40, 50, 60, 70, 80, 90, 100, 120, 140, 160, 180, or 200-fold greater MASP-1 and/or MASP-2 inhibition than a selected MASP inhibitory peptide reference compound.

In further particular embodiments, the MASP-1 and/or MASP-2 inhibitory activity of the MASP inhibitory peptides according to the present invention is determined by measurement of their $IC_{50}$ for MASP-1 and/or MASP-2 (e.g., rat human MASP-1 and/or MASP-2). Determination of the $IC_{50}$ for MASP-1 and/or MASP2 can be done with the biochemical assays shown herein. It is particularly preferred that a MASP inhibitory peptide of the present invention exhibits an $IC_{50}$ for MASP-1 and/or MASP-2 of <1,000 nM, preferably ≤500 nM, more preferably ≤300 nM, more preferably ≤250 nM, more preferably ≤200 nM, more preferably ≤150 nM, more preferably ≤100 nM, more preferably ≤75 nM, more preferably ≤50 nM, more preferably ≤45 nM, more preferably ≤40 nM, more preferably ≤35 nM, more preferably ≤30 nM.

In some embodiments, a MASP inhibitory peptide of the present invention has a lower $IC_{50}$ (i.e. higher binding affinity) for MASP-1 and/or MASP-2, (e.g., rat or human MASP-1 and/or MASP-2) compared to a selected MASP inhibitory peptide reference compound. In some embodiments, a MASP inhibitory peptide according to the present invention has an $IC_{50}$ in a MASP-1 and/or MASP-2 competitive binding assay which is at least about 5%, 10%, 20%, 30%, 40%, 50%, 60%, 70%, 80%, 90%, 100%, 200%, 300%, 400%, 500%, 700%, 1000% or 10000% lower than that of a selected MASP inhibitory peptide reference compound.

In some embodiments, a MASP inhibitory peptide of the present invention exhibits at least about 5%, 10%, 20%, 30%, 40%, 50%, 60%, 70%, 80%, 90%, 95%, 97%, 98%, 99%, or greater than 99%, 100%, 200%, 300%, 400%, 500%, 700%, 1000% or 10000% greater in vitro inhibition of human MASP-1 and/or MASP-2 activity as that of a selected MASP inhibitory peptide reference compound.

In some embodiments, a MASP inhibitory peptide of the present invention exhibits at least about 5%, 10%, 20%, 30%, 40%, 50%, 60%, 70%, 80%, 90%, 95%, 97%, 98%, 99%, or greater than 99%, 100%, 200%, 300%, 400%, 500%, 700%, 1000% or 10000% greater in vivo inhibition of human MASP-1 and/or MASP-2 activity as that of a selected MASP inhibitory peptide reference compound.

As used herein, in certain embodiments, a MASP inhibitory peptide having a "MASP-1 and/or MASP-2 inhibitory activity" means that the compound has the ability to inhibit C3 deposition in vitro or in subjects (e.g. mice or humans), when administered thereto (e.g. by the parenteral route, e.g. by injection, or by the pulmonary, nasal, sublingual, lingual, buccal, dermal, transdermal, conjunctival, optic route or as implant or stent orally administered), in a dose-dependent and time-dependent manner.

In some embodiments, a MASP inhibitory peptide of the present invention exhibits an inhibition of C3 deposition (e.g., human C3 deposition. In some embodiments, the inhibition of C3 deposition is determined by an in vitro or an in vivo inhibition. In some embodiments, a MASP inhibitory peptide of the present invention inhibits at least about 10%, 20%, 30%, 40%, 50%, 60%, 70%, 80%, 90%, 100%, 200%, 300%, 400%, 500%, 700%, 1000%, or 10000% of the C3 deposition inhibited by a selected MASP inhibitory peptide reference compound.

In certain embodiments, the MASP inhibitory peptide of the present invention exhibits 1.5, 2, 3, 4, 5, 6, 7, 8, 9, 10, 11, 12, 13, 14, 15, 16, 17, 18, 19, 20, 30, 40, 50, 60, 70, 80, 90, 100, 120, 140, 160, 180, or 200-fold greater inhibition of C3 deposition than a selected MASP inhibitory peptide reference compound.

In further particular embodiments, the MASP-1 and/or MASP-2 inhibitory activity of the MASP inhibitory peptides according to the present invention is determined by measurement of their $IC_{50}$ for inhibition of C3 deposition in vitro or in subjects (e.g. mice or humans). Determination of the $IC_{50}$ for C3-deposition can be done with the C3 Human Deposition assay shown herein. It is particularly preferred that a MASP inhibitory peptide of the present invention exhibits an $IC_{50}$ for C3 deposition of <1,000 nM, preferably ≤500 nM, more preferably ≤300 nM, more preferably ≤250 nM, more preferably ≤200 nM, more preferably ≤150 nM, more preferably ≤100 nM, more preferably ≤75 nM, more preferably ≤50 nM, more preferably ≤45 nM, more preferably ≤40 nM, more preferably ≤35 nM, more preferably ≤30 nM.

In some embodiments, a MASP inhibitory peptide of the present invention exhibits at least about 5%, 10%, 20%, 30%, 40%, 50%, 60%, 70%, 80%, 90%, 95%, 97%, 98%, 99%, or greater than 99%, 100%, 200% 300%, 400%, 500%, 700%, 1000% or 10000% greater in vitro inhibition of C3-deposition as that of a selected MASP inhibitory peptide reference compound.

In some embodiments, a MASP inhibitory peptide of the present invention exhibits at least about 5%, 10%, 20%, 30%, 40%, 50%, 60%, 70%, 80%, 90%, 95%, 97%, 98%, 99%, or greater than 99%, 100%, 200% 300%, 400%, 500%, 700%, 1000% or 10000% greater in vivo inhibition of C3-deposition as that of a selected MASP inhibitory peptide reference compound.

It is particularly preferred that a peptide according to the present invention acts as a MASP inhibitory peptide with its activity being determined in accordance with at least one of the specific assays and/or the in vivo studies according to the examples of the present invention.

Due to their aforesaid MASP-1 and/or MASP-2 inhibitory activity and inhibitory activity of C3-deposition, a compound containing the peptide or the peptide of the present invention (including analogues, derivatives, and pharmaceutically acceptable salts or solvates thereof as well as the above mentioned complex) are suitable for the use in in the prophylaxis and/or treatment of MASP-1 and/or MASP-2-associated disorders.

According to a further embodiment, the invention provides a compound containing a peptide which may be isolated and/or purified, comprising, essentially consisting of, or consisting of, formula (I) or formula (II) or a derivative, prodrug, analogue, pharmaceutically acceptable salt, solvate or solvate of the salt, which acts as a MASP-1 and/or MASP-2 inhibitor and/or which inhibits C3 deposition.

The compounds according to the invention can be used alone or in combination with other active compounds if necessary. The present invention further relates to medicaments containing at least one of the compounds according to the invention and one or more further active compounds, in particular for the treatment and/or prophylaxis of the aforementioned diseases. As suitable combination active compounds, we may mention for example and preferably:

compounds that inhibit the degradation of cyclic guanosine monophosphate (cGMP) and/or cyclic adenosine monophosphate (cAMP), for example inhibitors of phosphodiesterases (PDE) 1, 2, 3, 4 and/or 5, in particular PDE 4 inhibitors such as roflumilast or revamilast and PDE 5 inhibitors such as sildenafil, vardenafil, tadalafil, udenafil, dasantafil, avanafil, mirodenafil or lodenafil;

NO-independent but haem-dependent stimulators of guanylate cyclase, in particular riociguat, nelociguat, vericiguat and the compounds described in WO 00/06568, WO 00/06569, WO 02/42301, WO 03/095451, WO 2011/147809, WO 2012/004258, WO 2012/028647 and WO 2012/059549;

NO-independent and haem-independent activators of guanylate cyclase, in particular Runcaciguat, BI 703704 and the compounds described in WO2012/139888, WO 2001/019780 and WO2014/012934;

prostacyclin analogs and IP receptor agonists, for example and preferably iloprost, beraprost, treprostinil, epoprostenol, NS-304, selexipag, or ralinepag;

endothelin receptor antagonists, for example and preferably bosentan, darusentan, ambrisentan, macicentan or sitaxsentan;

vasopressin receptor antagonists, for example tolvaptan, conivaptan, relcovaptan;

human neutrophile elastase (HNE) inhibitors, for example and preferably sivelestat or DX-890 (Reltran);

compounds which inhibit the signal transduction cascade, in particular from the group of the tyrosine kinase inhibitors, for example and preferably dasatinib, nilotinib, bosutinib, regorafenib, sorafenib, sunitinib, cediranib, axitinib, telatinib, imatinib, brivanib, pazopanib, vatalanib, gefitinib, erlotinib, lapatinib, canertinib, lestaurtinib, pelitinib, semaxanib, masitinib, or tandutinib;

signal transductuion modulators from the group of ASK1 kinase inhibitors, for example selonsertib;

Rho kinase inhibitors, for example and preferably fasudil, Y-27632, SLx-2119, BF-66851, BF-66852, BF-66853, KI-23095 or BA-1049;

active ingredients which reduce vascular wall permeability (oedema formation), by way of example and with preference inhibitors of the ALK1-Smad1/5 signalling pathway, inhibitors of the VEGF and/or PDGF signalling pathways, cyclooxygenase inhibitors, inhibitors of the kallikrein-kinin system or inhibitors of the sphingosine-1-phosphate signalling pathways;

corticosteroids, for example cortisone, cortisol, prednisolone, methylprednisolone, triamcinolone or dexamethasone;

active ingredients which reduce damage to organs under oxidative stress, by way of example and with preference inhibitors of the complement system, especially antagonists of the complement C5a receptor, anti C5 antibodies or agonists of the 5-HT1A receptor;

modulators, stimulators and enhancers of the transcription factor Nrf2, for example CXA-10, Oltipraz, dimethyl fumarate or Bardoxolone;

adrenomedullin and adrenomedullin derivatives, for example pegylated adrenomedullin, and adrenomedullin stabilizing agents, for example adrecizumab;

compounds which inhibit hypoxia inducible factor prolyl hydroxylase (HIF-PH inhibitors), for example molidustat, vadadustat, roxadustat, daprodustat or desidustat;

compounds which inhibit induction of cell death and apoptosis pathway, for example QPI-1002;

- C-Met agonists and hepatocyte growth factor mimetics, for example refanalin;
- alkaline phosphatase and recombinant alkaline phosphatase;
- compounds which inhibit inflammatory response and T cell proliferation, for example CD28 antagonistic compounds such as Reltecimod;
- compounds which modulate the activation of Th17 T cells, for example modulators of the RORc/ROR-gamma transcription factor;
- compounds antagonizing the Th17 T cell response for example anti IL-17 and anti IL-23 antibodies, for example Ixekizumab, Secukinumab, Brodalumab, Ustekinumab, Guselkumab or PTG-200;
- antithrombotic agents, for example and preferably from the group of platelet aggregation inhibitors, anticoagulants or profibrinolytic substances;
- In a preferred embodiment of the invention, the compounds according to the invention are administered in combination with a platelet aggregation inhibitor, for example and preferably aspirin, clopidogrel, ticlopidine or dipyridamole.
- In a preferred embodiment of the invention, the compounds according to the invention are administered in combination with a thrombin inhibitor, for example and preferably ximelagatran, melagatran, dabigatran, bivalirudin or Clexane.
- In a preferred embodiment of the invention, the compounds according to the invention are administered in combination with a GPIIb/IIIa antagonist, for example and preferably tirofiban or abciximab.
- In a preferred embodiment of the invention, the compounds according to the invention are administered in combination with a factor Xa inhibitor, for example and preferably rivaroxaban, apixaban, fidexaban, razaxaban, fondaparinux, idraparinux, DU-176b, PMD-3112, YM-150, KFA-1982, EMD503982, MCM-17, MLN-1021, DX 9065a, DPC 906, JTV 803, SSR-126512 or SSR-128428.
- In a preferred embodiment of the invention, the compounds according to the invention are administered in combination with heparin or a low molecular weight (LMW) heparin derivative.
- In a preferred embodiment of the invention, the compounds according to the invention are administered in combination with direct inhibitors of coagulation factor XI, inhibitors of coagulation factor XI expression, and anti-coagulation factor XI antibodies such as Xisomab 3G3;
- In a preferred embodiment of the invention, the compounds according to the invention are administered in combination with a mineralocorticoid-receptor antagonist, for example and preferably spironolactone, eplerenone or finerenone.
- In a preferred embodiment of the invention, the compounds according to the invention are administered in combination with a diuretic, for example and preferably furosemide, bumetanide, Torsemide, bendroflumethiazide, chlorthiazide, hydrochlorthiazide, hydroflumethiazide, methyclothiazide, polythiazide, trichlormethiazide, chlorthalidone, indapamide, metolazone, quinethazone, acetazolamide, dichlorphenamide, methazolamide, glycerol, isosorbide, mannitol, amiloride or triamterene.
- In a preferred embodiment of the invention, the compounds according to the invention are administered in combination with a PPAR-gamma agonist, for example and preferably pioglitazone or rosiglitazone.
- In a preferred embodiment of the invention, the compounds according to the invention are administered in combination with a PPAR-delta agonist, for example and preferably GW 501516 or BAY 68-5042.

According to a further embodiment, the invention provides a pharmaceutical composition comprising at least one compound containing a peptide which may be isolated and/or purified, comprising, essentially consisting of, or consisting of, formula (I) or formula (II) or a derivative, prodrug, analogue, pharmaceutically acceptable salt, solvate or solvate of the salt, in combination with one or more further active ingredients selected from the group consisting of inhibitors of phosphodiesterases, stimulators or activators of guanylate cyclase, IP receptor agonists, mineralocorticoid-receptor antagonist, diuretic, PPAR-gamma agonist, PPAR-delta agonist, corticosteroids, active ingredients which reduce damage to organs under oxidative stress, compounds which inhibit induction of cell death and apoptosis pathway, compounds which inhibit inflammatory response and T cell proliferation, antithrombotic agents, platelet aggregation inhibitor, thrombin inhibitor, GPIIb/IIIa antagonist, factor Xa inhibitor, heparin or a low molecular weight (LMW) heparin derivative and inhibitors of coagulation factor XI.

The invention further relates to a kit-of-parts combination comprising at least one peptide, derivative or analogue as defined herein or a pharmaceutically acceptable salt or solvate thereof, a complex or a pharmaceutical composition as defined above, and at least one selected from a reagent, medical device, instruction letter or any combination thereof.

The invention further relates to a medical device comprising at least one peptide, derivative or analogue as defined herein or a pharmaceutically acceptable salt or solvate thereof, a complex or a pharmaceutical composition as defined above, for delivery of the peptide, derivative, analogue or complex thereof or of the pharmaceutical composition to a subject.

The pharmaceutical composition, kit-of-parts combination or medical device as defined above is in particular for the use in the prophylaxis and/or treatment of the disorders or diseases as defined as defined herein.

It is possible for the MASP inhibitory peptide of the present invention to have systemic and/or local activity. For this purpose, they can be administered in a suitable manner, such as, for example, via the oral, parenteral, pulmonary, nasal, sublingual, lingual, buccal, rectal, vaginal, dermal, transdermal, conjunctival, otic route or as an implant or stent.

For these administration routes, it is possible for the compounds according to the invention to be administered in suitable administration forms.

For oral administration, it is possible to formulate the compounds according to the invention to dosage forms known in the art that deliver the compounds of the invention rapidly and/or in a modified manner, such as, for example, tablets (uncoated or coated tablets, for example with enteric or controlled release coatings that dissolve with a delay or are insoluble), orally-disintegrating tablets, films/wafers, films/lyophylisates, capsules (for example hard or soft gelatine capsules), sugar-coated tablets, granules, pellets, powders, emulsions, suspensions, aerosols or solutions. It is possible to incorporate the compounds according to the invention in crystalline and/or amorphised and/or dissolved form into said dosage forms.

Parenteral administration can be effected with avoidance of an absorption step (for example intravenous, intraarterial, intracardial, intraspinal or intralumbal) or with inclusion of absorption (for example intramuscular, subcutaneous, intracutaneous, percutaneous or intraperitoneal, intraocular). Administration forms which are suitable for parenteral administration are, inter alia, preparations for injection and infusion in the form of solutions, suspensions, emulsions, lyophylisates or sterile powders.

Examples which are suitable for other administration routes are pharmaceutical forms for inhalation [inter alia powder inhalers, nebulizers], nasal drops, nasal solutions, nasal sprays; tablets/films/wafers/capsules for lingual, sublingual or buccal administration; suppositories; eye drops, eye ointments, eye baths, ocular inserts, ear drops, ear sprays, ear powders, ear-rinses, ear tampons; vaginal capsules, topical application, aqueous suspensions (lotions, mixture agitandae), lipophilic suspensions, emulsions, ointments, creams, transdermal therapeutic systems (such as, for example, patches), milk, pastes, foams, dusting powders, implants or stents.

According to a further embodiment, the invention provides a pharmaceutical composition comprising at least one compound containing a peptide which may be isolated and/or purified, comprising, essentially consisting of, or consisting of, formula (I) or formula (II) or a derivative, prodrug, analogue, pharmaceutically acceptable salt, solvate or solvate of the salt, in combination with one or more inert, nontoxic, pharmaceutically suitable excipients.

The compounds according to the invention can be incorporated into the stated administration forms. This can be effected in a manner known per se by mixing with pharmaceutically suitable excipients. Pharmaceutically suitable excipients include, inter alia, fillers and carriers (for example cellulose, microcrystalline cellulose (such as, for example, Avicel®), lactose, mannitol, starch, calcium phosphate (such as, for example, Di-Cafos®)), ointment bases (for example petroleum jelly, paraffins, triglycerides, waxes, wool wax, wool wax alcohols, lanolin, hydrophilic ointment, polyethylene glycols), bases for suppositories (for example polyethylene glycols, cacao butter, hard fat), solvents (for example water, ethanol, isopropanol, glycerol, propylene glycol, medium chain-length triglycerides fatty oils, liquid polyethylene glycols, paraffins), surfactants, emulsifiers, dispersants or wetters (for example sodium dodecyl sulfate), lecithin, phospholipids, fatty alcohols (such as, for example, Lanette®), sorbitan fatty acid esters (such as, for example, Span®), polyoxyethylene sorbitan fatty acid esters (such as, for example, Tween®), polyoxyethylene fatty acid glycerides (such as, for example, Cremophor®), polyoxethylene fatty acid esters, polyoxyethylene fatty alcohol ethers, glycerol fatty acid esters, poloxamers (such as, for example, Pluronic®), buffers, acids and bases (for example phosphates, carbonates, citric acid, acetic acid, hydrochloric acid, sodium hydroxide solution, ammonium carbonate, trometamol, triethanolamine), isotonicity agents (for example glucose, sodium chloride), adsorbents (for example highly-disperse silicas), viscosity-increasing agents, gel formers, thickeners and/or binders (for example polyvinylpyrrolidone, methylcellulose, hydroxypropylmethylcellulose, hydroxypropylcellulose, carboxymethylcellulose-sodium, starch, carbomers, polyacrylic acids (such as, for example, Carbopol®); alginates, gelatine), disintegrants (for example modified starch, carboxymethylcellulose-sodium, sodium starch glycolate (such as, for example, Explotab®), cross-linked polyvinylpyrrolidone, croscarmellose-sodium (such as, for example, AcDiSol®)), flow regulators, lubricants, glidants and mould release agents (for example magnesium stearate, stearic acid, talc, highly-disperse silicas (such as, for example, Aerosil®)), coating materials (for example sugar, shellac) and film formers for films or diffusion membranes which dissolve rapidly or in a modified manner (for example polyvinylpyrrolidones (such as, for example, Kollidon®), polyvinyl alcohol, hydroxypropylmethylcellulose, hydroxypropylcellulose, ethylcellulose, hydroxypropylmethylcellulose phthalate, cellulose acetate, cellulose acetate phthalate, polyacrylates, polymethacrylates such as, for example, Eudragit®)), capsule materials (for example gelatine, hydroxypropylmethylcellulose), synthetic polymers (for example polylactides, polyglycolides, polyacrylates, polymethacrylates (such as, for example, Eudragit®), polyvinylpyrrolidones (such as, for example, Kollidon®), polyvinyl alcohols, polyvinyl acetates, polyethylene oxides, polyethylene glycols and their copolymers and blockcopolymers), plasticizers (for example polyethylene glycols, propylene glycol, glycerol, triacetine, triacetyl citrate, dibutyl phthalate), penetration enhancers, stabilisers (for example antioxidants such as, for example, ascorbic acid, ascorbyl palmitate, sodium ascorbate, butylhydroxyanisole, butylhydroxytoluene, propyl gallate), preservatives (for example parabens, sorbic acid, thiomersal, benzalkonium chloride, chlorhexidine acetate, sodium benzoate), colourants (for example inorganic pigments such as, for example, iron oxides, titanium dioxide), flavourings, sweeteners, flavour- and/or odour-masking agents.

The present invention furthermore relates to a pharmaceutical composition comprising at least one peptide, derivative or analogue as defined herein or a pharmaceutically acceptable salt or solvate thereof or a complex as defined above.

In particular, the present invention relates to a pharmaceutical composition comprising at least one peptide, derivative or analogue as defined herein or a pharmaceutically acceptable salt or solvate thereof or a complex as defined above, conventionally together with one or more pharmaceutically suitable excipient(s), and to their use according to the present invention.

A pharmaceutical composition according to the present invention may comprise at least one additional active ingredient, such as preferably an additional active ingredient which is active in the prophylaxis and/or treatment of the disorders or diseases as defined herein.

The at least one peptide, derivative or analogue as defined herein or the pharmaceutically acceptable salt or solvate thereof or the complex or the pharmaceutical compositions as defined above may be administered enterally or parenterally, including intravenous, intramuscular, intraperitoneal, intrasternal, subcutaneous, intradermal and intraarticular injection and infusion, orally, intravaginally, intraperitoneally, intrarectally, topically or buccally. Suitable formulations for the respective administration routes are well known to a skilled person and include, without being limited thereto: pills, tablets, enteric-coated tablets, film tablets, layer tablets, sustained-release or extended-release formulations for oral administration, plasters, topical extended-release formulations, dragees, pessaries, gels, ointments, syrup, granules, suppositories, emulsions, dispersions, microcapsules, microformulations, nanoformulations, liposomal formulations, capsules, enteric-coated capsules, powders, inhalation powders, microcrystalline formulations, inhalation sprays, powders, drops, nose drops, nasal sprays, aerosols, ampoules, solutions, juices, suspensions, infusion solutions or injection solutions, etc.

According to a further embodiment, the invention provides a pharmaceutical composition comprising at least one compound containing a peptide which may be isolated and/or purified, comprising, essentially consisting of, or consisting of, formula (I) or formula (II) or a derivative, prodrug, analogue, pharmaceutically acceptable salt, solvate or solvate of the salt, in combination with one or more inert, nontoxic, pharmaceutically suitable excipients for the use in the prophylaxis and/or treatment of cardiovascular and cardiopulmonary disorders, shock, inflammatory disorders, cardiovascular, pulmonary, cerebral and renal sequels of sepsis, ischemia and/or reperfusion-related damage, acute kidney injury, transplant protection and delayed graft function, diseases of the blood and blood-forming organs and the immune system, sequels of diabetes mellitus, inflammatory diseases of the nervous system, diseases of the eye, diseases of the skin, diseases of the respiratory, digestive or genitourinary system and sequels of burns and injuries.

According to a further embodiment, the invention provides a pharmaceutical composition comprising at least one compound containing a peptide which may be isolated and/or purified, comprising, essentially consisting of, or consisting of, formula (I) or formula (II) or a derivative, prodrug, analogue, pharmaceutically acceptable salt, solvate or solvate of the salt, in combination with one or more further active ingredients selected from the group consisting of inhibitors of phosphodiesterases, stimulators or activators of guanylate cyclase, IP receptor agonists, mineralocorticoid-receptor antagonist, diuretic, PPAR-gamma agonist, PPAR-delta agonist, corticosteroids, active ingredients which reduce damage to organs under oxidative stress, compounds which inhibit induction of cell death and apoptosis pathway, compounds which inhibit inflammatory response and T cell proliferation, antithrombotic agents, platelet aggregation inhibitor, thrombin inhibitor, GPIIb/IIIa antagonist, factor Xa inhibitor, heparin or a low molecular weight (LMW) heparin derivative and inhibitors of coagulation factor XI for the use in the prophylaxis and/or treatment of cardiovascular and cardiopulmonary disorders, shock, inflammatory disorders, cardiovascular, pulmonary, cerebral and renal sequels of sepsis, ischemia and/or reperfusion-related damage, acute kidney injury, transplant protection and delayed graft function, diseases of the blood and blood-forming organs and the immune system, sequels of diabetes mellitus, inflammatory diseases of the nervous system, diseases of the eye, diseases of the skin, diseases of the respiratory, digestive or genitourinary system and sequels of burns and injuries.

According to a further embodiment, the invention provides a method for treatment and/or prevention of of cardiovascular and cardiopulmonary disorders, shock, inflammatory disorders, cardiovascular, pulmonary, cerebral and renal sequels of sepsis, ischemia and/or reperfusion-related damage, acute kidney injury, transplant protection and delayed graft function, diseases of the blood and blood-forming organs and the immune system, sequels of diabetes mellitus, inflammatory diseases of the nervous system, diseases of the eye, diseases of the skin, diseases of the respiratory, digestive or genitourinary system and sequels of burns and injuries in humans and animals by administration of an effective amount of a pharmaceutical composition comprising at least one compound containing a peptide which may be isolated and/or purified, comprising, essentially consisting of, or consisting of, formula (I) or formula (II) or a derivative, prodrug, analogue, pharmaceutically acceptable salt, solvate or solvate of the salt, or of a pharmaceutical composition comprising at least one compound containing a peptide which may be isolated and/or purified, comprising, essentially consisting of, or consisting of, formula (I) or formula (II) or a derivative, prodrug, analogue, pharmaceutically acceptable salt, solvate or solvate of the salt, in combination with one or more inert, nontoxic, pharmaceutically suitable excipients and/or one or more further active ingredients.

The suitable dosage of the MASP inhibitory peptide of the present invention can be decided by the attending physician within the scope of sound medical judgment. The specific therapeutically effective dose level for any particular subject will depend upon a variety of factors including: a) the disorder being treated and the severity of the disorder; b) activity of the specific compound employed; c) the specific composition employed, the age, body weight, general health, sex and diet of the patient; d) the time of administration, route of administration, and rate of excretion of the specific hepcidin analogue employed; e) the duration of the treatment; f) drugs used in combination or coincidental with the MASP inhibitory peptide employed, and like factors well known in the medical arts.

In particular embodiments, the total daily dose of the MASP inhibitory peptide of the invention to be administered to a subject or patient in single or divided doses may be in amounts, for example, from 0.0001 to 300 mg/kg body weight daily or 1 to 300 mg/kg body weight daily, or from about 0.0001 to about 100 mg/kg body weight per day, such as from about 0.0005 to about 50 mg/kg body weight per day, such as from about 0.001 to about 10 mg/kg body weight per day, e.g. from about 0.01 to about 1 mg/kg body weight per day, administered in one or more doses, such as from one to three doses. Generally, the MASP inhibitory peptide of the invention may be administered continuously (e.g. by intravenous administration or another continuous drug administration method), or may be administered to a subject at intervals, typically at regular time intervals, depending on the desired dosage and the pharmaceutical composition selected by the skilled practitioner for the particular subject. Regular administration dosing intervals include, e.g., once daily, twice daily, once every two, three, four, five or six days, once or twice weekly, once or twice monthly, and the like.

The invention further comprises the use of the MASP inhibitory peptide as described herein for the manufacture of a medicament, in particular for the manufacture of a medicament for the prophylaxis and/or treatment of a disorder or disease as defined herein.

The invention further comprises a process for manufacturing the peptids of the present invention, derivative or analogue or the pharmaceutically acceptable salt or solvate thereof or a complex, each as described herein. The process for manufacturing comprises the steps as shown in the examples of the present invention.

Generally, the MASP inhibitory peptide of the present invention may be manufactured synthetically, or semi-recombinantly.

According to a further embodiment, the invention provides a process for preparing a compound containing a peptide which may be isolated and/or purified, comprising, essentially consisting of, or consisting of, formula (I) or formula (II) or a derivative, prodrug, analogue or pharmaceutically acceptable salts or solvates thereof by using solid phase peptide synthesis.

According to a further embodiment, the invention provides a process for preparing a compound containing a peptide which may be isolated and/or purified, comprising, essentially consisting of, or consisting of, formula (I) or formula (II) or a derivative, prodrug, analogue, pharmaceutically acceptable salt, solvate or solvate of the salt, containing the steps 1. Use of a 2-chlorotrityl-type resin with a loading of 0.2-1.0 mmol/g, or a Wang-type resin with a loading of 0.2-1.0 mmol/gram,
2. Loading the c-terminal amino acid of the sequence onto the resin,
3. Removal of fmoc protection with a 15-25% piperidine solution in DMF or NMP,
4. Coupling of the next amino acid in the sequence with coupling reagents such as HBTU, HATU or DIC/Oxyma using stoichiometries between 3-8 equivalents,
5. Repeating steps 3 and 4 until the sequence is completed,
6. Cleavage of the peptide from the solid support using a cleavage cocktail that involves TFA and a thiol scavenger,
7. Cyclization of two cysteines in the sequence under oxidative conditions (air or I2),
8. Purification of the cleaved peptide using reversed-phase HPLC.

According to a further embodiment, the invention provides a process for preparing a compound containing a peptide which may be isolated and/or purified, comprising, essentially consisting of, or consisting of, formula (I) or formula (II) or a derivative, prodrug, analogue, pharmaceutically acceptable salt, solvate or solvate of the salt, containing the steps 1. Use of a 2-chlorotrityl-type resin with a loading of 0.2-1.0 mmol/g, or a Wang-type resin with a loading of 0.2-1.0 mmol/gram,
2. Loading the c-terminal amino acid of the sequence onto the resin,
3. Removal of fmoc protection with a 15-25% piperidine solution in DMF or NMP,
4. Coupling of the next amino acid in the sequence with coupling reagents such as HBTU, HATU or DIC/Oxyma using stoichiometries between 3-8 equivalents,
5. Repeating steps 3 and 4 until the sequence is completed,
6. Cleavage of the peptide from the solid support using a cleavage cocktail that involves TFA and a thiol scavenger,
7. Cyclization of two cysteines in the sequence under oxidative conditions (air or 12),
8. Purification of the cleaved peptide using reversed-phase HPLC,
9. Conversion to the HCl salt.

The at least one peptide, derivative or analogue as defined herein or the pharmaceutically acceptable salt or solvate thereof or the complex as defined herein may also be used as a biochemical agent in a biochemical assay, such as e.g. in a diagnostic assay to measure responsiveness to MASP inhibitors or in any biochemical assay being based on MASP inhibitor binding.

The present invention also includes polynucleotides comprising a sequence encoding a MASP inhibitory peptide according to the present invention, as well as a vector comprising a polynucleotide comprising a sequence encoding a MASP inhibitory peptide according to the present invention.

The invention is further illustrated by the following examples, which relate to certain specific embodiments of the present invention. The examples were carried out using well known standard techniques within the routine to those of skill in the art, unless indicated otherwise. The following examples are for illustrative purposes only and do not purport to be wholly definitive as to conditions or scope of the invention. As such, they should not be construed in any way as limiting the scope of the present invention.

EXAMPLES

List of Abbreviations Used in Experimental Section

Å Angstroms
aq. Aqueous, aqueous solution
bar Unit of pressure
BPR Back-pressure regulator
conc Concentrated
d Doublet (NMR)
dd Doublet of doublet (NMR)
DCM Dichloromethane
DEA Diethylamine
DIPEA N,N,-diisopropylethylamine (Hünig's base)
DMAP 4-Dimethylaminopyridine
DMF N,N-dimethylformamide
DMSO Dimethylsulfoxide
dt Doublet of triplet (NMR)
EA Ethyl acetate
ee Enantiomeric excess
ent Enantiomeric
eq Equivalent(s)
equiv Equivalent(s) (ion chromatography)
ESI Electrospray-ionisation (mass spectroscopy)
Fmoc-OSu 1-{[(9H-Fluoren-9-ylmethoxy)carbonyl]oxy}pyrrolidine-2,5-dione
GC-MS Gas chromatography coupled with mass spectrometry
h Hour(s)
HATU O-(7-Azabenzotriazol-1-yl)-N,N,N',N'-tetramethyluronium-hexafluorophosphate
HPLC High pressure liquid chromatography
IC Ion chromatography
ID Internal diameter
L Liter
LC-MS Liquid chromatography coupled to mass spectroscopy
LiHMDS Lithium bis(trimethylsilyl)amide
lit. Literature
m Multiplet (NMR)
MALDI Matrix Assisted Laser Desorption/Ionization (mass spectrometry)
Me Methyl
min Minute(s)
mm millimeter
μm micrometer (micron)
M Molar
MPLC Medium pressure liquid chromatography MS Mass spectroscopy
MTBE tert-Butyl methyl ether
MTP Microtiter plate
m/z mass-to-charge ratioi (mass spectrometry)
nm nanometer
NMP N-Methyl-2-pyrrolidone
NMR Nuclear magnetic resonance spectroscopy
PBS Phosphate buffered saline
PE Petroleum ether
PEG Polyethylene glycol
pos Positive
ppm parts per million
Pr Propyl
Psi Pounds per square inch (pressure)
q/quart Quartet (NMR)
qd Quartet of doublet (NMR)
quint Quintet (NMR)
rac racemic
Rf Retention factor (TLC)
RP reversed-phase (for liquid chromatography)
Rt Retention time (chromatography)
s Singlet (NMR)
s Seconds (time)
SPPS solid phase peptide synthesis
t Triplet (NMR)
TBTU O (Benzotriazol-1-yl)-N,N,N',N'-tetramethyluronium tetrafluoroborate
tBu tert-Butyl
TEA triethylamine
THF Tetrahydrofuran
TLC Thin layer chromatography
UPLC Ultra-performance liquid chromatography
UV Ultraviolet Further abbreviations can be found in Table 2 and 3.

Analytical LC-MS Methods

Method 1

Equipment type MS: ThermoFisherScientific LTQ-Orbitrap-XL; Equipment type HPLC: Agilent 1200SL; Column: Agilent, POROSHELL 120, 3×150 mm, SB—C18 2.7 μm; eluent A: 1 L water+0.1% trifluoroacetic acid; eluent B: 1 L acetonitrile+0.1% trifluoroacetic acid; gradient: 0.0 min 2% B→1.5 min 2% B→15.5 min 98% B→18.0 min 98% B; oven: 40° C.; flow rate: 0.75 mL/min; UV-detection: 210 nm Method 2

Equipment type MS: ThermoFisherScientific LTQ-Orbitrap-XL; Equipment type HPLC: Agilent 1200SL; Column: Agilent, POROSHELL 120; 3×150 mm, SB—C18 2.7 μm; eluent A: 1 L water+0.1% trifluoroacetic acid; eluent B: 1 L acetonitrile+0.1% trifluoroacetic acid; gradient: 0.0 min 5% B→0.3 min 5% B→7.0 min 98% B→10 min 98% B; oven: 40° C.; flow rate: 0.75 mL/min; UV-detection: 210 nm Method 3

Equipment type MS: Waters TOF instrument; Equipment type UPLC: Waters Acquity I-CLASS; Column: YMC, TRIART C18, 75×1 mm, 3.0 μm×12 nm; eluent A: 1 L water+0.01% formic acid; eluent B: 1 L acetonitrile+0.01% formic acid; gradient: 0.0 min 1% B→2.0 min 1% B→8.0 min 95% B→10.0 min 95% B; oven: 50° C.; flow rate: 0.63 mL/min; UV-detection: 210 nm Method 4

Equipment type MS: Waters TOF instrument; Equipment type UPLC: Waters Acquity I-CLASS; Column: YMC, TRIART C18, 75×1 mm, 3.0 μm 12 nm; eluent A: 1 L water+0.01% formic acid; eluent B: 1 L acetonitrile+0.01% formic acid; gradient: 0.0 min 1% B→1.0 min 1% B→15.0 min 50% B→18.0 min 95% B; oven: 50° C.; flow rate: 0.63 mL/min; UV-detection: 210 nm Method 5

Equipment type MS: Waters TOF instrument; Equipment type UPLC: Waters Acquity I-CLASS; Column: Waters, HSST3, 2.1×50 mm, C18 1.8 μm; eluent A: 1 L water+0.01% formic acid; eluent B: 1 L acetonitrile+0.01% formic acid; gradient: 0.0 min 2% B→0.5 min 2% B→7.5 min 95% B→10.0 min 95% B; oven: 50° C.; flow rate: 1.00 mL/min; UV-detection: 210 nm Method 6

Equipment type MS: Waters Synapt G2S; Equipment type UPLC: Waters Acquity I-CLASS; Column: Waters, BEH300, 2.1×150 mm, C18 1.7 μm; eluent A: 1 L water+0.01% formic acid; eluent B: 1 L acetonitrile+0.01% formic acid; gradient: 0.0 min 2% B→1.5 min 2% B→8.5 min 95% B→10.0 min 95% B; oven: 50° C.; flow rate: 0.50 mL/min; UV-detection: 220 nm Method 7

Instrument type MS: Agilent 6410 Triple Quad; Instrument type HPLC: Agilent 1200; Column: Gemini-NX C18 5 μm 110 Å 150×4.6 mm; eluent A: 0.1% TFA in $H_2O$; eluent B: 0.1% TFA in ACN; gradient: 0.0 min 20% B→20 min 50% B→20.1 min 90% B→23 min 90% B; oven temperature: 50° C.; flow rate: 1.0 mL/min; UV-detection: 220 nm Method 8

Instrument type MS: Agilent 6410 Triple Quad; Instrument type HPLC: Agilent 1200; Column: Discovery BIO Wide Pore C18 5 μm 300 Å×4.6 mm; eluent A: 0.1% TFA in $H_2O$; eluent B: 0.1% TFA in ACN; gradient: 0.0 min 10% B→20 min 80% B→20.1 min 90% B→23 min 90% B; oven temperature: 50° C.; flow rate: 1.0 mL/min; UV-detection: 220 nm Method 9

Instrument: Waters ACQUITY SQD UPLC System; column: Waters Acquity UPLC HSS T3 1.8 μm 50×1 mm; eluent A: 1 L water+0.25 mL 99% formic acid, eluent B: 1 L acetonitrile+0.25 mL 99% formic acid; gradient: 0.0 min 90% A→1.2 min 5% A→2.0 min 5% A; oven: 50° C.; flow: 0.40 mL/min; UV-detection: 210 nm Method 10

Instrument MS: Thermo Scientific FT-MS; Instrument UHPLC: Thermo Scientific UltiMate 3000; Column: Waters, HSST3, 2.1×75 mm, C18 1.8 μm; eluent A: 1 L watMethod 10er+0.01% formic acid; eluent B: 1 L acetonitrile+0.01% formic acid; gradient: 0.0 min 10% B→2.5 min 95% B→3.5 min 95% B; oven: 50° C.; flow rate: 0.90 mL/min; UV-detection: 210 nm/Optimum Integration Path 210-300 nm Method 11

MS Instrument: Agilent MS Quad 6150; HPLC: Agilent 1290; Column: Waters Acquity UPLC HSS T3 1.8 μm 50×2.1 mm; eluent A: 1 L water+0.25 mL formic acid, eluent B: 1 L acetonitrile+0.25 mL formic acid; gradient: 0.0 min 90% A→0.3 min 90% A→1.7 min 5% A→3.0 min 5% A oven: 50° C.; flow rate: 1.20 mL/min; UV-detection: 205-305 nm.

Method 12

Instrument: Waters ACQUITY SQD UPLC System; column: Waters Acquity UPLC HSST3 1.8 μm 50×1 mm; eluent A: 1 L water+0.25 mL 99% formic acid, eluent B: 1 L acetonitrile+0.25 mL 99% formic acid; gradient: 0.0 min 95% A→6.0 min 5% A→7.5 min 5% A oven: 50° C.; flow rate: 0.35 mL/min; UV-detection: 210 nm.

Method 13

Instrument: Waters Single Quad MS System; Instrument Waters UPLC Acquity; column: Waters BEH C18 1.7 μm 50×2.1 mm; eluent A: 1 L water+1.0 mL (25% ammonia)/L, eluent B: 1 L acetonitrile; gradient: 0.0 min 92% A→0.1 min 92% A→1.8 min 5% A→3.5 min 5% A; oven: 50° C.; flow rate: 0.45 mL/min; UV-detection: 210 nm.

Method 14

System MS: Waters TOF instrument; System UPLC: Waters Acquity I-CLASS; Column: Waters Acquity UPLC Peptide BEH C18 300 Å, 1.7 μm 150×2.1 mm; Eluent A: 1 l Water+0.100 ml 99% Formic acid, Eluent B: 1l Acetonitrile+0.100 ml 99% Formic acid; Gradient: 0.0 min 90% A→0.25 min 90% A→8.0 min 45% A→10.0 min 2%→12.0 min 2% A Oven: 50° C.; Flow: 0.475 ml/min; UV-Detection: 210 nm.

Method 15

MS instrument type: Agilent G6110A; HPLC instrument type: Agilent 1200 Series LC; UV DAD; column: Chromolith Flash RP-18e 25×2.0 mm; mobile phase A: 0.0375% TFA in water (v/v), mobile phase B: 0.01875% TFA in acetonitrile (V/V); gradient: 0.01 min 5% B→0.80 min 95% B→1.20 min 95% B→1.21 min 5% B→1.5 min 5% B; flow rate: 1.50 mL/min; oven temperature: 50° C.; UV detection: 220 nm & 254 nm.

MALDI Method

Exact mass measurements were performed on selected peptides using a Matrix Assisted Laser Desorption/Ionization (MALDI) mass spectrometry method on a Bruker autoflex maX LRF MALDI MS Time-of-Flight (ToF-MS) system. Samples were prepared on a Bruker MALDI target plate using α-cyano-4-hydroxycinnamic acid (CAS 28166-41-8) as the matrix. A solution of the sample peptide 0.1 to 1.0 mg in 1.0 mL acetonitrile-water (50/50 or 30/70) and a stock solution of the matrix (10 mg/mL) in 50% acetonitrile in water containing 0.05% trifluoroacetic acid are prepared. 1.0 uL of each solution is placed onto the MALDI target plate and allowed to dry. The sample is then ready for analysis. Recommended sample preparations for MALDI target plates can be found in the documentation provided by Bruker.

Analytical Ion Chromatography Method

Method: IC-Quantitative

Quantitative Measurement of Cations and Anions using external standards; Instrument: Thermo Scientific ICS 5000+; Capillary IC Columns: IonPac AS11-HC und IonPac CS16; eluent: gradient eluent [H]+[OH]−; Detector: Conductivity detection; routine anions possible: acetate, bromide, citrate, chloride, fluoride, formate, lactate, mesylate, phosphate, sulfate, tartrate, trifluoroacetate; routine cations possible: ammonium, barium, calcium, potassium, lithium, sodium, magnesium, choline.

Analytical Gas Chromatography Mass Spec Method

GC-MS Method 1

Instrument: Thermo Scientific DSQII, Thermo Scientific Trace GC Ultra; column: Restek RTX-35MS, 15 m×200 μm×0.33 μm; constant flow with Helium: 1.20 mL/min; oven: 60° C.; Inlet: 220° C.; gradient: 60° C., 30° C./min→300° C. (3.33 min hold).

NMR

The $^1$H-NMR data of selected compounds are listed in the form of $^1$H-NMR peaklists. Therein, for each signal peak the δ value in ppm is given, followed by the signal intensity, reported in round brackets. The δ value-signal intensity pairs from different peaks are separated by commas. Therefore, a peaklist is described by the general form: δ1 (intensity1), δ2 (intensity2), . . . , δi (intensityi), . . . , δn (intensityn).

The intensity of a sharp signal correlates with the height (in cm) of the signal in a printed NMR spectrum. When compared with other signals, this data can be correlated to the real ratios of the signal intensities. In the case of broad signals, more than one peak, or the center of the signal along with their relative intensity, compared to the most intense signal displayed in the spectrum, are shown. A $^1$H-NMR peaklist is similar to a classical $^1$H-NMR readout, and thus usually contains all the peaks listed in a classical NMR interpretation. Moreover, similar to classical 1H-NMR printouts, peaklists can show solvent signals, signals derived from stereoisomers of the particular target compound, peaks of impurities, 13C satellite peaks, and/or spinning sidebands. The peaks of stereoisomers, and/or peaks of impurities are typically displayed with a lower intensity compared to the peaks of the target compound (e.g., with a purity of >90%). Such stereoisomers and/or impurities may be typical for the particular manufacturing process, and therefore their peaks may help to identify a reproduction of the manufacturing process on the basis of "by-product fingerprints". An expert who calculates the peaks of the target compound by known methods (MestReC, ACD simulation, or by use of empirically evaluated expectation values), can isolate the peaks of the target compound as required, optionally using additional intensity filters. Such an operation would be similar to peak-picking in classical 1H-NMR interpretation. A detailed description of the reporting of NMR data in the form of peaklists can be found in the publication "Citation of NMR Peaklist Data within Patent Applications" (cf. http://www.researchdisclosure.com/searching-disclosures, Research Disclosure Database Number 605005, 2014, 1 Aug. 2014). In the peak picking routine, as described in the Research Disclosure Database Number 605005, the parameter "MinimumHeight" can be adjusted between 1% and 4%. However, depending on the chemical structure and/or depending on the concentration of the measured compound it may be reasonable to set the parameter "MinimumHeight"<1%.

PREPARATION EXAMPLES

General Methods for the Synthesis

Solid Phase Peptide Synthesis (SPPS) was carried out either using an automatic peptide synthesizer or performed manually by hand. Peptide synthesis was typically carried out in scale ranges from 0.1 to 1.0 mmol. When peptide synthesis was carried out by hand, the general procedures Methods C, D and E described below were used. Automated peptide synthesis was performed on a Symphony X peptide synthesizer (Gyros Protein Technologies).

Fmoc-protected amino acids (or intermediate amino acids used to prepare Fmoc amino acids) were purchased from Novabiochem, Bachem, Iris Biotech, Sigma-Aldrich, Alfa, Enamine, Amatek, Anichem, ACBR, ABC Laboratory, AP Bioscience, Combiblocks, ArZa Bioscience, Ark Pharm, Acroteinchem, Apollo Scientific, Biofine, Broadpharm, VWR, or Gyros Protein Technologies (Fluorenylmethoxycarbonyl=Fmoc), GL Biochem (Shanghai) Ltd, Chengdu Aminotp Pharmaceutical Technology Ltd, Suzhou Highfine Biotech Co., Ltd, WuXi AppTec, or sourced through other Chinese vendors. Some special fmoc-protected amino acids were synthesized internally, and these synthetic methods are described herein. Some of the fmoc amino acids synthesized internally are also commercially available. In some cases where the Fmoc-protected amino acid was not commercially available but the Boc-protected (tert-Butyloxycarbonyl=Boc) unnatural amino acid was commercially available, the fmoc-protected amino acid was prepared from the Boc-protected amino acid by deprotection and reprotection using methods commonly employed in the art. CAS Numbers for commercially available, unnatural amino acids used in the synthesis of peptides of this invention have in most cases been included in Table 5. In cases where a racemic amino acid (Fmoc or Boc) was purchased, one skilled in the art should recognize that the enantiomers can be separated using chiral chromatography, and this was in fact sometimes done to optain the enantiomerically pure amino acid prior to peptide synthesis.

The following unnatural amino acids have been used in preparing peptides of the invention. The Fmocor Boc-protected amino acids were either obtained through commercial sources (CAS Number is available) or, synthesized internally by methods described herein. Table 5 shows the CAS number of the chemical groups/amino acids which were used for the peptide synthesis (right column) and the corresponding chemical group/amino acid present in the peptides (left column).

TABLE 5

Availability of unnatural amino acids and chemical groups of this Invention

| Abbreviation/Expression Definition | CAS Number for Fmoc-/Boc-protected amino acid, chemical group or building block used for peptide synthesis |
|---|---|
| Cyclohexanecarboxylic acid | 98-89-5 |
| (2S)-Amino-2-[3-(Trifluoromethyl)bicyclo[1.1.1]pent-1-yl]acetic acid | 914082-67-0 |
| (S)-3-(2H-tetrazol-5-yl)propanoic acid | 954147-35-4 |
| (1R,3S)-3-(Amino)cyclopentanecarboxylic acid | 220497-67-6 |
| (1R,3S,4S)-2-azabicyclo[2.2.1]heptane-3-carboxylic acid | 291775-59-2 |
| (1R,3S,5R)-2-Azabicyclo[3.1.0]hexane-3-carboxylic acid | 1932624-93-5 |
| (1S,2S,4S)-Bicyclo[2.2.1]hept-5-en-2-ylacetic acid | 14734-13-5 |
| (1S,2S,5R)-3-azabicyclo[3.1.0]hexane-2-carboxylic acid | 400720-05-0 (Boc); 854113-43-2 |
| (1S,3R)-3-(Amino)cyclopentanecarboxylic acid | 220497-66-5 |
| (1S,3R,4R)-2-Azabicyclo[2.2.1]heptane-3-carboxylic acid | 291775-53-6; 291775-53-6 (Boc) |
| (2,4-Dioxoimidazolidin-1-yl)acetic acid | 94738-31-5; 94738-31-5 (NH) |
| 2-Cyano-L-phenylalanine | 401933-16-2 |
| 2-Fluoro-L-phenylalanine | 205526-26-7 |
| 2-Methyl-L-phenylalanine | 211637-75-1 |
| (2S)-(tetrahydro-2H-pyran-4-yl)ethanoic acid | 368866-31-3 |
| (2S,4S)-4-Trifluoromethyl-pyrrolidine-2-carboxylic acid | 1242934-32-2 |
| (3,3-difluorocyclobutyl)acetic acid | 1373503-48-0 |
| 3-Cyano-L-phenylalanine | 205526-36-9 |
| 3-Fluoro-L-phenylalanine | 8560-68-8 |
| 4-Fluoro-L-phenylalanine | 169243-86-1 |
| 5-Azaspiro[2.4]heptane-1-carboxylic acid | 150543-61-6 |
| D-(+)Biotin | 58-85-5 |
| L-N,N-Dimethylalanine | 2812-31-9 |
| N,N-Dimethylglycine | 1118-68-9 |
| 2-(N-Isopropyl-N-methylamino)acetic acid | 4747-21-1 |
| L-N-Methylalanine | 84000-07-7 |
| D-N-Methylalanine | 138774-92-2 |
| L-N-Methylcysteine | 944797-51-7 |
| L-N-Methylphenylalanine | 77128-73-5 |
| N-Methyl-Glycine | 77128-70-2 |
| L-N-Methylisoleucine | 138775-22-1 |
| N-Phenylglycine | 103-01-5 |
| (R)-3-Aminoadipic acid | 197006-18-1 |
| (R)-4-Amino-6-methylheptanoic acid | 269078-75-3 |
| (R)-Piperidine-3-Carboxylic Acid | 193693-67-3; 163438-09-3 (Boc) |
| (R)-Pyrrolidine-3-Carboxylic Acid | 68464-02-8 |
| (S)-(1-Piperidin-3-yl)-acetic acid | 1217646-18-8 |
| (S)-2-Amino-3-ethyl-pentanoic acid | 1310680-47-7 |
| (S)-3-(1-Pyrrolidine-2-yl)-propionic acid | 1013997-51-7 |
| (S)-3-(2H-Tetrazol-5-yl)propionic acid | 954147-35-4 |
| (S)-3-Methylvaleric Acid | 1730-92-3 |
| (S)-4-Piperazine-2-carboxylic acid | 1217628-46-0 |
| (S)-Piperidine-3-carboxylic acid | 193693-68-4 |
| (S)-Pyrrolidine-3-carboxylic acid | 193693-66-2; 140148-70-5 (Boc) |
| [(2R)-4,4-Difluoropyrrolidin-2-yl]acetic acid | 1402687-79-9 |
| [(6S)-5-Azaspiro[2.4]hept-6-yl]acetic acid | Omegachem (OC-0701) |
| 1,1-Dioxidotetrahydro-2H-thiopyran-4-yl)acetic acid | 1224869-02-6 |
| L-1-Napthylalanine | 96402-49-2 |
| 2-(3-Pyridyl)acetic acid | 501-81-5 |
| 2-(Aminomethyl)benzoic acid | 219640-94-5 |
| 2-(Cyclohexylamino)acetic acid | 108-91-8 |
| 2-(Diethylamino)acetic acid | 109-89-7 |
| 2-(Morpholine)acetic acid | 110-91-8 |
| 2-(N-Methyl-N-cyclopropylamino)acetic acid | 5163-20-2 |
| 2-(Piperidin)acetic acid | 110-89-4 |
| 2-(Pyrrolidine)acetic acid | 123-75-1 |
| 2-(Thian-4-yl)acetic acid | 137103-09-4 |
| 2-(Thiomorpholine)acetic acid | 123-90-0 |
| 2,3-Difluoro-L-phenylalanine | 1260605-30-8 |
| 2-Aminobenzoic acid | 150256-42-1 |
| 2-Azaspiro[3.3]heptane-6-carboxylic acid | 2138525-84-3 |

TABLE 5-continued

Availability of unnatural amino acids and chemical groups of this Invention

| Abbreviation/Expression Definition | CAS Number for Fmoc-/Boc-protected amino acid, chemical group or building block used for peptide synthesis |
|---|---|
| L-2-Bromophenylalanine | 220497-47-2 |
| 2-Chloro-L-phenylalanine | 198560-41-7 |
| 2-Cyanobenzoic acid | 3839-22-3 |
| 2-Fluorobenzoic acid | 445-29-4 |
| 2-Hydroxyacetic acid | 7732-18-5 |
| 2-Hydroxyisobutyric acid | 594-61-6 |
| 2-Methylbenzoic acid | 118-90-1 |
| 2-Methyl-L-phenylalanine | 211637-75-1 |
| L-2-Napthylalanine | 112883-43-9 |
| L-2-Pyridylalanine | 185379-40-2 |
| (2S)-Pyrrolidin-2-ylacetic acid | 19693-60-6 |
| 3-(2-Oxoimidazolidin-1-yl)benzoic acid | 884504-86-3 |
| 3-(3-Oxo-1,3,4,5,6,7-hexahydro-2H-indazol-2-yl)benzoic acid | 885949-86-0 |
| 3-(Aminomethyl)benzoic acid | 117445-22-4 |
| 3-(Isobutyrylamino)benzoic acid | 28533-44-0 |
| 3-(Trifluoromethyl)bicyclo[1.1.1]pent-1-yl]acetic acid | 914082-67-0 |
| 3-[(E)-(2-carboxycyclohexen-1-yl)azo]benzoic acid | 885949-86-0 |
| 3-Acetamidobenzoic acid | 587-48-4 |
| 3-Amino-2,2-dimethylpropionic acid | 1076197-00-6 |
| 3-Amino-3-methylbutyric acid | 244031-65-0; 129765-95-3 (Boc) |
| 3-Aminobenzoic acid | 185116-42-1 |
| 3-Aminomethylphenylacetic acid | 631915-50-9 |
| L-3-Bromophenylalanine | 220497-48-3 |
| 3-Carboxybenzoic acid | 121-91-5 |
| 3-Chloro-L-Phenylalanine | 198560-44-0 |
| 3-Chlorophenylglycine | 10242-05-4 |
| 3-Cyanobenzoic acid | 1877-72-1 |
| 3-Fluorobenzoic acid | 455-38-9 |
| 3-Methyl-L-phenylalanine | 211637-74-0 |
| 3-Methoxypropionic acid | 2544-06-1 |
| 3-Methylbenzoic acid | 99-04-7 |
| L-3-Pyridylalanine | 175453-07-3 |
| 4-(Aminomethyl)benzoic acid | 33233-67-9 |
| 4-Aminobenzoic acid | 185116-43-2 |
| 4-Aminomethylphenylacetic acid | 176504-01-1; 71420-92-3 (Boc) |
| L-4-Aminophenylalanine | 95753-56-3 |
| L-4-Bromophenylalanine | 198561-04-5 |
| 4-Carboxybenzoic acid | 100-21-0 |
| 4-Cyanobenzoic acid | 619-65-8 |
| 4-Fluorobenzoic acid | 456-22-4 |
| 4-Fluoro-L-Leucine | 1643928-01-1 |
| 4-Methyl-3-oxo-3,4-dihydro-2H-1,4-benzoxazine-8-carboxylic acid | 141762-02-9 |
| 4-Methylbenzoic acid | 99-94-5 |
| 4-Methylpentanoic acid | 646-07-1 |
| L-4-Pyridylalanine | 169555-95-7 |
| 4-Piperidinepropanoic acid | 154938-68-8 |
| 4-Tetrahydropyranoyl | 368866-31-3 |
| 5-Chlorothiophene-2-carboxylic acid | 24065-33-6 |
| 8-Aminocubane-1-carboxylic acid | Enamine EN300-88072 (MFCD09971721) |
| (S)-2-(Amino)-1,6-hexanedioic acid | 159751-47-0 |
| L-2-Aminobutyric acid | 135112-27-5 |
| 1-Aminocyclobutane-1-carboxylic acid | 885951-77-9 |
| Aminocyclobutanecarboxylic acid | 885951-77-9 |
| 1-(Aminomethyl)-cyclopropyl-1-carboxylic acid | 1263045-62-0 |
| (1S,2S)-2-Amino-1-cyclopentanecarboxylic acid | 359586-64-4 |
| (1R,2R)-2-Amino-1-cyclopentanecarboxylic acid | 359586-69-9 |
| rel-(1R,2S)-2-Amino-1-cyclopentanecarboxylic acid | 352707-76-7 |
| Adipic acid | 124-04-9 |
| 6-Aminohexanoic acid | 88574-06-5 |
| 2-Aminoisobutyric acid | 94744-50-0 |
| L-tert-Butylalanine | 139551-74-9 |
| allo-L-Isoleucine | 251316-98-0 |
| allo-L-Threonine | 201481-37-0 |
| 2-Methyl-L-Proline | 167275-47-0 |
| N(5)-methyl-L-arginine | 1135616-49-7 |
| (S)-Azetidine-2-carboxylic acid | 136552-06-2; 51077-14-6 (Boc) |
| Benzoic acid | 65-85-0 |
| L-2-Thienylalanine | 130309-35-2 |
| beta-Alanine | 35737-10-1 |
| Bromoacetyl | 79-08-3 |
| 4-(3,5-Dimethyl-1,2-oxazol-4-yl)-L-phenylalanine | 1381790-25-5 |
| (2S)-2-amino-3-(4-tert-butylphenyl)propanoic acid | 143415-62-7 |

TABLE 5-continued

| Availability of unnatural amino acids and chemical groups of this Invention | |
|---|---|
| Abbreviation/Expression Definition | CAS Number for Fmoc-/Boc-protected amino acid, chemical group or building block used for peptide synthesis |
| (2S)-2-Amino-5-methyl-hexanoic acid | 180414-94-2 |
| (2S)-2-Amino-4,4,4-trifluorobutanoic acid | 181128-48-3 |
| (2S)-3-(4-carboxyphenyl)-2-aminopropanoic acid | 183070-44-2 |
| (2S)-2-amino-3-(4-carbamoylphenyl)propanoic acid | 205126-71-2 |
| (2S)-2-Amino-3-(2,3,4,5,6-(pentafluorophenyl)propanoic acid | 205526-32-5 |
| (2S)-3-(3-Cyanophenyl)-2-aminopropanoic acid | 205526-36-9 |
| 3-Azido-L-Alanine | 684270-46-0 |
| 2-Amino-5,5,5-trifluoro-4-methyl-pentanoic acid | 777946-04-0 |
| (1R,2S,5S)-3-azabicyclo[3.1.0]hexane-2-carboxylic acid | 167611-99-6 (Boc); 1219181-14-2 (rac) |
| L-Cyclobutylalanine | 478183-62-9 |
| (S)-2-Amino-2-cyclobutylacetic acid | 1391630-31-1 |
| L-Cyclohexylalanine | 135673-97-1 |
| D-cyclohexylalanine | 144701-25-7 |
| L-Cyclohexylglycine | 161321-36-4 |
| L-4,4-Difluoroproline | |
| (2S,4S)-4-Fluoroproline | 203866-19-7 |
| L-Citrulline | 133174-15-9 |
| L-2-Amino-4-cyanobutyric acid | 913253-24-4 |
| 3,3-dimethyl-1,3-azasilolidine-5-carboxylic acid | 268224-29-9 (Boc) |
| (S)-(trifluoromethyl)-L-cysteine | 1994331-25-7 |
| (2S)-2-amino-3-(1-methylcyclopropyl)propanoic acid | 2350203-57-3 |
| (2S)-3-(indol-4-yl)-2-(amino)propanoic acid | 220499-20-7 |
| (2S)-3-(2,3-difluorophenyl)-2-aminopropanoic acid | 266360-64-9 |
| L-Cyclopentylalanine | 371770-32-0 |
| L-Cyclopentylglycine | 220497-61-0 |
| Cyclobutanecarboxylic acid | 3721-95-7 |
| 2-(Cyclobutyl)acetic acid | 6540-33-6 |
| L-Cyclobutylglycine | 49607-08-1 |
| Cyclohexylacetic acid | 5292-21-7 |
| Cyclopentanecarboxylic acid | 3400-45-1 |
| Cyclopentylacetic acid | 1123-00-8 |
| Cyclopropanecarboxylic acid | 1759-53-1 |
| Cyclopropylacetic acid | 5239-82-7 |
| D-2-Chlorophenylalanine | 205526-22-3 |
| L-2,4-Diaminobutyric acid | 125238-99-5; 607366-21-2 (ivDde); 851392-68-2 (MTT) |
| L-2,3-Diaminopropionic acid | 162558-25-0; 607366-20-1 (ivDde); 654670-89-0 (MTT) |
| D-beta-Proline | 193693-61-7 |
| D-Hydroxyproline | 464193-92-8 |
| (2S)-2-Amino-4-(benzylamino)-4-oxobutanecarboxylic acid | 100-46-9 |
| (2S)-2-[(3R)-3-Amino-2-oxopyrrolidin-1-yl]-4-methylpentanoic acid | 957507-85-6 |
| Fumaric acid | 110-17-8 |
| Gamma-Aminobutyric acid | 116821-47-7; 57294-38-9 (Boc) |
| L-tert-Butylglycine | 132684-60-7 |
| 1-Benzyl-L-histidine | 84030-19-3 |
| 1-Methyl-L-histidine | 202920-22-7 |
| L-3-Methylhistidine | 84030-19-3 |
| L-Homocysteine | 167015-23-8 |
| L-Dihydroorotic acid | 5988-19-2 |
| 3-Phenylpropanoic acid | 501-52-0 |
| L-Hydroxyproline | 122996-47-8 |
| Iminodiacetic acid | 142-73-4 |
| Isobutyric acid | 79-31-2 |
| Isonipecotic acid | 148928-15-8 |
| Isovaleric acid | 503-74-2 |
| N-e-Isopropyl-L-lysine | 201003-48-7 |
| 3-Ethyl-L-Norvaline | 1310680-47-7 |
| L-(+)-Lactic acid | 79-33-4 |
| 3-(1,3-Benzothiazol-2-yl)-L-alanine | 959583-56-3 |
| (S)-Pyrrolidine-2-carboxylic acid | 193693-60-6 |
| L-Propargylglycine | 1435854-95-7 |
| (3S)-Morpholine-3-carboxylic acid | 281655-37-6 |
| Nicotinic acid | 59-67-6 |
| L-Norleucine | 77284-32-3 |
| N-Methyl-L-proline | 475-11-6 |
| L-Norvaline | 135112-28-6 |
| 1,18-Octadecanedioic acid | 871-70-5 |
| 2,3,3a,4,5,6,7,7a-Octahydroindole-2-carboxylic acid | 130309-37-4 |
| L-Ornithine | 109425-55-0; 269062-80-8 (DDE); 1198321-33-3 (ivDDE); 147290-11-7 (Alloc) |

TABLE 5-continued

| Availability of unnatural amino acids and chemical groups of this Invention | |
|---|---|
| Abbreviation/Expression Definition | CAS Number for Fmoc-/Boc-protected amino acid, chemical group or building block used for peptide synthesis |
| Palmitic acid | 57-10-3 |
| 9-Amino-4,7-dioxanonanoic acid | 872679-70-4 |
| 12-Amino-4,7,10-trioxadodecanoic acid | 867062-95-1 |
| 15-Amino-4,7,10,13-tetraoxa(Pen)tadecanoic acid | 557756-85-1 |
| 18-Amino-4,7,10,13,16-(Pen)taoxaoctadecanoic acid | 882847-32-7 |
| 14-Amino-3,6,9,12-tetraoxatetradecanoic acid | 437655-95-3 |
| 1-Amino-3,6,9,12,15,18-hexaoxahenicosan-21-oic acid | 882847-34-9 |
| 17-Amino-3,6,9,12,15-(Pen)taoxaheptadecanoic acid | 635287-26-2 |
| 1-Amino-3,6,9,12,15,18,21-heptaoxatetracosan-24-oic acid | 1863885-74-8 |
| 1-Amino-3,6,9,12,15,18,21,24-octaoxaheptacosan-27-oic acid | 756526-02-0 |
| 1-Amino-3,6,9,12,15,18,21,24,27-nonaoxatriacontan-30-oic acid | 1191064-81-9 |
| L-Penicillamine | 201531-88-6 |
| Phenylacetic acid | 103-82-2 |
| L-Phenylglycine | 102410-65-1 |
| Picolinic acid | 98-98-6 |
| L-Pipecolic acid | 86069-86-5 |
| Piperidin-4-ylacetic acid | 157688-46-5 (Boc); 180181-05-9 |
| Pivalic acid | 75-98-9 |
| L-trans-3-Hydroxyproline | 4298-08-2 |
| L-Pyroglutamic acid | 53100-44-0 |
| S-2-amino-3-ethyl-pentanoic acid | 1310680-47-7 |
| S-3-1-Pyrrolidin-2-yl-propionic acid | MFCD09952617 |
| Suberic acid | 505-48-6 |
| tert-Butylacetic acid | 1070-83-3 |
| Tetrahydropyranyl-4-acetic acid | 85064-61-5 |
| Trifluoroacetic acid | 76-05-1 |
| L-2-Thienylalanine | 130309-35-2 |
| (2S,3S)-2-[(3R)-3-Amino-2-oxopyrrolidin-1-yl]-3-methylpentanoic acid | 301840-23-3 |
| (2S,3S)-2-[2-Oxopiperazin-1-yl]-3-methylpentanoic acid | — |
| (2S,3S)-2-[(3S)-2-oxopiperazin-1-yl]-3-methylpentanoic acid | — |
| (1R,3S,5R)-2-Azabicyclo[3.1.0]hexane-3-carboxylic acid | 1932624-93-5 |
| 3-(Trimethylsilyl)-L-alanine | 359766-59-9 |
| (6S)-5-Azaspiro[2.4]heptane-6-carboxylic acid | 2170726-27-7 |
| rel-(1R,3R,5R,6R)-6-(Trifluoromethyl)-2-aza-bicyclo[3.1.0]hexane-3-carboxylic acid | 1986905-54-7 |
| (4aR,6aR,9S,11aS)-11-Oxo-2,3,4,4a,6a,7,8,9,11,11a-decahy-dro-1H-pyrido[3,2-e]pyrrolo[1,2-a]azepine-9-carboxylic acid | 1637768-88-7 |
| (2S)-2[(Amino)-2-(tetrahydro-2H-pyran-4-yl)]acetic acid | 368866-31-3 |
| (2S,3S)-2-((Amino)methyl)-3-methylpentanoic acid | 671233-52-6 |
| 2-[(1S,2S)-1-(Amino)-2-methylbutyl]-1,3-oxazole-4-carboxylic acid | 1238864-23-7 |
| (2S)-Amino-(1-methyl-1H-indazol-5-yl)acetic acid | — |
| (2R)-Amino-(1-methyl-1H-indazol-5-yl)acetic acid | — |
| 3-Carboxyphenylalanine | — |
| 2-Methyl-D-alloisoleucine | 118904-37-3 |
| 4-Ethyl-L-norleucine | 1998613-43-6 |
| L-2,6-Difluorophenylalanine | 1235005-44-3 |
| 2,5-Difluoro-L-phenylalanine | 1004959-90-3 |
| (2S,3aS,6aS)-Octahydrocyclopenta[b]pyrrole-2-carboxylic acid | 87269-87-2 |
| (2S)-2-(Amino)-2-[(1S,3R)-3-hydroxycyclohexyl]acetic acid | — |
| (2S)-2-(Amino)-2-[(1S,3S)-3-hydroxycyclohexyl]acetic acid | — |
| 2-Amino-7-(tert-butoxy)-7-oxoheptanoic acid | 159751-46-9 |
| (2S)-3-(Triazol-1-yl)-2-(amino)propanoic acid | — |
| Tetrahydro-2H-pyran-3-ylacetic acid | 1395922-27-6 |
| rel-(1R,3S)-3-[(Amino)methyl]cyclohexanecarboxylic acid | 2138238-33-0 |
| (3R,6R)-1,1-Difluoro-5-azaspiro[2.4]heptane-6-carboxylic acid (enantiomer 1) | — |
| (3R,6R)-1,1-Difluoro-5-azaspiro[2.4]heptane-6-carboxylic acid (enantiomer 2) | — |
| Tranexamic acid | 167690-53-1; 27687-14-5 (Boc) |
| trans-2-(3-(Amino)cyclohexyl)acetic acid | 347185-01-7 |
| trans-4-Fluoroproline | 203866-20-0 |
| 1,13-Diamino-4,7,10-trioxatridecan-succinamic acid | 172089-14-4 |
| 4-Piperazine-2-carboxylic acid | 1034574-30-5 |
| (2-Pyrrolidine-1-yl) acetic acid | 37386-15-5 |
| (S)-2-(Amino)-1,6-hexanedioic acid (AAD) | 159751-47-0 |
| Freidinger's Lactam | 145484-45-3 |
| (R)-Pyrrolidine-3-acetic acid | 2137100-59-3 |
| (2S)-2-(morpholin-4-yl)propanoic acid | 110582-65-5 |
| L-dehydroproline | 135837-63-7 |
| (3S)-2-azaspiro[4.4]nonane-3-carboxylic acid | 394734-78-2 |

TABLE 5-continued

| Abbreviation/Expression Definition | CAS Number for Fmoc-/Boc-protected amino acid, chemical group or building block used for peptide synthesis |
|---|---|
| Availability of unnatural amino acids and chemical groups of this Invention | |
| (2R)-2-amino-3-(trifluoromethylsulfanyl)propanoic acid | 1994331-25-7 |
| Arg(13C6, 15N4) | 1217461-89-6 |

Solid-phase resins were purchased from Novabiochem, Bachem, Iris Biotech, Pcas Biomatrix, GL Biochem (Shanghai) Ltd, CEM, or Protein Technologies. The resin loading was 0.3-1.0 mmol/g. Peptides were synthesized on 2-Chlorotrityl resin, on Wang resin, or on Rink amide-type resins depending on the desired C-terminus. Cleavage of the fluorenylmethoxycarbonyl (Fmoc) protecting group was achieved using 20% piperidine in dimethylformamide at room temperature. Each Fmoc cleavage step was carried out twice. Amino acids were coupled on an automated synthesizer (Symphony X) using 8 equivalents of the Fmoc-amino acid, with 8 equivalents of DIC (Diispropylcarbodiimide) (0.5 M in DMF) and 8 equivalents of Oxyma (Ethyl cyanohydroxyiminoacetate) (0.5M in DMF). Amino acid couplings were conducted at room temperature and under a nitrogen atmosphere, when the Symphony X was used. When expensive or self-prepared fmoc-amino acids were used, the coupling was performed manually using 3 equivalents of the Fmoc-amino acid, with 3 equivalents of DIC (0.5 M in DMF) and 3 equivalents of Oxyma (0.5M in DMF). Each amino acid coupling step was carried out twice (double coupling). Alternatively, peptides were prepared by SPPS manually using 3 equivalents of the Fmoc-amino acid, 2.85 equivalents of HBTU ((2-(1H-benzotriazol-1-yl)-1,1,3,3-tetramethyluronium hexafluorophosphate, Hexafluorophosphate Benzotriazole Tetramethyl Uronium) (0.5 M in DMF) and 6 equivalents of DIPEA (0.5M in DMF). The coupling reaction was monitored using the ninhydrin test.

Peptides were completely deprotected using trifluoroacetic acid (TFA)/thioanisole (TA)/1,2-ethanedithiol (EDT) (90:7:3) or with 92.5% TFA/2.5% EDT/2.5% TIS (triisopropylsilane)/2.5% $H_2O$. For peptides containing methionine, the peptides were treated with a solution of 1.6% EDT and 1.2% trimethylsilylbromide in TFA for 2 h at room temperature to reduce oxidized methionine.

Disulfide Cyclization:

Disulfide bridges were formed by shaking peptides in 0.1 M ammonium bicarbonate buffer (pH 7.83) at a concentration of 0.5 mg/mL overnight. The solution was then lyophilized. Alternatively, disulfide bridges were formed by shaking peptides in mixture of acetonitrile/water (often 3:7) adjusted to pH 9.0 with solid ammonium bicarbonate buffer at a concentration of 1-3 mg/mL overnight. Alternatively, disulfide bridges were prepared by oxidation with iodine ($I_2$) (0.1 M in MeOH) at a concentration of 1-1.3 mg/mL in acetonitrile/water (1:1) at 20° C. for 2 min, followed by treatment with sodium thiosulfate (0.1 M in water) followed by lyophilization.

Optional Acetylation:

N-terminal acetylation was performed using 10 equivalents acetic anhydride in DMF (2 mL) and 2.5 equivalents DIPEA by shaking the suspension at RT for 1 h on an orbital shaker. The solvent was removed and the resin was washed with DMF (5×) and DCM (5×). The procedure was then repeated again. Alternatively, N-terminal acetylation was performed using 10 mL of a capping solution consisting of acetic anhydride/N-methyl morpholine (NMM)/DMF (10:5:85) by shaking the suspension at RT for 30 min on an orbital shaker.

Peptide Cleavage:

A cleavage cocktail containing TFA/EDT/Thioanisol (90:3:7) was prepared. The cleavage cocktail (2 mL) was added to the peptide containing resin and the suspension was shaken on an orbital shaker for 2.5 hours. Cold ether (−20° C.) was added to precipitate the peptide. The resulting solution was centrifuged under nitrogen (Sigma 2-16KL), and the resulting solid obtained after decantation was washed with cold ether 3 more times, by centrifugation and decantation. The resulting solid was purified by preparative HPLC.

Alternatively, a cleavage cocktail containing TFA/EDT/TIS/$H_2O$ (92.5:2.5:2.5:2.5) was prepared. The cleavage cocktail (6 mL (0.3 mmol scale)) was added to the peptide containing resin and the suspension was shaken on an orbital shaker for 2.5 hours. Cold tert-butyl methyl ether (−20° C.) was added to precipitate the peptide. The resulting solution was centrifuged at 3000 rpm for 3 min, and the resulting solid obtained after decantation was washed with cold tert-butyl methyl ether 3 more times (20 mL×3), by centrifugation and decantation. The resulting crude peptide was dried over vacuum for 2 hours and then purified by preparative HPLC.

Preparative HPLC:

An Agilent 1260 Prep reversed-phase HPLC or a Knauer AZURA Prep reversed-phase HPLC was used for purification. The column is chosen based on the results of a column screen. The peptide is dissolved in 10-30% ACN/water (typically the starting point of the gradient). Water and acetonitrile both contain 0.1% TFA. Flow rate 20 mL/min, 10-30% ACN/water to 85-90% ACN/water was typically used. Fractions were analysed by HPLC (Agilent 1260 Infinity) using using a Chromolith Speedrod column, 5-95% ACN/water gradient over 8 min) and by one or more of the following LC-MS methods: Method 1, Method 2, Method 3, Method 4, Method 5, Method 6.

Alternatively, a Gilson GX-281 Prep reversed-phase HPLC was used for purification. The column was chosen based on the results of a column screen. The peptide is dissolved in 10-30% ACN/water (typically the starting point of the gradient). The water contained 0.075% TFA. Normally a Luna column (25×200 mm, C18 10 μm, 110 Å) or a Gemini column (30×150 mm, C18 5 μm, 110 Å) was used. Conditions for prep HPLC: flow rate 20 mL/min, 10-30% ACN/water to 85-90% ACN/water, wavelength 214/254 nm, oven temperature 30° C. Fractions were analysed by HPLC (Agilent 1260 Infinity) using Method W1 or Method 7. The peptides were thereafter analyzed by one or more of the following methods: Method 1, Method 2, Method 3, Method 4, Method 5, Method 6.

Disulfide mimetics, wherein the —S—S— disulfide bond is replaced by a $—CH_2—S—$, $—S—CH_2—$, $—CH_2—CH_2—$, $—S—(CH_2)_2—$, $—(CH_2)_2—S—$ or a $—CH_2—S—$ $CH_2$— can be prepared according to procedure described in the following references in combination with methods described herein: (1) Hong-Kui Cui, Ye Guo, Yao He, Feng-Liang Wang, Hao-Nan Chang, Yu-Jia Wang, Fang-Ming Wu, Chang-Lin Tian, Lei Liu *Angew. Chem. Int. Ed.* 2013, 52, 9558-9562; (2) Ye Guo, De-Meng Sun, Feng-Liang Wang, Yao He, Lei Liu, Chang-Lin Tian *Angew. Chem. Int. Ed.* 2015, 54, 14276-14281; (3) Yang Xu, Tao Wang, Chao-Jian Guan, Yi-Ming Li, Lei Liu, Jing Shi, Donald Bierer *Tetrahedron Letters* 2017, 58, 1677-1680; (4) Tao Wang, Yi-Fu Kong, Yang Xu, Jian Fan, Hua-Jian Xu, Donald Bierer, Jun Wang, Jing Shi, Yi-Ming Li *Tetrahedron Letters* 2017, 58, 3970-3973; (5) Tao Wang, Jian Fan, Xiao-Xu Chen, Rui Zhao, Yang Xu, Donald Bierer, Lei Liu, Yi-Ming Li, Jing Shi, Ge-Min Fang *Org. Lett.* 2018, 20, 6074-6078; (6) Jan-Patrick Fischer, Ria Schönauer, Sylvia Els-Heindl, Donald Bierer, Johannes Koebberling, Bernd Riedl, Annette G. Beck-Sickinger *J Pep Sci.* 2019; e3147; (7) Dong-Liang Huang, Jing-Si Bai, Meng Wu, Xia Wang, Bernd Riedl, Elisabeth Pook, Carsten Alt, Marion Erny, Yi-Ming Li, Donald Bierer, Jing Shi, Ge-Min Fang *Chem. Commun.,* 2019, 55, 2821-2824; (8) Shuai-Shuai Sun, Junyou Chen, Rui Zhao, Donald Bierer, Jun Wang, Ge-Min Fang, Yi-Ming Li *Tetrahedron Letters* 2019, 60, 1197-1201; (9) C. M. B. K. Kourra and N. Cramer *Chem. Sci.,* 2016, 7, 7007-7012.

All peptides of this invention unless otherwise noted are TFA Salts.

General Method for the Automated SPPS of Masp Peptides (Method A) The synthesis of ((N-Me)G)-IC+SRSLP-(Oic)-I-(Pen)+IPD-$NH_2$ (Example 165) is representative.

The peptide was synthesized using standard Fmoc chemistry.

Automated SPPS was performed on a Symphony X peptide synthesizer (Protein Technologies). Chem-Matrix Rink Amide resin was typically used (loading 0.5 mmol/gram) on a 0.1 mmol scale. The resin was placed into the reaction vessel and placed onto the instrument. The following solutions were prepared and used during the synthesis:

1) Fmoc Amino Acids: 0.2 M (8 eq)
2) Activator 1: 0.5 M DIC in DMF (7.5 eq)
3) Activator 2: 0.5 M Oxyma in DMF (7.5 eq)
4) Fmoc Deprotection: 20% Piperidine in DMF
5) Acetic anhydride (10 equivalents) in 2 mL DMF Double couplings were typically performed for each amino acid. For expensive unnatural Fmoc or Boc amino acids, in-house synthesized Fmoc amino acids, or N-methylated amino acid, the sequence was interrupted and this amino acid was coupled manually (double coupling, but typically with less reagent (3-5 equiv). After this coupling was completed, the synthesis was typically continued on the synthesizer. If an N-methyl amino acid was added to the sequence, typically the next amino acid was coupled manually as well. All steps were performed at room temperature under nitrogen. Fmoc-Pen and Fmoc-Oic were typically coupled using automated SPPS. Fmoc(N-Me)G was typically coupled manually. Ahx was always coupled manually.

The resin was swelled and washed with DMF (3×3 mL, 10 min). If the resin contained Fmoc, then the Fmoc was removed with 20% piperidine solution (2×3 mL, 10 min). The resin was washed with DMF (6×3 mL, 30 sec).

Coupling:

Fmoc-Asp(t-Bu) (4.0 mL) was added. Activator 1 solution (DIC, 1.5 mL) and Activator 2 solution (Oxyma, 1.5 mL) were added and the coupling was allowed to proceed with nitrogen bubbling for 2 hours. The solution was drained and washed with DMF (1×3 mL, 30 sec). The coupling step was repeated.

Fmoc-Asp(Ot-Bu) (4.0 mL) was added. Activator 1 solution (DIC, 1.5 mL) and Activator 2 solution (Oxyma, 1.5 mL) were added and the coupling was allowed to proceed with nitrogen bubbling for 2 hours. The solution was drained and washed with DMF (6×3 mL, 30 sec).

Fmoc Cleavage:

The Fmoc protecting group was removed by adding 20% piperidine solution (2×3 mL, 10 min). The resin was washed with DMF (6×3 mL, 30 sec).

Coupling:

Fmoc-Pro (4.0 mL) was added. Activator 1 solution (DIC, 1.5 mL) and Activator 2 solution (Oxyma, 1.5 mL) were added and the coupling was allowed to proceed with nitrogen bubbling for 2 hours. The solution was drained and washed with DMF (1×3 mL, 30 sec). The coupling step was repeated. Fmoc-Pro (4.0 mL) was added. Activator 1 solution (DIC, 1.5 mL) and Activator 2 solution (Oxyma, 1.5 mL) were added and the coupling was allowed to proceed with nitrogen bubbling for 2 hours. The solution was drained and washed with DMF (6×3 mL, 30 sec).

Fmoc Cleavage:

The Fmoc protecting group was removed by adding 20% piperidine solution (2×3 mL, 10 min). The resin was washed with DMF (6×3 mL, 30 sec).

Coupling:

Fmoc-Ile (4.0 mL) was added. Activator 1 solution (DIC, 1.5 mL) and Activator 2 solution (Oxyma, 1.5 mL) were added and the coupling was allowed to proceed with nitrogen bubbling for 2 hours. The solution was drained and washed with DMF (1×3 mL, 30 sec). The coupling step was repeated. Fmoc-Ile (4.0 mL) was added. Activator 1 solution (DIC, 1.5 mL) and Activator 2 solution (Oxyma, 1.5 mL) were added and the coupling was allowed to proceed with nitrogen bubbling for 2 hours. The solution was drained and washed with DMF (6×3 mL, 30 sec).

Fmoc Cleavage:

The Fmoc protecting group was removed by adding 20% piperidine solution (2×3 mL, 10 min). The resin was washed with DMF (6×3 mL, 30 sec).

Coupling:

Fmoc-Pen(Trt) (4.0 mL) was added. Activator 1 solution (DIC, 1.5 mL) and Activator 2 solution (Oxyma, 1.5 mL) were added and the coupling was allowed to proceed with nitrogen bubbling for 2 hours. The solution was drained and washed with DMF (1×3 mL, 30 sec). The coupling step was repeated. Fmoc-Pen(Trt) (4.0 mL) was added. Activator 1 solution (DIC, 1.5 mL) and Activator 2 solution (Oxyma, 1.5 mL) were added and the coupling was allowed to proceed with nitrogen bubbling for 2 hours. The solution was drained and washed with DMF (6×3 mL, 30 sec).

Fmoc Cleavage:

The Fmoc protecting group was removed by adding 20% piperidine solution (2×3 mL, 10 min). The resin was washed with DMF (6×3 mL, 30 sec).

Coupling:

Fmoc-Ile (4.0 mL) was added. Activator 1 solution (DIC, 1.5 mL) and Activator 2 solution (Oxyma, 1.5 mL) were added and the coupling was allowed to proceed with nitrogen bubbling for 2 hours. The solution was drained and washed with DMF (1×3 mL, 30 sec). The coupling step was repeated. Fmoc-Ile (4.0 mL) was added. Activator 1 solution (DIC, 1.5 mL) and Activator 2 solution (Oxyma, 1.5 mL) were added and the coupling was allowed to proceed with nitrogen bubbling for 2 hours. The solution was drained and washed with DMF (6×3 mL, 30 sec).

Fmoc Cleavage:

The Fmoc protecting group was removed by adding 20% piperidine solution (2×3 mL, 10 min). The resin was washed with DMF (6×3 mL, 30 sec).

Coupling:

Fmoc-Oic (4.0 mL) was added. Activator 1 solution (DIC, 1.5 mL) and Activator 2 solution (Oxyma, 1.5 mL) were added and the coupling was allowed to proceed with nitrogen bubbling for 2 hours. The solution was drained and washed with DMF (1×3 mL, 30 sec). The coupling step was repeated. Fmoc-Oic (4.0 mL) was added. Activator 1 solution (DIC, 1.5 mL) and Activator 2 solution (Oxyma, 1.5 mL) were added and the coupling was allowed to proceed with nitrogen bubbling for 2 hours. The solution was drained and washed with DMF (6×3 mL, 30 sec).

Fmoc Cleavage:

The Fmoc protecting group was removed by adding 20% piperidine solution (2×3 mL, 10 min). The resin was washed with DMF (6×3 mL, 30 sec).

Coupling:

Fmoc-Pro (4.0 mL) was added. Activator 1 solution (DIC, 1.5 mL) and Activator 2 solution (Oxyma, 1.5 mL) were added and the coupling was allowed to proceed with nitrogen bubbling for 2 hours. The solution was drained and washed with DMF (1×3 mL, 30 sec). The coupling step was repeated. Fmoc-Pro (4.0 mL) was added. Activator 1 solution (DIC, 1.5 mL) and Activator 2 solution (Oxyma, 1.5 mL) were added and the coupling was allowed to proceed with nitrogen bubbling for 2 hours. The solution was drained and washed with DMF (6×3 mL, 30 sec).

Fmoc Cleavage:

The Fmoc protecting group was removed by adding 20% piperidine solution (2×3 mL, 10 min). The resin was washed with DMF (6×3 mL, 30 sec).

Coupling:

Fmoc-Leu (4.0 mL) was added. Activator 1 solution (DIC, 1.5 mL) and Activator 2 solution (Oxyma, 1.5 mL) were added and the coupling was allowed to proceed with nitrogen bubbling for 2 hours. The solution was drained and washed with DMF (1×3 mL, 30 sec). The coupling step was repeated. Fmoc-Leu (4.0 mL) was added. Activator 1 solution (DIC, 1.5 mL) and Activator 2 solution (Oxyma, 1.5 mL) were added and the coupling was allowed to proceed with nitrogen bubbling for 2 hours. The solution was drained and washed with DMF (6×3 mL, 30 sec).

Fmoc Cleavage:

The Fmoc protecting group was removed by adding 20% piperidine solution (2×3 mL, 10 min). The resin was washed with DMF (6×3 mL, 30 sec).

Coupling:

Fmoc-Ser(t-Bu) (4.0 mL) was added. Activator 1 solution (DIC, 1.5 mL) and Activator 2 solution (Oxyma, 1.5 mL) were added and the coupling was allowed to proceed with nitrogen bubbling for 2 hours. The solution was drained and washed with DMF (1×3 mL, 30 sec). The coupling step was repeated. Fmoc-Ser(t-Bu) (4.0 mL) was added. Activator 1 solution (DIC, 1.5 mL) and Activator 2 solution (Oxyma, 1.5 mL) were added and the coupling was allowed to proceed with nitrogen bubbling for 2 hours. The solution was drained and washed with DMF (6×3 mL, 30 sec).

Fmoc Cleavage:

The Fmoc protecting group was removed by adding 20% piperidine solution (2×3 mL, 10 min). The resin was washed with DMF (6×3 mL, 30 sec).

Coupling:

Fmoc-Arg(Pbf) (4.0 mL) was added. Activator 1 solution (DIC, 1.5 mL) and Activator 2 solution (Oxyma, 1.5 mL) were added and the coupling was allowed to proceed with nitrogen bubbling for 2 hours. The solution was drained and washed with DMF (1×3 mL, 30 sec). The coupling step was repeated. Fmoc-Arg(Pbf) (4.0 mL) was added. Activator 1 solution (DIC, 1.5 mL) and Activator 2 solution (Oxyma, 1.5 mL) were added and the coupling was allowed to proceed with nitrogen bubbling for 2 hours. The solution was drained and washed with DMF (6×3 mL, 30 sec).

Fmoc Cleavage:

The Fmoc protecting group was removed by adding 20% piperidine solution (2×3 mL, 10 min). The resin was washed with DMF (6×3 mL, 30 sec).

Coupling:

Fmoc-Ser(t-Bu) (4.0 mL) was added. Activator 1 solution (DIC, 1.5 mL) and Activator 2 solution (Oxyma, 1.5 mL) were added and the coupling was allowed to proceed with nitrogen bubbling for 2 hours. The solution was drained and washed with DMF (1×3 mL, 30 sec). The coupling step was repeated. Fmoc-Ser(t-Bu) (4.0 mL) was added. Activator 1 solution (DIC, 1.5 mL) and Activator 2 solution (Oxyma, 1.5 mL) were added and the coupling was allowed to proceed with nitrogen bubbling for 2 hours. The solution was drained and washed with DMF (6×3 mL, 30 sec).

Fmoc Cleavage:

The Fmoc protecting group was removed by adding 20% piperidine solution (2×3 mL, 10 min). The resin was washed with DMF (6×3 mL, 30 sec).

Coupling:

Fmoc-Cys(Trt) (4.0 mL) was added. Activator 1 solution (DIC, 1.5 mL) and Activator 2 solution (Oxyma, 1.5 mL) were added and the coupling was allowed to proceed with nitrogen bubbling for 2 hours. The solution was drained and washed with DMF (1×3 mL, 30 sec). The coupling step was repeated. Fmoc-Cys(Trt) (4.0 mL) was added. Activator 1 solution (DIC, 1.5 mL) and Activator 2 solution (Oxyma, 1.5 mL) were added and the coupling was allowed to proceed with nitrogen bubbling for 2 hours. The solution was drained and washed with DMF (6×3 mL, 30 sec).

Fmoc Cleavage:

The Fmoc protecting group was removed by adding 20% piperidine solution (2×3 mL, 10 min). The resin was washed with DMF (6×3 mL, 30 sec).

Coupling:

Fmoc-Ile (4.0 mL) was added. Activator 1 solution (DIC, 1.5 mL) and Activator 2 solution (Oxyma, 1.5 mL) were added and the coupling was allowed to proceed with nitrogen bubbling for 2 hours. The solution was drained and washed with DMF (1×3 mL, 30 sec). The coupling step was repeated. Fmoc-Ile (4.0 mL) was added. Activator 1 solution (DIC, 1.5 mL) and Activator 2 solution (Oxyma, 1.5 mL) were added and the coupling was allowed to proceed with nitrogen bubbling for 2 hours. The solution was drained and washed with DMF (6×3 mL, 30 sec).

Fmoc Cleavage:

The Fmoc protecting group was removed by adding 20% piperidine solution (2×3 mL, 10 min). The resin was washed with DMF (6×3 mL, 30 sec).

Manual Coupling During Automated SPPS:

Fmoc-(N-Me)G (0.2 M in DMF, 5 equiv) was added to the resin. Activator 1 solution (DIC, 1.5 mL) and Activator 2 solution (Oxyma, 1.5 mL) were added and the coupling was allowed to proceed with shaking (Thermomixer, rt) for 2 hours. The solution was filtered and washed with DMF (1×3 mL, 30 sec). The coupling step was repeated. Fmoc-(N-Me)G (0.2 M in DMF, 5 equiv) was added. Activator 1 solution (DIC, 1.5 mL) and Activator 2 solution (Oxyma, 1.5 mL) were added and the coupling was allowed to proceed with shaking (Thermomixer, rt) for 2 hours. The solution was filtered and washed with DMF (6×3 mL, 30 sec).

Fmoc Cleavage:

The Fmoc protecting group was removed by adding 20% piperidine solution (2×3 mL, 10 min). The resin was washed with DMF (6×3 mL, 30 sec).

If additional amino acids were present in the sequence, they were coupled using using the steps above.

Test Cleavage:

When manual couplings were performed, a test cleavage was typically performed to monitor the reactions.

The test cleavage cocktail was TFA/EDT/Thioanisol (90:3:7); 1.5 h shaking on a Thermomixer at room temperature and 750 rpm. Analysis was performed by LC-MS using one of the methods above.

Full Cleavage:

The resin containing the peptide was placed into a syringe and 3.0 mL of cleavage buffer TFA/EDT/Thioanisol (90:3:7) was added to the resin. The mixture was shaken at room temperature for 2.5 hours. The solution was collected by filtration and the peptide was precipitate by adding cold diethyl ether (−20° C.).

The solution was centrifuged (3000 rpm) in a Falcon tube (60 mL) under a nitrogen atmosphere. The ether was decanted and the solid residue was washed repeatedly with cold diethyl ether (5×10 mL). The solid residue was then dried.

Disulfide Cyclization:

The crude peptide was dissolved in 0.1M ammonium bicarbonate (pH 7.8-8.2) at a concentration of 1 mg/2 mL. The solution was allowed to shake on an orbital shaker overnight in a round-bottomed flask open to the air. The solution was then lyophilized to obtain a white powder.

Column Screening for HPLC Purification:

The peptide was dissolved in 5% $CH_3CN$ and 95% water. Column screening was performed on each peptide to determine which preparative HPLC method to use for purification. The following analytical columns were screened.

Two Methods are Available for Column Screening:

1) 5-60% ACN_8 Min_1 mL/min_25° C.
2) 30-85% ACN_8 Min_1 mL/min_25° C.

Available Columns (50 mm×ID 4.6 mm) (Available Also as as Prep Columns):

1) Aeris C18 (Phenomenex)
2) X-Bridge C18 (Waters)
3) Kinetex C18 (Coreshell Material) (Phenomenex)
4) YMC Triart C18 (elution with 100% water possible)
5) Kinetix Biphenyl (Phenomenex)
6) X-Select C18 (positive charge)
7) Jupiter Proteo C18 (Phenomenex)
8) Luna C18 (Phenomenex)

For Peptides of this Invention, One of the Following 5 Preparative Columns was Used:

1) Column: Phenomenex, *Aeris* Peptide 5μ XB—C18, AXIA Packed, 21.2×250 mm+Cartridge 5μ
2) Column: Phenomenex, Kinetex C18 5μ 21.5×250 mm+Cartridge 5μ
3) Column: Phenomenex, Kinetex 5μ Biphenyl 100A, AXIA Packed, 21.2×250 mm+Cartridge 5μ
4) Column: YMC Actus Triart Prep. C18 12 nm, S-10 μm 250×20 mm+Cartridge 3 μm (10×4 mm)
5) Column: Waters, Xbridge Prep.C18 5μ OBD 19×250 mm+Cartridge 10μ

Once the Column was Chosen, One of the Following Methods was Used:

1) method: Gradient 5-60% ACN in water (0.10% TFA)
2) method: Gradient 30-85% ACN in water (0.10% TFA)
3) focused gradient based on results of the column screening.

Flow rate 20 mL/min

The combined fractions were analyzed by HPLC (5-95 in 8 in, Chromolith SpeedROD & YMC C18 5-95 in 18 min) and using one of the LC-MS methods described above.

For Example 165, the crude peptide was dissolved in $CH_3CN$/water (1:1) and purified on a Phenomenex Kinetex column C18 5μ, 21.5×250 mm+5μ Cartridge, Flow rate: 20 mL/min, Method: 5-60% ACN in water (each containing 0.10% TFA) over 48 min. The combined fractions were lyophilized to provide 39 mg of example 165 (95% pure).

TABLE 6

Note of materials used and conditions

| # | Materials | Coupling reagents | Coupling time |
|---|---|---|---|
| 1 | Rink Amide ChemMatrix resin, loading 0.5 mmol/g (0.1 mmol) | — | |
| 2 | Fmoc-Asp(t-Bu)-OH (8.0 eq) | DIC (7.5 eq) Oxyma (7.5 eq) | 120 min |
| 3 | Fmoc-Pro-OH (8.0 eq) | DIC (7.5 eq) Oxyma (7.5 eq) | 120 min |
| 4 | Fmoc-Ile-OH (8.0 eq) | DIC (7.5 eq) Oxyma (7.5 eq) | 120 min |
| 5 | Fmoc-Pen(Trt)-OH (8.0 eq) | DIC (7.5 eq) Oxyma (7.5 eq) | 120 min |
| 6 | Fmoc-Ile-OH (8.0 eq) | DIC (7.5 eq) Oxyma (7.5 eq) | 120 min |
| 7 | Fmoc-Oic-OH (8.0 eq) | DIC (7.5 eq) Oxyma (7.5 eq) | 120 min |
| 8 | Fmoc-Pro-OH (8.0 eq) | DIC (7.5 eq) Oxyma (7.5 eq) | 120 min |
| 9 | Fmoc-Leu-OH (8.0 eq) | DIC (7.5 eq) Oxyma (7.5 eq) | 120 min |
| 10 | Fmoc-Ser(tBu)-OH (8.0 eq) | DIC (7.5 eq) Oxyma (7.5 eq) | 120 min |
| 11 | Fmoc-Arg(Pbf)-OH (8.0 eq) | DIC (7.5 eq) Oxyma (7.5 eq) | 120 min |
| 12 | Fmoc-Ser(t-Bu)-OH (8.0 eq) | DIC (7.5 eq) Oxyma (7.5 eq) | 120 min |
| 13 | Fmoc-Cys(Trt)-OH (8.0 eq) | DIC (7.5 eq) Oxyma (7.5 eq) | 120 min |
| 14 | Fmoc-Ile-OH (3.0 eq) | DIC (7.5 eq) Oxyma (7.5 eq) | 120 min |
| 15 | Fmoc-(N—Me)G-OH (8 eq) | DIC (7.5 eq) Oxyma (7.5 eq) | 120 min |

General Method for the Automated SPPS of Masp Peptides (Method B)

The synthesis of ((N-Me)G)-IC+SRSLP-(Oic)-I-(Pen)+I-((5-Azaspiro[2.4]heptane-1-carboxylic acid)OH (Example 164) is representative.

The peptide was synthesized using standard Fmoc chemistry.

When possible, preloaded Wang resin with the first amino acid (e.g. preloaded with Fmoc-Asp(t-Bu)-OH, Fmoc-Pro-OH, etc were used, with a typical loading of 0.55-0.7 mmol/g. When the first amino acid was not available, it was added manually.

When the first amino acid was not available as a preloaded resin, it was added manually and chlorotrityl resin was used for the synthesis.

Loading of First Amino Acid on 2-Chlorotrityl Resin:

2-Chlortritylresin (500 mg, 0.775 mmol) was allowed to swell with 10 mL of DCM in a 50 mL Falcon tube for 15 min 5-[(9H-fluoren-9-ylmethoxy)carbonyl]-5-azaspiro[2.4]heptane-1-carboxylic acid (281 mg, 0.775 mmol) was dissolved in DCM with DIEA (6 equiv, 0.81 mL) added, and the solution was added to the resin. The solution was purged with argon and shaken overnight at room temperature. The mixture was filtered and washed with DMF (3×5 mL) and DCM (3×5 mL). Methanol was added (5 mL), the mixture was shaken for 30 minutes, and then filtered. The resin was washed with DMF (3×5 mL) and DCM (3×5 mL). Methanol was again added (5 mL), the mixture was shaken for 30 minutes, and then filtered. The resin was washed with DMF (3×5 mL) and DCM (3×5 mL). The loading was determined to be 0.42 mmol/g based on the determination of loading procedure described below.

The resin was then used for automated SPPS on the Symphony X synthesizer from Protein Technologies on 0.1 mmol scale.

Determination of Resin Loading:

To determine the loading of a resin the FMOC protecting group is cleaved from a defined amount of resin and afterwards the concentration of the resulting fluorenyl compound in the supernatant cleavage solution is measured via photometry at 301 nm. This correlates directly with the amount of amino acid loaded on the resin.

1) 1-3 mg of resin are weighed into a 2 mL Eppendorf tube or similar (note the exact amount)
2) 1000 μL of a solution of 20% piperidine in DMF are added.
3) The mixture is agitated for 30 minutes to cleave the FMOC group.
4) 100 μL of the supernatant solution are then transferred into a quartz glass cuvette and diluted with 900 μL of 20% piperidine/DMF
5) A blank sample of 1000 μl piperidine/DMF is prepared in a second cuvette.
6) After determining the blank value from the reference sample, the extinction of the test sample at λ=301 nm is then measured in a UV-Vis photometer (Thermo Scientific Evolution 201).
7) For greater accuracy, multiple test samples (typically two) can be fashioned; the arithmetic mean of the measured extinctions is then used for calculation.

Calculation of Resin Loading:

The resin loading $L_{301}$ in mmol/g is calculated by the following formula:

$$L_{301} = \frac{E(301\text{ nm}) \cdot V}{\varepsilon(301\text{ nm}) \cdot D \cdot m} \cdot VF \cdot 1000$$

E=extinction

ε=extinction coefficient at 301 nm wavelength (7800 L/mol*cm)

m=amount of resin used (g)

V=volume of sample (L)

D=layer thickness of the cuvette (cm)

VF=dilution factor (=10)

Fmoc Cleavage:

The Fmoc protecting group was removed by adding 20% piperidine solution (2×3 mL, 10 min). The resin was washed with DMF (6×3 mL, 30 sec).

The coupling of the subsequent Fmoc amino acids proceeded as described in Method A.

The following solutions were prepared and used during the synthesis:

1) Fmoc Amino Acids: 0.2 M (8 eq)
2) Activator 1: 0.5 M DIC in DMF (7.5 eq)
3) Activator 2: 0.5 M Oxyma in DMF (7.5 eq)
4) Fmoc Deprotection: 20% Piperidine in DMF
5) Acetic anhydride (10 equivalents) in 2 mL DMF Double couplings were typically performed for each amino acid. For expensive unnatural Fmoc or Boc amino acids, in-house synthesized Fmoc amino acids, or N-methylated amino acid, the sequence was interrupted and this amino acid was coupled manually (double coupling, but typically with less reagent (3-5 equiv). After this coupling was completed, the synthesis was typically continued on the synthesizer. If an N-methyl amino acid was added to the sequence, typically the next amino acid was coupled manually as well. All steps were performed at room temperature under nitrogen. Fmoc-Pen and Fmoc-Oic were typically coupled using automated SPPS. Fmoc(N-Me)G was typically coupled manually. Ahx was always coupled manually.

Fmoc Cleavage:

The resin was swelled and washed with DMF (3×3 mL, 10 min). If the resin contained Fmoc, then the Fmoc was removed with 20% piperidine solution (2×3 mL, 10 min). The resin was washed with DMF (6×3 mL, 30 sec).

Coupling:

Fmoc-Ile (4.0 mL) was added. Activator 1 solution (DIC, 1.5 mL) and Activator 2 solution (Oxyma, 1.5 mL) were added and the coupling was allowed to proceed with nitrogen bubbling for 2 hours. The solution was drained and washed with DMF (1×3 mL, 30 sec). The coupling step was repeated. Fmoc-Ile (4.0 mL) was added. Activator 1 solution (DIC, 1.5 mL) and Activator 2 solution (Oxyma, 1.5 mL) were added and the coupling was allowed to proceed with nitrogen bubbling for 2 hours. The solution was drained and washed with DMF (6×3 mL, 30 sec).

Fmoc Cleavage:

The Fmoc protecting group was removed by adding 20% piperidine solution (2×3 mL, 10 min). The resin was washed with DMF (6×3 mL, 30 sec).

Coupling:

Fmoc-Pen(Trt) (4.0 mL) was added. Activator 1 solution (DIC, 1.5 mL) and Activator 2 solution (Oxyma, 1.5 mL) were added and the coupling was allowed to proceed with nitrogen bubbling for 2 hours. The solution was drained and washed with DMF (1×3 mL, 30 sec). The coupling step was repeated. Fmoc-Pen(Trt) (4.0 mL) was added. Activator 1 solution (DIC, 1.5 mL) and Activator 2 solution (Oxyma, 1.5 mL) were added and the coupling was allowed to proceed with nitrogen bubbling for 2 hours. The solution was drained and washed with DMF (6×3 mL, 30 sec).

Fmoc Cleavage:

The Fmoc protecting group was removed by adding 20% piperidine solution (2×3 mL, 10 min). The resin was washed with DMF (6×3 mL, 30 sec).

Coupling:

Fmoc-Ile (4.0 mL) was added. Activator 1 solution (DIC, 1.5 mL) and Activator 2 solution (Oxyma, 1.5 mL) were added and the coupling was allowed to proceed with nitrogen bubbling for 2 hours. The solution was drained and washed with DMF (1×3 mL, 30 sec). The coupling step was repeated. Fmoc-Ile (4.0 mL) was added. Activator 1 solution (DIC, 1.5 mL) and Activator 2 solution (Oxyma, 1.5 mL) were added and the coupling was allowed to proceed with nitrogen bubbling for 2 hours. The solution was drained and washed with DMF (6×3 mL, 30 sec).

Fmoc Cleavage:

The Fmoc protecting group was removed by adding 20% piperidine solution (2×3 mL, 10 min). The resin was washed with DMF (6×3 mL, 30 sec).

Coupling:

Fmoc-Oic (4.0 mL) was added. Activator 1 solution (DIC, 1.5 mL) and Activator 2 solution (Oxyma, 1.5 mL) were added and the coupling was allowed to proceed with nitrogen bubbling for 2 hours. The solution was drained and washed with DMF (1×3 mL, 30 sec). The coupling step was repeated. Fmoc-Oic (4.0 mL) was added. Activator 1 solution (DIC, 1.5 mL) and Activator 2 solution (Oxyma, 1.5 mL) were added and the coupling was allowed to proceed with nitrogen bubbling for 2 hours. The solution was drained and washed with DMF (6×3 mL, 30 sec).

Fmoc Cleavage:

The Fmoc protecting group was removed by adding 20% piperidine solution (2×3 mL, 10 min). The resin was washed with DMF (6×3 mL, 30 sec).

Coupling:

Fmoc-Pro (4.0 mL) was added. Activator 1 solution (DIC, 1.5 mL) and Activator 2 solution (Oxyma, 1.5 mL) were added and the coupling was allowed to proceed with nitrogen bubbling for 2 hours. The solution was drained and washed with DMF (1×3 mL, 30 sec). The coupling step was repeated. Fmoc-Pro (4.0 mL) was added. Activator 1 solution (DIC, 1.5 mL) and Activator 2 solution (Oxyma, 1.5 mL) were added and the coupling was allowed to proceed with nitrogen bubbling for 2 hours. The solution was drained and washed with DMF (6×3 mL, 30 sec).

Fmoc Cleavage:

The Fmoc protecting group was removed by adding 20% piperidine solution (2×3 mL, 10 min). The resin was washed with DMF (6×3 mL, 30 sec).

Coupling:

Fmoc-Leu (4.0 mL) was added. Activator 1 solution (DIC, 1.5 mL) and Activator 2 solution (Oxyma, 1.5 mL) were added and the coupling was allowed to proceed with nitrogen bubbling for 2 hours. The solution was drained and washed with DMF (1×3 mL, 30 sec). The coupling step was repeated. Fmoc-Leu (4.0 mL) was added. Activator 1 solution (DIC, 1.5 mL) and Activator 2 solution (Oxyma, 1.5 mL) were added and the coupling was allowed to proceed with nitrogen bubbling for 2 hours. The solution was drained and washed with DMF (6×3 mL, 30 sec).

Fmoc Cleavage:

The Fmoc protecting group was removed by adding 20% piperidine solution (2×3 mL, 10 min). The resin was washed with DMF (6×3 mL, 30 sec).

Coupling:

Fmoc-Ser(t-Bu) (4.0 mL) was added. Activator 1 solution (DIC, 1.5 mL) and Activator 2 solution (Oxyma, 1.5 mL) were added and the coupling was allowed to proceed with nitrogen bubbling for 2 hours. The solution was drained and washed with DMF (1×3 mL, 30 sec). The coupling step was repeated. Fmoc-Ser(t-Bu) (4.0 mL) was added. Activator 1 solution (DIC, 1.5 mL) and Activator 2 solution (Oxyma, 1.5 mL) were added and the coupling was allowed to proceed with nitrogen bubbling for 2 hours. The solution was drained and washed with DMF (6×3 mL, 30 sec).

Fmoc Cleavage:

The Fmoc protecting group was removed by adding 20% piperidine solution (2×3 mL, 10 min). The resin was washed with DMF (6×3 mL, 30 sec).

Coupling:

Fmoc-Arg(Pbf) (4.0 mL) was added. Activator 1 solution (DIC, 1.5 mL) and Activator 2 solution (Oxyma, 1.5 mL) were added and the coupling was allowed to proceed with nitrogen bubbling for 2 hours. The solution was drained and washed with DMF (1×3 mL, 30 sec). The coupling step was repeated. Fmoc-Arg(Pbf) (4.0 mL) was added. Activator 1 solution (DIC, 1.5 mL) and Activator 2 solution (Oxyma, 1.5 mL) were added and the coupling was allowed to proceed with nitrogen bubbling for 2 hours. The solution was drained and washed with DMF (6×3 mL, 30 sec).

Fmoc Cleavage:

The Fmoc protecting group was removed by adding 20% piperidine solution (2×3 mL, 10 min). The resin was washed with DMF (6×3 mL, 30 sec).

Coupling:

Fmoc-Ser(t-Bu) (4.0 mL) was added. Activator 1 solution (DIC, 1.5 mL) and Activator 2 solution (Oxyma, 1.5 mL) were added and the coupling was allowed to proceed with nitrogen bubbling for 2 hours. The solution was drained and washed with DMF (1×3 mL, 30 sec). The coupling step was repeated. Fmoc-Ser(t-Bu) (4.0 mL) was added. Activator 1 solution (DIC, 1.5 mL) and Activator 2 solution (Oxyma, 1.5 mL) were added and the coupling was allowed to proceed with nitrogen bubbling for 2 hours. The solution was drained and washed with DMF (6×3 mL, 30 sec).

Fmoc Cleavage:

The Fmoc protecting group was removed by adding 20% piperidine solution (2×3 mL, 10 min). The resin was washed with DMF (6×3 mL, 30 sec).

Coupling:

Fmoc-Cys(Trt) (4.0 mL) was added. Activator 1 solution (DIC, 1.5 mL) and Activator 2 solution (Oxyma, 1.5 mL) were added and the coupling was allowed to proceed with nitrogen bubbling for 2 hours. The solution was drained and washed with DMF (1×3 mL, 30 sec). The coupling step was repeated. Fmoc-Cys(Trt) (4.0 mL) was added. Activator 1 solution (DIC, 1.5 mL) and Activator 2 solution (Oxyma, 1.5 mL) were added and the coupling was allowed to proceed with nitrogen bubbling for 2 hours. The solution was drained and washed with DMF (6×3 mL, 30 sec).

Fmoc Cleavage:

The Fmoc protecting group was removed by adding 20% piperidine solution (2×3 mL, 10 min). The resin was washed with DMF (6×3 mL, 30 sec).

Coupling:

Fmoc-Ile (4.0 mL) was added. Activator 1 solution (DIC, 1.5 mL) and Activator 2 solution (Oxyma, 1.5 mL) were added and the coupling was allowed to proceed with nitrogen bubbling for 2 hours. The solution was drained and washed with DMF (1×3 mL, 30 sec). The coupling step was repeated. Fmoc-Ile (4.0 mL) was added. Activator 1 solution (DIC, 1.5 mL) and Activator 2 solution (Oxyma, 1.5 mL) were added and the coupling was allowed to proceed with nitrogen bubbling for 2 hours. The solution was drained and washed with DMF (6×3 mL, 30 sec).

Fmoc Cleavage:

The Fmoc protecting group was removed by adding 20% piperidine solution (2×3 mL, 10 min). The resin was washed with DMF (6×3 mL, 30 sec).

Manual Coupling During Automated SPPS:

Fmoc-(N-Me)G (0.2 M in DMF, 5 equiv) was added to the resin. Activator 1 solution (DIC, 1.5 mL) and Activator 2 solution (Oxyma, 1.5 mL) were added and the coupling was allowed to proceed with shaking (Thermomixer, rt) for 2 hours. The solution was filtered and washed with DMF (1×3 mL, 30 sec). The coupling step was repeated. Fmoc-(N-Me)G (0.2 M in DMF, 5 equiv) was added. Activator 1 solution (DIC, 1.5 mL) and Activator 2 solution (Oxyma, 1.5 mL) were added and the coupling was allowed to proceed with shaking (Thermomixer, rt) for 2 hours. The solution was filtered and washed with DMF (6×3 mL, 30 sec).

Fmoc Cleavage:

The Fmoc protecting group was removed by adding 20% piperidine solution (2×3 mL, 10 min). The resin was washed with DMF (6×3 mL, 30 sec).

If additional amino acids were present in the sequence, they were coupled using using the steps above.

Test Cleavage:

When manual couplings were performed, a test cleavage was typically performed to monitor the reactions.

The test cleavage cocktail was TFA/EDT/Thioanisol (90:3:7); 1.5 h shaking on a Thermomixer at room temperature and 750 rpm. Analysis was performed by LC-MS using one of the methods above.

Full Cleavage:

The resin containing the peptide was placed into a syringe and 3.0 mL of cleavage buffer TFA/EDT/Thioanisol (90:3:7) was added to the resin. The mixture was shaken at room temperature for 2.5 hours. The solution was collected by filtration and the peptide was precipitate by adding cold diethyl ether (−20° C.). The solution was centrifuged (3000 rpm) in a Falcon tube (60 mL) under a nitrogen atmosphere. The ether was decanted and the solid residue was washed repeatedly with cold diethyl ether (5×10 mL). The solid residue was then dried.

Disulfide Cyclization:

The crude peptide was dissolved in 0.1M ammonium bicarbonate (pH 7.8-8.2) at a concentration of 1 mg/2 mL. The solution was allowed to shake on an orbital shaker overnight in a round-bottomed flask open to the air. The solution was then lyophilized to obtain a white powder.

Column Screening for HPLC Purification:

The peptide was dissolved in 5% $CH_3CN$ and 95% water. Column screening was performed on each peptide to determine which preparative HPLC method to use for purification. The following analytical columns were screened.

Two Methods are Available for Column Screening:

1) 5-60% ACN_8 Min_1 mL/min_25° C.
2) 30-85% ACN_8 Min_1 mL/min_25° C.

Available Columns (50 mm×ID 4.6 mm) (Available Also as as Prep Columns):

1) Aeris C18 (Phenomenex)
2) X-Bridge C18 (Waters)
3) Kinetex C18 (Coreshell Material) (Phenomenex)
4) YMC Triart C18 (elution with 100% water possible)
5) Kinetix Biphenyl (Phenomenex)
6) X-Select C18 (positive charge)
7) Jupiter Proteo C18 (Phenomenex)
8) Luna C18 (Phenomenex)

For Peptides of this Invention, One of the Following 5 Preparative Columns was Used:

1) Column: Phenomenex, Aeris Peptide 5µ XB—C18, AXIA Packed, 21.2×250 mm+Cartridge 5µ
2) Column: Phenomenex, Kinetex C18 5µ 21.5×250 mm+Cartridge 5µ
3) Column: Phenomenex, Kinetex 5µ Biphenyl 100A, AXIA Packed, 21.2×250 mm+Cartridge 5µ
4) Column: YMC Actus Triart Prep. C18 12 nm, S-10 µm 250×20 mm+Cartridge 3 µm (10×4 mm)
5) Column: Waters, Xbridge Prep.C18 5µ OBD 19×250 mm+Cartridge 10µ

Once the column was chosen, one of the following methods was used:

1) method: Gradient 5-60% ACN in water (0.10% TFA)
2) method: Gradient 30-85% ACN in water (0.10% TFA)
3) focused gradient based on results of the column screening.

Flow rate 20 mL/min

The combined fractions were analyzed by HPLC (5-95 in 8 in, Chromolith SpeedROD & YMC C18 5-95 in 18 min) and using one of the LC-MS methods described about For example 164, the crude peptide was dissolved in $CH_3CN$/water (1:1) and purified on a Phenomenex Kinetex column C18 5µ, 21.5×250 mm+5µ Cartridge, Flow rate: 20 mL/min, Method: 5-60% ACN in water (each containing 0.10% TFA) over 48 min. The combined fractions were lyophilized to provide 29.8 mg of example 164 (98.3% pure).

TABLE 7

Note of materials used and conditions

| # | Materials | Coupling reagents | Coupling time |
|---|---|---|---|
| 1 | Rink Amide ChemMatrix resin, loading 0.5 mmol/g (0.1 mmol) | — | |
| 2 | 5-Fmoc-5-Azaspiro[2.4]heptane-1-carboxylic acid | DIPEA (6 eq) | ovenight |
| 3 | Fmoc-Ile-OH (8.0 eq) | DIC (7.5 eq) Oxyma (7.5 eq) | 120 min |
| 4 | Fmoc-Pen(Trt)-OH (8.0 eq) | DIC (7.5 eq) Oxyma (7.5 eq) | 120 min |
| 5 | Fmoc-Ile-OH (8.0 eq) | DIC (7.5 eq) Oxyma (7.5 eq) | 120 min |
| 6 | Fmoc-Oic-OH (8.0 eq) | DIC (7.5 eq) Oxyma (7.5 eq) | 120 min |
| 7 | Fmoc-Pro-OH (8.0 eq) | DIC (7.5 eq) Oxyma (7.5 eq) | 120 min |
| 8 | Fmoc-Leu-OH (8.0 eq) | DIC (7.5 eq) Oxyma (7.5 eq) | 120 min |
| 9 | Fmoc-Ser(tBu)-OH (8.0 eq) | DIC (7.5 eq) Oxyma (7.5 eq) | 120 min |
| 10 | Fmoc-Arg(Pbf)-OH (8.0 eq) | DIC (7.5 eq) Oxyma (7.5 eq) | 120 min |
| 11 | Fmoc-Ser(t-Bu)-OH (8.0 eq) | DIC (7.5 eq) Oxyma (7.5 eq) | 120 min |
| 12 | Fmoc-Cys(Trt)-OH (8.0 eq) | DIC (7.5 eq) Oxyma (7.5 eq) | 120 min |
| 13 | Fmoc-Ile-OH (3.0 eq) | DIC (7.5 eq) Oxyma (7.5 eq) | 120 min |
| 14 | Fmoc-(N—Me)G-OH (8 eq) | DIC (7.5 eq) Oxyma (7.5 eq) | 120 min |

General Method for the Manual SPPS of Masp Peptides (Method C)

The synthesis of sequence AIC+SRSLP-(Oic)-I-(Pen)+IPN-OH (Example 418) is representative.

Peptide Synthesis:

The peptide was synthesized using standard Fmoc chemistry.

1) Resin preparation: To the chlorotrityl resin (CTC Resin) (0.3 mmol, 0.3 g, 1.0 mmol/g) was added Fmoc-Asn(Trt)-OH (0.3 mmol, 0.18 g, 1.0 eq) and DIEA (0.21 mL, 1.2 mmol, 4.0 eq) in DCM (6.0 mL). The mixture was agitated with $N_2$ for 2 h at 20° C., then added MeOH (0.3 mL) and agitated with $N_2$ for another 30 min. The resin was washed with DMF (6.0 mL×3). Then 20% piperidine in DMF (6.0 mL) was added and the mixture was agitated with $N_2$ for 20 min at 20° C. Then the mixture was filtered to get the resin. The resin was washed with DMF (6.0 mL×3) and filtered to get the resin.
2) Coupling: Fmoc-Pro-OH (0.30 g, 0.9 mmol, 3.0 eq) HBTU (0.32 g, 0.85 mmol, 2.85 eq) and DIEA (1.80 mmol, 0.32 mL, 6.00 eq) in DMF (3.0 mL) was added to the resin and agitated with $N_2$ for 30 min at 20° C. The resin was then washed with DMF (6.0 mL×5).
3) Deprotection: 20% piperidine in DMF (6.0 mL) was added to the resin and the mixture was agitated with $N_2$ for 20 min at 20° C.
4) Repeat Step 2 to 3 for all other amino acids:

TABLE 8

Note of materials used and conditions

| # | Materials | Coupling reagents | Coupling time |
|---|---|---|---|
| 1 | Fmoc-Asn(Trt)-OH (1.0 eq) | DIEA(4.0 eq) | 2.0 h |
| 2 | Fmoc-Pro-OH (3.0 eq) | HBTU(2.85 eq) DIEA(6.0 eq) | 30 min |
| 3 | Fmoc-Ile-OH (3.0 eq) | HBTU(2.85 eq) DIEA(6.0 eq) | 30 min |
| 4 | Fmoc-Pen(Trt)-OH (3.0 eq) | HBTU(2.85 eq) DIEA(6.0 eq) | 30 min |
| 5 | Fmoc-Ile-OH (3.0 eq) | HBTU(2.85 eq) DIEA(6.0 eq) | 30 min |
| 6 | Fmoc-Oic-OH (3.0 eq) | HBTU(2.85 eq) DIEA(6.0 eq) | 30 min |
| 7 | Fmoc-Pro-OH (3.0 eq) | HBTU(2.85 eq) DIEA(6.0 eq) | 30 min |
| 8 | Fmoc-Leu-OH (3.0 eq) | HBTU(2.85 eq) DIEA(6.0 eq) | 30 min |
| 9 | Fmoc-Ser(tBu)-OH (3.0 eq) | HBTU(2.85 eq) DIEA(6.0 eq) | 30 min |
| 10 | Fmoc-Arg(Pbf)-OH (3.0 eq) | HBTU(2.85 eq) DIEA(6.0 eq) | 30 min |
| 11 | Fmoc-Ser(tBu)-OH (3.0 eq) | HBTU(2.85 eq) DIEA(6.0 eq) | 30 min |
| 12 | Fmoc-Cys(Trt)-OH (3.0 eq) | HBTU(2.85 eq) DIEA(6.0 eq) | 30 min |
| 13 | Fmoc-Ile-OH (3.0 eq) | HBTU(2.85 eq) DIEA(6.0 eq) | 30 min |
| 14 | Fmoc-Ala-OH (3.0 eq) | HBTU(2.85 eq) DIEA(6.0 eq) | 30 min |

20% piperidine in DMF was used for Fmoc deprotection for 30 min. The coupling reaction was monitored by ninhydrin (all amino acids except Pro) and chloranil test (Pro), and the resin was washed with DMF (5.0 mL) for 5 times.

Peptide Cleavage and Purification:

1) The resin was washed with MeOH (6.0 mL×5) and dried under vacuum to get 0.62 g peptide resin. Then 6.0 mL of cleavage buffer (92.5% TFA/2.5% EDT/2.5% TIS/2.5% $H_2O$) was added to the flask containing the side chain protected peptide resin at 20° C. and the mixture was stirred for 2.5 h.
2) The peptide was precipitated with cold tert-butyl methyl ether (50 mL) and centrifuged (3 min at 3000 rpm) to get the solid crude. Wash the crude peptide precipitation with tert-butyl methyl ether for two more times (20.0 mL×3). Dry the crude peptide over vacuum for 2.0 h to give 0.4 g crude peptide.
3) The crude (0.4 g) was dissolved in $CH_3CN$ (150 mL) and water (150 mL). Iodine ($I_2$) (0.1 M in MeOH, 1.5 mL) was added at 20° C. until yellow color persists. Then the mixture was stirred at 20° C. for 2 min. Then sodium thiosulfate (0.1 M in water, 0.05 mL) was added dropwise until yellow color disappears. The mixture was lyophilized to give the crude powder (0.41 g)
4) The crude peptide was purified by prep-HPLC (conditions: A: 0.075% TFA in water B: $CH_3CN$) and lyophilized to get the desired peptide (Example 418) (108.1 mg, 23.0% yield, 97.3% pure by Method W1; 97.4% pure by Method 7) as a white solid and TFA salt. Purification conditions: Peptide was dissolved in TFA/$H_2O$ (7:3); flow rate 20 mL/min; gradient 12-42% over 60 min; Retention time=42 min; purification over a Luna 25×200 mm, C18 10 um, 110 Å column, then again over a Gemini 150×30 mm, C18 5 um, 110 Å column to reach the desired purity.

If C-terminal amides were prepared according to this method, the synthesis began with Rink Amide MBHA resin (loading typically around 0.4-0.6 mmol/g, with the above steps being the same.

General Method for the Manual SPPS of Masp Peptides (Method D)

If C-terminal amides were prepared, the synthesis began with Rink Amide MBHA resin (loading typically around 0.4-0.6 mmol/g. The synthesis of sequence PIC+SRS-((tBu)A)-PPI-(Pen)+IPD-NH2 (Example 9) is representative.

If C-terminal acids were prepared, the synthesis began with 2-chlorotrityl resin, with the first Fmoc amino acid being added according to the method described in Method C.

Peptide Synthesis:

The peptide was synthesized using standard Fmoc chemistry.

1) Resin preparation: The Rink Amide MBHA resin (0.66 g, 0.30 mmol, loading=0.45 mmol/g) in DMF (10.0 mL) was agitated with $N_2$ for 0.5 h at 20° C. Then 20% piperidine in DMF (10 mL) was added and the mixture was agitated with $N_2$ for 20 min at 20° C. Then the mixture was filtered to get the resin. The resin was washed with DMF (10×5 mL) and filtered to get the resin.
2) Coupling: Fmoc-Asn(Trt)-OH (0.9 mmol, 0.37 g, 3.0 eq) HBTU (0.32 g, 0.85 mmol, 2.95 eq) and DIEA (1.80 mmol, 0.32 mL, 6.00 eq) in DMF (3.0 mL) was added to the resin and agitated with $N_2$ for 30 min at 20° C. The resin was then washed with DMF (10.0 mL×3).

3) Deprotection: 20% piperidine in DMF (10.0 mL) was added to the resin and the mixture was agitated with $N_2$ for 20 min at 20° C.
4) Repeat Step 2 to 3 for all other amino acids.

TABLE 9

| Note of materials used and conditions | | | |
|---|---|---|---|
| # | Materials | Coupling reagents | Coupling time |
| 1 | Fmoc-Asn(Trt)-OH (1.0 eq) | HBTU(2.85 eq) DIEA(6.0 eq) | 30 min |
| 2 | Fmoc-Pro-OH (3.0 eq) | HBTU(2.85 eq) DIEA(6.0 eq) | 30 min |
| 3 | Fmoc-Ile-OH (3.0 eq) | HBTU(2.85 eq) DIEA(6.0 eq) | 30 min |
| 4 | Fmoc-Pen(Trt)-OH (3.0 eq) | HBTU(2.85 eq) DIEA(6.0 eq) | 30 min |
| 5 | Fmoc-Ile-OH (3.0 eq) | HBTU(2.85 eq) DIEA(6.0 eq) | 30 min |
| 6 | Fmoc-Pro-OH (3.0 eq) | HBTU(2.85 eq) DIEA(6.0 eq) | 30 min |
| 7 | Fmoc-Pro-OH (3.0 eq) | HBTU(2.85 eq) DIEA(6.0 eq) | 30 min |
| 8 | Fmoc-Ala(t-Bu)-OH (3.0 eq) | HBTU(2.85 eq) DIEA(6.0 eq) | 30 min |
| 9 | Fmoc-Ser(tBu)-OH (3.0 eq) | HBTU(2.85 eq) DIEA(6.0 eq) | 30 min |
| 10 | Fmoc-Arg(Pbf)-OH (3.0 eq) | HBTU(2.85 eq) DIEA(6.0 eq) | 30 min |
| 11 | Fmoc-Ser(tBu)-OH (3.0 eq) | HBTU(2.85 eq) DIEA(6.0 eq) | 30 min |
| 12 | Fmoc-Cys(Trt)-OH (3.0 eq) | HBTU(2.85 eq) DIEA(6.0 eq) | 30 min |
| 13 | Fmoc-Ile-OH (3.0 eq) | HBTU(2.85 eq) DIEA(6.0 eq) | 30 min |
| 14 | Fmoc-Pro-OH (3.0 eq) | HBTU(2.85 eq) DIEA(6.0 eq) | 30 min |

20% piperidine in DMF was used for Fmoc deprotection for 30 min. The coupling reaction was monitored by ninhydrin (all amino acids except Pro) and chloranil test (Pro), and the resin was washed with DMF (5.0 mL) for 5 times.

Peptide Cleavage and Purification:

1) The resin was washed with MeOH (6.0 mL×5) and dried under vacuum to get 0.66 g peptide resin. Then 6.0 mL of cleavage buffer (90% TFA/5% EDT/2.5% TIS/2.5% $H_2O$) was added to the flask containing the side chain protected peptide resin at 20° C. and the mixture was stirred for 2.5 h.
2) The peptide was precipitated with cold tert-butyl methyl ether (50 mL) and centrifuged (3 min at 3000 rpm) to get the solid crude. The crude peptide precipitation was washed with tert-butyl methyl ether for three more times (20.0 mL×3). Dry the crude peptide over vacuum for 2.0 h to give 0.4 g crude peptide.
3) The crude (0.4 g) was dissolved in $CH_3CN$ (15 mL) and water (15 mL) to achieve a 0.1 mM concentration. $NH_4HCO_3$ solution (1M) was added to adjust the pH to about 8-9. The solution was allowed to shake at room temperature for about 8 hours. The reaction was monitored by HPLC. After the reaction was complete, the reaction was quenched with acetic acid to adjust the pH to about 6. The reaction mixture was then lyophilized and the resulting solid was purified by reversed-phase HPLC.
4) Purified the crude peptide by prep-HPLC (conditions: A: 0.075% TFA in water B: $CH_3CN$) and lyophilized to get the desired peptide (Example 9) (202.40 mg, 41.4.0% yield, 93.7% pure by Method W1; 95.1% pure by Method 7) as a white solid and TFA salt. Purification conditions: Peptide was dissolved in TFA/$H_2O$ (7:3); flow rate 20 mL/min; gradient 12-42% over 60 min; Retention time=42 min; purification over a Luna 25×200 mm, C18 10 μm, 110 Å column.

Alternative General Method for the Manual SPPS of Masp Peptides (Method E)

The synthesis of sequence ((2S)-2[(Amino)-2-(tetrahydro-2H-pyran-4-yl)]acetic acid)-IC+SRSLP-(Oic)IC+I-OH (Example 184) is representative.

Peptide Synthesis:

The peptide was synthesized using standard Fmoc chemistry.

The dark ball in the chemical structures below indicates the solid polymer support used for solid-phase peptide synthesis (SPPS), e.g. 2-chlorotrityl resin, Rink amide resin, etc.

Example 1A (2S)—({[(9H-fluoren-9-yl)methoxy]carbonyl}amino)(oxan-4-yl)acetic acid (Single Stereoisomer)

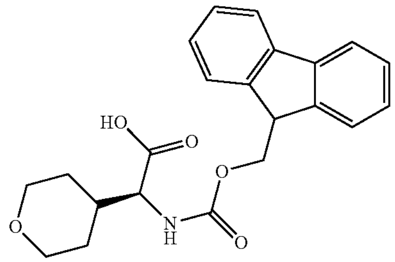 [SMILES: O=C(N[C@H](C(=O)O)C1CCOCC1)OCC1c2ccccc2-c2ccccc21]

To (2S)-amino(oxan-4-yl)acetic acid (950 mg, 5.97 mmol) in acetone/water (15 mL/10 mL) was added sodium bicarbonate (5.01 g, 59.7 mmol) and 1-({[(9H-fluoren-9-yl)methoxy]carbonyl}oxy)pyrrolidine-2,5-dione (2.11 g, 6.27 mmol). The mixture was stirred over the weekend at room temperature. The suspension was treated with water and extracted with MBTE two more times. The aqueous phase was acidified with 1 M aqueous hydrochloric acid and was extracted with dicloromethane three more times. The organic phase was washed with saturated aqueous sodium chloride solution, dried over magnesium sulfate, filtered and evaporated. The residue was purified via silica gel chromatography (Isolera; 50 g SNAP Ultra; gradient: cychohexane 50%/ethyl acetate 50%+1% acetic acid to cychohexane 20%/ethyl acetate 80%+1% acetic acid). The appropriate fractions were combined and evaporated. The residue was taken up in toluene and evaporated two more times, then the residue was dried under vacuum to give 1.08 g (100% purity, 47% yield) of the target compound.

LC-MS (Method 9): $R_t$=0.90 min; MS (ESIpos): m/z=382 $[M+H]^+$ $^1$H-NMR (400 MHz, DMSO-d6) δ[ppm]: −0.150 (0.43), −0.008 (4.33), 0.008 (3.74), 0.146 (0.43), 1.280 (1.03), 1.300 (2.26), 1.309 (2.36), 1.331 (2.75), 1.341 (2.92), 1.371 (2.77), 1.401 (2.54), 1.411 (2.32), 1.430 (1.49), 1.464 (6.34), 1.496 (3.49), 1.932 (1.76), 1.942 (2.14), 1.951 (1.93), 1.960 (2.08), 2.327 (0.64), 2.366 (0.64), 2.670 (0.64), 2.710 (0.65), 3.169 (2.11), 3.212 (2.67), 3.237 (6.32), 3.265 (6.90), 3.704 (0.49), 3.715 (0.49), 3.840 (4.66), 3.854 (5.62), 3.867 (4.30), 3.879 (6.28), 3.899 (5.14), 3.918 (3.56), 4.201 (2.11), 4.218 (5.83), 4.237 (9.07), 4.263 (8.42), 4.274 (9.80), 4.293 (5.14), 4.318 (1.05), 7.309 (6.35), 7.328 (15.12), 7.347 (9.86), 7.400 (9.65), 7.419 (15.88), 7.437 (7.02), 7.652 (5.77), 7.674 (5.52), 7.735 (8.21), 7.740 (8.28), 7.754 (7.63), 7.883 (16.00), 7.902 (14.80), 12.609 (0.56).

Example 2A

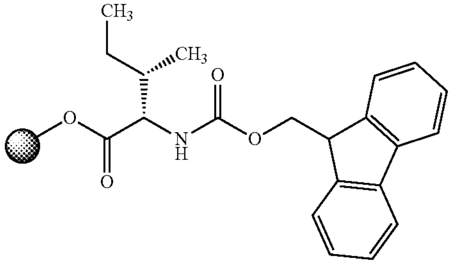 [SMILES: CC[C@H](C)[C@H](NC(=O)OCC1c2ccccc2-c2ccccc21)C(=O)OC]

The reaction was carried out under an argon atmosphere. To N-{[(9H-fluoren-9-yl)methoxy]carbonyl}-L-isoleucine (9.40 g, 26.6 mmol) in 53 mL dichloromethane was added N,N-diisopropylethylamine (19 mL, 110 mmol) and 2-chlorotritylchlorid resin (10.0 g, 13.3 mmol). The reaction mixture was shaken overnight at room temperature. The precipitate was collected by filtration and washed with DMF three times. The collected resin was shaken with dichloromethane/methanol 1:1 for 30 min. The resin was collected by filtration and washed three times in rotation with methanol and dichloromethane. The collected resin was dried under vacuum for the next step.

Example 3A

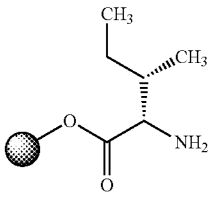

Example 2A (15.2 g, 6.82 mmol) in 200 mL DMF/piperidine 4:1 was shaken for 15 min at room temperature. The resin was collected by filtration and washed with DMF for three times. Both steps were repeated and washed three times in rotation with 200 mL methanol and 200 mL dichloromethane. The collected resin was dried under vacuum for the next step.

Example 4A

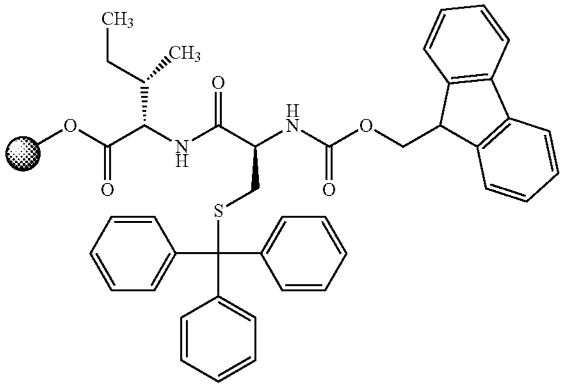 [SMILES: CC[C@H](C)[C@H](NC(=O)[C@H](CSC(c1ccccc1)(c1ccccc1)c1ccccc1)NC(=O)OCC1c2ccccc2-c2ccccc21)C(=O)OC]

Example 3A (11.4 g, 5.13 mmol) was swelled in 100 mL DMF at room temperature for 5 min. A mixture of N-{[(9H-fluoren-9-yl)methoxy]carbonyl}-S-(triphenylmethyl)-L-cysteine (6.01 g, 10.3 mmol) in 50 mL DMF, DIC (1.5 mL, 10 mmol) and Oxyma (1.42 g, 10.0 mmol) was added and the reaction mixture was shaken for 2 h at room temperature. The resin was collected by filtration and washed with DMF for three times. The coupling step was repeated overnight. The resin was collected by filtration and washed with 150 mL DMF for three times and then three more times in rotation with 150 mL methanol and 150 mL dichloromethane. The collected resin was dried under vacuum for the next step.

Example 5A

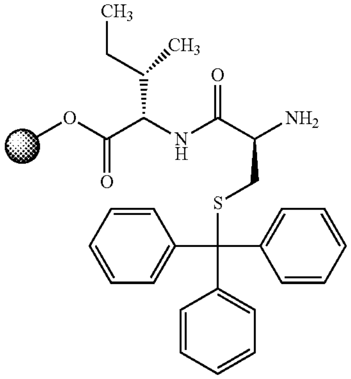 [SMILES: CC[C@H](C)[C@H](NC(=O)[C@@H](N)CSC(c1ccccc1)(c1ccccc1)c1ccccc1)C(=O)OC]

Example 4A (18.9 g, 8.51 mmol) in 200 mL DMF/piperidine 4:1 was shaken for 15 min at room temperature. The resin was collected by filtration and washed with DMF for three times. Both steps were repeated and the collected resin was washed three times in rotation with 200 mL methanol and 200 mL dichloromethane. The collected resin was dried under vacuum for the next step.

Example 6A

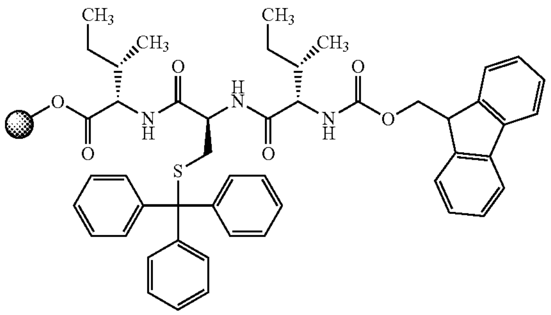 [SMILES: CC[C@H](C)[C@H](NC(=O)OCC1c2ccccc2-c2ccccc21)C(=O)N[C@@H](CSC(c1ccccc1)(c1ccccc1)c1ccccc1)C(=O)N[C@H](C(=O)OC)[C@@H](C)CC]

Example 5A (16.3 g, 7.32 mmol) was swelled in 150 mL DMF for 5 min at room temperature. A mixture of N-{[(9H-fluoren-9-yl)methoxy]carbonyl}-L-isoleucine (5.18 g, 14.6 mmol) in 50 mL DMF, DIC (2.2 mL, 14 mmol) and Oxyma (2.03 g, 14.3 mmol) was added and the reaction mixture was shaken for 2 h at room temperature. The resin was collected by filtration and washed with DMF for three times. The coupling step was repeated overnight. The resin was collected by filtration and washed with 200 mL DMF for three times and then three more times in rotation with 200 mL methanol and 200 mL dichloromethane. The collected resin was dried under vacuum for the next step.

Example 7A

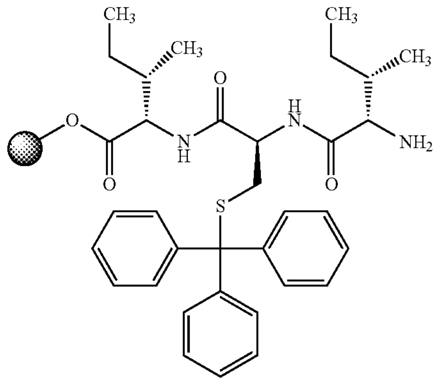 [SMILES: CC[C@H](C)[C@H](N)C(=O)N[C@@H](CSC(c1ccccc1)(c1ccccc1)c1ccccc1)C(=O)N[C@H](C(=O)OC)[C@@H](C)CC]

Example 6A (20.0 g, 8.98 mmol) in 200 mL DMF/piperidine 4:1 was shaken for 15 min at room temperature. The resin was collected by filtration and washed with DMF for three times. Both steps were repeated and the collected resin was washed three times in rotation with 200 mL methanol and 200 mL dichloromethane. The collected resin was dried under vacuum for the next step.

Example 8A

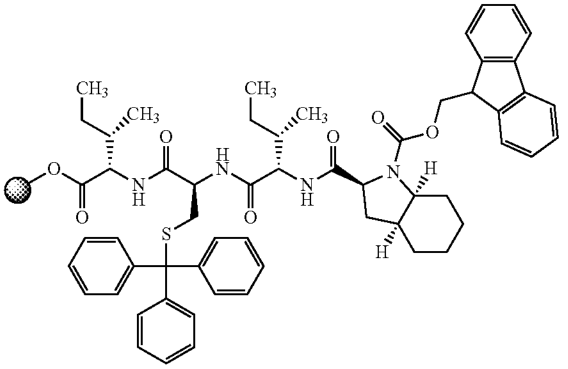 [SMILES: CC[C@H](C)[C@H](NC(=O)[C@@H]1C[C@@H]2CCCC[C@@H]2N1C(=O)OCC1c2ccccc2-c2ccccc21)C(=O)N[C@@H](CSC(c1ccccc1)(c1ccccc1)c1ccccc1)C(=O)N[C@H](C(=O)OC)[C@@H](C)CC]

Example 7A (17.8 g, 7.99 mmol) was swelled in 150 mL DMF for 5 min at room temperature. A mixture of (2S,3aS,7aS)-1-{[(9H-fluoren-9-yl)methoxy]carbonyl}octahydro-1H-indole-2-carboxylic acid (6.25 g, 16.0 mmol) in 50 mL DMF, DIC (2.4 mL, 16 mmol) and Oxyma (2.21 g, 15.6 mmol) was added and the reaction mixture was shaken for 2 h at room temperature. The resin was collected by filtration and washed with DMF for three times. The coupling step was repeated over the weekend. The resin was collected by filtration and washed with 200 mL DMF for three times and then three more times in rotation with 200 mL methanol and 200 mL dichloromethane. The collected resin was dried under vacuum for the next step.

Example 9A

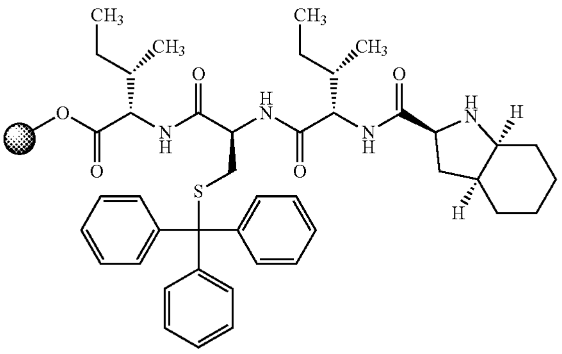 [SMILES: CC[C@H](C)[C@H](NC(=O)[C@@H]1C[C@@H]2CCCC[C@@H]2N1)C(=O)N[C@@H](CSC(c1ccccc1)(c1ccccc1)c1ccccc1)C(=O)N[C@H](C(=O)OC)[C@@H](C)CC]

Example 8A (21.5 g, 9.68 mmol) in 200 mL DMF/piperidine 4:1 was shaken for 30 min at room temperature. The resin was collected by filtration, washed with DMF for three times and then three more times in rotation with 200 mL methanol and 200 mL dichloromethane. To the collected resin was added 200 mL DMF/piperidine 4:1 and shaken for 1 h at room temperature. The resin was collected by filtration, washed with DMF for three times and then three more times in rotation with 200 mL methanol and 200 mL dichloromethane. The collected resin was dried under vacuum for the next step.

Example 10A

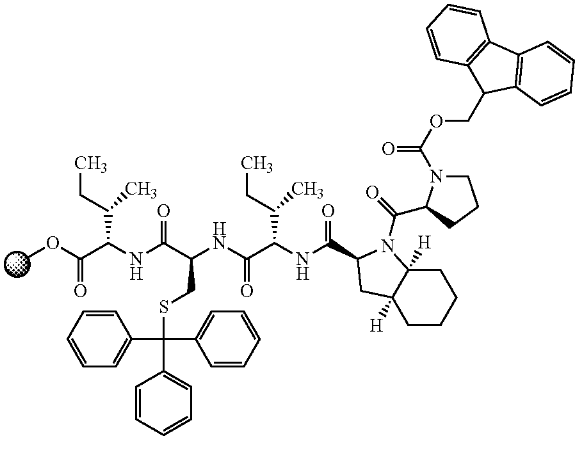 [SMILES: CC[C@H](C)[C@H](NC(=O)[C@@H]1C[C@@H]2CCCC[C@@H]2N1C(=O)[C@@H]1CCCN1C(=O)OCC1c2ccccc2-c2ccccc21)C(=O)N[C@@H](CSC(c1ccccc1)(c1ccccc1)c1ccccc1)C(=O)N[C@H](C(=O)OC)[C@@H](C)CC]

Example 9A (18.1 g, 8.13 mmol) was swelled in 150 mL DMF for 5 min at room temperature. A mixture of 1-{[(9H-fluoren-9-yl)methoxy]carbonyl}-L-proline (11.0 g, 32.5 mmol) in 50 mL DMF, DIC (4.9 mL, 32 mmol) and Oxyma (4.51 g, 31.7 mmol) was added and the reaction mixture was shaken over the weekend at room temperature. The resin was collected by filtration, washed with 200 mL DMF for three times and then three more times in rotation with 200 mL methanol and 200 mL dichloromethane. The collected resin was dried under vacuum for the next step.

Example 11A

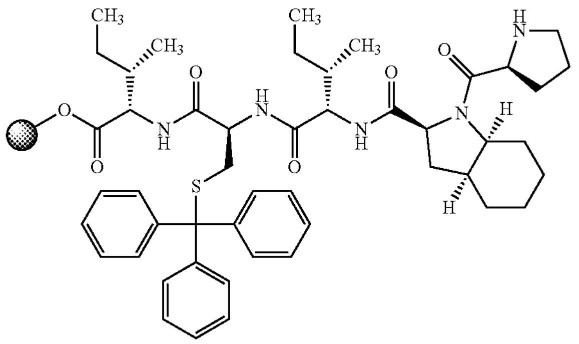 [SMILES: CC[C@H](C)[C@H](NC(=O)[C@@H]1C[C@@H]2CCCC[C@@H]2N1C(=O)[C@@H]1CCCN1)C(=O)N[C@@H](CSC(c1ccccc1)(c1ccccc1)c1ccccc1)C(=O)N[C@H](C(=O)OC)[C@@H](C)CC]

Example 10A (20.4 g, 9.16 mmol) in 150 mL DMF/piperidine 4:1 was shaken for 30 min at room temperature. The resin was collected by filtration and washed with DMF for three times. Both steps were repeated and the collected resin was washed three times in rotation with 200 mL methanol and 200 mL dichloromethane. The collected resin was dried under vacuum for the next step.

Example 12A

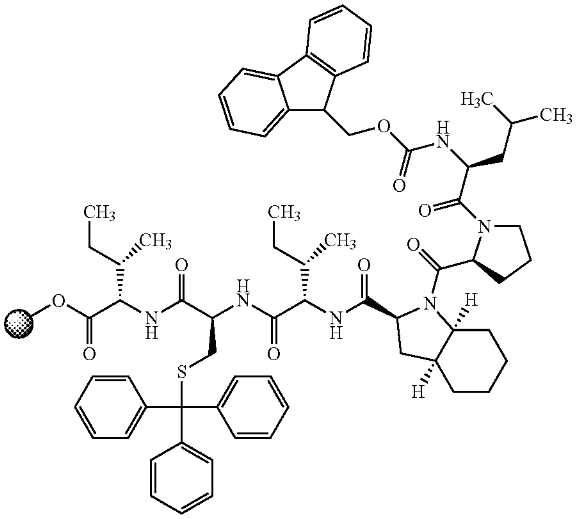 [SMILES: CC[C@H](C)[C@H](NC(=O)[C@@H]1C[C@@H]2CCCC[C@@H]2N1C(=O)[C@@H]1CCCN1C(=O)[C@H](CC(C)C)NC(=O)OCC1c2ccccc2-c2ccccc21)C(=O)N[C@@H](CSC(c1ccccc1)(c1ccccc1)c1ccccc1)C(=O)N[C@H](C(=O)OC)[C@@H](C)CC]

Example 11A (18.2 g, 8.18 mmol) was swelled in 150 mL DMF for 5 min at room temperature. A mixture of N-{[(9H-fluoren-9-yl)methoxy]carbonyl}-L-leucine (11.6 g, 32.7 mmol) in 50 mL DMF, DIC (4.9 mL, 32 mmol) and Oxyma (4.53 g, 31.9 mmol) was added and the reaction mixture was shaken overnight at room temperature. The resin was collected by filtration, washed with 200 mL DMF for three times and then three more times in rotation with 200 mL methanol and 200 mL dichloromethane. The collected resin was dried under vacuum for the next step.

Example 13A

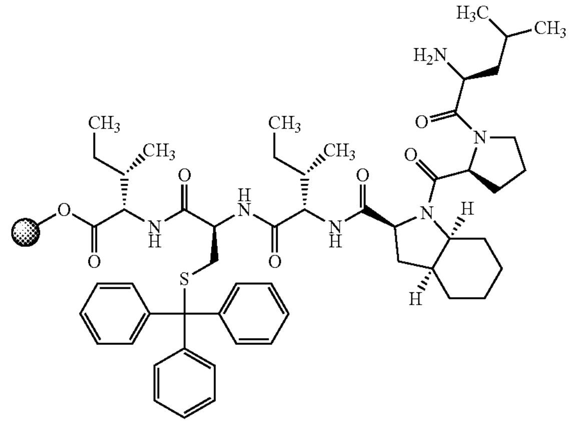 [SMILES: CC[C@H](C)[C@H](NC(=O)[C@@H]1C[C@@H]2CCCC[C@@H]2N1C(=O)[C@@H]1CCCN1C(=O)[C@@H](N)CC(C)C)C(=O)N[C@@H](CSC(c1ccccc1)(c1ccccc1)c1ccccc1)C(=O)N[C@H](C(=O)OC)[C@@H](C)CC]

Example 12A (20.9 g, 9.42 mmol) in 150 mL DMF/piperidine 4:1 was shaken for 30 min at room temperature. The resin was collected by filtration and washed with DMF for three times. Both steps were repeated and the collected resin was washed three times in rotation with 200 mL methanol and 200 mL dichloromethane. The collected resin was dried under vacuum for the next step.

Example 14A
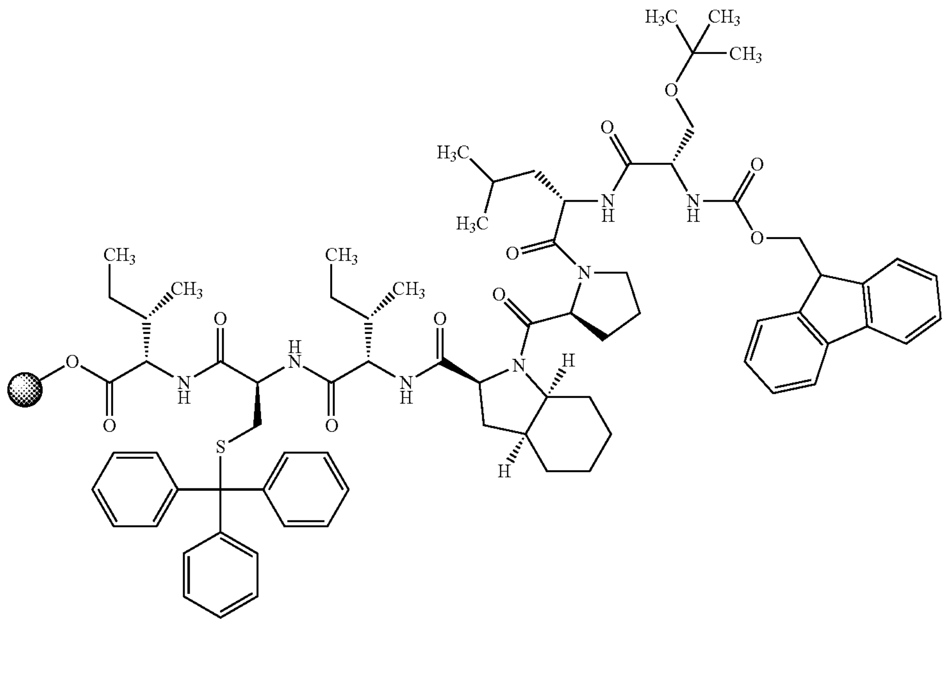 [SMILES: CC[C@H](C)[C@H](NC(=O)[C@@H]1C[C@@H]2CCCC[C@@H]2N1C(=O)[C@@H]1CCCN1C(=O)[C@H](CC(C)C)NC(=O)[C@H](COC(C)(C)C)NC(=O)OCC1c2ccccc2-c2ccccc21)C(=O)N[C@@H](CSC(c1ccccc1)(c1ccccc1)c1ccccc1)C(=O)N[C@H](C(=O)OC)[C@@H](C)CC]

Example 13A (18.0 g, 8.11 mmol) was swelled in 150 mL DMF for 5 min at room temperature. A mixture of O-tert-butyl-N-{[(9H-fluoren-9-yl)methoxy]carbonyl}-L-serine (12.4 g, 32.4 mmol) in 50 mL DMF, DIC (4.9 mL, 32 mmol) and Oxyma (4.49 g, 31.6 mmol) was added and the reaction mixture was shaken overnight at room temperature. The resin was collected by filtration, washed with 200 mL DMF for three times and then three more times in rotation with 200 mL methanol and 200 mL dichloromethane. The collected resin was dried under vacuum for the next step.

Example 15 A

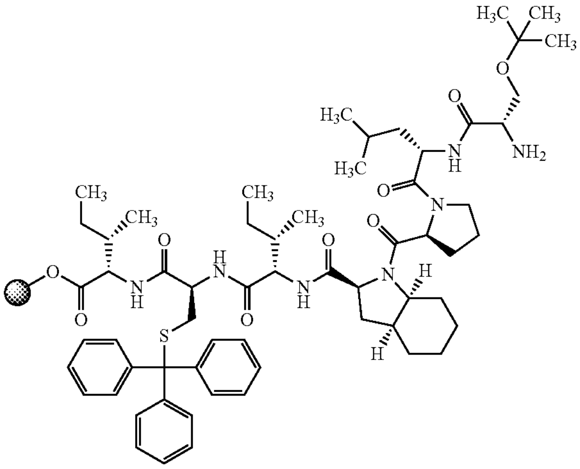 [SMILES: CC[C@H](C)[C@H](NC(=O)[C@@H]1C[C@@H]2CCCC[C@@H]2N1C(=O)[C@@H]1CCCN1C(=O)[C@H](CC(C)C)NC(=O)[C@@H](N)COC(C)(C)C)C(=O)N[C@@H](CSC(c1ccccc1)(c1ccccc1)c1ccccc1)C(=O)N[C@H](C(=O)OC)[C@@H](C)CC]

Example 14A (21.4 g, 9.64 mmol) in 200 mL DMF/piperidine 4:1 was shaken for 30 min at room temperature. The resin was collected by filtration and washed with DMF for three times. Both steps were repeated and the collected resin was washed three times in rotation with 200 mL methanol and 200 mL dichloromethane. The collected resin was dried under vacuum for the next step.

Example 16A

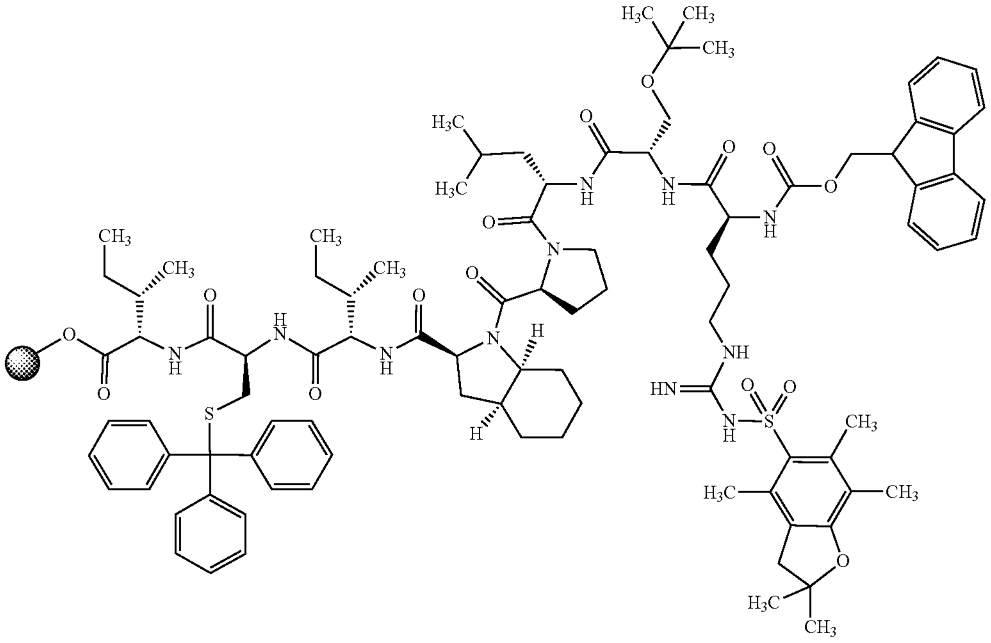 [SMILES: CC[C@H](C)[C@H](NC(=O)[C@@H]1C[C@@H]2CCCC[C@@H]2N1C(=O)[C@@H]1CCCN1C(=O)[C@H](CC(C)C)NC(=O)[C@H](COC(C)(C)C)NC(=O)[C@H](CCCNC(=N)NS(=O)(=O)c1c(C)c(C)c2c(c1C)CC(C)(C)O2)NC(=O)OCC1c2ccccc2-c2ccccc21)C(=O)N[C@@H](CSC(c1ccccc1)(c1ccccc1)c1ccccc1)C(=O)N[C@H](C(=O)OC)[C@@H](C)CC]

Example 15A (18.9 g, 8.51 mmol) was swelled in 150 mL DMF for 5 min at room temperature. A mixture of $N^2$—{[(9H-fluoren-9-yl)methoxy]carbonyl}-$N^5$—[N-(2,2,4,6,7-pentamethyl-2,3-dihydro-1-benzofuran-5-sulfonyl)carbamimidoyl]-L-ornithine (22.1 g, 34.0 mmol) in 50 mL DMF, DIC (5.1 mL, 33 mmol) and Oxyma (4.72 g, 33.2 mmol) was added and the reaction mixture was shaken overnight at room temperature. The resin was collected by filtration, washed with 200 mL DMF for three times and then three more times in rotation with 200 mL methanol and 200 mL dichloromethane. The collected resin was dried under vacuum for the next step.

Example 17A

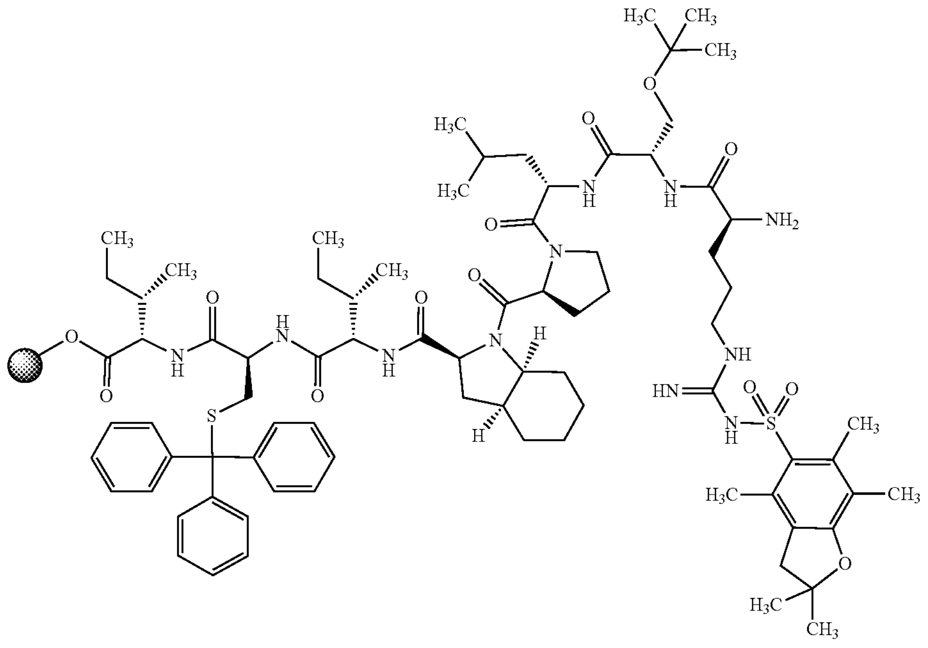

Example 16A (23.8 g, 10.7 mmol) in 200 mL DMF/piperidine 4:1 was shaken for 30 min at room temperature. The resin was collected by filtration and washed with DMF for three times. Both steps were repeated and the collected resin was washed three times in rotation with 200 mL methanol and 200 mL dichloromethane. The collected resin was dried under vacuum for the next step.
Example 18 A
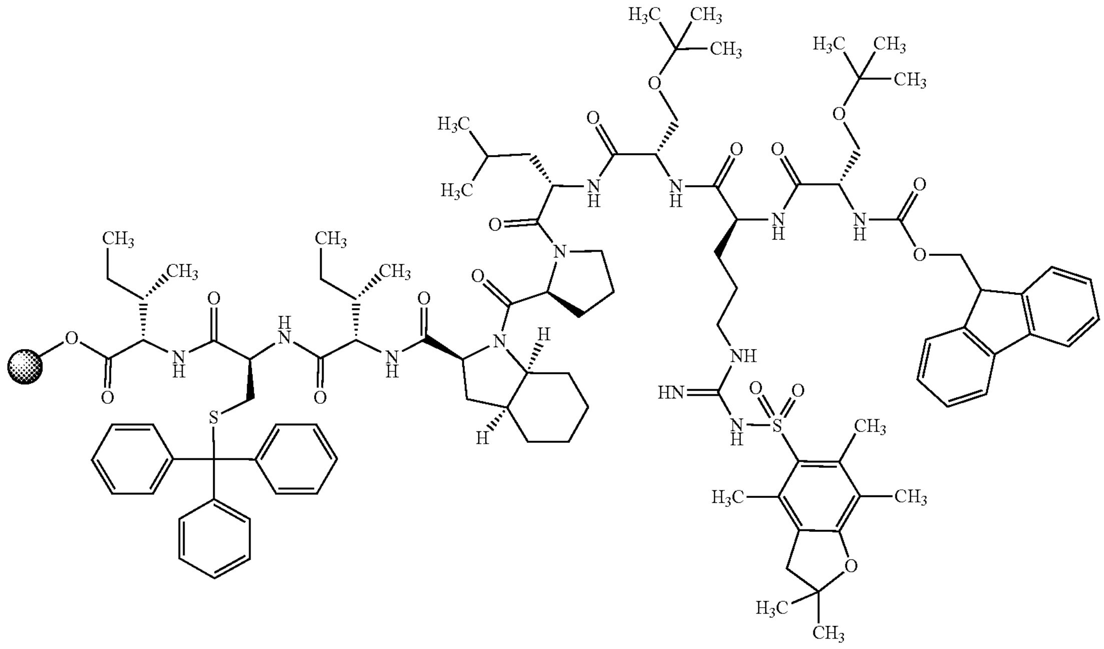 [SMILES: CC[C@H](C)[C@H](NC(=O)[C@@H]1C[C@@H]2CCCC[C@@H]2N1C(=O)[C@@H]1CCCN1C(=O)[C@H](CC(C)C)NC(=O)[C@H](COC(C)(C)C)NC(=O)[C@H](CCCNC(=N)NS(=O)(=O)c1c(C)c(C)c2c(c1C)CC(C)(C)O2)NC(=O)[C@H](COC(C)(C)C)NC(=O)OCC1c2ccccc2-c2ccccc21)C(=O)N[C@@H](CSC(c1ccccc1)(c1ccccc1)c1ccccc1)C(=O)N[C@H](C(=O)OC)[C@@H](C)CC]

Example 17A (22.1 g, 9.95 mmol) was swelled in 150 mL DMF for 5 min at room temperature. A mixture of O-tert-butyl-N-{[(9H-fluoren-9-yl)methoxy]carbonyl}-L-serine (15.3 g, 39.8 mmol) in 50 mL DMF, DIC (6.0 mL, 39 mmol) and Oxyma (5.51 g, 38.8 mmol) was added and the reaction mixture was shaken overnight at room temperature. The resin was collected by filtration, washed with 200 mL DMF for three times and then three more times in rotation with 200 mL methanol and 200 mL dichloromethane. The collected resin was dried under vacuum for the next step.

Example 19 A

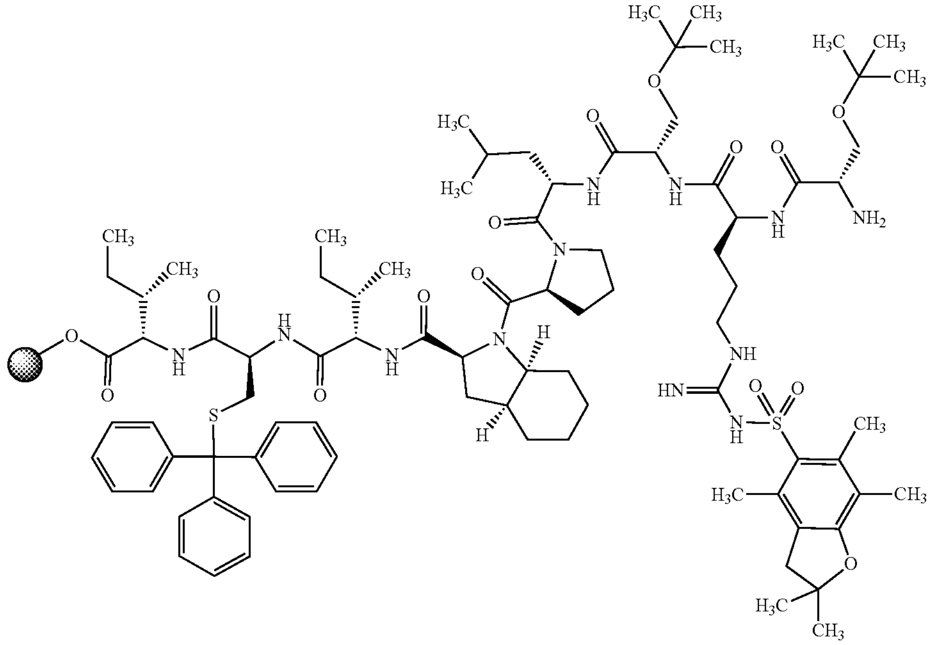

Example 18A (24.7 g, 11.1 mmol) in 200 mL DMF/piperidine 4:1 was shaken for 30 min at room temperature. The resin was collected by filtration and washed with DMF for three times. Both steps were repeated and the collected resin was washed three times in rotation with 200 mL methanol and 200 mL dichloromethane. The collected resin was dried under vacuum for the next step.
Example 20 A
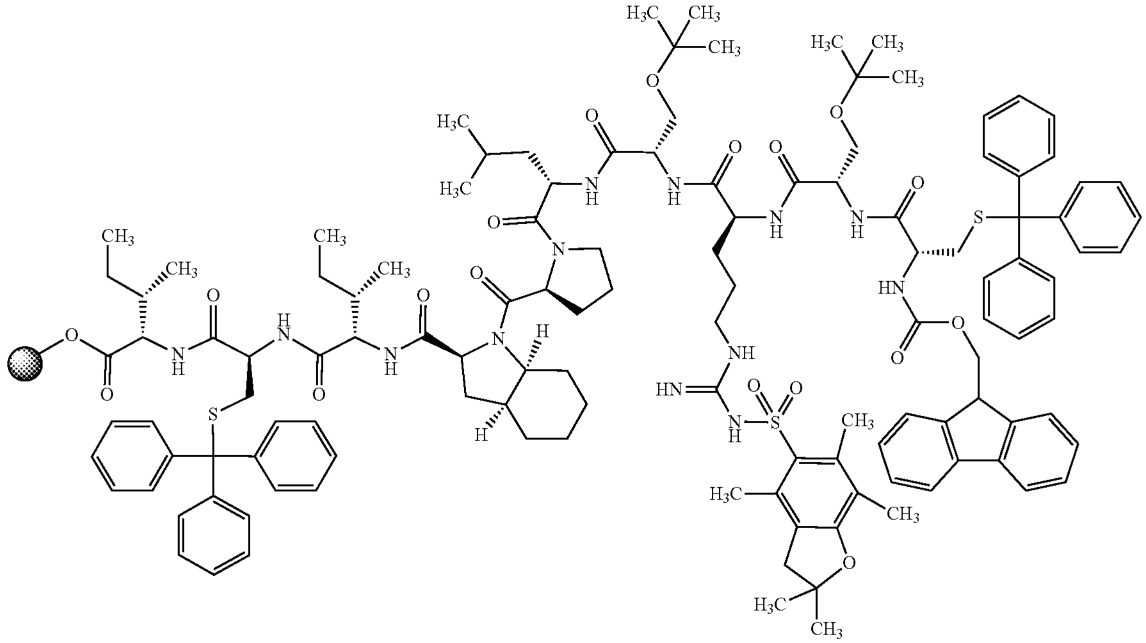 [SMILES: CC[C@H](C)[C@H](NC(=O)[C@@H]1C[C@@H]2CCCC[C@@H]2N1C(=O)[C@@H]1CCCN1C(=O)[C@H](CC(C)C)NC(=O)[C@H](COC(C)(C)C)NC(=O)[C@H](CCCNC(=N)NS(=O)(=O)c1c(C)c(C)c2c(c1C)CC(C)(C)O2)NC(=O)[C@H](COC(C)(C)C)NC(=O)[C@H](CSC(c1ccccc1)(c1ccccc1)c1ccccc1)NC(=O)OCC1c2ccccc2-c2ccccc21)C(=O)N[C@@H](CSC(c1ccccc1)(c1ccccc1)c1ccccc1)C(=O)N[C@H](C(=O)OC)[C@@H](C)CC]

Example 19A (22.2 g, 9.99 mmol) was swelled in 150 mL DMF for 5 min at room temperature. A mixture of N-{[(9H-fluoren-9-yl)methoxy]carbonyl}-S-(triphenylmethyl)-L-cysteine (23.4 g, 40.0 mmol) in 50 mL DMF, DIC (6.0 mL, 39 mmol) and Oxyma (5.54 g, 39.0 mmol) was added and the reaction mixture was shaken overnight at room temperature. The resin was collected by filtration, washed with 200 mL DMF for three times and then three more times in rotation with 200 mL methanol and 200 mL dichloromethane. The collected resin was dried under vacuum for the next step.

Example 21A

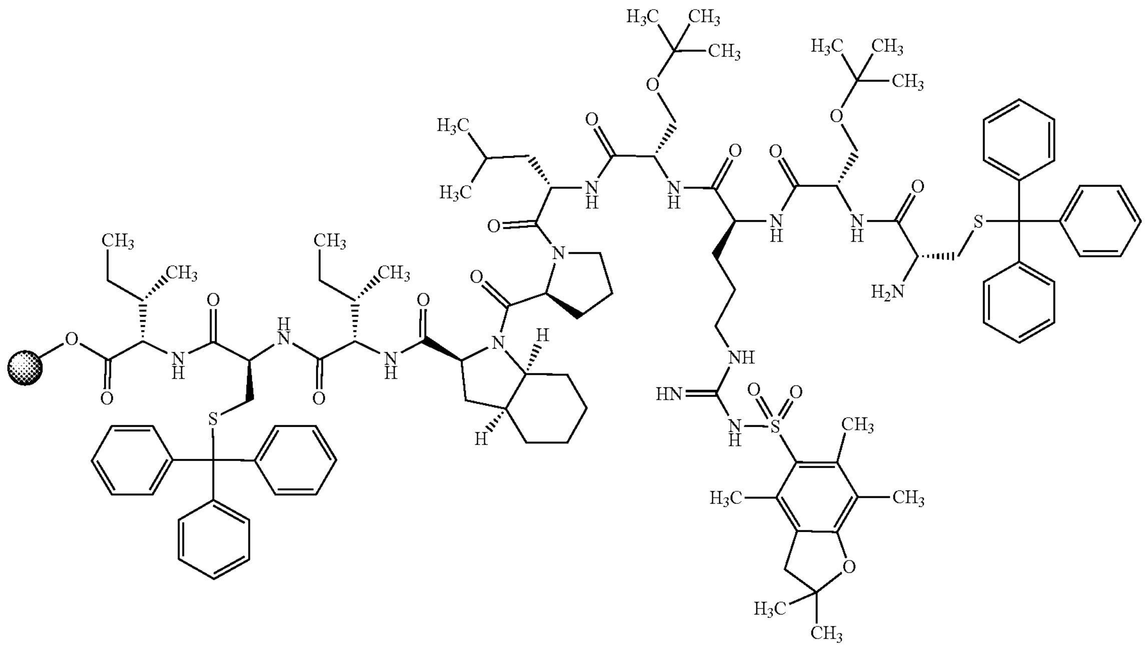 [SMILES: CC[C@H](C)[C@H](NC(=O)[C@@H]1C[C@@H]2CCCC[C@@H]2N1C(=O)[C@@H]1CCCN1C(=O)[C@H](CC(C)C)NC(=O)[C@H](COC(C)(C)C)NC(=O)[C@H](CCCNC(=N)NS(=O)(=O)c1c(C)c(C)c2c(c1C)CC(C)(C)O2)NC(=O)[C@H](COC(C)(C)C)NC(=O)[C@@H](N)CSC(c1ccccc1)(c1ccccc1)c1ccccc1)C(=O)N[C@@H](CSC(c1ccccc1)(c1ccccc1)c1ccccc1)C(=O)N[C@H](C(=O)OC)[C@@H](C)CC]

Example 20A (24.5 g, 11.0 mmol) in 200 mL DMF/piperidine 4:1 was shaken for 30 min at room temperature. The resin was collected by filtration and washed with DMF for three times. Both steps were repeated and the collected resin was washed three times in rotation with 200 mL methanol and 200 mL dichloromethane. The collected resin was dried under vacuum for the next step.
Example 22A
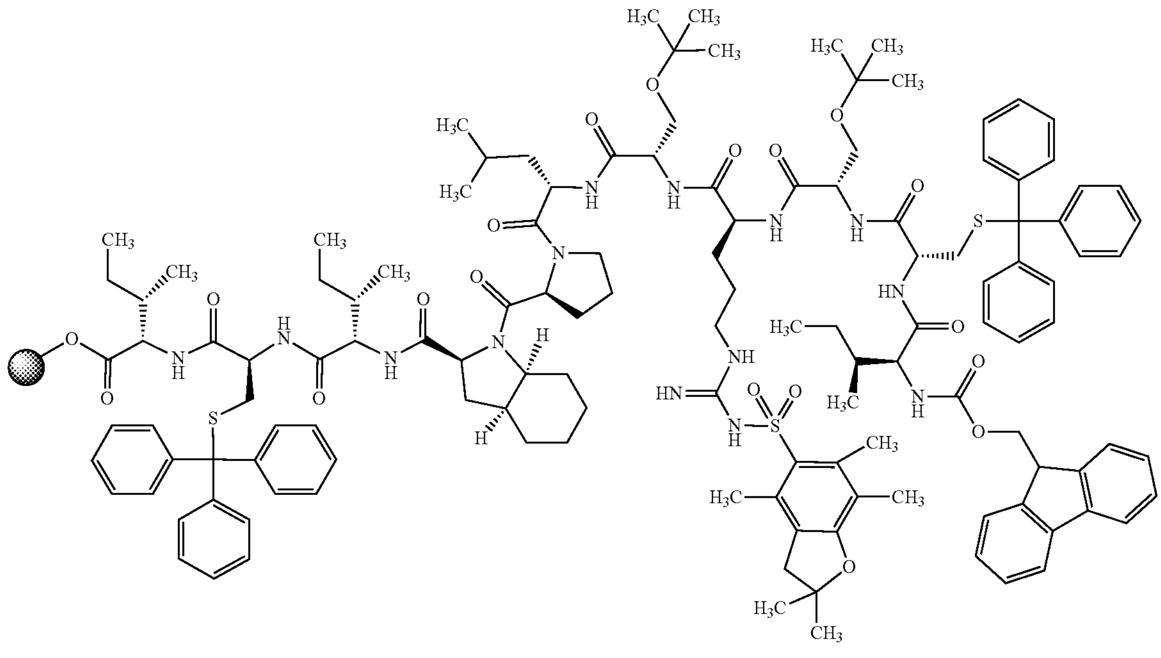 [SMILES: CC[C@H](C)[C@H](NC(=O)OCC1c2ccccc2-c2ccccc21)C(=O)N[C@@H](CSC(c1ccccc1)(c1ccccc1)c1ccccc1)C(=O)N[C@@H](COC(C)(C)C)C(=O)N[C@@H](CCCNC(=N)NS(=O)(=O)c1c(C)c(C)c2c(c1C)CC(C)(C)O2)C(=O)N[C@@H](COC(C)(C)C)C(=O)N[C@@H](CC(C)C)C(=O)N1CCC[C@H]1C(=O)N1[C@H](C(=O)N[C@H](C(=O)N[C@@H](CSC(c2ccccc2)(c2ccccc2)c2ccccc2)C(=O)N[C@H](C(=O)OC)[C@@H](C)CC)[C@@H](C)CC)C[C@@H]2CCCC[C@@H]21]

Example 21A (22.3 g, 10.0 mmol) was swelled in 150 mL DMF for 5 min at room temperature. A mixture of N-{[(9H-fluoren-9-yl)methoxy]carbonyl}-L-isoleucine (14.2 g, 40.1 mmol) in 50 mL DMF, DIC (6.0 mL, 39 mmol) and Oxyma (5.55 g, 39.0 mmol) was added and the reaction mixture was shaken over the weekend at room temperature. The resin was collected by filtration, washed with 200 mL DMF for three times and then three more times in rotation with 200 mL methanol and 200 mL dichloromethane. The collected resin was dried under vacuum for the next step.

Example 23A

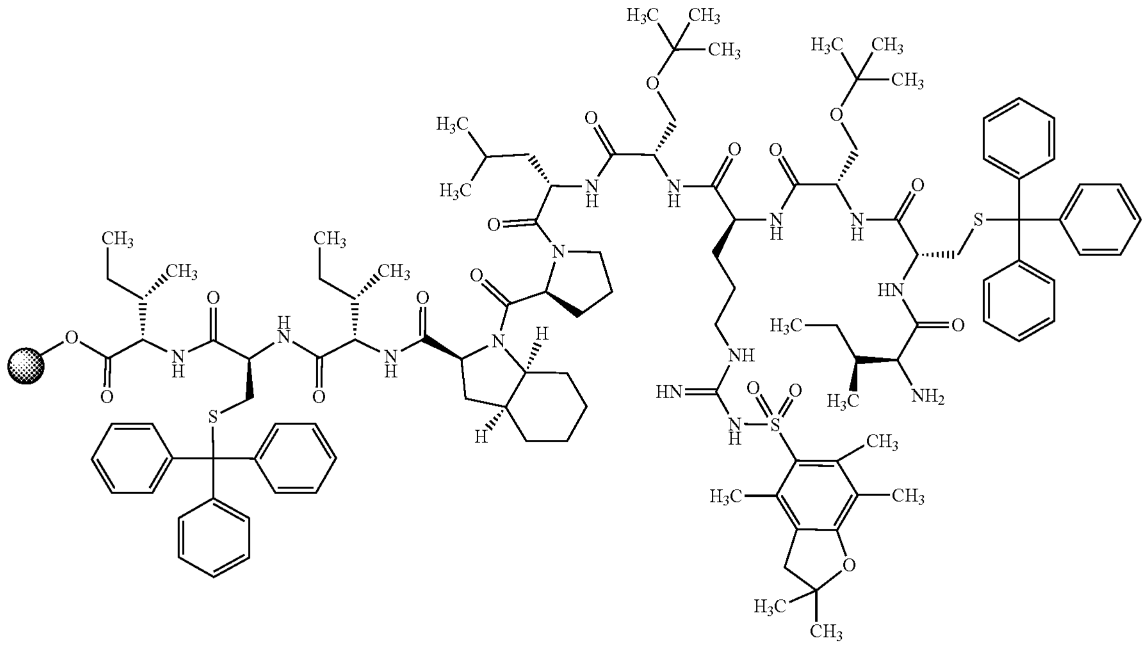 [SMILES: CC[C@H](C)[C@H](N)C(=O)N[C@@H](CSC(c1ccccc1)(c1ccccc1)c1ccccc1)C(=O)N[C@@H](COC(C)(C)C)C(=O)N[C@@H](CCCNC(=N)NS(=O)(=O)c1c(C)c(C)c2c(c1C)CC(C)(C)O2)C(=O)N[C@@H](COC(C)(C)C)C(=O)N[C@@H](CC(C)C)C(=O)N1CCC[C@H]1C(=O)N1[C@H](C(=O)N[C@H](C(=O)N[C@@H](CSC(c2ccccc2)(c2ccccc2)c2ccccc2)C(=O)N[C@H](C(=O)OC)[C@@H](C)CC)[C@@H](C)CC)C[C@@H]2CCCC[C@@H]21]

Example 22A (1.00 g, 250 μmol) in 7.5 mL DMF/piperidine 4:1 was shaken for 30 min at room temperature. The resin was collected by filtration and washed with DMF for three times. Both steps were repeated and the collected resin was washed three times in rotation with methanol and dichloromethane. The collected resin was dried under vacuum for the next step.
Example 24A
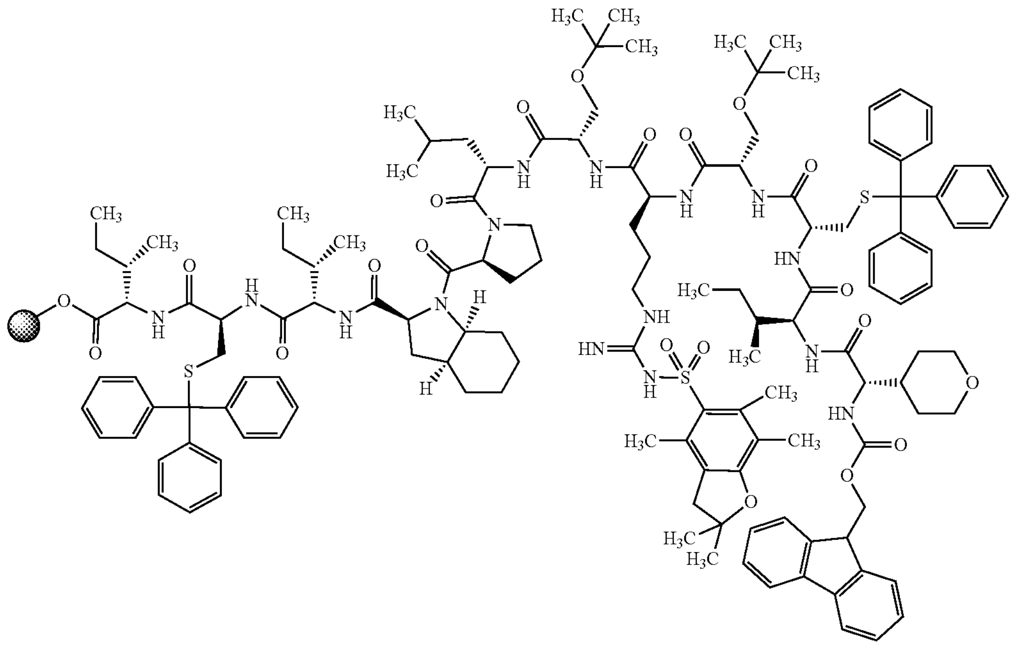 [SMILES: CC[C@H](C)[C@H](NC(=O)[C@@H](NC(=O)OCC1c2ccccc2-c2ccccc21)C1CCOCC1)C(=O)N[C@@H](CSC(c1ccccc1)(c1ccccc1)c1ccccc1)C(=O)N[C@@H](COC(C)(C)C)C(=O)N[C@@H](CCCNC(=N)NS(=O)(=O)c1c(C)c(C)c2c(c1C)CC(C)(C)O2)C(=O)N[C@@H](COC(C)(C)C)C(=O)N[C@@H](CC(C)C)C(=O)N1CCC[C@H]1C(=O)N1[C@H](C(=O)N[C@H](C(=O)N[C@@H](CSC(c2ccccc2)(c2ccccc2)c2ccccc2)C(=O)N[C@H](C(=O)OC)[C@@H](C)CC)[C@@H](C)CC)C[C@@H]2CCCC[C@@H]21]

Example 23A (1.00 g, 250 μmol) was swelled in 5 mL DMF for 5 min at room temperature. A mixture of (2S)—({[(9H-fluoren-9-yl)methoxy]carbonyl}amino)(oxan-4-yl) acetic acid (381 mg, 1.00 mmol) in 1 mL DMF, DIC (150 μL, 980 μmol) and Oxyma (139 mg, 975 μmol) was added and the reaction mixture was shaken over the weekend at room temperature. The resin was collected by filtration, washed with DMF for three times and then three more times in rotation with methanol and dichloromethane. The collected resin was dried under vacuum for the next step.

Example 25A

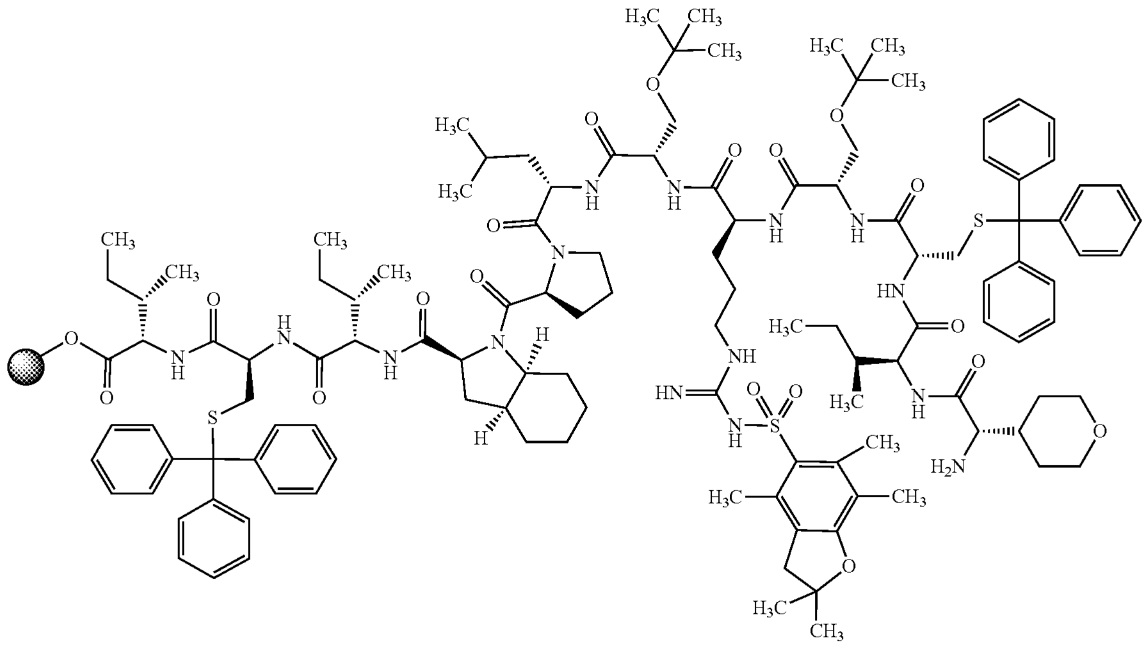 [SMILES: CC[C@H](C)[C@H](NC(=O)[C@@H](N)C1CCOCC1)C(=O)N[C@@H](CSC(c1ccccc1)(c1ccccc1)c1ccccc1)C(=O)N[C@@H](COC(C)(C)C)C(=O)N[C@@H](CCCNC(=N)NS(=O)(=O)c1c(C)c(C)c2c(c1C)CC(C)(C)O2)C(=O)N[C@@H](COC(C)(C)C)C(=O)N[C@@H](CC(C)C)C(=O)N1CCC[C@H]1C(=O)N1[C@H](C(=O)N[C@H](C(=O)N[C@@H](CSC(c2ccccc2)(c2ccccc2)c2ccccc2)C(=O)N[C@H](C(=O)OC)[C@@H](C)CC)[C@@H](C)CC)C[C@@H]2CCCC[C@@H]21]

Example 24A (1.00 g, 250 μmol) in 7.5 mL DMF/piperidine 4:1 was shaken for 30 min at room temperature. The resin was collected by filtration and washed with DMF for three times. Both steps were repeated and the collected resin was washed three times in rotation with methanol and dichloromethane. The collected resin was dried under vacuum for the next step.

Example 26A (2S,3S)-2-{[(2R)-2-{[(2S,3S)-2-{[(2S,3aS,7aS)-1-{(2S)-1-[(2S,5S,8S,11S,14R,17S,20S)-20-amino-17-[(2S)-butan-2-yl]-8-(3-carbamimidamidopropyl)-5,11-bis(hydroxymethyl)-2-(2-methylpropyl)-20-(oxan-4-yl)-4,7,10,13,16,19-hexaoxo-14-(sulfanylmethyl)-3,6,9,12,15,18-hexaazaicosanan-1-oyl]pyrrolidine-2-carbonyl}octahydro-1H-indole-2-carbonyl]amino}-3-methylpentanoyl]amino}-3-sulfanylpropanoyl]amino}-3-methylpentanoic acid (Single Stereoisomer)

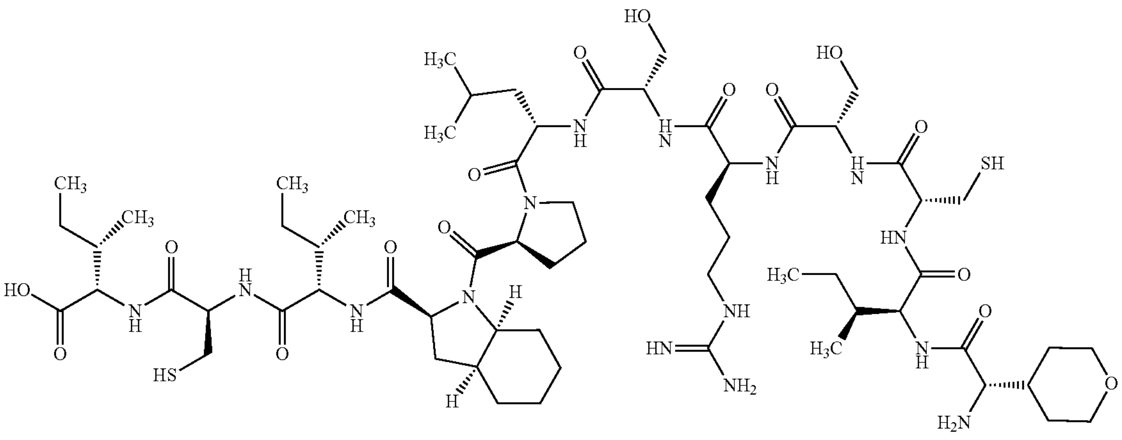 [SMILES: CC[C@H](C)[C@H](NC(=O)[C@H](CS)NC(=O)[C@@H](NC(=O)[C@@H]1C[C@@H]2CCCC[C@@H]2N1C(=O)[C@@H]1CCCN1C(=O)[C@H](CC(C)C)NC(=O)[C@H](CO)NC(=O)[C@H](CCCNC(=N)N)NC(=O)[C@H](CO)NC(=O)[C@H](CS)NC(=O)[C@@H](NC(=O)[C@@H](N)C1CCOCC1)[C@@H](C)CC)[C@@H](C)CC)C(=O)O]

To Example 25A (1.00 g, 250 μmol) was added the cleavage cocktail of TFA/EDT/Thioanisol (90:3:7) and the mixture was shaken for 2 h at room temperature. The filtrate was collected, and the resin was washed with dichloromethane. The combined filtrate was evaporated. The residue was stirred with diethyl ether and the solid was collected by filtration. The solid was washed several times with diethyl ether and dried under vacuum for the next step.

Example 184

((2S)-2[(Amino)-2-(tetrahydro-2H-pyran-4-yl)]acetic acid)-IC+SRSLP-(Oic)-IC+I-OH (Example 184)

N-[(6S,9S,12S,15S,18R,23R,26S,28aS,29aS,33aS,35aS)-18-({N-[(2S)-2-amino-2-(oxan-4-yl)acetyl]-L-isoleucyl}amino)-26-[(2S)-butan-2-yl]-12-(3-carbamimidamidopropyl)-9,15-bis(hydroxymethyl)-6-(2-methylpropyl)-5,8,11,14,17,25,28,35-octaoxodotriacontahydro-1H,5H,22H-pyrrolo[2',1':13,14][1,2,5,8,11,14,17,20,23,26]dithiaoctaazacyclononacosino[11,10-a]indole-23-carbonyl]-L-isoleucine (Single Stereoisomer)

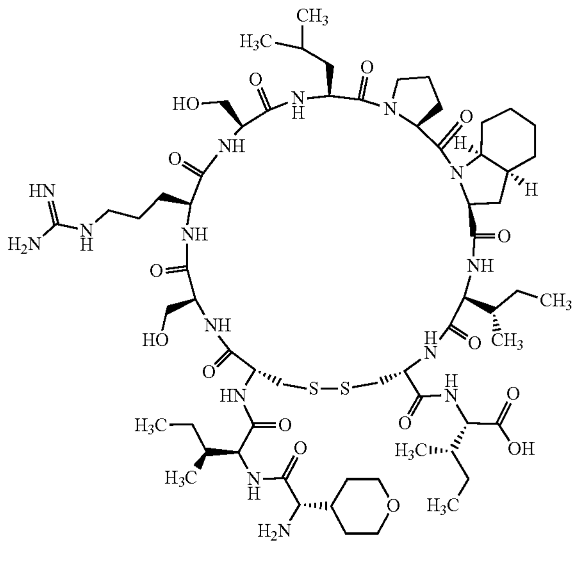 [SMILES: CC[C@H](C)[C@H](NC(=O)[C@@H]1CSSC[C@H](NC(=O)[C@@H](NC(=O)[C@@H](N)C2CCOCC2)[C@@H](C)CC)C(=O)N[C@@H](CO)C(=O)N[C@@H](CCCNC(=N)N)C(=O)N[C@@H](CO)C(=O)N[C@@H](CC(C)C)C(=O)N2CCC[C@H]2C(=O)N2[C@@H](C[C@@H]3CCCC[C@@H]32)C(=O)N[C@@H]([C@@H](C)CC)C(=O)N1)C(=O)O]

To Example 26A (425 mg, 304 μmol) was added 850 mL 0.1 M aqueous ammonium bicarbonate solution (pH 7.86). Air was bubbled though the reaction mixture for 5 min. The reaction mixture was stirred in a open flask overnight at room temperature. The solvents were lyophilized to give 580 mg of a white solid. Purification using reversed-phase HPLC as described above (Method B) gave three fractions 7.4 mg (>99%), 24.5 mg (98%) and 15 mg (95%) of the desired example 184.

General Method F: Conversion of Peptide TFA Salts to HCl Salts

The synthesis of AIC+SRS-((tBu)A)-PPI—((N-Me)C)+IPD-NH2 (HCl Salt) (Example 30) is representative.

Procedure of Automatic Ion Exchange Station:

Peristaltic pump of the company Hirschmann (Rotarus volume 50), Tubes: Tygon 2001 (ID 0.64 mm)

Settings:

Washing with $H_2O$: run-time 1200 s; 80 $min^{-1}$; 1 cycle (is 35 mL volume)

Sample circulation with peptide: run-time 1200 s; 80 $min^{-1}$; 1 cycle (is 70 mL volume)

Wash with $H_2O$ (or % ACN in $H_2O$: run-time 1200 s; 80 $min^{-1}$; 1 cycle (is 35 mL volume)

Amberlite IRA 410 (HCl form) was used. 1500 mg of the resin was placed into 2 filter cartridges and washed with deionized water (10 times).

The peptide dissolved in 3 mL of a 5% ACN/$H_2O$ solution was loaded onto the column and cycled through the column 10 times. The column was washed with water, and the solution collected into a Falcon tube and lyophilized 72.83 mg of the desired peptide was obtained as the HCl salt: LC-MS (>99%); Ion Chromatography analysis: 3.7 wt % Cl— (1.57 eq Cl—), <1 wt % TFA.

The Ion Exchange Process can Also be Performed Using the Following Protocol:

Amberlite IRA 410 resin (HCl form) (1-2 g) was placed into a 10 mL frit-syringe (100 mg Peptide needs 1 g IRA 410 resin)

1) The resin is washed with water (10 times×3 mL)
2) The resin is washed with 5% ACN in water (1 time×3 mL)
3) The peptide was dissolved in 5% ACN in water
4) The peptide was added to the syringe and the solution was cycled through the column 10-20 times. The eluent is collected into a Falcon Tube.
5) The resin is washed with 5% ACN in water (10 times×3 mL); this solution is added to the solution in the Falkon-tube
6) The combined solution is lyophilized.

General Method FA: Conversion of Peptide TFA Salts to Other Salts

Other Salt Forms:

The chloride counter ion can be exchanged with other counterions by passing a solution of the desired salt form (e.g sodium acetate) repeatedly through the column, then washing the column repeatedly with water.

The peptide is then loaded and the above procedures followed. Peptide acetate, tartrate, citrate, and lactate salts have thus been prepared. The following three examples are representative:

Example 249

Sequence: ((N-Me)G)-IC+SRSLP-(Oic)-I-(Pen)+IP-$NH_2$ (Acetate Salt) (Example 249)

N-[(6S,9S,12S,15S,18R,23R,26S,28aS,29aS,33aS,35aS)-26-[(2S)-butan-2-yl]-12-(3-carbamimidamidopropyl)-9,15-bis(hydroxymethyl)-22,22-dimethyl-18-[(N-methylglycyl-L-isoleucyl)amino]-6-(2-methylpropyl)-5,8,11,14,17,25,28,35-octaoxodotriacontahydro-1H,5H,22H-pyrrolo[2',1':13,14][1,2,5,8,11,14,17,20,23,26]dithiaoctaazacyclononacosino[11,10-a]indole-23-carbonyl]-L-isoleucyl-L-prolinamide, Acetic Acid salt IRA 410 chloride resin (12 g) was placed into an empty 20 mL Biotage column and the resin was washed with with a 5% solution of ACN-water (10 times). The cartridge was attached to the Automatic Ion Exchange Station. The resin was washed with 20 column volumes of a 1M NaOH solution (2×1800s rotation speed 80 $min^{-1}$). The column was washed with water until the pH of the eluent was <pH 9 (10 column volumes). The column was then eluted with 1 M acetic acid solution (10 column volumes), then washed with water until the pH of the eluent was >5 (about 10 column volumes). The peptide (N-Me)GIC+SRSLP-(Oic)-I-Pen+IP-$NH_2$ (TFA salt) (1200 mg) was loaded onto the column in 12 mL of 5% ACN/water and allowed to cycle through the column 10 times according to the General Method F. The resin was then washed with a 5% ACN/water solution 10 times and the eluent was collected into 50 mL Falcon tubes. The parameter settings used for this scale were:

Washing with $H_2O$: run-time 3085 s; 80 min-1; 1 cycle (is 90 mL volume)

Sample circulation with peptide: run-time 3085 s; 80 min-1; 1 cycle (is 180 mL volume)

Wash with $H_2O$ (or with % ACN in $H_2O$: run-time 3085 s; 80 min-1; 1 cycle (is 90 mL volume)

The combined eluent was lyophilized to give 1120 mg (100% purity, 97% yield) of the target acetate salt.

Ion chromatography (chloride content): <1% chloride

Ion chromatography (TFA content): <1% TFA

Ion chromatography (acetate content): 7.1% acetate=1.84 equiv

LC-MS (MCW-TOF-AQ-YMC-18 min): Rt=7.74 min; MS (ESIpos): m/z=725 $[M+2H]^+$

Example 264

Sequence: ((N-Me)G)-IC+SRSLP-(Oic)-I-(Pen)+IP-$NH_2$ (L-Tartaric acid salt) (Example 264)

N-[(6S,9S,12S,15S,18R,23R,26S,28aS,29aS,33aS,35aS)-26-[(2S)-butan-2-yl]-12-(3-carbamimidamidopropyl)-9,15-bis(hydroxymethyl)-22,22-dimethyl-18-[(N-methylglycyl-L-isoleucyl)amino]-6-(2-methylpropyl)-5,8,11,14,17,25,28,35-octaoxodotriacontahydro-1H,5H,22H-pyrrolo[2',1':13,14][1,2,5,8,11,14,17,20,23,26]dithiaoctaazacyclononacosino[11,10-a]indole-23-carbonyl]-L-isoleucyl-L-prolinamide (2R,3R)-2,3-dihydroxybutanedioic acid (L-(+) tartaric acid) salt IRA 410 chloride resin (12.5 g) was placed into an empty 20 mL Biotage column and the resin was washed with with a 5% solution of ACN-water (10 times). The cartridge was attached to the Automatic Ion Exchange Station. The resin was washed with 20 column volumes of a 1M NaOH solution (2×1800s rotation speed 80 $min^{-1}$). The column was washed with water until the pH of the eluent was <pH 9 (10 column volumes). The column was then eluted with 1 M L-tartaric acid solution (10 column volumes), then washed with water until the pH of the eluent was >5 (about 10 column volumes). The peptide ((N-Me)G)IC+SRSLP-(Oic)-I-(Pen)+IP-$NH_2$ (TFA salt) (1200 mg) was loaded onto the column in 12 mL of 5% ACN/water and allowed to cycle through the column 10 times according to the General Method F. The resin was then washed with a 5% ACN/water solution 10 times and the eluent was collected into 50 mL Falcon tubes. The parameter settings used for this scale were:

Washing with $H_2O$: run-time 3085 s; 80 $min^{-1}$; 1 cycle (is 90 mL volume)

Sample circulation with peptide: run-time 3085 s; 80 $min^{-1}$; 1 cycle (is 180 mL volume)

Wash with $H_2O$ (or % ACN in $H_2O$: run-time 3085 s; 80 $min^{-1}$; 1 cycle (is 90 mL volume)

The combined eluent was lyophilized to give 1170 mg (100% purity, 91% yield) of the target L-tartaric acid salt.

Ion Chromotography (chloride content): <1% chloride

Ion Chromotography (TFA content): <1% TFA

Ion chromatography (acetate content): 13.4% acetate=1.49 equiv

LC-MS (MCW-TOF-AQ-YMC-18 min): Rt=7.62 min; MS (ESIpos): m/z=725 $[M+2H]^+$

Example 376

Sequence: ((N-Me)G)-IC+SRSLP-(Oic)-I-(Pen)+IP-$NH_2$ (Citric acid salt) (Example 376)

N-[(6S,9S,12S,15S,18R,23R,26S,28aS,29aS,33aS,35aS)-26-[(2S)-butan-2-yl]-12-(3-carbamimidamidopropyl)-9,15-bis(hydroxymethyl)-22,22-dimethyl-18-[(N-methylglycyl-L-isoleucyl)amino]-6-(2-methylpropyl)-5,8,11,14,17,25,28,35-octaoxodotriacontahydro-1H,5H,22H-pyrrolo[2',1':13,14][1,2,5,8,11,14,17,20,23,26]dithiaoctaazacyclononacosino[11,10-a]indole-23-carbonyl]-L-isoleucyl-L-prolinamide, 2-hydroxypropane-1,2,3-tricarboxylic acid (citric acid) salt

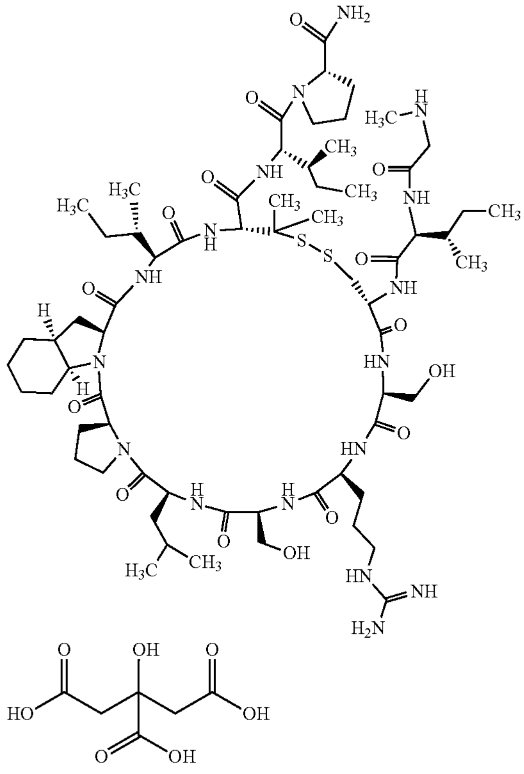

IRA 410 chloride resin (26 g) was placed into an empty 20 mL Biotage columns and the resin was washed with with a 5% solution of ACN-water (10 times). The cartridge was attached to the Automatic Ion Exchange Station. The resin was washed with 20 column volumes of a 1M NaOH solution (2×1800s rotation speed 80 min-1). The column was washed with water until the pH of the eluent was <pH 9 (10 column volumes). The column was then eluted with 1 M citric acid solution (10 column volumes), then washed with water until the pH of the eluent was >5 (about 10 column volumes). The peptide (NMe)GIC+SRSLP-(Oic)-I-Pen+IP-$NH_2$ (TFA salt) (1200 mg) was loaded onto the column in 12 mL of 5% ACN/water and allowed to cycle through the column 10 times according to the General Method F. The resin was then washed with a 5% ACN/water solution 10 times and the eluent was collected into 50 mL Falcon tubes. The parameter settings used for this scale were:

Washing with $H_2O$: run-time 3085 s; 80 $min^{-1}$; 1 cycle (is 90 mL volume)

Sample circulation with peptide: run-time 3085 s; 80 $min^{-1}$; 1 cycle (is 180 mL volume)

Wash with $H_2O$ (or % ACN in $H_2O$: run-time 3085 s; 80 $min^{-1}$; 1 cycle (is 90 mL volume)

The combined eluent was lyophilized to give 1370 mg (100% purity, 97% yield) of the target L-tartaric acid salt.

Ion Chromatography (chloride content): <1% chloride

Ion Chromatography (TFA content): <1% TFA

Ion chromatography (acetate content): 19.0% acetate=1.77 equiv

LC-MS (MCW-TOF-AQ-YMC-18 min): Rt=7.6 min; MS (ESIpos): m/z=725 $[M+2H]^+$

One skilled in the art will recognize that although the stoichiometry by ion chromatography is not always stoichiometric (e.g. 1:2 or 1:1), water content has not been taken into account, which where in a few cases that were measured, can be between 8-15% water content.

General Method G: Preparation of a Salt-Free Form

The preparation of AIC+SRSLP-(Oic)-I-(Pen)+IPD-$NH_2$ (salt free form) (Example 27) is representative.

5 Grams of the TFA salt (Example 75) was purified by reversed-phase HPLC using an acetonitrile water gradient at 70° C. with no acid modifier. The desired fractions were combined and lyophilized. 2.2 grams of the salt-free form (Example 27) was obtained; LC-MS (>99% pure); Ion Chromatography (<1% TFA)

General Method H: Large Scale Synthesis

The synthesis of AIC+SRS-((tBu)A)-PPI—((N-Me)C)+IPD-$NH_2$ (Example 48) is representative

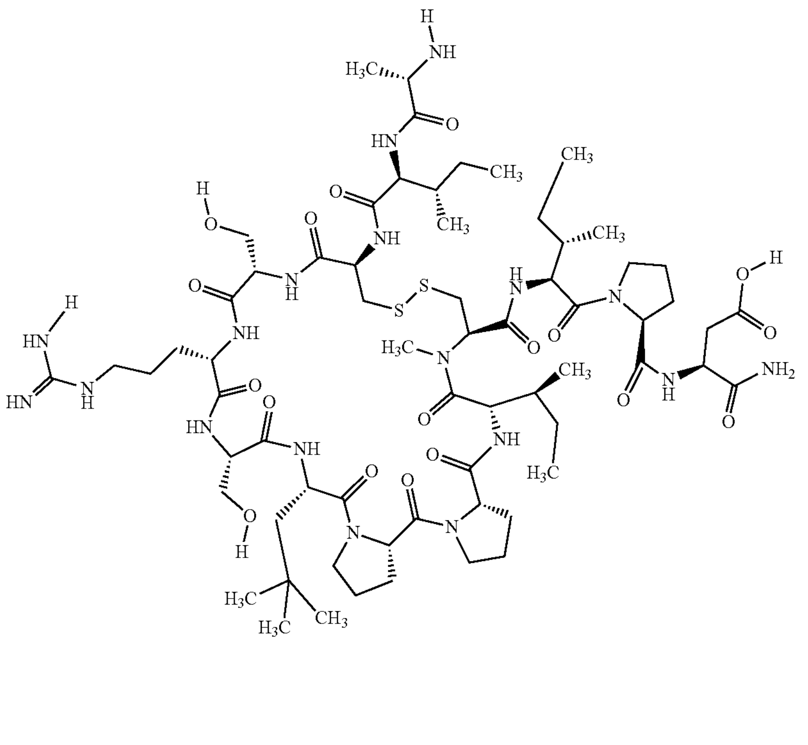 [SMILES: CC[C@H](C)[C@H](NC(=O)[C@H](C)N)C(=O)N[C@H]1CSSC[C@@H](C(=O)N[C@H](C(=O)N2CCC[C@H]2C(=O)N[C@@H](CC(=O)O)C(N)=O)[C@@H](C)CC)N(C)C(=O)[C@H]([C@@H](C)CC)NC(=O)[C@@H]2CCCN2C(=O)[C@@H]2CCCN2C(=O)[C@H](CC(C)(C)C)NC(=O)[C@H](CO)NC(=O)[C@H](CCCNC(=N)N)NC(=O)[C@H](CO)NC1=O]

The peptide was synthesized using standard Fmoc chemistry.

1) DMF was added to the vessel containing MBHA Resin (180 mmol) and the resin was allowed to swell for 2 hours.
2) The Fmoc-Rink amide linker was added and mixed for 30 seconds, then the activation buffer was added. Mixing was done using $N_2$ bubbling for about 1 hour.
3) The solution was drained from the resin and the resing was washed with DMF wash (30 sec×3 times).
4) A solution of 20% piperidine/DMF was added and mixed with nitrogen bubbling for 30 min.
5) The solution was drained and the resin was washed with DMF (5 times).
6) The Fmoc-amino acid solution was added and mixed for 30 seconds, then the activation buffer was added. Mixing was done using $N_2$ bubbling for about 1 hour.
7) Steps 3 to 6 were repeated for each amino acid coupling.

TABLE 10

Note of materials used and conditions

| # | Materials | Coupling reagents | Coupling time |
|---|---|---|---|
| 1 | Fmoc-Asp(OtBu)-OH | HBTU (3.0 eq) and DIEA (6.0 eq) | 1 h |
| 2 | Fmoc-Pro-OH | HBTU (3.0 eq) and DIEA (6.0 eq) | 1 h |
| 3 | Fmoc-Ile-OH | HBTU (3.0 eq) and DIEA (6.0 eq) | 1 h |
| 4 | Fmoc-NMe-Cys(Trt)-OH | HATU (2.0 eq) and DIEA (4.0 eq) | 1 h |
| 5 | Fmoc-Ile-OH | HBTU (3.0 eq) and DIEA (6.0 eq) | 1 h |
| 6 | Fmoc-Pro-OH | HBTU (3.0 eq) and DIEA (6.0 eq) | 1 h |
| 7 | Fmoc-Pro-OH | HBTU (3.0 eq) and DIEA (6.0 eq) | 1 h |
| 8 | Fmoc-tBuAla-OH | HATU (2.0 eq) and DIEA (4.0 eq) | 1 h |
| 9 | Fmoc-Ser(tBu)-OH | HBTU (3.0 eq) and DIEA (6.0 eq) | 1 h |
| 10 | Fmoc-Arg(pbf)-OH | HBTU (3.0 eq) and DIEA (6.0 eq) | 1 h |
| 11 | Fmoc-Ser(tBu)-OH | HBTU (3.0 eq) and DIEA (6.0 eq) | 1 h |
| 12 | Fmoc-Cys(Trt)-OH | HBTU (3.0 eq) and DIEA (6.0 eq) | 1 h |
| 13 | Fmoc-Ile-OH | HBTU (3.0 eq) and DIEA (6.0 eq) | 1 h |
| 14 | Fmoc-Ala-OH | HBTU (3.0 eq) and DIEA (6.0 eq) | 1 h |

A solution of 20% piperidine in DMF was used for Fmoc deprotection for 30 min. The coupling reaction was monitored by ninhydrin test, and the resin was washed with DMF for 5 times.

Peptide Cleavage and Purification:

1) The cleavage buffer (92.5% TFA: 2.5% EDT: 2.5% TIS: 2.5% $H_2O$) was added to the flask containing the side chain protected peptide at room temperature and the mixture was stirred for 2 hours.
2) The peptide was precipitated with cold isopropyl ether and centrifuged (2 min at 5000 rpm).
3) The peptide was washed twice more with isopropyl ether.
4) The crude peptide was dried under vacuum for 2 hours.

Disulfide Formation

To a solution of the crude linear peptide (15 g, 9.92 mmol, 1.0 eq) (20 batches) in $H_2O/I$ (3 L 2:1) was added $NH_4HCO_3$ (7.84 g, 99.2 mmol, 10 eq). The mixture was stirred at 30° C. for 16 h, quenched with the addition of HCl to PH-6, and then the mixture was lyophilized. The lyophilizate was purified by Prep-HPLC to give the desired example 48 (41.8 g, 95.8%, 13.3% yield) as a white solid, 156.8 grams total.

Purification Conditions

Equipment: Shimadzu 10A; Peptide was dissolved in $DMF/H_2O$. Mobile Phase: A ($H_2O$ (0.075% TFA in $H_2O$), B EtOH; gradient: 10-50%-60 min. Retention time: 47 min; Column: Luna, C18, 10 μm, 100A, 25 cm×50 mm; flow rate: 80 mL/min; wavelength: 220/254 nm; oven temp: room temperature.

Method I: Preparation of ((N-Me)A)-IC+SRSLP-(Oic)-I-(Pen)+IP-((N-Benzyl)D)-$NH_2$ (Example 462)
N-[(6S,9S,12S,15S,18R,23R,26S,28aS,29aS,33aS,35aS)-26-[(2S)-butan-2-yl]-12-(3-carbamimidamidopropyl)-9,15-bis(hydroxymethyl)-22,22-dimethyl-18-[(N-methyl-L-alanyl-L-isoleucyl)amino]-6-(2-methylpropyl)-5,8,11,14,17,25,28,35-octaoxodotriacontahydro-1H,5H,22H-pyrrolo[2',1':13,14][1,2,5,8,11,14,17,20,23,26]dithiaoctaazacyclononacosino [11,10-a]indole-23-carbonyl]-L-isoleucyl-L-prolyl-$N^4$-benzyl-L-aspartamide
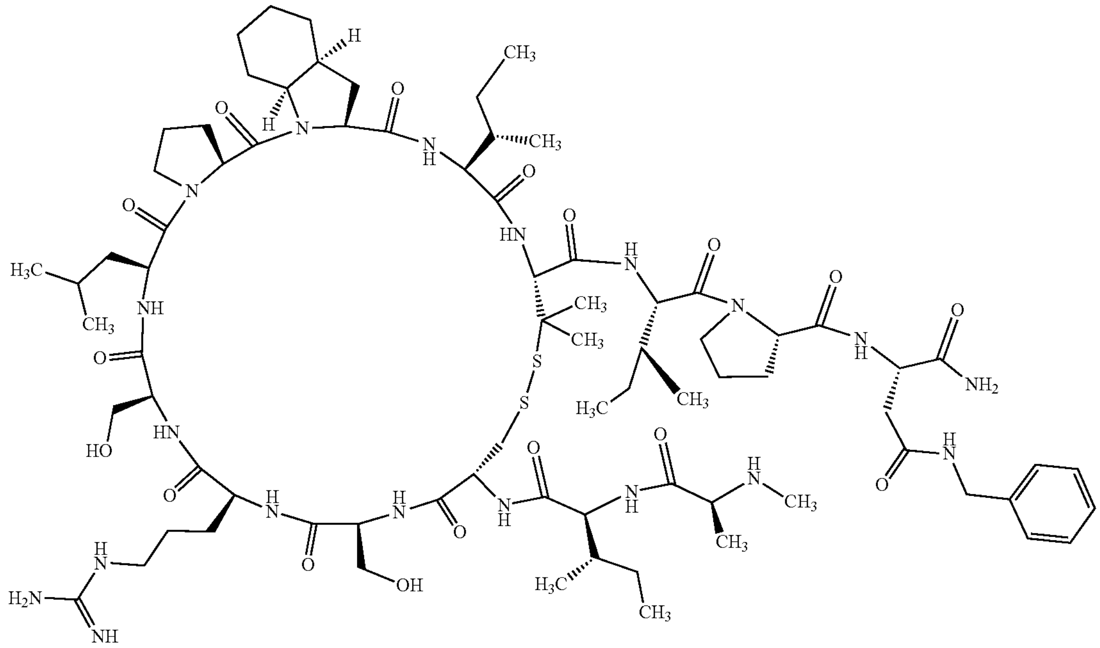 [SMILES: CC[C@@H](C)[C@H](NC(=O)[C@H]1NC(=O)[C@H]([C@@H](C)CC)NC(=O)[C@@H]2C[C@@H]3CCCC[C@@H]3N2C(=O)[C@@H]2CCCN2C(=O)[C@H](CC(C)C)NC(=O)[C@H](CO)NC(=O)[C@H](CCCNC(=N)N)NC(=O)[C@H](CO)NC(=O)[C@@H](NC(=O)[C@@H](NC(=O)[C@H](C)NC)[C@@H](C)CC)CSSC1(C)C)C(=O)N1CCC[C@H]1C(=O)N[C@@H](CC(=O)NCc1ccccc1)C(N)=O]

The peptide was prepared on Rink Amide MBHA resin (loading typically around 0.4-0.6 mmol/g) on 0.3 mmol scale. The first amino acid Fmoc-Asp(2-Phenylisopropyl ester)-OH (CAS 200336-86-3) was added to the resin using the method described in Method C. The peptide sequence was constructed using the steps described in Method C. Upon completion of the sequence, the 2-OPP protecting group was removed using 1% TFA in DCM, 30 minutes. N-Benzyl amine (3 equiv), DIC (3 equiv) and Oxyma (3 equiv) was added and the mixture was shaken for 2 hours. The peptide was cleaved, the disulfide bond was formed, and the peptide was purified according to Method C.

General Method J. Preparation of ((N-Me)G)-IC+SRSLP-(Oic)-I-(Pen)+IP-(*Dap)-OH (Example 467)

N-[(6S,9S,12S,15S,18R,23R,26S,28aS,29aS,33aS,35aS)-26-[(2S)-butan-2-yl]-12-(3-carbamimidamidopropyl)-9,15-bis(hydroxymethyl)-22,22-dimethyl-18-[(N-methylglycyl-L-isoleucyl)amino]-6-(2-methylpropyl)-5,8,11,14,17,25,28,35-octaoxodotriacontahydro-1H,5H,22H-pyrrolo[2',1':13,14][1,2,5,8,11,14,17,20,23,26]dithiaoctaazacyclononacosino[11,10-a]indole-23-carbonyl]-L-isoleucyl-N-[(2S)-2-amino-2-carboxyethyl]-L-prolinamide

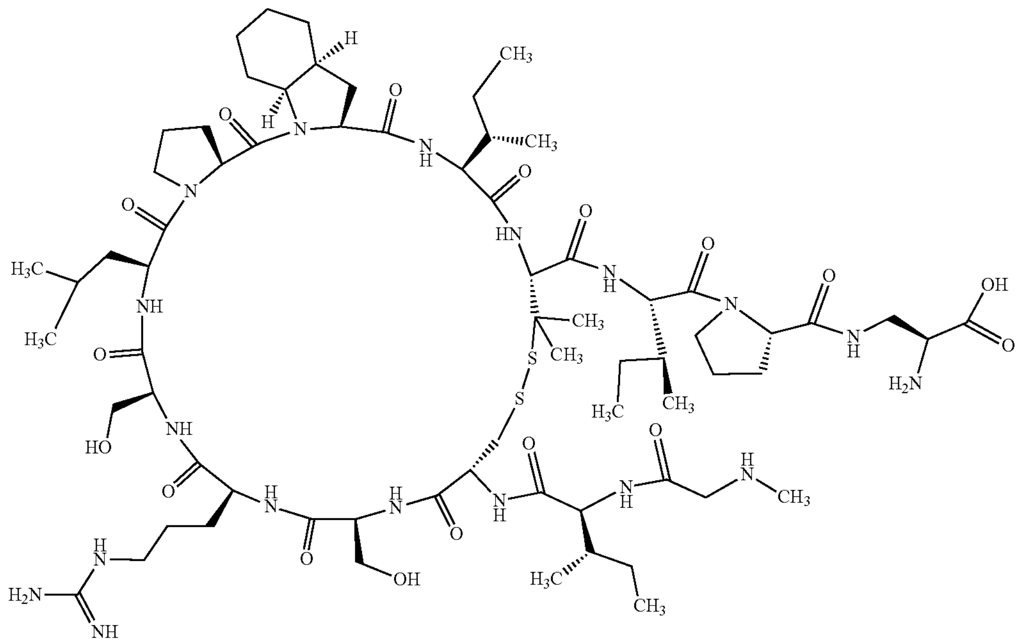

The peptide was prepared on 2-chlorotrityl resin according to Method C. BOC-Dap(Fmoc)-OH (CAS 122235-70-5) was added onto the resin according to Method C. The peptide was constructed and purified according to method C.

General Method K. Preparation of (2-(Morpholine) acetyl)-IC+SRS-((tBu)A)-PPI-(Pen)+IPD-NH2 (Example 283)

Example 27A

N-(bromoacetyl)-L-isoleucyl-L-cysteinyl-L-seryl-L-arginyl-L-seryl-4-methyl-L-leucyl-L-prolyl-L-prolyl-L-isoleucyl-3-sulfanyl-L-valyl-L-isoleucyl-L-prolyl-L-alpha-asparagine

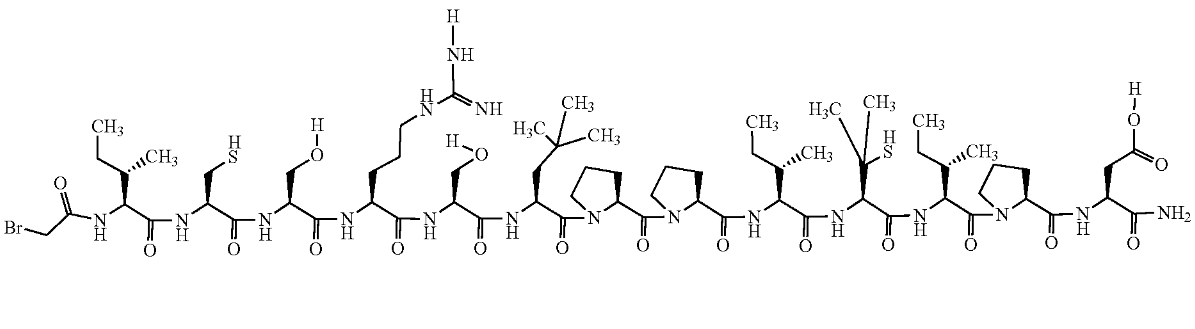 [SMILES: CC[C@H](C)[C@H](NC(=O)CBr)C(=O)N[C@@H](CS)C(=O)N[C@@H](CO)C(=O)N[C@@H](CCCNC(=N)N)C(=O)N[C@@H](CO)C(=O)N[C@@H](CC(C)(C)C)C(=O)N1CCC[C@H]1C(=O)N1CCC[C@H]1C(=O)N[C@H](C(=O)N[C@H](C(=O)N[C@H](C(=O)N1CCC[C@H]1C(=O)N[C@@H](CC(=O)O)C(N)=O)[C@@H](C)CC)C(C)(C)S)[C@@H](C)CC]

The sequence IC+SRS-((tBu)A)-PPI-(Pen)+IPD-NH2 was prepared 12 times on Rinkamide ChemMatrix resin at 0.1 mmol scale according to Method A. To the resin-containing peptide (200 mg 100 μmol) was added N,N'-diisopropylcarbodiimide (31 μL, 200 μmol), ethyl(hydroximino)cyanoacetate (28.4 mg, 200 μmol) and bromoacetic acid (14 μL, 200 μmol) and the mixture was shaken in 5 mL DMF overnight at room temperature on a thermomixer shaker. The resin was filtered, washed with DMF (6×5 mL), washed with DCM (6×5 mL) and then dried under vacuum for the next step.

Example 283

N-[(5aS,11S,14S,17S,20S,23R,28R,31S,33aS)-31-[(2S)-butan-2-yl]-17-(3-carbamimidamidopropyl)-11-(2,2-dimethylpropyl)-14,20-bis(hydroxymethyl)-27,27-dimethyl-23-({N-[(morpholin-4-yl)acetyl]-L-isoleucyl}amino)-5,10,13,16,19,22,30,33-octaoxooctacosahydro-1H,5H,10H-dipyrrolo[2,1-j:2',1'-m][1,2,5,8,11,14,17,20,23,26]dithiaoctaazacyclononacosine-28-carbonyl]-L-isoleucyl-L-prolyl-L-alpha-asparagine

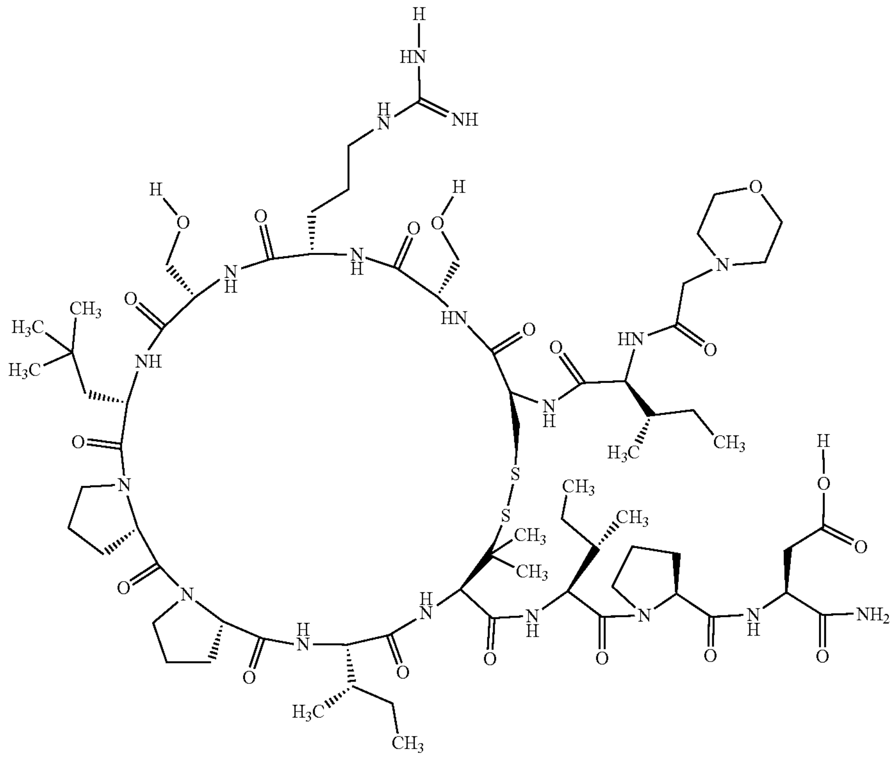

To example 27a (200 mg, 74% purity, 77.7 μmol) in NMP (10 mL) was added morpholine (34 μl, 390 μmol) and the suspension was shaken at 37° C. in thermomixer. The solid resin was collected by filtration, washed with 10 mL DMF and 10 mL dichloromethane each two times. The residue was treated with TFA/EDT/thionaisol (90:3:7) and shaken 2 h at room temperature. The reaction mixture was treated with cold diethyl ether (−10° C.), and then the suspension was centrifuged under nitrogen and washed three times (3x30 mL) with cold diethylether. To the residue was added a 0.1 M aqueous ammonium bicarbonate solution (400 mL) and the reaction mixture was shaken overnight in an open-to-the-air round-bottomed flask. The solution was lyophilized and the lyophilized powder was purified according to Method A, to provide 20.4 mg (98% purity, 16% yield) of example 283.

Example 300 (2-Hydroxyacetyl)-IC+SRS-((tBu)A)-PPI-(Pen)+IPD-$NH_2$ was isolated as a by-product.

General Method L. Preparation of Sodium and Choline Salt Forms

These salts were prepared from salt-free form peptides. The two examples below are representative of the general method:

Example 431

N-[(6S,9S,12S,15S,18R,23R,26S,28aS,29aS,33aS,35aS)-18-[(L-alanyl-L-isoleucyl)amino]-26-[(2S)-butan-2-yl]-12-(3-carbamimidamidopropyl)-9,15-bis(hydroxymethyl)-22,22-dimethyl-6-(2-methylpropyl)-5,8,11,14,17,25,28,35-octaoxodotriacontahydro-1H,5H,22H-pyrrolo[2',1':13,14][1,2,5,8,11,14,17,20,23,26]dithiaoctaazacyclononacosino[11,10-a]indole-23-carbonyl]-L-isoleucyl-N-[(1S)-1,2-dicarboxylatoethyl]-L-prolinamide, Sodium salt

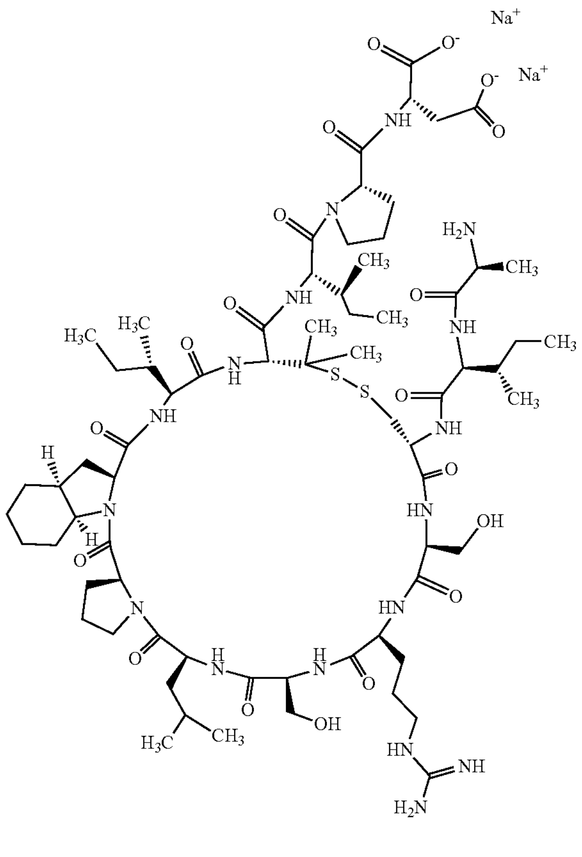 [SMILES: [Na+] ; CC[C@H](C)[C@H](NC(=O)[C@H](C)N)C(=O)N[C@H]1CSSC(C)(C)[C@@H](C(=O)N[C@H](C(=O)N2CCC[C@H]2C(=O)N[C@@H](CC(=O)[O-])C(=O)[O-])[C@@H](C)CC)NC(=O)[C@H]([C@@H](C)CC)NC(=O)[C@@H]2C[C@@H]3CCCC[C@@H]3N2C(=O)C[C@@H]2CCCN2C(=O)[C@H](CC(C)C)NC(=O)[C@H](CO)NC(=O)[C@H](CCCNC(=N)N)NC(=O)[C@H](CO)NC1=O ; [Na+]]

Sequence: AIC+SRSLP-(Oic)-I-(Pen)+IPD-OH (sodium salt) (Example 431)

To a solution of AIC+SRSLP-(Oic)-I-(Pen)+IPD-OH (salt-free form) (100 mg) in 20 mL acetonitrile/water 1:1 was added 1.3 mL of a 0.1 M sodium hydroxide solution. The mixture was dried under vacuum to give 109 mg (104% yield, 99% purity) of the target compound.

LC-MS (MCW-TOF-AQ-YMC-18 min): $R_t$=8.62 min; MS (ESIpos): m/z=783 [M+2H]2+

Ion chromatography (sodium content): 2.9% sodium=2.03 equiv

Example 432

N-[(6S,9S,12S,15S,18R,23R,26S,28aS,29aS,33aS,35aS)-18-[(L-alanyl-L-isoleucyl)amino]-26-[(2S)-butan-2-yl]-12-(3-carbamimidamidopropyl)-9,15-bis(hydroxymethyl)-22,22-dimethyl-6-(2-methylpropyl)-5,8,11,14,17,25,28,35-octaoxodotriacontahydro-1H,5H,22H-pyrrolo[2',1':13,14][1,2,5,8,11,14,17,20,23,26]dithiaoctaazacyclononacosino[11,10-a]indole-23-carbonyl]-L-isoleucyl-N-[(1S)-1,2-dicarboxylatoethyl]-L-prolinamide, 2-Hydroxy-N,N,N-trimethylethan-1-ammonium) (choline) salt

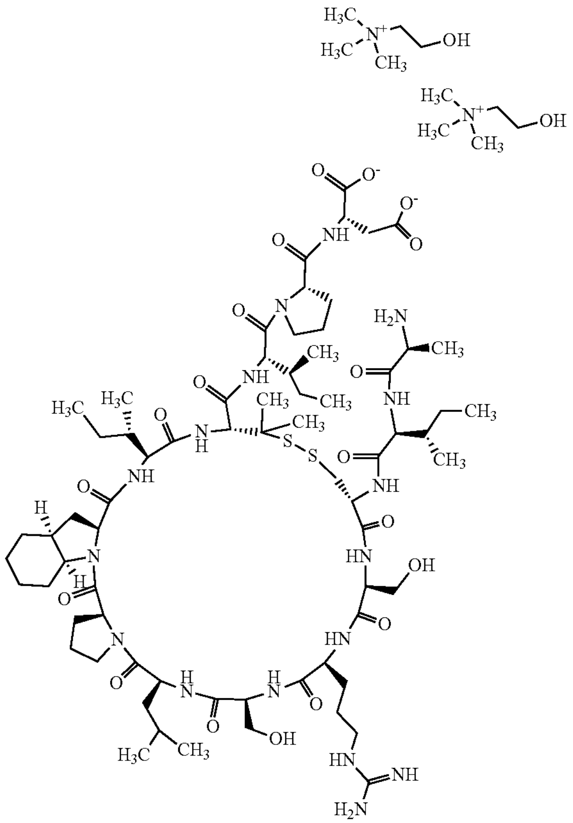

To a solution of AIC+SRSLP-(Oic)-I-(Pen)+IPD-OH (salt-free form) (100 mg) in 20 mL acetonitrile/water 1:1 was added 511 μL of a 0.25 M choline hydroxide solution. The mixture was dried under vacuum to give 122 mg (105% yield, 99% purity) of the target compound.

LC-MS (MCW-TOF-AQ-YMC-18 min): $R_t$=8.65 min; MS (ESIpos): m/z=783 [M+2H]2+

Ion chromatography (choline content): 11.7% choline=1.97 equiv

Example 13

AIC+SRSLP-(Oic)-I-(Pen)+IPD-OH (Example 13)

(3S)-4-amino-3-({(2S)-1-[(2S,3S)-2-{[(2R)-2-{[(2S,3S)-2-{[(2S,3aS,7aS)-1-{(2S)-1-[(2S,5S,8S,11S,14R,17S,20S)-20-amino-17-[(2S)-butan-2-yl]-8-(3-carbamimidamidopropyl)-5,11-bis(hydroxymethyl)-2-(2-methylpropyl)-4,7,10,13,16,19-hexaoxo-14-(sulfanylmethyl)-3,6,9,12,15,18-hexaazahenicosanan-1-oyl]pyrrolidine-2-carbonyl}octahydro-1H-indole-2-carbonyl]amino}-3-methylpentanoyl]amino}-3-methyl-3-sulfanylbutanoyl]amino}-3-methylpentanoyl]pyrrolidine-2-carbonyl}amino)-4-oxobutanoic acid

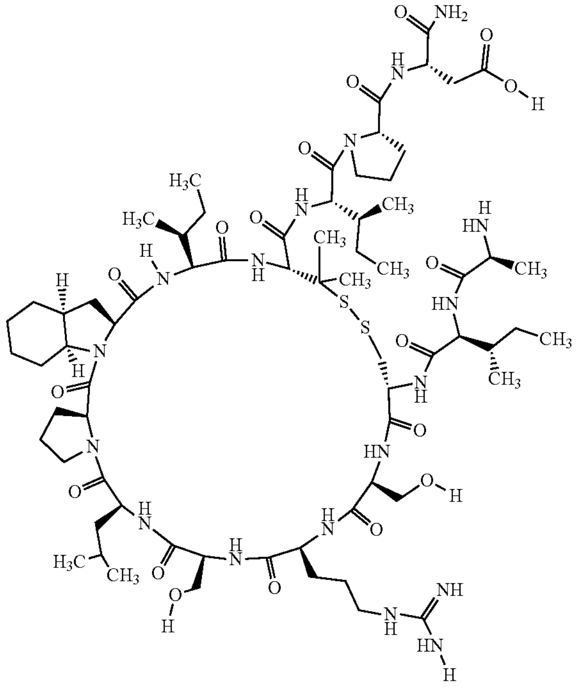

Peptide Synthesis

The peptide was synthesized using standard Fmoc chemistry.

1) Resin preparation: to the CTC Resin (15.0 mmol, 15.0 g, 1.0 mmol/g) was added Fmoc-Asp(OtBu)-OH (15.0 mmol, 6.17 g, 1.0 eq) and DIEA (10.4 mL, 60.0 mmol, 4.0 eq) in DCM (300 mL). The mixture was agitated with $N_2$ for 2 h at 20° C. Methanol was then added (15.0 mL) and the resin agitated with $N_2$ for another 30 min. The resin was washed with DMF (300 mL×3). Then a solution of 20% piperidine in DMF (300 mL) was added and the mixture was agitated with $N_2$ for 20 mH at 20° C. Then the mixture was filtered to give the resin. The resin was washed with DMF (300 mL×3) and filtered to give the resin.

2) Coupling: Fmoc-Pro-OH (15.2 g, 45.0 mmol, 3.0 eq), HBTU (16.2 g, 42.8 mmol, 2.85 eq) and DIEA (90.0 mmol, 15.6 mL, 6.00 eq) in DMF (100 mL) was added to the resin and the resin was agitated with $N_2$ for 30 mq at 20° C. The resin was then washed with DMF (300 mx5).

3) Deprotection: 20% piperidine in DMF (300 mL) was added to the resin and the mixture was agitated with $N_2$ for 20 min at 20° C.

4) Steps 2 and 3 were repeated for all other amino acids:

TABLE 11

Reagents used for example 13

| # | Materials | Coupling reagents | Coupling time | Supplier |
|---|---|---|---|---|
| 1 | Fmoc-Asp(OtBu)-OH (1.0 eq) | DIEA (4.0 eq) | 2.0 h | GL Biochem (shanghai) Ltd |
| 2 | Fmoc-Pro-OH (3.0 eq) | HBTU (2.85 eq) DIEA (6.0 eq) | 30 min | GL Biochem (shanghai) Ltd |
| 3 | Fmoc-Ile-OH (3.0 eq) | HBTU (2.85 eq) DIEA (6.0 eq) | 30 min | GL Biochem (shanghai) Ltd |
| 4 | Fmoc-Pen(Trt)-OH (3.0 eq) | HBTU (2.85 eq) DIEA (6.0 eq) | 30 min | GL Biochem (shanghai) Ltd |
| 5 | Fmoc-Ile-OH (3.0 eq) | HBTU (2.85 eq) DIEA (6.0 eq) | 30 min | GL Biochem (shanghai) Ltd |
| 6 | Fmoc-Oic-OH (3.0 eq) | HBTU (2.85 eq) DIEA (6.0 eq) | 30 min | GL Biochem (shanghai) Ltd |
| 7 | Fmoc-Pro-OH (3.0 eq) | HBTU (2.85 eq) DIEA (6.0 eq) | 30 min | GL Biochem (shanghai) Ltd |
| 8 | Fmoc-Leu-OH (3.0 eq) | HBTU (2.85 eq) DIEA (6.0 eq) | 30 min | GL Biochem (shanghai) Ltd |
| 9 | Fmoc-Ser(tBu)-OH (3.0 eq) | HBTU (2.85 eq) DIEA (6.0 eq) | 30 min | GL Biochem (shanghai) Ltd |

TABLE 11-continued

| Reagents used for example 13 | | | | |
|---|---|---|---|---|
| # | Materials | Coupling reagents | Coupling time | Supplier |
| 10 | Fmoc-Arg(Pbf)-OH (3.0 eq) | HBTU (2.85 eq) DIEA (6.0 eq) | 30 min | Chengdu aminotp Pharmaceutical Technology Ltd |
| 11 | Fmoc-Ser(tBu)-OH (3.0 eq) | HBTU (2.85 eq) DIEA (6.0 eq) | 30 min | GL Biochem (shanghai) Ltd |
| 12 | Fmoc-Cys(Trt)-OH (3.0 eq) | HBTU (2.85 eq) DIEA (6.0 eq) | 30 min | GL Biochem (shanghai) Ltd |
| 13 | Fmoc-Ile-OH (3.0 eq) | HBTU (2.85 eq) DIEA (6.0 eq) | 30 min | GL Biochem (shanghai) Ltd |
| 14 | Fmoc-Ala-OH (3.0 eq) | HBTU (2.85 eq) DIEA (6.0 eq) | 30 min | GL Biochem (shanghai) Ltd |

20% piperidine in DMF was used for Fmoc deprotection for 30 min. The coupling reaction was monitored by ninhydrin (all amino acids except Pro) and chloranil test (Pro), and the resin was washed with DMF (300 mL) for 5 times.

HBTU, DIEA supplier: Suzhou Highfine Biotech Co., Ltd

Peptide Cleavage and Purification

5) The resin was washed with MeOH (300 mL×5) and dried under vacuum to get 41.5 g of the peptide resin. Then 400 mL of cleavage buffer (92.5% TFA/2.5%3-mercaptopropionic acid/2.5% TIS/2.5% $H_2O$) was added to the flask containing the side chain protected peptide resin at 20° C. and the mixture was stirred for 2.5 h and then filtered.

6) The peptide was precipitated with cold tert-butyl methyl ether (4000 mL) and centrifuged (3 min at 3000 rpm) to get the crude solid peptide. The crude peptide precipitate was washed with tert-butyl methyl ether three more times (1000 mL×3). The crude peptide was then dried under vacuum for 2.0 h to give 21.8 g of the crude peptide.

7) The crude peptide (21.8 g) was dissolved in $CH_3CN$ (6.5 L) and water (6.5 L). I2 (0.1 M in MeOH, 55 mL) was added at 20° C. until a yellow color persisted. Then the mixture was stirred at 20° C. for 2 min. Sodium thiosulfate solution (0.1 M in water, 15 mL) was then added dropwise until the yellow color disappeared. The mixture was then lyophilized to give the crude powder (22.7 g).

8) Purification of the crude peptide by preparative HPLC (condition: A: 0.075% TFA in water B: $CH_3CN$), collection of product-containing fractions, and the lyophilization gave the target peptide (Sequence ID 13); (4305.1 mg, 18.3% yield, 99.1% by 110 Å C18 RP-HPLC column (Gemini C18 5 μm 110 Å 150×4.6 mm); 97.8% by 300 Å C18 RP-HPLC column (Discovery BIO Wide Pore C18 5 μm 300 Å 150×4.6 mm), TFA salt) as a white solid.

TABLE 12

| Purification conditions | |
|---|---|
| | Purification condition |
| Dissolution condition | TFA/$H_2O$ = 7/3 |
| Instrument | Gilson GX-281 |
| Mobile Phase | A: $H_2O$ (A: 0.075% TFA in $H_2O$, B: ACN) B: $CH_3CN$ |
| Gradient | 13-43%-60 min Retention time: 40 min |
| Column | Luna 25 × 200 mm, C18 10 μm, 110 Å + Gemini 150 × 30 mm, C18 5 μm, 110 Å |
| Flow Rate | 20 mL/Min |
| Wavelength | 214/254 nm |
| Oven Temperature | 30° C. |

LC-MS: Rt=1.369 min; 1564 [M+2H]+

Rt=8.72 min (99.1% pure) Gemini C18 5 m 110 Å 150×4.6 mm

Rt=9.42 min (97.8%) Discovery BIO Wide Porei C18 5 m 300 Å 150×4.6 mm

From example 13 (TFA salt), example 29 (HCl salt) can be prepared using General Method F; example 5 (salt-free form) can be prepared using General Method G. The preparations of example 431 (sodium salt) and example 432 (choline salt) from example 5 are shown below as Example 431 and Example 432, respectively.

Example 237

AIC+SRSL-(L-dehydroproline)-(Oic)-I-(Pen)+IPD-OH (Example 237)

N-[(6S,9S,12S,15S,18R,23R,26S,28aS,35aS)-18-[(L-alanyl-L-isoleucyl)amino]-26-[(2S)-butan-2-yl]-12-(3-carbamimidamidopropyl)-9,15-bis(hydroxymethyl)-22,22-dimethyl-6-(2-methylpropyl)-5,8,11,14,17,25,28,35-octaoxo-6,7,8,9,10,11,12,13,14,15,16,17,18,19,23,24,25,26,27,28,28a,29,29a,30,31,32,33,33a,35,35a-triacontahydro-3H,5H,22H-pyrrolo[2',1':13,14][1,2,5,8,11,14,17,20,23,26]dithiaoctaazacyclononacosino[11,10-a]indole-23-carbonyl]-L-isoleucyl-L-prolyl-L-aspartic acid

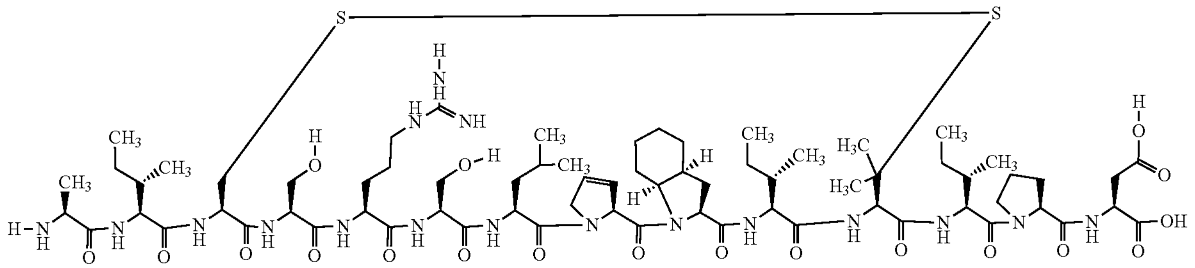 [SMILES: CC[C@H](C)[C@H](NC(=O)[C@H](C)N)C(=O)N[C@H]1CSSC(C)(C)[C@@H](C(=O)N[C@H](C(=O)N2CCC[C@H]2C(=O)N[C@@H](CC(=O)O)C(=O)O)[C@@H](C)CC)NC(=O)[C@H]([C@@H](C)CC)NC(=O)[C@@H]2C[C@@H]3CCCC[C@@H]3N2C(=O)[C@@H]2C=CCN2C(=O)[C@H](CC(C)C)NC(=O)[C@H](CO)NC(=O)[C@H](CCCNC(=N)N)NC(=O)[C@H](CO)NC1=O]

The peptide was prepared according to Method C (3.12 g). The analytical data for this peptide is shown in Table 16 and Table 17.

Example 142

AIC+SRSL-(Pro-D2)-(Oic)-I-(Pen)+IPD-OH (Example 142)

N-[(1R,2S,6S,9S,12S,15S,18R,23R,26S,28aS,35aS)-18-[(L-alanyl-L-isoleucyl)amino]-26-[(2S)-butan-2-yl]-12-(3-carbamimidamidopropyl)-9,15-bis(hydroxymethyl)-22,22-dimethyl-6-(2-methylpropyl)-5,8,11,14,17,25,28,35-octaoxo(1,2-$^{2}H_2$)dotriacontahydro-1H,5H,22H-pyrrolo[2',1':13,14][1,2,5,8,11,14,17,20,23,26]dithiaoctaazacyclononacosino[11,10-a]indole-23-carbonyl]-L-isoleucyl-L-prolyl-L-aspartic acid

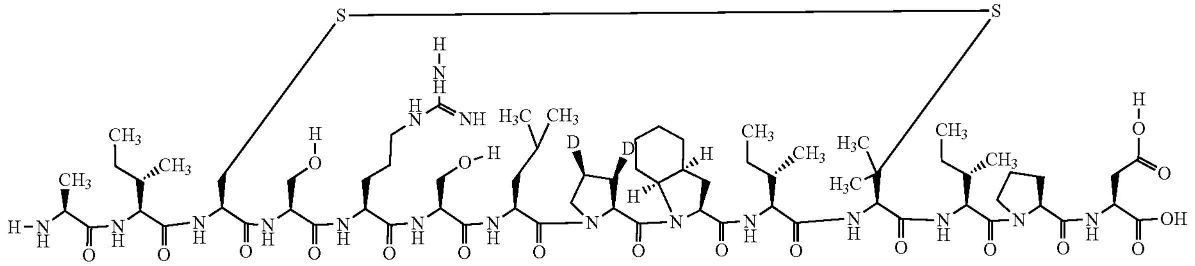 [SMILES: [2H][C@@H]1[C@H]([2H])CN2C(=O)[C@H](CC(C)C)NC(=O)[C@H](CO)NC(=O)[C@H](CCCNC(=N)N)NC(=O)[C@H](CO)NC(=O)[C@@H](NC(=O)[C@@H](NC(=O)[C@H](C)N)[C@@H](C)CC)CSSC(C)(C)[C@@H](C(=O)N[C@H](C(=O)N3CCC[C@H]3C(=O)N[C@@H](CC(=O)O)C(=O)O)[C@@H](C)CC)NC(=O)[C@H]([C@@H](C)CC)NC(=O)[C@@H]3C[C@@H]4CCCC[C@@H]4N3C(=O)[C@H]12]

The peptide from Example 237 (30 mg, 19.2 μmol) was dissolved in methanol-d4 (3 mL) (99.8% purity of D). Rhodium black (CAS 7440-16-6, ACBR, Article No. AB25746) (10 mol %, 1.9 μmol) was added to the solution under argon in an M-Braun Glovebox. The 8 mL reaction vial mixture was placed into an MTP pressure reactor block that is located on a Chemspeed Swing XL platform and is enclosed inside an M-Braun glovebox (Chemspeed Technologies AG, Wölferstrasse 8, 4414 Fullinsdorf, Switzerland, chemspeed@chemspeed.com). The reaction was shaken with an orbital speed of 650 rpm at room temperature under a pressure of 3 bar of deuterium gas for 16 h overnight. The pressure block was purged with argon and the vial was removed from the reactor block. The methanol-d4 was evaporated with a rotary evaporator and the resulting solid was dissolved in water (2 mL) and stirred for 1 hour to exchange the exchangeable deuterium atoms with hydrogen. After 1 hour, acetonitrile was added and the product was purified by reversed-phase HPLC [column: Phenomenex *Aeris* Peptide 5μ XB—C18, AXIA Packed, 21.2×250 mm+Cartridge 5μ, flow: 20 mL/min, focused gradient using $H_2O$/ACN with 0.1% TFA as acidic modifier. FOK30-40: 0 min 5% ACN, 0-13 min ramp to 30% ACN, 13-39 min flat ramp to 40% ACN, 39-46 min isocratic 40% ACN]. Chromatography fractions containing the product were analyzed by analytical HPLC (focused gradient) and by LC-MS and then pooled accordingly to provide two fractions of the pure product: 11.4 mg (90% purity, 34% yield) and 4.2 mg (99% purity, 14% yield). The analytical data for this peptide is in Table 16.

The product peptide was subjected to trypsin digestion followed by reaction with dithiothreitol and the resulting fragments were analyzed by TOF-MS-MS. Trypsin digestion cleaved the peptide between the arginine and serine (exact mass 1583.8384, found 1583.852 [M+2H]2+). Reaction with dithiothreitol produced two fragments, AICSR-OH (exact mass 548.2741, found 548.283 $[M+H]^+$) and SL-(Pro-D2)(Oic)-I-(Pen)+IPD-OH (exact mass 1037.5800, found 1038.587 $[M+H]^+$), with the fragments at 838.47 amu ((Pro-D2)-(Oic)-I-(Pen)+IPD-OH) and at 738.40 amu SL-((Oic)-I-(Pen)+IPD-OH) verifying the position of the deuterium atoms.

Example 28A

(2S,3aS,6aS)-Octahydrocyclopenta[b]pyrrole-2-carboxylic acid-hydrogen chloride (1/1) (single steremoisomer)

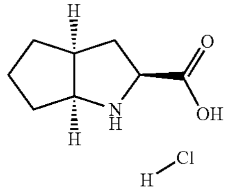

The reaction was performed under argon atmosphere. To palladium on carbon (200 mg, 10%) was added 20 mL methanol and benzyl (2S,3aS,6aS)-octahydrocyclopenta[b]pyrrole-2-carboxylate-hydrogen chloride (1/1) (1.00 g, 3.55 mmol). The reaction flask was charged with hydrogen gas (1 atm) and the reaction mixture was stirred under hydrogen atmosphere overnight at room temperature. The reaction mixture was filtered over diatomaceous earth and the filter cake was washed with methanol. The filtrate was evaporated and dried under vacuum to give 698 mg of the target compound.

(2S,3aS,6aS)-octahydrocyclopenta[b]pyrrole-2-carboxylic acid is also commercially available as a salt free form.

Example 29A

(2S,3aS,6aS)-1-{[(9H-Fluoren-9-yl)methoxy]carbonyl}octahydrocyclopenta[b]pyrrole-2-carboxylic acid (single steremoisomer)

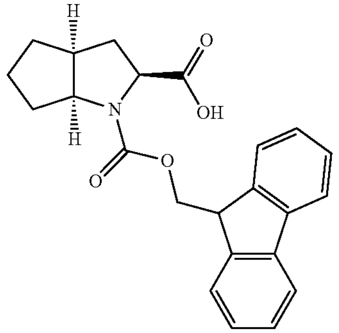 [SMILES: O=C(O)[C@@H]1C[C@@H]2CCC[C@@H]2N1C(=O)OCC1c2ccccc2-c2ccccc21]

To (2S,3aS,6aS)-octahydrocyclopenta[b]pyrrole-2-carboxylic acid-hydrogen chloride (1/1) (680 mg, 3.55 mmol) in 12 mL water was added sodium bicarbonate (2.98 g, 35.5 mmol) and a solution of 1-({[(9H-fluoren-9-yl)methoxy]carbonyl}oxy)pyrrolidine-2,5-dione (Fmoc-OSu) (1.26 g, 3.73 mmol) in 18 mL acetone. The reaction mixture was stirred overnight at room temperature. The reaction mixture was treated with water, acidified with 1 M hydrochloric acid and extracted with ethyl acetate two times. The organic phase was washed with saturated aqueous sodium chloride solution, dried over magnesium sulfate, filtrated and then evaporated. The residue was separated via silica gel chromatography (Biotage Isolera, column: 50 g SNAP Ultra; eluent: diechloromethan/methanol 100:2-100:5). The appropriate fractions were combined, evaporated and dried under vacuum to give 1.27 g (99% purity, 94% yield) of the target compound.

LC-MS (Method 10): $R_t$=2.08 min; MS (ESI pos): m/z=378 $[M+H]^+$ $^1$H-NMR (400 MHz, DMSO-d6) δ[ppm]: 1.260 (1.76), 1.274 (1.85), 1.299 (1.78), 1.321 (2.09), 1.335 (2.38), 1.440 (0.92), 1.455 (1.10), 1.473 (0.87), 1.521 (3.61), 1.537 (3.86), 1.551 (2.28), 1.607 (4.53), 1.620 (3.68), 1.640 (3.08), 1.653 (1.66), 1.712 (2.02), 1.781 (1.38), 1.816 (2.30), 1.827 (2.26), 1.839 (2.37), 1.855 (1.68), 2.073 (1.20), 2.305 (0.83), 2.328 (1.99), 2.351 (1.35), 2.360 (1.64), 2.384 (0.92), 2.468 (0.60), 2.606 (1.50), 2.670 (1.11), 3.860 (0.94), 3.874 (1.94), 3.893 (1.95), 3.907 (0.92), 4.143 (2.61), 4.156 (3.68), 4.167 (5.16), 4.186 (5.89), 4.266 (1.43), 4.280 (3.20), 4.294 (2.11), 4.345 (1.31), 4.371 (3.19), 4.386 (3.83), 4.396 (4.39), 4.411 (3.74), 4.422 (2.40), 4.437 (0.98), 7.292 (0.97), 7.311 (3.89), 7.329 (6.99), 7.346 (6.08), 7.363 (2.49), 7.395 (9.91), 7.414 (16.00), 7.432 (6.98), 7.663 (9.73), 7.680 (6.46), 7.879 (12.31), 7.897 (11.49), 12.586 (0.80).

Example 30A (1R,3S,5R)-2-azabicyclo[3.1.0]hexane-3-carboxylic acid (single stereoisomer)

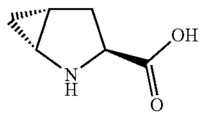

(1R,3S,5R)-2-(tert-butoxycarbonyl)-2-azabicyclo[3.1.0]hexane-3-carboxylic acid (CAS RN: 197142-34-0, 500 mg) was dissolved in 4M HCl-dioxane solution (3 mL) and stirred for 8 h at room temperature. The solvent was evaporated and the crude product was used directly for the next step Example 31A (1R,3S,5R)-2-{[(9H-fluoren-9-yl)methoxy]carbonyl}-2-azabicyclo[3.1.0]hexane-3-carboxylic acid (single stereoisomer)

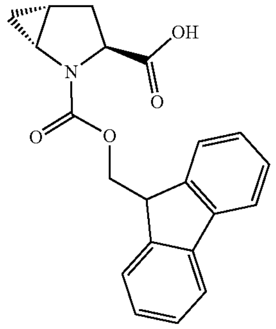 [SMILES: O=C(O)[C@@H]1C[C@H]2C[C@H]2N1C(=O)OCC1c2ccccc2-c2ccccc21]

To a solution of (1R,3S,5R)-2-azabicyclo[3.1.0]hexane-3-carboxylic acid (Example 30A, 280 mg, 2.20 mmol) in 3 mL water was added sodium bicarbonate (1.85 g, 22.0 mmol) and a solution of 1-({[(9H-fluoren-9-yl)methoxy]carbonyl}oxy)pyrrolidine-2,5-dione (0.78 g, 2.31 mmol) in 4.5 mL acetone. The reaction mixture was stirred overnight at room temperature. The reaction mixture was treated with water and extracted with twice with ethyl acetate. The organic phase was washed with saturated aqueous sodium chloride solution, dried over magnesium sulfate, filtrated, and then concentrated. The crude product was purified by preparative reversed-phase HPLC (Column: Reprosil; C18; 10 μm; 125×30 mm; eluant A: CAN, eluant B: water with 0.1% formic), and the product-containing fractions were combined and lyophilized to give 88.0 mg (96% purity, 11% yield) of the target compound.

LC-MS (Method 11): $R_t$=1.32 min; MS (ESI pos): m/z=372 $[M+Na]^+$ $^1$H-NMR (400 MHz, DMSO-d6) δ[ppm]: −0.149 (1.15), −0.008 (10.73), 0.008 (9.13), 0.146 (1.21), 0.468 (1.54), 0.534 (3.66), 0.803 (4.38), 1.682 (2.68), 2.072 (0.75), 2.128 (2.19), 2.142 (2.32), 2.223 (1.05), 2.293 (2.19), 2.327 (4.45), 2.349 (2.68), 2.366 (2.75), 2.523 (3.89), 2.670 (1.44), 2.710 (1.31), 2.816 (0.82), 3.413 (3.93), 3.757 (1.83), 4.010 (2.91), 4.140 (2.39), 4.211 (3.11), 4.285 (12.30), 6.929 (0.43), 6.950 (0.43), 7.340 (9.91), 7.358 (6.02), 7.406 (10.08), 7.425 (16.00), 7.443 (7.10), 7.650 (2.85), 7.702 (4.52), 7.724 (5.53), 7.746 (3.40), 7.892 (12.40), 7.910 (9.85), 12.680 (0.65).

This amino acid was used in Fmoc SPPS. This fmoc amino acid is also commercially available.

Example 32A

Benzyl (2R,4R)-4-[(2S)-butan-2-yl]-2-tert-butyl-5-oxo-1,3-oxazolidine-3-carboxylate (single stereoisomer)

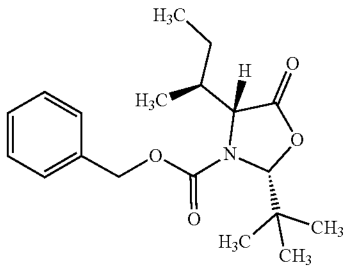 [SMILES: CC[C@H](C)[C@@H]1C(=O)O[C@H](C(C)(C)C)N1C(=O)OCc1ccccc1]

To a suspension of D-alloisoleucine (8.06 g, 61.4 mmol) in 120 mL ethanol, was added a sodium hydroxide solution made from 2.45 g sodium hydroxide in 11 mL water. The reaction mixture was stirred 90 min at room temperature and then evaporated. The residue was treated with 195 mL pentane and then 2,2-dimethylpropanal (10 mL, 92 mmol) was added. The reaction mixture was stirred 24 h at 45° C. with a Dean-Stark trap attached to the round-bottomed flask. After cooling, the solvents were evaporated and the residue was dried several times with toluene (azeotropic distillation). The residue was treated with 165 mL dichloromethane and cooled to 0° C. Benzyl carbonochloridate (13 mL, 92 mmol) was added and the the reaction mixture was stirred for one week at 0-4° C. 4-Dimethylaminopyridine (375 mg, 3.1 mmol) and 65 mL water were added to the reaction mixture, the reaction mixture was allowed to come to room temperature and then it was stirred overnight at room temperature. The reaction mixture was treated with ethyl acetate several times and extracted. The combined organic phase was washed twice with 10% aqueous citric acid and then twice with saturated aqueous sodium bicarbonate solution. The aqueous phase was reextracted with ethyl acetate. The combined organic phases were washed with saturated aqueous sodium chloride solution, dried over magnesium sulfate, filtrated and then evaporated. The residue was purified via silica gel chromatography (Isolera; eluent: cyclohexane/ethyl acetate 100:3-100:7). The product-containing fractions were combined, evaporated and then dried under vacuum to give 8.71 g of the target compound.

Example 33A

Benzyl (2R,4R)-4-[(2S)-butan-2-yl]-2-tert-butyl-4-methyl-5-oxo-1,3-oxazolidine-3-carboxylate (single stereoisomer)

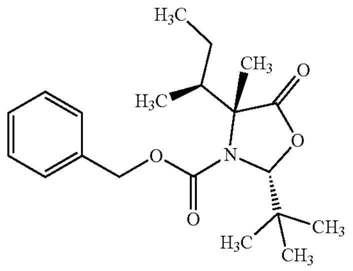 [SMILES: CC[C@H](C)[C@]1(C)C(=O)O[C@H](C(C)(C)C)N1C(=O)OCc1ccccc1]

The reaction was carried out under argon atmosphere. Benzyl (2R,4R)-4-[(2S)-butan-2-yl]-2-tert-butyl-5-oxo-1,3-oxazolidine-3-carboxylate (Example 32A, 8.12 g, 24.4 mmol) in 100 mL dry THF was cooled to −78° C. Potassium hexamethyldisilazide (44 mL, 29 mmol) was added dropwise and the reaction mixture stirred for 2 h at −78° C. Iodomethane (2.3 mL, 37 mmol) was added dropwise to the reaction mixture and the reaction mixture was stirred for 2.5 h at room temperature. Saturated aqueous ammonium chloride solution (20 mL) was added to the reaction mixture, the reaction mixture allowed to room temperature, and then the product was extracted into ethyl acetate. The combined organic phases were washed with saturated aqueous sodium bicarbonate solution, dried over magnesium sulfate, filtrated, and then concentrated. The residue was purified via silica gel chromatography (Isolera, column: 100 g SNAP Ultra; eluent: cyclohexane/ethyl acetate 100:3-100:7). The product-containing fractions were combined, evaporated and then dried under vacuum to give 3.2 g of the target compound.

Example 34A

N-[(Benzyloxy)carbonyl]-2-methyl-D-alloisoleucine (single stereoisomer)

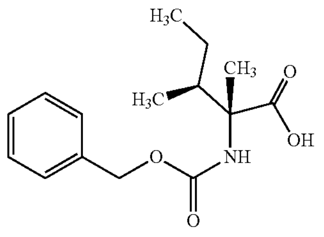 [SMILES: CC[C@H](C)[C@@](C)(NC(=O)OCc1ccccc1)C(=O)O]

To a solution of benzyl (2R,4R)-4-[(2S)-butan-2-yl]-2-tert-butyl-4-methyl-5-oxo-1,3-oxazolidine-3-carboxylate (Example 33A, 3.20 g, 9.21 mmol) in methanol (40 mL) was added 1 M sodium hydroxide solution (40 mL). The reaction mixture was stirred for 2 h at reflux. After cooling, the methanol was evaporated. The residue was treated with 10% citric acid solution and the product was extracted into ethyl acetate. The aqueous phase was extracted with ethyl acetate two more times. The combined organic phases were washed with saturated aqueous sodium chloride solution, dried over magnesium sulfate, filtrated, evaporated and then dried under vacuum to give 2.77 g of the target compound.

Example 35A

2-Methyl-D-alloisoleucine (single stereoisomer)

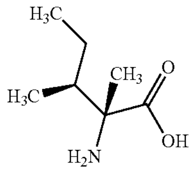

The reaction was carried out under argon atmosphere. To N-[(benzyloxy)carbonyl]-2-methyl-D-alloisoleucine (Example 34A, 2.57 g, 9.20 mmol) in 190 mL methanol was added palladium on carbon (390 mg, 10%). The reaction mixture was stirred under a hydrogen atmosphere for 4 h at room temperature and normal pressure. The reaction mixture was filtrated over diatomaceous earth and the filtrate was concentrated, then dried under vacuum to give 1.32 g (98% yield) of the target compound.

Example 36A

N-{[(9H-Fluoren-9-yl)methoxy]carbonyl}-2-methyl-D-alloisoleucine (single stereoisomer)

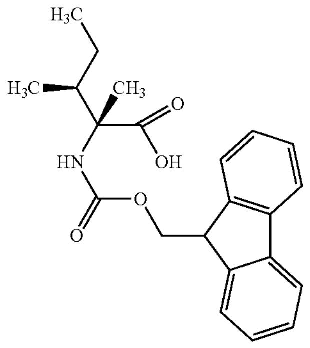 [SMILES: CC[C@H](C)[C@@](C)(NC(=O)OCC1c2ccccc2-c2ccccc21)C(=O)O]

To a solution of 2-methyl-D-alloisoleucine (Example 35 A, 1.32 g, 9.09 mmol) in a mixture of water (20 mL) and acetone (29 mL) was added sodium bicarbonate (7.64 g, 90.9 mmol) and then a solution of 1-({[(9H-fluoren-9-yl)methoxy]carbonyl}oxy)pyrrolidine-2,5-dione (3.22 g, 9.55 mmol) in acetone (20 mL) was added. The reaction mixture was stirred overnight at room temperature. The reaction mixture was treated with MTBE and extracted. The aqueous phase was acidified with conc. hydrochloric acid (pH 1) and extracted with ethyl acetate three more times. The combined organic phases were dried over magnesium sulfate, filtrated and evaporated. The residue was separated via silica gel chromatography (Isolera, column: 50 g SNAP Ultra; eluent: dichloromethane/methanol 100:3-100:5). The appropriate fractions were combined, evaporated and then dried under vacuum.

The MTBE phase was subsequently treated with a 5% sodium bicarbonate solution and extracted with ethyl acetate (600 mL). The aqueous phase was acidified with conc. hydrochloric acid (pH 1) and extracted with ethyl acetate each time. The combined organic phases were dried over magnesium sulfate, filtrated, evaporated and then dried under vacuum. The combined crude product yield was 2.53 g.

The residue was purified via silica gel chromatography (Isolera, column: 50 g SNAP Ultra; eluent: dichloromethane/methanol 97:3-97:5). The product-containing fractions were combined, evaporated and then dried under vacuum to give 967.4 mg of the target compound. The product was further dissolved in water/acetonitrile and lyophilized prior to use.

LC-MS (Method 10): $R_t$=2.10 min; MS (ESI pos): m/z=368.1857 $[M+H]^+$

This amino acid was used in Fmoc SPPS.

Example 37A (6S)-1,1-Difluoro-5-azaspiro[2.4]heptane-6-carboxylic acid (mixture of stereoisomers)

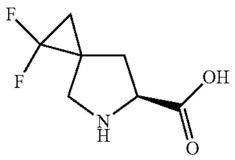 [SMILES: O=C(O)[C@@H]1CC2(CN1)CC2(F)F]

To (6S)-5-(tert-butoxycarbonyl)-1,1-difluoro-5-azaspiro[2.4]heptane-6-carboxylic acid (Omega, CAS 1357482-03-1) (2.50 g, 9.02 mmol) in 85 mL dichloromethane was added trifluoroacetic acid (15 mL, 250 mmol). The reaction mixture was stirred for 2 h at room temperature. The reaction mixture was concentrated and dried under vacuum for the next step.

Example 38A (6S)-5-{[(9H-Fluoren-9-yl)methoxy]carbonyl}-1,1-difluoro-5-azaspiro[2.4]heptane-6-carboxylic acid (mixture of stereoisomers)

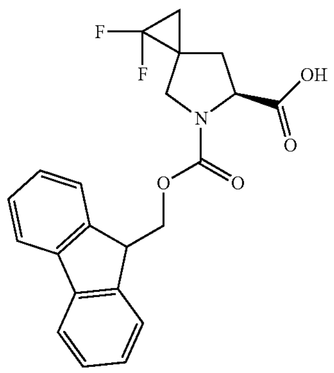 [SMILES: O=C(O)[C@@H]1CC2(CN1C(=O)OCC1c3ccccc3-c3ccccc31)CC2(F)F]

To a solution of (6S)-1,1-difluoro-5-azaspiro[2.4]heptane-6-carboxylic acid (mixture of stereoisomers) (Example 37A, 1.60 g, 9.03 mmol) in water (13 mL) was added sodium bicarbonate (7.59 g, 90.3 mmol) and then a solution of 1-({[(9H-fluoren-9-yl)methoxy]carbonyl}oxy)pyrrolidine-2,5-dione (3.20 g, 9.48 mmol) in acetone (20 mL). The reaction mixture was stirred overnight at room temperature. The reaction mixture was treated with water and extracted twice with MTBE. The aqueous phase was acidified with hydrochloric acid to pH3 and extracted with dichloromethane three times. The organic phase was washed with saturated aqueous sodium chloride solution, dried over magnesium sulfate, filtrated, evaporated and dried under vacuum to give 3.31 g (92% yield) of the target compound.

LC-MS (Method 10): $R_t$=1.99 min; MS (ESI pos): m/z=400 $[M+H]^+$ $^1$H-NMR (400 MHz, DMSO-d6) δ[ppm]: 1.106 (16.00), 1.589 (0.92), 1.605 (1.39), 1.619 (1.06), 1.627 (1.11), 1.655 (0.62), 1.682 (1.25), 1.703 (1.21), 1.916 (0.49), 1.949 (0.86), 1.978 (0.91), 2.012 (0.85), 2.042 (0.52), 2.086 (11.35), 2.558 (0.83), 2.568 (0.67), 2.591 (0.67), 2.645 (0.52), 2.670 (0.56), 3.077 (5.29), 3.442 (0.43), 3.452 (0.50), 3.471 (1.17), 3.479 (1.13), 3.500 (1.39), 3.527 (0.51), 3.562 (1.21), 3.627 (1.20), 3.652 (1.65), 3.677 (0.78), 4.186 (1.02), 4.200 (2.72), 4.223 (2.09), 4.238 (2.18), 4.257 (1.63), 4.279 (2.63), 4.294 (2.46), 4.306 (1.36), 4.322 (1.56), 4.348 (2.13), 4.359 (1.17), 4.372 (1.33), 4.382 (0.84), 4.477 (0.57), 4.499 (0.61), 4.510 (0.69), 4.518 (0.72), 4.533 (0.73), 4.541 (0.64), 5.754 (0.94), 7.300 (0.77), 7.316 (3.26), 7.334 (5.65), 7.353 (3.32), 7.406 (4.71), 7.425 (7.78), 7.443 (3.45), 7.640 (4.69), 7.659 (4.35), 7.683 (0.73), 7.884 (5.08), 7.903 (4.79).

Example 39A (6S)-5-{[(9H-Fluoren-9-yl)methoxy]carbonyl}-1,1-difluoro-5-azaspiro[2.4]heptane-6-carboxylic acid (enantiomer 1) and (enantiomer 2)

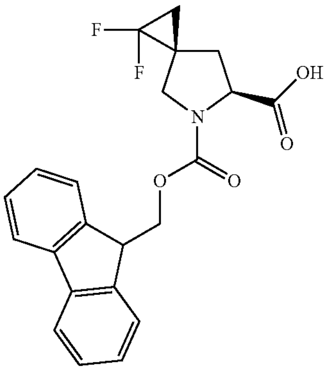 [SMILES: O=C(O)[C@@H]1C[C@@]2(CN1C(=O)OCC1c3ccccc3-c3ccccc31)CC2(F)F]

+

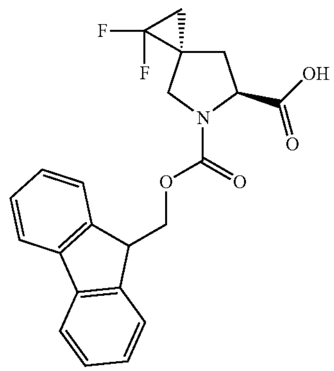

The diastereomeric mixture was separated using a THAR supercritical fluid chromatography Prep 200 instrument using a Chiralpcel AD-H (SFC) 5 µm, 250×30 mm column; eluent: $CO_2$/iso-propanol (83:17); pressure: 135 bar; temperature eluent: 38° C.; temperatur zyklon: 40° C.; pressure zyklon: 24 bar; flow rate: 100 g/min; detection: UV 210 nm; injection volume 0.4 mL/injection; under general operating conditions 1 g/min of $CO_2$ is approximately equivalent to 1 mL/min. Sequence Settings: cycle time=11.2 min Fraction 1 was collected between 5.85 min and 8.0 min (enantiomer 1)

Fraction 2 was collected between 8.4 min and 10.25 min (enantiomer 2)

The fractions were concentrated.

The fractions were analyzed using analytical SFC-MS (Agilent, column: Chiralpak AD-3 3 µm 100×4.6 mm, eluent: $CO_2$/iso-Propanol (85:15); BPR pressure: 130 bar; BPR temperature: 60° C.; column temperature: 40° C.; flow rate: 3 mL/min; UV 210 nm.

Fraction 1 (rt=2.081 min) was assigned the addition "(enantiomer 1)".

Fraction 2 (rt=2.838 min) was assigned the addition "(enantiomer 2)".

The stereochemistry of the two enantiomers was not assigned.

Example 40A (3R*,6S)-5-{[(9H-Fluoren-9-yl)methoxy]carbonyl}-1,1-difluoro-5-azaspiro[2.4]heptane-6-carboxylic acid (single enantiomer, enantiomer 1, stereochemistry at 3 position not defined)

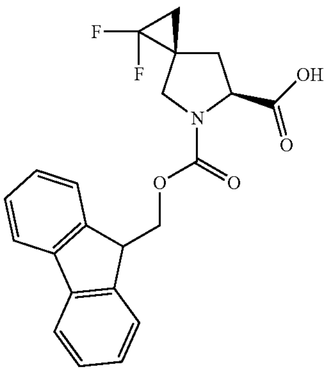

From the chiral SFC preparative purification, 2,015 g of the title compound was obtained, 100% ee LC-MS (Method 10): $R_t$=1.99 min; MS (ESI pos): m/z=400 $[M+H]^+$ $^1$H-NMR (400 MHz, DMSO-d6) δ[ppm]: −0.008 (0.70), 0.008 (0.74), 1.032 (15.85), 1.047 (16.00), 1.285 (1.59), 1.568 (0.69), 1.589 (1.52), 1.617 (1.57), 1.635 (0.96), 1.656 (0.63), 1.686 (1.36), 1.702 (1.37), 1.941 (0.90), 1.974 (1.05), 2.008 (0.87), 2.041 (0.90), 2.073 (1.11), 2.557 (1.08), 2.566 (0.95), 2.591 (0.80), 2.645 (0.71), 2.670 (0.95), 2.701 (0.65), 3.451 (0.87), 3.468 (1.64), 3.479 (1.88), 3.495 (1.12), 3.505 (1.17), 3.626 (2.11), 3.651 (2.91), 3.677 (1.38), 3.770 (0.41), 3.778 (0.42), 4.169 (0.43), 4.186 (1.17), 4.200 (3.11), 4.221 (2.05), 4.238 (1.40), 4.256 (1.57), 4.279 (3.79), 4.293 (3.74), 4.304 (1.62), 4.322 (2.70), 4.336 (1.12), 4.348 (2.93), 4.358 (1.92), 4.371 (1.64), 4.381 (1.52), 4.509 (1.14), 4.517 (1.25), 4.531 (1.28), 4.540 (1.12), 7.300 (0.91), 7.315 (3.87), 7.334 (7.04), 7.350 (3.82), 7.352 (4.21), 7.406 (5.88), 7.424 (9.76), 7.443 (4.35), 7.640 (7.54), 7.658 (6.74), 7.885 (6.80), 7.904 (6.34), 10.194 (0.55), 10.991 (0.42).

This amino acid was used in Fmoc SPPS.

Example 41A (3S*,6S)-5-{[(9H-Fluoren-9-yl)methoxy]carbonyl}-1,1-difluoro-5-azaspiro[2.4]heptane-6-carboxylic acid (single enantiomer, enantiomer 2, stereochemistry at cyclopropyl center not assigned)

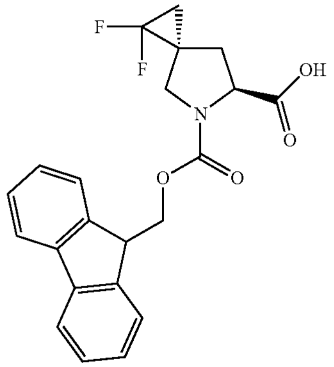 [SMILES: O=C(O)[C@@H]1C[C@]2(CN1C(=O)OCC1c3ccccc3-c3ccccc31)CC2(F)F]

From chiral SFC preparative purification, 1.041 g of the title compound was obtained, 94.58% ee LC-MS (Method 10): $R_t$=1.93 min; MS (ESI pos): m/z=400 $[M+H]^+$ $^1$H-NMR (400 MHz, DMSO-d6) δ[ppm]: −0.008 (1.19), 0.008 (1.31), 1.031 (0.55), 1.047 (0.56), 1.285 (0.60), 1.583 (1.53), 1.604 (4.87), 1.627 (5.45), 1.650 (3.25), 1.673 (2.78), 1.682 (3.76), 1.704 (3.11), 1.718 (0.95), 1.915 (3.17), 1.949 (3.55), 1.979 (3.13), 2.012 (3.33), 2.073 (3.85), 2.526 (1.60), 2.590 (1.44), 2.626 (1.61), 2.649 (0.89), 2.659 (0.80), 3.471 (2.04), 3.498 (5.50), 3.527 (3.26), 3.561 (7.96), 3.570 (4.68), 3.598 (0.84), 4.167 (0.94), 4.183 (2.75), 4.199 (6.46), 4.223 (7.75), 4.238 (9.60), 4.258 (5.95), 4.277 (4.06), 4.290 (3.98), 4.306 (3.80), 4.319 (4.63), 4.340 (4.17), 4.346 (4.47), 4.354 (2.34), 4.367 (3.96), 4.477 (3.66), 4.497 (3.66), 7.300 (1.97), 7.318 (8.34), 7.334 (11.70), 7.337 (12.42), 7.352 (6.35), 7.355 (6.41), 7.407 (9.62), 7.425 (16.00), 7.444 (7.11), 7.633 (6.46), 7.651 (10.65), 7.666 (6.62), 7.683 (4.36), 7.883 (9.71), 7.893 (10.32), 7.901 (9.57), 7.912 (8.99), 12.802 (0.79), 12.984 (0.67).

This amino acid was used in Fmoc SPPS.

Example 42A

3-[4-(tert-Butoxycarbonyl)-1H-1,2,3-triazol-1-yl]-N-{[(9H-fluoren-9-yl)methoxy]carbonyl}-L-alanine (single stereoisomer)

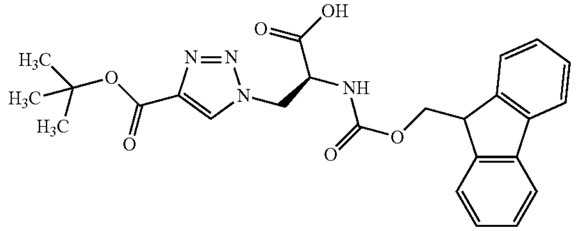 [SMILES: CC(C)(C)OC(=O)c1cn(C[C@H](NC(=O)OCC2c3ccccc3-c3ccccc32)C(=O)O)nn1]

To 3-azido-N-{[(9H-fluoren-9-yl)methoxy]carbonyl}-L-alanine (1.00 g, 2.84 mmol) in a mixture of 27 mL water/tert. butanol/dichloromethane (1:1:1) was added tert-butyl prop-2-ynoate (580 μL, 4.3 mmol), copper(II) sulfate pentahydrate (709 mg, 2.84 mmol) and a solution of sodium ascorbate (1.41 g, 7.10 mmol) in 14 mL water. The reaction mixture was stirred overnight at room temperature. The reaction mixture was treated with water, acidified with diluted citric acid and extracted with dichloromethane three times. The organic phase was dried over sodium sulfate, filtrated and then evaporated. The residue was taken up in acetonitrile/water and separated in 2 portions via preparative HPLC (column: Chromatorex C18 10 μm 125×40 mm; water-acetonitrile-gradient with 0.05% TFA: 0-2 min 25% acetonitrile, 2-22 min 25-75% acetonitrile, 23-26 min 75% acetonitrile, 26-28 min back to 25% acetonitrile; flow 100 mL/min). The product-containing fractions were combined, evaporated and dried under vacuum to give 1.02 g (100% purity, 75% yield) of the target compound.

LC-MS (Method 11): $R_t$=1.30 min; MS (ESI neg): m/z=477 $[M-H]^+$

This amino acid was used in Fmoc SPPS.

Example 43A

5-Azaspiro[2.4]heptane-1-carboxylic acid-trifluoroacetic acid (1/1)

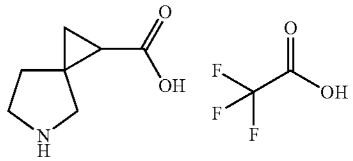

To a solution of 5-(tert-butoxycarbonyl)-5-azaspiro[2.4]heptane-1-carboxylic acid (1.00 g, 4.14 mmol) in 25 mL dichloromethane was added TFA (960 μL, 12 mmol). The reaction mixture stirred 2 h at room temperature. The reaction mixture was evaporated and dried under vacuum to give 0.80 g (76% yield) of the target compound.

LC-MS (Method 9): $R_t$=0.18 min; MS (ESI pos): m/z=142 $[M+H]^+$

Example 44A

5-{[(9H-Fluoren-9-yl)methoxy]carbonyl}-5-azaspiro[2.4]heptane-1-carboxylic acid

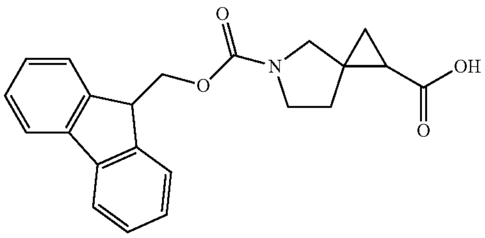 [SMILES: O=C(O)C1CC12CCN(C(=O)OCC1c3ccccc3-c3ccccc31)C2]

To a solution of 5-azaspiro[2.4]heptane-1-carboxylic acid-trifluoroacetic acid (1/1) (Example 43A, 994 mg, 3.90 mmol) in a mixture of 5 mL acetonitrile and 5 mL water was added 1-({[(9H-fluoren-9-yl)methoxy]carbonyl}oxy)pyrrolidine-2,5-dione (2.63 g, 7.79 mmol) and triethylamine (2.2 mL, 16 mmol). The reaction mixture was stirred overnight at room temperature. The reaction mixture was treated with water, acidified with 1 M hydrochloric acid to pH 4 and then extracted with dichloromethane three times. The combined organic phases were dried over sodium sulfate, filtrated and evaporated. The residue was triturated with acetonitrile, then the precipitate was collected by filtration and washed with acetonitrile. The filtrate was purified in 3 portions via preparative HPLC (column: Chromatorex C18 10 μm 125×40 mm; water-acetonitrile-gradient with 0.05% TFA: 0-2 min 25% acetonitrile, 2-22 min 25-75% acetonitrile, 23-26 min 75% acetonitrile, 26-28 min back to 25% acetonitrile; flow 100 mL/min). The appropriate fractions were combined, evaporated and dried under vacuum to give 1.16 g (95% purity, 78% yield) of the target compound.

LC-MS (Method 9): $R_t$=0.99 min; MS (ESI pos): m/z=364 $[M+H]^+$

This amino acid was used in Fmoc SPPS.

Example 45A tert-Butyl (3S,5S,6R)-3-(2-methylallyl)-2-oxo-5,6-diphenyl-morpholine-4-carboxylate

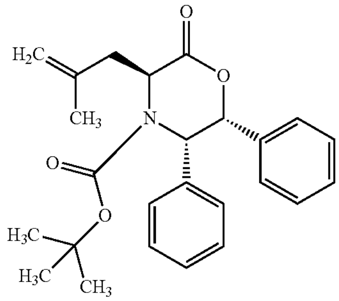 [SMILES: C=C(C)C[C@H]1C(=O)O[C@H](c2ccccc2)[C@H](c2ccccc2)N1C(=O)OC(C)(C)C]

Two batches were run in parallel: To a solution of tert-butyl (2R,3S)-6-oxo-2,3-diphenyl-morpholine-4-carboxylate (90.0 g, 255 mmol) and 3-bromo-2-methyl-prop-1-ene (37.0 g, 27.6 mL, 274 mmol) in THF (1.8 L) and HMPA (180 mL) was added sodium bis(trimethylsilyl)amide (279 mL, 1 M in THF) dropwise at −70° C. over a period of 60 mins under nitrogen atmosphere. Then the solution was stirred at −70° C. for 30 mins. The reaction was combined and quenched by saturated aqueous ammonium chloride solution (2.5 L), then extracted with ethyl acetate (2.0 L×2). The combined organic phase was washed with saturated aqueous sodium chloride solution (1.5 L×2), dried over sodium sulfate, filtered and concentrated in vacuo. The residue was purified by silica gel chromatography (petroleum ether/ethyl acetate=1/0, 10/1) to give the residue, the mixture of residue and Petroleum ether/EtOAc (2.0 L/0.2 L) was stirred for 0.5 h at 25° C., then filtered to give 145 g (89% purity, 62% yield) of the target compound.

LC-MS: Rt=1.027 min, MS+Na=430.2

$^1H$ NMR: $CDCl_3$: 7.35-7.00 (m, 8H), 6.52 (m, 2H), 6.35-6.28 (m, 1H), 5.15-4.82 (m, 4H), 2.95-2.70 (m, 2H), 1.87 (s, 3H), 1.41 (s, 3H), 1.03 (s, 6H)

Example 46A (3S,5S,6R)-3-[(1-Methylcyclopropyl)methyl]-5,6-diphenyl-morpholin-2-one

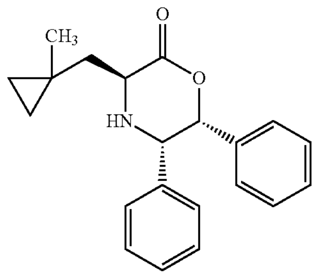 [SMILES: CC1(C[C@@H]2N[C@@H](c3ccccc3)[C@@H](c3ccccc3)OC2=O)CC1]

Three batches were run in parallel. To a solution of tert-butyl (3S,5S,6R)-3-(2-methylallyl)-2-oxo-5,6-diphenyl-morpholine-4-carboxylate (Example 45A, 35.0 g, 76 mmol) in 1.3 L dichloromethane was added diethylzinc (400 mL, 1M in toluene) at 0° C. over 30 min, then chloro(iodo) methane (140 g, 793 mmol, 57.6 mL) was added at 0° C. over 30 min. The reaction was stirred for 1.5 h at 0° C. The reaction was combined and poured into 2.0 L saturated aqueous sodium bicarbonate solution, the solution was filtered, and then the filtrate was extracted with dichloromethane (1.0 L×2). The combined organic phase was washed with 1.5 L saturated aqueous sodium chloride solution, dried over sodium sulfate, filtered through a short piece of silica. Then the filtrate was concentrated to give residue. The mixture of residue and petroleum ether/ethyl acetate/dichloromethane (10/1/1, 400 mL) was stirred for 0.5 h at 25° C. and filtered. The filtrate was concentrated to about 120 mL, then filtered to give 20 g (92% purity, 25% yield) of the target compound.

LC/MS: Rt=0.909 min, M+H+=322.2

Example 47A (2S)-2-(tert-Butoxycarbonylamino)-3-(1-methylcyclopropyl)propanoic acid

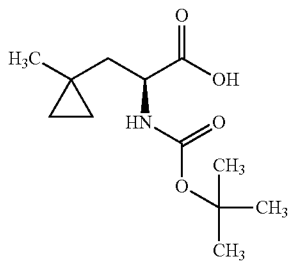 [SMILES: CC1(C[C@H](NC(=O)OC(C)(C)C)C(=O)O)CC1]

To a stirred solution containing ethanol (50 mL), liquid ammonia (600 mL), THF (500 mL) and (3S,5S,6R)-3-[(1-methylcyclopropyl)methyl]-5,6-diphenyl-morpholin-2-one (Example 46A, 57.4 g) that was cooled to −70° C. was added lithium (8 g, 1.15 mol) in small pieces over 0.5 h at −70° C. until a deep blue color persisted for 10 min at −70° C. The reaction was quenched by careful addition of 50 mL 20% aqueous ammonium chloride solution, the cold bath was removed, and the reaction was warmed to 25° C.

The reaction mixture was diluted with 300 mL water and extracted with MTBE (200 mL×2). The aqueous phase was cooled in ice, acidified to pH=1 with 1 M aqueous hxdrochlorid acid, and immediately extracted with ethyl acetate (800 mL×2). The combined ethyl acetate phases were washed with 300 mL saturated aqueous sodium chloride solution, dried over sodium sulfate and concentrated at reduced pressure to give 24 g (99 mmol) of the target compound.

Example 48A (2S)-2-amino-3-(1-methylcyclopropyl)propanoic acid hydrochloride

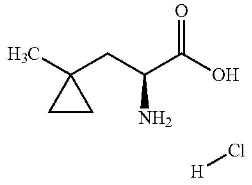

To the solution of (2S)-2-(tert-butoxycarbonylamino)-3-(1-methylcyclopropyl)propanoic acid (Example 47A, 24.0 g, 99 mmol) in dichloromethane (60 mL) was added hydrochloric acid/dioxane (200 mL, 4M) over 15 min at 25° C., then the solution was stirred for 0.5 h at 25° C. The reaction was concentrated to give a residue. The residue was treated with 150 mL of MTBE and stirred for 15 min at 25° C., then filtered to give 16 g (90% yield) of the target compound.

$^1$H NMR: DMSO-d6: 0.21-0.33 (3H, m), 0.37-0.51 (1H, m), 1.64-1.81 (2H, d), 3.88-3.92 (1H, t), 8.41 (3H, s), 13.73 (1H, s)

Example 49A (2S)-2-(9H-Fluoren-9-ylmethoxycarbonylamino)-3-(1-methylcyclopropyl)propanoic acid

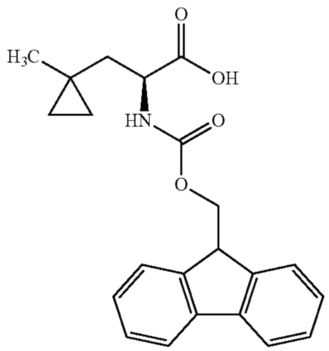 [SMILES: CC1(C[C@H](NC(=O)OCC2c3ccccc3-c3ccccc32)C(=O)O)CC1]

To a solution of ((2S)-2-amino-3-(1-methylcyclopropyl) propanoic acid hydrochloride (Example 48A, 14 g, 77.9 mmol) and sodium carbonate (25 g, 236 mmol) in THF (200 mL) and water (200 mL) was added 1-({[(9H-fluoren-9-yl) methoxy]carbonyl}oxy)pyrrolidine-2,5-dione (25 g, 74.1 mmol) over 30 min at 0° C., then the solution was stirred for 2 h at 0° C. 100 mL water was added. The solution was extracted with MTBE (300 mL×2) before the the pH of aqueous phase was adjusted to 2 with 2 M aqueous hydrochloric acid. The combined organic phase was washed with 150 mL saturated aqueous sodium chloride solution, dried over sodium sulfate, and filtered through a small column of silica. The filtrate was concentrated to give a residue. The combined residue (from previous runs) was purified by silica gel chromatography (petroleum ether/ethyl acetate (10:1, 3:1) to afford a semi-pure residue. The residue was further purified by preparative HPLC (column: Phenomenex Luna C18 250×50 mm, 10 μm; mobile phase: [water (0.05% HCl)-ACN]; B %: 38%-68%, 31 min, 50% min) to give 24.4 g (97% purity, 74% yield) of the target compound.

LC-MS: Rt=0.914 min, [M+H]+=366.1

$^{1}$H NMR: $CDCl_3$: δ ppm 0.23-0.40 (4H, m), 1.02-1.20 (3H, m), 1.48-1.95 (2H, m), 4.22-4.33 (1H, m), 4.39-4.61 (3H, m), 5.26-5.33 (1H, m), 7.31-7.49 (4H, m), 7.56-7.81 (4H, m).

This amino acid was used in Fmoc SPPS.

Example 50A

Methyl N-(tert-butoxycarbonyl)-D-methionyl-L-isoleucinate

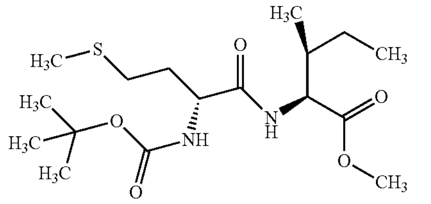 [SMILES: CC[C@H](C)[C@H](NC(=O)[C@@H](CCSC)NC(=O)OC(C)(C)C)C(=O)OC]

N-(tert-Butoxycarbonyl)-D-methionine (2.42 g, 9.71 mmol), methyl L-isoleucinate-hydrogen chloride (1/1) (1.76 g, 9.71 mmol), 1H-benzotriazol-1-ol (1.78 g, 11.6 mmol), 3-{[(Ethylimino)methylene]amino}-N,N-dimethylpropan-1-amine hydrochloride (1:1) (2.23 g, 11.6 mmol) and N,N-diisopropylethylamine (3.5 mL, 20 mmol) were dissolved in DMF (30 mL). The mixture was stirred at ambient temperature for 16 h. Water (100 mL) was then added, the mixture was extracted with two portions of ethyl acetate. The combined organic extract was washed sequentially with hydrochloric acid, water (10 mL), saturated aqueous sodium bicarbonate solution (10 mL) and brine, and then dried over anhydrous sodium sulfate. The organic layer was filtered and the filtrate was concentrated. The residue was dissolved in ether and the product crystallized. The solid was filtered and washed sequentially with ether and pentane. 3.13 g (99% purity, 86% yield) of the title compound were obtained.

Example 51A

Methyl (2S, 3S)-2-{(3R)-3-[(tert-butoxycarbonyl) amino]-2-oxopyrrolidin-1-yl}-3-methylpentanoate

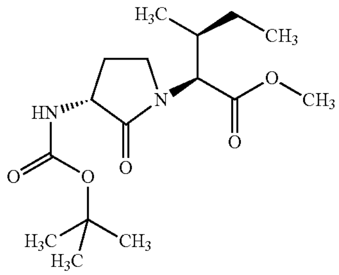 [SMILES: CC[C@H](C)[C@@H](C(=O)OC)N1CC[C@@H](NC(=O)OC(C)(C)C)C1=O]

Methyl N-(tert-butoxycarbonyl)-D-methionyl-L-isoleucinate (Example 50A, 2.85 g, 7.57 mmol) was dissolved in dichloromethane (40 mL) and the solution was cooled to 0° C. Trimethyloxonium tetrafluoroborate (1.12 g, 7.57 mmol) was added and the mixture was stirred at room temperature for 3 h. Potassium carbonate (3.13 g, 22.71 mmol) was added. Then the mixture was heated to reflux for 16 h. The reaction mixture was poured into 50 mL dichloromethane and washed with five portions of water. The organic layer was washed with brine, dried over anhydrous magnesium sulfate, and then filtered. The filtrate was concentrated and crystallized from hexane yielding 2.01 g (100% purity, 81% yield) of the title compound.

Example 52A (2S, 3S)-2-{(3R)-3-[(tert-Butoxycarbonyl)amino]-2-oxopyrrolidin-1-yl}-3-methylpentanoic acid

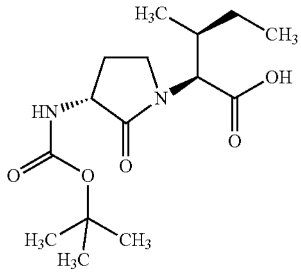 [SMILES: CC[C@H](C)[C@@H](C(=O)O)N1CC[C@@H](NC(=O)OC(C)(C)C)C1=O]

Methyl (2S,3S)-2-{(3R)-3-[(tert-Butoxycarbonyl) amino]-2-oxopyrrolidin-1-yl}-3-methylpentanoate (example 51A, 1.96 g, 5.97 mmol) was dissolved in THF (7.8 mL) and methanol (7.8 mL). A solution of lithium hydroxide (300 mg, 12.5 mmol) in 8 mL of water was added and the mixture was stirred for 1 h at room temperature. After the reaction mixture was concentrated, the white residue was dissolved in water (40 mL), washed with DCM (6 mL), and then acidified with 1 M hydrochloric acid (12 mL). The mixture was extracted with three portions of ethyl acetate. The combined organic extract was dried over anhydrous sodium sulfate, filtered, and then concentrated. The residue was crystallized from ethyl acetate and hexane to provide 1.3 g (100% purity, 67% yield) of the title compound.

LC-MS (Method 11): $R_t$=1.09 min; MS (ESI neg): m/z=313 $[M-H]^-$ $^1$H-NMR (400 MHz, DMSO-d6) δ[ppm]: 0.810 (0.96), 0.829 (2.41), 0.847 (1.25), 0.889 (2.53), 0.906 (2.59), 1.387 (16.00), 3.260 (0.71), 3.274 (0.56), 3.283 (0.75), 3.298 (0.64), 4.200 (0.97), 4.225 (0.94).

Example 53A

Methyl N-(tert-butoxycarbonyl)glycyl-L-isoleucinate

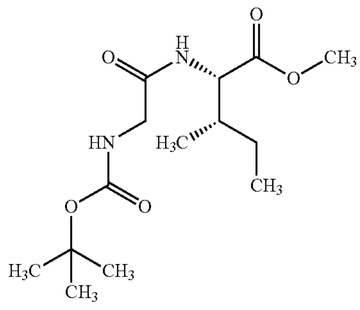 [SMILES: CC[C@H](C)[C@H](NC(=O)CNC(=O)OC(C)(C)C)C(=O)OC]

Methyl L-isoleucinate (3.00 g, 20.7 mmol) and N-(tert-butoxycarbonyl)glycine (3.98 g, 22.7 mmol) were dissolved in DMF (20 mL). This solution was cooled to 0-5° C. in an ice bath. N,N-diisopropylethylamine (3.6 mL, 21 mmol), 1H-benzotriazol-1-ol hydrate (316 mg, 2.07 mmol) and 1-(3-dimethylaminopropyl)-3-ethylcarbodiimidhydrochloride (4.36 g, 22.7 mmol) were added and the mixture was stirred at room temperature. The reaction mixture was quenched with concentrated aqueous ammonium chloride and extracted with three portions of ethyl acetate. The combined organic extracts were dried over anhydrous magnesium sulfate and concentrated. The crude product was purified by chromatography on silica gel (cyclohexane/ethyl acetate 0% to 10%) to give the title compound, 5.40 g (90% purity, 78% yield).

LC-MS (Method 11): $R_t$=1.13 min; MS (ESI pos): m/z=247 [M−tBu]$^+$ $^1$H-NMR (400 MHz, DMSO-d6) δ[ppm]: 0.819 (4.90), 0.835 (8.09), 0.853 (2.63), 1.152 (0.40), 1.174 (0.45), 1.354 (1.52), 1.375 (16.00), 1.459 (0.46), 3.561 (0.84), 3.571 (0.98), 3.577 (1.45), 3.594 (0.81), 3.630 (11.35), 4.220 (0.63), 4.237 (0.78), 4.240 (0.82), 4.257

Example 54A

Methyl glycyl-L-isoleucinate

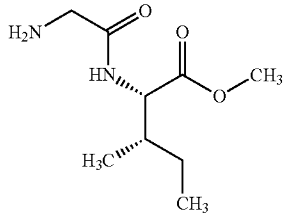

Methyl N-(tert-butoxycarbonyl)glycyl-L-isoleucinate (Example 53A, 1.50 g, 4.96 mmol) was dissolved in DCM (27 mL). Trifluoroacetic acid (3.0 mL, 39 mmol) was added and the reaction mixture was stirred for 30 min at room temperature. The reaction mixture was concentrated to afford the crude product, which was used directly for the next step.

Example 55A

Methyl N-(4-nitrobenzene-1-sulfonyl)glycyl-L-isoleucinate

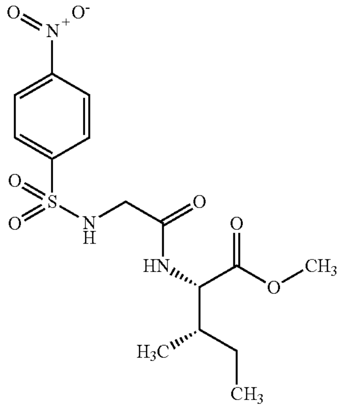

Methyl glycyl-L-isoleucinate (Example 54A, 1.00 g, 4.96 mmol) was dissolved in dichloromethane (40 mL, 620 mmol), triethylamine (2.4 mL, 17 mmol) was added, and then the solution was cooled to 0° C. 4-Nitrobenzene-1-sulfonyl chloride (1.21 g, 5.46 mmol) was added and the reaction mixture was stirred for 1 h. The reaction was then quenched with concentrated aqueous ammonium chloride and extracted with three portions of ethyl acetate. The combined organic extracts were dried over anhydrous magnesium sulfate, filtered, and then concentrated, to give 1.70 g (71% yield) of the title compound. The product was used directly for the next step.

Example 56A

Methyl (2S, 3S)-3-methyl-2-[4-(4-nitrobenzene-1-sulfonyl)-2-oxopiperazin-1-yl]pentanoate

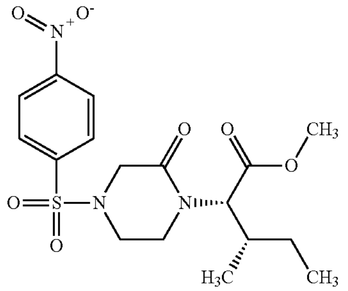

Methyl N-(4-nitrobenzene-1-sulfonyl)glycyl-L-isoleucinate (Example 55A, 1.92 g, 4.96 mmol) and 1,2-dibromoethane (4.3 mL, 50 mmol) were dissolved in DMF. Potassium carbonate (6.86 g, 49.6 mmol) was added and the mixture was heated to 60° C. for 3 h. The reaction was then quenched with concentrated aqueous ammonium chloride and extracted with three portions of ether. The combined organic extracts were dried over anhydrous magnesium sulfate, filtered, and then evaporated. The crude product was purified by column chromatography on silica gel (cyclohexane/ethyl acetate 6:1) to give title compound 1.40 g (97% purity, 66% yield).

LC-MS (Method 11): $R_1$=1.30 min; MS (ESI pos): m/z=414 $[M+H]^+$

Example 57A

Methyl (2S, 3S)-3-methyl-2-(2-oxopiperazin-1-yl) pentanoate

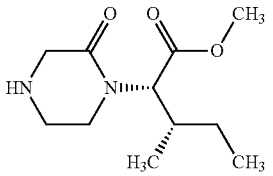 [SMILES: CC[C@H](C)[C@@H](C(=O)OC)N1CCNCC1=O]

Methyl (2S, 3S)-3-methyl-2-[4-(4-nitrobenzene-1-sulfonyl)-2-oxopiperazin-1-yl]pentanoate (Example 56A, 1.40 g, 3.39 mmol) and benzenethiol (1.0 mL, 10 mmol) were dissolved in acetonitrile (20 mL). Potassium carbonate (936 mg, 6.77 mmol) was added and the mixture was stirred at room temperature. The mixture was filtered and evaporated. The residue was purified by flash chromatography on silica gel (gradient dichlormethane/methanol 100:0 to 95:5) to afford 310 mg (40% yield) of the title compound, that was used directly for the next step.

Example 58A tert-Butyl 4-[(2S,3S)-1-methoxy-3-methyl-1-oxopentan-2-yl]-3-oxopiperazine-1-carboxylate

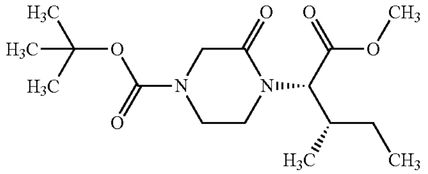 [SMILES: CC[C@H](C)[C@@H](C(=O)OC)N1CCN(C(=O)OC(C)(C)C)CC1=O]

Methyl (2S, 3S)-3-methyl-2-(2-oxopiperazin-1-yl)pentanoate (Example 57A, 310 mg, 1.36 mmol) was dissolved in dichloromethane (1.7 mL, 26 mmol). Di-tert-butyl dicarbonate (370 μL, 1.6 mmol) was added and the mixture was stirred at room temperature for 1 h. The reaction was then quenched with concentrated aqueous ammonium chloride and then extracted with three portions of DCM (20 mL). The combined organic extracts were dried over anhydrous magnesium sulfate, filtered and then concentrated, to afford 440 mg (99% purity, 98% yield) of the title compound.

LC-MS (§ Method 11): $R_t$=1.27 min; MS (ESI pos): m/z=273 $[M+H-tBu]^+$ $^1$H-NMR (400 MHz, DMSO-d6) δ[ppm]: 0.807 (0.86), 0.826 (2.27), 0.844 (1.20), 0.870 (2.25), 0.887 (2.30), 1.410 (16.00), 3.645 (6.00), 3.963 (0.63), 3.970 (0.62), 4.766 (0.82), 4.792 (0.80), 5.754 (0.87).

Example 59A (2S, 3S)-2-[4-(tert-butoxycarbonyl)-2-oxopiperazin-1-yl]-3-methylpentanoic acid

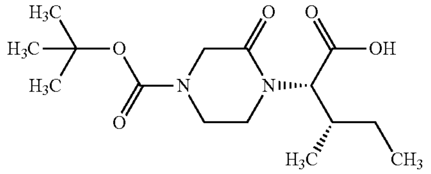 [SMILES: CC[C@H](C)[C@@H](C(=O)O)N1CCN(C(=O)OC(C)(C)C)CC1=O]

tert-Butyl 4-[(2S, 3S)-1-methoxy-3-methyl-1-oxopentan-2-yl]-3-oxopiperazine-1-carboxylate (Example 58A, 440 mg, 80% purity, 1.07 mmol) was dissolved in THF (1.4 mL) and methanol (1.4 mL). A solution of lithium hydroxide (53.9 mg, 2.25 mmol) in water (1.4 mL) was added and the mixture was stirred at room temperature for 1 h. The reaction mixture was concentrated and the residue was dissolved in water and then washed with DCM. The aqueous layer was separated, acidified to pH 3-4 with 1M hydrochloric acid, and then extracted three times with ethyl acetate. The combined organic layer was dried over anhydrous magnesium sulfate, filtered, and then concentrated under reduced pressure to give 310 mg (95% purity, 87% yield) of the title compound as a colorless oil.

LC-MS (Method 11): $R_1$=1.11 min; MS (ESI neg): m/z=313 $[M-H]^-$ $^1$H-NMR (400 MHz, DMSO-d6) δ[ppm]: 0.809 (0.81), 0.827 (2.06), 0.845 (1.12), 0.908 (2.11), 0.924 (2.09), 1.411 (16.00), 3.438 (0.43), 3.968 (0.78), 4.688 (0.79), 4.713 (0.77).

Example 60A

Methyl N-(tert-butoxycarbonyl)-L-alanyl-L-isoleucinate

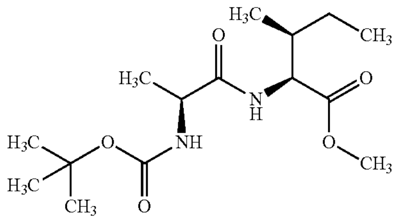 [SMILES: CC[C@H](C)[C@H](NC(=O)[C@H](C)NC(=O)OC(C)(C)C)C(=O)OC]

N-(tert-Butoxycarbonyl)-L-alanine (1.50 g, 7.93 mmol) and methyl L-isoleucinate-hydrogen chloride (1/1) (1.58 g, 8.72 mmol) were dissolved in DMF (7.7 mL). This solution was cooled to 0-5° C. in an ice bath. N,N-diisopropylethylamine (1.4 mL, 7.9 mmol), 1H-benzotriazol-1-ol hydrate (121 mg, 793 μmol) and 1-(3-dimethylaminopropyl)-3-ethylcarbodiimidhydrochloride (1.67 g, 8.72 mmol) were added and the mixture was stirred at room temperature. The reaction was then quenched with concentrated aqueous ammonium chloride and extracted with three portions of ethyl acetate. The combined organic extracts were dried over anhydrous magnesium sulfate, filtered, and then concentrated. The crude product was purified by chromatography on silica gel (cyclohexane/ethyl acetate 0% to 15%) to give 2.12 g (100% purity, 84% yield) of the title compound.

LC LC-MS (Method 10): $R_t$=1.70 min; MS (ESI pos): m/z=317 $[M+H]^+$ $^1$H-NMR (400 MHz, DMSO-d6) δ[ppm]: −0.008 (1.00), 0.008 (0.77), 0.818 (3.17), 0.825 (4.25), 0.836 (7.51), 0.842 (4.72), 0.855 (3.30), 1.144 (4.07), 1.161 (4.10), 1.179 (0.54), 1.200 (0.53), 1.371 (16.00), 1.398 (13.44), 1.775 (0.49), 2.523 (0.85), 3.621 (15.73), 4.021 (0.46), 4.039 (0.60), 4.207 (1.06), 4.223 (1.19), 4.228 (1.22), 4.244 (1.06), 6.908 (0.61), 6.928 (0.58), 7.886 (0.57), 7.907 (0.60).

Example 61A

Methyl L-alanyl-L-isoleucinate

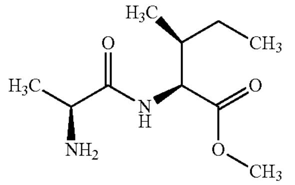

Methyl N-(tert-butoxycarbonyl)-L-alanyl-L-isoleucinate (Example 60A, 2.10 g, 6.64 mmol) was dissolved in DCM (20 mL). Trifluoroacetic acid (20 mL, 260 mmol) was added and the reaction mixture was stirred for 30 min at room temperature. The reaction mixture was concentrated and the crude dipeptide was used directly for the next step.

Example 62A

Methyl N-(4-nitrobenzene-1-sulfonyl)-L-alanyl-L-isoleucinate

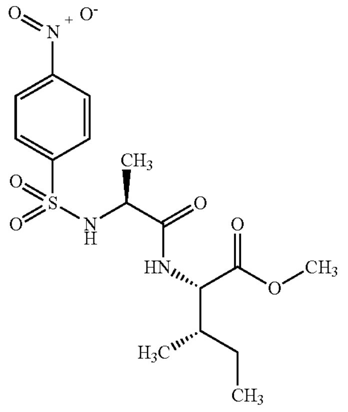

Methyl L-alanyl-L-isoleucinate (Example 61A, 1.44 g, 6.64 mmol) was dissolved in dichloromethane (54 mL), triethylamine (3.2 mL, 23 mmol) was added, and then the solution was cooled to 0° C. 4-Nitrobenzene-1-sulfonyl chloride (1.62 g, 7.30 mmol) was added and the reaction mixture was stirred. The reaction was then quenched with concentrated aqueous ammonium chloride and extracted with two portions of dichloromethane. The combined organic extracts were washed with saturated sodium chloride aqueous solution, dried over anhydrous magnesium sulfate, filtered, and the concentrated to afford 1.65 g (95% purity, 59% yield) of the title compound.

LC-MS (Method 11): $R_t$=1.18 min; MS (ESI neg): m/z=400 $[M-H]^-$ $^1$H-NMR (400 MHz, DMSO-d6) δ[ppm]: 0.008 (0.40), 0.676 (6.59), 0.693 (6.80), 0.740 (2.79), 0.758 (6.99), 0.777 (3.46), 1.013 (0.52), 1.025 (0.62), 1.047 (0.69), 1.066 (0.50), 1.117 (6.09), 1.135 (6.12), 1.175 (0.51), 1.192 (0.64), 1.203 (0.60), 1.210 (0.56), 1.222 (0.67), 1.237 (0.48), 1.243 (0.42), 1.551 (0.53), 1.568 (0.61), 1.578 (0.45), 1.584 (0.47), 1.988 (0.64), 3.577 (16.00), 3.933 (1.14), 3.948 (1.32), 3.953 (1.31), 3.968 (1.12), 4.056 (0.61), 4.073 (0.82), 4.091 (0.54), 7.994 (4.08), 7.999 (1.44), 8.012 (1.63), 8.016 (4.58), 8.135 (1.41), 8.155 (1.39), 8.365 (4.39), 8.383 (1.48), 8.388 (3.90), 8.463 (1.04), 8.482 (0.99).

Example 63A

Methyl (2S, 3S)-3-methyl-2-[(3S)-3-methyl-4-(4-nitrobenzene-1-sulfonyl)-2-oxopiperazin-1-yl]pentanoate

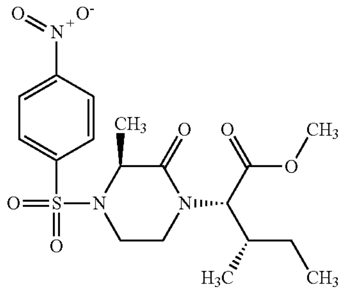

Methyl N-(4-nitrobenzene-1-sulfonyl)-L-alanyl-L-isoleucinate (Example 62A, 1.65 g, 4.11 mmol) and 1,2-dibromoethane (3.5 mL, 41 mmol) were dissolved in DMF (35 mL). Potassium carbonate (5.68 g, 41.1 mmol) was added and the reaction mixture was heated to 60° C. for 3 h. The reaction was then quenched with concentrated aqueous ammonium chloride and extracted with three portions of ether. The combined organic extracts were dried over anhydrous magnesium sulfate, filtered, and then concentrated. The crude product was purified by chromatography on silica gel (cyclohexane/ethyl acetate 6:1) to give 1.60 g (70% purity, 64% yield) of the title compound.

LC-MS (Method 11): $R_t$=1.30 min; MS (ESI pos): m/z=428 $[M+H]^+$

Example 64A

Methyl (2S,3S)-3-methyl-2-[(3S)-3-methyl-2-oxopiperazin-1-yl]pentanoate

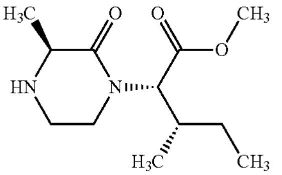 [SMILES: CC[C@H](C)[C@@H](C(=O)OC)N1CCN[C@@H](C)C1=O]

Methyl (2S, 3S)-3-methyl-2-[(3S)-3-methyl-4-(4-nitrobenzene-1-sulfonyl)-2-oxopiperazin-1-yl]pentanoate (Example 63A, 900 mg, 2.11 mmol) and benzenethiol (650 µL, 6.3 mmol) were dissolved in acetonitrile (12 mL). Potassium carbonate (582 mg, 4.21 mmol) was added and the reaction mixture was stirred at room temperature overnight. The mixture was filtered and concentrated. The residue was purified by flash chromatography on silica gel (gradient dichlormethane/methanol 100:0 to 95:5) to afford 336 mg (100% purity, 66% yield) of the title compound.

LC-MS (Method 13): $R_t$=1.09 min; MS (ESI pos): m/z=243 $[M+H]^+$

Example 65A tert-Butyl (2S)-4-[(2S, 3S)-1-methoxy-3-methyl-1-oxopentan-2-yl]-2-methyl-3-oxopiperazine-1-carboxylate

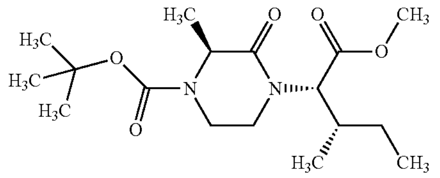 [SMILES: CC[C@H](C)[C@@H](C(=O)OC)N1CCN(C(=O)OC(C)(C)C)[C@@H](C)C1=O]

Methyl (2S, 3S)-3-methyl-2-[(3S)-3-methyl-2-oxopiperazin-1-yl]pentanoate (Example 64A, 736 mg, 3.04 mmol) was dissolved in dichloromethane (8 mL). Di-tert-butyl dicarbonate (1.0 mL, 4.6 mmol) was added, and the reaction mixture was stirred at room temperature over the weekend. The reaction was then quenched with concentrated aqueous ammonium chloride and extracted with two portions of DCM. The combined organic extracts were washed with sodium chloride solution, dried over anhydrous magnesium sulfate, filtered and then concentrated. The crude product was purified by chromatography on silica gel (cyclohexane/ethyl acetate 3:1) to afford 1.08 g (100% purity, 104% yield) of the title compound.

LC-MS (Method 10): $R_t$=1.98 min; MS (ESI pos): m/z=343 $[M+H]^+$ $^1$H-NMR (400 MHz, DMSO-d6) δ[ppm]: 0.800 (0.95), 0.818 (2.41), 0.837 (1.25), 0.875 (2.38), 0.892 (2.43), 1.305 (2.02), 1.323 (2.06), 1.414 (16.00), 3.645 (6.08), 4.769 (0.88), 4.795 (0.86).

Example 66A

(2S, 3S)-2-[(3S)-4-(tert-Butoxycarbonyl)-3-methyl-2-oxopiperazin-1-yl]-3-methylpentanoic acid

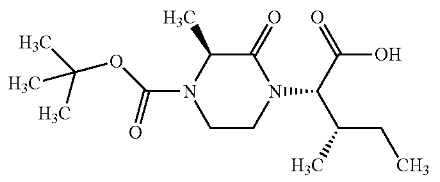 [SMILES: CC[C@H](C)[C@@H](C(=O)O)N1CCN(C(=O)OC(C)(C)C)[C@@H](C)C1=O]

tert-Butyl (2S)-4-[(2S,3S)-1-methoxy-3-methyl-1-oxopentan-2-yl]-2-methyl-3-oxopiperazine-1-carboxylate (Example 65A, 1.08 g, 3.15 mmol) was dissolved in a mixture of THF (4.5 mL) and methanol (4.5 mL). A solution of lithium hydroxide (159 mg, 6.62 mmol) in water (4.5 mL) was added and the reaction mixture was stirred at room temperature for 1 h. The reaction mixture was concentrated and the residue was dissolved in concentrated aqueous ammonium chloride. The aqueous layer was used acidified to pH 3-4 with 1M hydrochloric and extracted three times with DCM. The combined organic layer was dried over anhydrous magnesium sulfate, filtered, and then concentrated to afford 952 mg (100% purity, 92% yield) of the title compound.

LC-MS (Method 9): $R_t$=0.87 min; MS (ESI pos): m/z=329 $[M+H]^+$ $^1$H-NMR (400 MHz, DMSO-d6) δ[ppm]: 0.802 (1.09), 0.820 (2.24), 0.838 (1.18), 0.911 (2.22), 0.927 (2.28), 1.295 (0.50), 1.308 (2.03), 1.326 (1.99), 1.415 (16.00), 3.342 (0.65), 4.691 (0.84), 4.717 (0.82).

Example 67A

(2R, 5R)-3,6-Dimethoxy-2-(propan-2-yl)-5-[(trimethylsilyl)methyl]-2,5-dihydropyrazine

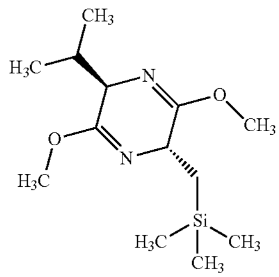 [SMILES: COC1=N[C@H](C(C)C)C(OC)=N[C@H]1C[Si](C)(C)C]

(2R)-3,6-Dimethoxy-2-(propan-2-yl)-2,5-dihydropyrazine (2.9 mL, 16 mmol) was dissolved in THF (58 mL) and the solution cooled to −78° C. n-Butyl lithium (10 mL, 1.6 M, 16 mmol) was added dropwise with stirring. Stirring was continued for 15 min at −78° C. (Chloromethyl)(trimethyl) silane (5.0 mL, 36 mmol) was added and the resulting mixture was stirred at ambient temperature overnight. The reaction mixture was diluted with water and extracted with diethyl ether. The combined organic layer was dried over anhydrous sodium sulfate, filtered, and then concentrated. The crude product was purified by chromatography on silica gel (cyclohexane/ethyl acetate 2%) to afford 3.0 g (87% purity, 60% yield) of the title compound.

LC-MS (Method 9): $R_t$=1.47 min; MS (ESI pos): m/z=271 $[M+H]^+$ $^1$H-NMR (400 MHz, DMSO-d6) δ[ppm]: −0.036 (0.45), −0.028 (9.14), −0.020 (0.46), −0.008 (1.38), 0.580 (3.69), 0.597 (3.75), 0.737 (0.61), 0.762 (0.63), 0.773 (0.73), 0.798 (0.73), 0.959 (3.60), 0.977 (3.69), 1.107 (0.73), 1.119 (0.75), 1.143 (0.66), 1.148 (0.47), 1.155 (0.63), 1.370 (1.30), 2.512 (16.00), 3.574 (8.95), 3.582 (8.85), 3.885 (0.64), 3.894 (1.26), 3.903 (0.72), 3.999 (0.49), 4.023 (0.47).

Example 68A

Methyl 3-(trimethylsilyl)-L-alaninate

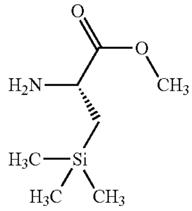

(2R, 5R)-3,6-Dimethoxy-2-(propan-2-yl)-5-[(trimethylsilyl)methyl]-2,5-dihydropyrazine (Example 67A, 3.00 g, 11.1 mmol) was dissolved in methanol (30 mL, 740 mmol) and the solution was cooled to 0° C. Hydrochloric acid (10 mL, 10%) was added and the solution was stirred for 2 h. The solution was evaporated and the residue was dissolved in DCM and sodium carbonate solution (100 mL, 2.0 M, 200 mmol). The aqueous layer was extracted with two portions of DCM. The DCM extract was dried over anhydrous magnesium sulfate, filtered, and then concentrated. The crude product was purified by chromatography on silica gel (2% methanol: (1% N,N-diethylethanamine in DCM)) to give 2.83 g (68% purity, 99% yield) of the title compound.

$^1$H-NMR (400 MHz, DMSO-d6) δ[ppm]: −0.010 (3.10), 0.008 (1.81), 0.736 (0.85), 0.759 (0.89), 0.772 (1.48), 0.795 (1.56), 0.803 (1.89), 0.820 (1.90), 0.841 (1.84), 0.858 (2.43), 0.875 (1.64), 0.900 (4.19), 0.911 (1.07), 0.918 (8.65), 0.936 (4.28), 1.682 (1.42), 2.384 (1.35), 2.402 (4.11), 2.420 (4.02), 2.438 (1.25), 3.088 (0.55), 3.102 (0.54), 3.302 (1.19), 3.306 (1.81), 3.321 (1.27), 3.330 (1.15), 3.345 (1.03), 3.583 (16.00), 3.591 (0.48), 3.605 (4.33), 5.742 (4.37).

Example 69A

N-{[(9H-Fluoren-9-yl)methoxy]carbonyl}-3-(trimethylsilyl)-L-alanine

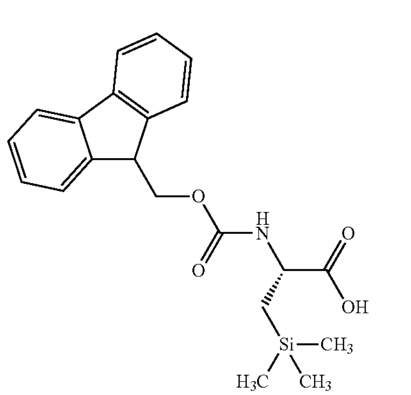 [SMILES: C[Si](C)(C)C[C@H](NC(=O)OCC1c2ccccc2-c2ccccc21)C(=O)O]

Methyl 3-(trimethylsilyl)-L-alaninate (Example 68A, 2.83 g, 68% purity, 11.0 mmol) was dissolved in methanol (44 mL) and the solution cooled to 0° C. A sodium hydroxide solution (11 mL, 1.0 M, 11 mmol) was added and the reaction mixture was stirred over night at room temperature. Water (40 mL), sodium hydrogen carbonate (922 mg, 11.0 mmol) and sodium carbonate (1.53 g, 14.4 mmol) were added. The methanol was removed under reduced pressure and then 1,4-dioxane (32 mL) was added to the aqueous solution. This solution was cooled to 0° C. in an ice bath. (9H-Fluoren-9-yl)methyl carbonochloridate (Fmoc-$C_1$) (4.26 g, 16.5 mmol) was then added and the reaction mixture was stirred for 5 h at room temperature. Additional Fmoc-$C_1$ (1.42 g, 5.5 mmol) was added and the reaction mixture was stirred for an additional 2 h. Equal portions of water and tert-butyl methyl ether were added to the reaction mixture. The aqueous phase was separated and washed further with tert-Butyl methyl ether, then acidified with 1 M hydrochloric acid (pH 3-4). The acidified mixture was extracted with three portions of MTBE. The combined organic layer was dried over anhydrous magnesium sulfate sulfate, filtered, and then concentrated. The crude product was purified by preparative HPLC (column: Reprosil; C18; 10 μm; 125×40 mm; eluant: AcCN/$H_2O$ with 0,1% HCOOH; flow rate: 100 mL/min; gradient: 0-5.50 min 10:90; sample injection at 3.00 min; 5.50-17.65 min to 95:5; 17.65-19.48 min 95:5; 19.48-19.66 min to 10:90; 19.66-20.72 min 10:90;) to give 1.65 g (99% purity, 39% yield) of the title compound.

LC-MS (Method 10): $R_t$=2.20 min; MS (ESI pos): m/z=384 $[M+H]^+$ $^1$H-NMR (400 MHz, DMSO-d6) δ[ppm]: −0.006 (16.00), 0.987 (3.81), 1.006 (3.64), 3.309 (2.95), 3.950 (0.67), 3.970 (1.71), 3.991 (1.59), 4.010 (0.53), 4.182 (0.67), 4.199 (1.66), 4.217 (1.67), 4.228 (1.08), 4.253 (2.79), 4.268 (3.86), 4.287 (1.60), 4.293 (0.85), 4.313 (0.41), 7.286 (1.24), 7.291 (1.27), 7.293 (1.31), 7.302 (2.68), 7.304 (2.70), 7.309 (2.55), 7.321 (1.75), 7.323 (1.70), 7.328 (1.57), 7.389 (2.90), 7.408 (4.73), 7.426 (2.11), 7.566 (1.81), 7.587 (1.74), 7.697 (2.14), 7.714 (3.62), 7.731 (1.81), 7.872 (4.43), 7.891 (4.02), 12.451 (0.54).

This amino acid was used in Fmoc SPPS.

Example 70A

Di-tert-butyl (2S)-5-hydroxypyrrolidine-1,2-dicarboxylate (mixture of isomers)

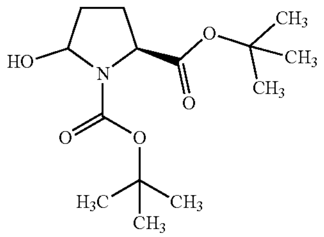 [SMILES: CC(C)(C)OC(=O)[C@@H]1CCC(O)N1C(=O)OC(C)(C)C]

Di-tert-butyl (2S)-5-oxopyrrolidine-1,2-dicarboxylate (CAS-RN: 91229-91-3, 21.0 g, 73.6 mmol) was dissolved in 250 mL THF and the solution was cooled to −78° C. Diisobutyl aluminum hydride (160 mL, 1.0 M, 160 mmol) was added dropwise and the mixture was stirred for 1 h at −78° C. The reaction was then quenched with 2-propanol (25 mL). Potassium sodium (2R,3R)-2,3-dihydroxybutanedioate solution (200 mL) was added, the mixture was stirred at room temperature, and then the reaction mixture was diluted with MTBE and water. The water layer was separated and extracted further with two portions of MTBE. The combined organic extract was dried over anhydrous magnesium sulfate, filtered, and the residue concentrated under reduced pressure to give 19.53 g (79% purity, 73% yield) of the title compound as a colorless oil.

Example 71A

Di-tert-butyl (2S,)-5-methoxypyrrolidine-1,2-dicarboxylate (mixture of isomers)

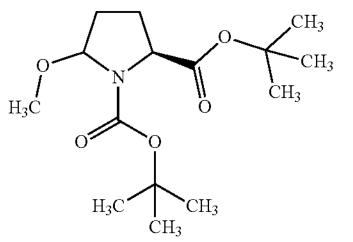 [SMILES: COC1CC[C@@H](C(=O)OC(C)(C)C)N1C(=O)OC(C)(C)C]

Di-tert-butyl (2S)-5-hydroxypyrrolidine-1,2-dicarboxylate (Example 70A, 19.5 g, 67.9 mmol) was dissolved in methanol (160 mL). Pyridinium para-toluenesulfonate (341 mg, 1.36 mmol) was added to the solution and the reaction mixture was stirred overnight at room temperature. The reaction mixture was concentrated and the crude product was purified by flash chromatography on silica gel (gradient cyclohexane-cyclohexane ethyl acetate 7:3) to afford 14.4 g (90% purity, 64% yield) of the title compound. $^{1}$H-NMR (400 MHz, DMSO-d6) δ[ppm]: 1.363 (9.51), 1.375 (8.10), 1.393 (2.67), 1.419 (16.00), 1.756 (0.58), 1.775 (0.93), 1.781 (0.88), 1.807 (0.46), 3.225 (3.77), 3.240 (1.93), 3.261 (2.02), 3.307 (4.01), 4.059 (0.64), 4.081 (0.82), 5.128 (0.56).

Example 72A

Di-tert-butyl (2S)-5-cyanopyrrolidine-1,2-dicarboxylate (mixture of isomers)

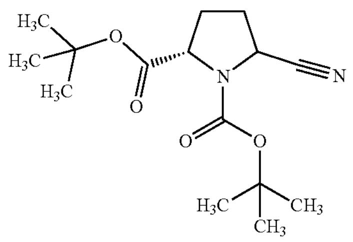 [SMILES: CC(C)(C)OC(=O)[C@@H]1CCC(C#N)N1C(=O)OC(C)(C)C]

Di-tert-butyl (2S,)-5-methoxypyrrolidine-1,2-dicarboxylate (Example 71A, 14.4 g, 47.8 mmol) was dissolved in DCM (125 mL) and the solution was cooled to −40° C. Trimethylsilyl trifluoromethanesulfonate (1.3 mL) (1 vol %) was added, then trimethylsilanecarbonitrile (7.0 mL, 53 mmol) was added dropwise over a 40 min period. The mixture was subsequently stirred for an additional 1.5 h at −40° C. The reaction mixture was quenched with methanol (19 mL) and then concentrated to afford 14.87 g (86% yield) of the title compound were isolated.

GC-MS (GC-MS Method 1): 195.2 (M+-Boc), 139.1 (-Boc, -t-Bu)

Example 73A

Di-tert-butyl (2S)-5-formylpyrrolidine-1,2-dicarboxylate (mixture of isomers)

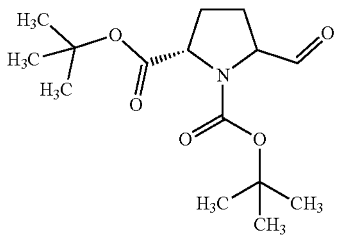 [SMILES: CC(C)(C)OC(=O)[C@@H]1CCC(C=O)N1C(=O)OC(C)(C)C]

Di-tert-butyl (2S)-5-cyanopyrrolidine-1,2-dicarboxylate (Example 72A, 14.0 g, 47.2 mmol) was dissolved in a mixture of pyridine (250 mL), acetic acid (130 mL) and water (130 mL). A Raney-Nickel-water suspension (70.0 g, 50% purity) was added and the mixture was hydrogenated over 7 h at ambient pressure at 80° C. The catalyst was then removed by filtration over a layer of diatomaceous earth and the solvent was washed with 250 mL of water. The aqueous phase was extracted three times with MTBE (650 mL). The combined organic layer was washed with water three times, washed with brine, dried over anhydrous magnesium sulfate and then filtered. The filtrate was evaporated under reduced pressure and the residue was purified by flash chromatography on silica gel (gradient cyclohexane-cyclohexane/ethyl acetate 7:3) to afford 7.40 g (85% purity, 44% yield) of a viscous oil.

GC-MS (GC-MS Method 1): ($M^{+}$-CO); (M+-CO, -Boc)

Example 74A

Di-tert-butyl (2S)-5-ethenylpyrrolidine-1,2-dicarboxylate (mixture of isomers)

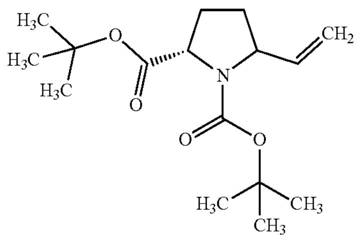 [SMILES: C=CC1CC[C@@H](C(=O)OC(C)(C)C)N1C(=O)OC(C)(C)C]

Methyl(triphenyl)phosphonium bromide (17.7 g, 49.4 mmol) was suspended in 180 mL of THF. Potassium bis (trimethylsilyl)amide solution (1M in toluene, 75 mL, 15% solution, 49 mmol) was added at dropwise at room temperature and stirred for 1 h. The mixture was cooled to −78° C. Di-tert-butyl (2S)-5-formylpyrrolidine-1,2-dicarboxylate (Example 73A, 7.40 g, 24.7 mmol) was dissolved in THF (60 mL).

The solution was added and stirred for 2 h at room temperature. The reaction mixture was poured into a solution of potassium sodium (2R,3R)-2,3-dihydroxybutanedioate (140 mL) and water (85 mL) and extracted with three portions of MTBE (210 mL). The combined organic extract was washed with sodium chloride solution, dried over anhydrous sodium sulfate, filtered and then concentrated. The crude product was purified by flash chromatography on silica gel (gradient cyclohexane-cyclohexane ethyl acetate (9:1)) to afford 4.25 g (100% purity, 58% yield) of the title compound were isolated.

GC-MS (GC-MS Method 1): Rt=5.07 min, 5.17 min; 197.3 (M+-Boc)

Example 75A tert-Butyl 5-vinyl-L-prolinate (mixture of isomers)

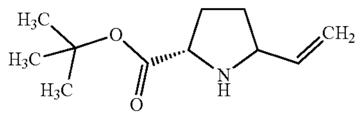

Di-tert-butyl (2S)-5-ethenylpyrrolidine-1,2-dicarboxylate (Example 74A, 4.25 g, 14.3 mmol) was dissolved in 45 mL DCM and the solution was cooled to 0° C. Trimethylsilyl trifluoromethanesulfonate (2.6 mL, 14 mmol) was added dropwise and the resulting mixture was stirred for 5 min at 0° C. The reaction was then quenched with concentrated aqueous sodium hydrogen carbonate solution (21 mL) and extracted with two portions of DCM. The combined organic layers were dried over magnesium sulfate, filtered and then concentrated. The crude product was purified by flash chromatography on silica gel (gradient methanol-dichlormethane (100:2)) to afford 2.09 g (100% purity, 74% yield) of the title compound.

GC-MS (GC-MS Method 1): Rt=3.37 min, 3.50 min; 197.3 (M+)

Example 76A tert-Butyl (5R)-5-ethenyl-L-prolinate (single stereoisomer)

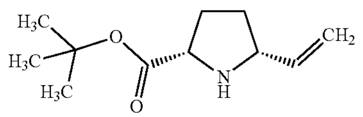

Isomeric separation of tert-Butyl-5-ethenyl-L-prolinate (diasteromeric mixture) (Example 75A, 2.55 g, 12.9 mmol) by flash chromatography on silica gel (gradient cyclohexane-ethyl acetate-trimethylamine (70:30:1)) afforded 1.35 g (100% purity, 53% yield) of the title compound.

GC-MS (GC-MS Method 1): Rt=3.50 min; 197.3 (M+)

$^1$H-NMR (400 MHz, DMSO-d6) δ[ppm]: 1.3-1.4 (1H), 1.40 (9H), 2.4 (1H), 3.5 (2H), 4.9 (1H), 5.15 (1H), 5.8 (1H).

Example 77A 1-tert-Butyl 2-methyl-3-ethenylpiperidine-1,2-dicarboxylate (mixture of isomers)

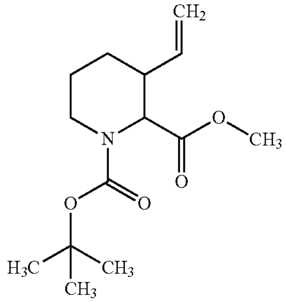 [SMILES: C=CC1CCCN(C(=O)OC(C)(C)C)C1C(=O)OC]

A solution of ethenylmagnesium bromide (39 mL, 0.70 M, 27 mmol) in anhydrous THF (20 mL) was cooled to −35° C. and then a solution of copper (I) bromide-dimethyl sulfide (1:1) (741 mg, 3.61 mmol) was added. The reaction mixture was stirred for 1 h at −35° C. A solution of 1-tert-Butyl 2-methyl 5,6-dihydropyridine-1,2(4H)-dicarboxylate (CAS-RN: 155905-80-9, 4.35 g, 18.0 mmol) in THF (10 mL) was added to the mixture, and then the reaction mixture was stirred for 6 h at −35° C. The mixture was quenched with a mixture of aqueous ammonium chloride (85 mL) and aqueous ammonia (85 mL) and extracted with two portions of MTBE (285 mL). The combined organic layers were washed sequentially with aqueous ammonium chloride (570 mL) and brine (570 mL), dried over magnesium sulfate, filtered, and then concentrated. The crude product was purified by chromatography on silica gel (gradient: cyclohexane-ethyl acetate (2%-20%)) to give 1.59 g (100% purity, 33% yield) of the title compound.

LC-MS (Method 12): $R_t$=3.33 min; MS (ESI pos): m/z=270 $[M+H]^+$ $^1$H-NMR (400 MHz, DMSO-d6) δ[ppm]: 1.038 (0.51), 1.087 (0.77), 1.382 (16.00), 1.419 (0.83), 1.429 (0.59), 1.448 (0.73), 1.459 (0.80), 1.466 (0.54), 1.479 (1.01), 1.485 (1.09), 1.496 (0.73), 1.502 (0.66), 1.506 (0.59), 1.514 (0.47), 1.532 (0.47), 1.544 (0.42), 1.600 (0.64), 1.627 (0.61), 2.899 (0.88), 3.690 (13.11), 3.817 (0.47), 3.849 (0.45), 5.120 (2.03), 5.148 (0.90), 5.164 (1.49), 5.869 (0.57).

Example 78A 1-(tert-Butoxycarbonyl)-3-ethenylpiperidine-2-carboxylic acid (mixture of isomers)

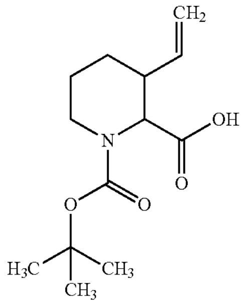 [SMILES: C=CC1CCCN(C(=O)OC(C)(C)C)C1C(=O)O]

1-tert-Butyl 2-methyl 3-ethenylpiperidine-1,2-dicarboxylate (Example 77A,1.59 g, 5.90 mmol) was dissolved in a mixture of methanol (5.9 mL) and THF (17.7 mL). A lithium hydroxide solution (5.9 mL, 2.0 M, 12 mmol) was added and the mixture was stirred for 5 h at 50° C., then cooled to room temperature. The reaction mixture was washed with MTBE (7.5 mL), cooled to 0° C., acidified with 1 M hydrochloric acid (14.5 mL), then extracted five times with DCM (15 mL). The combined organic extract was dried over magnesium sulfate, filtered, and then concentrated to afford 1.39 g (100% purity, 92% yield) of the title compound.

$^1$H-NMR (400 MHz, DMSO-d6) δ[ppm]: 1.381 (16.00), 1.423 (0.70), 1.434 (0.57), 1.455 (0.77), 1.465 (1.32), 1.473 (0.93), 1.488 (1.66), 1.495 (1.29), 1.519 (0.46), 1.530 (0.40), 1.608 (0.80), 1.632 (0.75), 2.911 (0.96), 3.815 (0.50), 3.842 (0.47), 5.113 (1.95), 5.140 (0.73), 5.156 (1.59), 5.753 (0.50), 5.874 (0.51), 12.910 (0.69).

Example 79A tert-Butyl 2-{[(2S, 5R)-2-(tert-butoxycarbonyl)-5-vinylpyrrolidin-1-yl]carbonyl}-3-vinylpiperidine-carboxylate (mixture of isomers)

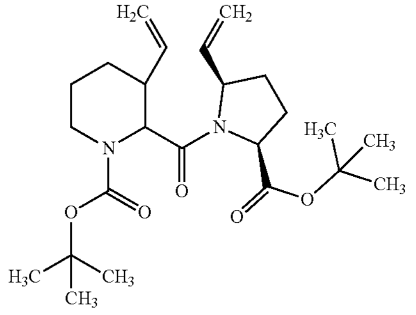 [SMILES: C=CC1CCCN(C(=O)OC(C)(C)C)C1C(=O)N1[C@@H](C=C)CC[C@H]1C(=O)OC(C)(C)C]

1-(tert-Butoxycarbonyl)-3-ethenylpiperidine-2-carboxylic acid (racemate) (Example 78A, 1.35 g, 5.30 mmol) and tert-butyl (5R)-5-ethenyl-L-prolinate (Example 76A, 950 mg, 4.82 mmol) were dissolved in acetonitrile (60 mL). N,N-diisopropylethylamine (2.5 mL, 14 mmol) was added and the reaction mixture was cooled to 0° C. A solution of 1H-benzotriazol-1-yloxy)(tripyrrolidin-1-yl)phosphonium hexafluorophosphate (3.26 g, 6.26 mmol) in acetonitrile (30 mL) was added to the mixture, and the reaction mixture was stirred for 20 h at room temperature. The reaction mixture was concentrated, redissolved in MTBE and washed with water. The aqueous phase re-extracted with MTBE. The combined organic layer was washed with brine, dried over magnesium sulfate, filtered, and then concentrated. The crude product was purified by chromatography on silica gel (cyclohexane/ethyl acetate (85:15)) to give 2.03 g (88% yield) of the title compound.

$^1$H-NMR (400 MHz, DMSO-d6) δ[ppm]: −0.008 (0.60), 1.373 (10.15), 1.392 (16.00), 1.396 (14.53), 1.458 (0.57), 1.489 (0.46), 1.763 (0.46), 1.780 (0.56), 2.105 (0.42), 2.122 (0.42), 2.524 (0.41), 5.050 (0.44), 5.090 (0.70), 5.116 (0.79), 5.754 (1.04).

Example 80A di-tert-Butyl (4aR,6aR,9S,11aS)-11-oxo-2,3,4,4a,6a,7,8,9,11,11a-decahydro-1H-pyrido[3,2-e]pyrrolo[1,2-a]azepine-1,9-dicarboxylate (single stereoisomer)

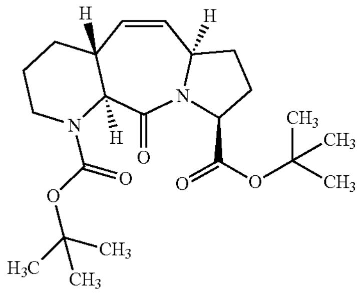 [SMILES: CC(C)(C)OC(=O)[C@@H]1CC[C@@H]2C=C[C@H]3CCCN(C(=O)OC(C)(C)C)[C@@H]3C(=O)N21]

tert-Butyl 2-{[(2S,5R)-2-(tert-butoxycarbonyl)-5-vinylpyrrolidin-1-yl]carbonyl}-3-vinylpiperidine-carboxylate (Example 79A, 2.00 g, 4.60 mmol) was dissolved in DCM (100 mL) and [1,3-bis(2,4,6-trimethylphenyl)imidazolidin-2-ylidene](dichloro)(phenylmethylidene)ruthenium-tricyclohexylphosphane (1:1) (781 mg, 920 μmol) was added. The reaction mixture was stirred for 48 h under reflux, then it was cooled to room temperature. DMSO (2.0 mL) was added and the reaction mixture was stirred overnight at room temperature. The reaction mixture was concentrated and the crude product was purified by chromatography on silica gel (cyclohexane/ethyl acetate (25%-50%)) to afford title 805 mg (99% purity, 42% yield) of the title compound.

LC-MS (Method 9): $R_t$=1.12 min; MS (ESI pos): m/z=407 $[M+H]^+$ $^1$H-NMR (400 MHz, DMSO-d6) δ[ppm]: 1.296 (5.30), 1.361 (16.00), 1.378 (2.93), 5.540 (0.72), 5.562 (0.51).

Example 81A (4aR,6aR,9S,11aS)-1-{[(9H-fluoren-9-yl)methoxy]carbonyl}-11-oxo-2,3,4,4a,6a,7,8,9,11,11a-decahydro-1H-pyrido[3,2-e]pyrrolo[1,2-a]azepine-9-carboxylic acid (single stereoisomer)

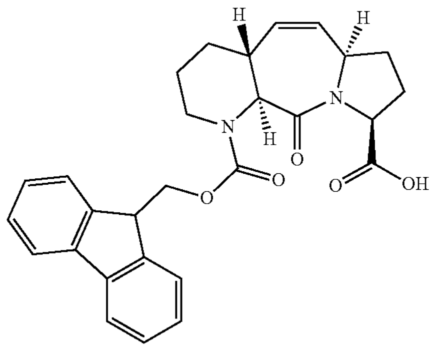 [SMILES: O=C(O)[C@@H]1CC[C@@H]2C=C[C@H]3CCCN(C(=O)OCC4c5ccccc5-c5ccccc54)[C@@H]3C(=O)N21]

Di-tert-Butyl-(4aR,6aR,9S,11aS)-11-oxo-2,3,4,4a,6a,7,8,9,11,11a-decahydro-1H-pyrido[3,2-e]pyrrolo[1,2-a]azepine-1,9-dicarboxylate (Example 80A,800 mg, 1.97 mmol) was dissolved in 8 mL DCM and the solution cooled to 0° C. Trifluoroacetic acid (8.0 mL, 100 mmol) was added and the reaction mixture was stirred for 1 h at room temperature. The reaction mixture was concentrated and the residue was diluted with sodium hydrogen carbonate solution (20 mL, pH=8). A solution of (9H-fluoren-9-yl)methyl carbonochloridate (CAS-RN: 28920-43-6, 764 mg, 2.95 mmol) in THF (24 mL) was added and the reaction mixture was stirred for 16 h at room temperature. The reaction mixture was diluted with DCM (100 mL) and acidified with 1 M hydrochloric acid (40 mL) (pH=1). The solution was extracted two times with DCM (50 mL) and the combined organic extract was dried over magnesium sulfate, filtered and then concentrated. Purification of the crude product by column chromatography on silica gel (DCM/MeOH 95/5) gave 676 mg (100% purity, 73% yield) of the title compound.

LC-MS (Method 10): $R_t$=1.86 min; MS (ESI pos): m/z=473 $[M+H]^+$ $^1$H-NMR (400 MHz, DMSO-d6) δ[ppm]: −0.008 (2.87), 0.008 (2.54), 0.778 (0.66), 0.800 (1.51), 0.808 (1.58), 0.832 (2.85), 0.856 (1.93), 0.865 (2.01), 0.889 (0.79), 1.125 (0.77), 1.157 (1.38), 1.182 (0.90), 1.215 (0.50), 1.235 (1.06), 1.517 (2.61), 1.538 (3.44), 1.563 (6.49), 1.593 (6.17), 1.610 (5.67), 1.636 (4.98), 1.660 (3.92), 1.684 (2.46), 1.719 (2.25), 1.747 (2.01), 1.846 (4.49), 1.858 (7.62), 1.868 (6.96), 1.901 (3.19), 2.010 (0.57), 2.073 (9.83), 2.189 (2.95), 2.200 (3.74), 2.241 (3.30), 2.276 (2.71), 2.307 (1.21), 2.327 (1.10), 2.366 (0.52), 2.398 (0.80), 2.428 (1.41), 2.456 (0.84), 2.670 (0.63), 2.710 (0.50), 2.816 (1.60), 2.833 (1.66), 2.849 (2.51), 2.862 (2.28), 2.877 (2.34), 2.895 (1.47), 3.040 (0.69), 3.075 (1.10), 3.086 (1.04), 3.101 (1.03), 3.121 (0.69), 3.690 (1.24), 3.724 (4.64), 3.744 (6.62), 3.756 (6.47), 3.777 (4.44), 3.823 (8.20), 3.852 (7.84), 4.120 (4.36), 4.137 (4.86), 4.148 (4.24), 4.191 (3.57), 4.202 (7.64), 4.212 (4.19), 4.261 (1.02), 4.276 (2.33), 4.291 (4.52), 4.316 (4.20), 4.328 (5.37), 4.346 (4.61), 4.370 (3.31), 4.383 (5.08), 4.395 (4.54), 4.411 (5.53), 4.422 (5.83), 4.456 (3.22), 4.595 (1.63), 4.761 (4.95), 4.773 (5.04), 4.788 (4.59), 4.800 (4.19), 5.364 (2.72), 5.393 (7.67), 5.422 (7.48), 5.451 (2.73), 5.510 (0.98), 5.540 (4.23), 5.553 (4.14), 5.585 (0.91), 7.282 (3.12), 7.300 (7.84), 7.319 (10.54), 7.337 (13.57), 7.355 (9.71), 7.366 (2.95), 7.377 (5.06), 7.399 (12.17), 7.420 (16.00), 7.438 (6.68), 7.521 (8.10), 7.539 (6.98), 7.613 (12.53), 7.631 (11.16), 7.646 (3.71), 7.665 (3.16), 7.847 (8.31), 7.865 (15.04), 7.884 (10.42), 7.908 (4.87), 12.429 (2.52).

This amino acid was used in Fmoc SPPS.

Example 82A (6S)-5-{[(9H-Fluoren-9-yl)methoxy]carbonyl}-5-azaspiro[2.4]heptane-6-carboxylic acid

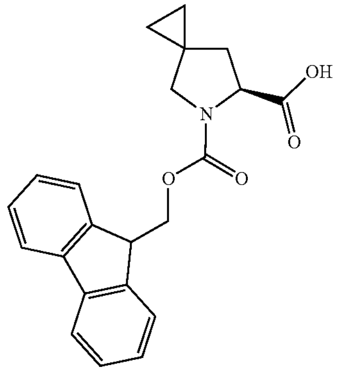 [SMILES: O=C(O)[C@@H]1CC2(CC2)CN1C(=O)OCC1c2ccccc2-c2ccccc21]

(6S)-5-Azaspiro[2.4]heptane-6-carboxylic acid (CAS-RN:152723-57-4, 1.38 g, 9.79 mmol) was dissolved in water (14 mL) and sodium hydrogen carbonate (8.23 g, 97.9 mmol) was added. Then a solution from 1-({[(9H-fluoren-9-yl)methoxy]carbonyl}oxy)pyrrolidine-2,5-dione (CAS-RN:82911-69-1, 3.47 g, 10.3 mmol) in acetone (21 mL) was added and the mixture was stirred overnight at room temperature. The reaction mixture was diluted with water and extracted two times with MTBE. The aqueous layer was acidified to pH 3-4 with 1M hydrochloric and extracted three times with DCM. The combined organic phase was dried over anhydrous magnesium sulfate, filtered, and then concentrated, to afford 3.3 g (100% purity, 93% yield) of the title compound.

LC-MS (Method 9): $R_t$=1.04 min; MS (ESI pos): m/z=364 $[M+H]^+$ $^1$H-NMR (400 MHz, DMSO-d6) δ[ppm]: 0.497 (1.67), 0.510 (2.34), 0.527 (5.55), 0.559 (3.82), 0.567 (5.51), 0.590 (9.33), 0.598 (11.21), 0.619 (1.87), 0.636 (0.58), 1.106 (9.23), 1.714 (2.14), 1.723 (2.15), 1.745 (2.40), 1.755 (2.50), 1.764 (1.94), 1.772 (1.85), 1.796 (2.02), 1.804 (1.93), 2.086 (7.36), 2.280 (2.12), 2.301 (2.47), 2.311 (2.21), 2.333 (2.24), 2.390 (1.75), 2.412 (2.07), 2.421 (1.87), 2.443 (1.71), 2.524 (0.88), 2.594 (3.10), 3.076 (2.73), 3.219 (3.24), 3.245 (4.13), 3.283 (3.41), 3.309 (5.19), 3.385 (5.05), 3.403 (4.32), 3.410 (3.56), 3.429 (3.16), 3.747 (1.01), 4.160 (0.68), 4.175 (1.57), 4.187 (3.09), 4.192 (3.69), 4.209 (6.08), 4.218 (4.18), 4.224 (3.09), 4.237 (2.43), 4.247 (1.22), 4.254 (2.15), 4.272 (16.00), 4.284 (3.83), 4.297 (4.75), 4.306 (2.72), 4.427 (2.10), 4.435 (2.31), 4.449 (2.34), 4.457 (2.02), 5.754 (0.45), 7.301 (1.47), 7.318 (5.18), 7.320 (5.43), 7.325 (2.74), 7.336 (7.24), 7.339 (7.37), 7.344 (4.81), 7.348 (3.25), 7.352 (3.50), 7.354 (3.84), 7.357 (3.67), 7.403 (9.03), 7.422 (14.80), 7.440 (6.64), 7.640 (8.10), 7.647 (7.82), 7.658 (7.43), 7.666 (6.87), 7.884 (10.09), 7.902 (9.58).

This amino acid was used in Fmoc SPPS.

This Fmoc amino acid was also prepared from (6S)-5-azaspiro[2.4]heptane-6-carboxylic acid prepared in Example 124A.

Example 83A (1S,3S,5S,6S)-2-{[(9H-Fluoren-9-yl)methoxy]carbonyl}-6-(trifluoromethyl)-2-azabicyclo[3.1.0]hexane-3-carboxylic acid and rel-(1R,3R,5R,6R)-2-{[(9H-Fluoren-9-yl)methoxy]carbonyl}-6-(trifluoromethyl)-2-azabicyclo[3.1.0]hexane-3-carboxylic acid

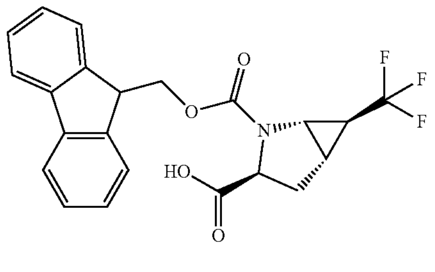

-continued

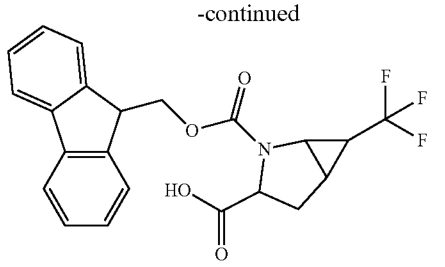

(1S, 3S, 5S, 6S)-6-(Trifluoromethyl)-2-azabicyclo[3.1.0]hexane-3-carboxylic acid (450 mg, 2.31 mmol) was dissolved in water (6 mL) and sodium hydrogen carbonate (1.94 g, 23.1 mmol) was added. Then a solution from 1-({[(9H-fluoren-9-yl)methoxy]carbonyl}oxy)pyrrolidine-2,5-dione (CAS-RN: 82911-69-1, 817 mg, 2.42 mmol) in acetone (9 mL) was added and the resulting suspension was stirred overnight at room temperature. The reaction mixture was diluted with water and extracted two times with MTBE. The aqueous layer was acidified to pH 3-4 with 1M hydrochloric and extracted three times with DCM. The combined organic phase was dried over anhydrous magnesium sulfate, filtered and then concentrated. The crude product was purified by preparative HPLC (column: Reprosil; C18; 10 μm; 125×40 mm; solvent: AcCN/$H_2O$ containing 0,1% HCOOH; flow rate: 100 mL/min; gradient: 0-5.50 min 10:90; sample injection at 3.00 min; 5.50-17.65 min gradient to 95:5; 17.65-19.48 min at 95:5; 19.48-19.66 min to 10:90; 19.66-20.72 min 10:90;), affording 571 mg (96% purity, 57% yield) of the title compound.

LC-MS (Method 9): $R_t$=1.06 min; MS (ESI pos): m/z=418 $[M+H]^+$ $^1$H-NMR (400 MHz, DMSO-d6) δ[ppm]: 2.073 (0.99), 2.203 (4.88), 2.345 (2.00), 2.366 (1.94), 3.755 (2.94), 4.078 (1.74), 4.221 (1.50), 4.253 (4.04), 4.270 (5.55), 4.290 (4.95), 4.337 (2.21), 7.293 (3.93), 7.301 (4.07), 7.312 (9.32), 7.319 (8.88), 7.330 (6.19), 7.337 (5.57), 7.407 (9.40), 7.425 (16.00), 7.444 (7.29), 7.695 (5.70), 7.887 (13.98), 7.906 (12.87), 12.866 (0.63).

The substance is also commercially available (CAS RN: 1986905-54-7)

The racemic amino acid using rel-(1R, 3R, 5R, 6R)-6-(Trifluoromethyl)-2-azabicyclo[3.1.0]hexane-3-carboxylic acid (Enamine) was prepared in a similar manner.

These amino acids were used in SPPS.

Example 84A

Methyl N-(tert-butoxycarbonyl)-L-isoleucylserinate (mixture of diastereomers)

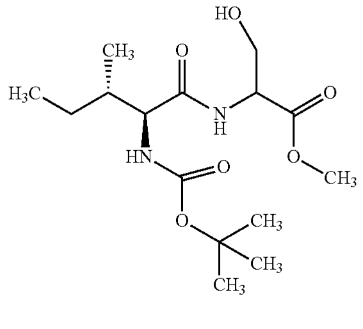 [SMILES: CC[C@H](C)[C@H](NC(=O)OC(C)(C)C)C(=O)NC(CO)C(=O)OC]

N-(tert-Butoxycarbonyl)-L-isoleucine (7.50 g, 32.4 mmol) and Methyl DL-serinate-hydrogen chloride (1/1) (5.05 g, 32.4 mmol) were dissolved in dichloromethane (65 mL). (Benzotriazol-1-yloxy)tris(dimethylamino)phosphonium hexafluorophosphate (14.9 g, 33.6 mmol) and N,N-diisopropylethylamine (11 mL, 65 mmol) were added and the reaction mixture was stirred overnight at room temperature. Dichloromethane (250 mL) was added and the reaction mixture was washed sequentially with water, aqueous hydrochloric acid (1M) and aqueous sodium hydrogen carbonate solution. The combined organic extract was dried over magnesium sulfate, filtered and then concentrated. The crude product was dissolved in DCM and thoroughly washed with water, two times again with aqueous hydrochloric acid (1M) and then two more times with aqueous sodium hydrogen carbonate. Subsequently the combined organic phase was dried over magnesium sulfate, filtered, and then concentrated. The crude product was used directly for the next step.

LC-MS (Method 11): 355.2 ($M^+Na^+$)

Example 85A

Methyl 2-{(1S,2S)-1-[(tert-butoxycarbonyl)amino]-2-methylbutyl}-4,5-dihydro-1,3-oxazole-4-carboxylate (mixture of diastereomers)

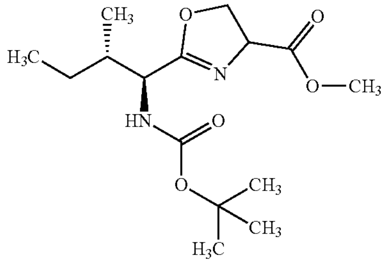 [SMILES: CC[C@H](C)[C@H](NC(=O)OC(C)(C)C)C1=NC(C(=O)OC)CO1]

Methyl N-(tert-butoxycarbonyl)-L-isoleucylserinate (Example 84A, 4.62 g, 13.9 mmol) was dissolved in dichloromethane (51 mL) and the solution cooled to −78° C. N-Ethyl-N-(trifluoro-lambda$^4$-sulfanyl)ethanamine (2.2 mL, 17 mmol) was added and the reaction mixture was stirred at −78° C. for 1.5 h. The reaction was quenched with potassium carbonate (7.68 g, 55.6 mmol) and then allowed to cool to room temperature. The solution was stirred for 1 h at room temperature. Then the solution was diluted with DCM (50 mL) and washed three times with saturated aqueous sodium hydrogen carbonate solution. The aqueous phase was further extracted with DCM. The combined organic phase was washed with brine, dried over anhydrous magnesium sulfate, filtered, and then concentrated to afford 5.75 g of the desired product.

LC-MS (Method 11): 315.2 ($M^+H^+$), 337.2 ($M^+Na^+$)

Example 86A

Methyl 2-{(1S,2S)-1-[(tert-butoxycarbonyl)amino]-2-methylbutyl}-1,3-oxazole-4-carboxylate

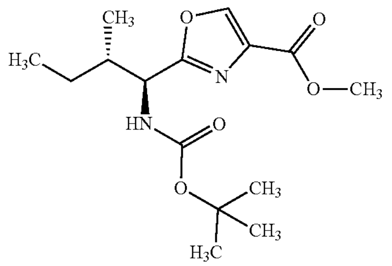 [SMILES: CC[C@H](C)[C@H](NC(=O)OC(C)(C)C)c1nc(C(=O)OC)co1]

Methyl 2-{(1S,2S)-1-[(tert-butoxycarbonyl)amino]-2-methylbutyl}-4,5-dihydro-1,3-oxazole-4-carboxylate (Example 85A, 4.37 g, 13.9 mmol) was dissolved in dichloromethane (35 mL, 540 mmol) and the solution was cooled at −40° C. Bromo(trichloro)methane (2.7 mL, 27 mmol) was added, then 2,3,4,6,7,8,9,10-octahydropyrimido[1,2-a] azepine (4.6 mL, 31 mmol) was also added. The reaction solution was stirred for 2.5 h at 0° C. and then diluted with DCM. The reaction mixture was washed five times with a 10% citric acid solution. The combined aqueous layer was extracted with DCM. The combined organic layer was washed with brine, dried over anhydrous magnesium sulfate, filtered and concentrated. The crude product was purified by chromatography on silica gel (gradient: cyclohexane/ethyl acetate (4:1)) to give 2.2 g (50.7% yield) of the title compound.

LC-MS (Method 10): 335.15 ($M^+Na^+$)

Example 87A

2-{(1S,2S)-1-[(tert-Butoxycarbonyl)amino]-2-methylbutyl}-1,3-oxazole-4-carboxylic acid

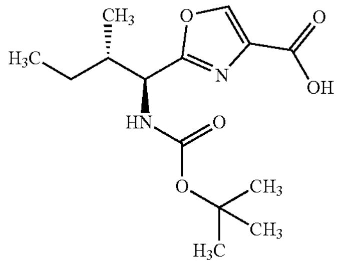 [SMILES: CC[C@H](C)[C@H](NC(=O)OC(C)(C)C)c1nc(C(=O)O)co1]

Methyl 2-{(1S,2S)-1-[(tert-butoxycarbonyl)amino]-2-methylbutyl}-1,3-oxazole-4-carboxylate (Example 86A, 2.21 g, 7.06 mmol) was dissolved in methanol (13.5 mL). Aqueous sodium hydroxide solution (4.3 mL, 3M) was added and the reaction mixture was stirred for 40 min and then concentrated to remove the methanol. The aqueous solution was acidified with aqueous 1M hydrochloric acid (14 mL) and extracted with ethyl acetate. The combined organic layer was dried over anhydrous magnesium sulfate, filtered and then concentrated under reduced pressure to give 12.0 g (95% purity, 51% yield) of the title compound.

LC-MS (MCW_OA_S1): $R_t$=1.13 min; MS (ESI neg): m/z=297 $[M+H]^-$

Example 88A (4R)-3-[(3S)-3-methylpentanoyl]-5,5-diphenyl-4-(propan-2-yl)-1,3-oxazolidin-2-one

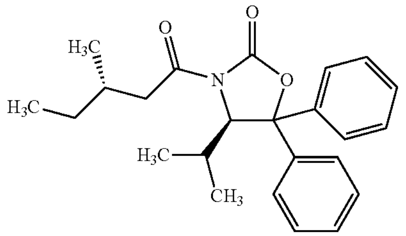 [SMILES: CC[C@H](C)CC(=O)N1C(=O)OC(c2ccccc2)(c2ccccc2)[C@H]1C(C)C]

A solution of (3S)-3-methylpentanoic acid (867 mg, 7.46 mmol) in anhydrous THF (50 mL) was cooled to −30° C. 2,2-Dimethylpropanoyl chloride (920 μl, 7.5 mmol) was added dropwise and the reaction mixture was stirred for 1.5 h at −30° C. Dry lithium chloride (347 mg, 8.17 mmol) and (4R)-5,5-diphenyl-4-(propan-2-yl)-1,3-oxazolidin-2-one (2.00 g, 7.11 mmol) ((R)-DIOZ) were sequentially added and the reaction mixture was slowly allowed to come to room temperature and stirred overnight. The reaction mixture was diluted with ethyl acetate and water. The water layer was separated and extracted with ethyl acetate. The combined ethyl acetate layer was washed with aqueous sodium chloride solution, dried over magnesium sulfate, filtered, and then concentrated, to give 2.87 g of a white solid. The crude product was dissolved in DCM with a small amount of methanol and was purified by column chromatography over silica gel (Biotage Isolera, 50 g cartridge) with cyclohexane/ethyl acetate (80:20) as eluant. The product-containing fractions were combined, concentrated and dried to give 2.25 g (98% purity, 82% yield) of the target compound.

LC-MS (Method 10): $R_t$=2.69 min; MS (ESI pos): m/z=380 $[M+H]^+$ $^1$H-NMR (400 MHz, DMSO-d6) δ[ppm]: 0.616 (13.33), 0.633 (13.58), 0.650 (7.84), 0.660 (16.00), 0.668 (15.61), 0.676 (15.27), 0.686 (7.40), 0.719 (0.40), 0.875 (12.87), 0.893 (12.59), 0.940 (0.92), 0.958 (1.50), 0.975 (2.08), 0.993 (2.23), 1.011 (1.38), 1.028 (0.84), 1.045 (1.41), 1.061 (1.93), 1.079 (1.89), 1.095 (1.16), 1.112 (0.62), 1.541 (0.55), 1.557 (1.29), 1.574 (1.91), 1.590 (1.82), 1.607 (1.10), 1.623 (0.40), 2.020 (0.71), 2.036 (1.44), 2.049 (1.78), 2.065 (1.28), 2.082 (0.50), 2.449 (2.60), 2.468 (2.84), 2.755 (2.63), 2.771 (2.50), 2.793 (2.05), 2.808 (1.92), 5.557 (5.98), 5.563 (5.64), 7.271 (2.61), 7.289 (6.37), 7.307 (5.02), 7.352 (5.04), 7.368 (10.74), 7.385 (9.60), 7.403 (3.47), 7.557 (8.45), 7.577 (6.54), 7.639 (8.45), 7.659 (6.92).

Example 89A

Benzyl {(2S,3S)-3-methyl-2-[(4R)-2-oxo-5,5-diphenyl-4-(propan-2-yl)-1,3-oxazolidine-3-carbonyl]pentyl}carbamate

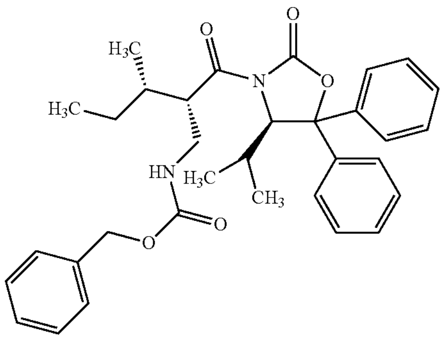 [SMILES: CC[C@H](C)[C@@H](CNC(=O)OCc1ccccc1)C(=O)N1C(=O)OC(c2ccccc2)(c2ccccc2)[C@H]1C(C)C]

The literature procedure (Sebesta and Seebach, *Helv. Chim. Acta* 2003, 86, 4061-4072) was followed. (4R)-3-[(3S)-3-methylpentanoyl]-5,5-diphenyl-4-(propan-2-yl)-1,3-oxazolidin-2-one (Example 88A, 2.20 g, 5.80 mmol) was dissolved in DCM (20 mL) and the solution was cooled to −15° C. A solution of Titanium (IV) chloride (6.1 mL, 1.0 M in DCM, 6.1 mmol) was added dropwise while maintaining the temperature at −15° C. Triethylamine (890 μl, 6.4 mmol) was then added and the reaction mixture was stirred for 30 min at −15° C.

In a separate round-bottomed flask a solution of benzyl (methoxymethyl)carbamate (1.24 g, 6.38 mmol, CAS RN: 94471-35-9) in DCM (10 mL) was cooled to 0° C. A solution of Titanium (IV) chloride (6.4 mL, 1.0 M in DCM, 6.4 mmol) was added dropwise, and then the entire solution was added dropwise to the flask containing (4R)-3-[(3S)-3-methylpentanoyl]-5,5-diphenyl-4-(propan-2-yl)-1,3-oxazolidin-2-one. The reaction mixture was stirred for 4 h at 0° C., then it was allowed to stir at room temperature overnight. The reaction was quenched by adding an aqueous ammonium chloride solution and then diluted with additional DCM. The separated organic layer was washed with aqueous 1M HCl solution, aqueous 1M NaOH solution, and then with aqueous sodium chloride solution. The organic layer was filtered and then concentrated, to give 3.39 g of a yellow oil. The crude product was purified by column chromatography over silica gel (Biotage Isolera 100 g cartridge) with cyclohexane/ethyl acetate (85:15) eluant. The product-containing fractions were combined, concentrated and then dried to give 1.50 g (96% purity, 46% yield, selectivity) of the title compound with a diastereoselectivity of 96.3% (lit. 96%).

LC-MS (Method 10): $R_t$=2.63 min; MS (ESI pos): m/z=543 $[M+H]^+$ $^1$H-NMR (400 MHz, DMSO-d6) δ[ppm]: 0.429 (3.22), 0.446 (3.32), 0.480 (1.44), 0.498 (3.18), 0.516 (1.79), 0.595 (4.27), 0.611 (4.65), 0.643 (0.49), 0.663 (0.46), 0.768 (0.45), 0.786 (0.46), 0.874 (3.86), 0.891 (4.01), 1.098 (0.48), 1.397 (16.00), 1.993 (0.45), 2.010 (0.57), 2.023 (0.45), 3.146 (0.44), 3.169 (0.66), 3.180 (1.02), 3.192 (0.63), 3.206 (0.44), 3.222 (0.53), 3.243 (0.48), 3.816 (0.57), 4.920 (0.59), 4.952 (1.85), 4.978 (2.04), 5.010 (0.65), 5.539 (1.70), 5.544 (1.73), 7.187 (0.53), 7.201 (0.87), 7.282 (3.41), 7.289 (5.28), 7.306 (4.14), 7.322 (1.84), 7.342 (2.69), 7.362 (3.73), 7.385 (3.47), 7.405 (1.52), 7.566 (3.08), 7.584 (2.46), 7.662 (2.88), 7.681 (2.48).

Example 90A (2S,3S)-2-({[(Benzyloxy)carbonyl]amino}methyl)-3-methylpentanoic acid

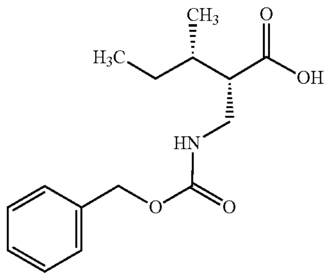 [SMILES: CC[C@H](C)[C@@H](CNC(=O)OCc1ccccc1)C(=O)O]

A solution of benzyl {(2S,3S)-3-methyl-2-[(4R)-2-oxo-5,5-diphenyl-4-(propan-2-yl)-1,3-oxazolidine-3-carbonyl]pentyl}carbamate (Example 89A, 1.49 g, 2.75 mmol) in THF (15 mL) was prepared. A solution of LiOH (105 mg, 4.39 mmol) in water (5 mL) was added and the reaction mixture was stirred at room temperature for 24 h. HPLC analysis indicated that the reaction was not completed, so an additional equivalent of LiOH (65.8 mg, 2.75 mmol) in water (3 mL) was added. The reaction mixture was stirred at room temperature overnight. The reaction mixture was diluted with diethyl ether, the mixture was stirred for 5 minutes, and then filtered. The filter cake was washed with water and with ether, and then the layers were separated. The aqueous layer was acidified with aqueous 1M HCl solution to pH 1 and extracted three times with diethyl ether. The combined ether phase was washed with sodium chloride solution, dried over magnesium sulfate, filtered, and then concentrated. After drying under high vacuum, 715 mg (100% purity, 93% yield) of the title compound was obtained.

LC-MS (Method 10): $R_t$=1.71 min; MS (ESI pos): m/z=280 $[M+H]^+$ $^1$H-NMR (400 MHz, DMSO-d6) δ[ppm]: 0.837 (6.34), 0.856 (14.23), 0.863 (13.72), 0.880 (12.65), 1.098 (0.91), 1.117 (1.35), 1.133 (1.47), 1.151 (1.49), 1.170 (0.95), 1.348 (0.42), 1.367 (1.02), 1.380 (1.33), 1.398 (1.53), 1.414 (1.09), 1.431 (0.72), 1.596 (0.82), 1.611 (1.42), 1.627 (1.61), 1.644 (1.16), 1.660 (0.53), 1.908 (3.41), 2.396 (1.17), 2.413 (2.79), 2.429 (2.67), 2.445 (1.07), 2.501 (16.00), 3.139 (4.27), 3.155 (7.41), 3.171 (4.60), 5.000 (15.52), 7.221 (1.46), 7.234 (2.66), 7.248 (1.41), 7.283 (0.89), 7.290 (0.97), 7.300 (2.98), 7.318 (5.22), 7.332 (11.34), 7.339 (12.29), 7.356 (5.30), 7.375 (1.45), 12.135 (3.58).

Example 91A (2S,3S)-2-(Aminomethyl)-3-methylpentanoic acid

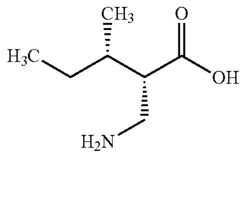

10% Palladium on carbon (100 mg) was weighed out into a round-bottomed flask and the flask was flushed with Argon. A solution of (2S,3S)-2-({[(benzyloxy)carbonyl] amino}methyl)-3-methylpentanoic acid (Example 90A, 710 mg, 2.54 mmol) in methanol (40 mL) was added and the reaction mixture was stirred at room temperature under a normal pressure of $H_2$ gas. HPLC analysis indicated that after 2 hours at room temperature, the reaction was completed. The reaction mixture was filtered through a plug of silica gel and the filter cake was washed several times with methanol. The combined filtrate was concentrated under reduced pressure to provide 345 mg (93%) of the title compound. The compound was used directly for the next step.

Example 92A (2S,3S)-2-[({[(9H-Fluoren-9-yl)methoxy] carbonyl}amino)methyl]-3-methylpentanoic acid

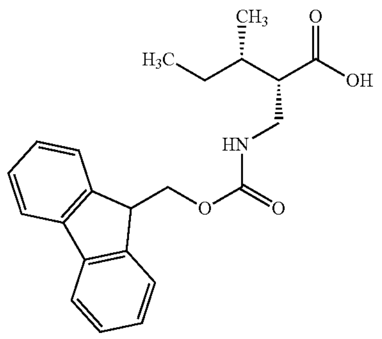 [SMILES: CC[C@H](C)[C@@H](CNC(=O)OCC1c2ccccc2-c2ccccc21)C(=O)O]

(2S,3S)-2-(Aminomethyl)-3-methylpentanoic acid (Example 91A, 344 mg, 2.37 mmol) was dissolved in aqueous sodium carbonate solution (32 mL, 0.15 M, 4.7 mmol). 1-([{9H-fluoren-9-yl)methoxy]carbonyl}oxy)pyrrolidine-2,5-dione (959 mg, 2.84 mmol) was dissolved in acetone (30 mL) and this solution was added to the previous solution and the reaction mixture was stirred for 2 h at room temperature. The reaction mixture was the concentrated to remove the acetone. The aqueous solution was diluted with water and extracted with ethyl acetate. The aqueous layer was acidified to pH 3-4 with 1M aqueous hydrochloric acid and extracted with ethyl acetate. The combined organic layers were washed with brine, dried over anhydrous magnesium sulfate, filtered and then concentrated. The crude product was purified by preparative HPLC (column: Reprosil; C18; 10 μm; 125×30 mm; solvents: AcCN/$H_2O$ containing 0.1% HCOOH; flow rate: 75 mL/min; gradient: 0-5.50 min (10:90); sample injection at 3.00 min; 5.50-17.65 min gradient to 95:5; 17.65-19.48 min (95:5); 19.48-19.66 min gradient to 10:90; 19.66-20.72 min (10:90) to give 795 mg (96% purity, 88% yield) of the title compound.

LC-MS (Method 9): $R_t$=1.06 min; MS (ESI pos): m/z=368 $[M+H]^+$ $^1$H-NMR (400 MHz, DMSO-d6) δ[ppm]: −0.008 (1.04), 0.008 (0.54), 0.752 (0.73), 0.841 (7.69), 0.860 (16.00), 0.870 (15.28), 0.878 (10.54), 0.887 (13.22), 1.085 (0.41), 1.103 (0.99), 1.123 (1.45), 1.139 (1.58), 1.157 (1.60), 1.176 (1.00), 1.371 (1.16), 1.384 (1.50), 1.403 (1.71), 1.418 (1.23), 1.435 (0.83), 1.604 (0.88), 1.619 (1.50), 1.636 (1.70), 1.651 (1.23), 2.408 (1.27), 2.425 (2.91), 2.441 (3.13), 2.458 (1.88), 2.524 (0.87), 2.749 (0.82), 3.143 (4.18), 3.158 (6.08), 3.174 (3.40), 4.176 (1.25), 4.194 (3.04), 4.211 (4.04), 4.241 (8.74), 4.255 (4.27), 4.263 (3.35), 7.303 (5.42), 7.322 (12.94), 7.340 (10.81), 7.353 (1.98), 7.394 (7.49), 7.413 (11.83), 7.431 (5.34), 7.673 (5.88), 7.683 (5.84), 7.691 (5.19), 7.701 (4.30), 7.876 (12.54), 7.895 (11.30), 12.176 (1.21).

This amino acid was used in SPPS.

Example 93A

2-[(1S,2S)-1-({[(9H-Fluoren-9-yl)methoxy] carbonyl}amino)-2-methylbutyl]-1,3-oxazole-4-carboxylic acid

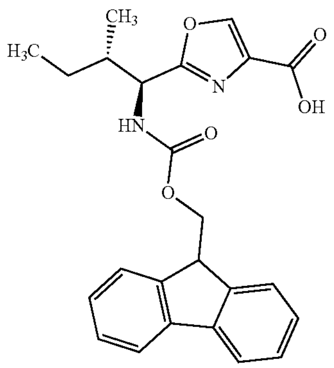 [SMILES: CC[C@H](C)[C@H](NC(=O)OCC1c2ccccc2-c2ccccc21)c1nc(C(=O)O)co1]

2-{(1S,2S)-1-[(tert-Butoxycarbonyl)amino]-2-methylbutyl}-1,3-oxazole-4-carboxylic acid (Example 87A, 1.85 g, 6.21 mmol) was dissolved in trifluoroacetic acid (7.6 mL, 99 mmol) and the solution was stirred for 15 min. Then the solution was diluted with toluene and evaporated. This step was repeated again. The crude product was dissolved in 1,4-dioxane (20 mL, 230 mmol) and water (20 mL). Potassium carbonate (1.60 g, 11.6 mmol) and 1-{[(9H-fluoren-9-ylmethoxy)carbonyl]oxy}pyrrolidine-2,5-dione (2.35 g, 6.96 mmol) was added and the reaction mixture was stirred overnight at room temperature. The reaction mixture was diluted with water (65 mL) and acidified to pH 2-3 with a 10% aqueous citric acid solution. The reaction mixture was extracted with ethyl acetate (three times), and the combined organic layer was washed with brine, dried over magnesium sulfate, filtered, and then concentrated under reduced pressure. The residue was purified by chromatography on silica gel (dichloromethane-methanol (3-7%+1% acetic acid), and the product-containing fractions were combined, diluted with toluene, and then concentrated. Toluene was then added again and then the solution was concentrated, to provide 2.09 g (100% purity, 80% yield) of the title compound.

LC-MS (MCW_FT_MS_M1): $R_t$=2.01 min; MS (ESI pos): m/z=421 $[M+H]^+$

This amino acid was used in SPPS.

Example 94A di(Prop-2-en-1-yl)amino](1-methyl-1H-indazol-5-yl) acetic acid (racemate)

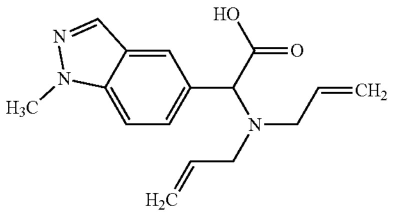 [SMILES: C=CCN(CC=C)C(C(=O)O)c1ccc2c(cnn2C)c1]

(1-Methyl-1H-indazol-5-yl)boronic acid (CAS-RN: 590418-08-9, 500 mg, 2.84 mmol), oxoacetic acid (CAS-RN: 298-12-4, 310 µl, 50% purity, 2.8 mmol) and N-(Prop-2-en-1-yl)prop-2-en-1-amine (CASRN:124-02-7, 350 µl, 2.8 mmol) were dissolved in acetonitrile (7.5 mL) and the reaction mixture was stirred for 40 h at 60° C. After cooling, the resulting solid was filtered, washed with ethyl acetate and dried to give 740 mg (100% purity, 91% yield) of the title compound.

LC-MS (Method 9): $R_t$=0.44 min; MS (ESI neg): m/z=284 $[M-H]^-$ $^1$H-NMR (400 MHz, DMSO-d6) δ[ppm]: 0.008 (1.87), 2.073 (0.51), 3.110 (0.68), 3.125 (0.77), 3.147 (2.14), 3.161 (2.16), 3.176 (2.32), 3.193 (2.28), 3.213 (0.90), 3.230 (0.96), 4.030 (16.00), 4.531 (3.61), 5.110 (2.47), 5.134 (4.58), 5.174 (2.56), 5.752 (0.60), 5.768 (1.07), 5.778 (0.73), 5.783 (0.73), 5.794 (1.49), 5.810 (1.35), 5.820 (0.63), 5.826 (0.67), 5.837 (0.87), 5.852 (0.49), 6.514 (1.52), 7.432 (1.39), 7.435 (1.47), 7.454 (1.77), 7.457 (1.87), 7.602 (2.26), 7.624 (1.75), 7.699 (3.10), 8.041 (4.18).

Example 95A ({[(9H-Fluoren-9-yl)methoxy]carbonyl}amino)(1-methyl-1H-indazol-5-yl)acetic acid (racemate)

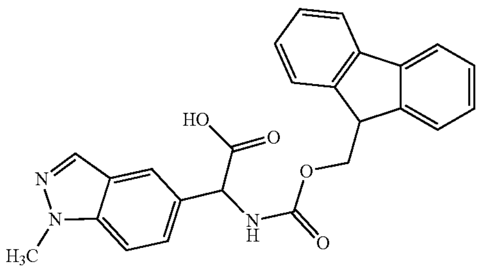 [SMILES: Cn1ncc2cc(C(NC(=O)OCC3c4ccccc4-c4ccccc43)C(=O)O)ccc21]

1,3-dimethyl-1,3-diazinane-2,4,6-trione (CAS-RN: 769-42-6, 1.97 g, 12.6 mmol) and tetrakis(triphenylphosphine) palladium(0) (48.6 mg, 42.1 µmol) were placed into a round-bottomed flask under Argon. A solution of [di(Prop-2-en-1-yl)amino](1-methyl-1H-indazol-5-yl)acetic acid (Example 94A, 600 mg, 2.10 mmol) in dry DCM was then added, and the reaction mixture was stirred for 2 h at 35° C. The suspension was diluted with water acetone and water and then the reaction mixture was concentrated to remove the DCM. Sodium hydrogen carbonate (2.65 g, 31.5 mmol) was added (attention gas formation). 1-({[(9H-fluoren-9-yl)methoxy]carbonyl}oxy)pyrrolidine-2,5-dione (780 mg, 2.31 mmol) was added to the suspension and the reaction mixture was stirred overnight at room temperature. Water and an aqueous solution of sodium carbonate (10%) were added and the solution was extracted two times with MTBE.

The aqueous phase was acidified with aqueous citric acid solution and then extracted three times with DCM. The combined organic layers were washed with brine, dried of magnesium sulfate, filtered, and then concentrated. The residue was purified by preparative HPLC (column: Reprosil; C18; 10 µm; 125×40 mm; solvent: AcCN/$H_2O$ containing 0.1% HCOOH; flow rate: 100 mL/min; gradient: 0-5.50 min (10:90); sample injection at 3.00 min; 5.50-17.65 min gradient to 95:5; 17.65-19.48 min (95:5); 19.48-19.66 min gradient to 10:90; 19.66-20.72 min (10:90) to give 422 mg (100% purity, 47% yield) of the title compound.

LC-MS (Method 9): $R_t$=0.94 min; MS (ESI pos): m/z=428 $[M+H]^+$ $^1$H-NMR (400 MHz, DMSO-d6) δ[ppm]: 2.073 (0.59), 4.041 (16.00), 4.198 (0.63), 4.215 (1.87), 4.231 (3.51), 4.253 (1.84), 4.269 (1.50), 4.280 (1.92), 4.298 (1.70), 4.319 (0.59), 5.256 (1.81), 5.276 (1.80), 7.275 (0.90), 7.293 (2.03), 7.320 (2.08), 7.339 (1.26), 7.388 (1.98), 7.406 (3.38), 7.424 (1.73), 7.445 (1.60), 7.467 (1.96), 7.621 (2.30), 7.643 (1.76), 7.744 (3.56), 7.763 (3.31), 7.792 (3.19), 7.875 (4.81), 7.893 (4.48), 8.063 (4.53), 8.213 (1.70), 8.232 (1.65), 12.835 (1.03).

Example 96A ({[(9H-Fluoren-9-yl)methoxy]carbonyl}amino)(1-methyl-1H-indazol-5-yl)acetic acid (enantiomer 1)

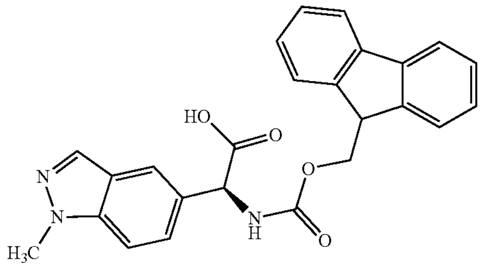 [SMILES: Cn1ncc2cc([C@H](NC(=O)OCC3c4ccccc4-c4ccccc43)C(=O)O)ccc21]

The diastereomeric mixture (Example 95A, 600 mg) was dissolved in methanol/acetonitrile (60 mL) and separated using a THAR supercritical fluid chromatography Prep 200 instrument using a Chiralpak AD-H (SFC) 5 µm, 250×30 mm column; eluent: CO2/iso-propanol (80:20); pressure: 135 bar; temperature eluent: 38° C.; flow rate: 100 g/min; detection: UV 210 nm; injection volume 0.4 mL/injection; under general operating conditions 1 g/min of CO2 is approximately equivalent to 1 mL/min.

Sequence Settings: cycle time=11.2 min

Fraction 1 was collected at 5.8 min (enantiomer 1); Fraction 2 was collected between 7.7 min (enantiomer 2). The fractions were concentrated.

The fractions were analyzed using analytical SFC-MS (Agilent, column: Daicel AD-3 3 µm 100×4.6 mm, eluent: CO2/methanol (80:20); BPR pressure: 130 bar; BPR temperature: 60° C.; column temperature: 40° C.; flow rate: 3 mL/min; UV 210 nm.

The stereochemistry of the two enantiomers was not assigned.

185 mg of enantiomer 1 (100% purity, 99.5% ee) were obtained (stereochemistry not determined)

LC-MS (Method 10): $R_t$=1.80 min; MS (ESI pos): m/z=428 $[M+H]^+$ $^1$H-NMR (400 MHz, DMSO-d6) δ[ppm]: 4.040 (16.00), 4.197 (0.54), 4.214 (1.44), 4.230 (2.80), 4.251 (1.59), 4.268 (1.38), 4.278 (1.68), 4.295 (1.46), 4.316 (0.48), 5.241 (1.20), 5.261 (1.19), 7.275 (0.78), 7.294 (1.73), 7.321 (1.78), 7.339 (1.11), 7.386 (1.77), 7.394 (1.54), 7.405 (2.97), 7.412 (2.26), 7.423 (1.63), 7.444 (1.36), 7.466 (1.53), 7.617 (1.85), 7.638 (1.42), 7.742 (3.01), 7.761 (2.84), 7.787 (2.53), 7.874 (4.50), 7.893 (4.19), 8.058 (4.56), 8.183 (0.93), 8.201 (0.92).

This amino acid was used in SPPS.

Example 97A ({[(9H-Fluoren-9-yl)methoxy]carbonyl}amino)(1-methyl-1H-indazol-5-yl)acetic acid (enantiomer 2)

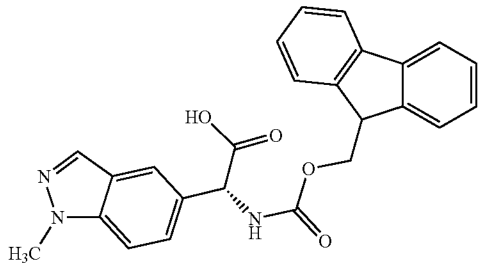 [SMILES: Cn1ncc2cc([C@@H](NC(=O)OCC3c4ccccc4-c4ccccc43)C(=O)O)ccc21]

Using the chiral separation method described in Example 96A, 145 mg (100% purity, 94.3%) of the enantiomer 2 were obtained (stereochemistry not determined).

LC-MS (Method 10): $R_t$=1.80 min; MS (ESI pos): m/z=428 $[M+H]^+$ $^1$H-NMR (400 MHz, DMSO-d6) δ[ppm]: −0.008 (0.78), 0.008 (0.70), 4.040 (16.00), 4.198 (0.41), 4.214 (1.16), 4.230 (2.33), 4.252 (1.27), 4.268 (1.03), 4.278 (1.36), 4.295 (1.14), 4.300 (0.99), 5.243 (0.98), 5.262 (0.98), 7.276 (0.59), 7.294 (1.34), 7.313 (1.11), 7.321 (1.38), 7.340 (0.86), 7.387 (1.36), 7.394 (1.12), 7.406 (2.32), 7.413 (1.70), 7.424 (1.22), 7.431 (0.89), 7.444 (1.06), 7.466 (1.21), 7.618 (1.52), 7.640 (1.16), 7.743 (2.38), 7.762 (2.23), 7.787 (2.02), 7.875 (3.68), 7.894 (3.45), 8.059 (3.94), 8.188 (0.73), 8.207 (0.72).

This amino acid was used in SPPS.

Example 98A

Benzyl N-[(benzyloxy)carbonyl]-3-bromo-L-phenylalaninate

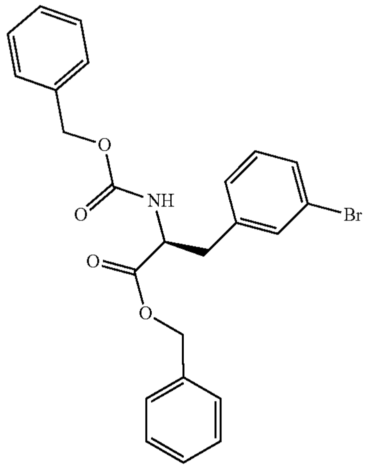 [SMILES: O=C(N[C@@H](Cc1cccc(Br)c1)C(=O)OCc1ccccc1)OCc1ccccc1]

N-[(Benzyloxy)carbonyl]-3-bromo-L-phenylalanine (15.3 g, 40.5 mmol) was dissolved in methanol (113 mL). Caesium carbonate (6.59 g, 20.2 mmol) was added and the mixture was stirred until gas no evolution ceased. The solution was evaporated to dryness. The residue was dissolved in DMF (140 mL, 1.8 mol) and (bromomethyl) benzene (5.3 mL, 44 mmol) was added dropwise. After a short time a solid precipitated. The suspension was diluted with ether and water. The organic phase was separated, and the aqueous phase was extracted two times with diethyl ether. The combined organic layers were washed with water, washed with brine, and then dried over magnesium sulfate. The crystalline residue was dissolved in ether and after the addition of pentane, a precipitate formed. The solid was filtered and dried. The ether/pentane solution was evaporated and dissolved in ether; after the addition of pentane a precipitate formed. The solid was filtered and dried, to give 16.0 g (100% purity, 84% yield) of the title compound.

LC-MS (Method 10): Rt=2.42 min; MS (ESI pos): m/z=468 [M+H]+

$^1$H-NMR (500 MHz, DMSO-d6) δ[ppm]: 2.874 (2.41), 2.895 (2.86), 2.902 (3.10), 2.923 (2.76), 3.071 (2.84), 3.082 (2.96), 3.099 (2.26), 3.109 (2.09), 3.636 (0.82), 4.336 (1.73), 4.347 (2.20), 4.353 (2.43), 4.357 (2.48), 4.363 (2.48), 4.373 (1.83), 4.383 (1.37), 4.921 (0.55), 4.963 (1.81), 4.989 (12.84), 4.994 (11.01), 5.020 (1.18), 5.043 (0.96), 5.093 (1.11), 5.119 (12.74), 5.139 (0.55), 5.147 (0.97), 7.174 (0.85), 7.211 (3.13), 7.226 (9.23), 7.241 (11.35), 7.248 (16.00), 7.263 (11.82), 7.298 (10.22), 7.313 (14.37), 7.316 (14.35), 7.321 (12.62), 7.332 (10.08), 7.336 (11.10), 7.344 (8.08), 7.351 (11.64), 7.366 (7.19), 7.379 (2.35), 7.414 (5.80), 7.429 (4.73), 7.499 (7.87), 7.880 (4.47), 7.896 (4.30).

Example 99A

3-[(2S)-3-(Benzyloxy)-2-{[(benzyloxy)carbonyl]amino}-3-oxopropyl]benzoic acid

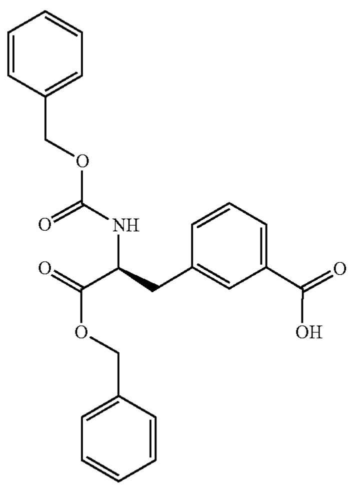 [SMILES: O=C(N[C@@H](Cc1cccc(C(=O)O)c1)C(=O)OCc1ccccc1)OCc1ccccc1]

The reaction was set up under argon. In a 2 L autoclave (stirring speed 750 rpm) are added palladium(II)acetate (2.16 g, 9.61 mmol), 1,1'-Bis(diphenylphosphino)ferrocene (10.63 g, 19.22 mmol) and potassium acetate (47.1 g, 480 mmol). The autoclave is flushed with argon and the reagents are dissolved by adding dry DMF (450 mL). A solution of benzyl N-[(benzyloxy)carbonyl]-3-bromo-L-phenylalaninate (Example 98A, 45.0 g, 96.1 mmol) in dry DMF (930 mL) was added to the autoclave, followed the addition of water (18 mL). The Autoclave was sealed, purged repeatedly with nitrogen and allowed to stir briefly. The autoclave was pressurized with carbon monoxide (3 bar) and then heated to 80° C. and 3 bar for 960 min. After the reaction was completed, the autoclave was purged, opened, and then the contents were dissolved in water (13 L). The reaction mixture was extracted 3 times with ethyl acetate (7 L) and the combined organic layer was washed with brine, and then concentrated. The crude product was purified by preparative normal phase chromatography (10 kg silica gel) with DCM/MeOH (95/5) and then further purified by preparative chromatography (DCM/MeOH gradient, Biotage Isolera) to provide 10.7 g (92% purity) of the title compound.

LC-MS (Method 10): $R_t$=1.92 min; MS (ESI neg): m/z=432.14 $[M-H]^-$

Example 100A

Benzyl N-[(benzyloxy)carbonyl]-3-(tert-butoxycarbonyl)-L-phenylalaninate

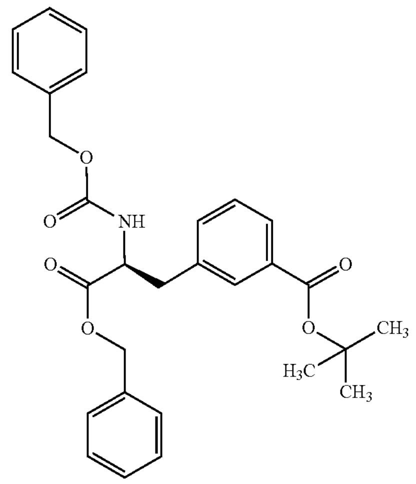 [SMILES: CC(C)(C)OC(=O)c1cccc(C[C@H](NC(=O)OCc2ccccc2)C(=O)OCc2ccccc2)c1]

To 3-[(2S)-3-(Benzyloxy)-2-{[(benzyloxy)carbonyl]amino}-3-oxopropyl]benzoic acid (Example 99A,18.0 g, 41.5 mmol) was added dichloromethane (280 mL, 4.4 mol). Cyclohexane (140 mL, 1.3 mol), tert-butyl 2,2,2-trichloroethanimidate (36.3 g, 166 mmol) and (diethyl ether)(trifluoro)boron (1.6 mL, 12 mmol) were added and the reaction mixture was stirred at room temperature. After 1 h, additional diethyl ether)(trifluoro)boron (1.6 mL, 12 mmol) was added and the reaction mixture was stirred overnight at room temperature. (diethyl ether)(trifluoro)boron (1 mL, 7.5 mmol) was added and reaction mixture was stirred for 2 h at room temperature. Additional tert-Butyl 2,2,2-trichloroethanimidate (9.0 g, 40.5 mmol) and additional (diethyl ether)(trifluoro)boron (1 mL, 7.5 mmol) were added and the reaction mixture was stirred overnight at room temperature. The suspension was filtered and the precipitate was washed with DCM: cyclohexane (2:1). The solution was diluted with concentrated aqueous sodium hydrogen carbonate solution. The combined water layers were extracted two times with DCM. The combined organic layers were then dried over magnesium sulfate, filtered and then evaporated. The resulting black oil was stirred with cyclohexane and ethyl acetate (2%), the precipitate was filtered, and the filtrate was evaporated. The resulting black oil was purified by column chromatography on silica gel (cyclohexane-ethyl acetate (9:1)) to yield 12.1 g (100% purity, 60% yield) of the title compound.

LC-MS (Method 9): $R_t$=1.34 min; MS (ESI pos): m/z=$[M+H]^+$ 490

Example 101A 3-(tert-Butoxycarbonyl)-L-phenylalanine

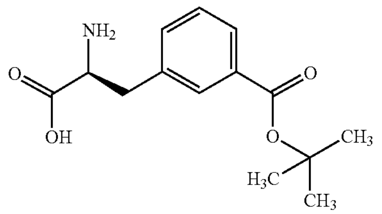 [SMILES: CC(C)(C)OC(=O)c1cccc(C[C@H](N)C(=O)O)c1]

Benzyl N-[(benzyloxy)carbonyl]-3-(tert-butoxycarbonyl)-L-phenylalaninate (Example 100A, 13.0 g, 26.6 mmol) was dissolved in methanol (250 mL). 10% Palladium on charcoal (1.54 g) was added and the mixture was hydrogenated at ambient pressure for 4 hours at room temperature. A precipitate was formed. The suspension was dissolved in methanol and was stirred at reflux. The warm solution was filtered over a layer of diatomaceous earth and the filter cake was washed with methanol (ca. 1 L). The combined filtrate was concentrated and dried, affording 6.10 g (94% purity, 81% yield) of the title compound.

LC-MS (Method 9): $R_t$=0.59 min; MS (ESI neg): m/z=264 $[M-H]^-$ $^1$H-NMR (400 MHz, DMSO-d6) δ[ppm]: 1.525 (5.74), 1.546 (16.00), 2.326 (0.50), 2.366 (0.48), 2.670 (0.50), 2.709 (0.48), 3.169 (0.57), 7.400 (0.89), 7.419 (0.66), 7.501 (0.76), 7.739 (0.84), 7.759 (0.85), 7.796 (1.02).

Example 102A 3-(tert-Butoxycarbonyl)-N-{[(9H-fluoren-9-yl) methoxy]carbonyl}-L-phenylalanine

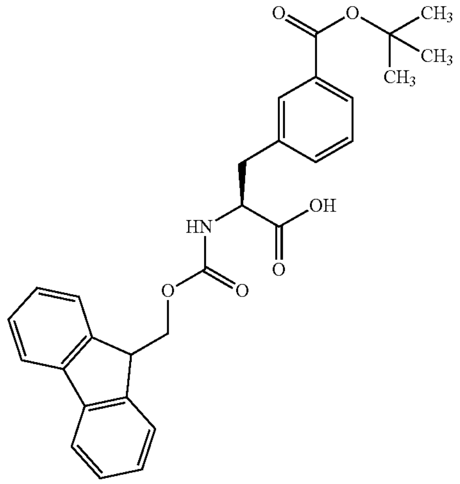 [SMILES: CC(C)(C)OC(=O)c1cccc(C[C@H](NC(=O)OCC2c3ccccc3-c3ccccc32)C(=O)O)c1]

3-(tert-Butoxycarbonyl)-L-phenylalanine (Example 101A, 6.10 g, 23.0 mmol) was dissolved in water (100 mL) and acetone (100 mL). Sodium hydrogen carbonate (19.3 g, 230 mmol) was added. A solution of 1-({[(9H-fluoren-9-yl) methoxy]carbonyl}oxy)pyrrolidine-2,5-dione (8.14 g, 24.1 mmol) was dissolved in acetone (100 mL) was added and the reaction mixture was stirred overnight at room temperature. The mixture was diluted with water and extracted with one portion of MTBE. The aqueous layer was acidified with 1M hydrochloric and extracted with DCM. The combined organic layer was washed with brine, dried over anhydrous magnesium sulfate, filtered, and then concentrated to afford 8.90 g (100% purity, 79% yield) of the title compound. Product was also present in the organic layer. The organic layer was concentrated. DCM and 1M hydrochloric were added to the residue and the mixture was stirred for 5 min. The residue was filtered and washed with water and DCM. The layers were separated, and the aqueous layer was extracted with DCM. The combined organic layer was then dried over anhydrous magnesium sulfate, filtered, and then concentrated. The crude product was purified by flash chromatography on silica gel (gradient DCM: methanol (0-10%)). The residue was taken up in acetonitrile and purified by preparative HPLC (column: Reprosil; C18; 10 μm; 125×40 mm; solvent: $AcCN/H_2O$ containing 0.1% HCOOH; flow rare: 100 mL/min; gradient: 0-5.50 min (10:90); sample injection at 3.00 min; 5.50-17.65 min gradient to 95:5; 17.65-19.48 min (95:5); 19.48-19.66 min gradient to 10:90; 19.66-20.72 min (10:90). In total, 1.58 g (100% purity, 14% yield) of the title compound was obtained.

LC-MS (Method 10): $R_t$=2.27 min; MS (ESI neg): m/z=486 $[M-H]^-$ $^1$H-NMR (400 MHz, DMSO-d6) δ[ppm]: 1.106 (1.34), 1.144 (4.63), 1.519 (16.00), 1.544 (0.64), 2.086 (1.34), 2.119 (1.97), 2.483 (1.16), 2.595 (0.68), 3.077 (0.43), 3.319 (1.89), 4.158 (0.42), 4.169 (0.81), 4.181 (2.03), 4.195 (0.76), 4.203 (0.48), 4.541 (0.43), 7.259 (0.80), 7.277 (0.76), 7.293 (0.68), 7.312 (0.44), 7.378 (0.62), 7.384 (0.86), 7.397 (1.11), 7.403 (1.62), 7.415 (0.62), 7.422 (0.90), 7.521 (0.63), 7.540 (0.45), 7.583 (0.68), 7.605 (0.86), 7.626 (0.62), 7.747 (0.59), 7.766 (0.57), 7.784 (0.68), 7.806 (0.63), 7.847 (1.02), 7.864 (1.58), 7.883 (1.42).

This amino acid was used in SPPS.

Example 103A (2S,5R)-2-(2-Ethylbutyl)-3,6-dimethoxy-5-(propan-2-yl)-2,5-dihydropyrazine

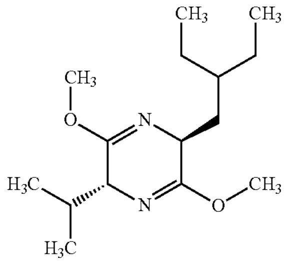 [SMILES: CCC(CC)C[C@@H]1N=C(OC)[C@@H](C(C)C)N=C1OC]

(2R)-3,6-Dimethoxy-2-(propan-2-yl)-2,5-dihydropyrazine (CAS-RN: 109838-859, 2.9 mL, 16 mmol) was dissolved in anhydrous THF (60 mL, 740 mmol) and the solution was cooled to −78° C. n-Butyllithium (10 mL, 1.6 M, 16 mmol) was added dropwise slowly and dropwise over a 15 minute period while stirring at −78° C. 3-(Bromomethyl)pentane (5.91 g, 35.8 mmol) was added and the reaction mixture was stirred for 2 h at −78° C., then allowed to come to room temperature overnight. The solution was cooled to 0° C. and slowly quenched with water. Diethyl ether was added and after stirring several minutes, the organic layer was separated. The aqueous phase was extracted two times with diethyl ether. The combined organic layers were washed with brine, dried over magnesium sulfate, filtered and evaporated. The crude product was purified by chromatography on silica gel (cyclohexane/ethyl acetate 2%) to give 2.60 g (95% purity, 57% yield) of the title compound.

LC-MS (Method 10): $R_t$=2.90 min; MS (ESI pos): m/z=269 $[M+H]^+$ $^1$H-NMR (400 MHz, DMSO-d6) δ[ppm]: −0.008 (0.51), 0.008 (0.45), 0.608 (6.77), 0.624 (6.91), 0.771 (3.04), 0.790 (7.57), 0.796 (3.51), 0.808 (4.20), 0.815 (7.45), 0.833 (3.54), 0.999 (6.56), 1.016 (6.71), 1.179 (0.65), 1.197 (0.97), 1.215 (0.95), 1.223 (0.51), 1.232 (0.73), 1.240 (0.81), 1.257 (1.26), 1.275 (1.64), 1.294 (1.28), 1.310 (0.57), 1.343 (0.55), 1.356 (1.67), 1.364 (0.66), 1.369 (0.83), 1.376 (1.52), 1.388 (1.40), 1.398 (0.66), 1.403 (0.63), 1.409 (1.04), 1.422 (0.43), 1.459 (0.56), 1.474 (0.63), 1.489 (0.45), 1.637 (0.66), 1.647 (0.68), 1.656 (0.56), 1.667 (0.69), 1.670 (0.69), 1.681 (0.54), 1.690 (0.48), 1.700 (0.44), 2.191 (0.54), 2.199 (0.55), 2.208 (0.71), 2.216 (0.71), 2.225 (0.52), 2.233 (0.51), 3.597 (16.00), 3.616 (15.85), 3.916 (1.08), 3.925 (2.24), 3.933 (1.46), 3.959 (0.67), 3.969 (1.06), 3.980 (0.99), 3.990 (1.00), 4.000 (0.49).

Example 104A

Methyl 4-ethyl-L-norleucinate

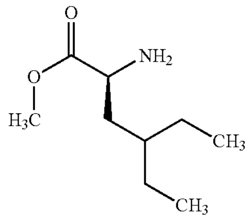

A solution (2S,5R)-2-(2-Ethylbutyl)-3,6-dimethoxy-5-(propan-2-yl)-2,5-dihydropyrazine (Example 103A, 2.60 g, 9.69 mmol) in methanol (30 mL) was cooled to 0° C. and a 10% aqueous solution of hydrochloric acid (10 mL) was added and then the reaction mixture was stirred for 2 h. The solution was evaporated and the residue was diluted with DCM and sodium carbonate solution (100 mL, 2.0 M). The separated aqueous layer was extracted two times with DCM. The combined organic layer was dried over magnesium sulfate, filtered and then concentrated to give 3.49 g (48% purity, 100% yield) of the title compound.

GC-MS (GC-MS Method 1): $R_t$=3.18 min, m/z=173 [M+]

Example 105A

4-Ethyl-N-{[(9H-fluoren-9-yl)methoxy]carbonyl}-L-norleucine

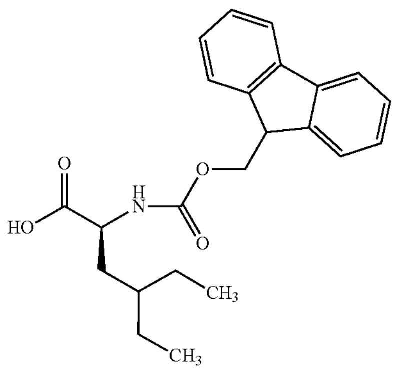 [SMILES: CCC(CC)C[C@H](NC(=O)OCC1c2ccccc2-c2ccccc21)C(=O)O]

To methyl 4-ethyl-L-norleucinate (Example 104A, 3.97 g, 48% purity, 11.0 mmol) was added methanol (100 mL) and the resulting solution was cooled to 0° C. Sodium hydroxide solution (24 mL, 1.0 M) was added and the reaction mixture was stirred for 1 h at 0° C., then warmed to room temperature and stirred further for 4 h. Water (80 mL), sodium hydrogen carbonate (2.03 g, 24.2 mmol) and sodium carbonate (4.00 g, 37.7 mmol) were sequentially added to the solution. The methanol was removed from the reaction mixture by rotary evaporation and the aqueous solution was diluted with 1,4-dioxane (60 mL). The suspension was cooled to 0° C. and (9H-fluoren-9-yl)methyl carbonochloridate (CAS-RN: 28920-43-6, 8.54 g, 33.0 mmol) was added. The reaction mixture was stirred overnight at room temperature. Water and MTBE were added, stirred briefly, and then the organic layer was separated. The aqueous layer was extracted with MTBE and then the combined organic layer was washed with 5% sodium carbonate solution. The combined aqueous layer was acidified to pH 1 with potassium hydrogen sulfate and the aqueous suspension was extracted three times with DCM. The combined organic layer was washed with brine, dried over anhydrous magnesium sulfate, filtered, and then concentrated. The crude product was purified by preparative HPLC (column: Reprosil; C18; 10 μm; 125×40 mm; solvent: AcCN/$H_2O$ containing 0.1% HCOOH; flow rate: 100 mL/min; gradient: 0-5.50 min (10:90); sample injection at 3.00 min; 5.50-17.65 min gradient to 95:5; 17.65-19.48 min (95:5); 19.48-19.66 min gradient to 10:90; 19.66-20.72 min (10:90), affording 1.57 g (100% purity, 37% yield) of the title compound.

LC-MS (Method 11): $R_t$=1.49 min; MS (ESI pos): m/z=404 $[M+Na]^+$ $^1$H-NMR (400 MHz, DMSO-d6) δ[ppm]: −0.008 (3.19), 0.008 (3.01), 0.774 (6.73), 0.792 (16.00), 0.809 (13.36), 0.826 (14.04), 0.844 (7.32), 1.181 (0.92), 1.197 (1.90), 1.216 (3.12), 1.234 (3.84), 1.253 (2.82), 1.273 (1.79), 1.293 (2.23), 1.308 (3.41), 1.331 (4.60), 1.339 (4.12), 1.505 (0.45), 1.557 (3.55), 1.575 (5.01), 1.590 (3.09), 3.950 (1.22), 3.970 (2.67), 3.989 (2.69), 4.009 (1.11), 4.204 (1.35), 4.220 (3.90), 4.238 (7.46), 4.263 (5.22), 4.279 (3.57), 4.286 (5.10), 4.304 (3.43), 4.310 (2.32), 4.328 (1.06), 7.299 (2.60), 7.306 (2.93), 7.317 (5.73), 7.322 (5.59), 7.336 (3.69), 7.341 (3.48), 7.400 (6.17), 7.419 (10.33), 7.437 (4.62), 7.626 (4.21), 7.647 (3.80), 7.711 (8.98), 7.729 (8.16), 7.884 (9.94), 7.903 (9.15), 12.540 (0.98).

This amino acid was used in SPPS.

Example 106A

N-{[(9H-Fluoren-9-yl)methoxy]carbonyl}-2,6-difluoro-L-phenylalanine

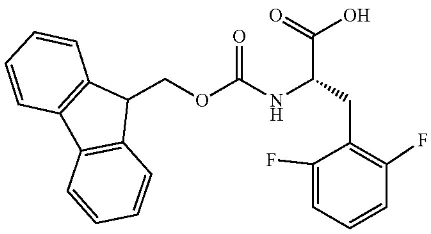 [SMILES: O=C(N[C@@H](Cc1c(F)cccc1F)C(=O)O)OCC1c2ccccc2-c2ccccc21]

To methyl 2,6-difluoro-L-phenylalaninate (CAS-RN: 1192057-28-5, 1.03 g, 4.79 mmol) was added methanol (18.5 mL) and the solution was cooled to 0° C. Sodium hydroxide solution (4.8 mL, 1.0 M) was added and the reaction mixture was stirred for 1 h at room temperature. Water (17 mL), sodium hydrogen carbonate (402 mg, 4.79 mmol) and sodium carbonate (667 mg, 6.29 mmol) were added to the solution. The methanol was removed by rotary evaporation and the aqueous layer was diluted with 1,4-dioxane (14 mL). The suspension was cooled to 0° C. and (9H-fluoren-9-yl)methyl carbonochloridate (CAS-RN: 28920-43-6, 1.86 g, 7.18 mmol) was added. The mixture was stirred for 2 h at room temperature. The reaction mixture was diluted with water and washed with MTBE. The aqueous layer was acidified to pH 1 with 1 M hydrochloric acid and extracted three times with ethyl acetate. The combined organic layers were washed with brine, dried over anhydrous magnesium sulfate, filtered and the concentrated, to afford 1.74 g (100% purity, 86% yield) of the title compound.

LC-MS (Method 10): $R_t$=2.00 min; MS (ESI pos): m/z=424 $[M+H]^+$ $^1$H-NMR (400 MHz, DMSO-d6) δ[ppm]: 1.157 (0.74), 1.175 (1.50), 1.193 (0.76), 1.988 (2.79), 2.992 (0.74), 3.014 (0.87), 3.025 (1.22), 3.048 (1.17), 3.118 (1.24), 3.134 (1.32), 3.153 (0.81), 3.169 (0.76), 3.316 (16.00), 4.021 (0.71), 4.039 (0.70), 4.131 (0.95), 4.149 (1.39), 4.166 (2.72), 4.194 (4.15), 4.213 (2.65), 4.235 (0.72), 7.013 (1.71), 7.033 (3.28), 7.053 (2.07), 7.290 (1.33), 7.307 (3.44), 7.323 (4.18), 7.341 (2.36), 7.357 (0.48), 7.397 (2.41), 7.415 (4.00), 7.434 (1.83), 7.639 (2.22), 7.659 (3.87), 7.679 (1.99), 7.818 (1.97), 7.839 (1.95), 7.876 (4.80), 7.894 (4.40), 12.793 (0.81).

This amino acid was used in SPPS.

Example 107A

N-{[(9H-Fluoren-9-yl)methoxy]carbonyl}-2,5-difluoro-L-phenylalanine

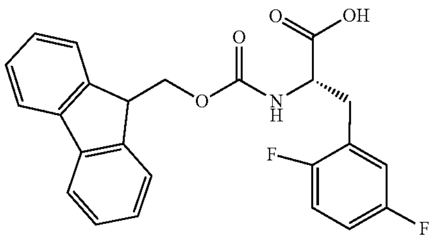 [SMILES: O=C(N[C@@H](Cc1cc(F)ccc1F)C(=O)O)OCC1c2ccccc2-c2ccccc21]

To methyl 2,5-difluoro-L-phenylalaninate (CAS-RN: 1213491-95-2) (2.27 g, 10.5 mmol) was added in methanol (40 mL) and the resulting solution was cooled to 0° C. Sodium hydroxide solution (11 mL, 1.0 M) was added and the reaction mixture was stirred for 1.5 h at room temperature. Water (35 mL), sodium hydrogen carbonate (886 mg, 10.5 mmol) and sodium carbonate (1.47 g, 13.9 mmol) were added to the solution. The methanol was removed by rotary evaporation and the aqueous layer was diluted with 1,4-dioxane (30 mL). The suspension was cooled to 0° C. and (9H-fluoren-9-yl)methyl carbonochloridate (CAS-RN: 28920-43-6, 4.09 g, 15.8 mmol) was added, and the reaction mixture was stirred for 2 h at room temperature. The mixture was diluted with water and washed with MTBE. The aqueous layer was acidified to pH 1 with 1 M hydrochloric acid solution and extracted three times with ethyl acetate. The combined organic layers were washed with brine, dried over anhydrous magnesium sulfate, filtered and the concentrated. The crude product was purified by flash chromatography on silica gel (gradient DCM: methanol 0-5%), then the residue was taken up in acetonitrile and purified again by preparative HPLC (column: Reprosil; C18; 10 μm; 125×40 mm; solvent: $AcCN/H_2O$ containing 0.1% HCOOH; flow rate: 100 mL/min; gradient: 0-5.50 min (10:90); sample injection at 3.00 min; 5.50-17.65 min gradient to 95:5; 17.65-19.48 min (95:5); 19.48-19.66 min bis 10:90; 19.66-20.72 min (10:90) to give 1.82 g (100% purity, 41% yield) of the title compound.

LC-MS (Method 9): $R_t$=1.04 min; MS (ESI pos): m/z=424 $[M+H]^+$ $^1$H-NMR (400 MHz, DMSO-d6) δ[ppm]: −0.008 (2.88), 0.008 (2.75), 1.234 (0.68), 2.329 (0.47), 2.671 (0.46), 2.843 (2.48), 2.870 (3.13), 2.877 (3.47), 2.904 (3.10), 3.166 (3.44), 3.177 (3.74), 3.200 (2.97), 3.212 (2.73), 4.141 (1.90), 4.158 (5.16), 4.173 (9.08), 4.196 (12.08), 4.201 (12.22), 4.211 (8.55), 4.221 (7.38), 4.233 (3.76), 4.246 (2.97), 4.259 (2.15), 7.084 (0.87), 7.093 (1.61), 7.106 (2.33), 7.114 (3.81), 7.124 (3.21), 7.135 (2.97), 7.144 (2.17), 7.175 (3.13), 7.187 (4.77), 7.197 (6.58), 7.210 (7.69), 7.220 (4.45), 7.232 (3.61), 7.263 (4.47), 7.282 (9.79), 7.301 (7.22), 7.305 (7.95), 7.325 (4.82), 7.349 (0.45), 7.389 (6.78), 7.408 (11.73), 7.426 (5.46), 7.489 (0.48), 7.509 (0.67), 7.532 (0.46), 7.610 (7.40), 7.628 (12.92), 7.646 (6.48), 7.791 (6.23), 7.812 (6.10), 7.871 (16.00), 7.890 (14.50), 12.862 (3.43).

This amino acid was used in SPPS.

This amino acid was also prepared from methyl 2,5-difluoro-L-phenylalaninate prepared in Example 126A. The amino acid can also be prepared from 2,5-difluoro-L-phenylalaninate (CAS RN: 31105-92-7) using the procedure described in Example 106A.

Example 108A

Benzyl tetrahydro-2H-pyran-3-ylacetate (racemate)

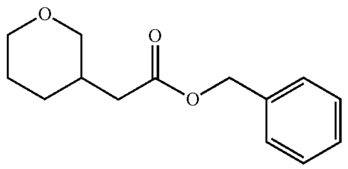 [SMILES: O=C(CC1CCCOC1)OCc1ccccc1]

Tetrahydro-2H-pyran-3-ylacetic acid (1.00 g, 6.94 mmol) was dissolved in methanol (10 mL, 250 mmol). Cesium carbonate (1.13 g, 3.47 mmol) was added and the reaction mixture was stirred at room temperature until the evolution of gas ceased. The solution was then evaporated. The residue was dissolved in DMF (10 mL), (bromomethyl)benzene (1.3 mL, 11 mmol) was added, and the reaction mixture was stirred overnight at room temperature. Additional (bromomethyl)benzene (325 μL, 2.75 mmol) was added and the reaction mixture was stirred for 3 h at room temperature. The suspension was then diluted with water and ether. After stirring for a few minutes, the organic layer was separated. The aqueous layer was extracted three times with diethyl ether. The combined organic layer was washed with brine, dried over anhydrous magnesium sulfate, filtered, and then concentrated. The crude product was purified by chromatography on silica gel (cyclohexane/ethyl acetate (85/15)) to give 1.50 g (100% purity, 92% yield) of the title compound.

LC-MS (Method 10): $R_t$=1.84 min; MS (ESI pos): m/z=235 $[M+H]^+$ $^1$H-NMR (500 MHz, DMSO-d6) δ[ppm]: 1.161 (0.45), 1.170 (0.51), 1.183 (0.89), 1.187 (0.68), 1.191 (0.98), 1.196 (0.60), 1.204 (0.68), 1.208 (1.03), 1.212 (0.77), 1.217 (1.00), 1.229 (0.62), 1.238 (0.63), 1.428 (0.47), 1.447 (0.62), 1.449 (0.74), 1.455 (0.95), 1.463 (0.63), 1.468 (0.83), 1.476 (1.42), 1.484 (0.80), 1.489 (0.56), 1.498 (0.98), 1.501 (0.53), 1.506 (1.11), 1.509 (1.00), 1.516 (1.65), 1.523 (1.08), 1.532 (0.56), 1.543 (0.70), 1.550 (0.40), 1.747 (0.90), 1.751 (0.77), 1.755 (0.89), 1.764 (0.62), 1.773 (0.82), 1.777 (0.69), 1.781 (0.77), 1.887 (0.41), 1.894 (0.68), 1.901 (0.68), 1.908 (0.76), 1.914 (0.90), 1.921 (0.74), 1.927 (0.68), 1.934 (0.63), 2.194 (1.30), 2.208 (1.18), 2.225 (3.67), 2.239 (3.41), 2.255 (3.55), 2.270 (3.23), 2.286 (1.23), 2.301 (1.12), 3.018 (2.02), 3.038 (2.30), 3.041 (2.34), 3.059 (2.06), 3.246 (1.05), 3.252 (1.07), 3.267 (1.61), 3.273 (1.61), 3.289 (1.21), 3.295 (1.19), 3.685 (0.75), 3.692 (1.34), 3.705 (1.77), 3.708 (1.89), 3.713 (2.24), 3.716 (2.16), 3.726 (1.17), 3.730 (1.14), 3.734 (1.08), 3.738 (0.97), 5.089 (16.00), 7.310 (0.41), 7.315 (0.73), 7.320 (0.71), 7.327 (2.21), 7.334 (1.16), 7.339 (1.36), 7.342 (1.95), 7.345 (2.49), 7.348 (2.36), 7.351 (1.63), 7.360 (9.48), 7.364 (11.33), 7.371 (1.08), 7.376 (3.55), 7.378 (3.74), 7.382 (1.62), 7.390 (0.55), 7.393 (1.20), 7.395 (0.74).

Example 109A

Benzyl tetrahydro-2H-pyran-3-yl acetate

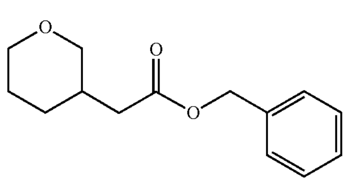 [SMILES: O=C(CC1CCCOC1)OCc1ccccc1]

The diastereomeric mixture (Example 108A, 1.5 g) was dissolved in methanol/acetonitrile (30 mL) and separated using a THAR supercritical fluid chromatography Prep 200 instrument using a Chiralpak AZ-H (SFC) 5 μm, 250×30 mm column; eluent: CO2/ethanol (90:10); pressure: 135 bar; temperature eluant: 35° C.; flow rate: 100 g/min; detection: UV 210 nm; injection volume 0.4 mL/injection; under general operating conditions 1 g/min of CO2 is approximately equivalent to 1 mL/min.

Sequence Settings: cycle time=11.2 min

Fraction 1 was collected at 1.48 min (enantiomer 1)

Fraction 2 was collected between 1.89 min (enantiomer 2)

The product-containing fractions combined and were concentrated.

The fractions were analyzed using analytical SFC-MS (Agilent, column: Daicel AZ-3 3 μm 100×4.6 mm, eluent: CO2/ethanol (90:10); BPR pressure: 130 bar; BPR temperature: 60° C.; column temperature: 40° C.; flow rate: 3 mL/min; UV 210 nm.

The stereochemistry of the two enantiomers was not assigned.

Benzyl tetrahydro-2H-pyran-3-ylacetate (enantiomer 1) was obtained with 99.5% ee (641 mg (100% purity).

LC-MS (Method 9): $R_t$=0.98 min; MS (ESI pos): m/z=235 $[M+H]^+$ $^1$H-NMR (500 MHz, DMSO-d6) δ[ppm]: 1.161 (0.45), 1.170 (0.51), 1.183 (0.89), 1.187 (0.67), 1.191 (0.98), 1.196 (0.61), 1.204 (0.67), 1.209 (1.03), 1.213 (0.77), 1.217 (1.00), 1.230 (0.61), 1.238 (0.62), 1.428 (0.48), 1.447 (0.61), 1.449 (0.75), 1.455 (0.95), 1.463 (0.64), 1.468 (0.82), 1.476 (1.41), 1.484 (0.79), 1.489 (0.56), 1.498 (0.98), 1.501 (0.52), 1.507 (1.05), 1.510 (1.00), 1.516 (1.65), 1.523 (1.07), 1.532 (0.55), 1.543 (0.70), 1.747 (0.90), 1.751 (0.78), 1.755 (0.89), 1.764 (0.63), 1.773 (0.81), 1.777 (0.69), 1.781 (0.78), 1.887 (0.40), 1.894 (0.69), 1.901 (0.68), 1.908 (0.76), 1.914 (0.91), 1.921 (0.74), 1.927 (0.67), 1.934 (0.64), 2.194 (1.30), 2.208 (1.18), 2.225 (3.69), 2.239 (3.42), 2.255 (3.56), 2.270 (3.24), 2.286 (1.23), 2.301 (1.12), 3.019 (2.02), 3.038 (2.29), 3.041 (2.36), 3.060 (2.07), 3.246 (1.05), 3.252 (1.08), 3.268 (1.63), 3.273 (1.63), 3.289 (1.24), 3.295 (1.23), 3.686 (0.75), 3.692 (1.34), 3.705 (1.73), 3.708 (1.90), 3.713 (2.19), 3.715 (2.20), 3.726 (1.19), 3.730 (1.13), 3.734 (1.08), 3.738 (0.97), 5.089 (16.00), 7.310 (0.40), 7.315 (0.74), 7.321 (0.69), 7.328 (2.23), 7.334 (1.13), 7.339 (1.36), 7.342 (1.99), 7.345 (2.52), 7.347 (2.34), 7.350 (1.66), 7.360 (9.33), 7.364 (11.16), 7.371 (1.09), 7.376 (3.58), 7.378 (3.72), 7.382 (1.63), 7.390 (0.54), 7.393 (1.20), 7.396 (0.75).

Benzyl tetrahydro-2H-pyran-3-ylacetate (enantiomer 2) was also obtained with 99.5% ee (611 mg (100% purity).

Example 110A

Tetrahydro-2H-pyran-3-ylacetic acid (enantiomer 1)

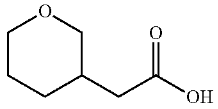

10% Palladium on charcoal (84.0 mg) was humidified with methanol under argon. A solution of benzyl tetrahydro-2H-pyran-3-ylacetate (Example 109A, 641 mg, 2.74 mmol) added. The reaction mixture was then hydrogenated for 2 h at ambient pressure at room temperature. The catalyst was removed by filtration over a layer of diatomaceous earth, the filter cake was washed with methanol, and the solvent was removed by rotary distillation, to provide 364 mg (100% purity, 92% yield) of the title compound.

GC-MS (GC-MS Method 1): $R_t$=3.57 min, m/z=144 [M+]

$^1$H-NMR (500 MHz, DMSO-d6) δ[ppm]: 1.145 (1.98), 1.154 (2.21), 1.166 (4.03), 1.171 (3.11), 1.175 (4.45), 1.180 (2.85), 1.188 (3.11), 1.192 (4.69), 1.196 (3.55), 1.201 (4.57), 1.213 (2.68), 1.222 (2.75), 1.428 (1.03), 1.436 (1.93), 1.445 (1.35), 1.449 (1.65), 1.455 (2.72), 1.458 (3.25), 1.463 (4.18), 1.471 (2.92), 1.476 (3.82), 1.484 (6.50), 1.493 (3.67), 1.498 (2.58), 1.506 (5.73), 1.514 (6.62), 1.521 (7.99), 1.528 (5.13), 1.537 (2.67), 1.548 (3.18), 1.554 (1.80), 1.563 (0.64), 1.759 (1.78), 1.767 (4.22), 1.771 (3.85), 1.775 (4.26), 1.784 (2.89), 1.793 (3.85), 1.797 (3.49), 1.801 (3.85), 1.809 (1.56), 1.824 (0.81), 1.832 (1.31), 1.839 (1.87), 1.846 (3.17), 1.853 (3.16), 1.859 (3.72), 1.866 (4.34), 1.873 (3.58), 1.879 (3.34), 1.886 (3.00), 1.893 (1.65), 1.900 (1.44), 1.908 (0.69), 2.023 (6.18), 2.036 (5.11), 2.054 (16.00), 2.068 (14.33), 2.087 (15.54), 2.101 (13.64), 2.118 (5.69), 2.133 (5.09), 2.999 (9.23), 3.018 (10.90), 3.021 (11.02), 3.040 (9.47), 3.134 (0.64), 3.247 (6.14), 3.253 (6.29), 3.269 (9.57), 3.275 (9.49), 3.291 (7.06), 3.297 (6.90), 3.586 (0.59), 3.696 (3.77), 3.703 (6.42), 3.709 (4.14), 3.717 (8.63), 3.725 (11.12), 3.739 (5.37), 3.743 (5.40), 3.747 (5.21), 3.750 (4.68).

This substance was used in SPPS.

Example 111A (3S)-3-[(2S,5R)-3,6-Dimethoxy-5-(propan-2-yl)-2,5-dihydropyrazin-2-yl]cyclohexan-1-one

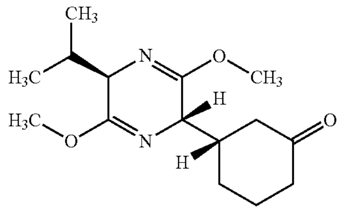 [SMILES: COC1=N[C@H](C(C)C)C(OC)=N[C@H]1[C@H]1CCCC(=O)C1]

(2R)-3,6-Dimethoxy-2-(propan-2-yl)-2,5-dihydropyrazine (4.61 g, 25.0 mmol) was dissolved in THF (20 mL) and cooled to −78° C. Butyllithium (16 mL, 1.6 M, 25 mmol) was added dropwise with stirring. Stirring was continued for 15 min at −78° C. Lithium (azanidylidenemethylidene)(thiophen-2-yl)copper (100 mL, 0.25 M, 25 mmol) was added and the mixture was stirred for 15 min at −78° C. A solution from cyclohex-2-en-1-one (2.4 mL, 25 mmol) in THF (10 mL) was added and the reaction mixture was stirred for 10 min at −78° C., then it was further stirred at ambient temperature for 2 h. The reaction was quenched with water and extracted two times with ethyl acetate. The combined organic layer was washed with sodium hydrogen carbonate solution and brine, dried over anhydrous magnesium sulfate, filtered, and then the residue was concentrated under reduced pressure to give 6.8 g of a colorless oil. The crude product was purified by flash chromatography on silica gel (gradient cyclohexane-ethyl acetate 85-15) to give 5.7 g (90% purity, 64% yield) of the title compound.

LC-MS (Method 12): $R_t$=3.14 min; MS (ESI pos): m/z=281.2 $[M+H]^+$ $^1$H-NMR (400 MHz, DMSO-d6) δ[ppm]: 0.587 (0.94), 0.604 (1.17), 0.617 (6.04), 0.634 (6.04), 0.971 (0.51), 0.988 (5.87), 0.995 (1.32), 1.005 (5.67), 1.012 (0.98), 1.032 (0.88), 1.049 (0.91), 1.575 (0.55), 1.596 (0.42), 1.607 (0.61), 1.750 (0.61), 1.760 (0.78), 1.784 (1.05), 1.794 (1.28), 1.816 (0.50), 1.837 (0.50), 1.843 (0.57), 1.874 (0.43), 1.979 (0.82), 2.012 (1.26), 2.024 (0.52), 2.032 (0.55), 2.044 (0.95), 2.057 (0.40), 2.122 (0.46), 2.148 (0.80), 2.156 (1.00), 2.164 (1.00), 2.173 (0.67), 2.181 (0.70), 2.190 (0.69), 2.199 (0.54), 2.207 (0.59), 2.225 (0.71), 2.242 (0.64), 2.259 (0.74), 2.275 (0.64), 2.294 (0.45), 2.310 (0.65), 2.319 (0.47), 2.329 (0.48), 2.338 (0.58), 2.348 (0.54), 3.602 (0.89), 3.631 (16.00), 3.642 (4.12), 3.652 (14.26), 3.902 (1.14), 3.911 (2.10), 3.920 (1.33), 3.943 (0.45), 4.069 (1.14), 4.078 (1.82), 4.086 (0.98), 4.492 (0.55), 5.674 (0.91).

Example 112A (1R,3S)-3-[(2S,5R)-3,6-Dimethoxy-5-(propan-2-yl)-2,5-dihydropyrazin-2-yl]cyclohexan-1-ol (2 stereoisomers present)

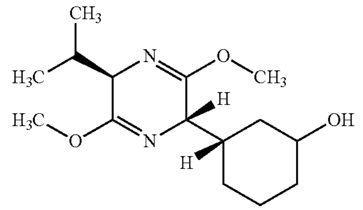 [SMILES: COC1=N[C@H](C(C)C)C(OC)=N[C@H]1[C@H]1CCCC(O)C1]

(3S)-3-[(2S,5R)-3,6-dimethoxy-5-(propan-2-yl)-2,5-dihydropyrazin-2-yl]cyclohexan-1-one (Example 111A, 5.70 g, 20.3 mmol) was dissolved in methanol (50 mL) and cooled to 0° C. Sodium tetrahydroborate (769 mg, 20.3 mmol) was added and the reaction mixture was stirred overnight at room temperature. Additional sodium tetrahydroborate (769 mg, 20.3 mmol) was added and stirring was continued at room temperature. This step is repeated 2 more times with 0.5 eq sodium tetrahydroborate. The methanol was evaporated and the residue was diluted with water and ethyl acetate. After stirring for several minutes, the layers were separated. The aqueous layer was extracted with ethyl acetate. The combined organic layer was washed with brine, dried over anhydrous magnesium sulfate, filtered, and the residue concentrated under reduced pressure to give 5.7 g of a yellow oil. The crude product was purified by flash chromatography on silica gel (gradient cyclohexane-cyclohexane ethyl acetate 5%-30%) to give 4.95 g (86% yield) of the title compound.

LC-MS (Method 10): $R_t$=1.87 min; MS (ESI pos): m/z=283.2 $[M+H]^+$; $R_t$=1.91 min; MS (ESI pos): m/z=283.2 $[M+H]^+$ $^1$H-NMR (400 MHz, DMSO-d6) δ[ppm]: 0.589 (1.83), 0.600 (6.10), 0.605 (2.52), 0.617 (6.02), 0.739 (0.91), 0.768 (0.96), 0.798 (0.42), 0.898 (0.47), 0.934 (0.50), 0.997 (6.80), 1.014 (7.00), 1.157 (0.53), 1.175 (0.92), 1.193 (0.73), 1.203 (0.72), 1.211 (0.59), 1.227 (0.47), 1.235 (0.72), 1.243 (0.51), 1.313 (0.52), 1.321 (0.63), 1.352 (0.99), 1.398 (2.43), 1.485 (0.59), 1.515 (0.56), 1.668 (0.44), 1.676 (0.56), 1.684 (0.44), 1.708 (0.51), 1.745 (0.57), 1.774 (0.54), 1.879 (0.58), 1.887 (0.56), 1.988 (1.39), 2.185 (0.54), 2.193 (0.57), 2.202 (0.73), 2.210 (0.75), 2.219 (0.55), 2.227 (0.55), 3.611 (7.06), 3.617 (3.03), 3.622 (16.00), 3.629 (14.28), 3.845 (0.55), 3.854 (0.50), 3.862 (1.17), 3.871 (2.39), 3.880 (1.79), 3.933 (1.11), 3.942 (1.74), 3.951 (0.86), 4.215 (0.59), 4.223 (0.57), 4.431 (2.16), 4.443 (2.10).

Example 113A

Methyl (2S)-amino[(1S)-3-hydroxycyclohexyl]acetate (2 stereoisomers present)

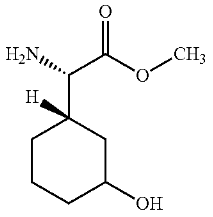

(3S)-3-[(2S,5R)-5-isopropyl-3,6-dimethoxy-2,5-dihydropyrazin-2-yl]cyclohexanol (Example 112A, 4.95 g, 17.5 mmol) was dissolved in methanol (45 mL) and the solution was cooled to 0° C. A 10% aqueous hydrochloric acid solution (15 mL) was added and the reaction mixture was stirred for a short time at 0° C., then it was allowed to stir at room temperature for 3 h. The reaction mixture was concentrated, the residue was diluted with DCM and then an aqueous sodium carbonate solution (150 mL, 2.0 M, 300 mmol) was added. The mixture was stirred and then the layers were separated. The aqueous layer was extracted two times with DCM. The combined organic layer was dried over anhydrous magnesium sulfate, filtered, and then concentrated. The crude product was purified by flash chromatography on silica gel (DCM: methanol 95+5) to give 1.92 g (58% yield) of the title compound.

$^1$H-NMR (400 MHz, DMSO-d6) δ[ppm]: −0.008 (1.04), 0.008 (0.93), 0.760 (0.69), 0.777 (0.71), 0.834 (0.61), 0.867 (1.92), 0.875 (1.16), 0.885 (1.54), 0.892 (1.18), 0.910 (0.45), 0.922 (0.61), 0.942 (1.05), 0.951 (0.95), 0.973 (1.17), 0.981 (1.06), 1.003 (0.54), 1.012 (0.50), 1.157 (0.67), 1.165 (0.41), 1.190 (0.65), 1.198 (0.44), 1.223 (0.42), 1.375 (0.69), 1.407 (0.79), 1.498 (0.52), 1.513 (0.89), 1.519 (0.95), 1.527 (0.74), 1.549 (0.69), 1.633 (2.72), 1.671 (0.69), 1.680 (0.78), 1.753 (1.26), 1.783 (1.67), 1.959 (0.49), 2.086 (0.85), 3.096 (0.46), 3.110 (0.48), 3.138 (1.12), 3.151 (1.10), 3.162 (1.07), 3.175 (1.02), 3.276 (0.43), 3.288 (0.55), 3.593 (0.71), 3.603 (4.85), 3.612 (16.00), 3.626 (1.87), 3.633 (0.96), 3.637 (1.57), 4.232 (0.60), 4.240 (0.55), 4.481 (1.83), 4.492 (1.73), 5.754 (0.68).

Example 114A (2S)-2-{[(9H-Fluoren-9-ylmethoxy)carbonyl]amino}-2-[(1S)-3-hydroxycyclohexyl]acetic acid (2 stereoisomers present)

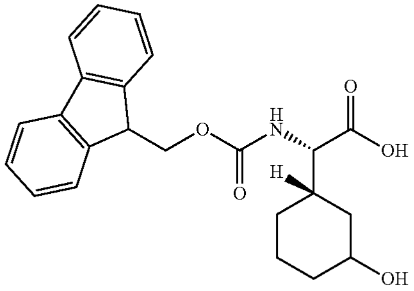 [SMILES: O=C(N[C@H](C(=O)O)[C@H]1CCCC(O)C1)OCC1c2ccccc2-c2ccccc21]

Methyl (2S)-amino[(1S)-3-hydroxycyclohexyl]acetate (Example 113A, 1.92 g, 10.3 mmol) was added to methanol (40 mL) and the solution was cooled to 0° C. Sodium hydroxide solution (10 mL, 1.0 M, 10 mmol) was added and the reaction mixture was stirred for 1.5 h at room temperature and then for 1 h at 50° C. Water (37 mL), sodium hydrogen carbonate (861 mg, 10.3 mmol), and sodium carbonate (1.43 g, 13.5 mmol) were added to the solution. The methanol was evaporated and the aqueous layer was diluted with 1,4-dioxane (30 mL). The suspension was cooled to 0° C. and (9H-fluoren-9-yl)methyl carbonochloridate (CAS-RN: 28920-43-6, 3.98 g, 15.4 mmol) was added. The mixture was stirred over night at room temperature. Water and MTBE were added and the organic layer was separated. The aqueous layer was acidified and extracted three times with DCM. The combined organic layers were washed with brine, dried over anhydrous magnesium sulfate, and filtered. The crude product was purified by flash chromatography on silica gel (DCM: methanol/HOAc 95+5+1) to give 2.22 g (55% yield) of the title compound.

LC-MS (Method 10): $R_t$=1.62 min; MS (ESI pos): m/z=396.18 $[M+H]^+$; $R_t$=1.67 min; MS (ESI pos): m/z=396.18 $[M+H]^+$ Example 115A (2S)-2-({[(9H-Fluoren-9-yl)methoxy]carbonyl}amino)-2-[(1S,3R)-3-hydroxycyclohexyl]acetic acid (diastereomer 1)

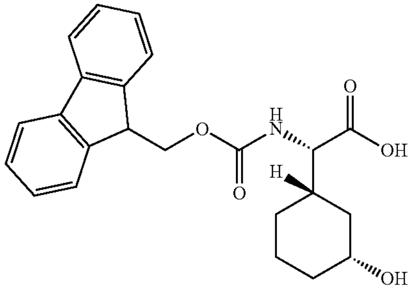

(2S)—{[(9H-Fluoren-9-ylmethoxy)carbonyl]amino}[(1S)-3-hydroxycyclohexyl]acetic acid (Example 114A, 2.22 g) was purified by chiral chromatography using the method described in Example 96 A to provide 890 mg (100% purity, 40% yield, 99% ee) of diastereomer 1.

LC-MS (Method 10): $R_t$=1.62 min; MS (ESI pos): m/z=396.2 $[M+H]^+$

H-NMR (400 MHz, DMSO-d6) δ[ppm]: 0.878 (0.88), 0.909 (1.80), 0.940 (2.23), 0.962 (1.87), 0.986 (2.99), 1.025 (4.63), 1.053 (3.69), 1.083 (1.14), 1.151 (1.18), 1.184 (2.16), 1.217 (1.71), 1.249 (0.53), 1.492 (2.55), 1.523 (2.32), 1.668 (2.86), 1.701 (2.42), 1.779 (6.54), 1.802 (4.90), 2.073 (4.22), 3.875 (0.46), 3.900 (3.08), 3.916 (3.51), 3.921 (3.52), 3.936 (2.67), 4.197 (1.31), 4.211 (3.35), 4.223 (9.23), 4.238 (12.01), 4.242 (10.59), 4.253 (6.34), 4.270 (3.91), 4.296 (0.72), 4.563 (2.04), 7.312 (6.21), 7.331 (14.61), 7.349 (9.50), 7.402 (9.30), 7.420 (15.31), 7.439 (6.83), 7.603 (4.81), 7.624 (4.95), 7.752 (11.74), 7.770 (10.65), 7.884 (16.00), 7.903 (14.82), 8.155 (0.69).

This amino acid was used in SPPS.

Example 116A (2S)-2-({[(9H-fluoren-9-yl)methoxy]carbonyl}amino)-2-[(1S,3S)-3-hydroxycyclohexyl]acetic acid (diastereomer 2)

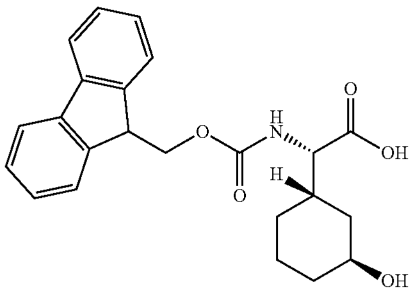 [SMILES: O=C(N[C@H](C(=O)O)[C@H]1CCC[C@H](O)C1)OCC1c2ccccc2-c2ccccc21]

Also isolated during the chiral chromatography of the diastereomeric mixture of (2S)—({[(9H-fluoren-9-yl)methoxy]carbonyl}amino)[(1S,3S)-3-hydroxycyclohexyl]acetic acid (Example 114A) was 280 mg (95% purity, 12% yield) of diastereomer 2.

LC-MS (Method 10): $R_t$=1.67 min; MS (ESI pos): m/z=396.2 $[M+H]^+$ $^1$H-NMR (400 MHz, DMSO-d6) δ[ppm]: 0.862 (0.81), 0.879 (0.71), 1.024 (0.76), 1.055 (1.68), 1.084 (1.84), 1.113 (1.00), 1.274 (1.39), 1.308 (2.53), 1.339 (1.79), 1.404 (4.60), 1.430 (3.90), 1.498 (3.23), 1.531 (6.31), 1.566 (4.20), 1.609 (2.04), 1.640 (1.55), 2.179 (1.80), 2.328 (0.51), 2.670 (0.47), 3.820 (0.62), 3.839 (0.86), 3.858 (0.76), 3.904 (4.71), 3.920 (3.46), 3.925 (3.34), 3.941 (2.46), 4.195 (1.38), 4.210 (3.69), 4.223 (9.20), 4.238 (10.72), 4.244 (8.66), 4.254 (7.18), 4.272 (6.16), 7.309 (5.80), 7.328 (13.47), 7.346 (8.67), 7.400 (9.17), 7.419 (15.07), 7.437 (6.77), 7.487 (3.68), 7.508 (3.60), 7.546 (0.67), 7.637 (0.61), 7.748 (11.33), 7.767 (10.18), 7.883 (16.00), 7.901 (14.74).

This amino acid was used in SPPS.

Example 117A 3-({[(9H-Fluoren-9-ylmethoxy)carbonyl]amino}methyl)cyclohexanecarboxylic acid (racemate)

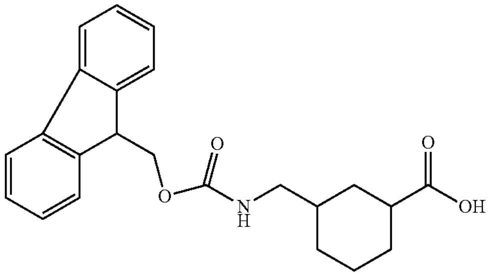 [SMILES: O=C(NCC1CCCC(C(=O)O)C1)OCC1c2ccccc2-c2ccccc21]

3-{[(tert-Butoxycarbonyl)amino]methyl}cyclohexanecarboxylic acid (racemate) (CAS RN: 145149-55-9, 1.00 g, 3.89 mmol) was dissolved in dichloromethane (20 mL, 310 mmol), trifluoroacetic acid (20 mL, 260 mmol) was added, and the reaction mixture was stirred for 30 min at room temperature. The solution was evaporated and the residue was dissolved in acetone (15 mL). Water (10 mL), sodium hydrogen carbonate (6.53 g, 77.7 mmol) and 1-({[(9H-fluoren-9-yl)methoxy]carbonyl}oxy)pyrrolidine-2,5-dione (CAS-RN: 82911-69-11.38 g, 4.08 mmol) were added. The suspension was stirred overnight at room temperature. Sodium hydrogen carbonate (6.53 g, 77.7 mmol) was added and the reaction mixture was allowed to stir for 1 h at room temperature. The suspension was diluted with water and extracted with MTBE. The aqueous layer was acidified with aqueous hydrochloric acid (1M) and then extracted three times with ethyl acetate. The combined organic layers were washed with brine, dried over magnesium sulfate, filtered, and then concentrated and evaporated, to provide three product-containing fractions: 130 mg (96% purity, 8% yield), 127 mg (96% purity, 8% yield), 51.0 mg (3% yield).

LC-MS (Method 9): $R_t$=1.01 min; MS (ESI pos): m/z=380 $[M+H]^+$ $^1$H-NMR (400 MHz, DMSO-d6) δ[ppm]: 0.736 (0.49), 0.759 (1.44), 0.790 (1.73), 0.821 (0.80), 0.851 (0.96), 0.882 (2.75), 0.913 (2.99), 0.944 (1.23), 1.083 (0.45), 1.120 (0.52), 1.153 (1.38), 1.182 (3.81), 1.206 (3.18), 1.235 (1.28), 1.418 (1.48), 1.598 (1.97), 1.630 (2.23), 1.717 (2.24), 1.739 (1.48), 1.747 (1.53), 1.835 (1.93), 1.862 (3.95), 1.897 (2.04), 2.074 (2.00), 2.123 (1.19), 2.130 (1.10), 2.152 (2.02), 2.174 (0.85), 2.181 (0.95), 2.524 (1.06), 2.785 (0.60), 2.801 (1.06), 2.818 (2.22), 2.835 (3.08), 2.849 (2.89), 2.862 (3.29), 2.878 (2.21), 2.895 (1.16), 2.911 (0.57), 4.188 (1.46), 4.206 (3.84), 4.223 (3.22), 4.238 (0.88), 4.253 (0.91), 4.287 (11.07), 4.304 (6.87), 4.333 (0.64), 4.351 (0.40), 4.451 (0.68), 7.306 (6.09), 7.324 (16.00), 7.341 (10.19), 7.392 (6.85), 7.410 (10.96), 7.429 (4.86), 7.459 (0.43), 7.626 (0.73), 7.643 (0.75), 7.683 (9.67), 7.702 (8.66), 7.875 (11.34), 7.894 (10.10), 12.028 (1.95).

This amino acid was used in SPPS.

Example 118A

Benzyl (2S)-2-(morpholin-4-yl)propanoate

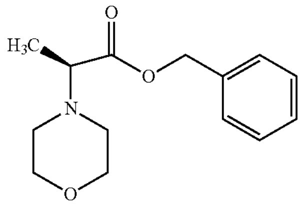 [SMILES: C[C@@H](C(=O)OCc1ccccc1)N1CCOCC1]

L-alanine (589 mg, 6.61 mmol), 1-bromo-2-(2-bromoethoxy)ethane (910 μL, 7.3 mmol) and sodium carbonate were dissolved in ethanol and the solution was refluxed for 2 days. The suspension was allowed to come to room temperature and the suspension was filtered. The filtrate was evaporated, suspended in ethanol (30 mL) and 3M hydrochloric acid was added to adjust the pH (to pH=3). The suspension was filtered, and the filtrate was evaporated. The residue was dissolved in DMF (20 mL). Cesium carbonate (1.08 g, 3.30 mmol) and (bromomethyl)benzene (1.6 mL, 13 mmol) were added and the mixture was stirred for 2 days at room temperature. Then water was added and then the solution was purified by reversed-phase HPLC (column: Reprosil; C18; 10 μm; 125×30 mm; eluent $ACN/H_2O$ with 0.1%

HCOOH modifier; flow: 75 mL/min; gradient: 0-5.50 min 10/90; Sample injection until 3.00 min; 5.50-17.65 min gradient to 95/5; 17.65-19.48 min 95/5; 19.48-19.66 min gradient to 10/90; 19.66-20.72 min 10/90;). The desired fractions were combined and lyophilized to provide 800 mg (98% purity, 48% yield) of the title compound as a colorless oil; ee >99%.

LC-MS (Method 9): $R_t$=0.51 min; MS (ESI pos): m/z=250 $[M+H]^+$ $^1$H-NMR (500 MHz, DMSO-d6) δ[ppm]: 1.191 (10.46), 1.205 (10.52), 2.462 (0.66), 2.469 (0.77), 2.473 (0.76), 2.485 (1.55), 2.521 (1.43), 2.562 (0.63), 3.330 (0.93), 3.344 (2.66), 3.358 (2.62), 3.372 (0.86), 3.499 (0.46), 3.506 (0.63), 3.511 (0.45), 3.521 (2.34), 3.530 (3.52), 3.532 (3.50), 3.538 (3.54), 3.549 (2.18), 3.564 (0.56), 5.101 (0.60), 5.126 (5.99), 5.131 (5.75), 5.156 (0.57), 7.323 (0.69), 7.327 (0.52), 7.332 (1.27), 7.341 (1.23), 7.343 (0.94), 7.350 (1.14), 7.358 (0.50), 7.369 (1.15), 7.377 (16.00), 7.386 (6.48), 7.392 (0.46).

Example 119A (2S)-2-(Morpholin-4-yl)propanoic acid

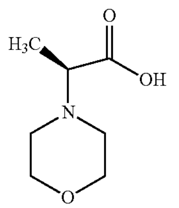

Palladium (10% on activated carbon) (100 mg) was moistened with methanol under argon. After that, benzyl (2S)-2-(morpholin-4-yl)propanoate (Example 118A, 800 mg, 3.21 mmol) was dissolved in methanol (100 mL) and the moistened palladium on activated carbon was added to the solution under argon. The suspension then was hydrogenated for 2 hours at ambient pressure under a hydrogen atmosphere. The vessel was purged of hydrogen with argon and the suspension was filtered over celite. The filtrate was evaporated, and the residue was dissolved in MeCN/$H_2O$ and lyophilized to provide 501 mg (>99% purity, 98% yield) of the title compound as a light-brown solid.

LC-MS (Method 9): $R_t$=0.16 min; MS (ESI pos): m/z=160 $[M+H]^+$ $^1$H-NMR (500 MHz, deuterium oxide) 6 [ppm]: 1.519 (16.00), 1.534 (15.96), 3.695 (1.39), 3.709 (4.02), 3.724 (3.89), 3.738 (1.30).

Example 120A 1-(Tert-butoxycarbonyl)-4-ethylidene-L-proline

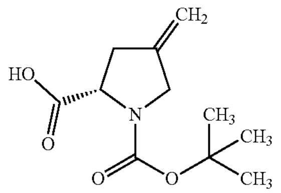 [SMILES: C=C1C[C@@H](C(=O)O)N(C(=O)OC(C)(C)C)C1]

Methyl(triphenyl)phosphonium bromide (34.7 g, 97.1 mmol) was suspended in 400 mL THF. A solution of KHMDS solution in toluene (146.6 mL, 15% w/v, 97.1 mmol) was added dropwise at room temperature and stirred for one hour at room temperature. After that, the solution was cooled to 0° C., and 1-(tertbutoxycarbonyl)-4-oxo-L-proline (11.1 g, 48.6 mmol) was added in portions. The mixture was stirred 2.5 hours at room temperature. Water was added to the reaction mixture. The mixture was made slightly acidic with 10% citric acid solution and the extracted three times with ethyl acetate. The combined ethyl acetate layer was washed with a saturated aqueous sodium chloride solution, dried over magnesium sulfate, and then dried under vacuum to give a thick orange resin. The crude product was used for the next step without further purification.

Example 121A

1-Tert-butyl 2-methyl (2S)-4-methylidenepyrrolidine-1,2-dicarboxylate

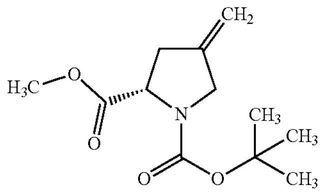 [SMILES: C=C1C[C@@H](C(=O)OC)N(C(=O)OC(C)(C)C)C1]

The crude 1-(tert-butoxycarbonyl)-4-ethylidene-L-proline (Example 120A) (11.0 g, 48.6 mmol) was dissolved in DMF (60 mL). Potassium carbonate (10.1 g, 72.9 mmol) was added, then iodomethane (4.5 ml, 73 mmol) was added, and then the mixture was stirred overnight at room temperature. The DMF was removed with a rotary evaporator, ethyl acetate was added, and then the mixture was washed one time with water. The aqueous phase was one time re-extracted with ethyl acetate. The combined organic phases were washed with a saturated aqueous sodium chloride solution, dried over magnesium sulfate, and then dried under vacuum to give the crude product. The crude product was dissolved in DCM and purified by normal-phase chromatography using a Biotage Isolara flash chromatography system, using an eluant of cyclohexane-ethyl acetate (85/15) to give 10.2 g (80%) of the title compound as a yellow oil.

LC-MS (Method 10): $R_t$=1.77 min; MS (ESI pos): m/z=186 $M-C_4H8^+$ $^1$H-NMR (500 MHz, DMSO-d6) δ[ppm]: 1.339 (16.00), 1.405 (10.53), 3.313 (10.02), 3.627 (3.90), 3.938 (2.21), 3.967 (0.60), 4.331 (0.51), 4.337 (0.54), 4.350 (0.57), 4.356 (0.59), 4.363 (0.47), 4.367 (0.42), 4.992 (1.33), 5.019 (1.17).

Example 122A

5-Tert-butyl 6-methyl (6S)-5-azaspiro[2.4]heptane-5,6-dicarboxylate

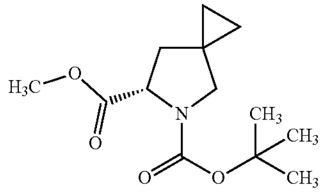 [SMILES: COC(=O)[C@@H]1CC2(CC2)CN1C(=O)OC(C)(C)C]

Under argon, diethylzinc (22 mL, 1.0 M in hexane, 22 mmol) was dissolved in anhydrous DCM (27 mL). The solution was cooled to 5° C. and then a solution of TFA (1.7 ml, 22 mmol) in DCM (17 mL) was added dropwise over a 1 hour period. The solution was stirred at 5° C. for an additional 30 min. A solution of diiodomethane (1.8 mL, 22 mmol) in anhydrous DCM (5 mL) was added dropwise quickly, and the resulting solution was stirred at 5° C. for 30 min. After that, a solution of 1-tert-butyl 2-methyl (2S)-4-methylidenepyrrolidine-1,2-dicarboxylate (Example 121A) (2.70 g, 11.2 mmol) in anhydrous DCM (5 mL) was added to the reaction mixture. The reaction mixture was stirred in a thawing ice-bath for 90 hours, then quenched with saturated, aqueous ammonium chloride solution. The phases were separated, and the aqueous phase was re-extracted with DCM one time. The organic phases were combined, dried over magnesium sulfate, and then evaporated to provide 1.57 g the crude product as a yellow oil. The oil was dissolved in ethyl acetate (54 mL), di-tert-butyldicarbonate (2.6 mL, 11 mmol) and triethylamine (3.1 mL, 22 mmol) were sequentially added, and then the reaction mixture was stirred overnight at room temperature. The reaction was controlled using TLC (petroleum ether/ethyl acetate 10/1; colored with ninhydrin). The crude product was purified by normal-phase chromatography using a Biotage Isolara flash chromatography system (100 g Biotage cartridge Ultra), using an eluant gradient of petroleum ether-ethyl acetate (EA) (2% to 18% EA) to provide 1.02 g of the title compound as a colorless oil.

Example 123A (6S)-5-(Tert-butoxycarbonyl)-5-azaspiro[2.4]heptane-6-carboxylic acid

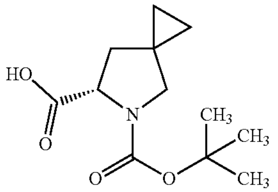

5-Tert-butyl 6-methyl (6S)-5-azaspiro[2.4]heptane-5,6-dicarboxylate (Example 122A) (2.50 g, 9.79 mmol) was dissolved in 50% THF/water (40 mL). Lithium hydroxide (703 mg, 29.4 mmol) was added, and the reaction mixture was stirred overnight at room temperature. The THF was removed using a rotary evaporator, and the aqueous solution was diluted with additional water (20 mL) water and washed once with MTBE. The separated aqueous phase was acidified with 1M hydrochloric acid (30 mL) and then extracted two times with DCM. The combined organic phase was dried over magnesium sulfate, filtered, and then concentrated to give 2.4 g of the title compound as a colorless oil.

Example 124A (6S)-5-azaspiro[2.4]heptane-6-carboxylic acid

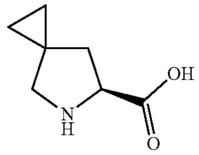

(6S)-5-(tert-butoxycarbonyl)-5-azaspiro[2.4]heptane-6-carboxylic acid (Example 123A) (2.36 g, 9.79 mmol) was dissolved in DCM (50 mL). Trifluoroacetic acid (10 mL, 250 mmol) was added, and the reaction mixture was stirred 2 hours at room temperature. The reaction control was made using TLC (DCM/MeOH 9/1). The solution was evaporated and the crude product was dried under vacuum to provide the title compound as a brown residue. This was used directly for the next step (Fmoc protection, see Example 82A).

Example 15A (2S,5R)-2-[(2,5-difluorophenyl)methyl]-3,6-dimethoxy-5-(propan-2-yl)-2,5-dihydropyrazine

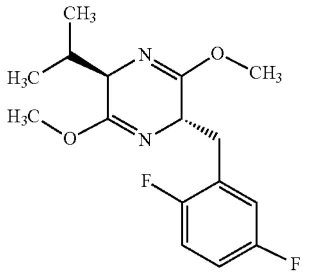 [SMILES: COC1=N[C@H](C(C)C)C(OC)=N[C@H]1Cc1cc(F)ccc1F]

The reaction was performed under argon. (2R)-3,6-dimethoxy-2-(propan-2-yl)-2,5-dihydropyrazine (CAS-RN: 109838-85-9) (2.9 ml, 16 mmol) was dissolved in anhydrous THF (40 mL) and the solution was cooled to −78° C. At this temperature, an n-butyl lithium solution (10 mL, 1.6 M in hexane, 16 mmol) was slowly added dropwise, and the resulting solution was stirred 15 min at −78° C. Then a solution of 2-(bromomethyl)-1,4-difluorobenzene (4.05 g, 19.5 mmol) in anhydrous THF (15 mL) was added and stirring was continued until the reaction came to room temperature. The reaction mixture was stirred for an additional hour at room temperature, while monitoring the reaction progress by HPLC. The mixture was quenched with water and extracted two times with ethyl acetate. The combined organic phases were washed one time with a saturated aqueous sodium chloride solution, dried over magnesium sulfate, and then concentrated to give 5.46 g of a crude yellow oil. The oil was purified by normal phase chromatography using a Biotage Isolara flash chromatography system (100 g Biotage cartridge Ultra), using an eluant of cyclohexane-ethyl acetate (EA) (95/5) to afford 4.16 g (82%) of the title compound as an oil.

LC-MS (Method 10): $R_t$=2.44 min; MS (ESI pos): m/z=311 $[M+H]^+$ $^1$H-NMR (400 MHz, DMSO-d6) δ[ppm]: 0.563 (6.79), 0.580 (6.97), 0.933 (6.65), 0.951 (6.88), 2.103 (0.58), 2.111 (0.61), 2.120 (0.78), 2.129 (0.79), 2.137 (0.59), 2.145 (0.57), 2.864 (0.79), 2.882 (0.83), 2.898 (1.08), 2.915 (1.09), 3.089 (1.06), 3.101 (1.10), 3.123 (0.82), 3.134 (0.81), 3.313 (7.20), 3.518 (1.28), 3.527 (2.46), 3.535 (1.37), 3.566 (16.00), 4.293 (0.58), 4.304 (1.07), 4.313 (1.08), 4.321 (1.01), 4.330 (0.58), 6.992 (0.47), 7.000 (0.66), 7.005 (0.63), 7.015 (1.06), 7.023 (0.71), 7.028 (0.64), 7.037 (0.63), 7.075 (0.63), 7.084 (0.91), 7.095 (0.74), 7.105 (0.66), 7.131 (0.68), 7.143 (0.73), 7.154 (1.05), 7.166 (1.04), 7.177 (0.45), 7.189 (0.40).

Example 126A

Methyl 2,5-difluoro-L-phenylalaninate

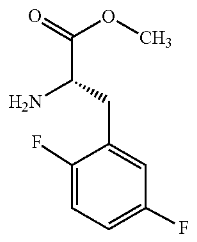

(2S,5R)-2-[(2,5-difluorophenyl)methyl]-3,6-dimethoxy-5-(propan-2-yl)-2,5-dihydropyrazine (example 125A) (4.15 g, 13.4 mmol) was dissolved in methanol (35 mL) and the solution was cooled to 0° C. A solution of a aqueous 10% hydrochloric acid (12 mL) was added and the solution was stirred 0° C. for some minutes. Then the reaction solution was allowed to come to room temperature and then stirred three hours at this temperature. The methanol was evaporated. The residue was diluted with DCM, 2M aqueous sodium carbonate solution (120 mL) was added and the resulting mixture was stirred vigorously for a few minutes. The layers were separated, and the aqueous phase was extracted two times with DCM. The combined organic phases were dried over magnesium sulfate, filtered, and then concentrated to give 3.97 g of a colorless liquid. The crude liquid was purified by normal phase chromatography using a Biotage Isolara flash chromatography system (100 g Biotage cartridge Ultra), using a gradient eluant of cyclohexane-ethyl acetate (EA) (10% to 75% EA) to provide 2.27 g (79%) of the title compound as a colorless liquid.

LC-MS (Method 13): $R_t$=1.20 min; MS (ESI pos): m/z=216 $[M+H]^+$ $^1$H-NMR (400 MHz, DMSO-d6) δ[ppm]: 1.833 (16.00), 2.733 (3.07), 2.753 (3.26), 2.767 (4.81), 2.787 (5.01), 2.889 (4.71), 2.904 (4.91), 2.923 (3.10), 2.938 (3.19), 3.315 (15.20), 3.401 (0.42), 3.553 (5.22), 3.568 (6.29), 3.572 (6.60), 3.768 (0.41), 7.060 (0.89), 7.069 (1.71), 7.081 (2.21), 7.090 (4.07), 7.101 (3.20), 7.111 (2.84), 7.120 (1.89), 7.151 (5.97), 7.163 (5.82), 7.174 (9.84), 7.186 (7.52), 7.196 (4.42), 7.208 (2.10).

Example 127A tert-Butyl (2R)-2-amino-3-[[(2R)-2-amino-3-tert-butoxy-3-oxo-propyl]disulfanyl]propanoate

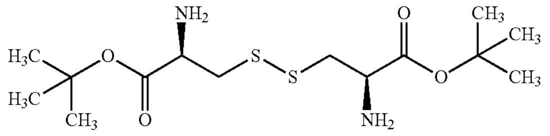 [SMILES: CC(C)(C)OC(=O)[C@@H](N)CSSC[C@H](N)C(=O)OC(C)(C)C]

To the suspension of L-Cystine (CAS RN: 56-89-3) (10.00 g, 41.61 mmol) in tert-butyl acetate (63.22 g, 544.24 mmol, 73 mL) was added $HClO_4$ (18.26 g, 127.23 mmol, 11 mL, 70% purity) (70% in $H_2O$) dropwise at 0° C. over 0.5 h, then the solution was stirred for 17 h at 20° C. Ice was added and the solution was used for the next step without further purification (14.67 g in theory).

Example 128A tert-Butyl (2R)-3-[[(2R)-3-tert-butoxy-2-(tert-butoxycarbonylamino)-3-oxo-propyl]disulfanyl]-2-(tertbutoxycarbonylamino)propanoate

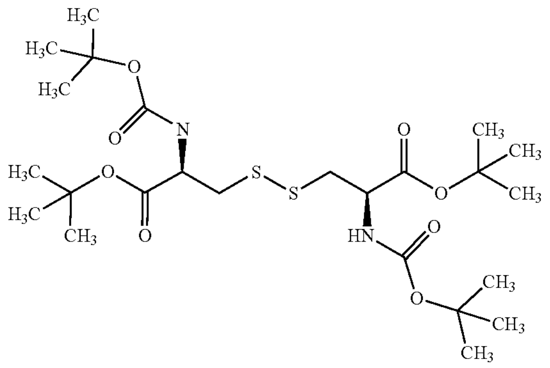

To the mixture of tert-butyl (2R)-2-amino-3-[[(2R)-2-amino-3-tert-butoxy-3-oxo-propyl]disulfanyl]propanoate (14.67 g in theory, from Example 127A) in water (200 mL) and EA (200 mL) was added $Na_2CO_3$ (30.00 g, 283.08 mmol) and $Boc_2O$ (27.25 g, 124.85 mmol) at 0° C., and the mixture (pH was 8-9) was stirred for 17 h at 20° C. The mixture was diluted with EA (100 mL) and water (200 mL). The organic layer was separated, and aqueous layer was extracted with EA (200 mL). The combined organic layer was washed with brine (200 mL), concentrated to give a residue, the residue was purified by silical gel chromatography (PE/EA=1/0 to 1/1) to give two batches of the title compound: 8.5 g crude as a light brown oil and 6.5 g as a light brown oil.

$^1$H-NMR (400 MHz, $CDCl_3$) δ [ppm]: 1.51, 1.61, 1.62. 1.64, 3.11, 3.12, 3.14, 3.16, 3.19, 3.203, 3.23, 3.24, 4.44, 4.46, 4.48, 4.49, 5.35, 5.37.

Example 129A tert-Butyl (2R)-2-(tert-butoxycarbonylamino)-3-sulfanyl-propanoate

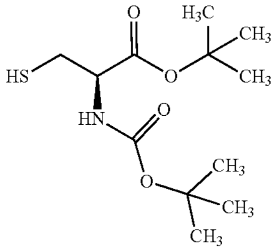 [SMILES: CC(C)(C)OC(=O)N[C@@H](CS)C(=O)OC(C)(C)C]

To the solution of tert-butyl (2R)-3-[[(2R)-3-tert-butoxy-2-(tert-butoxycarbonylamino)-3-oxo-propyl]disulfanyl]-2-(tert-butoxycarbonylamino)propanoate (8.5 g, crude, from example 128A) in THF (150 mL) and water (15 mL) was added tributylphosphane (3.77 g, 4.6 mL) at 0° C. over 0.5 h, then the solution was stirred for 2 h at 20° C. The mixture was worked up with another batch, prepared from 6.5 g of rare material (from Example 128A). Both reaction mixtures were poured into water (300 mL) and extracted with ethyl acetate (150 mL×2). The combined organic phase was washed with brine (300 mL), dried with anhydrous $Na_2SO_4$, filtered and concentrated in vacuum. The residue was purified by silica gel chromatography (PE/EA=40/1 to 10/1) to afford 12.5 g of the title compound as a colorless oil, which was used as pure. 6.5 g of an impure batch containing residual tributylphosphine was also obtained but discarded.

$^1$H-NMR (400 MHz, $CDCl_3$) δ [ppm]: 1.45, 2.94, 2.95, 2.96, 2.97, 4.46, 4.47, 4.48, 4.49, 5.39, 5.41

Example 130A tert-Butyl (2R)-2-(tert-butoxycarbonylamino)-3-(trifluoromethylsulfanyl)propanoate

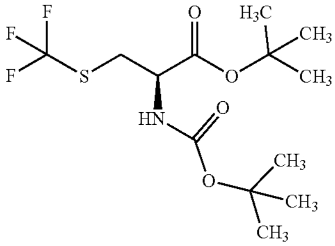 [SMILES: CC(C)(C)OC(=O)N[C@@H](CSC(F)(F)F)C(=O)OC(C)(C)C]

To a solution of 3,3-dimethyl-1-(trifluoromethyl)-1,2-benziodoxole (18 g, 54.53 mmol) in MeOH (150 mL) was added a solution of tert-butyl (2R)-2-(tert-butoxycarbonylamino)-3-sulfanyl-propanoate (14 g, 50.47 mmol, from Example 129A) in MeOH (20 mL) at −78° C. under $N_2$ over 30 min, and the reaction was stirred for 1 h at this temperature, upon which it becomes colorless solution. The reaction mixture was warmed to 20° C., stirred for 1 h, and concentrated to give a residue, which was purified by silica gel chromatography (PE/EA=1/0 to 40/1) twice to give 13.2 g of the title compound as a colorless oil.

$^1$H-NMR (400 MHz, $CDCl_3$) δ [ppm]: 1.47, 3.26, 3.28, 3.30, 3.31, 3.45, 3.46, 3.48, 3.50, 4.47, 4.48, 5.34, 5.35.

Example 131A tert-Butyl (2R)-2-amino-3-(trifluoromethylsulfanyl)propanoate hydrochloride

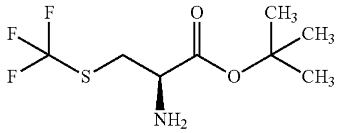

To a solution of tert-butyl (2R)-2-(tert-butoxycarbonylamino)-3-(trifluoromethylsulfanyl)-propanoate (12.20 g, 35.32 mmol, from example 130A) in DCM (10 mL) was added a solution of HCl/dioxane (4 M, 50 mL) and the reaction was stirred for 3 h at 10° C. The mixture was concentrated to give a white glassy solid, which was used for next step directly.

Example 132A tert-Butyl (2R)-2-(9H-fluoren-9-ylmethoxycarbonylamino)-3-(trifluoromethylsulfanyl)-propanoate

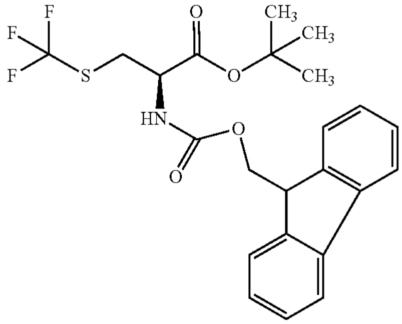 [SMILES: CC(C)(C)OC(=O)[C@H](CSC(F)(F)F)NC(=O)OCC1c2ccccc2-c2ccccc21]

To the mixture of tert-butyl (2R)-2-amino-3-(trifluoromethylsulfanyl)propanoate hydrochloride (crude from Example 131A) in dioxane (80 mL) was added saturated $NaHCO_3$ (80 mL), and Fmoc-OSu (19 g, 56.33 mmol), and the reaction (pH ~7-8) was stirred for 17 h at 10° C. The mixture was concentrated, and the residue was diluted with water (100 mL), then extracted with EA (100 mL×2). The organic layer was washed with brine (100 mL), concentrated, and then purified by silica gel chromatography (PE/EA=40/1-10/1) to give 13 g of the title compound as a colorless oil.

LC-MS (Method 15): $R_t$=1.028 min; MS (ESI pos): m/z=490.2 [M+Na]$^+$ $^1$H-NMR (400 MHz, $CDCl_3$) δ [ppm]: 1.45, 3.32, 3.47, 3.36, 3.49, 3.50, 4.16, 4.22, 4.24, 4.26, 4.37, 4.44, 4.46, 4.58, 5.62, 5.64, 7.33, 7.35, 7.40, 7.42, 7.44, 7.56, 7.61, 7.77, 7.79.

$^{19}$F-NMR: (376 MHz, $CDCl_3$) δ [ppm]: −40.85.

Example 133A

2R)-2-(9H-fluoren-9-ylmethoxycarbonylamino)-3-(trifluoromethylsulfanyl)propanoic acid

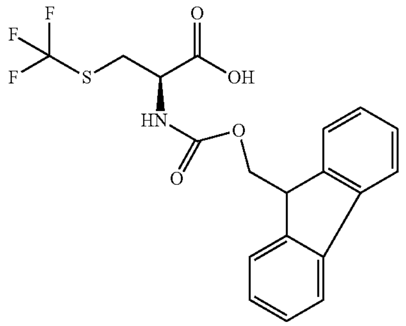 [SMILES: O=C(N[C@@H](CSC(F)(F)F)C(=O)O)OCC1c2ccccc2-c2ccccc21]

To a solution of tert-butyl (2R)-2-(9H-fluoren-9-ylmethoxycarbonylamino)-3-(trifluoromethylsulfanyl)propanoate (13 g, 27.81 mmol) in DCM (15 mL) was added TFA (30 mL) and thioanisole (15.75 g, 126.81 mmol, 15 mL), and the reaction mixture was stirred for 17 h at 10° C. The mixture was concentrated to give a residue, which was diluted with saturated $NaHCO_3$ solution (100 mL), and then extracted with EA (50 mL×2). The organic layer was washed with 1M HCl (50 mL), concentrated, and then purified by silica gel chromatography (PE/EA=10/1, then with DCM/MeOH=40/1 to 5/1) to give 10 g of the title compound as a white glassy solid purity: 98.8%. $^1$H-NMR indicated that the product contained ethyl acetate, so the solid was re-dissolved in DCM (80 mL), concentrated and then dried under high vacuum to give 9.67 g (23.22 mmol, 83.5% yield, 98.8% purity) of the title compound as a white glassy solid.

LC-MS (Method 15): $R_t$=0.895 min; MS (ESI pos): m/z=434.1 $[M+Na]^+$ $^1$H-NMR (400 MHz, $CDCl_3$) δ [ppm]: 3.25, 3.26, 3.32, 3.33, 3.93, 3.95, 4.22, 4.24, 4.26, 4.28, 4.30, 4.31, 6.95, 6.98, 7.31, 7.32, 7.33, 7.34, 7.39, 7.41, 7.42, 7.68, 7.70, 7.87, 7.89.

$^{19}$F-NMR: (376 MHz, $CDCl_3$) δ [ppm]: −40.89

Chiral SFC: $R_t$=2.49 min, 99% ee

Chiral SFC condition: AD-3_5CM_IPA (DEA)_10_20_3ML_T35 Column: Chiralpak AD-3 50×4.6 mm I.D., 3 μm Mobile phase: iso-propanol (0.05% DEA) in $CO_2$ from 10% to 20% Flow rate: 3 mL/min Wavelength: 220 nm.

This amino acid was used in SPPS. This amino acid is also commercially available (CAS-RN: 1994331-25-7.

Example 134A

Di-tert-butyl (2S)-5-oxopyrrolidine-1,2-dicarboxylate

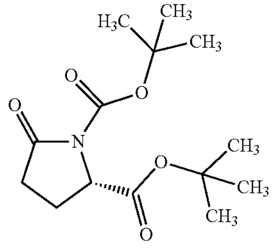 [SMILES: CC(C)(C)OC(=O)[C@@H]1CCC(=O)N1C(=O)OC(C)(C)C]

To a solution of compound tert-butyl (2S)-5-oxopyrrolidine-1,2-dicarboxylate (CAS-RN: 35418-16-7) (290 g, 1.57 mol, 1.00 eq) and DMAP (1.91 g, 15.66 mmol, 0.01 eq) in $CH_3CN$ (2.00 L), was added $Boc_2O$ (341 g, 1.57 mol, 359 mL, 1.00 eq) at 5° C. After the addition, the mixture was stirred at 20° C. for 12 h. TLC showed that the starting material was completely consumed, and two new spots (TLC) were formed (PE/EA=3/1, Rf=0.43, Rf=0.9). The reaction mixture was concentrated under reduced pressure to remove $CH_3CN$ and the residue was partitioned between DCM (1000 mL) and water (1000 mL). The organic layer was washed with brine (300 mL), dried over $Na_2SO_4$, filtered and concentrated under reduced pressure to give the crude product. The residue was purified by column chromatography ($SiO_2$, PE/EA=100/1 to 10/1) to afford the title compound (260.00 g, 874.75 mmol, 55.72% yield, 96% purity) as off-white solid.

LC-MS (Method 15): $R_t$=0.873 min; MS (ESI pos): m/z=308.0 $[M+Na]^+$, 331 $[M+2Na]^+$ $^1$H-NMR (400 MHz, $CDCl_3$) δ [ppm]: 1.44-1.42 (d, J=8.4, 8H), 1.97-1.92 (m, 1H), 2.22-2.19 (m, 1H), 2.43-2.40 (m, 1H), 2.58-2.49 (m, 1H), 4.42-4.39 (m, 1H).

Example 135A

Di-tert-butyl (2S)-4,4-diallyl-5-oxo-pyrrolidine-1,2-dicarboxylate

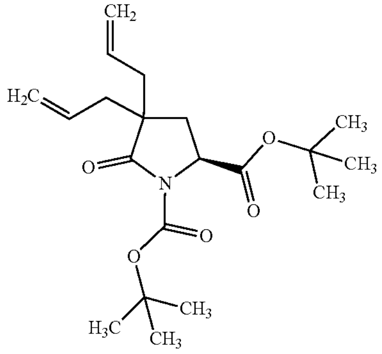 [SMILES: C=CCC1(CC=C)C[C@@H](C(=O)OC(C)(C)C)N(C(=O)OC(C)(C)C)C1=O]

To a solution of di-tert-butyl (2S)-5-oxopyrrolidine-1,2-dicarboxylate (61.9 g, 208 mmol, 1.00 eq, from Example 134A) in THF (40.0 mL) was added LiHMDS (1 M, 437 mL, 2.10 eq) dropwise at −73° C. and then stirred at −73° C. for 1 h. To the mixture was added compound allyl bromide (50.4 g, 416 mmol, 2.00 eq) dropwise. After the addition, the mixture was stirred at 15° C. for 2 h. TLC showed compound that the starting material was completely consumed, and four new spots were formed (PE/EA=3/1, $R_f$=0.9, $R_f$=0.8, Rf=0.7, Rf=0.1). The reaction mixture was quenched with saturated aqueous ammonium chloride (1000 mL), extracted with DCM (500 mL×3), dried over sodium sulfate, filtered, and then concentrated under reduced pressure to give a crude residue. The residue was purified by column chromatography ($SiO_2$, PE/EA=100/1 to 30/1) to afford the title compound (100 g, 38% yield, 86% purity) as a colorless oil.

LC-MS (Method 15): $R_t$=1.044 min; MS (ESI pos): m/z=411.4 $[M+2Na]^+$ $^1$H-NMR (400 MHz, $CDCl_3$) δ [ppm]: 1.49-1.43 (d, J=8.4, 8H), 1.87-1.82 (m, 1H), 2.22-2.18 (m, 3H), Example 136A Di-tert-butyl (2S)-4,4-diallylpyrrolidine-1,2-dicarboxylate

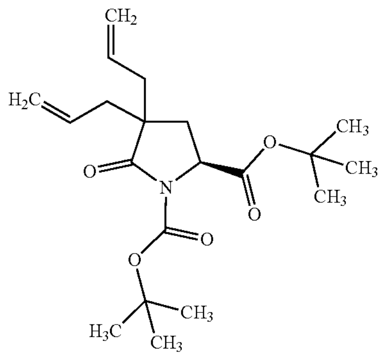 [SMILES: C=CCC1(CC=C)C[C@@H](C(=O)OC(C)(C)C)N(C(=O)OC(C)(C)C)C1=O]

To a solution of di-tert-butyl (2S)-4,4-diallyl-5-oxo-pyrrolidine-1,2-dicarboxylate (80.0 g, 188 mmol, 1.00 eq, from Example 135A) in THF (300 mL) was added $LiBHEt_3$ (1 M, 225 mL, 1.20 eq) at −78° C. After the addition, the mixture was stirred at −78° C. for 3 h. LCMS showed the desired MS was detected. TLC showed two new spots were formed (PE/EA=3/1, $R_f$=0.65, $R_f$=0.8). The reaction mixture was quenched with saturated aqueous sodium carbonate (50 mL) at 0° C. and then 30% $H_2O_2$ (1 mL) was added dropwise at 0° C. The mixture was concentrated under reduced pressure to remove the THF and then the residue was diluted with water (1000 mL) and DCM (1000 mL). The water phase was extracted with DCM (300 mL×3). The combined organic layer was dried over sodium sulfate, filtered, and then concentrated under reduced pressure to give the crude product. The crude residue was purified by column chromatography ($SiO_2$, PE/EA=80/1 to 30/1) to afford the title compound (56.0 g, 69% yield, 85% purity) as a colorless oil.

LC-MS (Method 15): $R_t$=1.192 min; MS (ESI pos): m/z=390.3 $[M+K]^+$ $^1$H-NMR (400 MHz, $CDCl_3$) δ [ppm]: 1.53-1.47 (m, 18H), 2.13-1.98 (m, 2H), 2.22-2.15 (m, 3H), 2.39-2.24 (m, 1H), 2.92-2.91 (m, 1H), 4.22-4.08 (m, 1H), 5.18-5.06 (m, 5H), 5.85-5.77 (m, 2H).

Example 137A

Di-tert-Butyl (3S)-2-azaspiro[4.4]non-7-ene-2,3-dicarboxylate

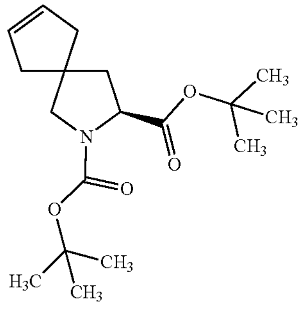 [SMILES: CC(C)(C)OC(=O)[C@@H]1CC2(CC=CC2)CN1C(=O)OC(C)(C)C]

To a solution of the Grubb's 1' generation catalyst (CAS RN: 172222-30-9) (2.85 g, 3.47 mmol, 0.05 eq) in DCM (400.00 mL) was added di-tert-butyl (2S)-4,4-diallylpyrrolidine-1,2-dicarboxylate (25.0 g, 69.4 mmol, 1.00 eq, from Example 136A) dropwise at 34° C. After the addition was completed, the mixture was stirred at 34° C. under $N_2$ for 1 h. TLC showed two new spots were formed (PE/EA=5/1, $R_f$=0.6, $R_f$=0.7). The reaction mixture was filtered and concentrated under reduced pressure to give the crude product. The residue was purified by column chromatography ($SiO_2$, PE/EA=1/0 to 80/1) to afford the title compound (12.0 g) as a colorless oil.

$^1$H-NMR (400 MHz, $CDCl_3$) δ [ppm]: 1.46-1.43 (m, 18H), 1.92-1.87 (m, 1H), 2.45-2.22 (m, 5H), 3.49-3.29 (m, 2H), 4.21-4.19 (m, 1H), 5.64 (s, 2H).

Example 138A

Di-tert-butyl (3S)-2-azaspiro[4.4]nonane-2,3-dicarboxylate

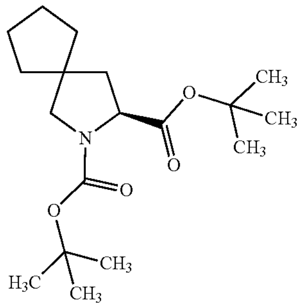 [SMILES: CC(C)(C)OC(=O)[C@@H]1CC2(CCCC2)CN1C(=O)OC(C)(C)C]

To a solution of di-tert-butyl (3S)-2-azaspiro[4.4]non-7-ene-2,3-dicarboxylate (12.0 g, 37.1 mmol, 1.0 eq, from Example 137A) in EtOH (100 mL) was added Pd/C (10%, 0.1 g) under a $N_2$ atmosphere. The suspension was degassed and purged 3 times with $H_2$ gas. The mixture was stirred under $H_2$ (15 Psi) at 25° C. for 16 h. Part of suspension was filtered, and the filtrate was concentrated, and proton NMR was taken, which showed that the desired product was formed. The reaction mixture was filtered, and the filtrate was concentrated to give 10.0 g (crude) of the title compound as a white solid.

$^1$H-NMR (400 MHz, $CDCl_3$) δ [ppm]: 4.12-4.02 (m, 1H), 3.65-3.60 (m, 2H), 3.12-3.38 (m, 5H), 2.11-2.06 (m, 1H), 1.80-1.77 (m, 1H), 1.57-1.56 (m, 6H), 1.40-1.36 (m, 18H).

Example 139A (3S)-2-Azaspiro[4.4]nonane-3-carboxylic acid

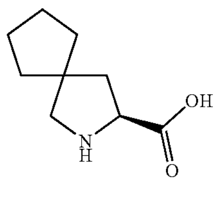 [SMILES: O=C(O)[C@@H]1CC2(CCCC2)CN1]

The compound di-tert-butyl (3S)-2-azaspiro[4.4]nonane-2,3-dicarboxylate (12 g, 36.8 mmol, 1 eq, from Example 138A) was added into a solution of HCl/EtOAc (150 mL), and then the mixture was stirred at 15° C. for 1 h. LC-MS analysis showed that the starting material was consumed, and the desired target mass was found. The reaction mixture was concentrated in vacuum to remove the solvent, affording 7.5 g (36.4 mmol, 99% yield) of the crude title compound as a white solid as a hydrochloride salt.

$^1$H-NMR (400 MHz, DMSO) δ [ppm]: 10.07 (s, 1H), 8.81 (s, 1H), 4.38-4.27 (m, 1H), 3.16-3.02 (m, 2H), 2.22-2.21 (m, 1H), 1.96-1.90 (m, 1H), 1.63-1.56 (m, 8H).

Example 140A (3S)-2-{[(9H-Fluoren-9-yl)methoxy]carbonyl}-2-azaspiro[4.4]nonane-3-carboxylic acid

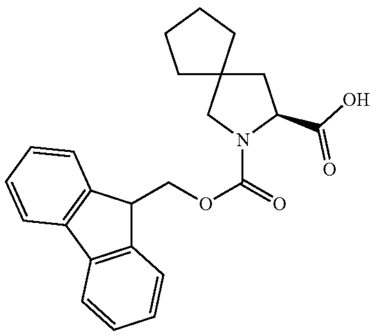 [SMILES: O=C(O)[C@@H]1CC2(CCCC2)CN1C(=O)OCC1c2ccccc2-c2ccccc21]

To a solution of (3S)-2-azaspiro[4.4]nonane-3-carboxylic acid (5.1 g, 24.8 mmol, from Example 139A) and Fmoc-OSu (10.0 g, 29.7 mmol, 1.2 eq) in THF (70 mL) and $H_2O$ (70 mL) was added $NaHCO_3$ (8.5 g, 101 mmol, 3.94, 4.08 eq). The mixture was stirred at 15° C. for 1 h. LCMS analysis showed that the starting material was consumed, and the desired target mass was obtained. Water (200 ml) was added, and then the mixture was extracted with DCM (200 mL×2). The combined organic layer was washed with brine (100 mL), dried over $Na_2SO_4$, filtered, and then concentrated. The crude product was purified for reversed-phase MPLC (EA) to afford 6.9 g (17.5 mmol, 70% yield, 99% purity) of the title compound as a yellow solid.

LC-MS (Method 15): $R_t$=2.501 min; MS (ESI pos): m/z=392.2 $[M+H]^+$ $^1$H-NMR (400 MHz, $CDCl_3$) δ [ppm]: 7.80-7.79 (d, J=7.2, 2H), 7.59-7.54 (m, 2H), 7.44-7.42 (m, 2H), 7.36-7.35 (m, 2H), 4.55-4.52 (m, 2H), 4.42-4.38 (m, 1H), 4.31-4.20 (m, 1H), 3.34-3.17 (m, 2H), 2.33-2.28 (m, 1H), 2.13-2.08 (m, 1H), 1.73-1.50 (m, 8H).

This amino acid was used in SPPS. This amino acid is also commercially available (CAS-RN: 394734-78-2).

Example 141A (2S,4R)-4-(Trifluoromethyl)pyrrolidine-2-carboxylic acid

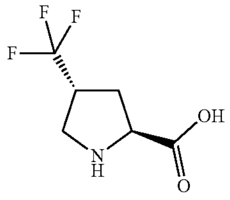 [SMILES: O=C(O)[C@@H]1C[C@@H](C(F)(F)F)CN1]

To a solution of (2S,4R)-1-tert-butoxycarbonyl-4-(trifluoromethyl)pyrrolidine-2-carboxylic acid (7 g, 24.7 mmol, 1 eq) in DCM (70 mL) was added TFA (8.00 mL, 108 mmol, 4.37 eq). The mixture was stirred at 10° C. for 4 h. LCMS analysis showed that the starting material was consumed and that the desired target mass was found. The reaction mixture was concentrated under vacuum and the crude product was used directly for the next step. The title compound (7.34 g, 24.7 mmol, 100% yield, TFA salt) was obtained as a white solid.

LC-MS (Method 15): $R_t$=0.18 min; MS (ESI pos): m/z=184.1 $[M+H]^+$ $^1$H-NMR (400 MHz, $CDCl_3$) δ [ppm]: 4.51-4.48 (m, 1H), 3.82 (m, 1H), 3.57-3.55 (m, 1H), 2.65-2.62 (m, 2H), 2.53-2.49 (m, 1H).

Example 142A (2S,4R)-1-(9H-Fluoren-9-ylmethoxycarbonyl)-4-(trifluoromethyl)pyrrolidine-2-carboxylic acid

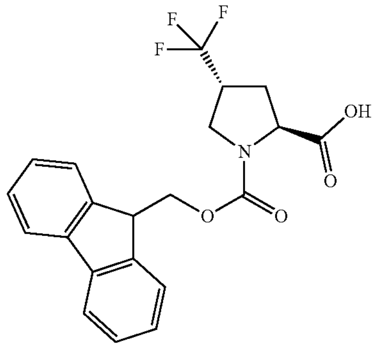 [SMILES: O=C(O)[C@@H]1C[C@@H](C(F)(F)F)CN1C(=O)OCC1c2ccccc2-c2ccccc21]

To a solution of the crude (2S,4R)-4-(trifluoromethyl)pyrrolidine-2-carboxylic acid (2 g, 6.73 mmol, 1 eq, TFA salt, from Example 141A) in $H_2O$ (70 mL) and acetone (70 mL) was added $Na_2CO_3$ (2.85 g, 26.9 mmol, 4 eq) and Fmoc-OSu (2.72 g, 8.08 mmol, 1.2 eq). The mixture was stirred at 10° C. for 12 h. LCMS analysis showed only one peak and that the desired mass was found. TLC analysis (DCM/MeOH=10/1) showed that the starting material was consumed, and that a main spot ($R_f$=0.4) appeared. HCl solution (1M, 30 mL) was added to the mixture until the pH=2. The mixture was extracted with DCM (70 mL×2), and the combined organic layer was washed with brine (70 ml), dried over $Na_2SO_4$, filtered, and then concentrated. The residue was purified by column chromatography ($SiO_2$, PE/EA=10/1 to 5/1), providing 1.7 g (61%, 97% purity) of the title compound as a yellow solid.

LC-MS (Method 15): $R_t$=2.425 min; MS (ESI pos): m/z=406.2 $[M+H]^+$, 406.2 $[M+Na]^+$ $^1$H-NMR (400 MHz, DMSO) δ [ppm]: 7.92-7.89 (m, 2H), 7.66-7.64 (m, 2H), 7.42-7.41 (m, 2H), 7.35-7.32 (m, 2H), 4.16-4.19 (m, 4H), 3.72-3.50 (m, 3H), 2.38-2.30 (m, 2H), 2.18 (s, 1H).

$^{19}$F-NMR (400 MHz, DMSO) δ [ppm]: −70.128, −70.275.

Chiral SFC: $R_t$=2.33 min, 99% ee

Chiral SFC condition: AD-3_5CM_IPA (DEA)_10_20_3ML_T35 Column: Chiralpak AD-3 50×4.6 mm I.D., 3 m Mobile phase: iso-propanol (0.05% DEA) in $CO_2$ from 10% to 20% Flow rate: 3 mL/min Wavelength: 220 nm.

This amino acid was used for SPPS.

TABLE 13

Reference peptides

| Reference No | SEQ ID NO | Identifier | Sequence | Method of Preparation |
|---|---|---|---|---|
| 1 | 11 | SFMI-1 | GIC + SRSLPPIC + IPD-OH | Method B |
| 2 | 12 | SFMI-1 HCl | GIC + SRSLPPIC + IPD-OH (HCl Salt) | Method B, F |
| 3 | 13 | SFMI-1 amide | GIC + SRSLPPIC + IPD-$NH_2$ | Method A |
| A | 14 | Ala-1 SFMI-1 | AIC + SRSLPPIC + IPD-OH | Method B |
| B | 15 | Ala-1 SFMI-1 amide | AIC + SRSLPPIC + IPD-$NH_2$ | Method A |
| C | 16 | Ala-1 SFMI-1 HCl amide | AIC + SRSLPPIC + IPD-$NH_2$ (HCl Salt) | Method A, F |

TABLE 14

Peptides according to the invention

| Example No | SEQ ID NO | Sequence | Method of Preparation |
|---|---|---|---|
| 4 | 17 | ((N—Me)G)-IC + SRSLP-(Oic)-I-(Pen) + IPD-(PEG1(10 atoms))-$NH_2$ | Method A |
| 5 | 18 | AIC + SRSLP-(Oic)-I-(Pen) + IPD-OH (salt free form) | Method B, C, G |
| 6 | 19 | (Nva)-IC + SRS-((tBu)A)-PPI-(((N—Me)C)) + I—$NH_2$ | Method D |
| 7 | 20 | ((N—Me)G)-IC + SRSLP-(Oic)-I-(Pen) + IP-(PEG2(13 atoms))-$NH_2$ | Method A |
| 8 | 21 | (beta-P)-IC + SRS-((tBu)A)-PPI-(Pen) + IP-$NH_2$ | Method A |
| 9 | 22 | PIC + SRS-((tBu)A)-PPI-(Pen) + IPD-$NH_2$ | Method D |
| 10 | 23 | (Aib)-IC + SRS-((tBu)A)-PPI-(Pen) + IPD-$NH_2$ | Method D |
| 11 | 24 | A-((N—Me)I)-C + SRS-((tBu)A)-PPI-((N—Me)C) + IPD-$NH_2$ | Method A |
| 12 | 25 | AIC + SRS-((tBu)A)-PPI-(Pen) + IPD-OH | Method B |
| 13 | 26 | AIC + SRSLP-(Oic)-I-(Pen) + IPD-OH | Method B, C, D |
| 14 | 27 | AIC + SRS-((tBu)A)-P-(Oic)-I-(Pen) + IPD-OH | Method B |
| 15 | 28 | (2-(Pyrrolidine)acetyl)-IC + SRS-((tBu)A)-PPI-(Pen) + IPD-$NH_2$ | Method K |
| 16 | 29 | ((N—Me)G)-IC + SRS-((tBu)A)-PPI-(Pen) + IP-(PEG3(16atoms))-$NH_2$ | Method A |
| 17 | 30 | AIC + SRSLP-((6S)-5-Azaspiro[2.4]heptane-6-carboxylic acid)-I-(Pen) + IPD-$NH_2$ | Method A |
| 18 | 31 | (Orn)-IC + SRS-((tBu)A)-PPI-(Pen) + IPD-OH | Method B |
| 19 | 32 | RIC + SRS-((tBu)A)-PPI-((N—Me)C) + IPD-$NH_2$ | Method A |
| 20 | 33 | AIC + SRS-((tBu)A)-PPI-((N—Me)C) + (2-[(1S,2S)-1-(Amino)-2-methylbutyl]-1,3-oxazole-4-carboxylic acid)-D-$NH_2$ | Method A |
| 21 | 34 | AIC + SRS-((tBu)A)-PPI-(Pen) + IPe-$NH_2$ | Method D |
| 22 | 35 | AIC + SRS-((tBu)A)-PPI-(Pen) + IPn-$NH_2$ | Method D |
| 23 | 36 | ((N—Me)A)-IC + SRS-((tBu)A)-P-(Oic)-I-(Pen) + IP-$NH_2$ | Method C |
| 24 | 37 | ((N—Me)A)-IC + SRS-((tBu)A)-PPI-(Pen) + IPD-$NH_2$ | Method D |
| 25 | 38 | AIC + SRS-((tBu)A)-PPI-((N—Me)C) + I—$NH_2$ | Method A |
| 26 | 39 | AIC + SRSLP-(Oic)-I-(Pen) + IPD-$NH_2$ (HCl salt) | Method A, F |
| 27 | 40 | AIC + SRSLP-(Oic)-I-(Pen) + IPD-$NH_2$ (salt free form) | Method A, G |
| 28 | 41 | (Nle)-IC + SRS-((tBu)A)-PPI-((N—Me)C) + I—$NH_2$ | Method D |
| 29 | 42 | AIC + SRSLP-(Oic)-I-(Pen) + IPD-OH (HCl salt) | Method B, C, F |
| 30 | 43 | AIC + SRS-((tBu)A)-PPI-((N—Me)C) + IPD-$NH_2$ (HCl salt) | Method A, F |
| 31 | 44 | AIC + SRS-((tBu)A)-P-((6S)-5-Azaspiro[2.4]heptane-6-carboxylic acid)-I-(Pen) + IPD-OH | Method B |
| 32 | 45 | (ACMP)-IC + SRS-((tBu)A)-PPI-(Pen) + IPD-$NH_2$ | Method D |
| 33 | 46 | ((1R,3S,4S)-2-azabicyclo[2.2.1]heptane-3-carboxylic acid)-IC + SRS-((tBu)A)-PPI-(Pen) + IP-$NH_2$ | Method A |
| 34 | 47 | ((N—Me)G)-IC + SRS-((tBu)A)-PPI-(Pen) + IP-(PEG7(25 atoms))-$NH_2$ | Method A |
| 35 | 48 | KIC + SRS-((tBu)A)-PPI-((N—Me)C) + IPD-$NH_2$ | Method A |
| 36 | 49 | AIC + SRSLP-((6S)-5-Azaspiro[2.4]heptane-6-carboxylic acid)-I-(Pen) + IPD-OH | Method B |
| 37 | 50 | AIC + SRS-((tBu)A)-PPIC + I—$NH_2$ | Method A |
| 38 | 51 | RIC + SRS-((tBu)A)-PPI-((N—Me)C) + I—$NH_2$ | Method A |
| 39 | 52 | ((N—Me)G)-IC + SRS-((tBu)A)-PPI-(Pen) + IP-(PEG1(10 atoms))-$NH_2$ (HCl salt) | Method A, F |
| 40 | 53 | (Cit)-IC + SRS-((tBu)A)-PPI-(Pen) + IPD-$NH_2$ | Method D |
| 41 | 54 | AIC + SRS-((tBu)A)-P-((6S)-5-Azaspiro[2.4]heptane-6-carboxylic acid)-I-((N—Me)C) + IPD-$NH_2$ | Method A |
| 42 | 55 | ((N—Me)G)-IC + SRS-((tBu)A)-PPI-(Pen) + IP-((S)-3-(2H-tetrazol-5-yl)propanoic acid)-$NH_2$ | Method D |
| 43 | 56 | ((N—Me)A)-IC + SRS-((tBu)A)-P-(Oic)-I-(Pen) + I—$NH_2$ | Method C |
| 44 | 57 | ((N—Me)G)-IC + SRS-((tBu)A)-PPI-(Pen) + IP-(PEG9(31 atoms))-$NH_2$ | Method A |
| 45 | 58 | AIC + SRS-((tBu)A)-P-((6S)-5-Azaspiro[2.4]heptane-6-carboxylic acid)-I-(Pen) + IPD-$NH_2$ | Method A |
| 46 | 59 | (Pip)-IC + SRS-((tBu)A)-PPI-((N—Me)C) + IPD-$NH_2$ | Method A |
| 47 | 60 | (3-Amino-3-methylbutyric acid)-IC + SRS-((tBu)A)-PPI-(Pen) + IPD-$NH_2$ | Method D |
| 48 | 61 | AIC + SRS-((tBu)A)-PPI-((N—Me)C) + IPD-$NH_2$ | Method A |
| 49 | 62 | (Orn)-IC + SRS-((tBu)A)-PPI-(Pen) + IPD-$NH_2$ | Method A |
| 50 | 63 | (Orn)-IC + SRSLP-(Oic)-I-(Pen) + IPD-$NH_2$ | Method A |

TABLE 14-continued

Peptides according to the invention

| Example No | SEQ ID NO | Sequence | Method of Preparation |
|---|---|---|---|
| 51 | 64 | aIC + SRS-((tBu)A)-PPI-(Pen) + IPD-$NH_2$ | Method D |
| 52 | 65 | A-(Cba)-C + SRS-((tBu)A)-PPI-(Pen) + IPD-$NH_2$ | Method D |
| 53 | 66 | TIC + SRS-((tBu)A)-PPI-((N—Me)C) + I—$NH_2$ | Method D |
| 54 | 67 | VIC + SRS-((tBu)A)-PPI-(Pen) + IPD-$NH_2$ | Method D |
| 55 | 68 | ((N—Me)G)-IC + SRS-((tBu)A)-PPI-(Pen) + IP-(PEG5-CH2CO2H (18 atoms))-$NH_2$ | Method A |
| 56 | 69 | ((N—Me)G)-IC + SRS-((tBu)A)-PPI-(Pen) + IPD-(Orn)-(Orn)-(Orn)-$NH_2$ | Method A |
| 57 | 70 | ((N—Me)G)-IC + SRS-((tBu)A)-PPI-(Pen) + IP-((N—Me)G)-((N—Me)G)-((N—Me)G)-$NH_2$ | Method A |
| 58 | 71 | ((N—Me)G)-IC + SRS-((tBu)A)-PPI-(Pen) + IP-((3-Carboxy)F)-$NH_2$ | Method A |
| 59 | 72 | Ac-G-((N—Me)I)-C + SRSLPPIC + IPD-OH | Method B |
| 60 | 73 | IIC + SRS-((tBu)A)-PPI-(Pen) + IPD-$NH_2$ | Method D |
| 61 | 74 | AIC + SRSLP-(Oic)-I-(Pen) + I—$NH_2$ | Method D |
| 62 | 75 | ((N—Me)G)-IC + SRSLP-(Oic)-I-(Pen) + IPD-(PEG2(13 atoms))-$NH_2$ | Method A |
| 63 | 76 | ((N—Me)G)-IC + SRSLP-(Oic)-I-(Pen) + IPD-(PEG5-CH2CO2H (18 atoms))-$NH_2$ | Method A |
| 64 | 77 | ((N—Me)G)-IC + SRSL-((1S,2S,5R)-3-azabicyclo[3.1.0]hexane-2-carboxylic acid)-PI-(Pen) + IP-$NH_2$ | Method A |
| 65 | 78 | LIC + SRS-((tBu)A)-PPI-((N—Me)C) + I—$NH_2$ | Method A |
| 66 | 79 | (Abu)-IC + SRS-((tBu)A)-PPIC + IPD-$NH_2$ | Method A |
| 67 | 80 | ((N—Me)G)-IC + SRSLP-(Oic)-I-(Pen) + IP-$NH_2$ (HCl salt) | Method A, F |
| 68 | 81 | LIC + SRS-((tBu)A)-PPI-(Pen) + IPD-$NH_2$ | Method D |
| 69 | 82 | (Nva)-IC + SRS-((tBu)A)-PPI-(Pen) + IPD-$NH_2$ | Method D |
| 70 | 83 | (Cit)-IC + SRS-((tBu)A)-PPI-(Pen) + IPD-OH | Method D |
| 71 | 84 | AIC + SRSLP-(Oic)-I-(Pen) + IP-$NH_2$ | Method D |
| 72 | 85 | ((N—Me)G)-IC + SRS-((tBu)A)-PPI-(Pen) + IP-(PEG2(13 atoms))-$NH_2$ | Method A |
| 73 | 86 | ((N—Me)G)-IC + SRS-((tBu)A)-PPI-(Pen) + IP-(PEG4-CH2CO2H (15 atoms))-$NH_2$ | Method A |
| 74 | 87 | ((N—Me)G)-IC + SRS-((tBu)A)-PPI-(Pen) + IP-(PEG8(28 atoms))-$NH_2$ | Method A |
| 75 | 88 | AIC + SRSLP-(Oic)-I-(Pen) + IPD-$NH_2$ | Method A, H |
| 76 | 89 | ((N—Me)G)-IC + SRSLP-(Oic)-I-(Pen) + IP-(PEG1(10 atoms))-$NH_2$ | Method A |
| 77 | 90 | (Orn)-IC + SRS-((tBu)A)-PPI-((N—Me)C) + IPD-$NH_2$ | Method A |
| 78 | 91 | (Orn)-IC + SRS-((tBu)A)-PPI-((N—Me)C) + IPD-$NH_2$ (HCl salt) | Method A, F |
| 79 | 92 | KIC + SRS-((tBu)A)-PPI-((N—Me)C) + I—$NH_2$ | Method A |
| 80 | 93 | ((N-Isopropyl-N-Methylamino)acetyl)-IC + SRS-((tBu)A)-PPI-(Pen) + IPD-$NH_2$ | Method K |
| 81 | 94 | WIC + SRS-((tBu)A)-PPI-(Pen) + IPD-$NH_2$ | Method D |
| 82 | 95 | (Azetidine-2-carboxylic acid)-IC + SRS-((tBu)A)-PPI-(Pen) + IPD-$NH_2$ | Method D |
| 83 | 96 | ((N—Me)G)-IC + SRSLP-(Oic)-I-(Pen) + IP-(PEG5-CH2CO2H (18 atoms))-$NH_2$ | Method A |
| 84 | 97 | ((N—Me)G)-IC + SRSLP-(Oic)-I-(Pen) + IPD-(PEG4(19 atoms))-$NH_2$ | Method A |
| 85 | 98 | ((N—Me)G)-IC + SRS-((tBu)A)-PPI-(Pen) + IP-(TTDS)-$NH_2$ | Method A |
| 86 | 99 | AIC + SRS-((tBu)A)-PPI-((N—Me)C) + IPD-OH | Method B |
| 87 | 100 | AIC + SRS-((tBu)A)-P-(Oic)-IC + IPD-$NH_2$ (HCl salt) | Method A, F |
| 88 | 101 | ((N—Me)G)-IC + SRSLP-(Oic)-I-(Pen) + IPD-OH | Method D |
| 89 | 102 | ((N—Me)G)-IC + SRS-((tBu)A)-PPI-(Pen) + IP-(PEG5(22 atoms))-$NH_2$ | Method A |
| 90 | 103 | ((N—Me)G)-IC + SRSL-((1S,2S,5R)-3-azabicyclo[3.1.0]hexane-2-carboxylic acid)-PI-(Pen) + IPE-$NH_2$ | Method A |
| 91 | 104 | (Orn)-IC + SRS-((tBu)A)-PPI-((N—Me)C) + I—$NH_2$ | Method A |
| 92 | 105 | (ACMP)-IC + SRS-((tBu)A)-PPI-((N—Me)C) + I—$NH_2$ | Method A |
| 93 | 106 | (3-Pal)-IC + SRS-((tBu)A)-PPI-(Pen) + IPD-$NH_2$ | Method D |
| 94 | 107 | (beta-2-thienylalanine)-IC + SRS-((tBu)A)-PPI-(Pen) + IPD-$NH_2$ | Method D |
| 95 | 108 | (Nle)-IC + SRS-((tBu)A)-PPI-(Pen) + IPD-$NH_2$ | Method D |
| 96 | 109 | aIC + SRSLP-(Oic)-I-(Pen) + I—OH | Method D |
| 97 | 110 | ((N—Me)G)-IC + SRSLP-(Oic)-I-(Pen) + IP-(PEG4(19 atoms))-$NH_2$ | Method A |
| 98 | 111 | AIC + SRS-((tBu)A)-PPI-(Pen) + IPD-$NH_2$ | Method A |
| 99 | 112 | AIC + SRS-((tBu)A)-P-(Oic)-IC + I—$NH_2$ | Method A |
| 100 | 113 | ((N—Me)G)-((N—Me)I)-C + SRS-((tBu)A)-PPI-(Pen) + I—$NH_2$ | Method D |
| 101 | 114 | ((N—Me)G)-IC + SRSLP-(Oic)-I-(Pen) + IPD-(PEG3(16 atoms))-$NH_2$ | Method A |
| 102 | 115 | AIC + SRSLP-(rel-(1R,3R,5R,6R)-6-(Trifluoromethyl)-2-azabicyclo[3.1.0]hexane-3-carboxylic acid)-IC + IPD-$NH_2$ | Method A |
| 103 | 116 | SIC + SRS-((tBu)A)-PPI-((N—Me)C) + I—$NH_2$ | Method A |
| 104 | 117 | AIC + SRS-((2-Bromo)F)-PPI-(Pen) + IPD-$NH_2$ | Method A |
| 105 | 118 | AIC + SRSLP-(Oic)-I-(Pen) + IPE-$NH_2$ | Method D |
| 106 | 119 | ((N—Me)A)-IC + SRSLP-(Oic)-I-(Pen) + IPD-$NH_2$ | Method A |
| 107 | 120 | ((N—Me)G)-IC + SRSLP-(Oic)-I-(Pen) + IPD-(PEG7(25 atoms))-$NH_2$ | Method A |
| 108 | 121 | AIC + SRS-((tBu)A)-P-(Oic)-I-(Pen) + IPD-$NH_2$ | Method A |
| 109 | 122 | ((N—Me)G)-IC + SRSLP-(Oic)-I-(Pen) + IP-$NH_2$ | Method A, H |
| 110 | 123 | ((N—Me)A)-IC + SRSLP-(Oic)-I-(Pen) + IP-OH | Method D |
| 111 | 124 | AIC + SRSLP-(Oic)-I-(Pen) + IP-OH | Method D |
| 112 | 125 | AIC + SRSLP-(Oic)-I-(Pen) + IPE-OH | Method D |
| 113 | 126 | ((N—Me)G)-IC + SRSLP-(Oic)-I-(Pen) + IP-(PEG4-CH2CO2H (15 atoms))-$NH_2$ | Method A |
| 114 | 127 | AIC + SRS-((tBu)A)-PP-((2S)-2-(Amino)-2-[(1S,3R)-3-hydroxycyclohexyl]acetic acid)-((N—Me)C) + IPD-$NH_2$ | Method A |
| 115 | 128 | (Hoo)-IC + SRS-((tBu)A)-PPI-(Pen) + IPD-$NH_2$ | Method D |
| 116 | 129 | (Gamma-Abu)-IC + SRS-((tBu)A)-PPI-(Pen) + IPD-$NH_2$ | Method D |
| 117 | 130 | AIC + SRSLP-(Oic)-I-(Pen) + I—OH | Method D |
| 118 | 131 | AIC + SRSLP-(Oic)-I-(Pen) + IPQ-OH | Method D |
| 119 | 132 | ((N—Me)G)-IC + SRSLP-(Oic)-I-(Pen) + IPD-(TTDS)-$NH_2$ | Method A |
| 120 | 133 | A-((N—Me)I)-C + SRS-((tBu)A)-P-(Oic)-I-((N—Me)C) + IPD-$NH_2$ | Method A |
| 121 | 134 | AIC + SRS-((t-Bu)A)-PPIC + ID-OH | Method B |
| 122 | 135 | AIC + SRSLP-(Oic)-I-(Pen) + IPE-$NH_2$ | Method D |
| 123 | 136 | AIC + SRSLP-(Oic)-I-((N—Me)C) + IP-$NH_2$ | Method A |

TABLE 14-continued

| Peptides according to the invention | | | |
|---|---|---|---|
| Example No | SEQ ID NO | Sequence | Method of Preparation |
| 124 | 137 | HIC + SRS-((tBu)A)-PPI-(Pen) + IPD-$NH_2$ | Method D |
| 125 | 138 | (Orn)-IC + SRS-((tBu)A)-PPI-(Pen) + IP-$NH_2$ | Method D |
| 126 | 139 | ((N—Me)A)-IC + SRS-((tBu)A)-PPI-(Pen) + IP-$NH_2$ | Method D |
| 127 | 140 | ((N—Me)G)-IC + SRSLP-(Oic)-I-(Pen) + IP-(PEG3(16 atoms))-$NH_2$ | Method A |
| 128 | 141 | AIC + SRS-((tBu)A)-P-((4-CF3)P)-I-((N—Me)C) + IPD-$NH_2$ | Method A |
| 129 | 142 | AIC + SRS-((tBu)A)-P-(Oic)-IC + I—$NH_2$ | Method A |
| 130 | 143 | (2-(Piperidin)acetyl)-IC + SRS-((tBu)A)-PPI-(Pen) + IPD-$NH_2$ | Method K |
| 131 | 144 | ((N—Me)A)-IC + SRSLP-(Oic)-I-(Pen) + IPE-$NH_2$ | Method D |
| 132 | 145 | AIC + SRSLP-(Oic)-I-(Pen) + IPQ-$NH_2$ | Method D |
| 133 | 146 | ((N—Me)G)-IC + SRSLP-(Oic)-I-(Pen) + IPD-(PEG4-CH2CO2H (15 atoms))-$NH_2$ | Method A |
| 134 | 147 | ((N—Me)A)-IC + SRSLP-(Oic)-I-(Pen) + I—OH | Method D |
| 135 | 148 | ((N—Me)A)-IC + SRSLP-(Oic)-I-(Pen) + IP-$NH_2$ | Method A |
| 136 | 149 | ((N—Me)G)-IC + SRSLP-(Oic)-I-(Pen) + IP-(TTDS)-$NH_2$ | Method A |
| 137 | 150 | (2-(Diethylamino)acetyl)-IC + SRS-((tBu)A)-PPI-(Pen) + IPD-$NH_2$ | Method K |
| 138 | 151 | AIC + SRSLP-(Oic)-I-(Pen) + IPE-OH | Method D |
| 139 | 152 | ((N—Me)A)-IC + SRSLP-(Oic)-I-(Pen) + IPQ-$NH_2$ | Method D |
| 140 | 153 | ((N—Me)G)-IC + SRSLP-(Oic)-I-(Pen) + IP-(PEG5(22 atoms))-$NH_2$ | Method A |
| 141 | 154 | ((N—Me)G)-IC + SRSLP-(Oic)-I-(Pen) + IPD-(PEG8(28 atoms))-$NH_2$ | Method A |
| 142 | 155 | AIC + SRSL-(Pro-D2)-(Oic)-I-(Pen) + IPD-OH | Deuterium |
| 143 | 156 | TIC + SRS-((tBu)A)-PPI-(Pen) + IPD-$NH_2$ | Method D |
| 144 | 157 | (Orn)-IC + SRS-((tBu)A)-PPI-(Pen) + IP-OH | Method D |
| 145 | 158 | ((N—Me)G)-IC + SRS-((tBu)A)-PPI-(Pen) + IP-(PEG4(19 atoms))-$NH_2$ | Method A |
| 146 | 159 | ((N—Me)G)-IC + SRSLP-(Oic)-I-(Pen) + IPD-(PEG5(22 atoms))-$NH_2$ | Method A |
| 147 | 160 | A-(Abu)-C + SRS-((tBu)A)-PPI-(Pen) + IPD-$NH_2$ | Method D |
| 148 | 161 | TIC + SRS-((tBu)A)-PPI-(Pen) + IPD-OH | Method D |
| 149 | 162 | ((N—Me)G)-((N—Me)I)-C + SRS-((tBu)A)-PPI-(Pen) + IP-$NH_2$ | Method D |
| 150 | 163 | ((N—Me)G)-IC + SRSLP-(Oic)-I-(Pen) + IP-(PEG7(25 atoms))-$NH_2$ | Method A |
| 151 | 164 | ((N—Me)G)-IC + SRSLP-(Oic)-I-(Pen) + IP-(PEG9(31 atoms))-$NH_2$ | Method A |
| 152 | 165 | ((N—Me)A)-IC + SRSLP-(Oic)-I-(Pen) + I—$NH_2$ | Method A |
| 153 | 166 | AIC + SRSLP-(Oic)-IC + IPD-OH | Method B |
| 154 | 167 | HIC + SRS-((tBu)A)-PPI-((N—Me)C) + I—$NH_2$ | Method A |
| 155 | 168 | AIC + SRS-((tBu)A)-P-(Oic)-I-((N—Me)C) + IPD-OH (HCl salt) | Method B, F |
| 156 | 169 | ((N—Me)G)-IC + SRS-((tBu)A)-PPI-(Pen) + IP-$NH_2$ | Method D |
| 157 | 170 | ((N—Me)G)-IC + SRS-((tBu)A)-PPI-(Pen) + IPP-$NH_2$ | Method D |
| 158 | 171 | AIC + SRS-((tBu)A)-P-((4-CF3)P)-IC + IPD-$NH_2$ | Method A, C |
| 159 | 172 | AIC + SRSLP-(Oic)-I-((N—Me)C) + I—$NH_2$ | Method A |
| 160 | 173 | aIC + SRSLP-(Oic)-I-(Pen) + I—$NH_2$ | Method D |
| 161 | 174 | ((N—Me)A)-IC + SRSLP-(Oic)-I-(Pen) + IPE-OH | Method D |
| 162 | 175 | ((N—Me)A)-IC + SRSLP-(Oic)-I-(Pen) + IPD-OH | Method D |
| 163 | 176 | (Dab)-IC + SRS-((tBu)A)-PPI-(Pen) + IP-$NH_2$ | Method A |
| 164 | 177 | ((N—Me)G)-IC + SRSLP-(Oic)-I-(Pen) + I-((5-Azaspiro[2.4]heptane-1-carboxylic acid)-OH | Method B |
| 165 | 178 | ((N—Me)G)-IC + SRSLP-(Oic)-I-(Pen) + IPD-$NH_2$ | Method A, D |
| 166 | 179 | (3-Amino-2,2-dimethylpropionic acid)-IC + SRS-((tBu)A)-PPI-(Pen) + IPD-$NH_2$ | Method A |
| 167 | 180 | ((N—Me)G)-IC + SRSLP-(Oic)-I-(Pen) + IP-OH | Method D |
| 168 | 181 | ((N—Me)G)-IC + SRSLP-(Oic)-I-(Pen) + IP-(PEG8(28 atoms))-$NH_2$ | Method A |
| 169 | 182 | (Abu)-IC + SRSLPP-(Chg)-C + IPD-$NH_2$ | Method A |
| 170 | 183 | AIC + SRSLPPI-(Pen) + IPD-$NH_2$ | Method A |
| 171 | 184 | AIC + SRS-((tBu)A)-PPI-(Pen) + IP-(Tranexamic)-$NH_2$ | Method A |
| 172 | 185 | aIC + SRS LP-(Oic)-I-(Pen) + IP-$NH_2$ | Method A |
| 173 | 186 | ((N—Me)G)-IC + SRSLP-(Oic)-I-(Pen) + IPE-$NH_2$ | Method D |
| 174 | 187 | ((N—Me)G)-IC + SRS-((tBu)A)-PPI-(Pen) + IP-(PEG3(16atoms))-$NH_2$ | Method A, D |
| 175 | 188 | ((N—Me)A)-IC + SRS-((tBu)A)-PPI-((N—Me)C) + IPD-$NH_2$ | Method A |
| 176 | 189 | AIC + SRS-((tBu)A)-P-((2S,3aS,6aS)-Octahydrocyclopenta[b]pyrrole-2-carboxylic acid)-I-((N—Me)C) + IPD-$NH_2$ | Method A |
| 177 | 190 | AIC + SRS-((tBu)A)-P-(Oic)-I-((N—Me)C) + I—OH | Method B |
| 178 | 191 | (2-Pal)-IC + SRS-((tBu)A)-PPI-(Pen) + IPD-$NH_2$ | Method D |
| 179 | 192 | ((N—Me)A)-IC + SRSLP-(Oic)-I-(Pen) + IPQ-OH | Method D |
| 180 | 193 | AIC + SRSLP-(Oic)-I-((N—Me)C) + IPD-OH | Method B |
| 181 | 194 | FIC + SRS-((tBu)A)-PPI-((N—Me)C) + I—$NH_2$ | Method A |
| 182 | 195 | YIC + SRS-((tBu)A)-PPI-((N—Me)C) + I—$NH_2$ | Method A |
| 183 | 196 | AIC + SRS-((tBu)A)-PP-((2S)-2-(Amino)-2-[(1S,3S)-3-hydroxycyclohexyl]acetic acid)-((N—Me)C) + IPD-$NH_2$ | Method A |
| 184 | 197 | ((2S)-2[(Amino)-2-(tetrahydro-2H-pyran-4-yl)]acetic acid)-IC + SRSLP-(Oic)-IC + I—OH | Method E |
| 185 | 198 | AIC + SRSLP-(Oic)-I-((N—Me)C) + IPD-$NH_2$ | Method A |
| 186 | 199 | (Orn)-IC + SRS-((tBu)A)-PPIC + I—$NH_2$ | Method A |
| 187 | 200 | (4-(Aminomethyl)benzoic acid)-IC + SRS-((tBu)A)-PPI-(Pen) + IPD-$NH_2$ | Method D |
| 188 | 201 | ((N—Me)G)-IC + SRSLP-(Oic)-I-(Pen) + I—OH | Method D |
| 189 | 202 | aIC + SRSLP-(Oic)-I-(Pen) + IPQ-OH | Method D |
| 190 | 203 | aIC + SRSLP-(Oic)-I-(Pen) + IP-OH | Method D |
| 191 | 204 | ((N—Me)G)-IC + SRSLP-(Oic)-I-(Pen) + IPE-$NH_2$ | Method D |
| 192 | 205 | aIC + SRSLP-(Oic)-I-(Pen) + IPE-$NH_2$ | Method D |
| 193 | 206 | ((N—Me)G)-IC + SRSLP-(Oic)-I-(Pen) + IP-((3-Carboxy)F)-$NH_2$ | Method A |
| 194 | 207 | ((N—Me)G)-IC + SRSLP-(Oic)-I-(Pen) + I-((5-Azaspiro[2.4]heptane-1-carboxylic acid)-OH | Method B |
| 195 | 208 | (Dap)-IC + SRS-((tBu)A)-PPI-(Pen) + I—$NH_2$ | Method D |
| 196 | 209 | ((N—Me)G)-IC + SRSLP-(Oic)-I-(Pen) + IPE-OH | Method D |

TABLE 14-continued

| Peptides according to the invention | | | |
|---|---|---|---|
| Example No | SEQ ID NO | Sequence | Method of Preparation |
| 197 | 210 | ((N—Me)G)-IC + SRS-((2S)-2-amino-3-(1-methylcyclopropyl)propanoic acid)-PPI-(Pen) + IP-$NH_2$ | Method A |
| 198 | 211 | AIC + SRS-((tBu)A)-P-(Oic)-I-((N—Me)C) + I—$NH_2$ | Method A |
| 199 | 212 | A-(Nva)-C + SRS-((tBu)A)-PPI-(Pen) + IPD-$NH_2$ | Method D |
| 200 | 213 | ((N—Me)G)-IC + SRSLP-(Oic)-I-(Pen) + IPQ-$NH_2$ | Method D |
| 201 | 214 | aIC + SRSLP-(Oic)-I-(Pen) + IPE-OH | Method D |
| 202 | 215 | aIC + SRSLP-(Oic)-I-(Pen) + IPQ-$NH_2$ | Method D |
| 203 | 216 | ((N—Me)G)-IC + SRSLP-(Oic)-I-(Pen) + IPQ-OH | Method D |
| 204 | 217 | (3-(Aminomethyl)benzoic acid)-IC + SRS-((tBu)A)-PPI-(Pen) + IP-$NH_2$ | Method D |
| 205 | 218 | G-((N—Me)I)-C + SRSLPPIC + IPD-$NH_2$ (HCl salt) | Method A, F |
| 206 | 219 | AIC + SRSLPP-(Chg)-(Pen) + IPD-$NH_2$ | Method D |
| 207 | 220 | ((N—Me)G)-IC + SRS-((tBu)A)-PPI-(Pen) + IP-(PEG1(10 atoms))-$NH_2$ | Method D |
| 208 | 221 | (ACBA)-IC + SRS-((tBu)A)-PPI-(Pen) + I—$NH_2$ | Method D |
| 209 | 222 | AIC + SRSLPP-((S)-2-amino-3-ethyl-pentanoic acid)-C + IPD-$NH_2$ | Method A |
| 210 | 223 | AIC + SRS-((tBu)A)-PPIC + IDD-OH | Method B |
| 211 | 224 | FIC + SRS-((tBu)A)-PPI-(Pen) + IPD-$NH_2$ | Method D |
| 212 | 225 | GIC + SRS-((tBu)A)-P-(Oic)-I-((N—Me)C) + IPD-$NH_2$ | Method A |
| 213 | 226 | ((N—Me)G)-GIC + SRS-((tBu)A)-PPI-(Pen) + IPD-$NH_2$ | Method D |
| 214 | 227 | ((N—Me)G)-IC + SRS-((S)-(trifluoromethyl)-L-cysteine)-PPI-(Pen) + IP-$NH_2$ | Method A |
| 215 | 228 | ((N—Me)G)-IC + SRSLP-(Oic)-I-(Pen) + IPE-OH | Method D |
| 216 | 229 | (Nva)-IC + SRSLPPIC + IPD-$NH_2$ | Method A |
| 217 | 230 | aIC + SRSLP-(Oic)-I-(Pen) + IPD-$NH_2$ | Method D |
| 218 | 231 | (4-Pal)-IC + SRS-((tBu)A)-PPI-(Pen) + IPD-$NH_2$ | Method D |
| 219 | 232 | (3-(Aminomethyl)benzoic acid)-IC + SRS-((tBu)A)-PP-(Pen) + IP-$NH_2$ | Method D |
| 220 | 233 | AIC + SRSLPPIC + (Cbg)-PD-$NH_2$ | Method A |
| 221 | 234 | (Tranexamic)-IC + SRS-((tBu)A)-PPI-(Pen) + IP-(PEG1(10 atoms))-$NH_2$ | Method A |
| 222 | 235 | AIC + SRSLPP-(Chg)-C + IPD-OH | Method B |
| 223 | 236 | WIC + SRS-((tBu)A)-PPI-((N—Me)C) + I—$NH_2$ | Method A |
| 224 | 237 | AIC + SRSLP-(Oic)-IC + IPD-$NH_2$ | Method A |
| 225 | 238 | (Orn)-IC + SRSLPP-(Chg)-C + IPD-OH | Method B |
| 226 | 239 | (2-(3-Pyridyl)acetic acid)-IC + SRS-((tBu)A)-PPI-(Pen) + IP-$NH_2$ | Method D |
| 227 | 240 | aIC + SRSLP-(Oic)-I-(Pen) + IPD-OH | Method D |
| 228 | 241 | ((N—Me)G)-IC + SRSLPPIC + IPD-$NH_2$ (HCl salt) | Method A, F |
| 229 | 242 | (2-(Cyclohexylamino)acetyl)-IC + SRS-((tBu)A)-PPI-(Pen) + IPD-$NH_2$ | Method K |
| 230 | 243 | (Abu)-IC + SRSLPPIC + IPD-$NH_2$ | Method A |
| 231 | 244 | AIC + SRS-((tBu)A)-P-(Oic)-I-((N—Me)C) + IPD-OH | Method B |
| 232 | 245 | ((N—Me)G)-IC + SRSLPPI-((N—Me)C) + IPD-OH | Method B, C |
| 233 | 246 | aIC + SRS-((S)-(trifluorornethyl)-L-cysteine)-PPI-(Pen) + IP-$NH_2$ | Method A |
| 234 | 247 | AIC + SRS-((tBu)A)-P-(Oic)-I—C + IPD-$NH_2$ | Method A |
| 235 | 248 | AIC + SRS-((2,5-Difluoro)F)-PPI-((N—Me)C) + IPD-$NH_2$ | Method A |
| 236 | 249 | (Orn)-IC + SRSLPPIC + I—NH2 | Method A |
| 237 | 250 | AIC + SRSL-(L-dehydroproline)-(Oic)-I-(Pen) + IPD-OH | Method C |
| 238 | 251 | AIC + SRS-((2-Chloro)F)-PPI-((N—Me)C) + IPD-$NH_2$ | Method A |
| 239 | 252 | (4-(Aminomethyl)benzoic acid)-IC + SRS-((tBu)A)-PPI-((N—Me)C) + IPD-$NH_2$ | Method A |
| 240 | 253 | (Orn)-IC + SRS-((S)-(trifluoromethyl)-L-cysteine)-PPI-(Pen) + IP-$NH_2$ | Method A |
| 241 | 254 | AIC + SRSL-((4aR,6aR,9S,11aS)-11-Oxo-2,3,4,4a,6a,7,8,9,11,11a-decahydro-1H-pyrido[3,2-e]pyrrolo[1,2-a]azepine-9-carboxylic acid)-IC + IPD-$NH_2$ | Method A |
| 242 | 255 | (trans-2-(3-(Amino)cyclohexyl)acetic acid)-IC + SRS-((tBu)A)-PPI-(Pen) + IP-$NH_2$ (diastereomer #2) | Method A |
| 243 | 256 | ((N,N-diMe)A)-IC + SRS-((tBu)A)-PPIC + IPD-$NH_2$ | Method A |
| 244 | 257 | ((N—Me)G)-IC + SRSLP-(Oic)-I-(Pen) + I—$NH_2$ | Method A, D |
| 245 | 258 | AIC + SRSLP-((6S)-5-Azaspiro[2.4]heptane-6-carboxylic acid)-IC + IPD-$NH_2$ | Method A |
| 246 | 259 | ((N—Me)G)-IC + SRS-((tBu)A)-PPIC + IPD-OH | Method B |
| 247 | 260 | AIC + SRSLPP-(Chg)-C + I—$NH_2$ | Method A |
| 248 | 261 | AIC + SRS-((4-Fluoro)L)-PPIC + IPD-NH2 | Method A |
| 249 | 262 | ((N—Me)G)-IC + SRSLP-(Oic)-I-(Pen) + IP-$NH_2$ (Acetate) | Method FA |
| 250 | 263 | ((N—Me)P)-IC + SRS-((tBu)A)-PPIC + IPD-$NH_2$ | Method A |
| 251 | 264 | (trans-2-(3-(Amino)cyclohexyl)acetic acid)-IC + SRS-((tBu)A)-PPI-(Pen) + IP-$NH_2$ (diastereomer #1) | Method A |
| 252 | 265 | AIC + SRSNPPI-(Pen) + IPD-$NH_2$ | Method D |
| 253 | 266 | ((N—Me)A)-IC + SRS-((tBu)A)-PPIC + IPD-$NH_2$ | Method A |
| 254 | 267 | AIC + SRSLPP-(Chg)-C + IPD-$NH_2$ | Method A |
| 255 | 268 | (Ahx)-IC + SRS-((tBu)A)-PPI-(Pen) + IP-$NH_2$ | Method D |
| 256 | 269 | IC + SRS-((tBu)A)-PP-I-((N—Me)C) + IPD-$NH_2$ | Method A |
| 257 | 270 | kIC + SRS-((tBu)A)-PPI-(Pen) + I—$NH_2$ | Method D |
| 258 | 271 | IC + SRS-((tBu)A)-PPI-(Pen) + IP-OH | Method D |
| 259 | 272 | (Piperidin-4-ylacetic acid)-IC + SRS-((tBu)A)-PPI-((N—Me)C) + I—$NH_2$ | Method K |
| 260 | 273 | A-((N—Me)I)-C + SRSLPPIC + IPD-$NH_2$ | Method A |
| 261 | 274 | G-((N—Me)I)-C + SRSLPPIC + IPD-$NH_2$ | Method A |
| 262 | 275 | AIC + SRSLPP-(Cpg)-C + IPD-$NH_2$ | Method A |
| 263 | 276 | (Gamma-Abu)-IC + SRS-((tBu)A)-PPI-((N—Me)C) + IPD-$NH_2$ | Method D |
| 264 | 277 | ((N—Me)G)-IC + SRSLP-(Oic)-I-(Pen) + IP-$NH_2$ (Tartrate) | Method FA |
| 265 | 278 | IC + SRSLP-(Oic)-I-(Pen) + IP-OH | Method D |
| 266 | 279 | ((N—Me)G)-((N—Me)G)-((N—Me)G)-((N—Me)G)-((N—Me)G)-IC + SRS-((tBu)A)-PPI-(Pen) + IP-$NH_2$ | Method A |
| 267 | 280 | ((N—Me)G)-IC + SRS-((2S)-2-amino-3-(1-methylcyclopropyl)propanoic acid)-P-(Oic)-I-(Pen) + IP-$NH_2$ | Method A |
| 268 | 281 | AIC + SRS-((tBu)A)-P-(Oic)-I-((N—Me)C) + IPD-$NH_2$ | Method A |
| 269 | 282 | (Tranexamic)-IC + SRS-((tBu)A)-PPI-(Pen) + IP-$NH_2$ | Method D |

TABLE 14-continued

| Peptides according to the invention | | | |
|---|---|---|---|
| Example No | SEQ ID NO | Sequence | Method of Preparation |
| 270 | 283 | AIC + SRSLP-(Oic)-(Chg)-C + IPD-$NH_2$ | Method A |
| 271 | 284 | ((N—Me)G)-IC + SRSLPPIC + IPD-$NH_2$ | Method A |
| 272 | 285 | ((2-Thiomorpholine)acetyl)-IC + SRS-((tBu)A)-PPI-(Pen) + IPD-$NH_2$ | Method K |
| 273 | 286 | (Cyclopropylacetic acid)-IC + SRS-((tBu)A)-PPI-(Pen) + IPD-$NH_2$ | Method D |
| 274 | 287 | (Cyclopropylacetic acid)-IC + SRS-((tBu)A)-PPI-((N—Me)C) + I—$NH_2$ | Method A |
| 275 | 288 | G-((N—Me)I)-C + SRSLPPIC + IPD-OH | Method B |
| 276 | 289 | G-((N—Me)I)-C + SRSLPPIC + IPd-OH | Method B |
| 277 | 290 | ((N—Me)G)-IC + SRSLPPIC + (allo-I)-PD-$NH_2$ | Method A |
| 278 | 291 | AIC + SR-(allo-T)-LPPIC + IPD-$NH_2$ | Method A |
| 279 | 292 | AIC + SRS-(3-(Trimethylsilyl)-L-alanine)-P-(Oic)-I-((N—Me)C) + IPD-$NH_2$ | Method A |
| 280 | 293 | Ac-IC + SRS-((tBu)A)-PPI-((N—Me)C) + I—$NH_2$ | Method D |
| 281 | 294 | ((N—Me)G)-IC + SRSLPPIC + IPD-OH | Method B, C |
| 282 | 295 | ((N—Me)G)-IC + SRSLPP-(Chg)-C + IPD-$NH_2$ | Method A |
| 283 | 296 | (2-(Morpholine)acetyl)-IC + SRS-((tBu)A)-PPI-(Pen) + IPD-$NH_2$ | Method K |
| 284 | 297 | (Cyclobutylacetic)-IC + SRS-((tBu)A)-PPI-(Pen) + IP-$NH_2$ | Method D |
| 285 | 298 | (Tranexamic)-IC + SRS-((tBu)A)-PPI-((N—Me)C) + I—$NH_2$ | Method A |
| 286 | 299 | GIC + SRSLPPIC + I-(Aib)-D-OH | Method B |
| 287 | 300 | ((N—Me)G)-IC + SRSLPPIC + I-((trans-4-Fluoro)P)-D-OH | Method B |
| 288 | 301 | ((N—Me)G)-IC + TRSLPPIC + IPD-OH | Method B |
| 289 | 302 | ((N—Me)G)-IC + SRSLPP-IC + I-((2-Me)P)-D-OH | Method B |
| 290 | 303 | Ac-IC + SRS-((tBu)A)-PPI-(Pen) + IPD-$NH_2$ | Method D |
| 291 | 304 | FIC + SRSLP-(Oic)-I-(Pen) + IP-$NH_2$ | Method C |
| 292 | 305 | AIC + SRSLP-(Oic)-IC + I—OH | Method E |
| 293 | 306 | IC + SRSLP-(Oic)-I-(Pen) + IPD-$NH_2$ | Method A, D |
| 294 | 307 | (Benzoic)-IC + SRS-((tBu)A)-PPI-(Pen) + IPD-$NH_2$ | Method D |
| 295 | 308 | (Phenylacetic acid)-IC + SRS-((tBu)A)-PPI-(Pen) + IPD-$NH_2$ | Method D |
| 296 | 309 | (Tetrahydro-2H-pyran-3-ylacetic acid)-IC + SRSLP-(Oic)-I-(Pen) + IP-$NH_2$ | Method A |
| 297 | 310 | ((N—Me)A)-IC + SRSLPPIC + IPD-$NH_2$ | Method A |
| 298 | 311 | ((N—Ph)G)-IC + SRS-((tBu)A)-PPI-((N—Me)C) + I—$NH_2$ | Method A |
| 299 | 312 | (Orn)-IC + SRS-((tBu)A)-PPI-((N—Me)C) + (2-[(1S,2S)-1-(Amino)-2-methylbutyl]-1,3-oxazole-4-carboxylic acid)-D-$NH_2$ | Method A |
| 300 | 313 | (2-Hydroxyacetyl)-IC + SRS-((tBu)A)-PPI-(Pen) + IPD-$NH_2$ | Method K |
| 301 | 314 | (Cyclobutanecarboxylic)-IC + SRS-((tBu)A)-PPI-((N—Me)C) + I—$NH_2$ | Method A |
| 302 | 315 | AIC + SRSLPP-((3-Chloro-Ph)G)-C + IPD-$NH_2$ | Method A |
| 303 | 316 | IC + SRS-((tBu)A)-PPI-(Pen) + IPP-$NH_2$ | Method D |
| 304 | 317 | (Tetrahydro-2H-pyran-3-ylacetic acid)-IC + SRSLP-(Oic)-I-(Pen) + IP-$NH_2$ | Method A |
| 305 | 318 | (Tetrahydropyranyl-4-acetic acid)-IC + SRS-((tBu)A)-PPI-((N—Me)C) + I—$NH_2$ | Method A |
| 306 | 319 | (beta-A)-IC + SRSLPPIC + IPD-OH | Method B |
| 307 | 320 | (2-(N-Methyl-N-cyclopropylamino)acetyl)-IC + SRS-((tBu)A)-PPI-(Pen) + IPD-$NH_2$ | Method K |
| 308 | 321 | (Cyclobutanecarboxylic)-IC + SRS-((tBu)A)-PPI-(Pen) + IPD-$NH_2$ | Method D |
| 309 | 322 | (Isovaleric)-IC + SRS-((tBu)A)-PPI-(Pen) + IPD-$NH_2$ | Method D |
| 310 | 323 | ((N—Me)G)-I-(Pen) + SRS-((tBu)A)-PPI-C + IP-$NH_2$ | Method D |
| 311 | 324 | ((N—Ph)G)-IC + SRS-((tBu)A)-PPI-(Pen) + IP-$NH_2$ | Method D |
| 312 | 325 | ((N—Me)G)-IC + SRSLPPIC + IPd-OH | Method B |
| 313 | 326 | ((N—Me)G)-IC + SRSLPPIC + I-(Abu)-D-OH | Method B |
| 314 | 327 | AIC + SRS-(AAD)-PP-I-((N—Me)C) + IPD-$NH_2$ | Method A |
| 315 | 328 | (Cyclopropanecarboxylic)-IC + SRS-((tBu)A)-PPI-(Pen) + IPD-$NH_2$ | Method D |
| 316 | 329 | IC + SRS-((tBu)A)-PPI-(Pen) + IP-$NH_2$ | Method D |
| 317 | 330 | ((N—Me)G)-IC + SRSLPPIC + ID-$NH_2$ | Method A |
| 318 | 331 | ((N—Me)G)-IC + SRSLPPIC + IPD-OH (HCl- Salt) | Method B, F |
| 319 | 332 | (Tranexamic)-IC + SRS-((tBu)A)-PPI-((N—Me)C) + IPD-$NH_2$ | Method A |
| 320 | 333 | (PEG1(10 atoms))-AIC + SRS-((tBu)A)-PPI-(Pen) + IPD-$NH_2$ | Method D |
| 321 | 334 | ((N—Me)G)-IC + SRS-(Cnba)-PPI-(Pen) + IPD-$NH_2$ | Method D |
| 322 | 335 | ((tBu)A)-GIC + SRSLP-(Oic)-I-(Pen) + IP-$NH_2$ | Method D |
| 323 | 336 | GIC + SRSLP-(Oic)-IC + IPD-OH | Method B |
| 324 | 337 | ((N—Me)G)-IC + SRSLP-((1R,3S,5R)-2-Azabicyclo[3.1.0]hexane-3-carboxylic acid)-IC + IPD-OH | Method B |
| 325 | 338 | ((N—Me)G)-IC + SRSLPPIC + (Phg)-PD-OH | Method B |
| 326 | 339 | AIC + SRSLP-(3,3-dimethyl-1,3-azasilolidine-5-carboxylic acid)-IC + IPD-$NH_2$ | Method A |
| 327 | 340 | (3-Methoxypropionic acid)-IC + SRS-((tBu)A)-PPI-(Pen) + IPD-$NH_2$ | Method D |
| 328 | 341 | ((1S,2S,4S)-Bicyclo[2.2.1]hept-5-en-2-ylacetic acid)-IC + SRS-((tBu)A)-PPI-(Pen) + IPD-$NH_2$ (unknown hydroxylation by-product) | Method D |
| 329 | 342 | ((N—Me)G)-IC + SRSLPPIC + I-((N—Me)G)-D-OH | Method B |
| 330 | 343 | ((3-Bromo)F)-IC + SRS-((tBu)A)-PPI-(Pen) + IPD-$NH_2$ | Method D |
| 331 | 344 | A-(allo-I)C + SRSLPPIC + IPD-$NH_2$ | Method A |
| 332 | 345 | (Ahx)-IC + SRS-((tBu)A)-PPI-((N—Me)C) + IPD-$NH_2$ | Method A |
| 333 | 346 | (tert-Butylacetic acid)-IC + SRS-((tBu)A)-PPI-((N—Me)C) + I—$NH_2$ | Method A |
| 334 | 347 | (Cyclopentanecarboxylic acid)-IC + SRS-((tBu)A)-PPI-(Pen) + IPD-$NH_2$ | Method A |
| 335 | 348 | ((tBu)A)-IC + SRSLP-(Oic)-I-(Pen) + IP-OH | Method D |
| 336 | 349 | IC + SRSLP-(Oic)-I-(Pen) + IP-$NH_2$ | Method D |
| 337 | 350 | AIC + SRS-((2S)-2-Amino-4,4,4-trifluorobutanoic acid)-PPI-((N—Me)C) + IPD-$NH_2$ | Method A |
| 338 | 351 | ((2S,3S)-2-[(3R)-3-Amino-2-oxopyrrolidin-1-yl]-3-niethylpentanoic acid)-C + SRSLPPIC + IAD-OH | Method B |
| 339 | 352 | ((N—Me)G)-IC + SRSLPPIC + IPE-OH | Method B |
| 340 | 353 | ((N—Me)G)-((N—Me)I)-C + SRSLPPIC + IPD-$NH_2$ | Method A |
| 341 | 354 | IC + SRSLP-(Oic)-I-(Pen) + I—$NH_2$ | Method D |
| 342 | 355 | (Tetrahydropyranyl-4-acetic acid)-IC + SRS-((tBu)A)-PPIC + IPD-$NH_2$ | Method D |

TABLE 14-continued

| Example No | SEQ ID NO | Sequence | Method of Preparation |
|---|---|---|---|
| | | Peptides according to the invention | |
| 343 | 356 | (Cyclopentylacetic)-IC + SRS-((tBu)A)-PPI-(Pen) + IPD-$NH_2$ | Method A |
| 344 | 357 | AIC + SRS-(2-Amino-7-(tert-butoxy)-7-oxoheptanoic acid)-PPI-(Pen) + IPD-$NH_2$ | Method A |
| 345 | 358 | IC + SRS-((tBu)A)-PPI-(Pen) + I—$NH_2$ | Method D |
| 346 | 359 | AIC + SRSLPP-(allo-I)-C + IPD-$NH_2$ | Method A |
| 347 | 360 | IC + SRSLP-(Oic)-I-(Pen) + IPD-OH | Method B, D |
| 348 | 361 | GIC + SRSLPPIC + I-(Hyp)-D-OH | Method B |
| 349 | 362 | ((N—Me)G)-IC + SRSLP-(Oic)-IC + IPD-OH | Method B |
| 350 | 363 | ((N,N-diMe)G)-IC + SRSLPPIC + IPD-$NH_2$ | Method A |
| 351 | 364 | (Cyclobutylacetic)-IC + SRS-((tBu)A)-PPI-(Pen) + IPD-$NH_2$ | Method D |
| 352 | 365 | (D-(+)Biotin)-(Ahx)-AIC + SRS-((tBu)A)-PPI-(Pen) + IPD-OH | Method D |
| 353 | 366 | (Cyclopropanecarboxylic)-IC + SRS-((tBu)A)-PPI-((N—Me)C) + I—$NH_2$ | Method A |
| 354 | 367 | ((N—Me)G)-IC + SRSL-((trans-4-Fluoro)P)-PIC + IPD-OH | Method B |
| 355 | 368 | AIC + SRSLP-((3S-OH)P)-IC + IPD-$NH_2$ | Method A |
| 356 | 369 | ((S)-3-Methylpentanoic acid)-IC + SRS-((tBu)A)-PPI-(Pen) + IPD-$NH_2$ | Method A |
| 357 | 370 | GIC + SRSL-(Morpholine-3-carboxylic)-PIC + IPD-OH | Method B |
| 358 | 371 | (Isovaleric)-IC + SRS-((tBu)A)-PPI-((N—Me)C) + I—$NH_2$ | Method D |
| 359 | 372 | (tert-Butylacetic acid)-IC + SRS-((tBu)A)-PPI-(Pen) + IP-$NH_2$ | Method D |
| 360 | 373 | (4-(3,5-Dimethyl-1,2-oxazol-4-yl)-L-phenylalanine)-IC + SRSLP-(Oic)-I-(Pen) + IP-$NH_2$ | Method C |
| 361 | 374 | ((N—Me)G)-PIC + SRS-((tBu)A)-PPI-(Pen) + IP-$NH_2$ | Method D |
| 362 | 375 | (4-(Aminomethyl)benzoic acid)-IC + SRSLPPI-((N—Me)C) + IPD-$NH_2$ | Method A |
| 363 | 376 | (D-(+)Biotin)-(Ahx)-AIC + SRS-((tBu)A)-PPI-(Pen) + IPD-$NH_2$ | Method D |
| 364 | 377 | (Tranexamic)-IC + SRSLPPI-((N—Me)C) + IPD-$NH_2$ | Method A |
| 365 | 378 | (4-Methylvaleric)-IC + SRS-((tBu)A)-PPI-(Pen) + IPD-NH2 | Method D |
| 366 | 379 | (5-Chlorothiophene-2-carboxylic acid)-IC + SRS-((tBu)A)-PPI-(Pen) + IPD-$NH_2$ | Method D |
| 367 | 380 | ((N—Me)G)-IC + SRSLPPIC + I-(Oic)-D-OH | Method B |
| 368 | 381 | IC + SRSLP-(Oic)-I-(Pen) + I—OH | Method D |
| 369 | 382 | IC + SRSLP-(Oic)-I-(Pen) + IPE-OH | Method D |
| 370 | 383 | fIC + SRSLP-(Oic)-I-(Pen) + IP-$NH_2$ | Method C |
| 371 | 384 | PPIC + SRS-((tBu)A)-PPI-(Pen) + I—$NH_2$ | Method D |
| 372 | 385 | IC + SRSLP-(Oic)-I-(Pen) + IPE-$NH_2$ | Method D |
| 373 | 386 | (Aib)-IC + SRSLPPIC + IPD-$NH_2$ | Method A |
| 374 | 387 | AIC + SRSLPPIC + (2-Methyl-D-alloisoleucine)-PD-$NH_2$ | Method A |
| 375 | 388 | (4-Methylvaleric)-IC + SRS-((tBu)A)-PPI-(Pen) + IPD-OH | Method D |
| 376 | 389 | ((N—Me)G)-IC + SRSLP-(Oic)-I-(Pen) + IP-$NH_2$ (Citrate) | Method FA |
| 377 | 390 | IC + SRSLP-(Oic)-I-(Pen) + IPQ-$NH_2$ | Method D |
| 378 | 391 | PPIC + SRS-((tBu)A)-PPI-(Pen) + IP-$NH_2$ | Method D |
| 379 | 392 | ((N—Me)I)-C + SRS-((tBu)A)-PPI-(Pen) + IP-$NH_2$ | Method D |
| 380 | 393 | GIC + SRSL-(Hyp)-PIC + IPD-OH | Method B |
| 381 | 394 | ((N—Me)G)-(Orn)-(Orn)-(Orn)-IC + SRS-((tBu)A)-PPI-(Pen) + IP-$NH_2$ | Method C |
| 382 | 395 | (Cyclobutylacetic)-IC + SRS-((tBu)A)-PPI-((N—Me)C) + I—$NH_2$ | Method A |
| 383 | 396 | (Ahx)-IC + SRSLP-(Oic)-IC + I—OH | Method E |
| 384 | 397 | GIC + SRS-((Trifluoro)l/L)-PPIC + IPD-OH | Method B |
| 385 | 398 | (Hydrocinnamic)-IC + SRS-((tBu)A)-PPI-(Pen) + IPD-$NH_2$ | Method D |
| 386 | 399 | ((N—Me)G)-IC + SRSLPPIC + IpD-OH | Method B |
| 387 | 400 | (Lactic)-IC + SRS-((tBu)A)-PPIC + IPD-$NH_2$ | Method A |
| 388 | 401 | IC + SRSLP-(Oic)-I-(Pen) + IPQ-OH | Method D |
| 389 | 402 | AIC + SRSLPP-(Cyclobutylglycine)-C + IPD-$NH_2$ | Method A |
| 390 | 403 | ((N—Me)G)-IC + SRSLP-((trans-4-Fluoro)P)-IC + IPD-OH | Method B |
| 391 | 404 | (Cyclohexylcarboxylic)-IC + SRS-((tBu)A)-PPI-((N—Me)C) + IPD-$NH_2$ | Method A |
| 392 | 405 | (2-Hydroxyisobutyric)-IC + SRS-((tBu)A)-PPIC + IPD-$NH_2$ | Method A |
| 393 | 406 | ((2S,3S)-2-[(3S)-2-oxopiperazin-1-yl]-3-methylpentanoic acid)-C + SRSLPPIC + IAD-OH | Method B |
| 394 | 407 | ((N—Me)G)-IC + SRSLPPIC + IPN-OH | Method B |
| 395 | 408 | (Adipic acid)-IC + SRS-((tBu)A)-PPI-(Pen) + IPD-$NH_2$ | Method D |
| 396 | 409 | (tert-Butylacetic acid)-IC + SRS-((tBu)A)-PPI-(Pen) + I—$NH_2$ | Method D |
| 397 | 410 | ((2S,3S)-2-[2-Oxopiperazin-1-yl]-3-methylpentanoic acid)-C + SRSLPPIC + IPD-OH | Method B |
| 398 | 411 | (Pivalic)-IC + SRS-((tBu)A)-PPI-((N—Me)C) + I—$NH_2$ | Method A |
| 399 | 412 | (Orn)-AIC + SRS-((tBu)A)-PPI-((N—Me)C) + IPD-$NH_2$ | Method A |
| 400 | 413 | (Fumaric acid)-IC + SRS-((tBu)A)-PPI-(Pen) + IPD-$NH_2$ | Method D |
| 401 | 414 | GIC + SRSL-(Pip)-PIC + ID-OH | Method B |
| 402 | 415 | ((N—Me)G)-I-(Pen) + SRSLPPIC + IPD-OH | Method B |
| 403 | 416 | AIC + S-((Me)R)-S-((tBu)A)-PPI-(Pen) + IPD-$NH_2$ | Method A |
| 404 | 417 | (Isobutyric acid)-IC + SRS-((tBu)A)-PPI-((N—Me)C) + IPD-$NH_2$ | Method A |
| 405 | 418 | ((N—Me)G)-(Orn)-(Orn)-(Orn)-IC + SRSLP-(Oic)-I-(Pen) + IP-$NH_2$ | Method C |
| 406 | 419 | (Hydrocinnamic)-IC + SRS-((tBu)A)-PPI-(Pen) + IPD-OH | Method D |
| 407 | 420 | (Suberic acid)-IC + SRS-((tBu)A)-PPI-(Pen) + IPD-$NH_2$ | Method D |
| 408 | 421 | (Cyclopentanecarboxylic acid)-IC + SRS-((tBu)A)-PPI-((N—Me)C) + I—$NH_2$ | Method A |
| 409 | 422 | (PEG1(10 atoms))-GIC + SRSLPPIC + IPD-OH | Method B |
| 410 | 423 | GIC + SRSLP-(Hyp)-IC + IPD-OH | Method B |
| 411 | 424 | AIC + SRS-((tBu)G)-PPI-C + IPD-$NH_2$ | Method A |
| 412 | 425 | ((N—Me)G)-IC + KRS-((tBu)A)-PPI-(Pen) + IP-$NH_2$ | Method D |
| 413 | 426 | ((N—Me)G)-IC + SR-(Dap)-LPPIC + IPD-OH | Method B |
| 414 | 427 | GIC + SRSLP-((cis-Fluoro)P)-IC + IPD-OH | Method B |
| 415 | 428 | (Cyclohexylacetic)-IC + SRS-((tBu)A)-PPI-(Pen) + IPD-$NH_2$ | Method A |
| 416 | 429 | GIC + SRS-((4-Bromo)F)-PPIC + IPD-OH | Method B |
| 417 | 430 | AIC + SRSLPPIC + ((2S,3S)-2-((Amino)methyl)-3-methylpentanoic acid)-PD-$NH_2$ | Method A |

TABLE 14-continued

| Peptides according to the invention | | | |
|---|---|---|---|
| Example No | SEQ ID NO | Sequence | Method of Preparation |
| 418 | 431 | AIC + SRSLP-(Oic)-I-(Pen) + IPN-OH | Method C |
| 419 | 432 | ((N—Me)G)-IC + SRSLP-(Oic)-I-(Pen) + I-((5-Azaspiro[2.4]heptane-1-carboxylic acid)-OH | Method B |
| 420 | 433 | AIC + SRSLP-(Oic)-I-(Pen) + IPD-$NH_2$ (Acetate) | Method FA |
| 421 | 434 | (Tranexamic)-IC + SRS-((tBu)A)-PPI-(Pen) + IP-(PEG2(13 atoms))-$NH_2$ | Method A |
| 422 | 435 | (Tranexamic)-IC + SRS-((tBu)A)-PPI-(Pen) + IP-(PEG4-CH2CO2H (15 atoms))-$NH_2$ | Method A |
| 423 | 436 | (Tranexamic)-IC + SRS-((tBu)A)-PPI-(Pen) + IP-(PEG3(16 atoms))-$NH_2$ | Method A |
| 424 | 437 | (Tranexamic)-IC + SRS-((tBu)A)-PPI-(Pen) + IP-(PEG5-CH2CO2H (18 atoms))-$NH_2$ | Method A |
| 425 | 438 | (Tranexamic)-IC + SRS-((tBu)A)-PPI-(Pen) + IP-(PEG5(22 atoms))-$NH_2$ | Method A |
| 426 | 439 | (Tranexamic)-IC + SRS-((tBu)A)-PPI-(Pen) + IP-(PEG7(25 atoms))-$NH_2$ | Method A |
| 427 | 440 | (Tranexamic)-IC + SRS-((tBu)A)-PPI-(Pen) + IP-(PEG8(28 atoms))-$NH_2$ | Method A |
| 428 | 441 | ((N—Me)G)-IC + SRSLP-(Oic)-I-(Pen) + IPD-(PEG9(31 atoms))-$NH_2$ | Method A |
| 429 | 442 | (Tranexamic)-IC + SRS-((tBu)A)-PPI-(Pen) + IP-(TTDS)-$NH_2$ | Method A |
| 430 | 443 | ((N—Me)G)-IC + SRS-((tBu)A)-PPI-(Pen) + IP-(Orn)-(Orn)-(Orn)-$NH_2$ | Method A |
| 431 | 444 | AIC + SRSLP-(Oic)-I-(Pen) + IPD-OH (sodium salt) | Method B, L |
| 432 | 445 | AIC + SRSLP-(Oic)-I-(Pen) + IPD-OH (choline-salt) | Method B, L |
| 433 | 446 | ((N—Me)G)-IC + SRS-((tBu)A)-PPI-(Pen) + IPD-((N—Me)G)-((N—Me)G)-((N—Me)G)-$NH_2$ | Method A |
| 434 | 447 | (ODD)-AIC + SRSLP-(Oic)-I-(Pen) + IPD-OH | Method B |
| 435 | 448 | (Tranexamic)-IC + SRS-((tBu)A)-PPI-(Pen) + IP-(PEG4(19 atoms))-$NH_2$ | Method A |
| 436 | 449 | ((N—Me)G)-IC + SRSLP-(Oic)-I-(Pen) + IPP-((2S)-3-(Triazol-1-yl)-2-(amino)propanoic acid)-$NH_2$ | Method A |
| 437 | 450 | ((N—Me)G)-IC + SRSLP-(Oic)-I-(Pen) + IP-((2S)-3-(Triazol-1-yl)-2-(amino)propanoic acid)-$NH_2$ | Method A |
| 438 | 451 | ((N—Me)G)-IC + SRSLP-(Oic)-I-(Pen) + IP-((5-Azaspiro[2.4]heptane-1-carboxylic acid)-OH | Method B |
| 439 | 452 | ((N—Me)G)-IC + SRS-((tBu)A)-P-((6S)-5-Azaspiro[2.4]heptane-6-carboxylic acid)-I-(Pen) + IP-$NH_2$ | Method A |
| 440 | 453 | ((N—Me)G)-IC + SRS-((2S)-3-(2,3-difluorophenyl)-2-aminopropanoic acid)-PPI-(Pen) + IP-$NH_2$ | Method A |
| 441 | 454 | ((N—Me)G)-IC + SRS-((2S)-3-(2,3-difluorophenyl)-2-aminopropanoic acid)-P-(Oic)-I-(Pen) + IP-$NH_2$ | Method A |
| 442 | 455 | ((N—Me)G)-IC + SRS-((tBu)A)-P-((1S,2S,5R)-3-azabicyclo[3.1.0]hexane-2-carboxylic acid)-I-(Pen) + IPD-OH | Method C |
| 443 | 456 | ((N—Me)A)-IC + SRS-((tBu)A)-P-((3R,6R)-1,1-Difluoro-5-azaspiro[2.4]heptane-6-carboxylic acid (enantiomer 1))-I-(Pen) + IP-$NH_2$ | Method A |
| 444 | 457 | ((3-Me)H)-IC + SRSLP-(Oic)-I-(Pen) + IP-$NH_2$ | Method A |
| 445 | 458 | ((N—Me)A)-IC + SRS-((tBu)A)-P-((3R,6R)-1,1-Difluoro-5-azaspiro[2.4]heptane-6-carboxylic acid (enantiomer 2))-I-(Pen) + IP-$NH_2$ | Method A |
| 446 | 459 | ((N—Me)G)-IC + SRSLP-(Oic)-I-(Pen) + IP-(Ida)-OH | Method C |
| 447 | 460 | ((N—Me)G)-IC + SRS-((tBu)A)-PPI-(Pen) + IP-((1-Bn)H)-OH | Method C |
| 448 | 461 | ((N—Me)G)-IC + RRS-((tBu)A)-PP-(Nva)-(Pen) + IP-$NH_2$ | Method D |
| 449 | 462 | ((N—Me)G)-IC + SRSLP-(Oic)-I-(Pen) + IP-((1R,3S)-3-(Amino)cyclopentanecarboxylic acid)-OH | Method B |
| 450 | 463 | ((N—Me)G)-IC + SRSLP-(Oic)-I-(Pen) + IP-((R)-4-Amino-6-methylheptanoic acid)-OH | Method B |
| 451 | 464 | ((N—Me)G)-IC + SRSLP-(Oic)-I-(Pen) + IP-((S)-(1-Piperidin-3-yl)-acetic acid)-OH | Method B |
| 452 | 465 | ((N—Me)G)-IC + SRSLP-(Oic)-I-(Pen) + IP-((1S,3R)-3-(Amino)cyclopentanecarboxylic acid)-OH | Method B |
| 453 | 466 | ((N—Me)G)-IC + SRSLP-(Oic)-I-(Pen) + IP-((S)-3-(1-Pyrrolidine-2-yl)-propionic acid)-OH | Method B |
| 454 | 467 | ((N—Me)G)-IC + SRSLP-(Oic)-I-(Pen) + IPN-OH | Method B, C |
| 455 | 468 | ((N—Me)G)-IC + SRSLP-(Oic)-I-(Pen) + IP-(beta-homo-P)-OH | Method B |
| 456 | 469 | ((N—Me)G)-IC + SRSLP-(Oic)-I-(Pen) + IP-((S)-Pyrrolidine-3-carboxylic acid)-OH | Method B |
| 457 | 470 | ((2,4-dioxoimidazolidin-1-yl)acetic acid)-IC + SRSLP-(Oic)-I-(Pen) + IPD-OH | Method B |
| 458 | 471 | AIC + SRSLP-(Oic)-I-(Pen) + IP-(*Dap)-OH | Method C |
| 459 | 472 | ((R)-Piperidine-3-carboxylic acid)-IC + SRSLP-(Oic)-I-(Pen) + I—OH | Method C |
| 460 | 473 | ((S)-Piperidine-3-carboxylic acid)-IC + SRSLP-(Oic)-I-(Pen) + I—OH | Method C |
| 461 | 474 | (8-aminocubane-1-carboxylic acid)-IC + SRS-((tBu)A)-PPI-(Pen) + IPD-OH | Method B |
| 462 | 475 | ((N—Me)A)-IC + SRSLP-(Oic)-I-(Pen) + IP-((N-Benzyl)D)-$NH_2$ | Method I |
| 463 | 476 | ((N—Me)G)-IC + SRSLP-(Oic)-I-(Pen) + IPDK-OH | Method C |
| 464 | 477 | ((N—Me)G)-IC + SRSLP-(Oic)-I-(Pen) + IPGD-OH | Method C |
| 465 | 478 | ((N—Me)G)-IC + SRSLP-(Oic)-I-(Pen) + IPD-(Ahx)-OH | Method C |
| 466 | 479 | ((N—Me)G)-IC + SRSLP-(Oic)-I-(Pen) + IPDD-OH | Method C |
| 467 | 480 | ((N—Me)G)-IC + SRSLP-(Oic)-I-(Pen) + IP-(*Dap)-OH | Method J |
| 468 | 481 | ((N—Me)G)-IC + SRSLP-(Oic)-I-(Pen) + IP-(PEG2(13 atoms))-OH | Method C |
| 469 | 482 | (Orn)-IC + SRSLP-(Oic)-I-(Pen) + IPD-OH | Method C |
| 470 | 483 | ((N—Me)G)-IC + SRSLP-(Oic)-I-(Pen) + IP-(PEG4-CH2CO2H (15 atoms))-OH | Method C |
| 471 | 484 | ((N—Me)G)-IC + SRSLP-(Oic)-I-(Pen) + IPD-(PEG4-CH2CO2H (15 atoms))-OH | Method C |
| 472 | 485 | ((N—Me)G)-IC + SRSLP-(Oic)-I-(Pen) + IP-(PEG5(22 atoms))-OH | Method C |
| 473 | 486 | AIC + SRSLP-(Oic)-I-(Pen) + IPD-OH (Acetate) | Method FA |
| 474 | 487 | ((N—Me))-GIC + SRSLP-(Oic)-I-(Pen) + I-((S)-4-Piperazine-2-carboxylic acid)-OH | Method B |
| 475 | 488 | (Piperidin-4-ylacetic acid)-IC + SRS-((tBu)A)-PPIC + IPD-OH | Method C |
| 476 | 489 | ((N—Me)G)-IC + SRSLP-(Oic)-I-(Pen) + IP-(4-Aminomethylphenylacetic acid)-OH | Method C |
| 477 | 490 | ((N—Me)G)-IC + SRSLP-(Oic)-I-(Pen) + IP-(3-Aminomethylphenylacetic acid)-OH | Method C |
| 478 | 491 | aIC + SRSLP-(Oic)-I-(Pen)- + IP-(3-Aminomethylphenylacetic acid)-OH | Method C |
| 479 | 492 | (Orn)-IC + SRS-((tBu)A)-PPI-((N—Me)C) + IPD-OH | Method C |
| 480 | 493 | (beta-P)-IC + SRS-((tBu)A)-PPI-(Pen) + IPD-OH | Method C |
| 481 | 494 | (beta-p)-IC + SRS-((tBu)A)-PPI-(Pen) + IPD-OH | Method C |
| 482 | 495 | ((N—Me)G)-IC + SRS-((tBu)A)-PPI-(Pen) + IP-((3-Carboxy)F)-OH | Method C |
| 483 | 496 | ((N—Me)G)-IC + SRSLP-(Oic)-I-(Pen) + IP-((3-Carboxy)F)-OH | Method C |
| 484 | 497 | ((N—Me)G)-IC + SRSLP-(Oic)-I-(Pen) + IPD-(PEG2(13 atoms))-OH | Method C |
| 485 | 498 | ((N—Me)G)-IC + SRS-((tBu)A)-PPI-(Pen) + IP-(PEG3(16atoms))-OH | Method C |
| 486 | 499 | ((N—Me)G)-IC + SRS-((tBu)A)-PPI-(Pen) + IP-(Orn)-D-OH | Method C |
| 487 | 500 | ((N—Me)G)-IC + SRSLP-(Oic)-I-(Pen) + IPR-OH | Method C |
| 488 | 501 | ((R)-Piperidine-3-Carboxylic Acid)-IC + SRSLP-(Oic)-I-(Pen) + IPD-OH | Method C |
| 489 | 502 | ((S)-Piperidine-3-Carboxylic Acid)-IC + SRSLP-(Oic)-I-(Pen) + IPD-OH | Method C |

TABLE 14-continued

| Peptides according to the invention | | | |
|---|---|---|---|
| Example No | SEQ ID NO | Sequence | Method of Preparation |
| 490 | 503 | (4-Carboxybenzoic acid)-GIC + SRSLP-(Oic)-I-(Pen) + IPD-OH | Method C |
| 491 | 504 | (3-Carboxybenzoic acid)-GIC + SRSLP-(Oic)-I-(Pen) + IPD-OH | Method C |
| 492 | 505 | ((N—Me)G)-IC + SRSLP-(Oic)-I-(Pen) + IPT-OH | Method C |
| 493 | 506 | ((N—Me)G)-IC + SRSLP-(Oic)-I-(Pen) + IPY-OH | Method C |
| 494 | 507 | ((N—Me)G)-IC + SRSLP-(Oic)-I-(Pen) + IPDA-OH | Method C |
| 495 | 508 | ((N—Me)G)-IC + SRSLP-(Oic)-I-(Pen) + IPGd-OH | Method C |
| 496 | 509 | ((N—Me)G)-IC + SRS-((tBu)A)-PPI-(Pen) + IP-(PEG5-CH2CO2H(18 atoms))-OH | Method C |
| 497 | 510 | ((N—Me)G)-IC + SRS-((tBu)A)-PPI-(Pen) + IP-((N—Me)G)-((N—Me)G)-((N—Me)G)-OH | Method C |
| 498 | 511 | ((N—Me)G)-IC + SRS-((tBu)A)-PPI-(Pen) + IP-(PEG1(10 atoms))-OH | Method C |
| 499 | 512 | AIC + S-(Arg(13C6,15N4))-SLP-(Oic)-I-(Pen) + IPD-OH (HCl Salt) | Method B, F |
| 500 | 513 | ((N—Me)G)IC + SRSLP-(Oic)-I-(Pen) + IPD-(PEG1(10 atoms))-OH | Method C |
| 501 | 514 | ((N—Me)G)-IC + SRS-((tBu)A)-PPI-(Pen) + IPD-(PEG3(16atoms))-OH | Method C |
| 502 | 515 | (Pyrrolidineacetyl)-IC + SRS-((tBu)A)-PPI-(Pen) + IPD-OH | Method C |
| 503 | 516 | ((N—Me)G)-IC + SRS-((tBu)A)-PPI-(Pen) + IP-(PEG9(31 atoms))-OH | Method C |
| 504 | 517 | ((N—Me)G)-IC + SRS-((tBu)A)-PPI-(Pen) + IPD-(PEG9(31 atoms))-OH | Method C |
| 505 | 518 | ((N—Me)G)-IC + SRS-((tBu)A)-PPI-(Pen) + IP-(PEG8(28 atoms))-OH | Method C |
| 506 | 519 | ((N—Me)G)-IC + SRS-((tBu)A)-PPI-(Pen) + IP-(PEG4-CH2CO2H(15 atoms))-OH | Method C |
| 507 | 520 | AIC + SRSL-((1S,2S,5R)-3-Azabicyclo[3.1.0]hexane-2-carboxylic acid)-PI-(Pen) + IPD-OH | Method B |
| 508 | 521 | ((N—Me)G)-IC + SRS-(2-Amino-5,5,5-trifluoro-4-methyl-pentanoic acid)-PPI-(Pen) + IPD-OH | Method B |
| 509 | 522 | ((N—Me)G)-IC + SRS-((2S)-2-Amino-5-methyl-hexanoic acid)-PPI-(Pen) + IPD-OH | Method B |
| 510 | 523 | ((2S)-2-(morpholin-4-yl)propanoic acid)-IC + SRSLP-(Oic)-I-(Pen) + IPD-OH | Method B |
| 511 | 524 | AIC + SRSLPP-((3-Chloro-Ph)G)-C + IPD-OH | Method C |
| 512 | 525 | (ODD)-AIC + SRSLP-(Oic)-I-(Pen) + IPD-(Orn)-OH | Method C |
| 513 | 526 | (ODD)-(Orn)-IC + SRSLP-(Oic)-I-(Pen) + IPD-OH | Method C |
| 514 | 527 | ((N—Me)G)-IC + SRS-((tBu)A)-PPI-(Pen) + IP-(PEG2(13 atoms))-OH | Method C |
| 515 | 528 | ((N—Me)G)-IC + SRSLP-(Oic)-I-(Pen) + IP-(AAD)-OH | Method C |
| 516 | 529 | AIC + SRSLP-((4-CF3)P)-IC + IPD-OH | Method C |
| 517 | 530 | AIC + SRS-((tBu)A)-P-((4-CF3)P)-I-(Pen) + IPD-OH | Method C |
| 518 | 531 | ((N—Me)G)-FC + TRK-((tBu)A)-(Pen) + YPD-OH | Method C |
| 519 | 532 | ((N—Me)G)-IC + SRS-((2,5-Difluoro)F)-PPI-(Pen) + IPD-OH | Method C |
| 520 | 533 | ((N—Me)G)-IC + SRS-((2,5-Difluoro)F)-PPI-(Pen) + IPe-OH | Method C |
| 521 | 534 | ((N—Me)G)-IC + SRS-((2,5-Difluoro)F)-PPI-(Pen) + IPDd-OH | Method C |
| 522 | 535 | aIC + SRS-((tBu)A)-P-((6S)-5-Azaspiro[2.4]heptane-6-carboxylic acid)-I-(Pen) + IPD-OH | Method C |
| 523 | 536 | aIC + SRS-((tBu)A)-P-((6S)-5-Azaspiro[2.4]heptane-6-carboxylic acid)-I-(Pen) + IPe-OH | Method C |
| 524 | 537 | AIC + SRS-((tBu)A)-P-((4-CF3)P)-IC + IPD-OH | Method C |
| 525 | 538 | ((N—Me)G)-IC + SRS-((2S)-2-amino-3-(1-methylcyclopropyl)propanoic acid)-P-(Oic)-I-(Pen) + IPD-OH | Method B |
| 526 | 539 | ((N—Me)G)-IC + SRS-((tBu)A)-P-((1S,2S,5R)-3-azabicyclo[3.1.0]hexane-2-carboxylic acid)-I-(Pen) + IPD-OH | Method C |
| 527 | 540 | ((N—Me)G)-IC + SRSLP-(Oic)-I-(Pen) + IP-(Freidinger's Lactam)-OH | Method C |
| 528 | 541 | pIC + SRSLP-(Oic)-I-(Pen) + IP-(Ida)-OH (HCl salt) | Method C |
| 529 | 542 | (Orn)-IC + SRS-((2R)-2-amino-3-(trifluoromethylsulfanyl)propanoic acid)-PPI-(Pen) + IPD-OH | Method C |
| 530 | 543 | ((N—Me)G)-IC + SRSLP-(Oic)-I-(Pen) + IP-((R)-Pyrrolidine-3-acetic acid)-OH | Method C |
| 531 | 544 | ((N—Me)G)-IC + SRS-((tBu)A)-P-((3S)-2-azaspiro[4.4]nonane-3-carboxylic acid)-I-(Pen) + IPD-OH | Method C |
| 532 | 545 | ((N—Me)G)-IC + SRSLP-(Oic)-I-(Pen) + IP-((R)-Pyrrolidine-3-carboxylic acid)-OH | Method C |

TABLE 15

| Analytical data for the reference peptides | | | | | | | | |
|---|---|---|---|---|---|---|---|---|
| Reference No | Retention time (min) | LC-MS Method 1 | Purity (%) | Exact Mass Calcd (g/mol) | Exact Mass Found (g/mol) | Ionization | LC-MS Purity (%) Method W2 | LC-MS Purity (%) Method W3 |
| 1 | 8.68 | Method 1 | >99 | 1467.7214 | 1467.7344 | [M + 2H]2+ | | |
| 2 | 8.75 | Method 1 | >99 | 1467.7200 | 1467.7400 | [M + 2H]2+ | | |
| 3 | 4.37 | Method 2 | 94.79 | 1466.7374 | 1466.7408 | [M + 2H]2+ | | |
| A | 4.66 | Method 6 | >99 | 1481.7371 | 1481.7600 | [M + 2H]2+ | | |
| B | 8.59 | Method 1 | >99 | 1480.7500 | 1480.7600 | [M + 2H]2+ | | |
| C | 8.88 | Method 1 | 95.00 | 1480.7530 | 1480.7632 | [M + 2H]2+ | | |

TABLE 16

| Analytical data for the peptides prepared according to the invention | | | | | | | | | |
|---|---|---|---|---|---|---|---|---|---|
| Example No | Retention time (min) | LC-MS Method 1 | Purity (%) | Exact Mass Calcd (g/mol) | Exact Mass Found (g/mol) | Ionization | LC-MS Purity (%) Method W2 | LC-MS Purity (%) Method W3 |
| 4 | 7.98 | Method 4 | 93.11 | 1721.9208 | 1721.9344 | [M + 2H]2+ | | |
| 5 | 8.61 | Method 4 | 96.38 | 1563.8153 | 1563.8286 | [M + 2H]2+ | | |
| 6 | 9.69 | Method 1 | >99 | 1324.7359 | 1325.7380 | [M + H]+ | 98.49 | 98.16 |
| 7 | 7.92 | Method 4 | 96.55 | 1650.9201 | 1650.9384 | [M + 2H]2+ | | |
| 8 | 6.90 | Method 4 | 100 | 1433.7887 | 1433.807 | [M + 2H]2+ | | |
| 9 | 7.78 | Method 4 | 97.50 | 1548.8156 | 1548.8322 | [M + 2H]2+ | 93.70 | 95.10 |
| 10 | 9.22 | Method 1 | 82.28 | 1536.8156 | 1536.8320 | [M + 2H]2+ | 91.50 | 90.10 |
| 11 | 9.26 | Method 1 | 93.15 | 1522.8000 | 1522.8258 | [M + 2H]2+ | | |
| 12 | 9.41 | Method 1 | >99 | 1523.7840 | 1523.8060 | [M + 2H]2+ | | |
| 13 | 8.52 | Method 4 | >99 | 1563.8153 | 1563.8346 | [M + 2H]2+ | 98.68 | 97.99 |
| 14 | 9.97 | Method 1 | 99.07 | 1577.8310 | 1577.8558 | [M + 2H]2+ | | |
| 15 | 9.33 | Method 1 | 92.48 | 1562.8313 | 1562.8476 | [M + 2H]2+ | | |
| 16 | 7.67 | Method 4 | 95.58 | 1654.915 | 1654.9296 | [M + 2H]2+ | | |
| 17 | 9.21 | Method 1 | 95.00 | 1534.8000 | 1534.8246 | [M + 2H]2+ | | |
| 18 | 8.8 | Method 1 | >99 | 1566.8262 | 1566.8502 | [M + 2H]2+ | | |
| 19 | 8.94 | Method 1 | 90.00 | 1593.8483 | 1593.8616 | [M + 2H]2+ | | |
| 20 | 9.71 | Method 1 | 95.90 | 1478.7374 | 1478.7458 | [M + 2H]2+ | | |
| 21 | 9.3 | Method 1 | 95.59 | 1537.7997 | 1536.8342 | [M + 2H]2+ | 97.00 | 95.80 |
| 22 | 9.14 | Method 1 | 94.83 | 1521.8160 | 1521.8338 | [M + 2H]2+ | 96.30 | 95.60 |
| 23 | 8.09 | Method 4 | >99 | 1475.8356 | 1475.8488 | [M + 2H]2+ | 88.40 | 89.20 |
| 24 | 9.21 | Method 1 | 92.48 | 1536.8156 | 1536.8304 | [M + 2H]2+ | 97.40 | 93.20 |
| 25 | 9.48 | Method 1 | 98.21 | 1296.7046 | 1297.7152 | [M + H]+ | | |
| 26 | 9.72 | Method 1 | >99 | 1562.8313 | 1562.8562 | [M + 2H]2+ | | |
| 27 | 4.00 | Method 3 | >99 | 1562.8313 | 1562.8518 | [M + 2H]2+ | | |
| 28 | 9.87 | Method 1 | >99 | 1338.7516 | 1338.7530 | [M + H]+ | 98.77 | 97.66 |
| 29 | 8.56 | Method 4 | >99 | 1563.8153 | 1563.82 | [M + 2H]2+ | | |
| 30 | 4.71 | Method 2 | >99 | 1508.7843 | 1508.7874 | [M + 2H]2+ | | |
| 31 | 9.64 | Method 1 | >99 | 1549.7997 | 1549.8095 | [M + H]+ | | |
| 32 | 9.2 | Method 1 | 86.00 | 1548.8156 | 1548.8232 | [M + 2H]2+ | 92.70 | 90.10 |
| 33 | 7.28 | Method 4 | 100 | 1459.8043 | 1459.8218 | [M + 2H]2+ | | |
| 34 | 8.08 | Method 4 | 100 | 1786.9937 | 1788.024 | [M + 2H]2+ | | |
| 35 | 8.87 | Method 1 | 95.00 | 1565.8422 | 1565.8538 | [M + 2H]2+ | | |
| 36 | 9.29 | Method 1 | 95.00 | 1535.7840 | 1535.8108 | [M + 2H]2+ | | |
| 37 | 9.14 | Method 1 | >99 | 1282.6890 | 1282.7012 | [M + 2H]2+ | | |
| 38 | 8.9 | Method 1 | >99 | 1381.7686 | 1381.7800 | [M + H]+ | | |
| 39 | 7.70 | Method 4 | 97.08 | 1566.8626 | 1566.8794 | [M + 2H]2+ | | |
| 40 | 9.01 | Method 1 | 83.81 | 1608.8480 | 1608.8640 | [M + 2H]2+ | 96.30 | 92.40 |
| 41 | 9.64 | Method 1 | 95.00 | 1534.8000 | 1534.9346 | [M + 2H]2+ | | |
| 42 | 7.23 | Method 4 | >99 | 1546.8225 | 1546.8388 | [M + 2H]2+ | 96.40 | 96.10 |
| 43 | 7.9 | Method 4 | >99 | 1378.7829 | 1378.8 | [M + 2H]2+ | 96.27 | 97.01 |
| 44 | 8.10 | Method 4 | 96.58 | 1875.0461 | 1876.06 | [1M + 2H]2+ | | |
| 45 | 9.49 | Method 1 | 88.00 | 1548.8156 | 1548.8380 | [M + 2H]2+ | | |
| 46 | 9.59 | Method 1 | 91.55 | 1548.8156 | 1548.8286 | [M + 2H]2+ | | |
| 47 | 9.24 | Method 1 | 80.00 | 1550.8313 | 1550.8442 | [M + 2H]2+ | 96.50 | 93.60 |
| 48 | 9.57 | Method 1 | >99 | 1508.7843 | 1508.7916 | [M + 2H]2+ | | |
| 49 | 8.67 | Method 1 | >99 | 1565.8422 | 1565.8560 | [M + 2H]2+ | | |
| 50 | 9.08 | Method 1 | >99 | 1605.8735 | 1605.8984 | [M + 2H]2+ | | |
| 51 | 9.16 | Method 1 | 71.28 | 1522.8000 | 1522.8128 | [M + 2H]2+ | 95.10 | 94.50 |
| 52 | 9.28 | Method 1 | 78/21 | 1534.8000 | 1534.8128 | [M + 2H]2+ | 95.76 | 92.92 |
| 53 | 9.41 | Method 1 | >99 | 1326.7152 | 1326.7209 | [M + H]+ | 98.66 | 97.12 |
| 54 | 9.45 | Method 1 | 91.46 | 1550.8313 | 1550.8464 | [M + 2H]2+ | 94.20 | 94.70 |
| 55 | 7.83 | Method 4 | 94.68 | 1684.9256 | 1685.9558 | [M + 2H]2+ | | |
| 56 | 4.60 | Method 4 | 90.76 | 1865.0379 | 1866.0744 | [M + 4H]4+ | | |
| 57 | 7.15 | Method 4 | 98.44 | 1620.8844 | 1620.8984 | [M + 2H]2+ | | |
| 58 | 8.21 | Method 4 | 100 | 1598.8313 | 1598.8554 | [M + 2H]2+ | | |
| 59 | 9.07 | Method 1 | >99 | 1523.7476 | 1523.7686 | [M + 2H]2+ | | |
| 60 | 9.63 | Method 1 | 94.50 | 1564.8469 | 1564.8598 | [M + 2H]2+ | 93.30 | 92.20 |
| 61 | 7.50 | Method 4 | >99 | 1350.7516 | 1350.7642 | [M + 2H]2+ | 96.00 | 97.10 |
| 62 | 8.23 | Method 4 | 100 | 1765.947 | 1765.9622 | [M + 2H]2+ | | |
| 63 | 8.59 | Method 4 | 100 | 1839.9838 | 1841.0094 | [M + 2H]2+ | | |
| 64 | 7.12 | Method 4 | 100 | 1405.7574 | 1405.7800 | [M + 2H]2+ | | |
| 65 | 9.75 | Method 1 | >99 | 1338.7516 | 1338.7650 | [M + H]+ | | |
| 66 | 9.11 | Method 1 | 95.21 | 1508.7843 | 1508.8020 | [M + 2H]2+ | | |
| 67 | 7.72 | Method 4 | >99 | 1447.8043 | 1447.8184 | [M + 2H]2+ | | |
| 68 | 9.62 | Method 1 | 84.01 | 1564.8469 | 1564.8638 | [M + 2H]2+ | 95.30 | 95.80 |
| 69 | 9.5 | Method 1 | 85.69 | 1550.8313 | 1550.8490 | [M + 2H]2+ | 93.00 | 93.90 |
| 70 | 7.58 | Method 4 | >99 | 1609.832 | 1609.8478 | [M + 2H]2+ | | |
| 71 | 5.06 | Method 4 | 99.17 | 1447.8043 | 1447.7710 | [M + 2H]2+ | 98.10 | 96.30 |
| 72 | 7.34 | Method 4 | 97.29 | 1610.8888 | 1610.9054 | [M + 2H]2+ | | |
| 73 | 7.5 | Method 4 | 94.66 | 1640.8994 | 1640.913 | [M + 2H]2+ | | |
| 74 | 7.94 | Method 4 | 95.69 | 1831.0199 | 1831.04 | [M + 2H]2+ | | |
| 75 | 8.19 | Method 4 | >99 | 1562.8313 | 1562.842 | [M + 2H]2+ | | |
| 76 | 7.78/7.80 | Method 4 | 100/100 | 1606.8939 | 1606.9108/ 1606.9078 | [M + 2H]2+ | | |

TABLE 16-continued

Analytical data for the peptides prepared according to the invention

| Example No | Retention time (min) | LC-MS Method 1 | Purity (%) | Exact Mass Calcd (g/mol) | Exact Mass Found (g/mol) | Ionization | LC-MS Purity (%) Method W2 | LC-MS Purity (%) Method W3 |
|---|---|---|---|---|---|---|---|---|
| 77 | 8.96 | Method 1 | >99 | 1551.8265 | 1551.8418 | [M + 2H]2+ | | |
| 78 | 8.92 | Method 1 | >99 | 1551.8265 | 1551.8382 | [M + 2H]2+ | | |
| 79 | 8.79 | Method 1 | >99 | 1353.7625 | 1353.7738 | [M + 2H]2+ | | |
| 80 | 9.41 | Method 1 | 98.76 | 1564.8469 | 1564.8612 | [M + 2H]2+ | | |
| 81 | 9.9 | Method 1 | 87.34 | 1637.8422 | 1637.8578 | [M + 2H]2+ | 94.30 | 94.50 |
| 82 | 9.25 | Method 1 | 87.40 | 1534.8000 | 1534.8166 | [M + 2H]2+ | 94.40 | 93.10 |
| 83 | 8.22 | Method 4 | 100 | 1724.9569 | 1724.9722 | [M + 2H]2+ | | |
| 84 | 8.37 | Method 4 | 100 | 1853.9995 | 1854.0168 | [M + 2H]2+ | | |
| 85 | 7.64 | Method 4 | 100 | 1709.9572 | 1709.98 | [M + 2H]2+ | | |
| 86 | 9.56 | Method 1 | >99 | 1509.7684 | 1509.7790 | [M + 2H]2+ | | |
| 87 | 9.71 | Method 1 | 88.65 | 1548.8156 | 1548.8324 | [M + 2H]2+ | | |
| 88 | 8.56 | Method 4 | >99 | 1563.8153 | 1563.8338 | [M + 2H]2+ | 99.49 | 98.88 |
| 89 | 7.71 | Method 4 | 94.93 | 1742.9674 | 1742.9808 | [M + 2H]2+ | | |
| 90 | 7.25 | Method 4 | 100 | 1534.8 | 1534.8136 | [M + 2H]2+ | | |
| 91 | 8.93 | Method 1 | 92.60 | 1339.7468 | 1339.7460 | [M + 2H]2+ | | |
| 92 | 9.59 | Method 1 | 98.22 | 1322.7203 | 1322.7270 | [M + 2H]2+ | | |
| 93 | 8.92 | Method 1 | 79.37 | 1599.8265 | 1599.8390 | [M + 2H]2+ | 97.20 | 94.40 |
| 94 | 9.69 | Method 1 | 91.51 | 1604.7877 | 1604.7942 | [M + 2H]2+ | 92.80 | 92.70 |
| 95 | 9.71 | Method 1 | 85.46 | 1564.8469 | 1564.8626 | [M + 2H]2+ | 93.20 | 91.60 |
| 96 | 7.53 | Method 4 | >99 | 1351.7356 | 1351.7356 | [M + 2H]2+ | 95.30 | 96.20 |
| 97 | 8.19 | Method 4 | 96.25 | 1738.9725 | 1739.98 | [M + 2H]2+ | | |
| 98 | 9.19 | Method 1 | 97.50 | 1522.8000 | 1522.8170 | [M + 2H]2+ | | |
| 99 | 9.75 | Method 1 | >99 | 1336.7359 | 1337.7410 | [M + H]+ | | |
| 100 | 6.83 | Method 4 | >99 | 1324.7359 | 1324.7552 | [M + 2H]2+ | 99.60 | 99.50 |
| 101 | 8.25 | Method 4 | 99.42 | 1809.9733 | 1810.9926 | [M + 2H]2+ | | |
| 102 | 9.59 | Method 1 | 92.37 | 1560.7404 | 1560.7566 | [M + 2H]2+ | | |
| 103 | 9.31 | Method 1 | >99 | 1312.6995 | 1312.7116 | [M + 2H]2+ | | |
| 104 | 9.44 | Method 1 | >99 | 1620.6792 | 1622.6874 | [M + 2H]2+ | | |
| 105 | 7.82 | Method 4 | 96.96 | 1576.8469 | 1576.8664 | [M + 2H]2+ | 96.10 | 97.20 |
| 106 | 8.12 | Method 4 | 96.29 | 1576.8469 | 1576.8624 | [M + 2H]2+ | 91.60 | 93.40 |
| 107 | 8.74 | Method 4 | 93.03 | 1942.0519 | 1943.0778 | [M + 2H]2+ | | |
| 108 | 9.87 | Method 1 | 98.00 | 1576.8469 | 1576.8632 | [M + 2H]2+ | | |
| 109 | 8.05 | Method 4 | >99 | 1447.8043 | 1447.8228 | [M + 2H]2+ | 99.50 | 99.30 |
| 110 | 8.57 | Method 4 | >99 | 1462.8040 | 1462.8150 | [M + 2H]2+ | 97.30 | 96.70 |
| 111 | 8.5 | Method 4 | >99 | 1448.7884 | 1448.8082 | [M + 2H]2+ | 99.00 | 99.20 |
| 112 | 8.34 | Method 4 | >99 | 1577.8310 | 1577.8388 | [M + 2H]2+ | 97.20 | 95.20 |
| 113 | 8.22 | Method 4 | 91.92 | 1680.9307 | 1680.9486 | [M + 2H]2+ | | |
| 114 | 8.76 | Method 1 | 97.00 | 1550.7949 | 1550.8186 | [M + 2H]2+ | | |
| 115 | 9.43 | Method 1 | 85.65 | 1591.7851 | 1591.8010 | [M + 2H]2+ | 95.50 | 93.70 |
| 116 | 9.13 | Method 1 | 85.75 | 1536.8156 | 1536.8316 | [M + 2H]2+ | 95.90 | 92.90 |
| 117 | 8.12 | Method 4 | >99 | 1351.7356 | 1351.7492 | [M + 2H]2+ | 99.10 | 98.90 |
| 118 | 5.19 | Method 4 | >99 | 1576.8469 | 1576.8658 | [M + 2H]2+ | 98.00 | 98.00 |
| 119 | 8.32 | Method 4 | 100 | 1865.0155 | 1866.0304 | [M + 2H]2+ | | |
| 120 | 9.9 | Method 1 | 97.00 | 1576.8469 | 1576.8738 | [M + 2H]2+ | | |
| 121 | 8.95 | Method 1 | >99 | 1398.6999 | 1398.7090 | [M + H]+ | | |
| 122 | 7.77 | Method 4 | >99 | 1576.8469 | 1576.8580 | [M + 2H]2+ | 96.70 | 96.70 |
| 123 | 10 | Method 1 | >99 | 1433.7887 | 1433.7986 | [M + 2H]2+ | | |
| 124 | 8.84 | Method 1 | 88.44 | 1588.8218 | 1588.8398 | [M + 2H]2+ | 96.90 | 94.40 |
| 125 | 5.83 | Method 4 | >99 | 1450.8152 | 1450.8322 | [M + 2H]2+ | 99.60 | 98.60 |
| 126 | 7.35 | Method 4 | >99 | 1421.7887 | 1421.8074 | [M + 2H]2+ | 99.30 | 98.24 |
| 127 | 8.04 | Method 4 | 94.16 | 1694.9463 | 1694.9594 | [M + 2H]2+ | | |
| 128 | 9.87 | Method 1 | >99 | 1576.7717 | 1576.7832 | [M + 2H]2+ | | |
| 129 | 9.79 | Method 1 | >99 | 1336.7359 | 1336.7440 | [M + H]+ | | |
| 130 | 7.76 | Method 4 | >99 | 1576.8469 | 1576.8588 | [M + 2H]2+ | | |
| 131 | 7.98 | Method 4 | >99 | 1590.8626 | 1590.8774 | [M + 2H]2+ | 98.50 | 98.20 |
| 132 | 7.63 | Method 4 | 98.57 | 1575.8620 | 1575.8764 | [M + 2H]2+ | 92.10 | 98.00 |
| 133 | 8.41 | Method 4 | 100 | 1795.9576 | 1796.9876 | [M + 2H]2+ | | |
| 134 | 8.24 | Method 4 | >99 | 1365.7512 | 1365.7660 | [M + 2H]2+ | 99.60 | 98.90 |
| 135 | 8.00 | Method 4 | >99 | 1461.8200 | 1461.8346 | [M + 2H]2+ | 95.70 | 95.31 |
| 136 | 8.36 | Method 4 | 100 | 1749.9885 | 1751.0162 | [M + 2H]2+ | | |
| 137 | 7.68 | Method 4 | >99 | 1564.8469 | 1564.8598 | [M + 2H]2+ | | |
| 138 | 8.39 | Method 4 | >99 | 1577.8310 | 1577.9858 | [M + 2H]2+ | 98.90 | 98.80 |
| 139 | 7.91 | Method 4 | >99 | 1589.8786 | 1589.8942 | [M + 2H]2+ | 96.50 | 98.40 |
| 140 | 7.91 | Method 4 | 94.59 | 1782.9987 | 1783.02 | [M + 2H]2+ | | |
| 141 | 8.78 | Method 4 | 100 | 1986.0781 | 1987.1064 | [M + 2H]2+ | | |
| 142 | 2.95 | Method 14 | 90.10 | 1565.7997 | 1565.8520 | [M + 2H]2+ | | |
| 143 | 7.42 | Method 4 | 94.92 | 1552.8106 | 1552.8338 | [M + 2H]2+ | 95.10 | 93.50 |
| 144 | 6.45 | Method 4 | >99 | 1451.7993 | 1451.8158 | [M + 2H]2+ | 96.00 | 96.00 |
| 145 | 7.92 | Method 4 | 93.08 | 1698.9412 | 1699.9666 | [M + 2H]2+ | | |
| 146 | 8.54 | Method 4 | 98.92 | 1898.0257 | 1899.0438 | [M + 2H]2+ | | |
| 147 | 9.03 | Method 1 | 82.90 | 1494.7687 | 1494.7820 | [M + 2H]2+ | 96.98 | 95.66 |
| 148 | 7.95 | Method 4 | >99 | 1553.7946 | 1553.8008 | [M + 2H]2+ | 95.10 | 93.50 |
| 149 | 7.15 | Method 4 | >99 | 1421.7887 | 1421.8082 | [M + 2H]2+ | 98.50 | 98.90 |
| 150 | 8.30 | Method 4 | 96.95 | 1827.025 | 1827.04 | [M + 2H]2+ | | |

TABLE 16-continued

Analytical data for the peptides prepared according to the invention

| Example No | Retention time (min) | LC-MS Method 1 | Purity (%) | Exact Mass Calcd (g/mol) | Exact Mass Found (g/mol) | Ionization | LC-MS Purity (%) Method W2 | LC-MS Purity (%) Method W3 |
|---|---|---|---|---|---|---|---|---|
| 151 | 8.75 | Method 4 | 90.85 | 1915.0774 | 1916.1114 | [M + 2H]2+ | | |
| 152 | 7.63 | Method 4 | >99 | 1364.7672 | 1364.7830 | [M + 2H]2+ | 99.30 | 98.10 |
| 153 | 9.6 | Method 1 | >99 | 1535.7840 | 1535.7904 | [M + 2H]2+ | | |
| 154 | 8.94 | Method 1 | >99 | 1362.7264 | 1362.7502 | [M + 2H]2+ | | |
| 155 | 10.26 | Method 1 | >99 | 1563.8153 | 1563.8318 | [M + 2H]2+ | | |
| 156 | 7.06 | Method 4 | >99 | 1407.7730 | 1407.7902 | [M + 2H]2+ | 99.30 | 98.40 |
| 157 | 7.85 | Method 4 | >99 | 1504.8258 | 1504.8416 | [M + 2H]2+ | 98.20 | 99.30 |
| 158 | 9.49 | Method 1 | 96.07 | 1562.7561 | 1562.7722 | [M + 2H]2+ | | |
| 159 | 9.93 | Method 1 | >99 | 1336.7359 | 1336.7485 | [M + H]+ | | |
| 160 | 7.63 | Method 4 | >99 | 1350.7516 | 1350.7670 | [M + 2H]2+ | 95.20 | 96.10 |
| 161 | 8.27 | Method 4 | >99 | 1591.8466 | 1591.8658 | [M + 2H]2+ | 98.20 | 98.50 |
| 162 | 8.52 | Method 4 | >99 | 1577.8310 | 1577.8426 | [M + 2H]2+ | 96.50 | 97.00 |
| 163 | 8.98 | Method 1 | >99 | 1436.7996 | 1436.8210 | [M + 2H]2+ | | |
| 164 | 7.99 | Method 4 | 98.33 | 1474.804 | 1476.84 | [M + 2H]2+ | | |
| 165 | 7.93 | Method 4 | 96.48 | 1562.8313 | 1562.8510 | [M + 2H]2+ | 96.70 | 96.70 |
| 166 | 7.37 | Method 4 | 79.60 | 1550.8313 | 1550.8446 | [M + 2H]2+ | 94.20 | 92.20 |
| 167 | 8.5 | Method 4 | >99 | 1448.7884 | 1448.8034 | [M + 2H]2+ | 96.60 | 98.20 |
| 168 | 8.45 | Method 4 | 100 | 1871.0512 | 1871.06 | [M + 2H]2+ | | |
| 169 | 9.22 | Method 1 | >99 | 1520.7843 | 1520.7968 | [M + 2H]2+ | | |
| 170 | 8.98 | Method 1 | 91.66 | 1508.7843 | 1508.7936 | [M + 2H]2+ | | |
| 171 | 7.51 | Method 4 | >99 | 1546.8728 | 1546.8896 | [M + 2H]2+ | 97.10 | 96.20 |
| 172 | 5.14 | Method 4 | >99 | 1447.8043 | 1447.8228 | [M + 2H]2+ | 97.00 | 97.90 |
| 173 | 7.77 | Method 4 | >99 | 1576.8469 | 1576.8678 | [M + 2H]2+ | 98.00 | 97.30 |
| 174 | 7.54 | Method 4 | 95.17 | 1654.9150 | 1654.9334 | [M + 2H]2+ | 98.00 | 98.00 |
| 175 | 9.4 | Method 1 | 93.13 | 1522.8000 | 1522.8092 | [M + 2H]2+ | | |
| 176 | 10.05 | Method 1 | >99 | 1548.8156 | 1548.8388 | [M + 2H]2+ | | |
| 177 | 10.55 | Method 1 | >99 | 1351.7356 | 1351.7490 | [M + H]+ | | |
| 178 | 9.44 | Method 1 | 87.65 | 1598.8313 | 1598.8368 | [M + 2H]2+ | 92.00 | 95.40 |
| 179 | 8.11 | Method 4 | >99 | 1590.8626 | 1590.8774 | [M + 2H]2+ | 97.70 | 98.00 |
| 180 | 10 | Method 1 | >99 | 1549.7997 | 1549.8112 | [M + 2H]2+ | | |
| 181 | 9.86 | Method 1 | 99.00 | 1372.7359 | 1373.7382 | [M + H]+ | | |
| 182 | 9.57 | Method 1 | >99 | 1388.7308 | 1388.7400 | [M + H]+ | | |
| 183 | 8.95 | Method 1 | >99 | 1550.7949 | 1551.8000 | [M + H]+ | | |
| 184 | 9.89 | Method 1 | >99 | 1393.7462 | 1393.7700 | [M + 2H]2+ | | |
| 185 | 9.83 | Method 1 | >99 | 1548.8156 | 1548.8244 | [M + 2H]2+ | | |
| 186 | 8.76 | Method 1 | >99 | 1325.7312 | 1325.7359 | [M + H]+ | | |
| 187 | 9.2 | Method 1 | 85.96 | 1584.8156 | 1584.8334 | [M + 2H]2+ | 97.10 | 95.00 |
| 188 | 7.97 | Method 4 | >99 | 1351.7356 | 1351.7524 | [M + 2H]2+ | 99.30 | 99.80 |
| 189 | 7.97 | Method 4 | >99 | 1576.8469 | 1576.8658 | [M + 2H]2+ | 97.60 | 98.50 |
| 190 | 8.42 | Method 4 | >99 | 1448.7884 | 1448.8150 | [M + 2H]2+ | 98.00 | 98.60 |
| 191 | 7.78 | Method 4 | >99 | 1576.8469 | 1576.8650 | [M + 2H]2+ | 98.40 | 96.60 |
| 192 | 8.07 | Method 4 | 88.36 | 1576.8469 | 1576.8638 | [M + 2H]2+ | 99.20 | 98.20 |
| 193 | 8.58 | Method 4 | 95.98 | 1638.8626 | 1638.88 | [M + 2H]2+ | | |
| 194 | 4.08 | Method 3 | 100 | 1474.804 | 1474.8212 | [M + 2H]2+ | | |
| 195 | 6.52 | Method 4 | >99 | 1325.7312 | 1325.7488 | [M + 2H]2+ | 99.10 | 95.10 |
| 196 | 8.11 | Method 4 | >99 | 1577.8310 | 1577.8456 | [M + 2H]2+ | 95.60 | 95.20 |
| 197 | 7.06 | Method 4 | 100 | 1405.7574 | 1405.78 | [M + 2H]2+ | | |
| 198 | 10.17 | Method 1 | >99 | 1350.7516 | 1350.7656 | [M + H]+ | | |
| 199 | 9.16 | Method 1 | 81.04 | 1508.7843 | 1508.7950 | [M + 2H]2+ | 94.25 | 92.02 |
| 200 | 7.55 | Method 4 | >99 | 1575.8629 | 1575.8758 | [M + 2H]2+ | 91.60 | 95.90 |
| 201 | 8.14 | Method 4 | >99 | 1577.8310 | 1577.8466 | [M + 2H]2+ | 98.80 | 99.10 |
| 202 | 7.62 | Method 4 | >99 | 1575.8629 | 1575.9792 | [M + 2H]2+ | 98.60 | 99.10 |
| 203 | 7.95 | Method 4 | >99 | 1576.8469 | 1576.8588 | [M + 2H]2+ | 98.80 | 97.50 |
| 204 | 7.57 | Method 4 | >99 | 1469.7887 | 1469.8062 | [M + 2H]2+ | 95.90 | 96.20 |
| 205 | 8.81 | Method 1 | 95.10 | 1480.7530 | 1480.7638 | [M + 2H]2+ | | |
| 206 | 7.55 | Method 4 | 84.01 | 1534.8000 | 1534.8172 | [M + 2H]2+ | 96.70 | 95.80 |
| 207 | 7.18 | Method 4 | 97.74 | 1566.8626 | 1566.8881 | [M + 2H]2+ | 98.30 | 98.10 |
| 208 | 7.16 | Method 4 | >99 | 1336.7359 | 1336.7542 | [M + 2H]2+ | 98.50 | 97.50 |
| 209 | 9.17 | Method 1 | 94.43 | 1494.7687 | 1494.7826 | [M + 2H]2+ | | |
| 210 | 8.78 | Method 1 | >99 | 1513.7269 | 1513.7372 | [M + 2H]2+ | | |
| 211 | 9.79 | Method 1 | 86.55 | 1598.8313 | 1598.8430 | [M + 2H]2+ | 96.39 | 97.13 |
| 212 | 10.07 | Method 1 | >99 | 1548.8156 | 1548.8266 | [M + 2H]2+ | | |
| 213 | 9.14 | Method 1 | 84.10 | 1579.8215 | 1579.8394 | [M + 2H]2+ | 97.50 | 94.80 |
| 214 | 6.82 | Method 4 | 94.98 | 1451.6699 | 1451.6876 | [M + 2H]2+ | | |
| 215 | 8.17 | Method 4 | >99 | 1577.8310 | 1577.8580 | [M + 2H]2+ | 98.70 | 98.20 |
| 216 | 9.02 | Method 1 | 95.47 | 1508.7843 | 1508.8030 | [M + 2H]2+ | | |
| 217 | 8.00 | Method 4 | 94.67 | 1562.8313 | 1562.8420 | [M + 2H]2+ | 90.20 | 94.10 |
| 218 | 7.38 | Method 4 | 83.21 | 1599.8265 | 1599.8452 | [M + 2H]2+ | 95.50 | 95.40 |
| 219 | 7.29 | Method 4 | 98.29 | 1469.7887 | 1469.8074 | [M + 2H]2+ | 91.60 | 92.60 |
| 220 | 8.75 | Method 1 | 91.37 | 1478.7374 | 1478.8566 | [M + 2H]2+ | | |
| 221 | 7.37 | Method 4 | 98.49 | 1634.9252 | 1634.9396 | [M + 2H]2+ | | |
| 222 | 9.36 | Method 1 | >99 | 1507.7527 | 1507.7598 | [M + 2H]2+ | | |
| 223 | 10.02 | Method 1 | >99 | 1411.7500 | 1411.7640 | [M + 2H]2+ | | |
| 224 | 9.49 | Method 1 | >99 | 1534.8000 | 1534.8034 | [M + 2H]2+ | | |

TABLE 16-continued

Analytical data for the peptides prepared according to the invention

| Example No | Retention time (min) | LC-MS Method 1 | Purity (%) | Exact Mass Calcd (g/mol) | Exact Mass Found (g/mol) | Ionization | LC-MS Purity (%) Method W2 | LC-MS Purity (%) Method W3 |
|---|---|---|---|---|---|---|---|---|
| 225 | 8.92 | Method 1 | 98.52 | 1550.7949 | 1550.8112 | [M + 2H]2+ | | |
| 226 | 8.52 | Method 4 | >99 | 1455.7730 | 1455.7904 | [M + 2H]2+ | 98.90 | 98.80 |
| 227 | 8.32 | Method 4 | 98.31 | 1563.8153 | 1563.8276 | [M + 2H]2+ | 93.90 | 92.60 |
| 228 | 8.86 | Method 1 | 94.17 | 1480.7530 | 1480.7624 | [M + 2H]2+ | | |
| 229 | 8.26 | Method 4 | 97.70 | 1590.8626 | 1590.8782 | [M + 2H]2+ | | |
| 230 | 4.54 | Method 2 | 94.53 | 1494.7687 | 1494.7734 | [M + 2H]2+ | | |
| 231 | 10.19 | Method 1 | >99 | 1563.8153 | 1563.8254 | [M + 2H]2+ | | |
| 232 | 9.27 | Method 1 | >99 | 1495.7527 | 1495.7612 | [M + 2H]2+ | | |
| 233 | 7.05 | Method 4 | 100 | 1451.6699 | 1451.69 | [M + 2H]2+ | | |
| 234 | 9.66 | Method 1 | >99 | 1548.8156 | 1548.8260 | [M + 2H]2+ | | |
| 235 | 9.52 | Method 1 | 92.00 | 1564.7342 | 1564.7572 | [M + 2H]2+ | | |
| 236 | 8.62 | Method 1 | >99 | 1311.7155 | 1311.7100 | [M + H]+ | | |
| 237 | 8.30 | Method 4 | >99 | 1561.7997 | 1561.8138 | [M + 2H]2+ | 97.11 | 96.94 |
| 238 | 9.52 | Method 1 | 99.00 | 1562.7141 | 1562.7204 | [M + 2H]2+ | | |
| 239 | 9.37 | Method 1 | 96.86 | 1570.8190 | 1570.8000 | [M + 2H]2+ | | |
| 240 | 5.43 | Method 4 | 98.27 | 1494.7121 | 1494.7317 | [M + 3H]3+ | | |
| 241 | 9.15 | Method 1 | >99 | 1518.7687 | 1518.7814 | [M + 2H]2+ | | |
| 242 | 7.41 | Method 4 | 100 | 1475.8356 | 1475.8544 | [M + 2H]2+ | | |
| 243 | 9.08 | Method 1 | >99 | 1522.8000 | 1522.8114 | [M + 2H]2+ | | |
| 244 | 7.58 | Method 4 | >99 | 1350.7516 | 1350.7668 | [M + 2H]2+ | 96.10 | 96.70 |
| 245 | 9.28 | Method 1 | >99 | 1506.7687 | 1506.7754 | [M + 2H]2+ | | |
| 246 | 9.14 | Method 1 | >99 | 1495.7527 | 1495.7622 | [M + 2H]2+ | | |
| 247 | 9.33 | Method 1 | >99 | 1294.6890 | 1294.7038 | [M + 2H]2+ | | |
| 248 | 8.77 | Method 1 | 97.35 | 1498.7436 | 1498.7550 | [M + 2H]2+ | | |
| 249 | 7.81 | Method 1 | >99 | 1447.8043 | 1447.8232 | [M + 2H]2+ | | |
| 250 | 9.16 | Method 1 | 96.08 | 1534.8000 | 1534.8168 | [M + 2H]2+ | | |
| 251 | 7.55 | Method 4 | 87.23 | 1475.8356 | 1475.849 | [M + 2H]2+ | | |
| 252 | 8.3 | Method 1 | 85.87 | 1509.7432 | 1509.7608 | [M + 2H]2+ | 96.30 | 96.70 |
| 253 | 9.04 | Method 1 | 95.92 | 1508.7843 | 1508.7908 | [M + 2H]2+ | | |
| 254 | 9.18 | Method 1 | 95.70 | 1506.7687 | 1506.7768 | [M + 2H]2+ | | |
| 255 | 7.26 | Method 4 | >99 | 1449.8200 | 1449.8404 | [M + 2H]2+ | 97.70 | 96.50 |
| 256 | 9.45 | Method 1 | 94.64 | 1437.7472 | 1437.7622 | [M + 2H]2+ | | |
| 257 | 5.48 | Method 4 | >99 | 1367.7781 | 1367.7956 | [M + 2H]2+ | 95.40 | 97.30 |
| 258 | 7.51 | Method 4 | >99 | 1337.7199 | 1337.7416 | [M + 2H]2+ | 98.79 | 99.40 |
| 259 | 9.36 | Method 1 | >99 | 1350.7516 | 1350.7566 | [M + H]+ | | |
| 260 | 8.85 | Method 1 | >99 | 1494.7687 | 1494.7762 | [M + 2H]2+ | | |
| 261 | 8.69 | Method 1 | >99 | 1480.7530 | 1480.7618 | [M + 2H]2+ | | |
| 262 | 8.97 | Method 1 | 94.47 | 1492.7530 | 1492.7622 | [M + 2H]2+ | | |
| 263 | 7.63 | Method 4 | 86.77 | 1522.8000 | 1522.8100 | [M + 2H]2+ | 97.20 | 93.30 |
| 264 | 8.07 | Method 1 | >99 | 1447.8043 | 1447.8224 | [M + 2H]2+ | | |
| 265 | 8.26 | Method 4 | >99 | 1377.7512 | 1377.7666 | [M + 2H]2+ | 97.60 | 96.50 |
| 266 | 7.17 | Method 4 | 100 | 1691.9215 | 1691.9382 | [M + 2H]2+ | | |
| 267 | 7.84 | Method 4 | 100 | 1459.8043 | 1459.8176 | [M + 2H]2+ | | |
| 268 | 10.3 | Method 1 | >99 | 1562.8313 | 1562.8400 | [M + 2H]2+ | | |
| 269 | 7.32 | Method 4 | >99 | 1475.8356 | 1475.8540 | [M + 2H]2+ | 98.50 | 98.50 |
| 270 | 9.77 | Method 1 | >99 | 1560.8156 | 1560.8218 | [M + 2H]2+ | | |
| 271 | 8.7 | Method 1 | 97.00 | 1480.7530 | 1480.7600 | [M + 2H]2+ | | |
| 272 | 9.47 | Method 1 | 97.47 | 1594.8034 | 1594.8198 | [M + 2H]2+ | | |
| 273 | 10.12 | Method 1 | 84.96 | 1533.8047 | 1533.8212 | [M + 2H]2+ | 93.10 | 91.60 |
| 274 | 10.75 | Method 1 | >99 | 1307.7094 | 1307.7134 | [M + H]+ | | |
| 275 | 4.62 | Method 6 | 92.32 | 1481.7371 | 1481.74 | [M + H]+ | | |
| 276 | 4.43 | Method 2 | >99 | 1481.7371 | 1481.7500 | [M + 2H]2+ | | |
| 277 | 8.83 | Method 1 | 96.32 | 1480.7530 | 1480.7588 | [M + 2H]2+ | | |
| 278 | 4.56 | Method 2 | 93.63 | 1494.7687 | 1494.7814 | [M + 2H]2+ | | |
| 279 | 10.29 | Method 1 | 98.00 | 1578.8082 | 1578.8230 | [M + 2H]2+ | | |
| 280 | 10.19 | Method 1 | 98.00 | 1267.6781 | 1267.6785 | [M + H]+ | 99.10 | 95.80 |
| 281 | 4.39 | Method 2 | >99 | 1481.7371 | 1481.7378 | [M + 2H]2+ | | |
| 282 | 9.11 | Method 1 | 93.00 | 1506.7687 | 1506.7738 | [M + 2H]2+ | | |
| 283 | 9.28 | Method 1 | >99 | 1578.8262 | 1578.8412 | [M + 2H]2+ | | |
| 284 | 10.26 | Method 4 | >99 | 1432.7934 | 1432.8096 | [M + 2H]2+ | 99.40 | 99.10 |
| 285 | 9.45 | Method 1 | >99 | 1364.7672 | 1364.7725 | [M + H]+ | | |
| 286 | 4.43 | Method 2 | 95.85 | 1455.7214 | 1455.7370 | [M + 2H]2+ | | |
| 287 | 8.81 | Method 1 | >99 | 1499.7276 | 1499.7358 | [M + 2H]2+ | | |
| 288 | 8.94 | Method 1 | >99 | 1495.7527 | 1495.7644 | [M + 2H]2+ | | |
| 289 | 9.01 | Method 1 | >99 | 1495.7527 | 1495.7592 | [M + 2H]2+ | | |
| 290 | 9.66 | Method 1 | 84.19 | 1493.7734 | 1493.7802 | [M + H]+ | 93.60 | 90.80 |
| 291 | 8.86 | Method 4 | 93.41 | 1523.8356 | 1523.85 | [M + 2H]2+ | | |
| 292 | 4.85 | Method 2 | >99 | 1323.7043 | 1323.7204 | [M + 2H]2+ | | |
| 293 | 9.8 | Method 1 | 95.00 | 1491.7942 | 1491.8200 | [M + 2H]2+ | | |
| 294 | 10.33 | Method 1 | 78.00 | 1555.7891 | 1555.8006 | [M + 2H]2+ | 95.19 | 92.10 |
| 295 | 10.4 | Method 1 | 86.71 | 1569.8047 | 1569.8000 | [M + H]+ | 93.00 | 90.90 |
| 296 | 10.43 | Method 4 | 100 | 1502.8353 | 1502.8522 | [M + 2H]2+ | | |
| 297 | 8.91 | Method 1 | 95.00 | 1494.7687 | 1494.7766 | [M + 2H]2+ | | |
| 298 | 11.01 | Method 1 | >99 | 1358.7203 | 1358.7314 | [M + 2H]2+ | | |

TABLE 16-continued

Analytical data for the peptides prepared according to the invention

| Example No | Retention time (min) | LC-MS Method 1 | Purity (%) | Exact Mass Calcd (g/mol) | Exact Mass Found (g/mol) | Ionization | LC-MS Purity (%) Method W2 | LC-MS Purity (%) Method W3 |
|---|---|---|---|---|---|---|---|---|
| 299 | 9.01 | Method 1 | >99 | 1521.7796 | 1521.7836 | [M + 2H]2+ | | |
| 300 | 9.51 | Method 1 | >99 | 1509.7684 | 1509.7814 | [M + 2H]2+ | | |
| 301 | 10.82 | Method 1 | >99 | 1307.7094 | 1307.7118 | [M + H]+ | | |
| 302 | 9.26 | Method 1 | >99 | 1534.6828 | 1534.6974 | [M + 2H]2+ | | |
| 303 | 7.31 | Method 4 | >99 | 1433.7887 | 1433.8066 | [M + 2H]2+ | 96.50 | 96.30 |
| 304 | 10.30 | Method 4 | 98.25 | 1502.8353 | 1502.8516 | [M + 2H]2+ | | |
| 305 | 10.41 | Method 1 | >99 | 1351.7400 | 1351.7415 | [M + H]+ | | |
| 306 | 8.8 | Method 1 | >99 | 1481.7371 | 1481.7496 | [M + 2H]2+ | | |
| 307 | 7.79 | Method 4 | >99 | 1562.8313 | 1562.8488 | [M + 2H]2+ | | |
| 308 | 10.14 | Method 1 | 87.08 | 1533.8047 | 1533.8218 | [M + 2H]2+ | 96.70 | 95.10 |
| 309 | 10.3 | Method 1 | 86.87 | 1535.8204 | 1535.8376 | [M + 2H]2+ | 96.90 | 90.20 |
| 310 | 7.09 | Method 4 | >99 | 1407.7730 | 1407.7906 | [M + 2H]2+ | 99.20 | 99.20 |
| 311 | 10.27 | Method 4 | >99 | 1469.7887 | 1469.8040 | [M + 2H]2+ | 99.00 | 99.40 |
| 312 | 4.46 | Method 2 | >99 | 1481.7371 | 1481.7504 | [M + 2H]2+ | | |
| 313 | 8.7 | Method 1 | >99 | 1469.7371 | 1469.7474 | [M + 2H]2+ | | |
| 314 | 8.75 | Method 1 | 91.20 | 1524.7429 | 1524.7560 | [M + 2H]2+ | | |
| 315 | 9.91 | Method 1 | 83.68 | 1519.7891 | 1519.8056 | [M + 2H]2+ | 95.10 | 93.60 |
| 316 | 7.06 | Method 4 | >99 | 1336.7359 | 1336.7536 | [M + 2H]2+ | 99.60 | 99.90 |
| 317 | 8.66 | Method 1 | 93.96 | 1383.7003 | 1383.7078 | [M + 2H]2+ | | |
| 318 | 8.96 | Method 1 | >99 | 1481.7371 | 1481.7454 | [M + 2H]2+ | | |
| 319 | 9.35 | Method 1 | 89.58 | 1576.8469 | 1576.8584 | [M + 2H]2+ | | |
| 320 | 9.31 | Method 1 | 89.56 | 1610.8524 | 1681.9082 | [M + 2H]2+ | 97.20 | 95.40 |
| 321 | 6.48 | Method 4 | 92.95 | 1505.7483 | 1505.7668 | [M + 2H]2+ | 92.90 | 88.80 |
| 322 | 9.00 | Method 4 | 98.26 | 1503.8669 | 1503.8840 | [M + 2H]2+ | 96.60 | 95.10 |
| 323 | 9.35 | Method 1 | >99 | 1521.7684 | 1521.7868 | [M + 2H]2+ | | |
| 324 | 9.09 | Method 1 | >99 | 1493.7371 | 1493.7424 | [M + 2H]2+ | | |
| 325 | 8.9 | Method 1 | 97.47 | 1501.7058 | 1501.7144 | [M + 2H]2+ | | |
| 326 | 4.71 | Method 2 | >99 | 1524.7613 | 1524.7768 | [M + 2H]2+ | | |
| 327 | 9.77 | Method 1 | 87.14 | 1537.7997 | 1537.8162 | [M + 2H]2+ | 96.70 | 92.20 |
| 328 | 8.99 | Method 4 | 94.93 | 1603.8466 | 1603.8682 | [M + 2H]2+ | 98.50 | 97.80 |
| 329 | 8.74 | Method 1 | 99.70 | 1455.7214 | 1455.7486 | [M + 2H]2+ | | |
| 330 | 9.05 | Method 4 | 85.36 | 1676.7418 | 1676.7586 | [M + 2H]2+ | 91.30 | 91.40 |
| 331 | 9.01 | Method 1 | 82.76 | 1480.7530 | 1480.7602 | [M + 2H]2+ | | |
| 332 | 9.35 | Method 1 | 92.34 | 1550.8313 | 1550.8400 | [M + 2H]2+ | | |
| 333 | 11.32 | Method 1 | >99 | 1323.7407 | 1323.7457 | [M + H]+ | | |
| 334 | 10.37 | Method 1 | 85.11 | 1547.8204 | 1547.8366 | [M + 2H]2+ | 95.80 | 93.90 |
| 335 | 10.04 | Method 4 | >99 | 1504.8510 | 1504.8710 | [M + 2H]2+ | 95.80 | 96.80 |
| 336 | 7.75 | Method 4 | >99 | 1376.7672 | 1376.7836 | [M + 2H]2+ | 98.00 | 98.50 |
| 337 | 9.06 | Method 1 | 96.83 | 1520.7091 | 1520.7232 | [M + 2H]2+ | | |
| 338 | 8.42 | Method 1 | 99.32 | 1467.7214 | 1467.7260 | [M + 2H]2+ | | |
| 339 | 8.81 | Method 1 | >99 | 1495.7527 | 1495.7684 | [M + 2H]2+ | | |
| 340 | 8.87 | Method 1 | >99 | 1494.7687 | 1494.7724 | [M + 2H]2+ | | |
| 341 | 7.26 | Method 4 | >99 | 1279.7145 | 1279.7288 | [M + 2H]2+ | 96.50 | 96.60 |
| 342 | 8.71 | Method 4 | 89.03 | 1549.7997 | 1549.8172 | [M + 2H]2+ | 90.40 | 89.40 |
| 343 | 10.63 | Method 1 | 92.89 | 1561.8360 | 1561.8516 | [M + 2H]2+ | | |
| 344 | 8.6 | Method 1 | 94.15 | 1552.7742 | 1552.7908 | [M + 2H]2+ | | |
| 345 | 6.62 | Method 4 | 94.45 | 1239.6832 | 1239.6998 | [M + 2H]2+ | 97.10 | 95.30 |
| 346 | 8.95 | Method 1 | >99 | 1480.7530 | 1480.7568 | [M + 2H]2+ | | |
| 347 | 8.59 | Method 4 | >99 | 1492.7782 | 1492.7972 | [M + 2H]2+ | 98.80 | 98.90 |
| 348 | 8.48 | Method 1 | 97.31 | 1483.7163 | 1483.7342 | [M + 2H]2+ | | |
| 349 | 9.6 | Method 1 | >99 | 1535.7840 | 1535.7942 | [M + 2H]2+ | | |
| 350 | 8.88 | Method 1 | 95.86 | 1494.7687 | 1494.7754 | [M + 2H]2+ | | |
| 351 | 10.41 | Method 1 | 84.00 | 1547.8204 | 1547.8358 | [M + 2H]2+ | 96.10 | 94.10 |
| 352 | 9.51 | Method 4 | >99 | 1862.9457 | 1862.9551 | [M + 2H]2+ | 97.70 | 95.00 |
| 353 | 10.54 | Method 1 | >99 | 1293.6937 | 1293.6958 | [M + H]+ | | |
| 354 | 8.97 | Method 1 | >99 | 1499.7276 | 1499.7348 | [M + 2H]2+ | | |
| 355 | 4.52 | Method 2 | 90.00 | 1496.7480 | 1496.7520 | [M + 2H]2+ | | |
| 356 | 10.58 | Method 1 | 93.20 | 1549.8360 | 1549.8502 | [M + 2H]2+ | | |
| 357 | 8.82 | Method 1 | >99 | 1483.7163 | 1483.7282 | [M + 2H]2+ | | |
| 358 | 11.05 | Method 1 | >99 | 1309.7250 | 1309.6000 | [M + 2H]2+ | 98.30 | 97.50 |
| 359 | 10.49 | Method 4 | >99 | 1434.8091 | 1434.8240 | [M + 2H]2+ | 98.60 | 98.90 |
| 360 | 9.22 | Method 4 | 96.98 | 1618.8728 | 1618.8882 | [M + 2H]2+ | 96.18 | 97.30 |
| 361 | 7.43 | Method 4 | 95.37 | 1504.8258 | 1504.8430 | [M + 2H]2+ | 98.20 | 97.20 |
| 362 | 9.2 | Method 1 | 94.52 | 1556.7843 | 1556.8050 | [M + 2H]2+ | | |
| 363 | 9.35 | Method 4 | 85.07 | 1861.9617 | 1861.9685 | [M + H]+ | 97.70 | 95.00 |
| 364 | 9.21 | Method 1 | 97.74 | 1562.8313 | 1562.8390 | [M + 2H]2+ | | |
| 365 | 10.56 | Method 1 | 80.41 | 1549.8360 | 1549.8518 | [M + 2H]2+ | 94.70 | 92.90 |
| 366 | 10.82 | Method 1 | >99 | 1595.7065 | 1595.7192 | [M + 2H]2+ | 97.30 | 94.40 |
| 367 | 9.64 | Method 1 | 99.58 | 1535.7840 | 1535.8040 | [M + 2H]2+ | | |
| 368 | 7.84 | Method 4 | >99 | 1280.6985 | 1280.7178 | [M + 2H]2+ | 99.60 | 99.70 |
| 369 | 8.24 | Method 4 | >99 | 1506.7938 | 1506.8094 | [M + 2H]2+ | 95.40 | 95.80 |
| 370 | 8.98 | Method 4 | >99 | 1523.8356 | 1523.8492 | [M + 2H]2+ | 97.12 | 97.08 |
| 371 | 7.10 | Method 4 | >99 | 1433.7887 | 1433.8050 | [M + 2H]2+ | 93.50 | 91.70 |
| 372 | 8.07 | Method 4 | >99 | 1505.8098 | 1505.9486 | [M + 2H]2+ | 99.40 | 98.80 |

TABLE 16-continued

Analytical data for the peptides prepared according to the invention

| Example No | Retention time (min) | LC-MS Method 1 | Purity (%) | Exact Mass Calcd (g/mol) | Exact Mass Found (g/mol) | Ionization | LC-MS Purity (%) Method W2 | LC-MS Purity (%) Method W3 |
|---|---|---|---|---|---|---|---|---|
| 373 | 4.37 | Method 2 | >99 | 1494.7687 | 1494.7726 | [M + 2H]2+ | | |
| 374 | 9.06 | Method 1 | 92.43 | 1494.7700 | 1494.7854 | [M + 2H]2+ | | |
| 375 | 10.32 | Method 4 | 95.26 | 1550.8201 | 1550.8392 | [M + 2H]2+ | | |
| 376 | 7.60 | Method 1 | >99 | 1447.8043 | 1447.8248 | [M + 2H]2+ | | |
| 377 | 7.50 | Method 4 | >99 | 1504.8258 | 1504.8388 | [M + 2H]2+ | 93.50 | 96.90 |
| 378 | 7.51 | Method 4 | >99 | 1530.8415 | 1530.8574 | [M + 2H]2+ | 99.10 | 99.70 |
| 379 | 7.20 | Method 4 | >99 | 1350.7516 | 1350.7680 | [M + 2H]2+ | 97.30 | 99.00 |
| 380 | 8.26/8.34 | Method 1 | 70/29 | 1483.7163 | 1483.7374 | [M + 2H]2+ | | |
| 381 | 3.9 | Method 4 | >99 | 1750.011 | 1750.0326 | [M + 3H]3+ | 99.37 | 98.66 |
| 382 | 11.06 | Method 1 | >99 | 1321.7250 | 1321.7286 | [M + H]+ | | |
| 383 | 9.91 | Method 1 | >99 | 1365.7500 | 1365.7630 | [M + 2H]2+ | | |
| 384 | 9.15 | Method 1 | 87.43 | 1521.6931 | 1521.6976 | [M + 2H]2+ | | |
| 385 | 10.68 | Method 1 | 83.28 | 1583.8204 | 1583.8368 | [M + 2H]2+ | 96.30 | 91.20 |
| 386 | 4.55 | Method 2 | >99 | 1481.7371 | 1481.7494 | [M + 2H]2+ | | |
| 387 | 9.46 | Method 1 | 93.47 | 1495.7527 | 1495.7636 | [M + 2H]2+ | | |
| 388 | 8.07 | Method 4 | >99 | 1505.8098 | 1505.8246 | [M + 2H]2+ | 97.80 | 97.10 |
| 389 | 8.75 | Method 1 | 93.22 | 1478.7374 | 1478.7462 | [M + 2H]2+ | | |
| 390 | 8.89 | Method 1 | >99 | 1499.7276 | 1499.7360 | [M + 2H]2+ | | |
| 391 | 10.75 | Method 1 | 91.00 | 1547.8204 | 1547.8280 | [M + 2H]2+ | | |
| 392 | 9.55 | Method 1 | 88.42 | 1509.7684 | 1509.7812 | [M + 2H]2+ | | |
| 393 | 8.73 | Method 1 | >99 | 1481.7371 | 1481.7432 | [M + 2H]2+ | | |
| 394 | 4.39 | Method 2 | 95.41 | 1480.7530 | 1480.7642 | [M + 2H]2+ | | |
| 395 | 9.64 | Method 1 | 84.41 | 1579.8102 | 1579.8260 | [M + 2H]2+ | 93.40 | 90.50 |
| 396 | 10.54 | Method 4 | >99 | 1337.7563 | 1337.7660 | [M + H]+ | 99.30 | 98.20 |
| 397 | 8.79 | Method 1 | >99 | 1493.7371 | 1493.7510 | [M + 2H]2+ | | |
| 398 | 11.13 | Method 1 | >99 | 1309.7250 | 1309.7295 | [M + H]+ | | |
| 399 | 9.16 | Method 1 | 88.00 | 1622.8637 | 1622.8866 | [M + 2H]2+ | | |
| 400 | 9.66 | Method 1 | 85.00 | 1549.7633 | 1549.7778 | [M + 2H]2+ | 95.50 | 93.80 |
| 401 | 4.54 | Method 2 | 94.46 | 1384.6843 | 1384.7002 | [M + 2H]2+ | | |
| 402 | 8.86 | Method 1 | >99 | 1509.7684 | 1509.7802 | [M + 2H]2+ | | |
| 403 | 9.29 | Method 1 | 93.30 | 1536.8156 | 1536.8306 | [M + 2H]2+ | | |
| 404 | 10.21 | Method 1 | >99 | 1507.7891 | 1507.7944 | [M + 2H]2+ | | |
| 405 | 4.24 | Method 4 | >99 | 1790.0423 | 1791.0678 | [M + 3H]3+ | 99.08 | 98.69 |
| 406 | 10.45 | Method 4 | 98.71 | 1584.8044 | 1584.8186 | [M + 2H]2+ | | |
| 407 | 9.21 | Method 4 | 83.34 | 1607.8415 | 1607.8578 | [M + 2H]2+ | 96.00 | 94.40 |
| 408 | 11.12 | Method 1 | >99 | 1321.7250 | 1321.7258 | [M + H]+ | | |
| 409 | 8.77 | Method 1 | 97.00 | 1626.8109 | 1626.8200 | [M + 2H]2+ | | |
| 410 | 8.59/8.66 | Method 1 | 59/40 | 1483.7163 | 1483.7370 | [M + 2H]2+ | | |
| 411 | 8.95 | Method 1 | 94.75 | 1480.7530 | 1480.7630 | [M + 2H]2+ | | |
| 412 | 5.62 | Method 4 | 97.66 | 1448.836 | 1448.8554 | [M + 3H]3+ | 96.30 | 97.40 |
| 413 | 4.36 | Method 2 | >99 | 1480.7530 | 1480.7612 | [M + 2H]2+ | | |
| 414 | 8.7 | Method 1 | >99 | 1485.7120 | 1485.7238 | [M + 2H]2+ | | |
| 415 | 10.87 | Method 1 | 91.80 | 1575.8517 | 1575.8652 | [M + 2H]2+ | | |
| 416 | 9.36 | Method 1 | >99 | 1579.6163 | 1579.6200 | [M + 2H]2+ | | |
| 417 | 9.15 | Method 1 | >99 | 1494.7687 | 1494.7736 | [M + 2H]2+ | | |
| 418 | 8.39 | Method 4 | >99 | 1562.8313 | 1562.9000 | [M + 2H]2+ | 97.31 | 97.42 |
| 419 | 8.44 | Method 4 | >99 | 1474.8040 | 1476.8178 | [M + 2H]2+ | | |
| 420 | 4.01 | Method 3 | >99 | 1562.8313 | 1562.8422 | [M + 2H]2+ | | |
| 421 | 7.57 | Method 4 | 98.63 | 1678.9514 | 1680.9710 | [M + 2H]2+ | | |
| 422 | 7.67 | Method 4 | 95.55 | 1708.9620 | 1710.9742 | [M + 2H]2+ | | |
| 423 | 7.72 | Method 4 | >99 | 1722.9776 | 1724.9942 | [M + 2H]2+ | | |
| 424 | 7.85 | Method 4 | 94.30 | 1752.9882 | 1755.0024 | [M + 2H]2+ | | |
| 425 | 7.80 | Method 4 | 97.93 | 1811.0300 | 1814.0484 | [M + 2H]2+ | | |
| 426 | 7.96 | Method 4 | 98.96 | 1855.0563 | 1858.0758 | [M + 2H]2+ | | |
| 427 | 8.19 | Method 4 | >99 | 1899.0825 | 1902.1006 | [M + 2H]2+ | | |
| 428 | 8.73 | Method 4 | 94.64 | 2030.1043 | 2032.1148 | [M + 2H]2+ | | |
| 429 | 7.84 | Method 4 | >99 | 1778.0198 | 1780.0348 | [M + 2H]2+ | | |
| 430 | 4.37 | Method 4 | >99 | 1750.0110 | 1753.0326 | [M + 3H]3+ | | |
| 431 | 8.62 | Method 4 | >99 | 1561.7997 | 1565.8452 | [M + 2H]2+ | | |
| 432 | 8.65 | Method 4 | >99 | 1561.7997 | 1565.4816 | [M + 2H]2+ | | |
| 433 | 2.85 | Method 5 | 85.05 | 1735.9113 | 1737.9288 | [M + 2H]2+ | | |
| 435 | 2.70 | Method 5 | 94.14 | 1767.0038 | 1770.0200 | [M + 2H]2+ | | |
| 436 | 8.33 | Method 4 | 98.11 | 1726.9011 | 1728.9172 | [M + 2H]2+ | | |
| 437 | 8.43 | Method 4 | >99 | 1629.8483 | 1631.8630 | [M + 2H]2+ | | |
| 438 | 8.54 | Method 4 | 97.07 | 1571.8568 | 1573.8716 | [M + 2H]2+ | | |
| 439 | 7.58 | Method 4 | >99 | 1433.7887 | 1435.8152 | [M + 2H]2+ | | |
| 440 | 7.43 | Method 4 | >99 | 1463.7229 | 1465.7404 | [M + 2H]2+ | | |
| 441 | 8.34 | Method 4 | >99 | 1517.7699 | 1519.7886 | [M + 2H]2+ | | |
| 443 | 7.73 | Method 4 | >99 | 1483.7855 | 1485.8006 | [M + 2H]2+ | | |
| 444 | 6.79 | Method 4 | >99 | 1527.8418 | 1529.8576 | [M + 2H]2+ | | |
| 445 | 7.63 | Method 4 | >99 | 1483.7855 | 1485.8018 | [M + 2H]2+ | | |
| 446 | 8.65 | Method 4 | 91.93 | 1563.8153 | 1563.8272 | [M + 2H]2+ | 95.35 | 98.58 |
| 447 | 2.65 | Method 5 | >99 | 1635.8629 | 1635.8760 | [M + 2H]2+ | 98.66 | 99.22 |
| 448 | 5.44 | Method 4 | 97.04 | 1462.8265 | 1465.8501 | [M + 3H]3+ | 95.79% | 97.26% |

TABLE 16-continued

Analytical data for the peptides prepared according to the invention

| Example No | Retention time (min) | LC-MS Method 1 | Purity (%) | Exact Mass Calcd (g/mol) | Exact Mass Found (g/mol) | Ionization | LC-MS Purity (%) Method W2 | LC-MS Purity (%) Method W3 |
|---|---|---|---|---|---|---|---|---|
| 449 | 8.33 | Method 4 | 86.83 | 1559.8568 | 1561.8714 | [M + 2H]2+ | | |
| 450 | 9.24 | Method 4 | 90.97 | 1589.9037 | 1591.9208 | [M + 2H]2+ | | |
| 451 | 8.61 | Method 4 | 95.66 | 1573.8724 | 1575.8884 | [M + 2H]2+ | | |
| 452 | 8.24 | Method 4 | 96.26 | 1559.8568 | 1561.8714 | [M + 2H]2+ | | |
| 453 | 8.53 | Method 4 | 94.00 | 1573.8724 | 1575.8874 | [M + 2H]2+ | | |
| 454 | 7.96 | Method 4 | >99 | 1562.8313 | 1564.8458 | [M + 2H]2+ | | |
| 455 | 8.47 | Method 4 | >99 | 1559.8568 | 1561.8710 | [M + 2H]2+ | | |
| 456 | 8.28 | Method 4 | >99 | 1545.8411 | 1547.8552 | [M + 2H]2+ | | |
| 457 | 9.44 | Method 4 | >99 | 1632.8004 | 1634.8240 | [M + 2H]2+ | | |
| 458 | 2.61 | Method 5 | >99 | 1534.8364 | 1536.8654 | [M + 2H]2+ | 96.68% | 96.99% |
| 459 | 2.85 | Method 5 | >99 | 1391.7669 | 1393.7826 | [M + 2H]2+ | 89.95% | 99.44% |
| 460 | 2.84 | Method 5 | >99 | 1391.7669 | 1393.7810 | [M + 2H]2+ | 97.71% | 98.46% |
| 462 | 8.76 | Method 4 | 78.21 | 1665.9099 | 1667.9238 | [M + 2H]2+ | 95.17% | 93.69% |
| 463 | 7.12 | Method 4 | 94.14 | 1691.9103 | 1694.9349 | [M + 3H]3+ | 97.30% | 90.79% |
| 464 | 8.26 | Method 4 | >99 | 1620.8368 | 1622.8530 | [M + 2H]2+ | 97.37% | 94.11% |
| 465 | 8.39 | Method 4 | >99 | 1676.8994 | 1678.9132 | [M + 2H]2+ | 98.76% | 99.20% |
| 466 | 8.11 | Method 4 | >99 | 1678.8422 | 1680.8566 | [M + 2H]2+ | 99.18% | 98.78% |
| 467 | 6.96 | Method 4 | >99 | 1534.8364 | 1537.8579 | [M + 3H]3+ | 99.05% | 99.51% |
| 468 | 8.26 | Method 4 | 94.77 | 1651.9041 | 1653.9234 | [M + 2H]2+ | 96.08% | 96.72% |
| 469 | 6.87 | Method 4 | >99 | 1606.8575 | 1609.8813 | [M + 3H]3+ | 97.93% | 96.22% |
| 470 | 8.71 | Method 4 | >99 | 1681.9147 | 1683.9302 | [M + 2H]2+ | 96.68% | 92.70% |
| 471 | 8.40 | Method 4 | >99 | 1796.9416 | 1798.9566 | [M + 2H]2+ | 97.03% | 95.29% |
| 472 | 8.56 | Method 4 | >99 | 1783.9828 | 1785.9958 | [M + 2H]2+ | 97.03% | 95.29% |
| 473 | 8.39 | Method 4 | >99 | 1563.8153 | 1563.8244 | [M + 2H]2+ | | |
| 474 | 6.65 | Method 4 | 95.2 | 1463.7993 | 1463.816 | [M + 2H]2+ | | |
| 475 | 7.74 | Method 4 | >99 | 1549.7997 | 1549.8134 | [M + 2H]2+ | 97.03 | 95.07 |
| 476 | 9.69 | Method 4 | >99 | 1595.8568 | 1595.8710 | [M + 2H]2+ | 95.68 | 96.16 |
| 477 | 9.87 | Method 4 | >99 | 1595.8568 | 1595.8712 | [M + 2H]2+ | 96.85 | 97.09 |
| 478 | 9.84 | Method 4 | >99 | 1595.8568 | 1595.8668 | [M + 2H]2+ | 96.50 | 94.73 |
| 479 | 6.83 | Method 4 | >99 | 1552.8106 | 1552.8284 | [M + 2H]2+ | 96.16 | 94.86 |
| 480 | 7.51 | Method 4 | 99.0 | 1549.7997 | 1549.8132 | [M + 2H]2+ | 94.8 | 96.2 |
| 481 | 7.59 | Method 4 | >99 | 1549.7997 | 1549.8206 | [M + 2H]2+ | 97.55 | 97.23 |
| 482 | 8.32 | Method 4 | >99 | 1599.8153 | 1599.8326 | [M + 2H]2+ | 98.99 | 98.86 |
| 483 | 8.85 | Method 4 | 94.52 | 1639.8466 | 1639.8596 | [M + 2H]2+ | 98.56 | 98.33 |
| 484 | 8.50 | Method 4 | >99 | 1766.9311 | 1766.9468 | [M + 2H]2+ | 98.65 | 97.21 |
| 485 | 7.77 | Method 4 | >99 | 1655.8990 | 1655.9152 | [M + 2H]2+ | 98.60 | 99.16 |
| 486 | 2.31 | Method 5 | 97.6 | 1637.8633 | 1637.8754 | [M + 2H]2+ | 95.81 | 96.13 |
| 487 | 2.52 | Method 5 | >99 | 1604.8895 | 1604.9038 | [M + 2H]2+ | 99.01 | 98.81 |
| 488 | 2.95 | Method 5 | >99 | 1603.8466 | 1603.8610 | [M + 2H]2+ | 98.08 | 98.25 |
| 489 | 2.84 | Method 5 | >99 | 1603.8466 | 1603.8684 | [M + 2H]2+ | 99.49 | 98.23 |
| 490 | 3.40 | Method 5 | >99 | 1697.8157 | 1697.8294 | [M + 2H]2+ | 99.38 | 99.17 |
| 491 | 3.43 | Method 5 | >99 | 1697.8157 | 1697.8316 | [M + 2H]2+ | 96.36 | 96.84 |
| 492 | 2.86 | Method 5 | >99 | 1549.8360 | 1549.8488 | [M + 2H]2+ | 98.14 | 98.16 |
| 493 | 2.93 | Method 5 | 97.60 | 1611.8517 | 1611.8664 | [M + 2H]2+ | 97.58 | 97.80 |
| 494 | 2.88 | Method 5 | 97.96 | 1634.8524 | 1634.8662 | [M + 2H]2+ | 97.13 | 97.02 |
| 495 | 2.97 | Method 5 | >99 | 1620.8368 | 1620.8538 | [M + 2H]2+ | 98.60 | 98.29 |
| 496 | 8.11 | Method 4 | >99 | 1685.9096 | 1685.9238 | [M + 2H]2+ | 95.64 | 96.06 |
| 497 | 7.90 | Method 4 | 95.72 | 1621.8684 | 1621.8810 | [M + 2H]2+ | 92.88 | 92.81 |
| 498 | 7.49 | Method 4 | >99 | 1567.8466 | 1567.8568 | [M + 2H]2+ | 98.13 | 98.05 |
| 499 | 8.47 | Method 4 | >99 | 1573.8030 | 1573.8528 | [M + 2H]2+ | | |
| 500 | 8.40 | Method 4 | >99 | 1722.9048 | 1722.9200 | [M + 2H]2+ | 98.10 | 99.55 |
| 501 | 7.86 | Method 4 | 98.44 | 1770.9260 | 1770.9408 | [M + 2H]2+ | 97.32 | 96.25 |
| 502 | 7.70 | Method 4 | 99.09 | 1563.8153 | 1563.8320 | [M + 2H]2+ | 97.46 | 96.62 |
| 503 | 8.29 | Method 4 | >99 | 1876.0301 | 1876.0302 | [M + 2H]2+ | 95.23 | 94.54 |
| 504 | 8.41 | Method 4 | >99 | 1991.0571 | 1991.0740 | [M + 2H]2+ | 96.55 | 96.43 |
| 505 | 8.23 | Method 4 | >99 | 1832.0039 | 1832.0216 | [M + 2H]2+ | 95.43 | 96.86 |
| 506 | 7.98 | Method 4 | 98.67 | 1641.8834 | 1641.8986 | [M + 2H]2+ | 97.81 | 97.21 |
| 507 | 7.86 | Method 4 | >99 | 1521.7684 | 1521.7926 | [M + 2H]2+ | | |
| 508 | 7.63 | Method 4 | >99 | 1563.7401 | 1563.7564 | [M + 2H]2+ | | |
| 509 | 7.75 | Method 4 | >99 | 1523.7840 | 1523.8000 | [M + 2H]2+ | | |
| 510 | 8.35 | Method 4 | >99 | 1633.8572 | 1633.8688 | [M + 2H]2+ | | |
| 511 | 2.58 | Method 5 | >99 | 1535.6668 | 1535.6802 | [M + 2H]2+ | 87.38 | 89.08 |
| 512 | 4.12 | Method 5 | >99 | 1974.1298 | 1974.1506 | [M + 2H]2+ | 95.15 | 95.33 |
| 513 | 3.96 | Method 5 | >99 | 1903.0927 | 1903.1106 | [M + 2H]2+ | 96.44 | 95.38 |
| 514 | 2.65 | Method 5 | >99 | 1611.8728 | 1611.8852 | [M + 2H]2+ | 95.68 | 95.22 |
| 515 | 2.79 | Method 5 | >99 | 1591.8466 | 1591.8600 | [M + 2H]2+ | 97.20 | 97.37 |
| 516 | 2.73 | Method 5 | >99 | 1549.7244 | 1549.7380 | [M + 2H]2+ | 93.87 | 95.17 |
| 517 | 2.90 | Method 5 | >99 | 1591.7714 | 1591.7908 | [M + 2H]2+ | 91.59 | 93.39 |

TABLE 16-continued

| Analytical data for the peptides prepared according to the invention | | | | | | | | |
|---|---|---|---|---|---|---|---|---|
| Example No | Retention time (min) | LC-MS Method 1 | Purity (%) | Exact Mass Calcd (g/mol) | Exact Mass Found (g/mol) | Ionization | LC-MS Purity (%) Method W2 | LC-MS Purity (%) Method W3 |
| 518 | 1.75 | Method 5 | >99 | 1355.6366 | 1355.6494 | [M + 2H]2+ | 97.11 | 98.05 |
| 519 | 2.67 | Method 5 | >99 | 1579.7339 | 1579.7548 | [M + 2H]2+ | 95.69 | 96.40 |
| 520 | 2.68 | Method 5 | >99 | 1593.7495 | 1595.7636 | [M + 2H]2+ | 97.27 | 96.99 |
| 521 | 2.66 | Method 5 | >99 | 1694.7608 | 1694.7798 | [M + 2H]2+ | 95.48 | 95.35 |
| 522 | 2.79 | Method 5 | >99 | 1549.7997 | 1549.8140 | [M + 2H]2+ | 97.12 | 96.45 |
| 523 | 2.82 | Method 5 | >99 | 1563.8153 | 1563.8312 | [M + 2H]2+ | 95.87 | 96.34 |
| 524 | 2.82 | Method 5 | >99 | 1563.7401 | 1573.7518 | [M + 2H]2+ | 91.95 | 92.65 |
| 525 | 8.24 | Method 4 | 84.39 | 1575.8153 | 1575.8416 | [M + 2H]2+ | | |
| 526 | 2.70 | Method 5 | >99 | 1535.7840 | 1535.7966 | [M + 2H]2+ | 96.07 | 95.73 |
| 527 | 3.11 | Method 5 | 98.08 | 1644.9095 | 1644.9230 | [M + 2H]2+ | 98.01 | 96.26 |
| 528 | 2.99 | Method 5 | 95.62 | 1589.8310 | 1589.8490 | [M + 2H]2+ | 75.28 | 75.57 |
| 529 | 6.47 | Method 4 | 95.44 | 1610.7231 | 1610.7386 | [M + 2H]2+ | 84.42 | 82.86 |
| 530 | 2.89 | Method 5 | >99 | 1559.8568 | 1559.8754 | [M + 2H]2+ | 97.07 | 96.79 |
| 531 | 2.94 | Method 5 | >99 | 1577.8310 | 1577.8492 | [M + 2H]2+ | 95.26 | 97.20 |
| 532 | 2.89 | Method 5 | >99 | 1545.8411 | 1545.8590 | [M + 2H]2+ | 97.87 | 96.49 |

TABLE 17

| Maldi mass spectral data for selected peptides | |
|---|---|
| Example No | Method MALDI (Amu + 1) |
| 512 | 1975.223 |
| 526 | 1536.827 |
| 527 | 1645.817 |
| 529 | 1611.761 |
| 530 | 1560.875 |
| 531 | 1578.866 |
| 532 | 1546.821 |
| 142 | 1566.863 |
| 237 | 1562.785 |

In the following, examples 29, 44, 45, 67, 75, 109, 166, 185, 347, 443, 466 and 499 are exemplified by their chemical structure. The present invention includes pharmaceutically acceptable salts, solvates or solvates of the salts of these examples. Chemical structures are displayed as salt free forms.

Example 29, Sequence: AIC+SRSLP-(Oic)-I-(Pen)+IPD-OH (HCl salt)

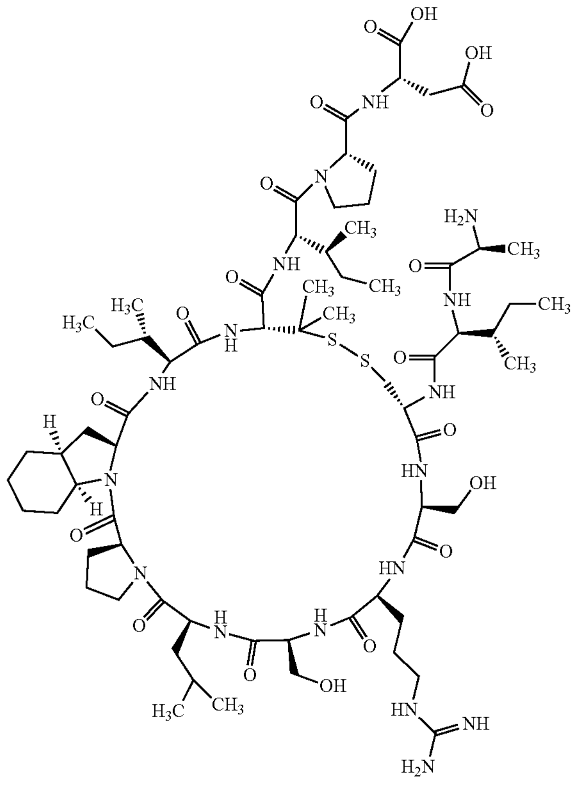 [SMILES: CC[C@H](C)[C@H](NC(=O)[C@H](C)N)C(=O)N[C@H]1CSSC(C)(C)[C@@H](C(=O)N[C@H](C(=O)N2CCC[C@H]2C(=O)N[C@@H](CC(=O)O)C(=O)O)[C@@H](C)CC)NC(=O)[C@H]([C@@H](C)CC)NC(=O)[C@@H]2C[C@@H]3CCCC[C@@H]3N2C(=O)[C@@H]2CCCN2C(=O)[C@H](CC(C)C)NC(=O)[C@H](CO)NC(=O)[C@H](CCCNC(=N)N)NC(=O)[C@H](CO)NC1=O]

Example 44, Sequence: ((N-Me)G)-IC+SRS-((tBu)A)-PPI-(Pen)+IP-(PEG9 (31 atoms))-NH2
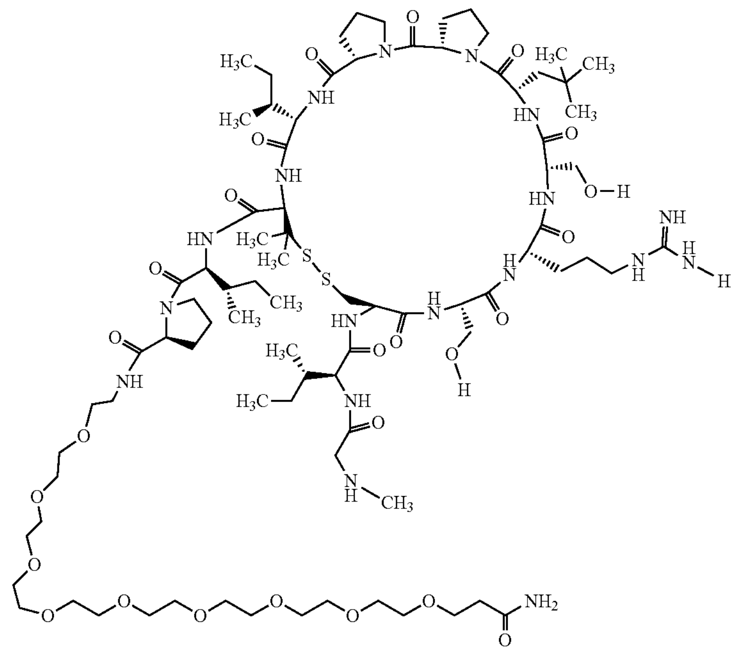 [SMILES: CC[C@H](C)[C@H](NC(=O)CNC)C(=O)N[C@H]1CSSC(C)(C)[C@@H](C(=O)N[C@H](C(=O)N2CCC[C@H]2C(=O)NCCOCCOCCOCCOCCOCCOCCOCCOCCOCCC(N)=O)[C@@H](C)CC)NC(=O)[C@H]([C@@H](C)CC)NC(=O)[C@@H]2CCCN2C(=O)[C@@H]2CCCN2C(=O)[C@H](CC(C)(C)C)NC(=O)[C@H](CO)NC(=O)[C@H](CCCNC(=N)N)NC(=O)[C@H](CO)NC1=O]
Example 45, Sequence: AI-C+SRS-((tBu)A)-P-((6S)-5-Azaspiro[2.4]heptane-6-carboxylic acid)-I-(Pen)+IPD-NH2
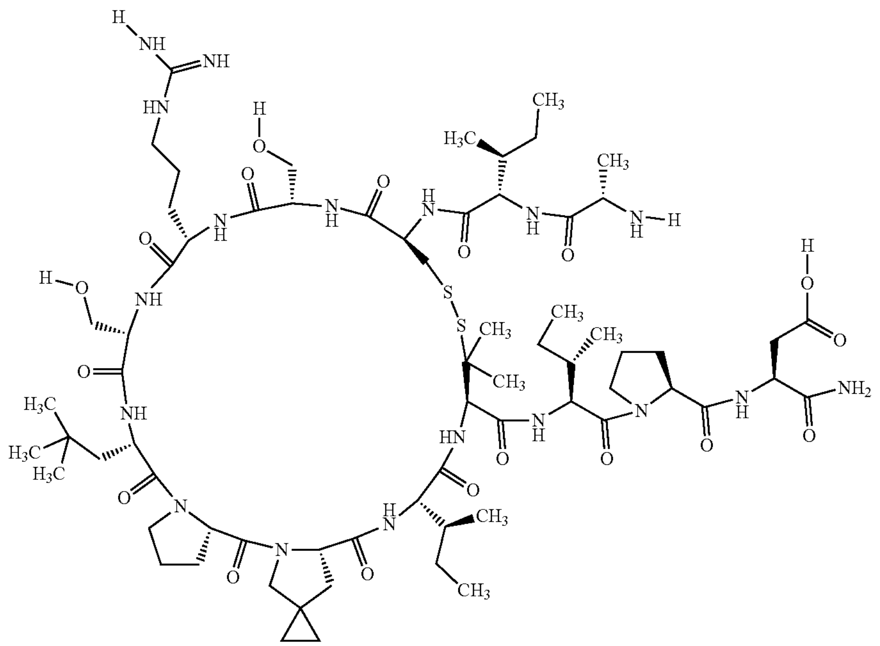 [SMILES: CC[C@H](C)[C@H](NC(=O)[C@H](C)N)C(=O)N[C@H]1CSSC(C)(C)[C@@H](C(=O)N[C@H](C(=O)N2CCC[C@H]2C(=O)N[C@@H](CC(=O)O)C(N)=O)[C@@H](C)CC)NC(=O)[C@H]([C@@H](C)CC)NC(=O)[C@@H]2CC3(CC3)CN2C(=O)[C@@H]2CCCN2C(=O)[C@H](CC(C)(C)C)NC(=O)[C@H](CO)NC(=O)[C@H](CCCNC(=N)N)NC(=O)[C@H](CO)NC1=O]

Example 67, Sequence: ((N-Me)G)-IC+SRSLP-(Oic)-I-(Pen)+IP-NH2 (HCl salt)
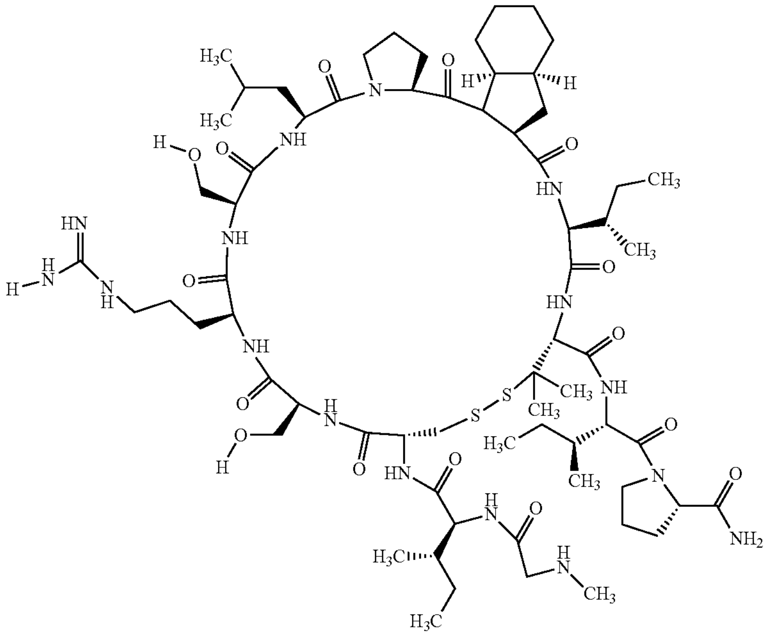

Example 75, Sequence: AIC+SRSLP-(Oic)-I-(Pen)+IPD-NH2
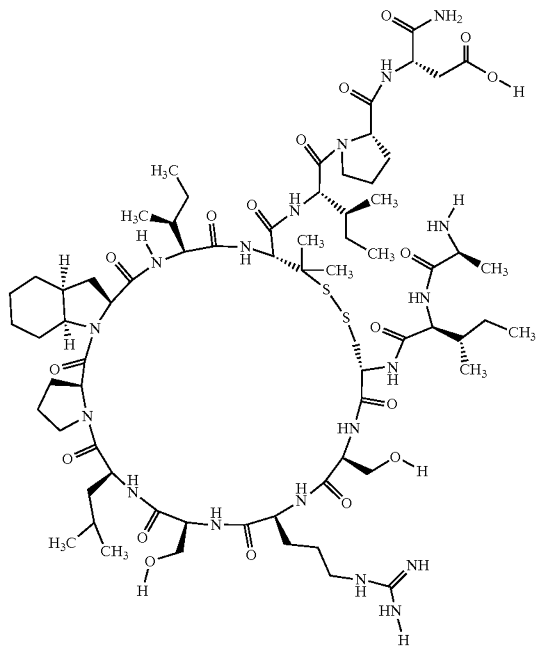 [SMILES: CC[C@H](C)[C@H](NC(=O)[C@H](C)N)C(=O)N[C@H]1CSSC(C)(C)[C@@H](C(=O)N[C@H](C(=O)N2CCC[C@H]2C(=O)N[C@@H](CC(=O)O)C(N)=O)[C@@H](C)CC)NC(=O)[C@H]([C@@H](C)CC)NC(=O)[C@@H]2C[C@@H]3CCCC[C@@H]3N2C(=O)[C@@H]2CCCN2C(=O)[C@H](CC(C)C)NC(=O)[C@H](CO)NC(=O)[C@H](CCCNC(=N)N)NC(=O)[C@H](CO)NC1=O]
Example 109, Sequence: ((N-Me)G)-IC+SRSLP-(Oic)-I-(Pen)+IP-NH2
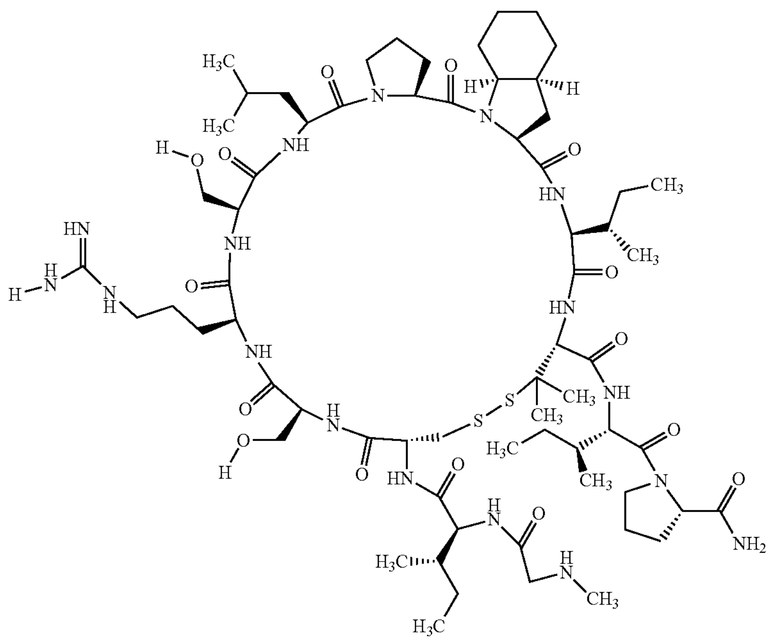 [SMILES: CC[C@H](C)[C@H](NC(=O)CNC)C(=O)N[C@H]1CSSC(C)(C)[C@@H](C(=O)N[C@H](C(=O)N2CCC[C@H]2C(N)=O)[C@@H](C)CC)NC(=O)[C@H]([C@@H](C)CC)NC(=O)[C@@H]2C[C@@H]3CCCC[C@@H]3N2C(=O)[C@@H]2CCCN2C(=O)[C@H](CC(C)C)NC(=O)[C@H](CO)NC(=O)[C@H](CCCNC(=N)N)NC(=O)[C@H](CO)NC1=O]

Example 166, Sequence: (3-Amino-2,2-dimethyl-propionic acid)-IC+SRS-((tBu)A)-PPI-(Pen)+IPD-NH2
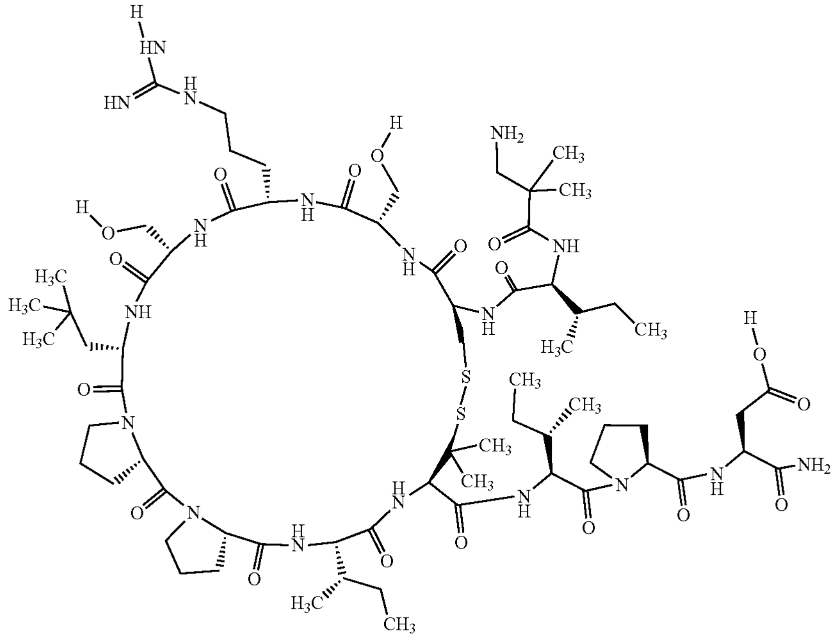
Example 185, Sequence: AIC+SRSLP-(Oic)-I—((N-Me)C)+IPD-NH2
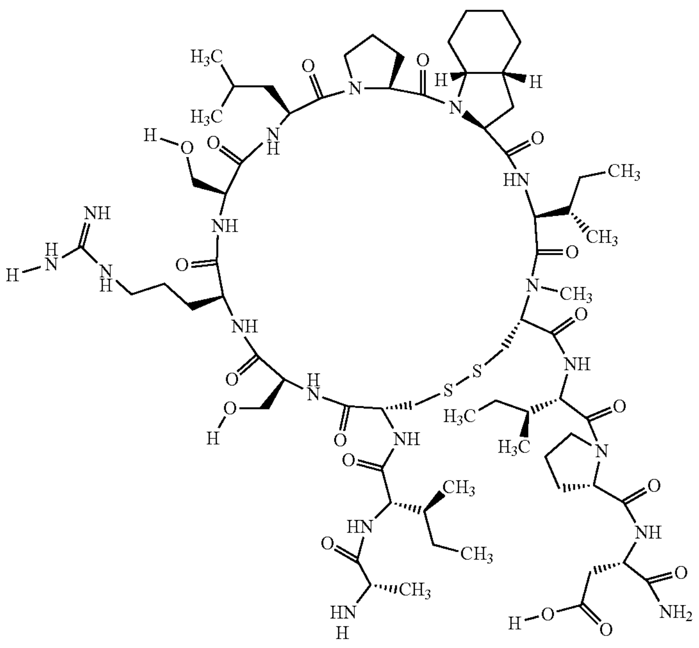

Example 347, Sequence: IC+SRSLP-(Oic)-I-(Pen)+IPD-OH
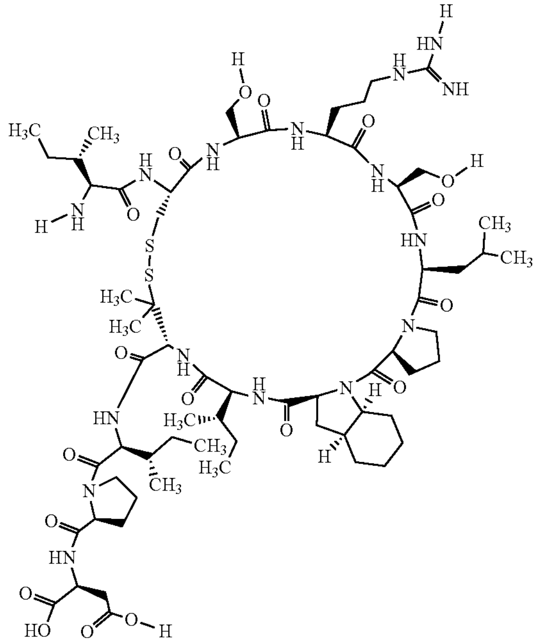 [SMILES: CC[C@H](C)[C@H](N)C(=O)N[C@H]1CSSC(C)(C)[C@@H](C(=O)N[C@H](C(=O)N2CCC[C@H]2C(=O)N[C@@H](CC(=O)O)C(=O)O)[C@@H](C)CC)NC(=O)[C@H]([C@@H](C)CC)NC(=O)[C@@H]2C[C@@H]3CCCC[C@@H]3N2CC(=O)[C@@H]2CCCN2C(=O)[C@H](CC(C)C)NC(=O)[C@H](CO)NC(=O)[C@H](CCCNC(=N)N)NC(=O)[C@H](CO)NC1=O]
Example 443, Sequence: ((N-Me)A)-IC+SRS-((tBu) A)-P-((3R,6R)-1,1-Difluoro-5-azaspiro[2.4]heptane-6-carboxylic acid (enantiomer 1))—I-(Pen)+IP-NH2
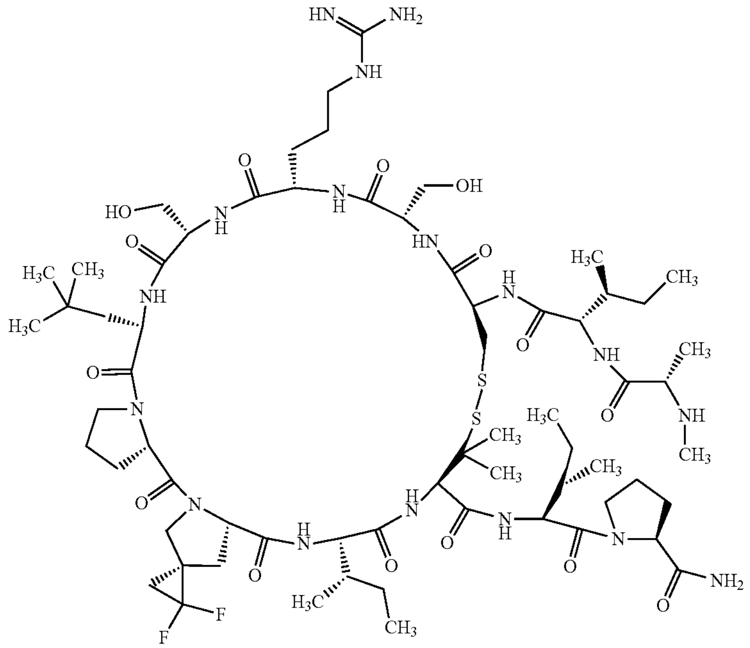 [SMILES: CC[C@H](C)[C@H](NC(=O)[C@H](C)NC)C(=O)N[C@H]1CSSC(C)(C)[C@@H](C(=O)N[C@H](C(=O)N2CCC[C@H]2C(N)=O)[C@@H](C)CC)NC(=O)[C@H]([C@@H](C)CC)NC(=O)[C@@H]2C[C@@]3(CN2C(=O)[C@@H]2CCCN2C(=O)[C@@H](CC(C)(C)C)NC(=O)[C@H](CO)NC(=O)[C@H](CCCNC(=N)N)NC(=O)[C@H](CO)NC1=O)CC3(F)F]

Example 466, Sequence: ((N-Me)G)-IC+SRSLP-(Oic)-I-(Pen)+IPDD-OH
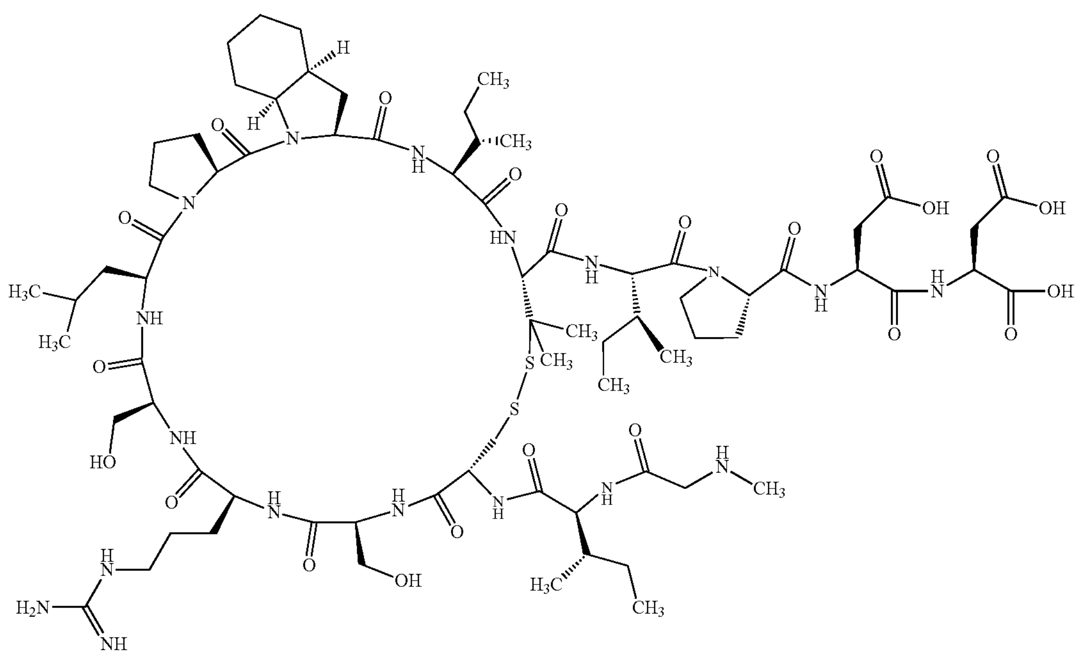 [SMILES: CC[C@H](C)[C@H](NC(=O)CNC)C(=O)N[C@H]1CSSC(C)(C)[C@@H](C(=O)N[C@H](C(=O)N2CCC[C@H]2C(=O)N[C@@H](CC(=O)O)C(=O)N[C@@H](CC(=O)O)C(=O)O)[C@@H](C)CC)NC(=O)[C@H]([C@@H](C)CC)NC(=O)[C@@H]2C[C@@H]3CCCC[C@@H]3N2C(=O)[C@@H]2CCCN2C(=O)[C@H](CC(C)C)NC(=O)[C@H](CO)NC(=O)[C@H](CCCNC(=N)N)NC(=O)[C@H](CO)NC1=O]
Example 499, Sequence: AIC+S-(Arg (13C6.15N4))—SLP-(Oic)-I-(Pen)+IPD-OH
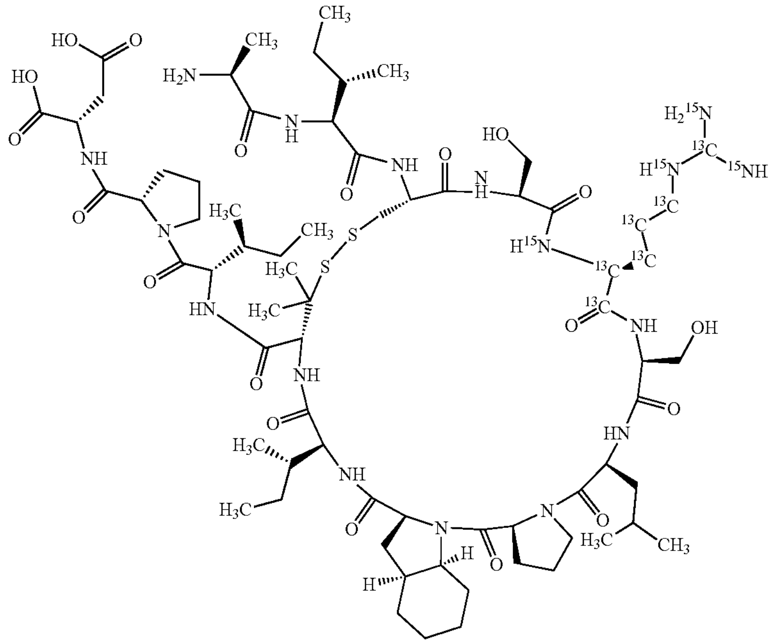 [SMILES: CC[C@H](C)[C@H](NC(=O)[C@H](C)N)C(=O)N[C@H]1CSSC(C)(C)[C@@H](C(=O)N[C@H](C(=O)N2CCC[C@H]2C(=O)N[C@@H](CC(=O)O)C(=O)O)[C@@H](C)CC)NC(=O)[C@H]([C@@H](C)CC)NC(=O)[C@@H]2C[C@@H]3CCCC[C@@H]3N2C(=O)[C@@H]2CCCN2C(=O)[C@H](CC(C)C)NC(=O)[C@H](CO)N[13C](=O)[13C@H]([13CH2][13CH2][13CH2][15NH][13CH]([15NH2])[15NH2])[15NH]C(=O)[C@H](CO)NC1=O]

Biological In Vitro Testings

1. Serine Protease Profiling of Test Compounds

Test compounds were tested in a protease panel consisting of different human serine proteases including kallikrein, plasmin, FXIa, thrombin, factor Xa, tPA, and trypsin.

Test Description

Inhibitory potency and/or selectivity of test compounds were determined. The assays are based on the fluorescent detection of aminomethylcoumarine (AMC), released from the fluorogenic peptidic protease substrates upon protease catalyzed cleavage. The active proteases or zymogenes, typically purified from human plasma or for trypsin from human pancreas, and corresponding substrates are commercially available.

Serine protease assays comprise of the following enzymes and substrates. All enzymes and substrates are diluted in assay buffer (50 mM Tris/HCl pH7.4, 100 mM NaCl, 5 mM CaCl2), 0.1% BSA). The final assay concentrations are given:

Kallikrein (Kordia; 0.2 nM), H-Pro-Phe-Arg-AMC (Bachem I-1295; 5 μM)

Plasmin (Kordia; 0.1 μg/mL, 1.2 nM), MeOSuc-Ala-Phe-Lys-AMC (Bachem I-1275; 50 μM)

Factor XIa (Kordia; 0.15 nM), Boc-Glu(OBzl)-Ala-Arg-AMC (Bachem I-1575; 5 μM)

Thrombin (Kordia; 0.02 nM), Boc-Asp(OBzl)-Pro-Arg-AMC (Bachem I-1560; 5 μM)

Factor Xa (Kordia; 1.3 nM), Boc-Ile-Glu-Gly-Arg-AMC (Bachem I-1100; 5 μM)

Tissue plasminogen activator (tPA, Loxo; 2 nM), CH3SO2-D-Phe-Gly-Arg-AMC (Pentapharm 091-06; 5 μM)

Trypsin (Sigma; 0.042 U/mL), substrate Boc-Ile-Glu-Gly-Arg-AMC (Bachem I-1100; 5 μM)

For determination of test compound potency, the enzyme and corresponding substrate dilutions are used to perform protease assays:

To 384 well microtiter plates (white, Greiner), containing 1 μL/well serial dilutions of test or reference compounds, 20 μL assay buffer, 20 μl enzyme dilution, and 20 μl substrate are added. Control reactions do not contain test compound (DMSO only). After incubation for typically 30 min (linear reaction kinetics) at room temperature, fluorescence (ex 360 nm, em 465 nm) is measured in a microtiter plate fluorescence reader (e.g Tecan Safire II). $IC_{50}$ values are determined by plotting log test compound concentration against the percentage protease activity.

2. Biochemical Human MASP-1 and MASP-2 Assay 2.1 Recombinant Expression and Protein Production of Recombinant Human MASP1 and MASP2 Active Proteases.

A truncated cDNA sequence of human MASP1 encoding the fragment corresponding to the amino acids 297-699 with an C-terminal His Tag and N-terminal Ig-kappa secretion signal (SEQ ID No: 2) was subcloned into the mammalian expression vector pcDNA3.1 (Invitrogen).

A truncated cDNA sequence of human MASP1 encoding the fragment corresponding to the amino acids 297-686 with an C-terminal His Tag and N-terminal Ig-kappa secretion signal (SEQ ID No: 3) was subcloned into the mammalian expression vector pcDNA3.1 (Invitrogen).

The MASP1 or MASP2 expression vectors were transfected into the HEK293 (ATCC No. CRL-1573) cell line using Lipofectamine LTX® Reagent (Thermo-Fischer), as described by the manufacturer. The mature form of the recombinant human MASP1 and MASP2 proteases were secreted into the culture medium. The MASP1 and MASP2 proteins were purified from the conditioned media by affinity chromatography on Ni-NTA Superflow resin (Qiagen) as described by the manufacturer.

2.2 Biochemical Human MASP1 Assay

Recombinant human MASP1 enzyme produced in the HEK 293 cells was diluted in the reaction buffer (50 mM HEPES pH 8.0; 100 mM NaCl; 0.01% CHAPS; 0.5 mM Gluthathione) to the concentration of 20 nM and 25 μl was transferred into each single well of 384-well white microtiter plate (Greiner Bio One 781075). 1 μl of the inhibitor compound solution (dissolved in DMSO, at the corresponding concentration) or pure DMSO as a control was added to the same wells. The enzymatic reaction was initiated by addition of 25 μl of 20 μM solution of the FRET substrate ABZ-MYGGARRL-Lys (Dnp)-NH2; (ABZ-2-aminobenzoyl; DNP-2,4-dinitrophenyl; custom synthesis by Jerini Peptide Technologies, Berlin) in the reaction buffer. The microtiter plate was incubated for 60-120 min at the temperature of 32 C. The increase of fluorescence intensity was measured in appropriate fluorescence plate reader (e.g. TECAN Ultra) using excitation wavelength of 320 nm and emission wavelength of 420 nm. IC50 values were calculated from percentage of inhibition of human MASP1 activity as a function of test compound concentration.

2.3 Biochemical Human MASP2 Assay

Recombinant human MASP2 enzyme produced in the HEK 293 cells was diluted in the reaction buffer (50 mM HEPES pH 8.0; 100 mM NaCl; 0.01% CHAPS; 0.5 mM Gluthathione) to the concentration of 20 nM and 25 μl was transferred into each single well of 384-well white microtiter plate (Greiner Bio One 781075). 1 μl of the inhibitor compound solution (dissolved in DMSO, at the corresponding concentration) or pure DMSO as a control was added to the same wells. The enzymatic reaction was initiated by addition of 25 μl of 60 μM solution of the FRET substrate DABCYL-KISPQGYGRR-Glu(EDANS)—NH2; (Dabcyl-4-((4-(dimethylamino)phenyl)azo)benzoic acid; Edans-5-[(2-Aminoethyl) amino]naphthalene-1-sulfonyl; custom synthesis by Jerini Peptide Technologies, Berlin) in the reaction buffer. The microtiter plate was incubated for 60-120 min at the temperature of 32 C. The increase of fluorescence intensity was measured in appropriate fluorescence plate reader (e.g. TECAN Ultra) using excitation wavelength of 340 nm and emission wavelength of 490 nm. IC50 values were calculated from percentage of inhibition of human MASP2 activity as a function of test compound concentration.

3. C3 Deposition Assay (Human, Rat, Mouse, Dog, Mini-Pig)

The C3 deposition assay was conducted essentially as described (reference). Multiwell plates (Greiner-Nunc 384 Maxi Sorp #464718) were coated over night with Mannan from *Saccharomyces cerevisiae* (Sigma M7504, 10 μg/mL in 0.05 M carbonate-bicarbonate buffer, pH 9.6) at 4° C. Wells were washed three times with TBS and subsequently incubated for 2 hours with 50 μL of 1% bovine serum albumin (BSA) in Tris-buffered saline (TBS) at 37° C. in order to block non-specific binding. After this step and each of the following incubation steps wells were washed three times with C3 wash buffer (TBS; 0.05% Tween 20; 5 mM $CaCl_2$). Wells were next incubated for 30 min at 37° C. with 50 μL of a mixture of test compounds with diluted serum in Veronal buffer (Veronal Puffer (Lonza 12624E). Serum was used at concentrations that did not show detectable C3 deposition to uncoated plates in pre-tests. Appropriate dilutions were found to be in the range of 1:100-1:200 for human, rat, mouse and dog serum and 1:20-1:100 for mini pig serum, respectively. In typical experiments compounds were tested in a range of concentrations between $1\times10^{-9}$ and $5\times10^{-5}$ mol/L. After washing C3 deposition was detected by incubation with a polyclonal rabbit anti-human C3 antibody (Dako (Biozol) A0062) for 1 hour followed by washing and incubation with a peroxidase conjugated Anti Rabbit IgG (Sigma A1949) for 30 min at 37° C. and subsequent washing and incubation with TMB substrate solution in the dark. When appropriately developed the color reaction was stopped by addition of 25 μL of stop solution (Sigma S5814) and quantified on a photometer by measuring absorption at a wavelength of 450 nm. Antibodies were diluted in C3 wash buffer supplemented with 0.5% BSA.

4. Biochemical Rat MASP-1 and MASP-2 Assay 4.1 Recombinant Expression and Protein Production of Recombinant Human and Rat MASP1 and MASP2 Active Proteases.

A truncated cDNA sequence of rat MASP1 encoding the fragment corresponding to the amino acids 302-704 with an C-terminal His Tag and N-terminal Ig-kappa secretion signal (SEQ ID No: 4) was subcloned into the mammalian expression vector pcDNA3.1 (Invitrogen).

A truncated cDNA sequence of rat MASP2 encoding the fragment corresponding to the amino acids 296-685 with a C-terminal His Tag and N-terminal Ig-kappa secretion signal (SEQ ID No: 5) was subcloned into the mammalian expression vector pcDNA3.1 (Invitrogen).

The MASP1 or MASP2 expression vectors were transfected into the HEK293 (ATCC No. CRL-1573) cell line using Lipofectamine LTX® Reagent (Thermo-Fischer), as described by the manufacturer. The mature form of the recombinant rat MASP1 and MASP2 proteases were secreted into the culture medium.

The MASP1 and MASP2 proteins were purified from the conditioned media by affinity chromatography on Ni-NTA Superflow resin (Qiagen) as described by the manufacturer.

4.2 Biochemical Rat MASP1 Assay.

Recombinant rat MASP1 enzyme produced in the HEK 293 cells was diluted in the reaction buffer (50 mM HEPES pH 8.0; 100 mM NaCl; 0.01% CHAPS; 0.5 mM Gluthathione) to the concentration of 4 nM and 25 μl was transferred into each single well of 384-well white microtiter plate (Greiner Bio One 781075). 1 μl of the inhibitor compound solution (dissolved in DMSO, at the corresponding concentration) or pure DMSO as a control was added to the same wells. The enzymatic reaction was initiated by addition of 25 μl of 40 μM solution of the FRET substrate Dabcyl-MYGGARRL-Glu(Edans)-NH2; (Dabcyl-4 ((4-(dimethylamino)phenyl)azo)benzoic acid; Edans-5-[(2-Aminoethyl) amino]naphthalene-1-sulfonyl; custom synthesis by Jerini Peptide Technologies, Berlin) in the reaction buffer. The microtiter plate was incubated for 60-120 min at the temperature of 32 C. The increase of fluorescence intensity was measured in appropriate fluorescence plate reader (e.g. TECAN Ultra) using excitation wavelength of 340 nm and emission wavelength of 490 nm. IC50 values were calculated from percentage of inhibition of rat MASP2 activity as a function of test compound concentration.

4.3 Biochemical Rat MASP2 Assay.

Recombinant rat MASP2 enzyme produced in the HEK 293 cells was diluted in the reaction buffer (50 mM HEPES pH 8.0; 100 mM NaCl; 0.01% CHAPS; 0.5 mM Gluthathione) to the concentration of 20 nM and 25 μl was transferred into each single well of 384-well white microtiter plate (Greiner Bio One 781075). 1 μl of the inhibitor compound solution (dissolved in DMSO, at the corresponding concentration) or pure DMSO as a control was added to the same wells. The enzymatic reaction was initiated by addition of 25 μl of 30 μM solution of the FRET substrate Abz-IEGRTSED-(Lys)Dnp-NH2; (ABZ-2-aminobenzoyl; DNP-2,4-dinitrophenyl; custom synthesis by Jerini Peptide Technologies, Berlin) in the reaction buffer. The microtiter plate was incubated for 60-120 min at the temperature of 32 C. The increase of fluorescence intensity was measured in appropriate fluorescence plate reader (e.g. TECAN Ultra) using excitation wavelength of 320 nm and emission wavelength of 420 nm. IC50 values were calculated from percentage of inhibition of rat MASP2 activity as a function of test compound concentration.

TABLE 18

Average IC50 of the reference peptides

| Reference No | human MASP1 IC50 [mol/L] | human MASP2 |IC50 [mol/L] | Human C3-DEPOSITION SERUM| IC50 [mol/L] |
|---|---|---|---|
| 1 | 1.56E−08 | 1.09E−06 | 1.52E−07 |
| 2 | 1.80E−08 | 6.10E−07 | 1.85E−07 |
| 3 | 1.80E−08 | 6.10E−07 | 5.10E−08 |
| A | 7.45E−09 | 9.14E−07 | 3.94E−08 |
| B | 8.00E−09 | 3.90E−07 | 2.82E−08 |
| C | 3.60E−09 | 3.00E−06 | 2.57E−08 |

TABLE 19

Average IC50 of the peptides of the invention

| Example No | human MASP1 IC50 [mol/L] | human MASP2 |IC50 [mol/L] | Human C3-DEPOSITION SERUM| IC50 [mol/L] |
|---|---|---|---|
| 4 | 9.30E−10 | 6.80E−08 | 8.11E−09 |
| 5 | 9.60E−10 | 9.70E−08 | 1.03E−08 |
| 6 | 1.10E−09 | 5.00E−08 | 1.39E−08 |
| 7 | 1.10E−09 | 2.30E−08 | 8.71E−08 |
| 8 | 1.10E−09 | | 1.45E−08 |
| 9 | 1.14E−09 | 5.00E−08 | 2.85E−08 |
| 10 | 1.19E−09 | 3.60E−08 | 2.75E−08 |
| 11 | 1.20E−09 | 6.20E−07 | 3.86E−08 |
| 12 | 1.20E−09 | 3.70E−08 | 1.42E−07 |
| 13 | 1.85E−09 | 1.00E−07 | 6.62E−09 |
| 14 | 1.30E−09 | 6.20E−08 | 1.18E−07 |
| 15 | 1.30E−09 | 8.70E−08 | 1.56E−08 |
| 16 | 1.30E−09 | 2.80E−08 | 5.01E−09 |
| 17 | 1.33E−09 | 1.80E−08 | 3.82E−07 |
| 18 | 1.35E−09 | 4.00E−08 | 2.09E−07 |
| 19 | 1.36E−09 | 1.00E−07 | 1.24E−07 |
| 20 | 1.40E−09 | 7.20E−07 | 3.65E−08 |
| 21 | 1.40E−09 | 6.20E−08 | 1.63E−08 |
| 22 | 1.40E−09 | 5.30E−08 | 1.39E−08 |
| 23 | 1.40E−09 | 4.00E−08 | 6.25E−09 |
| 24 | 1.43E−09 | 9.80E−08 | 2.83E−08 |
| 25 | 1.50E−09 | 1.00E−07 | 1.28E−08 |
| 26 | 1.50E−09 | 9.30E−08 | 1.04E−08 |
| 27 | 1.50E−09 | 1.40E−07 | 8.50E−09 |
| 28 | 1.50E−09 | 5.60E−08 | 1.31E−08 |
| 29 | 2.45E−09 | 4.20E−08 | 6.99E−09 |
| 30 | 1.53E−09 | 1.40E−07 | 3.61E−08 |
| 31 | 1.57E−09 | 1.77E−08 | 4.28E−08 |
| 32 | 1.60E−09 | 1.10E−07 | 2.93E−08 |
| 33 | 1.60E−09 | | 1.02E−08 |
| 34 | 1.60E−09 | 4.50E−08 | 3.92E−08 |
| 35 | 1.65E−09 | 1.20E−07 | 1.57E−07 |
| 36 | 1.65E−09 | 2.60E−08 | 4.51E−07 |
| 37 | 1.70E−09 | 1.20E−07 | 1.46E−08 |
| 38 | 1.70E−09 | 8.70E−08 | 7.26E−08 |
| 39 | 1.70E−09 | 3.10E−08 | 1.08E−08 |
| 40 | 1.70E−09 | 5.90E−08 | 1.21E−08 |
| 41 | 1.80E−09 | 4.00E−08 | 1.21E−08 |
| 42 | 1.80E−09 | 3.60E−08 | 1.41E−08 |
| 43 | 1.80E−09 | 7.60E−08 | 2.73E−08 |

TABLE 19-continued

Average IC50 of the peptides of the invention

| Example No | human MASP1 IC50 [mol/L] | human MASP2 |IC50 [mol/L] | Human C3-DEPOSITION SERUM| IC50 [mol/L] |
|---|---|---|---|
| 44 | 1.80E−09 | 7.30E−08 | 6.85E−08 |
| 45 | 1.83E−09 | 2.45E−08 | 1.86E−08 |
| 46 | 1.90E−09 | 4.30E−07 | 2.57E−08 |
| 47 | 1.90E−09 | 1.20E−07 | 4.34E−08 |
| 48 | 1.95E−09 | 2.25E−07 | 1.02E−07 |
| 49 | 2.00E−09 | 1.10E−07 | 3.56E−07 |
| 50 | 2.00E−09 | 7.60E−08 | 3.19E−08 |
| 51 | 2.00E−09 | 4.40E−08 | 3.95E−08 |
| 52 | 2.00E−09 | 2.40E−08 | 2.30E−08 |
| 53 | 2.00E−09 | 8.00E−08 | 3.03E−08 |
| 54 | 2.00E−09 | 7.30E−08 | 8.81E−09 |
| 55 | 2.00E−09 | 4.20E−08 | 5.40E−08 |
| 56 | 2.00E−09 | 1.30E−07 | 6.97E−09 |
| 57 | 2.00E−09 | 4.70E−08 | 1.17E−08 |
| 58 | 2.00E−09 | 4.20E−08 | 2.13E−08 |
| 59 | 2.09E−09 | | 2.38E−07 |
| 60 | 2.10E−09 | 7.20E−08 | 1.15E−08 |
| 61 | 2.10E−09 | 9.80E−08 | 3.94E−08 |
| 62 | 2.10E−09 | 9.60E−08 | 5.91E−08 |
| 63 | 2.10E−09 | 1.30E−07 | 7.91E−08 |
| 64 | 2.10E−09 | 2.00E−08 | 2.98E−08 |
| 65 | 2.20E−09 | 9.80E−08 | 9.82E−08 |
| 66 | 2.20E−09 | 1.20E−07 | 3.60E−07 |
| 67 | 2.20E−09 | 4.30E−08 | 1.21E−07 |
| 68 | 2.20E−09 | 7.00E−08 | 1.40E−08 |
| 69 | 2.20E−09 | 5.10E−08 | 1.31E−08 |
| 70 | 2.20E−09 | 6.50E−08 | 4.84E−08 |
| 71 | 2.20E−09 | 6.30E−08 | 7.11E−08 |
| 72 | 2.20E−09 | 4.20E−08 | 5.98E−08 |
| 73 | 2.20E−09 | 3.00E−08 | 7.04E−08 |
| 74 | 2.20E−09 | 5.20E−08 | 5.20E−08 |
| 75 | 2.23E−09 | 1.50E−07 | 3.20E−08 |
| 76 | 2.30E−09 | 8.70E−08 | 1.18E−08 |
| 77 | 2.40E−09 | 1.50E−07 | 5.33E−08 |
| 78 | 2.40E−09 | 1.70E−07 | 1.46E−08 |
| 79 | 2.40E−09 | 1.10E−07 | 2.59E−07 |
| 80 | 2.40E−09 | 5.70E−08 | 2.00E−08 |
| 81 | 2.40E−09 | 6.40E−08 | 1.62E−08 |
| 82 | 2.40E−09 | 6.80E−08 | 1.33E−08 |
| 83 | 2.40E−09 | 1.10E−07 | 3.48E−08 |
| 84 | 2.40E−09 | 1.00E−07 | 7.00E−08 |
| 85 | 2.40E−09 | 5.80E−08 | 4.82E−08 |
| 86 | 2.45E−09 | 1.85E−07 | 1.21E−06 |
| 87 | 2.50E−09 | 1.90E−07 | 1.52E−08 |
| 88 | 2.50E−09 | 1.20E−07 | 8.08E−08 |
| 89 | 2.50E−09 | 4.80E−08 | 4.30E−08 |
| 90 | 2.50E−09 | 7.00E−08 | 1.21E−07 |
| 91 | 2.60E−09 | 1.30E−07 | 1.12E−08 |
| 92 | 2.60E−09 | 3.60E−07 | 3.77E−08 |
| 93 | 2.60E−09 | 3.00E−08 | 4.00E−08 |
| 94 | 2.60E−09 | 4.70E−08 | 2.98E−08 |
| 95 | 2.60E−09 | 3.80E−08 | 1.21E−08 |
| 96 | 2.60E−09 | 9.20E−08 | 1.89E−08 |
| 97 | 2.60E−09 | 1.30E−07 | 4.84E−08 |
| 98 | 2.60E−09 | 8.30E−08 | 1.04E−07 |
| 99 | 2.70E−09 | 4.90E−07 | 1.35E−08 |
| 100 | 2.70E−09 | 3.20E−07 | 1.09E−08 |
| 101 | 2.70E−09 | 2.00E−07 | 8.13E−08 |
| 102 | 2.80E−09 | 2.80E−06 | 2.51E−07 |
| 103 | 2.80E−09 | 2.30E−07 | 4.30E−07 |
| 104 | 2.80E−09 | 4.80E−08 | 3.29E−07 |
| 105 | 2.80E−09 | 1.50E−07 | 5.69E−08 |
| 106 | 2.80E−09 | 1.45E−07 | 1.21E−08 |
| 107 | 2.80E−09 | 1.80E−07 | 1.10E−07 |
| 108 | 2.80E−09 | 1.30E−07 | 1.07E−07 |
| 109 | 2.90E−09 | 6.96E−08 | 1.35E−07 |
| 110 | 2.90E−09 | 2.00E−07 | 8.24E−08 |
| 111 | 2.90E−09 | 1.60E−07 | 4.87E−08 |
| 112 | 2.90E−09 | 1.30E−07 | 4.50E−08 |
| 113 | 2.90E−09 | 8.90E−08 | 3.89E−08 |
| 114 | 3.00E−09 | 3.30E−07 | 1.40E−08 |
| 115 | 3.00E−09 | 3.00E−08 | 1.92E−08 |
| 116 | 3.00E−09 | 4.60E−08 | 1.54E−08 |

TABLE 19-continued

Average IC50 of the peptides of the invention

| Example No | human MASP1 IC50 [mol/L] | human MASP2 |IC50 [mol/L] | Human C3-DEPOSITION SERUM| IC50 [mol/L] |
|---|---|---|---|
| 117 | 3.00E−09 | 3.60E−07 | 6.81E−08 |
| 118 | 3.00E−09 | 1.40E−07 | 5.03E−08 |
| 119 | 3.00E−09 | 2.00E−07 | 7.81E−08 |
| 120 | 3.10E−09 | 5.90E−07 | 3.65E−08 |
| 121 | 3.10E−09 | 8.30E−08 | 5.78E−08 |
| 122 | 3.10E−09 | 1.60E−07 | 8.44E−08 |
| 123 | 3.20E−09 | 9.70E−08 | 5.55E−09 |
| 124 | 3.20E−09 | 7.50E−08 | 1.40E−08 |
| 125 | 3.20E−09 | 9.30E−08 | 2.83E−08 |
| 126 | 3.20E−09 | 2.40E−08 | 1.49E−08 |
| 127 | 3.20E−09 | 7.90E−08 | 3.96E−08 |
| 128 | 3.20E−09 | 1.60E−06 | 1.24E−07 |
| 129 | 3.30E−09 | 1.60E−07 | 2.76E−08 |
| 130 | 3.30E−09 | 7.10E−08 | 5.43E−08 |
| 131 | 3.30E−09 | 2.00E−07 | 4.02E−08 |
| 132 | 3.30E−09 | 1.40E−07 | 1.07E−07 |
| 133 | 3.30E−09 | 1.60E−07 | 1.17E−07 |
| 134 | 3.40E−09 | 4.10E−07 | 5.12E−08 |
| 135 | 3.40E−09 | 9.90E−08 | 5.12E−08 |
| 136 | 3.40E−09 | 8.70E−08 | 5.53E−08 |
| 137 | 3.50E−09 | 9.80E−08 | 5.34E−08 |
| 138 | 3.50E−09 | 1.40E−07 | 1.14E−07 |
| 139 | 3.50E−09 | 1.90E−07 | 6.94E−08 |
| 140 | 3.50E−09 | 9.00E−08 | 6.80E−08 |
| 141 | 3.50E−09 | 2.10E−07 | 1.83E−07 |
| 142 | 2.13E−09 | 1.26E−07 | 1.24E−08 |
| 143 | 3.60E−09 | 7.45E−08 | 4.11E−08 |
| 144 | 3.60E−09 | 1.30E−07 | 5.53E−08 |
| 145 | 3.60E−09 | 6.00E−08 | 1.01E−07 |
| 146 | 3.60E−09 | 1.70E−07 | 9.88E−08 |
| 147 | 3.70E−09 | 6.80E−08 | 6.12E−08 |
| 148 | 3.70E−09 | 5.60E−08 | 5.00E−08 |
| 149 | 3.70E−09 | 5.90E−07 | 7.80E−08 |
| 150 | 3.70E−09 | 9.70E−08 | 7.41E−08 |
| 151 | 3.70E−09 | 1.00E−07 | 3.00E−08 |
| 152 | 3.75E−09 | 1.95E−07 | 4.23E−08 |
| 153 | 4.65E−09 | 3.16E−07 | 2.05E−08 |
| 154 | 3.80E−09 | 1.40E−07 | 2.24E−07 |
| 155 | 3.80E−09 | 2.10E−07 | 2.24E−08 |
| 156 | 3.80E−09 | 4.40E−08 | 2.73E−08 |
| 157 | 3.80E−09 | 6.30E−08 | 1.57E−06 |
| 158 | 3.90E−09 | 9.30E−07 | 1.21E−08 |
| 159 | 3.90E−09 | 1.70E−07 | 2.10E−08 |
| 160 | 3.90E−09 | 1.00E−07 | 6.39E−08 |
| 161 | 3.90E−09 | 1.70E−07 | 7.56E−08 |
| 162 | 3.90E−09 | 1.60E−07 | 8.22E−08 |
| 163 | 4.00E−09 | 6.40E−08 | 1.77E−08 |
| 164 | 4.00E−09 | 5.70E−08 | 8.16E−08 |
| 165 | 4.05E−09 | 1.50E−07 | 3.60E−08 |
| 166 | 4.20E−09 | 1.30E−07 | 3.34E−08 |
| 167 | 4.20E−09 | 2.30E−07 | 7.05E−08 |
| 168 | 4.20E−09 | 1.20E−07 | 4.75E−08 |
| 169 | 4.25E−09 | 5.20E−08 | 8.68E−07 |
| 170 | 4.30E−09 | 6.80E−08 | 1.33E−08 |
| 171 | 4.30E−09 | 3.00E−08 | 1.95E−08 |
| 172 | 4.30E−09 | 5.90E−08 | 3.59E−08 |
| 173 | 4.30E−09 | 2.00E−07 | 1.03E−07 |
| 174 | 4.35E−09 | 6.55E−08 | 2.80E−07 |
| 175 | 4.40E−09 | 1.30E−07 | 1.31E−08 |
| 176 | 4.40E−09 | 2.40E−07 | 1.37E−08 |
| 177 | 4.40E−09 | 8.50E−07 | 2.75E−08 |
| 178 | 4.40E−09 | 6.80E−08 | 4.68E−08 |
| 179 | 4.40E−09 | 1.70E−07 | 8.65E−08 |
| 180 | 4.40E−09 | 1.80E−07 | 1.11E−08 |
| 181 | 4.50E−09 | 1.70E−07 | 1.35E−05 |
| 182 | 4.50E−09 | 6.80E−08 | 1.25E−07 |
| 183 | 4.70E−09 | 1.10E−06 | 4.07E−08 |
| 184 | 4.70E−09 | 2.00E−07 | 4.30E−08 |
| 185 | 4.80E−09 | 2.45E−07 | 6.74E−09 |
| 186 | 4.80E−09 | 1.70E−07 | 1.16E−08 |
| 187 | 4.90E−09 | 8.10E−09 | 1.65E−08 |
| 188 | 4.90E−09 | 5.50E−07 | 9.66E−08 |
| 189 | 4.90E−09 | 1.40E−07 | 9.90E−08 |

TABLE 19-continued

Average IC50 of the peptides of the invention

| Example No | human MASP1 IC50 [mol/L] | human MASP2 |IC50 [mol/L] | Human C3-DEPOSITION SERUM| IC50 [mol/L] |
|---|---|---|---|
| 190 | 4.90E−09 | 2.00E−07 | 2.81E−07 |
| 191 | 5.00E−09 | 2.00E−07 | 9.12E−08 |
| 192 | 5.00E−09 | 1.50E−07 | 1.15E−07 |
| 193 | 5.00E−09 | 1.40E−07 | 4.15E−08 |
| 194 | 5.10E−09 | 1.00E−07 | 8.29E−08 |
| 195 | 5.10E−09 | 8.10E−08 | 2.27E−08 |
| 196 | 5.10E−09 | 1.80E−07 | 9.68E−08 |
| 197 | 5.10E−09 | 1.70E−08 | 6.34E−08 |
| 198 | 5.20E−09 | 2.50E−07 | 3.89E−08 |
| 199 | 5.20E−09 | 1.90E−08 | 4.36E−08 |
| 200 | 5.20E−09 | 1.90E−07 | 5.26E−08 |
| 201 | 5.30E−09 | 1.00E−07 | 1.56E−07 |
| 202 | 5.30E−09 | 1.30E−07 | 1.10E−07 |
| 203 | 5.40E−09 | 1.70E−07 | 1.53E−07 |
| 204 | 5.40E−09 | 1.60E−08 | 2.17E−08 |
| 205 | 5.50E−09 | 1.40E−05 | 2.51E−08 |
| 206 | 5.70E−09 | 4.40E−08 | 3.34E−08 |
| 207 | 5.70E−09 | 7.40E−08 | 2.89E−07 |
| 208 | 5.70E−09 | 1.50E−08 | 1.39E−08 |
| 209 | 5.80E−09 | 5.10E−08 | 1.48E−08 |
| 210 | 5.80E−09 | 6.10E−08 | 2.29E−08 |
| 211 | 5.80E−09 | 7.30E−08 | 3.55E−08 |
| 212 | 6.00E−09 | 7.40E−07 | 1.43E−08 |
| 213 | 6.10E−09 | 1.70E−07 | 5.82E−08 |
| 214 | 6.10E−09 | 2.70E−08 | 2.24E−08 |
| 215 | 6.20E−09 | 1.80E−07 | 1.27E−07 |
| 216 | 6.30E−09 | 2.20E−07 | 2.51E−08 |
| 217 | 6.30E−09 | 1.30E−07 | 6.43E−08 |
| 218 | 6.40E−09 | 6.50E−08 | 2.86E−08 |
| 219 | 6.40E−09 | 1.60E−08 | 2.89E−08 |
| 220 | 6.50E−09 | 4.10E−07 | 1.48E−07 |
| 221 | 6.50E−09 | 1.30E−08 | 1.67E−08 |
| 222 | 6.50E−09 | 1.40E−07 | 7.36E−08 |
| 223 | 6.60E−09 | 1.20E−07 | 2.70E−07 |
| 224 | 6.90E−09 | 4.00E−07 | 1.55E−08 |
| 225 | 6.90E−09 | 4.90E−08 | 6.88E−08 |
| 226 | 7.00E−09 | 8.50E−09 | 3.03E−08 |
| 227 | 7.00E−09 | 1.00E−07 | 1.20E−07 |
| 228 | 7.10E−09 | 4.20E−06 | 3.10E−08 |
| 229 | 7.10E−09 | 2.00E−07 | 2.97E−08 |
| 230 | 7.20E−09 | 3.00E−07 | 4.31E−07 |
| 231 | 7.20E−09 | 1.90E−07 | 9.22E−09 |
| 232 | 7.30E−09 | 1.70E−06 | 1.25E−07 |
| 233 | 7.30E−09 | 1.90E−08 | 1.48E−08 |
| 234 | 7.40E−09 | 2.60E−07 | 9.46E−09 |
| 235 | 7.60E−09 | 6.30E−08 | 4.91E−08 |
| 236 | 7.80E−09 | 1.90E−07 | 2.72E−08 |
| 237 | 9.30E−09 | 6.40E−08 | 1.47E−08 |
| 238 | 8.10E−09 | 1.30E−07 | 1.25E−07 |
| 239 | 8.10E−09 | 3.50E−08 | 5.19E−08 |
| 240 | 8.10E−09 | 5.60E−08 | 2.99E−08 |
| 241 | 8.20E−09 | 7.25E−08 | 2.20E−08 |
| 242 | 8.20E−09 | | 1.98E−08 |
| 243 | 8.30E−09 | 1.20E−07 | 3.36E−08 |
| 244 | 8.45E−09 | 2.95E−07 | 1.74E−07 |
| 245 | 8.50E−09 | 3.30E−08 | 2.08E−08 |
| 246 | 8.80E−09 | 2.60E−06 | 2.17E−07 |
| 247 | 8.90E−09 | 9.20E−08 | 2.67E−08 |
| 248 | 8.90E−09 | 3.00E−07 | 2.71E−08 |
| 249 | 1.40E−09 | 3.70E−08 | |
| 250 | 9.30E−09 | 2.60E−07 | 2.53E−08 |
| 251 | 9.30E−09 | | 1.66E−08 |
| 252 | 9.40E−09 | 4.80E−07 | 6.48E−08 |
| 253 | 9.50E−09 | 4.40E−07 | 7.70E−08 |
| 254 | 9.80E−09 | 7.35E−08 | 1.53E−08 |
| 255 | 9.90E−09 | 1.60E−08 | 2.82E−08 |
| 256 | 1.00E−08 | 6.20E−07 | 1.94E−07 |
| 257 | 1.00E−08 | 1.10E−07 | 2.48E−08 |
| 258 | 1.00E−08 | 4.00E−07 | 1.40E−08 |
| 259 | 1.00E−08 | 3.20E−08 | 7.83E−08 |
| 260 | 1.01E−08 | 2.70E−06 | 5.63E−08 |
| 261 | 1.10E−08 | 1.50E−06 | 1.62E−07 |
| 262 | 1.10E−08 | 1.70E−07 | 3.55E−08 |

TABLE 19-continued

Average IC50 of the peptides of the invention

| Example No | human MASP1 IC50 [mol/L] | human MASP2 |IC50 [mol/L] | Human C3-DEPOSITION SERUM| IC50 [mol/L] |
|---|---|---|---|
| 263 | 1.10E−08 | 2.10E−07 | 6.34E−08 |
| 264 | 1.10E−09 | 3.50E−08 | 7.17E−09 |
| 265 | 1.10E−08 | 1.20E−06 | 3.20E−06 |
| 266 | 1.10E−08 | 3.80E−08 | 2.18E−08 |
| 267 | 1.10E−08 | 5.70E−08 | 8.29E−08 |
| 268 | 1.20E−08 | 3.70E−07 | 1.62E−07 |
| 269 | 1.20E−08 | 1.70E−08 | 2.23E−08 |
| 270 | 1.20E−08 | 2.90E−07 | 1.35E−07 |
| 271 | 1.30E−08 | 5.00E−07 | 3.48E−08 |
| 272 | 1.30E−08 | 2.90E−08 | 2.96E−08 |
| 273 | 1.30E−08 | 4.70E−09 | 1.82E−08 |
| 274 | 1.30E−08 | 5.50E−08 | 1.79E−07 |
| 275 | 1.40E−08 | 1.10E−06 | 4.71E−08 |
| 276 | 1.40E−08 | 1.30E−06 | 3.38E−06 |
| 277 | 1.40E−08 | 1.70E−07 | 2.45E−07 |
| 278 | 1.40E−08 | 3.30E−07 | 2.16E−08 |
| 279 | 1.40E−08 | 1.10E−06 | 3.44E−08 |
| 280 | 1.40E−08 | 6.10E−08 | 8.78E−08 |
| 281 | 1.50E−08 | 5.35E−07 | 4.47E−08 |
| 282 | 1.50E−08 | 8.91E−07 | 1.59E−07 |
| 283 | 1.50E−08 | 4.20E−08 | 6.98E−08 |
| 284 | 1.50E−08 | 9.30E−09 | 1.86E−08 |
| 285 | 1.50E−08 | 2.60E−08 | 2.64E−07 |
| 286 | 1.60E−08 | 1.60E−07 | 4.29E−06 |
| 287 | 1.60E−08 | 4.90E−07 | 2.70E−07 |
| 288 | 1.60E−08 | 6.50E−06 | 6.96E−07 |
| 289 | 1.60E−08 | 1.60E−07 | 4.11E−07 |
| 290 | 1.60E−08 | 2.50E−08 | 2.54E−08 |
| 291 | 1.60E−08 | 8.10E−08 | 3.29E−08 |
| 292 | 1.60E−08 | 9.30E−07 | 1.30E−08 |
| 293 | 1.70E−08 | 6.03E−07 | 3.87E−07 |
| 294 | 1.70E−08 | 4.90E−09 | 4.19E−08 |
| 295 | 1.70E−08 | 1.10E−08 | 6.37E−08 |
| 296 | 1.70E−08 | 1.20E−08 | 1.26E−08 |
| 297 | 1.80E−08 | 5.00E−07 | 1.20E−07 |
| 298 | 1.80E−08 | 4.20E−08 | 2.32E−08 |
| 299 | 1.80E−08 | 9.10E−07 | 7.36E−07 |
| 300 | 1.80E−08 | 4.50E−08 | 5.98E−08 |
| 301 | 1.80E−08 | 1.90E−08 | 1.46E−07 |
| 302 | 1.90E−08 | 1.40E−06 | 7.96E−08 |
| 303 | 1.90E−08 | 5.00E−07 | 1.67E−07 |
| 304 | 1.90E−08 | 2.70E−08 | 1.84E−08 |
| 305 | 1.90E−08 | 9.40E−09 | 7.34E−08 |
| 306 | 2.00E−08 | 4.50E−07 | 3.17E−07 |
| 307 | 2.00E−08 | 4.30E−08 | 2.65E−08 |
| 308 | 2.00E−08 | 5.00E−09 | 1.68E−08 |
| 309 | 2.00E−08 | 1.20E−08 | 2.06E−08 |
| 310 | 2.00E−08 | 3.00E−06 | 2.26E−07 |
| 311 | 2.00E−08 | 4.90E−08 | 1.94E−08 |
| 312 | 2.10E−08 | 5.30E−07 | 2.45E−06 |
| 313 | 2.10E−08 | 2.50E−07 | 3.16E−07 |
| 314 | 2.10E−08 | 2.60E−07 | 2.09E−07 |
| 315 | 2.10E−08 | 4.50E−09 | 2.27E−08 |
| 316 | 2.10E−08 | 6.60E−07 | 2.00E−07 |
| 317 | 2.20E−08 | 2.10E−07 | 3.86E−07 |
| 318 | 2.20E−08 | 6.10E−07 | 3.47E−07 |
| 319 | 2.20E−08 | 1.80E−08 | 2.13E−08 |
| 320 | 2.20E−08 | 1.90E−07 | 6.43E−08 |
| 321 | 2.20E−08 | 1.80E−06 | 2.74E−07 |
| 322 | 2.20E−08 | 1.50E−07 | 1.13E−07 |
| 323 | 6.96E−09 | 5.60E−07 | 2.32E−08 |
| 324 | 2.30E−08 | 7.20E−08 | 3.51E−07 |
| 325 | 2.30E−08 | 4.50E−07 | 1.19E−06 |
| 326 | 2.30E−08 | 7.10E−07 | 2.15E−08 |
| 327 | 2.30E−08 | 2.50E−08 | 1.94E−08 |
| 328 | 2.30E−08 | 1.30E−08 | 3.16E−08 |
| 329 | 2.40E−08 | 2.60E−07 | 6.86E−06 |
| 330 | 2.40E−08 | 1.30E−07 | 3.30E−08 |
| 331 | 2.40E−08 | 6.10E−07 | 1.81E−07 |
| 332 | 2.50E−08 | 2.30E−08 | 2.43E−08 |
| 333 | 2.50E−08 | 8.40E−09 | 1.40E−08 |
| 334 | 2.50E−08 | 5.50E−09 | 7.97E−09 |
| 335 | 2.50E−08 | 1.80E−07 | 5.66E−08 |

TABLE 19-continued

Average IC50 of the peptides of the invention

| Example No | human MASP1 IC50 [mol/L] | human MASP2 |IC50 [mol/L] | Human C3-DEPOSITION SERUM| IC50 [mol/L] |
|---|---|---|---|
| 336 | 2.50E−08 | 6.90E−07 | 2.72E−07 |
| 337 | 2.50E−08 | 2.00E−06 | 2.51E−05 |
| 338 | 2.60E−08 | 3.60E−07 | 3.35E−07 |
| 339 | 2.60E−08 | 6.40E−07 | 4.73E−07 |
| 340 | 2.60E−08 | 3.00E−07 | 8.69E−07 |
| 341 | 2.60E−08 | 4.30E−07 | 2.89E−07 |
| 342 | 2.60E−08 | 1.70E−08 | 4.06E−08 |
| 343 | 2.70E−08 | 1.20E−08 | 1.60E−08 |
| 344 | 2.70E−08 | 5.10E−08 | 4.43E−08 |
| 345 | 2.70E−08 | 3.90E−07 | 1.93E−07 |
| 346 | 2.70E−08 | 1.90E−07 | 6.84E−08 |
| 347 | 2.75E−08 | 8.55E−07 | 1.51E−07 |
| 348 | 2.80E−08 | 6.90E−07 | 4.91E−06 |
| 349 | 9.60E−09 | 4.20E−07 | 7.06E−08 |
| 350 | 2.80E−08 | 3.70E−07 | 1.68E−07 |
| 351 | 2.80E−08 | 1.20E−08 | 7.74E−09 |
| 352 | 2.80E−08 | 7.10E−08 | 2.85E−07 |
| 353 | 2.80E−08 | 5.00E−08 | 4.47E−07 |
| 354 | 2.90E−08 | 5.10E−07 | 5.94E−07 |
| 355 | 2.90E−08 | 9.30E−07 | 1.62E−07 |
| 356 | 2.90E−08 | 1.60E−08 | 2.88E−08 |
| 357 | 3.10E−08 | 1.30E−06 | 1.15E−05 |
| 358 | 3.10E−08 | 1.90E−08 | 4.38E−08 |
| 359 | 3.10E−08 | 3.40E−08 | 3.26E−08 |
| 360 | 3.10E−08 | 5.50E−08 | 9.13E−08 |
| 361 | 3.20E−08 | 1.00E−06 | 2.30E−07 |
| 362 | 3.30E−08 | 6.50E−08 | 3.94E−08 |
| 363 | 3.30E−08 | 1.20E−07 | 1.30E−07 |
| 364 | 3.30E−08 | 9.80E−08 | 2.28E−08 |
| 365 | 3.40E−08 | 1.04E−08 | 4.57E−08 |
| 366 | 3.40E−08 | 9.00E−09 | 4.71E−09 |
| 367 | 3.50E−08 | 6.00E−07 | 1.31E−06 |
| 368 | 3.50E−08 | 1.20E−06 | 5.58E−07 |
| 369 | 3.50E−08 | 4.20E−07 | 6.06E−08 |
| 370 | 3.50E−08 | 9.35E−08 | 1.30E−08 |
| 371 | 3.60E−08 | 8.10E−07 | 3.15E−07 |
| 372 | 3.60E−08 | 6.60E−07 | 4.55E−07 |
| 373 | 3.70E−08 | 4.50E−07 | 5.24E−07 |
| 374 | 3.70E−08 | 1.40E−05 | 6.70E−05 |
| 375 | 3.70E−08 | 9.60E−09 | 1.13E−07 |
| 376 | 1.10E−09 | 3.50E−08 | 1.38E−08 |
| 377 | 3.70E−08 | 8.10E−07 | 2.67E−07 |
| 378 | 3.80E−08 | 1.10E−06 | 3.10E−07 |
| 379 | 3.90E−08 | 3.60E−07 | 1.92E−07 |
| 380 | 4.00E−08 | 8.10E−07 | 9.47E−07 |
| 381 | 4.00E−08 | 5.50E−07 | 5.47E−08 |
| 382 | 4.00E−08 | 4.10E−08 | 1.27E−07 |
| 383 | 4.00E−08 | 8.00E−07 | 1.53E−05 |
| 384 | 4.20E−08 | 2.60E−07 | 8.12E−07 |
| 385 | 4.25E−08 | 8.95E−09 | 5.64E−08 |
| 386 | 4.30E−08 | 7.50E−07 | 3.05E−07 |
| 387 | 4.40E−08 | 2.20E−06 | 8.76E−08 |
| 388 | 4.50E−08 | 7.50E−07 | 4.33E−07 |
| 389 | 4.60E−08 | 3.30E−07 | 6.03E−08 |
| 390 | 4.70E−08 | 1.30E−06 | 1.15E−06 |
| 391 | 4.70E−08 | 9.50E−09 | 2.57E−08 |
| 392 | 4.70E−08 | 8.00E−08 | 6.24E−08 |
| 393 | 4.90E−08 | 3.80E−06 | 5.45E−07 |
| 394 | 5.20E−08 | | 1.12E−07 |
| 395 | 5.20E−08 | 1.20E−08 | 4.59E−08 |
| 396 | 5.30E−08 | 2.80E−08 | 2.55E−08 |
| 397 | 5.40E−08 | 3.80E−06 | 7.20E−07 |
| 398 | 5.40E−08 | 2.20E−08 | 1.92E−08 |
| 399 | 5.50E−08 | 5.20E−07 | 3.42E−07 |
| 400 | 5.50E−08 | 9.00E−09 | 5.26E−08 |
| 401 | 5.60E−08 | | 4.48E−07 |
| 402 | 5.80E−08 | 2.10E−06 | 2.55E−05 |
| 403 | 5.90E−08 | 7.40E−07 | 6.59E−07 |
| 404 | 6.20E−08 | 1.70E−08 | 3.51E−08 |
| 405 | 6.30E−08 | 9.80E−07 | 8.69E−08 |
| 406 | 6.40E−08 | 1.30E−08 | 6.13E−08 |
| 407 | 6.40E−08 | 1.20E−08 | 1.54E−08 |
| 408 | 6.90E−08 | 3.20E−08 | 2.86E−07 |
| 409 | 7.10E−08 | 5.70E−07 | 1.53E−05 |
| 410 | 7.60E−08 | 2.70E−06 | 4.32E−06 |
| 411 | 7.60E−08 | 2.50E−06 | 2.84E−07 |
| 412 | 7.70E−08 | 5.00E−06 | 1.83E−07 |
| 413 | 7.80E−08 | 2.00E−06 | 1.05E−05 |
| 414 | 8.60E−08 | 4.00E−06 | 2.38E−05 |
| 415 | 8.60E−08 | 2.00E−08 | 1.86E−08 |
| 416 | 8.70E−08 | 1.90E−07 | 4.14E−05 |
| 417 | 8.90E−08 | 1.70E−05 | 2.07E−07 |
| 418 | 1.80E−09 | 1.30E−07 | 5.39E−08 |
| 419 | 5.10E−09 | 1.00E−07 | 8.29E−08 |
| 421 | 5.00E−09 | 9.80E−09 | 5.22E−08 |
| 422 | 8.10E−09 | 1.20E−08 | 5.91E−08 |
| 423 | 5.70E−09 | 1.20E−08 | 4.77E−08 |
| 424 | 6.60E−09 | 1.10E−08 | 5.26E−08 |
| 425 | 7.70E−09 | 1.30E−08 | 4.78E−08 |
| 426 | 9.10E−09 | 1.50E−08 | 4.60E−08 |
| 427 | 1.00E−08 | 1.50E−08 | 6.39E−08 |
| 428 | 3.70E−09 | 3.20E−07 | 6.03E−08 |
| 429 | 6.90E−09 | 1.20E−08 | 4.72E−08 |
| 430 | 1.40E−09 | 9.10E−08 | 4.05E−08 |
| 431 | 2.00E−09 | 1.70E−07 | 8.64E−08 |
| 432 | 2.70E−09 | 3.70E−07 | 1.73E−07 |
| 433 | 1.70E−09 | 1.20E−07 | 8.02E−08 |
| 434 | 1.00E−06 | 1.00E−06 | |
| 435 | 9.20E−09 | 1.70E−08 | 5.82E−08 |
| 436 | 2.30E−09 | 4.40E−08 | 5.19E−08 |
| 437 | 2.20E−09 | 7.60E−08 | 5.61E−08 |
| 438 | 2.90E−09 | 8.30E−08 | 5.08E−08 |
| 439 | 3.20E−09 | 1.50E−08 | 2.84E−08 |
| 440 | 1.80E−08 | 2.60E−08 | 2.15E−07 |
| 441 | 6.50E−08 | 2.20E−07 | 2.53E−07 |
| 443 | 7.80E−10 | 7.40E−08 | 2.52E−08 |
| 444 | 2.80E−09 | 6.10E−08 | 2.95E−08 |
| 445 | 3.00E−09 | 3.00E−07 | 4.99E−08 |
| 446 | 2.70E−09 | 7.20E−08 | |
| 447 | 4.70E−09 | 6.55E−08 | |
| 448 | 4.40E−07 | 1.00E−06 | 3.45E−06 |
| 449 | 1.80E−09 | 9.30E−08 | 5.58E−08 |
| 450 | 5.80E−09 | 2.30E−07 | 7.34E−08 |
| 451 | 2.60E−09 | 6.10E−08 | 5.69E−08 |
| 452 | 2.00E−09 | 1.00E−07 | 3.78E−08 |
| 453 | 2.50E−09 | 5.60E−08 | 5.98E−08 |
| 454 | 2.00E−09 | 9.90E−08 | 6.57E−08 |
| 455 | 2.90E−09 | 8.50E−08 | |
| 456 | 1.90E−09 | 1.10E−07 | 5.55E−08 |
| 457 | 1.70E−08 | 4.50E−08 | 5.06E−08 |
| 458 | 5.10E−09 | 2.10E−07 | 1.07E−07 |
| 459 | 4.30E−09 | 2.00E−07 | 1.04E−07 |
| 460 | 8.20E−09 | 1.40E−07 | 6.20E−08 |
| 462 | 1.20E−08 | 1.30E−07 | 6.10E−08 |
| 463 | 3.80E−09 | 2.60E−07 | 6.39E−08 |
| 464 | 1.00E−09 | 4.50E−08 | 7.76E−08 |
| 465 | 4.10E−10 | 1.20E−07 | 9.94E−08 |
| 466 | 7.20E−10 | 4.00E−08 | 7.16E−08 |
| 467 | 6.60E−09 | 5.50E−08 | 4.15E−08 |
| 468 | 4.50E−09 | 9.70E−08 | 5.77E−08 |
| 469 | 1.90E−09 | 1.10E−07 | 4.00E−08 |
| 470 | 1.80E−09 | 5.80E−08 | 4.12E−08 |
| 471 | 2.60E−09 | 8.20E−08 | 4.49E−08 |
| 472 | 4.00E−09 | 5.10E−08 | 4.39E−08 |
| 474 | 2.40E−09 | 7.80E−08 | |
| 475 | 2.60E−08 | 1.80E−08 | |
| 476 | 3.80E−09 | 6.10E−08 | |
| 477 | 9.60E−09 | 1.72E−07 | |
| 478 | 3.70E−09 | 3.70E−08 | |
| 479 | 5.85E−09 | 1.75E−07 | |
| 480 | 3.00E−09 | 3.50E−08 | |
| 481 | 2.50E−09 | 5.50E−08 | |
| 482 | 2.80E−09 | 2.50E−08 | |
| 483 | 5.40E−09 | 6.40E−08 | |
| 484 | 5.50E−09 | 1.20E−07 | |
| 485 | 2.10E−09 | 3.50E−08 | |

TABLE 19-continued

Average IC50 of the peptides of the invention

| Example No | human MASP1 IC50 [mol/L] | human MASP2 \|IC50 [mol/L] | Human C3-DEPOSITION SERUM\| IC50 [mol/L] |
|---|---|---|---|
| 486 | 3.80E−09 | 3.20E−08 | |
| 487 | 2.35E−09 | 4.80E−08 | |
| 488 | 5.20E−09 | 1.10E−07 | |
| 489 | 2.40E−09 | 3.20E−08 | |
| 490 | 1.95E−08 | 2.10E−08 | 4.64E−08 |
| 491 | 5.80E−08 | 4.30E−08 | |
| 492 | 3.00E−09 | 1.80E−07 | |
| 493 | 3.20E−09 | 1.20E−07 | |
| 494 | 2.60E−09 | 8.40E−08 | |
| 495 | 3.40E−09 | 3.70E−08 | |
| 496 | 2.00E−09 | 3.10E−08 | |
| 497 | 2.30E−09 | 4.70E−08 | |
| 498 | 2.30E−09 | 3.90E−08 | |
| 500 | 7.70E−09 | 1.50E−07 | |
| 501 | 4.80E−09 | 5.90E−08 | |
| 502 | 6.50E−09 | 1.10E−07 | |
| 503 | 6.30E−09 | 6.20E−08 | |
| 504 | 6.80E−09 | 1.20E−07 | |
| 505 | 7.90E−09 | 7.60E−08 | |
| 506 | 6.20E−09 | 7.60E−08 | |
| 507 | 1.70E−09 | 2.70E−08 | |
| 508 | 1.40E−08 | 3.30E−07 | |
| 509 | 6.50E−08 | 7.00E−08 | |
| 510 | 7.00E−08 | 1.70E−07 | |
| 511 | 5.26E−07 | 1.00E−06 | |
| 512 | 1.00E−06 | 1.00E−06 | |
| 513 | 7.40E−07 | 1.00E−06 | |
| 514 | 5.30E−09 | 4.60E−08 | |
| 515 | 7.00E−09 | 1.50E−07 | |
| 516 | 7.50E−09 | 1.00E−06 | |
| 517 | 3.10E−09 | 5.10E−07 | |
| 518 | 1.00E−06 | 1.00E−06 | |
| 519 | 1.80E−08 | 4.70E−08 | |
| 520 | 2.10E−08 | 6.40E−08 | |
| 521 | 1.70E−08 | 2.00E−08 | |
| 522 | 4.40E−09 | 2.20E−08 | |
| 523 | 4.40E−09 | 2.40E−08 | |
| 524 | 7.80E−09 | 1.00E−06 | |
| 525 | 2.00E−08 | 2.30E−07 | |
| 526 | 6.60E−09 | 1.04E−07 | 4.85E−08 |
| 527 | 2.30E−08 | 9.60E−08 | 1.54E−08 |
| 528 | 7.50E−09 | 6.50E−08 | 2.03E−08 |
| 529 | 3.10E−09 | 5.40E−08 | 3.95E−08 |
| 530 | 6.78E−09 | 1.16E−07 | 2.14E−08 |
| 531 | 1.71E−08 | 2.61E−07 | 3.41E−08 |
| 532 | 2.80E−08 | 1.66E−07 | 2.03E−08 |

TABLE 20

Average IC50 of the reference peptides

| Reference No | rat MASP1 IC50 [mol/L] | rat MASP2 \|IC50 [mol/L] | rat C3-DEPOSITION SERUM\| IC50 [mol/L] |
|---|---|---|---|
| 1 | 6.86E−08 | 6.80E−08 | 1.70E−06 |
| 3 | | | 1.14E−06 |
| A | 5.02E−08 | 6.84E−08 | 1.41E−06 |
| B | 8.34E−08 | 5.42E−08 | 6.49E−07 |
| C | 2.10E−07 | | 5.79E−07 |

TABLE 21

Average IC50 of the peptides of the invention

| Example No | rat MASP1 IC50 [mol/L] | rat MASP2 \|IC50 [mol/L] | rat C3-DEPOSITION SERUM\| IC50 [mol/L] |
|---|---|---|---|
| 5 | 2.80E−08 | 4.90E−08 | 2.14E−07 |
| 7 | 3.00E−08 | 1.60E−08 | |
| 12 | 1.30E−08 | | |
| 13 | 9.32E−09 | 1.64E−08 | 2.42E−07 |
| 14 | 2.30E−08 | | |
| 17 | 3.10E−08 | | |
| 18 | 2.60E−08 | | |
| 19 | 2.30E−08 | | |
| 20 | 1.30E−08 | | |
| 21 | 6.70E−08 | 4.00E−08 | |
| 26 | 5.50E−08 | 5.34E−08 | 1.50E−07 |
| 27 | 9.81E−09 | 9.10E−09 | 1.46E−07 |
| 29 | 1.05E−08 | 1.74E−08 | 1.96E−07 |
| 30 | 2.80E−08 | | |
| 31 | 2.20E−08 | | |
| 32 | 5.60E−08 | 4.80E−08 | |
| 35 | 4.60E−08 | | |
| 36 | 2.40E−08 | | |
| 37 | 1.40E−07 | | |
| 38 | 1.20E−08 | | |
| 39 | 4.90E−08 | 3.70E−08 | |
| 41 | 2.80E−08 | 1.30E−08 | |
| 44 | 8.70E−08 | 3.50E−08 | |
| 45 | 4.00E−08 | | |
| 48 | 5.15E−08 | | |
| 49 | 6.00E−08 | | |
| 54 | 1.60E−07 | 4.80E−08 | |
| 55 | 6.50E−08 | 2.70E−08 | |
| 59 | 2.50E−07 | | |
| 62 | 5.50E−08 | 5.00E−08 | |
| 65 | 7.20E−09 | | |
| 66 | 7.00E−08 | | |
| 67 | 7.20E−08 | 3.60E−08 | |
| 72 | 4.30E−08 | 2.70E−08 | |
| 73 | 4.30E−08 | 2.80E−08 | |
| 74 | 7.10E−08 | 2.80E−08 | |
| 75 | 3.50E−08 | 3.49E−08 | 1.83E−07 |
| 77 | 6.60E−08 | | |
| 78 | 4.80E−08 | | |
| 79 | 8.50E−08 | | |
| 83 | 1.20E−07 | 4.80E−08 | |
| 85 | 7.50E−08 | 3.70E−08 | |
| 86 | 1.60E−08 | | |
| 88 | 3.60E−08 | 6.80E−08 | |
| 90 | 6.70E−08 | 5.50E−08 | |
| 97 | 1.20E−07 | 5.10E−08 | |
| 98 | 1.70E−08 | | |
| 99 | 2.20E−07 | | |
| 101 | 7.60E−08 | 5.00E−08 | |
| 102 | 1.40E−07 | | |
| 103 | 1.10E−07 | | |
| 104 | 7.70E−08 | | |
| 108 | 1.10E−08 | | |
| 109 | 7.60E−08 | 4.20E−08 | |
| 119 | 1.30E−07 | 7.00E−08 | |
| 123 | 5.90E−08 | | |
| 126 | 1.10E−08 | 1.00E−08 | |
| 128 | 3.50E−08 | | |
| 133 | 9.80E−08 | 6.70E−08 | |
| 140 | 1.00E−07 | 5.00E−08 | |
| 141 | 1.40E−07 | 9.50E−08 | |
| 142 | 1.09E−08 | 1.71E−08 | 4.72E−07 |
| 146 | 1.10E−07 | 6.80E−08 | |
| 150 | 1.20E−07 | 5.30E−08 | |
| 153 | 4.00E−08 | 5.03E−08 | 8.00E−07 |
| 154 | 7.20E−08 | | |
| 156 | 2.10E−08 | 1.60E−08 | |
| 158 | 2.47E−07 | 4.20E−07 | |
| 164 | 7.90E−08 | 2.80E−08 | |
| 168 | 1.40E−07 | 5.30E−08 | |
| 169 | 3.70E−07 | | |
| 170 | 5.40E−08 | 9.82E−09 | 2.36E−07 |
| 171 | 4.20E−08 | 2.10E−08 | |

TABLE 21-continued

Average IC50 of the peptides of the invention

| Example No | rat MASP1 IC50 [mol/L] | rat MASP2 \|IC50 [mol/L] | rat C3-DEPOSITION SERUM\| IC50 [mol/L] |
|---|---|---|---|
| 174 | 6.56E−08 | 3.51E−08 | |
| 175 | 2.80E−08 | | |
| 180 | 4.20E−08 | | |
| 181 | 1.30E−07 | | |
| 182 | 1.30E−08 | | |
| 185 | 5.70E−08 | 1.09E−08 | 2.36E−07 |
| 186 | 3.80E−07 | | |
| 187 | 7.70E−08 | 3.70E−09 | |
| 194 | 7.00E−08 | 4.20E−08 | |
| 197 | 1.00E−07 | 1.50E−08 | |
| 199 | 1.80E−07 | 4.90E−08 | |
| 205 | 3.00E−07 | | |
| 207 | 4.30E−08 | 3.36E−08 | |
| 208 | 6.10E−08 | 8.60E−09 | |
| 209 | 3.30E−07 | | |
| 210 | 1.90E−08 | | |
| 211 | 7.50E−08 | 2.30E−08 | |
| 212 | 2.46E−08 | 3.45E−08 | 2.31E−07 |
| 216 | 2.40E−07 | | |
| 222 | 2.40E−07 | | |
| 223 | 1.20E−07 | | |
| 224 | 6.04E−08 | 4.24E−08 | 7.83E−07 |
| 225 | 2.30E−07 | | |
| 226 | 2.90E−08 | 2.90E−09 | |
| 228 | 2.60E−07 | | |
| 230 | 3.70E−07 | | |
| 231 | 3.80E−08 | | |
| 232 | 6.73E−08 | 1.25E−07 | |
| 234 | 7.80E−08 | | |
| 235 | 3.80E−07 | 2.90E−08 | |
| 236 | 8.90E−07 | | |
| 237 | 1.00E−06 | 1.00E−06 | |
| 238 | 1.50E−07 | | |
| 241 | 1.30E−07 | | |
| 243 | 1.40E−07 | | |
| 246 | 7.80E−08 | | |
| 247 | 7.00E−07 | | |
| 248 | 2.60E−07 | | |
| 250 | 7.70E−08 | | |
| 253 | 1.30E−07 | | |
| 254 | 3.20E−07 | | |
| 259 | 2.70E−08 | | |
| 260 | 1.60E−07 | | |
| 261 | 3.00E−07 | | |
| 262 | 4.90E−07 | | |
| 267 | 1.30E−07 | 4.20E−08 | |
| 268 | 1.00E−07 | | |
| 269 | 1.20E−07 | 9.60E−09 | |
| 270 | 1.70E−07 | | |
| 271 | 8.87E−08 | 5.52E−08 | 1.06E−06 |
| 274 | 8.90E−08 | | |
| 275 | 1.50E−07 | | |
| 276 | 2.00E−07 | | |
| 277 | 1.90E−07 | | |
| 278 | 8.30E−08 | | |
| 281 | 2.70E−07 | 3.08E−07 | 1.41E−06 |
| 282 | 4.70E−07 | | |
| 284 | 6.00E−08 | 9.70E−09 | |
| 286 | 2.30E−07 | | |
| 287 | 2.50E−07 | | |
| 289 | 1.80E−07 | | |
| 294 | 9.70E−08 | 9.60E−09 | |
| 305 | 7.60E−08 | 5.30E−09 | |
| 313 | 2.20E−07 | | |
| 323 | 5.18E−08 | 6.01E−08 | 1.14E−06 |
| 343 | 1.40E−07 | 1.90E−08 | |
| 347 | 1.00E−06 | 1.00E−06 | |
| 348 | 3.50E−07 | | |
| 360 | 1.20E−07 | 7.30E−08 | |
| 367 | 1.20E−07 | | |
| 370 | 2.35E−07 | 1.70E−07 | |
| 381 | 6.00E−07 | 4.70E−07 | |
| 400 | 4.50E−08 | 1.10E−08 | |

TABLE 21-continued

Average IC50 of the peptides of the invention

| Example No | rat MASP1 IC50 [mol/L] | rat MASP2 \|IC50 [mol/L] | rat C3-DEPOSITION SERUM\| IC50 [mol/L] |
|---|---|---|---|
| 405 | 6.50E−07 | 5.10E−07 | |
| 419 | 7.00E−08 | 4.20E−08 | |
| 436 | 3.90E−08 | 3.10E−08 | |
| 437 | 4.60E−08 | 4.00E−08 | |
| 438 | 3.10E−08 | 2.20E−08 | |
| 439 | 3.60E−08 | 9.40E−09 | |
| 440 | 6.10E−07 | 1.40E−08 | |
| 441 | 4.10E−07 | 1.20E−07 | |
| 443 | 2.90E−08 | 4.70E−09 | |
| 444 | 1.30E−07 | 9.80E−09 | |
| 445 | 1.50E−07 | 9.40E−08 | |
| 447 | 2.10E−08 | 3.50E−08 | |
| 448 | 5.00E−06 | 5.00E−06 | |
| 449 | 4.50E−08 | 4.45E−08 | |
| 450 | 3.10E−08 | 5.20E−08 | |
| 451 | 4.60E−08 | 4.60E−08 | |
| 452 | 3.60E−08 | 3.70E−08 | |
| 453 | 3.80E−08 | 3.20E−08 | |
| 454 | 1.27E−07 | 7.90E−08 | |
| 455 | 4.10E−08 | 3.20E−08 | |
| 456 | 3.90E−08 | 3.00E−08 | |
| 457 | 2.00E−08 | 5.00E−09 | 2.34E−07 |
| 458 | 2.50E−07 | 1.00E−07 | |
| 459 | 1.80E−07 | 5.10E−08 | |
| 460 | 2.10E−07 | 6.90E−08 | |
| 462 | 1.60E−07 | 1.50E−07 | |
| 463 | 1.90E−07 | 1.00E−07 | |
| 464 | 9.40E−08 | 1.20E−07 | |
| 465 | 7.20E−08 | 1.40E−07 | |
| 466 | 1.76E−08 | 7.20E−08 | |
| 467 | 1.70E−07 | 7.00E−08 | |
| 468 | 1.30E−07 | 8.00E−08 | |
| 469 | 1.20E−07 | 3.40E−08 | |
| 470 | 1.00E−07 | 5.40E−08 | |
| 471 | 7.80E−08 | 7.10E−08 | |
| 472 | 1.00E−07 | 4.90E−08 | |
| 474 | 8.70E−08 | 2.60E−08 | |
| 475 | 2.50E−07 | 2.50E−08 | |
| 476 | 5.30E−08 | 6.10E−08 | |
| 477 | 1.54E−07 | 1.23E−07 | |
| 478 | 6.80E−08 | 4.90E−08 | |
| 479 | 8.40E−08 | 4.50E−08 | |
| 480 | 2.40E−08 | 4.10E−08 | |
| 481 | 2.00E−08 | 3.60E−08 | |
| 482 | 1.80E−08 | 3.30E−08 | |
| 483 | 3.40E−08 | 5.00E−08 | |
| 484 | 6.30E−08 | 8.80E−08 | |
| 485 | 3.60E−08 | 3.20E−08 | |
| 486 | 6.90E−08 | 6.80E−08 | |
| 487 | 6.70E−08 | 3.80E−08 | |
| 488 | 4.10E−08 | 3.60E−08 | |
| 489 | 4.20E−08 | 2.20E−08 | |
| 490 | 1.25E−08 | 1.50E−08 | 3.66E−07 |
| 491 | 2.00E−08 | 2.30E−08 | |
| 492 | 6.50E−08 | 8.10E−08 | |
| 493 | 4.40E−08 | 4.90E−08 | |
| 494 | 3.80E−08 | 6.20E−08 | |
| 495 | 4.50E−08 | 6.60E−08 | |
| 496 | 3.10E−08 | 3.10E−08 | |
| 497 | 5.80E−08 | 3.90E−08 | |
| 498 | 4.40E−08 | 4.20E−08 | |
| 526 | 4.85E−07 | 2.53E−07 | |
| 527 | 2.40E−07 | 4.20E−08 | |
| 528 | 4.20E−07 | 8.20E−09 | |
| 529 | 7.30E−07 | 1.00E−07 | |
| 530 | 2.33E−08 | 1.84E−08 | 2.82E−07 |
| 531 | 2.60E−08 | 7.41E−08 | |
| 532 | 2.42E−08 | 1.76E−08 | |

4. Kidney Ischemia Reperfusion Injury (IRI) in Rats after Unilateral Nephrectomy All procedures conformed to national legislation (dt. Tierschutzgesetz) and EU directives for the use of animals for scientific purposes and were approved by the institutional animal care office of Bayer AG and by the competent regional authority (LANUV Recklinghausen). Standard laboratory diet and tap water were available ad libitum. In a typical experiment, the number of animals used was n=6 to 12. Animals were randomly assigned to experimental groups. Kidney ischemia reperfusion injury (IRI) was performed in male unilaterally nephrectomized Wistar rats of a preferred body weight in the range of 250 to 350 g. For unilateral nephrectomy rats were kept anesthetized under inhalation of 2% isoflurane in air. Analgesia was provided as a subcutaneous injection of 400 μl/kg of a mixture of 25% Ketavet and 8% Rompun in 0.9 NaCl. Unilateral nephrectomy was performed after protruding the right kidney through a small incision in the dorsolateral abdominal wall and ligating of its peduncle. After unilateral nephrectomy abdominal incision was closed by surgical sutures in layers and animals were allowed to recover for 7 to 8 days before IRI. IRI was performed under anesthesia and analgesia as described above. The remnant left kidney was protruded through a small incision of the abdominal wall and blood vessels of the kidney peduncle were clamped with an atraumatic microvascular clamp for 45 minutes in a typical setting. During this time the kidney together with the clamp in situ was repositioned into the abdominal cavity to ensure warm ischemia. After 45 min the clamp was opened and removed, and the incision closed by sutures as described above. Test compound or vehicle was administered intravenously via a polyethylene catheter placed before surgery into the jugular vein.

Compounds were dissolved in appropriate vehicle and administered either preventive before IRI or therapeutically after completion of IRI. Typical dose range applied was 0.1-30 mg/kg i.v. Vehicle without compound was administered to animals that served as controls. Sham control animals underwent the whole procedure described above without closure of the clamp for induction of ischemia.

Blood samples were taken under anesthesia at day 1 and 8 after IRI. In a typical setting, animals were sacrificed 8 days after IRI and kidneys were sampled and frozen in liquid nitrogen. In another typical setting the animals were sacrificed 1 day after IRI.

Typical laboratory parameters measured in plasma samples to assess kidney function were creatinine and urea. For determination of creatinine clearance animals were kept in metabolic cages and urine was collected for at least 16 hours. After determination of urine volume flow ($V_U$) and determination of urinary and plasma creatinine concentrations ($[Crea]_U$ and $[Crea]_{Pl}$, respectively) creatinine clearance ($Cl_{Crea}$) was calculated according to the standard formula: $Cl_{Crea}=V_U*[Crea]_U/[Crea]_{Pl}$ RNA Extraction and Quantitative Real-Time Polymerase Chain Reaction: Total RNA was extracted from tissue samples by the Trizol method. Integrity of obtained RNA was checked on a Bioanalyzer (Agilent). For reverse transcription, 1 μg of total RNA was first digested with RNase-free DNase I (Gibco) for 15 min at room temperature and then reverse transcribed using Promiscript (Promega) in a total reaction volume of 40 μl according to the standard protocol of the kit supplier. After inactivation of the enzyme by heating for 15 min to 65° C., the obtained cDNA was diluted to a final volume of 150 μl with bidest. water and 4 μl were chosen per PCR reaction. Real-Time PCR including normalization of raw data to cytosolic beta-actin as a housekeeping gene was carried out as described (Ellinghaus et al., 2005). The resulting expression is given in arbitrary units. Sequences of used oligonucleotide primers and probes are given in table 1.

5. Kidney Ischemia Reperfusion Injury (IRI) in Pigs after Aortic Balloon Occlusion All procedures conformed to national legislation (dt. Tierschutzgesetz) and EU directives for the use of animals for scientific purposes and were approved by the institutional animal care office of Bayer AG and by the competent regional authority (LANUV Recklinghausen). Female Göttingen mini pigs (Ellegaard, Denmark) of a body weight ranging preferably from 12 to 16 kg were used for the experiments. Animals were randomly assigned to experimental groups.

Minimal invasive methods were applied with modifications as described (Simon et al., Effects of intravenous sulfide during porcine aortic occlusion-induced kidney ischemia/reperfusion injury. Shock. 2011; 35:156-163; Matejkova et al., Carbamylated erythropoietin-FC fusion protein and recombinant human erythropoietin during porcine kidney ischemia/reperfusion injury. Intensive Care Med. 2011; 39:497-510). In brief: Pigs were kept anesthetized by a continuous i.v.-infusion of Ketavet®, Dormicum® and Pancuronium® after premedication with an intramuscular injection of Ketavet®/Stresnil®. After intratracheal intubation animals were artificially ventilated using a pediatric respirator (Avance $CS^2$, GE Healthcare) with an oxygen air mixture at a tidal volume of 6 to 8 mL/kg at a constant positive end-expiratory pressure (PEEP) of 3-4 cm $H_2O$ and a frequency of 13 to 20 $min^{-1}$. Ventilation was adjusted to keep arterial PaCO2 at about 40 mmHg at baseline. A catheter was placed into the right jugular vein for drug and fluid administration. Ringer-lactate solution was infused intravenously at a constant rate of 10 mL/kg/h. Animals received 50 i.E./kg Heparin i.v. Routinely the following cardiovascular and respiratory parameters were measured after placement of necessary probes and catheters fitted to appropriate pressure transducers and recording equipment: central venous pressure (via left jugular vein), arterial blood pressure and heart rate (BP and HR; via left carotid artery) and cardiac output (CO) and systemic vascular resistance (SVR) by use of the PiCCO® system (Pulsion, Germany) connected to a Pulsion 4F Thermodilution-catheter (PV2014L08N) placed into the right carotid artery. Catheters for measurement of CVP, BP and HR were fitted to a Ponemah recording system via Combitrans transducers (Braun, REF 5203660). A Fogarty occlusion catheter (8F/14F, Edwards Lifesiences, REF 6208014F) was inserted into the abdominal aorta via the left femoral artery so that the tip with the inflatable balloon was placed upstream of the kidney arteries. A catheter was introduced into the urinary bladder via a small abdominal incision and urine continuously collected. Arterial blood samples were collected at regular intervals in which creatinine, urea, liver enzymes, blood cells and compound concentrations were determined. Arterial $pO_2$, $pCO_2$ and pH were determined on a Stat Profile®PRIME® (Nova Biomedical) blood gas analyzer at regular intervals in arterial blood samples. Kidney perfusion was assessed at regular intervals by Doppler ultrasound determination of the resistive index using a LOGIQ e Veterinary ultrasound apparatus (General Electrics) fitted with a 2.0 to 5.0 MHz broad-spectrum convex transducer (C1-5-RS, REF 5384874). Renal resistive index (RRI) is a suitable parameter to assess severity of acute kidney injury in patients (Darmon et al., Diagnostic accuracy of Doppler renal resistive index for reversibility of acute kidney injury in critically ill patients. Intensive Care Med. 2011; 37(1): 68-76)

When cardiovascular parameters showed a stable baseline (which was normally the case 60 min after surgery) recordings were started and samples for baseline parameters were collected. HR and MABP were continuously measured and for recording averaged over 2 min intervals. At the end of experimentation pigs were sacrificed by exsanguination.

Kidney injury was induced by inflating the balloon of the Fogarty balloon catheter with saline which immediately interrupted blood flow to the kidneys and the abdominal organs and led to a sharp increase of aortic blood pressure upstream of the balloon. Stop of blood flow was further confirmed by Doppler ultrasound examination of the kidney blood vessels. In typical experiments the aorta is kept occluded for 90 to 120 min until reperfusion by deflating the balloon. After reperfusion the Ringer-lactate infusion rate is doubled to 20 mL/kg/h in order to stabilize blood pressure and to enable diuresis. All parameters were monitored for up to 6 hours after reperfusion.

Compounds were dissolved in appropriate vehicle and administered either preventive before IRI or therapeutically after completion of IRI. Typical dose range applied was 0.1-10 mg/kg i.v. In a typical experiment up to three doses were tested in up to 6 animals per dose group. Vehicle without compound was administered to animals that served as controls. Sham control animals underwent the whole procedure described above without induction of ischemia.

As a measure for kidney function after reperfusion preferably but not exclusively changes in diuresis, serum creatinine, serum potassium, serum bicarbonate and in resistive index determined by Doppler ultrasound examination were used.

TABLE 22

Sequence Listing

| SEQ ID No | Sequence |
|---|---|
| SEQ ID 1 | GIC+SRSLPPIC+IPD-OH |
| SEQ ID 2 | METDTLLLWVLLLWVPGSTGDAGNECPELQPPVHG-<br>KIEPSQAKYFFKDQVLVSCDTGYKVLKDNVEMDTFQIECLKDGTWSNKIP<br>TCKIVDCRAPGELEHGLITFSTRNNLTTYKSEIKYSCQEPYYKMLNNNT-<br>GIYTCSAQGVWMNKVLGRSLPTCLPVCGLPKFSRKLMARIFNGRPAQKGT<br>TPWIAMLSHLNGQPFCGGSLLGSSWIVTAAHCLHQSLDPEDPTLRDSDLL-<br>SPSDFKIILGKHWRLRSDENEQHLGVKHTTLHPQYDPNTFENDVALVELLE<br>SPVLNAFVMPICLPEGPQQEGAMVIVSGWGKQFLQRF-<br>PETLMEIEIPIVDHSTCQKAYA-<br>PLKKKVTRDMICAGEKEGGKDACAGDSGGPMVTLNRERGQWYLVGTVS<br>WGDDCGKKDRYGVYSYIHHNKDWIQRVTGVRNHHHHHH |
| SEQ ID 3 | METDTLLLWVLLLWVPGSTGDAQPCPYPMAPPNGHVSPVQAKY-<br>ILKDSFSIFCETGYELLQGHLPLKSFTAVCQKDGSWDRPMPACSIVDCGPP<br>DDLPSGRVEYITGPGVTTYKAVIQYSCEETFYTMKVNDGKYVCEAD-<br>GFWTSSKGEKSLPVCEPVCGLSARTTGGRIYGGQKAKPGDFPWQVLILGG<br>TTAAGALLYDNWVLTAAHAVYEQKHDASALDIRMGTLKRL-<br>SPHYTQAWSEAVFI-<br>HEGYTHDAGFDNDIALIKLNNKVVINSNITPICLPRKEAESFMRTDDIGTAS<br>GWGLTQRGFLARNLMYVDIPIVDHQKCTAAY-<br>EKPPYPRGSVTANMLCAGLESGGKD-<br>SCRGDSGGALVFLDSETERWFVGGIVSWGSMNCGEAGQYGVYTKVINYI<br>PWIENIISDFHHHHHH |
| SEQ ID 4 | METDTLLLWVLLLWVPGSTGDAGNECPKLQPPVYGKIEPSQAVYS-<br>FKDQVLISCDTGYKVLKDNEVMDTFQIECLKDGAWSNKIPTCKIVDCGVP<br>AVLKHGLVTFSTRN-<br>NLTTYKSEIRYSCQQPYYKMLHNTTGVYTCSAHGTWT-<br>NEVLKRSLPTCLPVCGLPKFSRKHISRIFNGRPAQKGTTPWIAMLSQLNGQ<br>PFCGGSLLGSNWVLTAAHCLHHPLDPEEPILHNSHLL-<br>SPSDFKIIMGKHWRRRSDEDEQHL-<br>HVKHIMLHPLYNPSTFENDLGLVELSESPRLNDFVMPVCLPEHPSTEGTM<br>VIVSGWGKQFLQRLPENLMEIEIPIVNYHTCQEAYTPLGKKVTQDMI-<br>CAGEKEGGKDACAGDSGGPMVTKDAERDQWYLVGVVSWGEDCGKKDR<br>YGVYSYIYPNKDWIQRVTGVRNHHHHHH |
| SEQ ID 5 | METDTLLLWVLLLWVPGSTGDTAQPCPDPTAPPN-<br>GHISPVQATYVLKDSFSVFCKTGFELLQGSVPLKSFrAVCQKDGSWDRPIP<br>ECSIIDCGPPDDLPNGHVDYITGPEVTTYKAVIQYSCEET-<br>FYTMSSNGKYVCEAD-<br>GFWTSSKGEKSLPVCKPVCGLSTHTSGGRIIGGQPAKPGDFPWQVLLLGET<br>TAAGALIHDDWVLTAAHAVYGKTEAMSSLDIRMGILKRLSLIYTQAW-<br>PEAVFIHEGYTHGAG-<br>FDNDIALIKLKNKVTINRNIMPICLPRKEAASLMKTDFVGTVAGWGLTQK<br>GFLARNLMFVDIPIVDHQKCATAYTKQPYP-<br>GAKVTVNMLCAGLDRGGKDSCRGDSGGAL-<br>VFLDNETQRWFVGGIVSWGSINCGGSEQYGVYTKVTNYIPWIENIINNFHH<br>HHHH |
| SEQ ID 6 | ABZ-MYGGARRL-Lys (Dnp)-NH2 |
| SEQ ID 7 | DABCYL-KISPQGYGRR-Glu(EDANS)-NH2 |

TABLE 22-continued

| Sequence Listing | |
|---|---|
| SEQ ID No | Sequence |
| SEQ ID 8 | Dabcyl-MYGGARRL-Glu(Edans)-NH2 |
| SEQ ID 9 | Abz-IEGRTSED-(Lys)Dnp-NH2 |
| SEQ ID 10 | AIC+SRSLPPIC+IPD-OH |

REFERENCES

Caliceti P., Veronese F. M., Adv. Drug Deliv. Rev. 2003, 55, 1261-1277

Darmon et al., Diagnostic accuracy of Doppler renal resistive index for reversibility of acute kidney injury in critically ill patients. Intensive Care Med. 2011; 37(1): 68-76

Dong-Liang Huang, Jing-Si Bai, Meng Wu, Xia Wang, Bernd Riedl, Elisabeth Pook, Carsten Alt, Marion Erny, Yi-Ming Li, Donald Bierer, Jing Shi, Ge-Min Fang Chem. Commun., 2019, 55, 2821-2824

Dunkelberger and Song, Complement and its role in innate and adaptive immune responses. Cell Res. 2010; 20(1): 34-50

Ellinghaus et al., J Thorac Cardiovasc Surg. 2005 June; 129(6):1383-90

Encyclopedia of Pharmaceutical Technology", 3rd edition, James Swarbrick (Ed.), pp. 3177-3187

Farrar et al., Collectin-11 detects stress-induced L-fucose pattern to trigger renal epithelial injury. J Clin Invest. 2016; 126(5):1911-1925

Garred et al., A journey through the lectin pathway of complement-MBL and beyond. Immunol Rev. 2016; 274 (1):74-97

Handbook of Pharmaceutical Salts: Properties, Selection, and Use by Stahl and Wermuth (Wiley-VCH, 2002)

Héja et al, Revised mechanism of complement lectin-pathway activation revealing the role of serine protease MASP-1 as the exclusive activator of MASP-2. Proc Natl Acad Sci USA. 2012; 109(26):10498-503

Héja et al., Monospecific inhibitors show that both mannan-binding lectin-associated serine protease-1 (MASP-1) and are essential for lectin pathway activation and reveal structural plasticity of MASP-2. J Biol Chem. 2012; 287(24):20290-300

Hong-Kui Cui, Ye Guo, Yao He, Feng-Liang Wang, Hao-Nan Chang, Yu-Jia Wang, Fang-Ming Wu, Chang-Lin Tian, Lei Liu Angew. Chem. Int. Ed. 2013, 52, 9558-9562 http://www.researchdisclosure.com/searching-disclosures, Research Disclosure Database Number 605005, 2014, 1 Aug. 2014

Jan-Patrick Fischer, Ria Schönauer, Sylvia Els-Heindl, Donald Bierer, Johannes Koebberling, Bernd Riedl, Annette G. Beck-Sickinger J Pep Sci. 2019; e3147

Kocsis et al., Selective inhibition of the lectin pathway of complement with phage display selected peptides against mannose-binding lectin-associated serine protease (MASP)-1 and -2: significant contribution of MASP-1 to lectin pathway activation. J Immunol. 2010; 185(7):4169-78

Kourra CMBK and Cramer N; Chem. Sci., 2016, 7, 7007-7012

Matejkova et al., Carbamylated erythropoietin-FC fusion protein and recombinant human erythropoietin during porcine kidney ischemia/reperfusion injury. Intensive Care Med. 2011; 39:497-510

Møller-Kristensen et al., Mannan-binding lectin recognizes structures on ischaemic reperfused mouse kidneys and is implicated in tissue injury. Scand J Immunol. 2005; 61(5):426-34

Nomenclature of α-Amino Acids (Recommendations, 1974), Biochemistry, 14(2), (1975)

Remington's Pharmaceutical Sciences, 17th edition, Alfonso R. Gennaro (Ed.), Mark Publishing Company, Easton, PA, USA, 1985

Schwaeble et al., Targeting of mannan-binding lectin-associated serine protease-2 confers protection from myocardial and gastrointestinal ischemia/reperfusion injury. Proc Natl Acad Sci USA. 2011; 108(18):7523-8

Sebesta and Seebach, Helv. Chim. Acta 2003, 86, 4061-4072

Shuai-Shuai Sun, Junyou Chen, Rui Zhao, Donald Bierer, Jun Wang, Ge-Min Fang, Yi-Ming Li Tetrahedron Letters 2019, 60, 1197-1201

Sieve et al., Regulation and function of endothelial glycocalyx layer in vascular diseases. Vascul Pharmacol. 2018; 100:26-33

Simon et al., Effects of intravenous sulfide during porcine aortic occlusion-induced kidney ischemia/reperfusion injury. Shock. 2011; 35:156-163

T. Peleg-Shulman et al., J. Med. Chem., 2004, 47, 4897-4904

Tao Wang, Jian Fan, Xiao-Xu Chen, Rui Zhao, Yang Xu, Donald Bierer, Lei Liu, Yi-Ming Li, Jing Shi, Ge-Min Fang Org. Lett. 2018, 20, 6074-6078

Tao Wang, Yi-Fu Kong, Yang Xu, Jian Fan, Hua-Jian Xu, Donald Bierer, Jun Wang, Jing Shi, Yi-Ming Li Tetrahedron Letters 2017, 58, 3970-3973;

Yang Xu, Tao Wang, Chao-Jian Guan, Yi-Ming Li, Lei Liu, Jing Shi, Donald Bierer Tetrahedron Letters 2017, 58, 1677-1680

Ye Guo, De-Meng Sun, Feng-Liang Wang, Yao He, Lei Liu, Chang-Lin Tian Angew. Chem. Int. Ed. 2015, 54, 14276-14281

The invention claimed is:

1. A method for treating a disease, disorder or condition in a subject in need thereof, wherein the disease, disorder or condition is acute kidney injury, wherein the method comprises:

administering to the subject an effective amount of a compound having the structure:

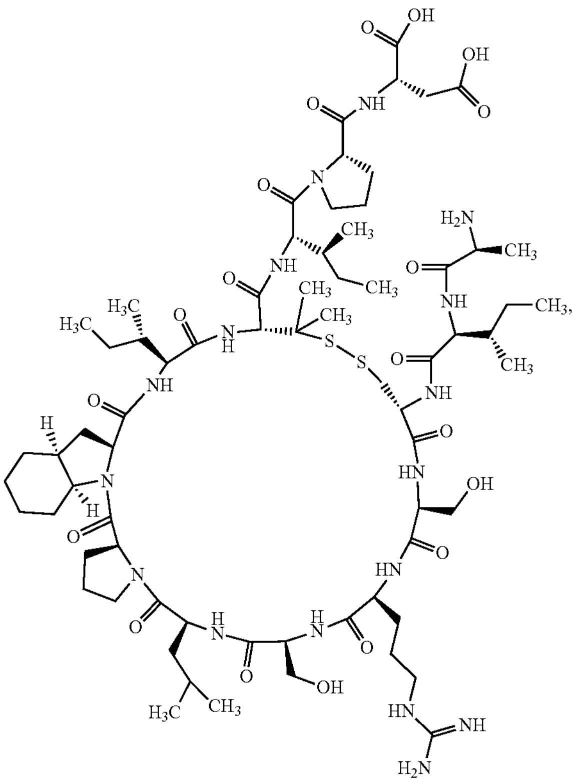 [SMILES: CC[C@H](C)[C@H](NC(=O)[C@H](C)N)C(=O)N[C@H]1CSSC(C)(C)[C@@H](C(=O)N[C@H](C(=O)N2CCC[C@H]2C(=O)N[C@@H](CC(=O)O)C(=O)O)[C@@H](C)CC)NC(=O)[C@H]([C@@H](C)CC)NC(=O)[C@@H]2C[C@@H]3CCCC[C@@H]3N2C(=O)[C@@H]2CCCN2C(=O)[C@H](CC(C)C)NC(=O)[C@H](CO)NC(=O)[C@H](CCCNC(=N)N)NC(=O)[C@H](CO)NC1=O]

or a pharmaceutically acceptable salt, solvate or solvate of the salt thereof.

2. The method of claim 1, wherein the compound is in salt free form, or is a trifluoroacetate acid salt, a hydrochloride salt, a sodium salt, or a choline salt.

3. The method of claim 1, wherein the subject is a human.

4. The method of claim 1, wherein the subject is a non-human animal.

5. A method for treating a disease, disorder or condition in a subject in need thereof, wherein the disease, disorder or condition is acute kidney injury, wherein the method comprises:

administering to the subject an effective amount of a pharmaceutical composition comprising a compound having the structure:

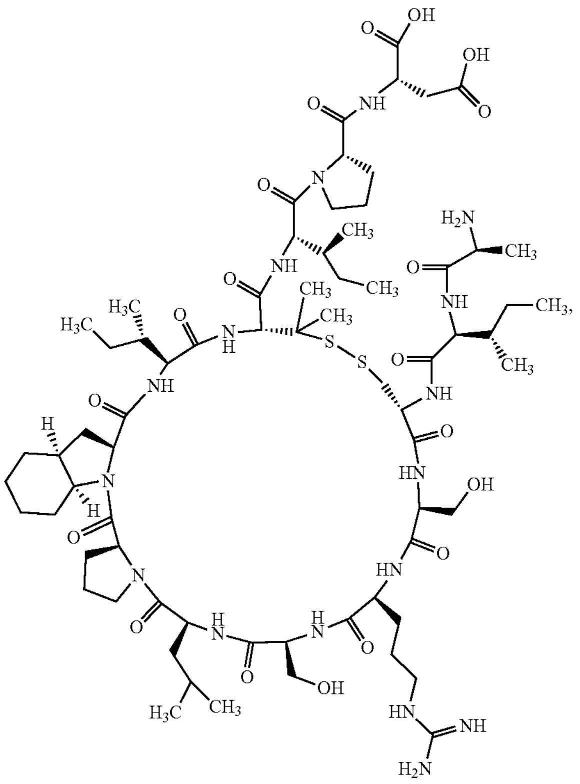 [SMILES: CC[C@H](C)[C@H](NC(=O)[C@H](C)N)C(=O)N[C@H]1CSSC(C)(C)[C@@H](C(=O)N[C@H](C(=O)N2CCC[C@H]2C(=O)N[C@@H](CC(=O)O)C(=O)O)[C@@H](C)CC)NC(=O)[C@H]([C@@H](C)CC)NC(=O)[C@@H]2C[C@@H]3CCCC[C@@H]3N2C(=O)[C@@H]2CCCN2C(=O)[C@H](CC(C)C)NC(=O)[C@H](CO)NC(=O)[C@H](CCCNC(=N)N)NC(=O)[C@H](CO)NC1=O]

or a pharmaceutically acceptable salt, solvate or solvate of the salt thereof, in combination with one or more inert, nontoxic, pharmaceutically suitable excipients.

6. The method of claim 5, wherein the compound is in salt free form, or is a trifluoroacetate acid salt, a hydrochloride salt, a sodium salt, or a choline salt.

7. The method of claim 5, wherein the subject is a human.

8. The method of claim 5, wherein the subject is a non-human animal.

* * * * *

SEQUENCE LISTING

```
Sequence total quantity: 545
SEQ ID NO: 1           moltype = AA  length = 14
FEATURE                Location/Qualifiers
REGION                 1..14
```

-continued

```
                        note = SFMI-1
DISULFID                3..11
                        note = disulfide bond
source                  1..14
                        mol_type = protein
                        organism = synthetic construct
SEQUENCE: 1
GICSRSLPPI CIPD                                                    14

SEQ ID NO: 2            moltype = AA  length = 430
FEATURE                 Location/Qualifiers
REGION                  1..430
                        note = MASP-1_Human_Sequence fragment_C-terminal His Tag
                         and N-terminal Ig-kappa secretion signal
source                  1..430
                        mol_type = protein
                        organism = synthetic construct
SEQUENCE: 2
METDTLLLWV LLLWVPGSTG DAGNECPELQ PPVHGKIEPS QAKYFFKDQV LVSCDTGYKV  60
LKDNVEMDTF QIECLKDGTW SNKIPTCKIV DCRAPGELEH GLITFSTRNN LTTYKSEIKY  120
SCQEPYYKML NNNTGIYTCS AQGVWMNKVL GRSLPTCLPV CGLPKFSRKL MARIFNGRPA  180
QKGTTPWIAM LSHLNGQPFC GGSLLGSSWI VTAAHCLHQS LDPEDPTLRD SDLLSPSDFK  240
IILGKHWRLR SDENEQHLGV KHTTLHPQYD PNTFENDVAL VELLESPVLN AFVMPICLPE  300
GPQQEGAMVI VSGWGKQFLQ RFPETLMEIE IPIVDHSTCQ KAYAPLKKKV TRDMICAGEK  360
EGGKDACAGD SGGPMVTLNR ERGQWYLVGT VSWGDDCGKK DRYGVYSYIH HNKDWIQRVT  420
GVRNHHHHHH                                                         430

SEQ ID NO: 3            moltype = AA  length = 417
FEATURE                 Location/Qualifiers
REGION                  1..417
                        note = MASP-2_Human_Sequence fragment_C-terminal His Tag
                         and N-terminal Ig-kappa secretion signal
source                  1..417
                        mol_type = protein
                        organism = synthetic construct
SEQUENCE: 3
METDTLLLWV LLLWVPGSTG DAQPCPYPMA PPNGHVSPVQ AKYILKDSFS IFCETGYELL  60
QGHLPLKSFT AVCQKDGSWD RPMPACSIVD CGPPDDLPSG RVEYITGPGV TTYKAVIQYS  120
CEETFYTMKV NDGKYVCEAD GFWTSSKGEK SLPVCEPVCG LSARTTGGRI YGGQKAKPGD  180
FPWQVLILGG TTAAGALLYD NWVLTAAHAV YEQKHDASAL DIRMGTLKRL SPHYTQAWSE  240
AVFIHEGYTH DAGFDNDIAL IKLNNKVVIN SNITPICLPR KEAESFMRTD DIGTASGWGL  300
TQRGFLARNL MYVDIPIVDH QKCTAAYEKP PYPRGSVTAN MLCAGLESGG KDSCRGDSGG  360
ALVFLDSETE RWFVGGIVSW GSMNCGEAGQ YGVYTKVINY IPWIENIISD FHHHHHH     417

SEQ ID NO: 4            moltype = AA  length = 430
FEATURE                 Location/Qualifiers
REGION                  1..430
                        note = MASP-1_Rat_Sequence fragment_C-terminal His Tag and
                         N-terminal Ig-kappa secretion signal
source                  1..430
                        mol_type = protein
                        organism = synthetic construct
SEQUENCE: 4
METDTLLLWV LLLWVPGSTG DAGNECPKLQ PPVYGKIEPS QAVYSFKDQV LISCDTGYKV  60
LKDNEVMDTF QIECLKDGAW SNKIPTCKIV DCGVPAVLKH GLVTFSTRNN LTTYKSEIRY  120
SCQQPYYKML HNTTGVYTCS AHGTWTNEVL KRSLPTCLPV CGLPKFSRKH ISRIFNGRPA  180
QKGTTPWIAM LSQLNGQPFC GGSLLGSNWV LTAAHCLHHP LDPEEPILHN SHLLSPSDFK  240
IIMGKHWRRR SDEDEQHLHV KHIMLHPLYN PSTFENDLGL VELSESPRLN DFVMPVCLPE  300
HPSTEGTMVI VSGWGKQFLQ RLPENLMEIE IPIVNYHTCQ EAYTPLGKKV TQDMICAGEK  360
EGGKDACAGD SGGPMVTKDA ERDQWYLVGV VSWGEDCGKK DRYGVYSYIY PNKDWIQRVT  420
GVRNHHHHHH                                                         430

SEQ ID NO: 5            moltype = AA  length = 417
FEATURE                 Location/Qualifiers
REGION                  1..417
                        note = MASP-2_Rat_Sequence fragment_C-terminal His Tag and
                         N-terminal Ig-kappa secretion signal
source                  1..417
                        mol_type = protein
                        organism = synthetic construct
SEQUENCE: 5
METDTLLLWV LLLWVPGSTG DTAQPCPDPT APPNGHISPV QATYVLKDSF SVFCKTGFEL  60
LQGSVPLKSF TAVCQKDGSW DRPIPECSII DCGPPDDLPN GHVDYITGPE VTTYKAVIQY  120
SCEETFYTMS SNGKYVCEAD GFWTSSKGEK SLPVCKPVCG LSTHTSGGRI IGGQPAKPGD  180
FPWQVLLLGE TTAAGALIHD DWVLTAAHAV YGKTEAMSSL DIRMGILKRL SLIYTQAWPE  240
AVFIHEGYTH GAGFDNDIAL IKLKNKVTIN RNIMPICLPR KEAASLMKTD FVGTVAGWGL  300
TQKGFLARNL MFVDIPIVDH QKCATAYTKQ PYPGAKVTVN MLCAGLDRGG KDSCRGDSGG  360
ALVFLDNETQ RWFVGGIVSW GSINCGGSEQ YGVYTKVTNY IPWIENIINN FHHHHHH     417
```

-continued

```
SEQ ID NO: 6            moltype = AA  length = 10
FEATURE                 Location/Qualifiers
REGION                  1..10
                        note = Fluorescence Resonance Energy Transfer substrate
MOD_RES                 1
                        note = Xaa is 2-aminobenzoyl
MOD_RES                 10
                        note = AMIDATION
MOD_RES                 10
                        note = Xaa is 2-amino-6-(2,4-dinitroanilino)hexanoic acid
source                  1..10
                        mol_type = protein
                        organism = synthetic construct
SEQUENCE: 6
XMYGGARRLX                                                  10

SEQ ID NO: 7            moltype = AA  length = 12
FEATURE                 Location/Qualifiers
REGION                  1..12
                        note = Fluorescence resonance energy transfer substrate
MOD_RES                 1
                        note = Xaa is 4-((4-(dimethylamino)phenyl)azo)benzoic acid
MOD_RES                 12
                        note = AMIDATION
MOD_RES                 12
                        note = Xaa is
                         2-amino-5-oxo-5-[2-[(5-sulfo-1-naphthyl)amino]ethylamino]pe
                         ntanoi c acid
source                  1..12
                        mol_type = protein
                        organism = synthetic construct
SEQUENCE: 7
XKISPQGYGR RX                                               12

SEQ ID NO: 8            moltype = AA  length = 10
FEATURE                 Location/Qualifiers
REGION                  1..10
                        note = Fluorescence resonance energy transfer substrate
MOD_RES                 1
                        note = Xaa is 4-((4-(dimethylamino)phenyl)azo)benzoic acid
MOD_RES                 10
                        note = AMIDATION
MOD_RES                 10
                        note = Xaa is
                         2-amino-5-oxo-5-[2-[(5-sulfo-1-naphthyl)amino]ethylamino]pe
                         ntanoi c acid
source                  1..10
                        mol_type = protein
                        organism = synthetic construct
SEQUENCE: 8
XMYGGARRLX                                                  10

SEQ ID NO: 9            moltype = AA  length = 10
FEATURE                 Location/Qualifiers
REGION                  1..10
                        note = Fluorescence resonance energy transfer substrate
MOD_RES                 1
                        note = Xaa is 2-aminobenzoyl
MOD_RES                 10
                        note = AMIDATION
MOD_RES                 10
                        note = Xaa is 2-amino-6-(2,4-dinitroanilino)hexanoic acid
source                  1..10
                        mol_type = protein
                        organism = synthetic construct
SEQUENCE: 9
XIEGRTSEDX                                                  10

SEQ ID NO: 10           moltype = AA  length = 14
FEATURE                 Location/Qualifiers
REGION                  1..14
                        note = Ala-1 SFMI-1
DISULFID                3..11
                        note = disulfide bond
source                  1..14
                        mol_type = protein
                        organism = synthetic construct
SEQUENCE: 10
AICSRSLPPI CIPD                                             14
```

```
SEQ ID NO: 11          moltype = AA  length = 14
FEATURE                Location/Qualifiers
REGION                 1..14
                       note = Synthetic Construct
DISULFID               3..11
                       note = disulfide bond
source                 1..14
                       mol_type = protein
                       organism = synthetic construct
SEQUENCE: 11
GICSRSLPPI CIPD                                                    14

SEQ ID NO: 12          moltype = AA  length = 14
FEATURE                Location/Qualifiers
REGION                 1..14
                       note = Synthetic Construct
DISULFID               3..11
                       note = disulfide bond
source                 1..14
                       mol_type = protein
                       organism = synthetic construct
SEQUENCE: 12
GICSRSLPPI CIPD                                                    14

SEQ ID NO: 13          moltype = AA  length = 14
FEATURE                Location/Qualifiers
REGION                 1..14
                       note = Synthetic Construct
DISULFID               3..11
                       note = disulfide bond
MOD_RES                14
                       note = AMIDATION
source                 1..14
                       mol_type = protein
                       organism = synthetic construct
SEQUENCE: 13
GICSRSLPPI CIPD                                                    14

SEQ ID NO: 14          moltype = AA  length = 14
FEATURE                Location/Qualifiers
REGION                 1..14
                       note = Synthetic Construct
DISULFID               3..11
                       note = disulfide bond
source                 1..14
                       mol_type = protein
                       organism = synthetic construct
SEQUENCE: 14
AICSRSLPPI CIPD                                                    14

SEQ ID NO: 15          moltype = AA  length = 14
FEATURE                Location/Qualifiers
REGION                 1..14
                       note = Synthetic Construct
DISULFID               3..11
                       note = disulfide bond
MOD_RES                14
                       note = AMIDATION
source                 1..14
                       mol_type = protein
                       organism = synthetic construct
SEQUENCE: 15
AICSRSLPPI CIPD                                                    14

SEQ ID NO: 16          moltype = AA  length = 14
FEATURE                Location/Qualifiers
REGION                 1..14
                       note = Synthetic Construct
DISULFID               3..11
                       note = disulfide bond
MOD_RES                14
                       note = AMIDATION
source                 1..14
                       mol_type = protein
                       organism = synthetic construct
SEQUENCE: 16
AICSRSLPPI CIPD                                                    14
```

```
SEQ ID NO: 17           moltype = AA  length = 15
FEATURE                 Location/Qualifiers
REGION                  1..15
                        note = Synthetic Construct
MOD_RES                 1
                        note = MeGly
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
MOD_RES                 15
                        note = AMIDATION
MOD_RES                 15
                        note = Xaa is 9-Amino-4,7-dioxanonanoic acid
source                  1..15
                        mol_type = protein
                        organism = synthetic construct
SEQUENCE: 17
XICSRSLPXI XIPDX                                                            15

SEQ ID NO: 18           moltype = AA  length = 14
FEATURE                 Location/Qualifiers
REGION                  1..14
                        note = Synthetic Construct
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
source                  1..14
                        mol_type = protein
                        organism = synthetic construct
SEQUENCE: 18
AICSRSLPXI XIPD                                                             14

SEQ ID NO: 19           moltype = AA  length = 12
FEATURE                 Location/Qualifiers
REGION                  1..12
                        note = Synthetic Construct
MOD_RES                 1
                        note = Nva
DISULFID                3..11
                        note = disulfide bond
MOD_RES                 7
                        note = Xaa is L-tert-Butylalanine
MOD_RES                 11
                        note = Xaa is L-N-Methylcysteine
MOD_RES                 12
                        note = AMIDATION
source                  1..12
                        mol_type = protein
                        organism = synthetic construct
SEQUENCE: 19
XICSRSXPPI XI                                                               12

SEQ ID NO: 20           moltype = AA  length = 14
FEATURE                 Location/Qualifiers
REGION                  1..14
                        note = Synthetic Construct
MOD_RES                 1
                        note = MeGly
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
MOD_RES                 14
                        note = AMIDATION
MOD_RES                 14
                        note = Xaa is 12-Amino-4,7,10-trioxadodecanoic acid
source                  1..14
                        mol_type = protein
```

```
                        organism = synthetic construct
SEQUENCE: 20
XICSRSLPXI XIPX                                                             14

SEQ ID NO: 21           moltype = AA  length = 13
FEATURE                 Location/Qualifiers
REGION                  1..13
                        note = Synthetic Construct
MOD_RES                 1
                        note = Xaa is (S)-Pyrrolidine-2-carboxylic acid
DISULFID                3..11
                        note = disulfide bond
MOD_RES                 7
                        note = Xaa is L-tert-Butylalanine
MOD_RES                 11
                        note = Xaa is L-Penicillamine
MOD_RES                 13
                        note = AMIDATION
source                  1..13
                        mol_type = protein
                        organism = synthetic construct
SEQUENCE: 21
XICSRSXPPI XIP                                                              13

SEQ ID NO: 22           moltype = AA  length = 14
FEATURE                 Location/Qualifiers
REGION                  1..14
                        note = Synthetic Construct
DISULFID                3..11
                        note = disulfide bond
MOD_RES                 7
                        note = Xaa is L-tert-Butylalanine
MOD_RES                 11
                        note = Xaa is L-Penicillamine
MOD_RES                 14
                        note = AMIDATION
source                  1..14
                        mol_type = protein
                        organism = synthetic construct
SEQUENCE: 22
PICSRSXPPI XIPD                                                             14

SEQ ID NO: 23           moltype = AA  length = 14
FEATURE                 Location/Qualifiers
REGION                  1..14
                        note = Synthetic Construct
MOD_RES                 1
                        note = Aib
DISULFID                3..11
                        note = disulfide bond
MOD_RES                 7
                        note = Xaa is L-tert-Butylalanine
MOD_RES                 11
                        note = Xaa is L-Penicillamine
MOD_RES                 14
                        note = AMIDATION
source                  1..14
                        mol_type = protein
                        organism = synthetic construct
SEQUENCE: 23
XICSRSXPPI XIPD                                                             14

SEQ ID NO: 24           moltype = AA  length = 14
FEATURE                 Location/Qualifiers
REGION                  1..14
                        note = Synthetic Construct
MOD_RES                 2
                        note = MeIle
DISULFID                3..11
                        note = disulfide bond
MOD_RES                 7
                        note = Xaa is L-tert-Butylalanine
MOD_RES                 11
                        note = Xaa is L-N-Methylcysteine
MOD_RES                 14
                        note = AMIDATION
source                  1..14
                        mol_type = protein
                        organism = synthetic construct
```

```
SEQUENCE: 24
AXCSRSXPPI XIPD                                              14

SEQ ID NO: 25          moltype = AA  length = 14
FEATURE                Location/Qualifiers
REGION                 1..14
                       note = Synthetic Construct
DISULFID               3..11
                       note = disulfide bond
MOD_RES                7
                       note = Xaa is L-tert-Butylalanine
MOD_RES                11
                       note = Xaa is L-Penicillamine
source                 1..14
                       mol_type = protein
                       organism = synthetic construct
SEQUENCE: 25
AICSRSXPPI XIPD                                              14

SEQ ID NO: 26          moltype = AA  length = 14
FEATURE                Location/Qualifiers
REGION                 1..14
                       note = Synthetic Construct
DISULFID               3..11
                       note = disulfide bond
MOD_RES                9
                       note = Xaa is
                        2,3,3a,4,5,6,7,7a-Octahydroindole-2-carboxylic acid
MOD_RES                11
                       note = Xaa is L-Penicillamine
source                 1..14
                       mol_type = protein
                       organism = synthetic construct
SEQUENCE: 26
AICSRSLPXI XIPD                                              14

SEQ ID NO: 27          moltype = AA  length = 14
FEATURE                Location/Qualifiers
REGION                 1..14
                       note = Synthetic Construct
DISULFID               3..11
                       note = disulfide bond
MOD_RES                7
                       note = Xaa is L-tert-Butylalanine
MOD_RES                9
                       note = Xaa is
                        2,3,3a,4,5,6,7,7a-Octahydroindole-2-carboxylic acid
MOD_RES                11
                       note = Xaa is L-Penicillamine
source                 1..14
                       mol_type = protein
                       organism = synthetic construct
SEQUENCE: 27
AICSRSXPXI XIPD                                              14

SEQ ID NO: 28          moltype = AA  length = 14
FEATURE                Location/Qualifiers
REGION                 1..14
                       note = Synthetic Construct
MOD_RES                1
                       note = Xaa is 2-(Pyrrolidine)acetic acid
MOD_RES                3..11
                       note = disulfide bond
MOD_RES                7
                       note = Xaa is L-tert-Butylalanine
MOD_RES                11
                       note = Xaa is L-Penicillamine
MOD_RES                14
                       note = AMIDATION
source                 1..14
                       mol_type = protein
                       organism = synthetic construct
SEQUENCE: 28
XICSRSXPPI XIPD                                              14

SEQ ID NO: 29          moltype = AA  length = 14
FEATURE                Location/Qualifiers
REGION                 1..14
                       note = Synthetic Construct
```

-continued

```
MOD_RES                 1
                        note = MeGly
DISULFID                3..11
                        note = disulfide bond
MOD_RES                 7
                        note = Xaa is L-tert-Butylalanine
MOD_RES                 11
                        note = Xaa is L-Penicillamine
MOD_RES                 14
                        note = AMIDATION
MOD_RES                 14
                        note = Xaa is 15-Amino-4,7,10,13-tetraoxapentadecanoic acid
source                  1..14
                        mol_type = protein
                        organism = synthetic construct
SEQUENCE: 29
XICSRSXPPI XIPX                                                             14

SEQ ID NO: 30           moltype = AA  length = 14
FEATURE                 Location/Qualifiers
REGION                  1..14
                        note = Synthetic Construct
DISULFID                3..11
                        note = disulfide bond
MOD_RES                 9
                        note = Xaa is (6S)-5-Azaspiro[2.4]heptane-6-carboxylic acid
MOD_RES                 11
                        note = Xaa is L-Penicillamine
MOD_RES                 14
                        note = AMIDATION
source                  1..14
                        mol_type = protein
                        organism = synthetic construct
SEQUENCE: 30
AICSRSLPXI XIPD                                                             14

SEQ ID NO: 31           moltype = AA  length = 14
FEATURE                 Location/Qualifiers
REGION                  1..14
                        note = Synthetic Construct
MOD_RES                 1
                        note = Orn
DISULFID                3..11
                        note = disulfide bond
MOD_RES                 7
                        note = Xaa is L-tert-Butylalanine
MOD_RES                 11
                        note = Xaa is L-Penicillamine
source                  1..14
                        mol_type = protein
                        organism = synthetic construct
SEQUENCE: 31
XICSRSXPPI XIPD                                                             14

SEQ ID NO: 32           moltype = AA  length = 14
FEATURE                 Location/Qualifiers
REGION                  1..14
                        note = Synthetic Construct
DISULFID                3..11
                        note = disulfide bond
MOD_RES                 7
                        note = Xaa is L-tert-Butylalanine
MOD_RES                 11
                        note = Xaa is L-N-Methylcysteine
MOD_RES                 14
                        note = AMIDATION
source                  1..14
                        mol_type = protein
                        organism = synthetic construct
SEQUENCE: 32
RICSRSXPPI XIPD                                                             14

SEQ ID NO: 33           moltype = AA  length = 13
FEATURE                 Location/Qualifiers
REGION                  1..13
                        note = Synthetic Construct
DISULFID                3..11
                        note = disulfide bond
MOD_RES                 7
```

```
                         note = Xaa is L-tert-Butylalanine
MOD_RES                  11
                         note = Xaa is L-N-Methylcysteine
MOD_RES                  12
                         note = Xaa is
                          2-[(1S,2S)-1-(Amino)-2-methylbutyl]-1,3-oxazole-4-carboxyli
                          c acid
MOD_RES                  13
                         note = AMIDATION
source                   1..13
                         mol_type = protein
                         organism = synthetic construct
SEQUENCE: 33
AICSRSXPPI XXD                                                            13

SEQ ID NO: 34            moltype = AA  length = 14
FEATURE                  Location/Qualifiers
REGION                   1..14
                         note = Synthetic Construct
DISULFID                 3..11
                         note = disulfide bond
MOD_RES                  7
                         note = Xaa is L-tert-Butylalanine
MOD_RES                  11
                         note = Xaa is L-Penicillamine
MOD_RES                  14
                         note = AMIDATION
SITE                     14
                         note = Xaa is D-Glutamic acid
source                   1..14
                         mol_type = protein
                         organism = synthetic construct
SEQUENCE: 34
AICSRSXPPI XIPX                                                           14

SEQ ID NO: 35            moltype = AA  length = 14
FEATURE                  Location/Qualifiers
REGION                   1..14
                         note = Synthetic Construct
DISULFID                 3..11
                         note = disulfide bond
MOD_RES                  7
                         note = Xaa is L-tert-Butylalanine
MOD_RES                  11
                         note = Xaa is L-Penicillamine
MOD_RES                  14
                         note = AMIDATION
SITE                     14
                         note = Xaa is D-Asparagine
source                   1..14
                         mol_type = protein
                         organism = synthetic construct
SEQUENCE: 35
AICSRSXPPI XIPX                                                           14

SEQ ID NO: 36            moltype = AA  length = 13
FEATURE                  Location/Qualifiers
REGION                   1..13
                         note = Synthetic Construct
MOD_RES                  1
                         note = Xaa is L-N-Methylalanine
DISULFID                 3..11
                         note = disulfide bond
MOD_RES                  7
                         note = Xaa is L-tert-Butylalanine
MOD_RES                  9
                         note = Xaa is
                          2,3,3a,4,5,6,7,7a-Octahydroindole-2-carboxylic acid
MOD_RES                  11
                         note = Xaa is L-Penicillamine
MOD_RES                  13
                         note = AMIDATION
source                   1..13
                         mol_type = protein
                         organism = synthetic construct
SEQUENCE: 36
XICSRSXPXI XIP                                                            13

SEQ ID NO: 37            moltype = AA  length = 14
```

-continued

```
FEATURE                Location/Qualifiers
REGION                 1..14
                       note = Synthetic Construct
MOD_RES                1
                       note = Xaa is L-N-Methylalanine
DISULFID               3..11
                       note = disulfide bond
MOD_RES                7
                       note = Xaa is L-tert-Butylalanine
MOD_RES                11
                       note = Xaa is L-Penicillamine
MOD_RES                14
                       note = AMIDATION
source                 1..14
                       mol_type = protein
                       organism = synthetic construct
SEQUENCE: 37
XICSRSXPPI XIPD                                                        14

SEQ ID NO: 38          moltype = AA  length = 12
FEATURE                Location/Qualifiers
REGION                 1..12
                       note = Synthetic Construct
DISULFID               3..11
                       note = disulfide bond
MOD_RES                7
                       note = Xaa is L-tert-Butylalanine
MOD_RES                11
                       note = Xaa is L-N-Methylcysteine
MOD_RES                12
                       note = AMIDATION
source                 1..12
                       mol_type = protein
                       organism = synthetic construct
SEQUENCE: 38
AICSRSXPPI XI                                                          12

SEQ ID NO: 39          moltype = AA  length = 14
FEATURE                Location/Qualifiers
REGION                 1..14
                       note = Synthetic Construct
DISULFID               3..11
                       note = disulfide bond
MOD_RES                9
                       note = Xaa is
                        2,3,3a,4,5,6,7,7a-Octahydroindole-2-carboxylic acid
MOD_RES                11
                       note = Xaa is L-Penicillamine
MOD_RES                14
                       note = AMIDATION
source                 1..14
                       mol_type = protein
                       organism = synthetic construct
SEQUENCE: 39
AICSRSLPXI XIPD                                                        14

SEQ ID NO: 40          moltype = AA  length = 14
FEATURE                Location/Qualifiers
REGION                 1..14
                       note = Synthetic Construct
DISULFID               3..11
                       note = disulfide bond
MOD_RES                9
                       note = Xaa is
                        2,3,3a,4,5,6,7,7a-Octahydroindole-2-carboxylic acid
MOD_RES                11
                       note = Xaa is L-Penicillamine
MOD_RES                14
                       note = AMIDATION
source                 1..14
                       mol_type = protein
                       organism = synthetic construct
SEQUENCE: 40
AICSRSLPXI XIPD                                                        14

SEQ ID NO: 41          moltype = AA  length = 12
FEATURE                Location/Qualifiers
REGION                 1..12
                       note = Synthetic Construct
```

```
MOD_RES                 1
                        note = Nle
DISULFID                3..11
                        note = disulfide bond
MOD_RES                 7
                        note = Xaa is L-tert-Butylalanine
MOD_RES                 11
                        note = Xaa is L-N-Methylcysteine
MOD_RES                 12
                        note = AMIDATION
source                  1..12
                        mol_type = protein
                        organism = synthetic construct
SEQUENCE: 41
XICSRSXPPI XI                                                       12

SEQ ID NO: 42           moltype = AA  length = 14
FEATURE                 Location/Qualifiers
REGION                  1..14
                        note = Synthetic Construct
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
source                  1..14
                        mol_type = protein
                        organism = synthetic construct
SEQUENCE: 42
AICSRSLPXI XIPD                                                     14

SEQ ID NO: 43           moltype = AA  length = 14
FEATURE                 Location/Qualifiers
REGION                  1..14
                        note = Synthetic Construct
DISULFID                3..11
                        note = disulfide bond
MOD_RES                 7
                        note = Xaa is L-tert-Butylalanine
MOD_RES                 11
                        note = Xaa is L-N-Methylcysteine
MOD_RES                 14
                        note = AMIDATION
source                  1..14
                        mol_type = protein
                        organism = synthetic construct
SEQUENCE: 43
AICSRSXPPI XIPD                                                     14

SEQ ID NO: 44           moltype = AA  length = 14
FEATURE                 Location/Qualifiers
REGION                  1..14
                        note = Synthetic Construct
DISULFID                3..11
                        note = disulfide bond
MOD_RES                 7
                        note = Xaa is L-tert-Butylalanine
MOD_RES                 9
                        note = Xaa is (6S)-5-Azaspiro[2.4]heptane-6-carboxylic acid
MOD_RES                 11
                        note = Xaa is L-Penicillamine
source                  1..14
                        mol_type = protein
                        organism = synthetic construct
SEQUENCE: 44
AICSRSXPXI XIPD                                                     14

SEQ ID NO: 45           moltype = AA  length = 14
FEATURE                 Location/Qualifiers
REGION                  1..14
                        note = Synthetic Construct
MOD_RES                 1
                        note = Xaa is 1-(Aminomethyl)-cyclopropyl-1-carboxylic acid
DISULFID                3..11
                        note = disulfide bond
MOD_RES                 7
                        note = Xaa is L-tert-Butylalanine
```

```
MOD_RES                 11
                        note = Xaa is L-Penicillamine
MOD_RES                 14
                        note = AMIDATION
source                  1..14
                        mol_type = protein
                        organism = synthetic construct
SEQUENCE: 45
XICSRSXPPI XIPD                                                     14

SEQ ID NO: 46           moltype = AA  length = 13
FEATURE                 Location/Qualifiers
REGION                  1..13
                        note = Synthetic Construct
MOD_RES                 1
                        note = Xaa is
                         (1R,3S,4S)-2-azabicyclo[2.2.1]heptane-3-carboxylic acid
DISULFID                3..11
                        note = disulfide bond
MOD_RES                 7
                        note = Xaa is L-tert-Butylalanine
MOD_RES                 11
                        note = Xaa is L-Penicillamine
MOD_RES                 13
                        note = AMIDATION
source                  1..13
                        mol_type = protein
                        organism = synthetic construct
SEQUENCE: 46
XICSRSXPPI XIP                                                      13

SEQ ID NO: 47           moltype = AA  length = 14
FEATURE                 Location/Qualifiers
REGION                  1..14
                        note = Synthetic Construct
MOD_RES                 1
                        note = MeGly
DISULFID                3..11
                        note = disulfide bond
MOD_RES                 7
                        note = Xaa is L-tert-Butylalanine
MOD_RES                 11
                        note = Xaa is L-Penicillamine
MOD_RES                 14
                        note = AMIDATION
MOD_RES                 14
                        note = Xaa is
                         1-Amino-3,6,9,12,15,18,21-heptaoxatetracosan-24-oic acid
source                  1..14
                        mol_type = protein
                        organism = synthetic construct
SEQUENCE: 47
XICSRSXPPI XIPX                                                     14

SEQ ID NO: 48           moltype = AA  length = 14
FEATURE                 Location/Qualifiers
REGION                  1..14
                        note = Synthetic Construct
DISULFID                3..11
                        note = disulfide bond
MOD_RES                 7
                        note = Xaa is L-tert-Butylalanine
MOD_RES                 11
                        note = Xaa is L-N-Methylcysteine
MOD_RES                 14
                        note = AMIDATION
source                  1..14
                        mol_type = protein
                        organism = synthetic construct
SEQUENCE: 48
KICSRSXPPI XIPD                                                     14

SEQ ID NO: 49           moltype = AA  length = 14
FEATURE                 Location/Qualifiers
REGION                  1..14
                        note = Synthetic Construct
DISULFID                3..11
                        note = disulfide bond
MOD_RES                 9
```

-continued

```
                        note = Xaa is (6S)-5-Azaspiro[2.4]heptane-6-carboxylic acid
MOD_RES                 11
                        note = Xaa is L-Penicillamine
source                  1..14
                        mol_type = protein
                        organism = synthetic construct
SEQUENCE: 49
AICSRSLPXI XIPD                                                             14

SEQ ID NO: 50           moltype = AA  length = 12
FEATURE                 Location/Qualifiers
REGION                  1..12
                        note = Synthetic Construct
DISULFID                3..11
                        note = disulfide bond
MOD_RES                 7
                        note = Xaa is L-tert-Butylalanine
MOD_RES                 12
                        note = AMIDATION
source                  1..12
                        mol_type = protein
                        organism = synthetic construct
SEQUENCE: 50
AICSRSXPPI CI                                                               12

SEQ ID NO: 51           moltype = AA  length = 12
FEATURE                 Location/Qualifiers
REGION                  1..12
                        note = Synthetic Construct
DISULFID                3..11
                        note = disulfide bond
MOD_RES                 7
                        note = Xaa is L-tert-Butylalanine
MOD_RES                 11
                        note = Xaa is L-N-Methylcysteine
MOD_RES                 12
                        note = AMIDATION
source                  1..12
                        mol_type = protein
                        organism = synthetic construct
SEQUENCE: 51
RICSRSXPPI XI                                                               12

SEQ ID NO: 52           moltype = AA  length = 14
FEATURE                 Location/Qualifiers
REGION                  1..14
                        note = Synthetic Construct
MOD_RES                 1
                        note = MeGly
DISULFID                3..11
                        note = disulfide bond
MOD_RES                 7
                        note = Xaa is L-tert-Butylalanine
MOD_RES                 11
                        note = Xaa is L-Penicillamine
MOD_RES                 14
                        note = AMIDATION
MOD_RES                 14
                        note = Xaa is 9-Amino-4,7-dioxanonanoic acid
source                  1..14
                        mol_type = protein
                        organism = synthetic construct
SEQUENCE: 52
XICSRSXPPI XIPX                                                             14

SEQ ID NO: 53           moltype = AA  length = 14
FEATURE                 Location/Qualifiers
REGION                  1..14
                        note = Synthetic Construct
MOD_RES                 1
                        note = Xaa is L-Citrulline
DISULFID                3..11
                        note = disulfide bond
MOD_RES                 7
                        note = Xaa is L-tert-Butylalanine
MOD_RES                 11
                        note = Xaa is L-Penicillamine
MOD_RES                 14
                        note = AMIDATION
```

```
source                  1..14
                        mol_type = protein
                        organism = synthetic construct
SEQUENCE: 53
XICSRSXPPI XIPD                                                           14

SEQ ID NO: 54           moltype = AA  length = 14
FEATURE                 Location/Qualifiers
REGION                  1..14
                        note = Synthetic Construct
DISULFID                3..11
                        note = disulfide bond
MOD_RES                 7
                        note = Xaa is L-tert-Butylalanine
MOD_RES                 9
                        note = Xaa is (6S)-5-Azaspiro[2.4]heptane-6-carboxylic acid
MOD_RES                 11
                        note = Xaa is L-N-Methylcysteine
MOD_RES                 14
                        note = AMIDATION
source                  1..14
                        mol_type = protein
                        organism = synthetic construct
SEQUENCE: 54
AICSRSXPXI XIPD                                                           14

SEQ ID NO: 55           moltype = AA  length = 14
FEATURE                 Location/Qualifiers
REGION                  1..14
                        note = Synthetic Construct
MOD_RES                 1
                        note = MeGly
DISULFID                3..11
                        note = disulfide bond
MOD_RES                 7
                        note = Xaa is L-tert-Butylalanine
MOD_RES                 11
                        note = Xaa is L-Penicillamine
MOD_RES                 14
                        note = AMIDATION
MOD_RES                 14
                        note = Xaa is (S)-3-(2H-tetrazol-5-yl)propanoic acid
source                  1..14
                        mol_type = protein
                        organism = synthetic construct
SEQUENCE: 55
XICSRSXPPI XIPX                                                           14

SEQ ID NO: 56           moltype = AA  length = 12
FEATURE                 Location/Qualifiers
REGION                  1..12
                        note = Synthetic Construct
MOD_RES                 1
                        note = Xaa is L-N-Methylalanine
DISULFID                3..11
                        note = disulfide bond
MOD_RES                 7
                        note = Xaa is L-tert-Butylalanine
MOD_RES                 9
                        note = Xaa is
                         2,3,3a,4,5,6,7,7a-Octahydroindole-2-carboxylic acid
MOD_RES                 11
                        note = Xaa is L-Penicillamine
MOD_RES                 12
                        note = AMIDATION
source                  1..12
                        mol_type = protein
                        organism = synthetic construct
SEQUENCE: 56
XICSRSXPXI XI                                                             12

SEQ ID NO: 57           moltype = AA  length = 14
FEATURE                 Location/Qualifiers
REGION                  1..14
                        note = Synthetic Construct
MOD_RES                 1
                        note = MeGly
DISULFID                3..11
                        note = disulfide bond
```

```
MOD_RES                  7
                         note = Xaa is L-tert-Butylalanine
MOD_RES                  11
                         note = Xaa is L-Penicillamine
MOD_RES                  14
                         note = AMIDATION
MOD_RES                  14
                         note = Xaa is
                          1-Amino-3,6,9,12,15,18,21,24,27-nonaoxatriacontan-30-oic
                          acid
source                   1..14
                         mol_type = protein
                         organism = synthetic construct
SEQUENCE: 57
XICSRSXPPI XIPX                                                      14

SEQ ID NO: 58            moltype = AA  length = 14
FEATURE                  Location/Qualifiers
REGION                   1..14
                         note = Synthetic Construct
DISULFID                 3..11
                         note = disulfide bond
MOD_RES                  7
                         note = Xaa is L-tert-Butylalanine
MOD_RES                  9
                         note = Xaa is (6S)-5-Azaspiro[2.4]heptane-6-carboxylic acid
MOD_RES                  11
                         note = Xaa is L-Penicillamine
MOD_RES                  14
                         note = AMIDATION
source                   1..14
                         mol_type = protein
                         organism = synthetic construct
SEQUENCE: 58
AICSRSXPXI XIPD                                                      14

SEQ ID NO: 59            moltype = AA  length = 14
FEATURE                  Location/Qualifiers
REGION                   1..14
                         note = Synthetic Construct
MOD_RES                  1
                         note = Xaa is L-Pipecolic acid
DISULFID                 3..11
                         note = disulfide bond
MOD_RES                  7
                         note = Xaa is L-tert-Butylalanine
MOD_RES                  11
                         note = Xaa is L-N-Methylcysteine
MOD_RES                  14
                         note = AMIDATION
source                   1..14
                         mol_type = protein
                         organism = synthetic construct
SEQUENCE: 59
XICSRSXPPI XIPD                                                      14

SEQ ID NO: 60            moltype = AA  length = 14
FEATURE                  Location/Qualifiers
REGION                   1..14
                         note = Synthetic Construct
MOD_RES                  1
                         note = Xaa is 3-Amino-3-methylbutyric acid
DISULFID                 3..11
                         note = disulfide bond
MOD_RES                  7
                         note = Xaa is L-tert-Butylalanine
MOD_RES                  11
                         note = Xaa is L-Penicillamine
MOD_RES                  14
                         note = AMIDATION
source                   1..14
                         mol_type = protein
                         organism = synthetic construct
SEQUENCE: 60
XICSRSXPPI XIPD                                                      14

SEQ ID NO: 61            moltype = AA  length = 14
FEATURE                  Location/Qualifiers
REGION                   1..14
```

-continued

```
                        note = Synthetic Construct
DISULFID                3..11
                        note = disulfide bond
MOD_RES                 7
                        note = Xaa is L-tert-Butylalanine
MOD_RES                 11
                        note = Xaa is L-N-Methylcysteine
MOD_RES                 14
                        note = AMIDATION
source                  1..14
                        mol_type = protein
                        organism = synthetic construct
SEQUENCE: 61
AICSRSXPPI XIPD                                              14

SEQ ID NO: 62           moltype = AA  length = 14
FEATURE                 Location/Qualifiers
REGION                  1..14
                        note = Synthetic Construct
MOD_RES                 1
                        note = Orn
DISULFID                3..11
                        note = disulfide bond
MOD_RES                 7
                        note = Xaa is L-tert-Butylalanine
MOD_RES                 11
                        note = Xaa is L-Penicillamine
MOD_RES                 14
                        note = AMIDATION
source                  1..14
                        mol_type = protein
                        organism = synthetic construct
SEQUENCE: 62
XICSRSXPPI XIPD                                              14

SEQ ID NO: 63           moltype = AA  length = 14
FEATURE                 Location/Qualifiers
REGION                  1..14
                        note = Synthetic Construct
MOD_RES                 1
                        note = Orn
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
MOD_RES                 14
                        note = AMIDATION
source                  1..14
                        mol_type = protein
                        organism = synthetic construct
SEQUENCE: 63
XICSRSLPXI XIPD                                              14

SEQ ID NO: 64           moltype = AA  length = 14
FEATURE                 Location/Qualifiers
REGION                  1..14
                        note = Synthetic Construct
SITE                    1
                        note = Xaa is D-Alanine
DISULFID                3..11
                        note = disulfide bond
MOD_RES                 7
                        note = Xaa is L-tert-Butylalanine
MOD_RES                 11
                        note = Xaa is L-Penicillamine
MOD_RES                 14
                        note = AMIDATION
source                  1..14
                        mol_type = protein
                        organism = synthetic construct
SEQUENCE: 64
XICSRSXPPI XIPD                                              14

SEQ ID NO: 65           moltype = AA  length = 14
FEATURE                 Location/Qualifiers
REGION                  1..14
```

```
                        note = Synthetic Construct
MOD_RES                 2
                        note = Xaa is L-Cyclobutylalanine
DISULFID                3..11
                        note = disulfide bond
MOD_RES                 7
                        note = Xaa is L-tert-Butylalanine
MOD_RES                 11
                        note = Xaa is L-Penicillamine
MOD_RES                 14
                        note = AMIDATION
source                  1..14
                        mol_type = protein
                        organism = synthetic construct
SEQUENCE: 65
AXCSRSXPPI XIPD                                                       14

SEQ ID NO: 66           moltype = AA  length = 12
FEATURE                 Location/Qualifiers
REGION                  1..12
                        note = Synthetic Construct
DISULFID                3..11
                        note = disulfide bond
MOD_RES                 7
                        note = Xaa is L-tert-Butylalanine
MOD_RES                 11
                        note = Xaa is L-N-Methylcysteine
MOD_RES                 12
                        note = AMIDATION
source                  1..12
                        mol_type = protein
                        organism = synthetic construct
SEQUENCE: 66
TICSRSXPPI XI                                                         12

SEQ ID NO: 67           moltype = AA  length = 14
FEATURE                 Location/Qualifiers
REGION                  1..14
                        note = Synthetic Construct
DISULFID                3..11
                        note = disulfide bond
MOD_RES                 7
                        note = Xaa is L-tert-Butylalanine
MOD_RES                 11
                        note = Xaa is L-Penicillamine
MOD_RES                 14
                        note = AMIDATION
source                  1..14
                        mol_type = protein
                        organism = synthetic construct
SEQUENCE: 67
VICSRSXPPI XIPD                                                       14

SEQ ID NO: 68           moltype = AA  length = 14
FEATURE                 Location/Qualifiers
REGION                  1..14
                        note = Synthetic Construct
MOD_RES                 1
                        note = MeGly
DISULFID                3..11
                        note = disulfide bond
MOD_RES                 7
                        note = Xaa is L-tert-Butylalanine
MOD_RES                 11
                        note = Xaa is L-Penicillamine
MOD_RES                 14
                        note = AMIDATION
MOD_RES                 14
                        note = Xaa is 17-Amino-3,6,9,12,15-pentaoxaheptadecanoic
                         acid
source                  1..14
                        mol_type = protein
                        organism = synthetic construct
SEQUENCE: 68
XICSRSXPPI XIPX                                                       14

SEQ ID NO: 69           moltype = AA  length = 17
FEATURE                 Location/Qualifiers
REGION                  1..17
```

-continued

```
                        note = Synthetic Construct
MOD_RES                 1
                        note = MeGly
DISULFID                3..11
                        note = disulfide bond
MOD_RES                 7
                        note = Xaa is L-tert-Butylalanine
MOD_RES                 11
                        note = Xaa is L-Penicillamine
MOD_RES                 15
                        note = Orn
MOD_RES                 16
                        note = Orn
MOD_RES                 17
                        note = AMIDATION
MOD_RES                 17
                        note = Orn
source                  1..17
                        mol_type = protein
                        organism = synthetic construct
SEQUENCE: 69
XICSRSXPPI XIPDXXX                                                17

SEQ ID NO: 70           moltype = AA  length = 16
FEATURE                 Location/Qualifiers
REGION                  1..16
                        note = Synthetic Construct
MOD_RES                 1
                        note = MeGly
DISULFID                3..11
                        note = disulfide bond
MOD_RES                 7
                        note = Xaa is L-tert-Butylalanine
MOD_RES                 11
                        note = Xaa is L-Penicillamine
MOD_RES                 14
                        note = MeGly
MOD_RES                 15
                        note = MeGly
MOD_RES                 16
                        note = AMIDATION
MOD_RES                 16
                        note = MeGly
source                  1..16
                        mol_type = protein
                        organism = synthetic construct
SEQUENCE: 70
XICSRSXPPI XIPXXX                                                 16

SEQ ID NO: 71           moltype = AA  length = 14
FEATURE                 Location/Qualifiers
REGION                  1..14
                        note = Synthetic Construct
MOD_RES                 1
                        note = MeGly
DISULFID                3..11
                        note = disulfide bond
MOD_RES                 7
                        note = Xaa is L-tert-Butylalanine
MOD_RES                 11
                        note = Xaa is L-Penicillamine
MOD_RES                 14
                        note = AMIDATION
MOD_RES                 14
                        note = Xaa is 3-Carboxyphenylalanine
source                  1..14
                        mol_type = protein
                        organism = synthetic construct
SEQUENCE: 71
XICSRSXPPI XIPX                                                   14

SEQ ID NO: 72           moltype = AA  length = 14
FEATURE                 Location/Qualifiers
REGION                  1..14
                        note = Synthetic Construct
MOD_RES                 1
                        note = ACETYLATION
MOD_RES                 2
                        note = MeIle
```

```
DISULFID                3..11
                        note = disulfide bond
source                  1..14
                        mol_type = protein
                        organism = synthetic construct
SEQUENCE: 72
GXCSRSLPPI CIPD                                                     14

SEQ ID NO: 73           moltype = AA  length = 14
FEATURE                 Location/Qualifiers
REGION                  1..14
                        note = Synthetic Construct
DISULFID                3..11
                        note = disulfide bond
MOD_RES                 7
                        note = Xaa is L-tert-Butylalanine
MOD_RES                 11
                        note = Xaa is L-Penicillamine
MOD_RES                 14
                        note = AMIDATION
source                  1..14
                        mol_type = protein
                        organism = synthetic construct
SEQUENCE: 73
IICSRSXPPI XIPD                                                     14

SEQ ID NO: 74           moltype = AA  length = 12
FEATURE                 Location/Qualifiers
REGION                  1..12
                        note = Synthetic Construct
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
MOD_RES                 12
                        note = AMIDATION
source                  1..12
                        mol_type = protein
                        organism = synthetic construct
SEQUENCE: 74
AICSRSLPXI XI                                                       12

SEQ ID NO: 75           moltype = AA  length = 15
FEATURE                 Location/Qualifiers
REGION                  1..15
                        note = Synthetic Construct
MOD_RES                 1
                        note = MeGly
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
MOD_RES                 15
                        note = AMIDATION
MOD_RES                 15
                        note = Xaa is 12-Amino-4,7,10-trioxadodecanoic acid
source                  1..15
                        mol_type = protein
                        organism = synthetic construct
SEQUENCE: 75
XICSRSLPXI XIPDX                                                    15

SEQ ID NO: 76           moltype = AA  length = 15
FEATURE                 Location/Qualifiers
REGION                  1..15
                        note = Synthetic Construct
MOD_RES                 1
                        note = MeGly
DISULFID                3..11
                        note = disulfide bond
MOD_RES                 9
                        note = Xaa is
                         2,3,3a,4,5,6,7,7a-Octahydroindole-2-carboxylic acid
```

-continued

```
MOD_RES                 11
                        note = Xaa is L-Penicillamine
MOD_RES                 15
                        note = AMIDATION
MOD_RES                 15
                        note = Xaa is 17-Amino-3,6,9,12,15-pentaoxaheptadecanoic
                         acid
source                  1..15
                        mol_type = protein
                        organism = synthetic construct
SEQUENCE: 76
XICSRSLPXI XIPDX                                                           15

SEQ ID NO: 77           moltype = AA  length = 13
FEATURE                 Location/Qualifiers
REGION                  1..13
                        note = Synthetic Construct
MOD_RES                 1
                        note = MeGly
DISULFID                3..11
                        note = disulfide bond
MOD_RES                 8
                        note = Xaa is
                         (1S,2S,5R)-3-azabicyclo[3.1.0]hexane-2-carboxylic acid
MOD_RES                 11
                        note = Xaa is L-Penicillamine
MOD_RES                 13
                        note = AMIDATION
source                  1..13
                        mol_type = protein
                        organism = synthetic construct
SEQUENCE: 77
XICSRSLXPI XIP                                                             13

SEQ ID NO: 78           moltype = AA  length = 12
FEATURE                 Location/Qualifiers
REGION                  1..12
                        note = Synthetic Construct
DISULFID                3..11
                        note = disulfide bond
MOD_RES                 7
                        note = Xaa is L-tert-Butylalanine
MOD_RES                 11
                        note = Xaa is L-N-Methylcysteine
MOD_RES                 12
                        note = AMIDATION
source                  1..12
                        mol_type = protein
                        organism = synthetic construct
SEQUENCE: 78
LICSRSXPPI XI                                                              12

SEQ ID NO: 79           moltype = AA  length = 14
FEATURE                 Location/Qualifiers
REGION                  1..14
                        note = Synthetic Construct
MOD_RES                 1
                        note = Abu
DISULFID                3..11
                        note = disulfide bond
MOD_RES                 7
                        note = Xaa is L-tert-Butylalanine
MOD_RES                 14
                        note = AMIDATION
source                  1..14
                        mol_type = protein
                        organism = synthetic construct
SEQUENCE: 79
XICSRSXPPI CIPD                                                            14

SEQ ID NO: 80           moltype = AA  length = 13
FEATURE                 Location/Qualifiers
REGION                  1..13
                        note = Synthetic Construct
MOD_RES                 1
                        note = MeGly
DISULFID                3..11
                        note = disulfide bond
MOD_RES                 9
```

```
                         note = Xaa is
                          2,3,3a,4,5,6,7,7a-Octahydroindole-2-carboxylic acid
MOD_RES                  11
                         note = Xaa is L-Penicillamine
MOD_RES                  13
                         note = AMIDATION
source                   1..13
                         mol_type = protein
                         organism = synthetic construct
SEQUENCE: 80
XICSRSLPXI XIP                                                             13

SEQ ID NO: 81            moltype = AA  length = 14
FEATURE                  Location/Qualifiers
REGION                   1..14
                         note = Synthetic Construct
DISULFID                 3..11
                         note = disulfide bond
MOD_RES                  7
                         note = Xaa is L-tert-Butylalanine
MOD_RES                  11
                         note = Xaa is L-Penicillamine
MOD_RES                  14
                         note = AMIDATION
source                   1..14
                         mol_type = protein
                         organism = synthetic construct
SEQUENCE: 81
LICSRSXPPI XIPD                                                            14

SEQ ID NO: 82            moltype = AA  length = 14
FEATURE                  Location/Qualifiers
REGION                   1..14
                         note = Synthetic Construct
MOD_RES                  1
                         note = Nva
DISULFID                 3..11
                         note = disulfide bond
MOD_RES                  7
                         note = Xaa is L-tert-Butylalanine
MOD_RES                  11
                         note = Xaa is L-Penicillamine
MOD_RES                  14
                         note = AMIDATION
source                   1..14
                         mol_type = protein
                         organism = synthetic construct
SEQUENCE: 82
XICSRSXPPI XIPD                                                            14

SEQ ID NO: 83            moltype = AA  length = 14
FEATURE                  Location/Qualifiers
REGION                   1..14
                         note = Synthetic Construct
MOD_RES                  1
                         note = Xaa is L-Citrulline
DISULFID                 3..11
                         note = disulfide bond
MOD_RES                  7
                         note = Xaa is L-tert-Butylalanine
MOD_RES                  11
                         note = Xaa is L-Penicillamine
source                   1..14
                         mol_type = protein
                         organism = synthetic construct
SEQUENCE: 83
XICSRSXPPI XIPD                                                            14

SEQ ID NO: 84            moltype = AA  length = 13
FEATURE                  Location/Qualifiers
REGION                   1..13
                         note = Synthetic Construct
DISULFID                 3..11
                         note = disulfide bond
MOD_RES                  9
                         note = Xaa is
                          2,3,3a,4,5,6,7,7a-Octahydroindole-2-carboxylic acid
MOD_RES                  11
                         note = Xaa is L-Penicillamine
```

```
MOD_RES                 13
                        note = AMIDATION
source                  1..13
                        mol_type = protein
                        organism = synthetic construct
SEQUENCE: 84
AICSRSLPXI XIP                                                      13

SEQ ID NO: 85           moltype = AA  length = 14
FEATURE                 Location/Qualifiers
REGION                  1..14
                        note = Synthetic Construct
MOD_RES                 1
                        note = MeGly
DISULFID                3..11
                        note = disulfide bond
MOD_RES                 7
                        note = Xaa is L-tert-Butylalanine
MOD_RES                 11
                        note = Xaa is L-Penicillamine
MOD_RES                 14
                        note = AMIDATION
MOD_RES                 14
                        note = Xaa is 12-Amino-4,7,10-trioxadodecanoic acid
source                  1..14
                        mol_type = protein
                        organism = synthetic construct
SEQUENCE: 85
XICSRSXPPI XIPX                                                     14

SEQ ID NO: 86           moltype = AA  length = 14
FEATURE                 Location/Qualifiers
REGION                  1..14
                        note = Synthetic Construct
MOD_RES                 1
                        note = MeGly
DISULFID                3..11
                        note = disulfide bond
MOD_RES                 7
                        note = Xaa is L-tert-Butylalanine
MOD_RES                 11
                        note = Xaa is L-Penicillamine
MOD_RES                 14
                        note = AMIDATION
MOD_RES                 14
                        note = Xaa is 14-Amino-3,6,9,12-tetraoxatetradecanoic acid
source                  1..14
                        mol_type = protein
                        organism = synthetic construct
SEQUENCE: 86
XICSRSXPPI XIPX                                                     14

SEQ ID NO: 87           moltype = AA  length = 14
FEATURE                 Location/Qualifiers
REGION                  1..14
                        note = Synthetic Construct
MOD_RES                 1
                        note = MeGly
DISULFID                3..11
                        note = disulfide bond
MOD_RES                 7
                        note = Xaa is L-tert-Butylalanine
MOD_RES                 11
                        note = Xaa is L-Penicillamine
MOD_RES                 14
                        note = AMIDATION
MOD_RES                 14
                        note = Xaa is
                         1-Amino-3,6,9,12,15,18,21,24-octaoxaheptacosan-27-oic acid
source                  1..14
                        mol_type = protein
                        organism = synthetic construct
SEQUENCE: 87
XICSRSXPPI XIPX                                                     14

SEQ ID NO: 88           moltype = AA  length = 14
FEATURE                 Location/Qualifiers
REGION                  1..14
                        note = Synthetic Construct
```

```
DISULFID              3..11
                      note = disulfide bond
MOD_RES               9
                      note = Xaa is
                       2,3,3a,4,5,6,7,7a-Octahydroindole-2-carboxylic acid
MOD_RES               11
                      note = Xaa is L-Penicillamine
MOD_RES               14
                      note = AMIDATION
source                1..14
                      mol_type = protein
                      organism = synthetic construct
SEQUENCE: 88
AICSRSLPXI XIPD                                                          14

SEQ ID NO: 89         moltype = AA  length = 14
FEATURE               Location/Qualifiers
REGION                1..14
                      note = Synthetic Construct
MOD_RES               1
                      note = MeGly
DISULFID              3..11
                      note = disulfide bond
MOD_RES               9
                      note = Xaa is
                       2,3,3a,4,5,6,7,7a-Octahydroindole-2-carboxylic acid
MOD_RES               11
                      note = Xaa is L-Penicillamine
MOD_RES               14
                      note = AMIDATION
MOD_RES               14
                      note = Xaa is 9-Amino-4,7-dioxanonanoic acid
source                1..14
                      mol_type = protein
                      organism = synthetic construct
SEQUENCE: 89
XICSRSLPXI XIPX                                                          14

SEQ ID NO: 90         moltype = AA  length = 14
FEATURE               Location/Qualifiers
REGION                1..14
                      note = Synthetic Construct
MOD_RES               1
                      note = Orn
DISULFID              3..11
                      note = disulfide bond
MOD_RES               7
                      note = Xaa is L-tert-Butylalanine
MOD_RES               11
                      note = Xaa is L-N-Methylcysteine
MOD_RES               14
                      note = AMIDATION
source                1..14
                      mol_type = protein
                      organism = synthetic construct
SEQUENCE: 90
XICSRSXPPI XIPD                                                          14

SEQ ID NO: 91         moltype = AA  length = 14
FEATURE               Location/Qualifiers
REGION                1..14
                      note = Synthetic Construct
MOD_RES               1
                      note = Orn
DISULFID              3..11
                      note = disulfide bond
MOD_RES               7
                      note = Xaa is L-tert-Butylalanine
MOD_RES               11
                      note = Xaa is L-N-Methylcysteine
MOD_RES               14
                      note = AMIDATION
source                1..14
                      mol_type = protein
                      organism = synthetic construct
SEQUENCE: 91
XICSRSXPPI XIPD                                                          14

SEQ ID NO: 92         moltype = AA  length = 12
```

-continued

```
FEATURE                Location/Qualifiers
REGION                 1..12
                       note = Synthetic Construct
DISULFID               3..11
                       note = disulfide bond
MOD_RES                7
                       note = Xaa is L-tert-Butylalanine
MOD_RES                11
                       note = Xaa is L-N-Methylcysteine
MOD_RES                12
                       note = AMIDATION
source                 1..12
                       mol_type = protein
                       organism = synthetic construct
SEQUENCE: 92
KICSRSXPPI XI                                                       12

SEQ ID NO: 93          moltype = AA  length = 14
FEATURE                Location/Qualifiers
REGION                 1..14
                       note = Synthetic Construct
MOD_RES                1
                       note = Xaa is 2-(N-Isopropyl-N-methylamino)acetic acid
DISULFID               3..11
                       note = disulfide bond
MOD_RES                7
                       note = Xaa is L-tert-Butylalanine
MOD_RES                11
                       note = Xaa is L-Penicillamine
MOD_RES                14
                       note = AMIDATION
source                 1..14
                       mol_type = protein
                       organism = synthetic construct
SEQUENCE: 93
XICSRSXPPI XIPD                                                     14

SEQ ID NO: 94          moltype = AA  length = 14
FEATURE                Location/Qualifiers
REGION                 1..14
                       note = Synthetic Construct
DISULFID               3..11
                       note = disulfide bond
MOD_RES                7
                       note = Xaa is L-tert-Butylalanine
MOD_RES                11
                       note = Xaa is L-Penicillamine
MOD_RES                14
                       note = AMIDATION
source                 1..14
                       mol_type = protein
                       organism = synthetic construct
SEQUENCE: 94
WICSRSXPPI XIPD                                                     14

SEQ ID NO: 95          moltype = AA  length = 14
FEATURE                Location/Qualifiers
REGION                 1..14
                       note = Synthetic Construct
MOD_RES                1
                       note = Xaa is (S)-Azetidine-2-carboxylic acid
DISULFID               3..11
                       note = disulfide bond
MOD_RES                7
                       note = Xaa is L-tert-Butylalanine
MOD_RES                11
                       note = Xaa is L-Penicillamine
MOD_RES                14
                       note = AMIDATION
source                 1..14
                       mol_type = protein
                       organism = synthetic construct
SEQUENCE: 95
XICSRSXPPI XIPD                                                     14

SEQ ID NO: 96          moltype = AA  length = 14
FEATURE                Location/Qualifiers
REGION                 1..14
                       note = Synthetic Construct
```

```
MOD_RES                 1
                        note = MeGly
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
MOD_RES                 14
                        note = AMIDATION
MOD_RES                 14
                        note = Xaa is 17-Amino-3,6,9,12,15-pentaoxaheptadecanoic
                         acid
source                  1..14
                        mol_type = protein
                        organism = synthetic construct
SEQUENCE: 96
XICSRSLPXI XIPX                                                     14

SEQ ID NO: 97           moltype = AA  length = 15
FEATURE                 Location/Qualifiers
REGION                  1..15
                        note = Synthetic Construct
MOD_RES                 1
                        note = MeGly
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
MOD_RES                 15
                        note = AMIDATION
MOD_RES                 15
                        note = Xaa is 18-Amino-4,7,10,13,16-pentaoxaoctadecanoic
                         acid
source                  1..15
                        mol_type = protein
                        organism = synthetic construct
SEQUENCE: 97
XICSRSLPXI XIPDX                                                    15

SEQ ID NO: 98           moltype = AA  length = 14
FEATURE                 Location/Qualifiers
REGION                  1..14
                        note = Synthetic Construct
MOD_RES                 1
                        note = MeGly
DISULFID                3..11
                        note = disulfide bond
MOD_RES                 7
                        note = Xaa is L-tert-Butylalanine
MOD_RES                 11
                        note = Xaa is L-Penicillamine
MOD_RES                 14
                        note = AMIDATION
MOD_RES                 14
                        note = Xaa is 1,13-Diamino-4,7,10-trioxatridecan-succinamic
                         acid
source                  1..14
                        mol_type = protein
                        organism = synthetic construct
SEQUENCE: 98
XICSRSXPPI XIPX                                                     14

SEQ ID NO: 99           moltype = AA  length = 14
FEATURE                 Location/Qualifiers
REGION                  1..14
                        note = Synthetic Construct
DISULFID                3..11
                        note = disulfide bond
MOD_RES                 7
                        note = Xaa is L-tert-Butylalanine
MOD_RES                 11
                        note = Xaa is L-N-Methylcysteine
source                  1..14
                        mol_type = protein
```

-continued

```
                        organism = synthetic construct
SEQUENCE: 99
AICSRSXPPI XIPD                                                           14

SEQ ID NO: 100          moltype = AA  length = 14
FEATURE                 Location/Qualifiers
REGION                  1..14
                        note = Synthetic Construct
DISULFID                3..11
                        note = disulfide bond
MOD_RES                 7
                        note = Xaa is L-tert-Butylalanine
MOD_RES                 9
                        note = Xaa is
                         2,3,3a,4,5,6,7,7a-Octahydroindole-2-carboxylic acid
MOD_RES                 14
                        note = AMIDATION
source                  1..14
                        mol_type = protein
                        organism = synthetic construct
SEQUENCE: 100
AICSRSXPXI CIPD                                                           14

SEQ ID NO: 101          moltype = AA  length = 14
FEATURE                 Location/Qualifiers
REGION                  1..14
                        note = Synthetic Construct
MOD_RES                 1
                        note = MeGly
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
source                  1..14
                        mol_type = protein
                        organism = synthetic construct
SEQUENCE: 101
XICSRSLPXI XIPD                                                           14

SEQ ID NO: 102          moltype = AA  length = 14
FEATURE                 Location/Qualifiers
REGION                  1..14
                        note = Synthetic Construct
MOD_RES                 1
                        note = MeGly
DISULFID                3..11
                        note = disulfide bond
MOD_RES                 7
                        note = Xaa is L-tert-Butylalanine
MOD_RES                 11
                        note = Xaa is L-Penicillamine
MOD_RES                 14
                        note = AMIDATION
MOD_RES                 14
                        note = Xaa is
                         1-Amino-3,6,9,12,15,18-hexaoxahenicosan-21-oic acid
source                  1..14
                        mol_type = protein
                        organism = synthetic construct
SEQUENCE: 102
XICSRSXPPI XIPX                                                           14

SEQ ID NO: 103          moltype = AA  length = 14
FEATURE                 Location/Qualifiers
REGION                  1..14
                        note = Synthetic Construct
MOD_RES                 1
                        note = MeGly
DISULFID                3..11
                        note = disulfide bond
MOD_RES                 8
                        note = Xaa is
                         (1S,2S,5R)-3-Azabicyclo[3.1.0]hexane-2-carboxylic acid
MOD_RES                 11
                        note = Xaa is L-Penicillamine
MOD_RES                 14
```

```
                        note = AMIDATION
source                  1..14
                        mol_type = protein
                        organism = synthetic construct
SEQUENCE: 103
XICSRSLXPI XIPE                                                     14

SEQ ID NO: 104          moltype = AA  length = 12
FEATURE                 Location/Qualifiers
REGION                  1..12
                        note = Synthetic Construct
MOD_RES                 1
                        note = Orn
DISULFID                3..11
                        note = disulfide bond
MOD_RES                 7
                        note = Xaa is L-tert-Butylalanine
MOD_RES                 11
                        note = Xaa is L-N-Methylcysteine
MOD_RES                 12
                        note = AMIDATION
source                  1..12
                        mol_type = protein
                        organism = synthetic construct
SEQUENCE: 104
XICSRSXPPI XI                                                       12

SEQ ID NO: 105          moltype = AA  length = 12
FEATURE                 Location/Qualifiers
REGION                  1..12
                        note = Synthetic Construct
MOD_RES                 1
                        note = Xaa is 1-(Aminomethyl)-cyclopropyl-1-carboxylic acid
DISULFID                3..11
                        note = disulfide bond
MOD_RES                 7
                        note = Xaa is L-tert-Butylalanine
MOD_RES                 11
                        note = Xaa is L-N-Methylcysteine
MOD_RES                 12
                        note = AMIDATION
source                  1..12
                        mol_type = protein
                        organism = synthetic construct
SEQUENCE: 105
XICSRSXPPI XI                                                       12

SEQ ID NO: 106          moltype = AA  length = 14
FEATURE                 Location/Qualifiers
REGION                  1..14
                        note = Synthetic Construct
MOD_RES                 1
                        note = Xaa is L-3-Pyridylalanine
DISULFID                3..11
                        note = disulfide bond
MOD_RES                 7
                        note = Xaa is L-tert-Butylalanine
MOD_RES                 11
                        note = Xaa is L-Penicillamine
MOD_RES                 14
                        note = AMIDATION
source                  1..14
                        mol_type = protein
                        organism = synthetic construct
SEQUENCE: 106
XICSRSXPPI XIPD                                                     14

SEQ ID NO: 107          moltype = AA  length = 14
FEATURE                 Location/Qualifiers
REGION                  1..14
                        note = Synthetic Construct
MOD_RES                 1
                        note = Xaa is L-2-Thienylalanine
DISULFID                3..11
                        note = disulfide bond
MOD_RES                 7
                        note = Xaa is L-tert-Butylalanine
MOD_RES                 11
                        note = Xaa is L-Penicillamine
```

```
MOD_RES                 14
                        note = AMIDATION
source                  1..14
                        mol_type = protein
                        organism = synthetic construct
SEQUENCE: 107
XICSRSXPPI XIPD                                                       14

SEQ ID NO: 108          moltype = AA  length = 14
FEATURE                 Location/Qualifiers
REGION                  1..14
                        note = Synthetic Construct
MOD_RES                 1
                        note = Nle
DISULFID                3..11
                        note = disulfide bond
MOD_RES                 7
                        note = Xaa is L-tert-Butylalanine
MOD_RES                 11
                        note = Xaa is L-Penicillamine
MOD_RES                 14
                        note = AMIDATION
source                  1..14
                        mol_type = protein
                        organism = synthetic construct
SEQUENCE: 108
XICSRSXPPI XIPD                                                       14

SEQ ID NO: 109          moltype = AA  length = 12
FEATURE                 Location/Qualifiers
REGION                  1..12
                        note = Synthetic Construct
SITE                    1
                        note = Xaa is D-Alanine
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
source                  1..12
                        mol_type = protein
                        organism = synthetic construct
SEQUENCE: 109
XICSRSLPXI XI                                                         12

SEQ ID NO: 110          moltype = AA  length = 14
FEATURE                 Location/Qualifiers
REGION                  1..14
                        note = Synthetic Construct
MOD_RES                 1
                        note = MeGly
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
MOD_RES                 14
                        note = AMIDATION
MOD_RES                 14
                        note = Xaa is 18-Amino-4,7,10,13,16-pentaoxaoctadecanoic
                         acid
source                  1..14
                        mol_type = protein
                        organism = synthetic construct
SEQUENCE: 110
XICSRSLPXI XIPX                                                       14

SEQ ID NO: 111          moltype = AA  length = 14
FEATURE                 Location/Qualifiers
REGION                  1..14
                        note = Synthetic Construct
DISULFID                3..11
                        note = disulfide bond
MOD_RES                 7
                        note = Xaa is L-tert-Butylalanine
```

-continued

```
MOD_RES                11
                       note = Xaa is L-Penicillamine
MOD_RES                14
                       note = AMIDATION
source                 1..14
                       mol_type = protein
                       organism = synthetic construct
SEQUENCE: 111
AICSRSXPPI XIPD                                                   14

SEQ ID NO: 112         moltype = AA  length = 12
FEATURE                Location/Qualifiers
REGION                 1..12
                       note = Synthetic Construct
DISULFID               3..11
                       note = disulfide bond
MOD_RES                7
                       note = Xaa is L-tert-Butylalanine
MOD_RES                9
                       note = Xaa is
                        2,3,3a,4,5,6,7,7a-Octahydroindole-2-carboxylic acid
MOD_RES                12
                       note = AMIDATION
source                 1..12
                       mol_type = protein
                       organism = synthetic construct
SEQUENCE: 112
AICSRSXPXI CI                                                     12

SEQ ID NO: 113         moltype = AA  length = 12
FEATURE                Location/Qualifiers
REGION                 1..12
                       note = Synthetic Construct
MOD_RES                1
                       note = MeGly
MOD_RES                2
                       note = MeIle
DISULFID               3..11
                       note = disulfide bond
MOD_RES                7
                       note = Xaa is L-tert-Butylalanine
MOD_RES                11
                       note = Xaa is L-Penicillamine
MOD_RES                12
                       note = AMIDATION
source                 1..12
                       mol_type = protein
                       organism = synthetic construct
SEQUENCE: 113
XXCSRSXPPI XI                                                     12

SEQ ID NO: 114         moltype = AA  length = 15
FEATURE                Location/Qualifiers
REGION                 1..15
                       note = Synthetic Construct
MOD_RES                1
                       note = MeGly
DISULFID               3..11
                       note = disulfide bond
MOD_RES                9
                       note = Xaa is
                        2,3,3a,4,5,6,7,7a-Octahydroindole-2-carboxylic acid
MOD_RES                11
                       note = Xaa is L-Penicillamine
MOD_RES                15
                       note = AMIDATION
MOD_RES                15
                       note = Xaa is 15-Amino-4,7,10,13-tetraoxapentadecanoic acid
source                 1..15
                       mol_type = protein
                       organism = synthetic construct
SEQUENCE: 114
XICSRSLPXI XIPDX                                                  15

SEQ ID NO: 115         moltype = AA  length = 14
FEATURE                Location/Qualifiers
REGION                 1..14
                       note = Synthetic Construct
DISULFID               3..11
```

-continued

```
                       note = disulfide bond
MOD_RES                9
                       note = Xaa is
                        rel-(1R,3R,5R,6R)-6-(Trifluoromethyl)-2-azabicyclo[3.1.0]he
                        xane-3 -carboxylic acid
MOD_RES                14
                       note = AMIDATION
source                 1..14
                       mol_type = protein
                       organism = synthetic construct
SEQUENCE: 115
AICSRSLPXI CIPD                                                      14

SEQ ID NO: 116         moltype = AA  length = 12
FEATURE                Location/Qualifiers
REGION                 1..12
                       note = Synthetic Construct
DISULFID               3..11
                       note = disulfide bond
MOD_RES                7
                       note = Xaa is L-tert-Butylalanine
MOD_RES                11
                       note = Xaa is L-N-Methylcysteine
MOD_RES                12
                       note = AMIDATION
source                 1..12
                       mol_type = protein
                       organism = synthetic construct
SEQUENCE: 116
SICSRSXPPI XI                                                        12

SEQ ID NO: 117         moltype = AA  length = 14
FEATURE                Location/Qualifiers
REGION                 1..14
                       note = Synthetic Construct
DISULFID               3..11
                       note = disulfide bond
MOD_RES                7
                       note = Xaa is L-2-Bromophenylalanine
MOD_RES                11
                       note = Xaa is L-Penicillamine
MOD_RES                14
                       note = AMIDATION
source                 1..14
                       mol_type = protein
                       organism = synthetic construct
SEQUENCE: 117
AICSRSXPPI XIPD                                                      14

SEQ ID NO: 118         moltype = AA  length = 14
FEATURE                Location/Qualifiers
REGION                 1..14
                       note = Synthetic Construct
DISULFID               3..11
                       note = disulfide bond
MOD_RES                9
                       note = Xaa is
                        2,3,3a,4,5,6,7,7a-Octahydroindole-2-carboxylic acid
MOD_RES                11
                       note = Xaa is L-Penicillamine
MOD_RES                14
                       note = AMIDATION
source                 1..14
                       mol_type = protein
                       organism = synthetic construct
SEQUENCE: 118
AICSRSLPXI XIPE                                                      14

SEQ ID NO: 119         moltype = AA  length = 14
FEATURE                Location/Qualifiers
REGION                 1..14
                       note = Synthetic Construct
MOD_RES                1
                       note = Xaa is L-N-Methylalanine
DISULFID               3..11
                       note = disulfide bond
MOD_RES                9
                       note = Xaa is
                        2,3,3a,4,5,6,7,7a-Octahydroindole-2-carboxylic acid
```

-continued

```
MOD_RES                 11
                        note = Xaa is L-Penicillamine
MOD_RES                 14
                        note = AMIDATION
source                  1..14
                        mol_type = protein
                        organism = synthetic construct
SEQUENCE: 119
XICSRSLPXI XIPD                                                      14

SEQ ID NO: 120          moltype = AA  length = 15
FEATURE                 Location/Qualifiers
REGION                  1..15
                        note = Synthetic Construct
MOD_RES                 1
                        note = MeGly
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
MOD_RES                 15
                        note = AMIDATION
MOD_RES                 15
                        note = Xaa is
                         1-Amino-3,6,9,12,15,18,21-heptaoxatetracosan-24-oic acid
source                  1..15
                        mol_type = protein
                        organism = synthetic construct
SEQUENCE: 120
XICSRSLPXI XIPDX                                                     15

SEQ ID NO: 121          moltype = AA  length = 14
FEATURE                 Location/Qualifiers
REGION                  1..14
                        note = Synthetic Construct
DISULFID                3..11
                        note = disulfide bond
MOD_RES                 7
                        note = Xaa is L-tert-Butylalanine
MOD_RES                 9
                        note = Xaa is
                         2,3,3a,4,5,6,7,7a-Octahydroindole-2-carboxylic acid
MOD_RES                 11
                        note = Xaa is L-Penicillamine
MOD_RES                 14
                        note = AMIDATION
source                  1..14
                        mol_type = protein
                        organism = synthetic construct
SEQUENCE: 121
AICSRSXPXI XIPD                                                      14

SEQ ID NO: 122          moltype = AA  length = 13
FEATURE                 Location/Qualifiers
REGION                  1..13
                        note = Synthetic Construct
MOD_RES                 1
                        note = MeGly
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
MOD_RES                 13
                        note = AMIDATION
source                  1..13
                        mol_type = protein
                        organism = synthetic construct
SEQUENCE: 122
XICSRSLPXI XIP                                                       13

SEQ ID NO: 123          moltype = AA  length = 13
FEATURE                 Location/Qualifiers
REGION                  1..13
```

```
                         note = Synthetic Construct
MOD_RES                  1
                         note = Xaa is L-N-Methylalanine
DISULFID                 3..11
                         note = disulfide bond
MOD_RES                  9
                         note = Xaa is
                          2,3,3a,4,5,6,7,7a-Octahydroindole-2-carboxylic acid
MOD_RES                  11
                         note = Xaa is L-Penicillamine
source                   1..13
                         mol_type = protein
                         organism = synthetic construct
SEQUENCE: 123
XICSRSLPXI XIP                                                 13

SEQ ID NO: 124           moltype = AA  length = 13
FEATURE                  Location/Qualifiers
REGION                   1..13
                         note = Synthetic Construct
DISULFID                 3..11
                         note = disulfide bond
MOD_RES                  9
                         note = Xaa is
                          2,3,3a,4,5,6,7,7a-Octahydroindole-2-carboxylic acid
MOD_RES                  11
                         note = Xaa is L-Penicillamine
source                   1..13
                         mol_type = protein
                         organism = synthetic construct
SEQUENCE: 124
AICSRSLPXI XIP                                                 13

SEQ ID NO: 125           moltype = AA  length = 14
FEATURE                  Location/Qualifiers
REGION                   1..14
                         note = Synthetic Construct
DISULFID                 3..11
                         note = disulfide bond
MOD_RES                  9
                         note = Xaa is
                          2,3,3a,4,5,6,7,7a-Octahydroindole-2-carboxylic acid
MOD_RES                  11
                         note = Xaa is L-Penicillamine
source                   1..14
                         mol_type = protein
                         organism = synthetic construct
SEQUENCE: 125
AICSRSLPXI XIPE                                                14

SEQ ID NO: 126           moltype = AA  length = 14
FEATURE                  Location/Qualifiers
REGION                   1..14
                         note = Synthetic Construct
MOD_RES                  1
                         note = MeGly
DISULFID                 3..11
                         note = disulfide bond
MOD_RES                  9
                         note = Xaa is
                          2,3,3a,4,5,6,7,7a-Octahydroindole-2-carboxylic acid
MOD_RES                  11
                         note = Xaa is L-Penicillamine
MOD_RES                  14
                         note = AMIDATION
MOD_RES                  14
                         note = Xaa is 14-Amino-3,6,9,12-tetraoxatetradecanoic acid
source                   1..14
                         mol_type = protein
                         organism = synthetic construct
SEQUENCE: 126
XICSRSLPXI XIPX                                                14

SEQ ID NO: 127           moltype = AA  length = 14
FEATURE                  Location/Qualifiers
REGION                   1..14
                         note = Synthetic Construct
DISULFID                 3..11
                         note = disulfide bond
```

```
MOD_RES                 7
                        note = Xaa is L-tert-Butylalanine
MOD_RES                 10
                        note = Xaa is
                         (2S)-2-(Amino)-2-[(1S,3R)-3-hydroxycyclohexyl]acetic acid
MOD_RES                 11
                        note = Xaa is L-N-Methylcysteine
MOD_RES                 14
                        note = AMIDATION
source                  1..14
                        mol_type = protein
                        organism = synthetic construct
SEQUENCE: 127
AICSRSXPPX XIPD                                                              14

SEQ ID NO: 128          moltype = AA  length = 14
FEATURE                 Location/Qualifiers
REGION                  1..14
                        note = Synthetic Construct
MOD_RES                 1
                        note = Xaa is L-Dihydroorotic acid
DISULFID                3..11
                        note = disulfide bond
MOD_RES                 7
                        note = Xaa is L-tert-Butylalanine
MOD_RES                 11
                        note = Xaa is L-Penicillamine
MOD_RES                 14
                        note = AMIDATION
source                  1..14
                        mol_type = protein
                        organism = synthetic construct
SEQUENCE: 128
XICSRSXPPI XIPD                                                              14

SEQ ID NO: 129          moltype = AA  length = 14
FEATURE                 Location/Qualifiers
REGION                  1..14
                        note = Synthetic Construct
MOD_RES                 1
                        note = 4Abu
DISULFID                3..11
                        note = disulfide bond
MOD_RES                 7
                        note = Xaa is L-tert-Butylalanine
MOD_RES                 11
                        note = Xaa is L-Penicillamine
MOD_RES                 14
                        note = AMIDATION
source                  1..14
                        mol_type = protein
                        organism = synthetic construct
SEQUENCE: 129
XICSRSXPPI XIPD                                                              14

SEQ ID NO: 130          moltype = AA  length = 12
FEATURE                 Location/Qualifiers
REGION                  1..12
                        note = Synthetic Construct
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
source                  1..12
                        mol_type = protein
                        organism = synthetic construct
SEQUENCE: 130
AICSRSLPXI XI                                                                12

SEQ ID NO: 131          moltype = AA  length = 14
FEATURE                 Location/Qualifiers
REGION                  1..14
                        note = Synthetic Construct
DISULFID                3..11
                        note = disulfide bond
MOD_RES                 9
```

```
                         note = Xaa is
                          2,3,3a,4,5,6,7,7a-Octahydroindole-2-carboxylic acid
MOD_RES                  11
                         note = Xaa is L-Penicillamine
source                   1..14
                         mol_type = protein
                         organism = synthetic construct
SEQUENCE: 131
AICSRSLPXI XIPQ                                                    14

SEQ ID NO: 132           moltype = AA  length = 15
FEATURE                  Location/Qualifiers
REGION                   1..15
                         note = Synthetic Construct
MOD_RES                  1
                         note = MeGly
DISULFID                 3..11
                         note = disulfide bond
MOD_RES                  9
                         note = Xaa is
                          2,3,3a,4,5,6,7,7a-Octahydroindole-2-carboxylic acid
MOD_RES                  11
                         note = Xaa is L-Penicillamine
MOD_RES                  15
                         note = Xaa is 1,13-Diamino-4,7,10-trioxatridecan-succinamic
                          acid
MOD_RES                  15
                         note = AMIDATION
source                   1..15
                         mol_type = protein
                         organism = synthetic construct
SEQUENCE: 132
XICSRSLPXI XIPDX                                                   15

SEQ ID NO: 133           moltype = AA  length = 14
FEATURE                  Location/Qualifiers
REGION                   1..14
                         note = Synthetic Construct
MOD_RES                  2
                         note = MeIle
DISULFID                 3..11
                         note = disulfide bond
MOD_RES                  7
                         note = Xaa is L-tert-Butylalanine
MOD_RES                  9
                         note = Xaa is
                          2,3,3a,4,5,6,7,7a-Octahydroindole-2-carboxylic acid
MOD_RES                  11
                         note = Xaa is L-N-Methylcysteine
MOD_RES                  14
                         note = AMIDATION
source                   1..14
                         mol_type = protein
                         organism = synthetic construct
SEQUENCE: 133
AXCSRSXPXI XIPD                                                    14

SEQ ID NO: 134           moltype = AA  length = 13
FEATURE                  Location/Qualifiers
REGION                   1..13
                         note = Synthetic Construct
DISULFID                 3..11
                         note = disulfide bond
MOD_RES                  7
                         note = Xaa is L-tert-Butylalanine
source                   1..13
                         mol_type = protein
                         organism = synthetic construct
SEQUENCE: 134
AICSRSXPPI CID                                                     13

SEQ ID NO: 135           moltype = AA  length = 14
FEATURE                  Location/Qualifiers
REGION                   1..14
                         note = Synthetic Construct
DISULFID                 3..11
                         note = disulfide bond
MOD_RES                  9
                         note = Xaa is
```

```
                          2,3,3a,4,5,6,7,7a-Octahydroindole-2-carboxylic acid
MOD_RES                  11
                         note = Xaa is L-Penicillamine
MOD_RES                  14
                         note = AMIDATION
source                   1..14
                         mol_type = protein
                         organism = synthetic construct
SEQUENCE: 135
AICSRSLPXI XIPE                                                             14

SEQ ID NO: 136           moltype = AA  length = 13
FEATURE                  Location/Qualifiers
REGION                   1..13
                         note = Synthetic Construct
DISULFID                 3..11
                         note = disulfide bond
MOD_RES                  9
                         note = Xaa is
                          2,3,3a,4,5,6,7,7a-Octahydroindole-2-carboxylic acid
MOD_RES                  11
                         note = Xaa is L-N-Methylcysteine
MOD_RES                  13
                         note = AMIDATION
source                   1..13
                         mol_type = protein
                         organism = synthetic construct
SEQUENCE: 136
AICSRSLPXI XIP                                                              13

SEQ ID NO: 137           moltype = AA  length = 14
FEATURE                  Location/Qualifiers
REGION                   1..14
                         note = Synthetic Construct
DISULFID                 3..11
                         note = disulfide bond
MOD_RES                  7
                         note = Xaa is L-tert-Butylalanine
MOD_RES                  11
                         note = Xaa is L-Penicillamine
MOD_RES                  14
                         note = AMIDATION
source                   1..14
                         mol_type = protein
                         organism = synthetic construct
SEQUENCE: 137
HICSRSXPPI XIPD                                                             14

SEQ ID NO: 138           moltype = AA  length = 13
FEATURE                  Location/Qualifiers
REGION                   1..13
                         note = Synthetic Construct
MOD_RES                  1
                         note = Orn
DISULFID                 3..11
                         note = disulfide bond
MOD_RES                  7
                         note = Xaa is L-tert-Butylalanine
MOD_RES                  11
                         note = Xaa is L-Penicillamine
MOD_RES                  13
                         note = AMIDATION
source                   1..13
                         mol_type = protein
                         organism = synthetic construct
SEQUENCE: 138
XICSRSXPPI XIP                                                              13

SEQ ID NO: 139           moltype = AA  length = 13
FEATURE                  Location/Qualifiers
REGION                   1..13
                         note = Synthetic Construct
MOD_RES                  1
                         note = Xaa is L-N-Methylalanine
DISULFID                 3..11
                         note = disulfide bond
MOD_RES                  7
                         note = Xaa is L-tert-Butylalanine
MOD_RES                  11
```

```
                        note = Xaa is L-Penicillamine
MOD_RES                 13
                        note = AMIDATION
source                  1..13
                        mol_type = protein
                        organism = synthetic construct
SEQUENCE: 139
XICSRSXPPI XIP                                              13

SEQ ID NO: 140          moltype = AA  length = 14
FEATURE                 Location/Qualifiers
REGION                  1..14
                        note = Synthetic Construct
MOD_RES                 1
                        note = MeGly
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
MOD_RES                 14
                        note = Xaa is 15-Amino-4,7,10,13-tetraoxapentadecanoic acid
MOD_RES                 14
                        note = AMIDATION
source                  1..14
                        mol_type = protein
                        organism = synthetic construct
SEQUENCE: 140
XICSRSLPXI XIPX                                             14

SEQ ID NO: 141          moltype = AA  length = 14
FEATURE                 Location/Qualifiers
REGION                  1..14
                        note = Synthetic Construct
DISULFID                3..11
                        note = disulfide bond
MOD_RES                 7
                        note = Xaa is L-tert-Butylalanine
MOD_RES                 9
                        note = Xaa is
                         (2S,4S)-4-Trifluoromethyl-pyrrolidine-2-carboxylic acid
MOD_RES                 11
                        note = Xaa is L-N-Methylcysteine
MOD_RES                 14
                        note = AMIDATION
source                  1..14
                        mol_type = protein
                        organism = synthetic construct
SEQUENCE: 141
AICSRSXPXI XIPD                                             14

SEQ ID NO: 142          moltype = AA  length = 12
FEATURE                 Location/Qualifiers
REGION                  1..12
                        note = Synthetic Construct
DISULFID                3..11
                        note = disulfide bond
MOD_RES                 7
                        note = Xaa is L-tert-Butylalanine
MOD_RES                 9
                        note = Xaa is
                         2,3,3a,4,5,6,7,7a-Octahydroindole-2-carboxylic acid
MOD_RES                 12
                        note = AMIDATION
source                  1..12
                        mol_type = protein
                        organism = synthetic construct
SEQUENCE: 142
AICSRSXPXI CI                                               12

SEQ ID NO: 143          moltype = AA  length = 14
FEATURE                 Location/Qualifiers
REGION                  1..14
                        note = Synthetic Construct
MOD_RES                 1
                        note = Xaa is 2-(Piperidin)acetic acid
DISULFID                3..11
```

-continued

```
                        note = disulfide bond
MOD_RES                 7
                        note = Xaa is L-tert-Butylalanine
MOD_RES                 11
                        note = Xaa is L-Penicillamine
MOD_RES                 14
                        note = AMIDATION
source                  1..14
                        mol_type = protein
                        organism = synthetic construct
SEQUENCE: 143
XICSRSXPPI XIPD                                                     14

SEQ ID NO: 144          moltype = AA  length = 14
FEATURE                 Location/Qualifiers
REGION                  1..14
                        note = Synthetic Construct
MOD_RES                 1
                        note = Xaa is L-N-Methylalanine
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
MOD_RES                 14
                        note = AMIDATION
source                  1..14
                        mol_type = protein
                        organism = synthetic construct
SEQUENCE: 144
XICSRSLPXI XIPE                                                     14

SEQ ID NO: 145          moltype = AA  length = 14
FEATURE                 Location/Qualifiers
REGION                  1..14
                        note = Synthetic Construct
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
MOD_RES                 14
                        note = AMIDATION
source                  1..14
                        mol_type = protein
                        organism = synthetic construct
SEQUENCE: 145
AICSRSLPXI XIPQ                                                     14

SEQ ID NO: 146          moltype = AA  length = 15
FEATURE                 Location/Qualifiers
REGION                  1..15
                        note = Synthetic Construct
MOD_RES                 1
                        note = MeGly
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
MOD_RES                 15
                        note = AMIDATION
MOD_RES                 15
                        note = Xaa is 14-Amino-3,6,9,12-tetraoxatetradecanoic acid
source                  1..15
                        mol_type = protein
                        organism = synthetic construct
SEQUENCE: 146
XICSRSLPXI XIPDX                                                    15

SEQ ID NO: 147          moltype = AA  length = 12
FEATURE                 Location/Qualifiers
REGION                  1..12
```

```
                        note = Synthetic Construct
MOD_RES                 1
                        note = Xaa is L-N-Methylalanine
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
source                  1..12
                        mol_type = protein
                        organism = synthetic construct
SEQUENCE: 147
XICSRSLPXI XI                                                   12

SEQ ID NO: 148          moltype = AA  length = 13
FEATURE                 Location/Qualifiers
REGION                  1..13
                        note = Synthetic Construct
MOD_RES                 1
                        note = Xaa is L-N-Methylalanine
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
MOD_RES                 13
                        note = AMIDATION
source                  1..13
                        mol_type = protein
                        organism = synthetic construct
SEQUENCE: 148
XICSRSLPXI XIP                                                  13

SEQ ID NO: 149          moltype = AA  length = 14
FEATURE                 Location/Qualifiers
REGION                  1..14
                        note = Synthetic Construct
MOD_RES                 1
                        note = MeGly
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
MOD_RES                 14
                        note = AMIDATION
MOD_RES                 14
                        note = Xaa is 1,13-Diamino-4,7,10-trioxatridecan-succinamic
                         acid
source                  1..14
                        mol_type = protein
                        organism = synthetic construct
SEQUENCE: 149
XICSRSLPXI XIPX                                                 14

SEQ ID NO: 150          moltype = AA  length = 14
FEATURE                 Location/Qualifiers
REGION                  1..14
                        note = Synthetic Construct
MOD_RES                 1
                        note = Xaa is 2-(Diethylamino)acetic acid
DISULFID                3..11
                        note = disulfide bond
MOD_RES                 7
                        note = Xaa is L-tert-Butylalanine
MOD_RES                 11
                        note = Xaa is L-Penicillamine
MOD_RES                 14
                        note = AMIDATION
source                  1..14
                        mol_type = protein
                        organism = synthetic construct
SEQUENCE: 150
```

-continued

```
XICSRSXPPI XIPD                                                       14

SEQ ID NO: 151          moltype = AA  length = 14
FEATURE                 Location/Qualifiers
REGION                  1..14
                        note = Synthetic Construct
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
source                  1..14
                        mol_type = protein
                        organism = synthetic construct
SEQUENCE: 151
AICSRSLPXI XIPE                                                       14

SEQ ID NO: 152          moltype = AA  length = 14
FEATURE                 Location/Qualifiers
REGION                  1..14
                        note = Synthetic Construct
MOD_RES                 1
                        note = Xaa is L-N-Methylalanine
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
MOD_RES                 14
                        note = AMIDATION
source                  1..14
                        mol_type = protein
                        organism = synthetic construct
SEQUENCE: 152
XICSRSLPXI XIPQ                                                       14

SEQ ID NO: 153          moltype = AA  length = 14
FEATURE                 Location/Qualifiers
REGION                  1..14
                        note = Synthetic Construct
MOD_RES                 1
                        note = MeGly
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
MOD_RES                 14
                        note = AMIDATION
MOD_RES                 14
                        note = Xaa is
                         1-Amino-3,6,9,12,15,18-hexaoxahenicosan-21-oic acid
source                  1..14
                        mol_type = protein
                        organism = synthetic construct
SEQUENCE: 153
XICSRSLPXI XIPX                                                       14

SEQ ID NO: 154          moltype = AA  length = 15
FEATURE                 Location/Qualifiers
REGION                  1..15
                        note = Synthetic Construct
MOD_RES                 1
                        note = MeGly
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
MOD_RES                 15
                        note = AMIDATION
```

-continued

```
MOD_RES                 15
                        note = Xaa is
                         1-Amino-3,6,9,12,15,18,21,24-octaoxaheptacosan-27-oic acid
source                  1..15
                        mol_type = protein
                        organism = synthetic construct
SEQUENCE: 154
XICSRSLPXI XIPDX                                                           15

SEQ ID NO: 155          moltype = AA  length = 14
FEATURE                 Location/Qualifiers
REGION                  1..14
                        note = Synthetic Construct
DISULFID                3..11
                        note = disulfide bond
MOD_RES                 8
                        note = Xaa is L-Proline (3,4-dideuterium), deuterated
                         L-Proline
MOD_RES                 9
                        note = Xaa is
                         2,3,3a,4,5,6,7,7a-Octahydroindole-2-carboxylic acid
MOD_RES                 11
                        note = Xaa is L-Penicillamine
source                  1..14
                        mol_type = protein
                        organism = synthetic construct
SEQUENCE: 155
AICSRSLXXI XIPD                                                            14

SEQ ID NO: 156          moltype = AA  length = 14
FEATURE                 Location/Qualifiers
REGION                  1..14
                        note = Synthetic Construct
DISULFID                3..11
                        note = disulfide bond
MOD_RES                 7
                        note = Xaa is L-tert-Butylalanine
MOD_RES                 11
                        note = Xaa is L-Penicillamine
MOD_RES                 14
                        note = AMIDATION
source                  1..14
                        mol_type = protein
                        organism = synthetic construct
SEQUENCE: 156
TICSRSXPPI XIPD                                                            14

SEQ ID NO: 157          moltype = AA  length = 13
FEATURE                 Location/Qualifiers
REGION                  1..13
                        note = Synthetic Construct
MOD_RES                 1
                        note = Orn
DISULFID                3..11
                        note = disulfide bond
MOD_RES                 7
                        note = Xaa is L-tert-Butylalanine
MOD_RES                 11
                        note = Xaa is L-Penicillamine
source                  1..13
                        mol_type = protein
                        organism = synthetic construct
SEQUENCE: 157
XICSRSXPPI XIP                                                             13

SEQ ID NO: 158          moltype = AA  length = 14
FEATURE                 Location/Qualifiers
REGION                  1..14
                        note = Synthetic Construct
MOD_RES                 1
                        note = MeGly
DISULFID                3..11
                        note = disulfide bond
MOD_RES                 7
                        note = Xaa is L-tert-Butylalanine
MOD_RES                 11
                        note = Xaa is L-Penicillamine
MOD_RES                 14
                        note = AMIDATION
```

```
MOD_RES                 14
                        note = Xaa is 18-Amino-4,7,10,13,16-pentaoxaoctadecanoic
                         acid
source                  1..14
                        mol_type = protein
                        organism = synthetic construct
SEQUENCE: 158
XICSRSXPPI XIPX                                                            14

SEQ ID NO: 159          moltype = AA  length = 15
FEATURE                 Location/Qualifiers
REGION                  1..15
                        note = Synthetic Construct
MOD_RES                 1
                        note = MeGly
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
MOD_RES                 15
                        note = AMIDATION
MOD_RES                 15
                        note = Xaa is
                         1-Amino-3,6,9,12,15,18-hexaoxahenicosan-21-oic acid
source                  1..15
                        mol_type = protein
                        organism = synthetic construct
SEQUENCE: 159
XICSRSLPXI XIPDX                                                           15

SEQ ID NO: 160          moltype = AA  length = 14
FEATURE                 Location/Qualifiers
REGION                  1..14
                        note = Synthetic Construct
MOD_RES                 2
                        note = Abu
DISULFID                3..11
                        note = disulfide bond
MOD_RES                 7
                        note = Xaa is L-tert-Butylalanine
MOD_RES                 11
                        note = Xaa is L-Penicillamine
MOD_RES                 14
                        note = AMIDATION
source                  1..14
                        mol_type = protein
                        organism = synthetic construct
SEQUENCE: 160
AXCSRSXPPI XIPD                                                            14

SEQ ID NO: 161          moltype = AA  length = 14
FEATURE                 Location/Qualifiers
REGION                  1..14
                        note = Synthetic Construct
DISULFID                3..11
                        note = disulfide bond
MOD_RES                 7
                        note = Xaa is L-tert-Butylalanine
MOD_RES                 11
                        note = Xaa is L-Penicillamine
source                  1..14
                        mol_type = protein
                        organism = synthetic construct
SEQUENCE: 161
TICSRSXPPI XIPD                                                            14

SEQ ID NO: 162          moltype = AA  length = 13
FEATURE                 Location/Qualifiers
REGION                  1..13
                        note = Synthetic Construct
MOD_RES                 1
                        note = MeGly
MOD_RES                 2
                        note = MeIle
DISULFID                3..11
                        note = disulfide bond
```

-continued

```
MOD_RES                 7
                        note = Xaa is L-tert-Butylalanine
MOD_RES                 11
                        note = Xaa is L-Penicillamine
MOD_RES                 13
                        note = AMIDATION
source                  1..13
                        mol_type = protein
                        organism = synthetic construct
SEQUENCE: 162
XXCSRSXPPI XIP                                                   13

SEQ ID NO: 163          moltype = AA  length = 14
FEATURE                 Location/Qualifiers
REGION                  1..14
                        note = Synthetic Construct
MOD_RES                 1
                        note = MeGly
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
MOD_RES                 14
                        note = AMIDATION
MOD_RES                 14
                        note = Xaa is
                         1-Amino-3,6,9,12,15,18,21-heptaoxatetracosan-24-oic acid
source                  1..14
                        mol_type = protein
                        organism = synthetic construct
SEQUENCE: 163
XICSRSLPXI XIPX                                                  14

SEQ ID NO: 164          moltype = AA  length = 14
FEATURE                 Location/Qualifiers
REGION                  1..14
                        note = Synthetic Construct
MOD_RES                 1
                        note = MeGly
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
MOD_RES                 14
                        note = AMIDATION
MOD_RES                 14
                        note = Xaa is
                         1-Amino-3,6,9,12,15,18,21,24,27-nonaoxatriacontan-30-oic
                         acid
source                  1..14
                        mol_type = protein
                        organism = synthetic construct
SEQUENCE: 164
XICSRSLPXI XIPX                                                  14

SEQ ID NO: 165          moltype = AA  length = 12
FEATURE                 Location/Qualifiers
REGION                  1..12
                        note = Synthetic Construct
MOD_RES                 1
                        note = Xaa is L-N-Methylalanine
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
MOD_RES                 12
                        note = AMIDATION
source                  1..12
                        mol_type = protein
                        organism = synthetic construct
```

```
SEQUENCE: 165
XICSRSLPXI XI                                                          12

SEQ ID NO: 166          moltype = AA  length = 14
FEATURE                 Location/Qualifiers
REGION                  1..14
                        note = Synthetic Construct
DISULFID                3..11
                        note = disulfide bond
MOD_RES                 9
                        note = Xaa is
                         2,3,3a,4,5,6,7,7a-Octahydroindole-2-carboxylic acid
source                  1..14
                        mol_type = protein
                        organism = synthetic construct
SEQUENCE: 166
AICSRSLPXI CIPD                                                        14

SEQ ID NO: 167          moltype = AA  length = 12
FEATURE                 Location/Qualifiers
REGION                  1..12
                        note = Synthetic Construct
DISULFID                3..11
                        note = disulfide bond
MOD_RES                 7
                        note = Xaa is L-tert-Butylalanine
MOD_RES                 11
                        note = Xaa is L-N-Methylcysteine
MOD_RES                 12
                        note = AMIDATION
source                  1..12
                        mol_type = protein
                        organism = synthetic construct
SEQUENCE: 167
HICSRSXPPI XI                                                          12

SEQ ID NO: 168          moltype = AA  length = 14
FEATURE                 Location/Qualifiers
REGION                  1..14
                        note = Synthetic Construct
DISULFID                3..11
                        note = disulfide bond
MOD_RES                 7
                        note = Xaa is L-tert-Butylalanine
MOD_RES                 9
                        note = Xaa is
                         2,3,3a,4,5,6,7,7a-Octahydroindole-2-carboxylic acid
MOD_RES                 11
                        note = Xaa is L-N-Methylcysteine
source                  1..14
                        mol_type = protein
                        organism = synthetic construct
SEQUENCE: 168
AICSRSXPXI XIPD                                                        14

SEQ ID NO: 169          moltype = AA  length = 13
FEATURE                 Location/Qualifiers
REGION                  1..13
                        note = Synthetic Construct
MOD_RES                 1
                        note = MeGly
DISULFID                3..11
                        note = disulfide bond
MOD_RES                 7
                        note = Xaa is L-tert-Butylalanine
MOD_RES                 11
                        note = Xaa is L-Penicillamine
MOD_RES                 13
                        note = AMIDATION
source                  1..13
                        mol_type = protein
                        organism = synthetic construct
SEQUENCE: 169
XICSRSXPPI XIP                                                         13

SEQ ID NO: 170          moltype = AA  length = 14
FEATURE                 Location/Qualifiers
REGION                  1..14
                        note = Synthetic Construct
```

-continued

```
MOD_RES                 1
                        note = MeGly
DISULFID                3..11
                        note = disulfide bond
MOD_RES                 7
                        note = Xaa is L-tert-Butylalanine
MOD_RES                 11
                        note = Xaa is L-Penicillamine
MOD_RES                 14
                        note = AMIDATION
source                  1..14
                        mol_type = protein
                        organism = synthetic construct
SEQUENCE: 170
XICSRSXPPI XIPP                                                        14

SEQ ID NO: 171          moltype = AA  length = 14
FEATURE                 Location/Qualifiers
REGION                  1..14
                        note = Synthetic Construct
DISULFID                3..11
                        note = disulfide bond
MOD_RES                 7
                        note = Xaa is L-tert-Butylalanine
MOD_RES                 9
                        note = Xaa is
                         (2S,4S)-4-Trifluoromethyl-pyrrolidine-2-carboxylic acid
MOD_RES                 14
                        note = AMIDATION
source                  1..14
                        mol_type = protein
                        organism = synthetic construct
SEQUENCE: 171
AICSRSXPXI CIPD                                                        14

SEQ ID NO: 172          moltype = AA  length = 12
FEATURE                 Location/Qualifiers
REGION                  1..12
                        note = Synthetic Construct
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-N-Methylcysteine
MOD_RES                 12
                        note = AMIDATION
source                  1..12
                        mol_type = protein
                        organism = synthetic construct
SEQUENCE: 172
AICSRSLPXI XI                                                          12

SEQ ID NO: 173          moltype = AA  length = 12
FEATURE                 Location/Qualifiers
REGION                  1..12
                        note = Synthetic Construct
SITE                    1
                        note = Xaa is D-Alanine
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
MOD_RES                 12
                        note = AMIDATION
source                  1..12
                        mol_type = protein
                        organism = synthetic construct
SEQUENCE: 173
XICSRSLPXI XI                                                          12

SEQ ID NO: 174          moltype = AA  length = 14
FEATURE                 Location/Qualifiers
REGION                  1..14
                        note = Synthetic Construct
```

-continued

```
MOD_RES                1
                       note = Xaa is L-N-Methylalanine
DISULFID               3..11
                       note = disulfide bond
MOD_RES                9
                       note = Xaa is
                        2,3,3a,4,5,6,7,7a-Octahydroindole-2-carboxylic acid
MOD_RES                11
                       note = Xaa is L-Penicillamine
source                 1..14
                       mol_type = protein
                       organism = synthetic construct
SEQUENCE: 174
XICSRSLPXI XIPE                                                    14

SEQ ID NO: 175         moltype = AA  length = 14
FEATURE                Location/Qualifiers
REGION                 1..14
                       note = Synthetic Construct
MOD_RES                1
                       note = Xaa is L-N-Methylalanine
DISULFID               3..11
                       note = disulfide bond
MOD_RES                9
                       note = Xaa is
                        2,3,3a,4,5,6,7,7a-Octahydroindole-2-carboxylic acid
MOD_RES                11
                       note = Xaa is L-Penicillamine
source                 1..14
                       mol_type = protein
                       organism = synthetic construct
SEQUENCE: 175
XICSRSLPXI XIPD                                                    14

SEQ ID NO: 176         moltype = AA  length = 13
FEATURE                Location/Qualifiers
REGION                 1..13
                       note = Synthetic Construct
MOD_RES                1
                       note = Dbu
DISULFID               3..11
                       note = disulfide bond
MOD_RES                7
                       note = Xaa is L-tert-Butylalanine
MOD_RES                11
                       note = Xaa is L-Penicillamine
MOD_RES                13
                       note = AMIDATION
source                 1..13
                       mol_type = protein
                       organism = synthetic construct
SEQUENCE: 176
XICSRSXPPI XIP                                                     13

SEQ ID NO: 177         moltype = AA  length = 13
FEATURE                Location/Qualifiers
REGION                 1..13
                       note = Synthetic Construct
MOD_RES                1
                       note = Xaa is MeGly
DISULFID               3..11
                       note = disulfide bond
MOD_RES                9
                       note = Xaa is
                        2,3,3a,4,5,6,7,7a-Octahydroindole-2-carboxylic acid
MOD_RES                11
                       note = Xaa is L-Penicillamine
MOD_RES                13
                       note = Xaa is 5-Azaspiro[2.4]heptane-1-carboxylic acid
source                 1..13
                       mol_type = protein
                       organism = synthetic construct
SEQUENCE: 177
XICSRSLPXI XIX                                                     13

SEQ ID NO: 178         moltype = AA  length = 14
FEATURE                Location/Qualifiers
REGION                 1..14
                       note = Synthetic Construct
```

-continued

```
MOD_RES                 1
                        note = MeGly
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
MOD_RES                 14
                        note = AMIDATION
source                  1..14
                        mol_type = protein
                        organism = synthetic construct
SEQUENCE: 178
XICSRSLPXI XIPD                                                     14

SEQ ID NO: 179          moltype = AA  length = 14
FEATURE                 Location/Qualifiers
REGION                  1..14
                        note = Synthetic Construct
MOD_RES                 1
                        note = Xaa is 3-Amino-2,2-dimethylpropionic acid
DISULFID                3..11
                        note = disulfide bond
MOD_RES                 7
                        note = Xaa is L-tert-Butylalanine
MOD_RES                 11
                        note = Xaa is L-Penicillamine
MOD_RES                 14
                        note = AMIDATION
source                  1..14
                        mol_type = protein
                        organism = synthetic construct
SEQUENCE: 179
XICSRSXPPI XIPD                                                     14

SEQ ID NO: 180          moltype = AA  length = 13
FEATURE                 Location/Qualifiers
REGION                  1..13
                        note = Synthetic Construct
MOD_RES                 1
                        note = MeGly
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
source                  1..13
                        mol_type = protein
                        organism = synthetic construct
SEQUENCE: 180
XICSRSLPXI XIP                                                      13

SEQ ID NO: 181          moltype = AA  length = 14
FEATURE                 Location/Qualifiers
REGION                  1..14
                        note = Synthetic Construct
MOD_RES                 1
                        note = MeGly
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
MOD_RES                 14
                        note = AMIDATION
MOD_RES                 14
                        note = Xaa is
                         1-Amino-3,6,9,12,15,18,21,24-octaoxaheptacosan-27-oic acid
source                  1..14
                        mol_type = protein
                        organism = synthetic construct
SEQUENCE: 181
XICSRSLPXI XIPX                                                     14
```

```
SEQ ID NO: 182          moltype = AA  length = 14
FEATURE                 Location/Qualifiers
REGION                  1..14
                        note = Synthetic Construct
MOD_RES                 1
                        note = Abu
DISULFID                3..11
                        note = disulfide bond
MOD_RES                 10
                        note = Xaa is L-Cyclohexylglycine
MOD_RES                 14
                        note = AMIDATION
source                  1..14
                        mol_type = protein
                        organism = synthetic construct
SEQUENCE: 182
XICSRSLPPX CIPD                                                    14

SEQ ID NO: 183          moltype = AA  length = 14
FEATURE                 Location/Qualifiers
REGION                  1..14
                        note = Synthetic Construct
DISULFID                3..11
                        note = disulfide bond
MOD_RES                 11
                        note = Xaa is L-Penicillamine
MOD_RES                 14
                        note = AMIDATION
source                  1..14
                        mol_type = protein
                        organism = synthetic construct
SEQUENCE: 183
AICSRSLPPI XIPD                                                    14

SEQ ID NO: 184          moltype = AA  length = 14
FEATURE                 Location/Qualifiers
REGION                  1..14
                        note = Synthetic Construct
DISULFID                3..11
                        note = disulfide bond
MOD_RES                 7
                        note = Xaa is L-tert-Butylalanine
MOD_RES                 11
                        note = Xaa is L-Penicillamine
MOD_RES                 14
                        note = AMIDATION
MOD_RES                 14
                        note = Xaa is Tranexamic acid
source                  1..14
                        mol_type = protein
                        organism = synthetic construct
SEQUENCE: 184
AICSRSXPPI XIPX                                                    14

SEQ ID NO: 185          moltype = AA  length = 13
FEATURE                 Location/Qualifiers
REGION                  1..13
                        note = Synthetic Construct
SITE                    1
                        note = Xaa is D-Alanine
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
MOD_RES                 13
                        note = AMIDATION
source                  1..13
                        mol_type = protein
                        organism = synthetic construct
SEQUENCE: 185
XICSRSLPXI XIP                                                     13

SEQ ID NO: 186          moltype = AA  length = 14
FEATURE                 Location/Qualifiers
REGION                  1..14
```

-continued

```
                        note = Synthetic Construct
MOD_RES                 1
                        note = MeGly
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
MOD_RES                 14
                        note = AMIDATION
source                  1..14
                        mol_type = protein
                        organism = synthetic construct
SEQUENCE: 186
XICSRSLPXI XIPE                                                            14

SEQ ID NO: 187          moltype = AA  length = 14
FEATURE                 Location/Qualifiers
REGION                  1..14
                        note = Synthetic Construct
MOD_RES                 1
                        note = MeGly
DISULFID                3..11
                        note = disulfide bond
MOD_RES                 7
                        note = Xaa is L-tert-Butylalanine
MOD_RES                 11
                        note = Xaa is L-Penicillamine
MOD_RES                 14
                        note = AMIDATION
MOD_RES                 14
                        note = Xaa is 15-Amino-4,7,10,13-tetraoxapentadecanoic acid
source                  1..14
                        mol_type = protein
                        organism = synthetic construct
SEQUENCE: 187
XICSRSXPPI XIPX                                                            14

SEQ ID NO: 188          moltype = AA  length = 14
FEATURE                 Location/Qualifiers
REGION                  1..14
                        note = Synthetic Construct
MOD_RES                 1
                        note = Xaa is L-N-Methylalanine
DISULFID                3..11
                        note = disulfide bond
MOD_RES                 7
                        note = Xaa is L-tert-Butylalanine
MOD_RES                 11
                        note = Xaa is L-N-Methylcysteine
MOD_RES                 14
                        note = AMIDATION
source                  1..14
                        mol_type = protein
                        organism = synthetic construct
SEQUENCE: 188
XICSRSXPPI XIPD                                                            14

SEQ ID NO: 189          moltype = AA  length = 14
FEATURE                 Location/Qualifiers
REGION                  1..14
                        note = Synthetic Construct
DISULFID                3..11
                        note = disulfide bond
MOD_RES                 7
                        note = Xaa is L-tert-Butylalanine
MOD_RES                 9
                        note = Xaa is
                         (2S,3aS,6aS)-Octahydrocyclopenta[b]pyrrole-2-carboxylic
                         acid
MOD_RES                 11
                        note = Xaa is L-N-Methylcysteine
MOD_RES                 14
                        note = AMIDATION
source                  1..14
                        mol_type = protein
                        organism = synthetic construct
```

```
SEQUENCE: 189
AICSRSXPXI XIPD                                                    14

SEQ ID NO: 190         moltype = AA  length = 12
FEATURE                Location/Qualifiers
REGION                 1..12
                       note = Synthetic Construct
DISULFID               3..11
                       note = disulfide bond
MOD_RES                7
                       note = Xaa is L-tert-Butylalanine
MOD_RES                9
                       note = Xaa is
                        2,3,3a,4,5,6,7,7a-Octahydroindole-2-carboxylic acid
MOD_RES                11
                       note = Xaa is L-N-Methylcysteine
source                 1..12
                       mol_type = protein
                       organism = synthetic construct
SEQUENCE: 190
AICSRSXPXI XI                                                      12

SEQ ID NO: 191         moltype = AA  length = 14
FEATURE                Location/Qualifiers
REGION                 1..14
                       note = Synthetic Construct
MOD_RES                1
                       note = Xaa is L-2-Pyridylalanine
DISULFID               3..11
                       note = disulfide bond
MOD_RES                7
                       note = Xaa is L-tert-Butylalanine
MOD_RES                11
                       note = Xaa is L-Penicillamine
MOD_RES                14
                       note = AMIDATION
source                 1..14
                       mol_type = protein
                       organism = synthetic construct
SEQUENCE: 191
XICSRSXPPI XIPD                                                    14

SEQ ID NO: 192         moltype = AA  length = 14
FEATURE                Location/Qualifiers
REGION                 1..14
                       note = Synthetic Construct
MOD_RES                1
                       note = Xaa is L-N-Methylalanine
DISULFID               3..11
                       note = disulfide bond
MOD_RES                9
                       note = Xaa is
                        2,3,3a,4,5,6,7,7a-Octahydroindole-2-carboxylic acid
MOD_RES                11
                       note = Xaa is L-Penicillamine
source                 1..14
                       mol_type = protein
                       organism = synthetic construct
SEQUENCE: 192
XICSRSLPXI XIPQ                                                    14

SEQ ID NO: 193         moltype = AA  length = 14
FEATURE                Location/Qualifiers
REGION                 1..14
                       note = Synthetic Construct
DISULFID               3..11
                       note = disulfide bond
MOD_RES                9
                       note = Xaa is
                        2,3,3a,4,5,6,7,7a-Octahydroindole-2-carboxylic acid
MOD_RES                11
                       note = Xaa is L-N-Methylcysteine
source                 1..14
                       mol_type = protein
                       organism = synthetic construct
SEQUENCE: 193
AICSRSLPXI XIPD                                                    14

SEQ ID NO: 194         moltype = AA  length = 12
```

```
FEATURE                 Location/Qualifiers
REGION                  1..12
                        note = Synthetic Construct
DISULFID                3..11
                        note = disulfide bond
MOD_RES                 7
                        note = Xaa is L-tert-Butylalanine
MOD_RES                 11
                        note = Xaa is L-N-Methylcysteine
MOD_RES                 12
                        note = AMIDATION
source                  1..12
                        mol_type = protein
                        organism = synthetic construct
SEQUENCE: 194
FICSRSXPPI XI                                                   12

SEQ ID NO: 195          moltype = AA  length = 12
FEATURE                 Location/Qualifiers
REGION                  1..12
                        note = Synthetic Construct
DISULFID                3..11
                        note = disulfide bond
MOD_RES                 7
                        note = Xaa is L-tert-Butylalanine
MOD_RES                 11
                        note = Xaa is L-N-Methylcysteine
MOD_RES                 12
                        note = AMIDATION
source                  1..12
                        mol_type = protein
                        organism = synthetic construct
SEQUENCE: 195
YICSRSXPPI XI                                                   12

SEQ ID NO: 196          moltype = AA  length = 14
FEATURE                 Location/Qualifiers
REGION                  1..14
                        note = Synthetic Construct
DISULFID                3..11
                        note = disulfide bond
MOD_RES                 7
                        note = Xaa is L-tert-Butylalanine
MOD_RES                 10
                        note = Xaa is (2S)-2-(Amino
                         )-2-[(1S,3S)-3-hydroxycyclohexyl]acetic acid)
MOD_RES                 11
                        note = Xaa is L-N-Methylcysteine
MOD_RES                 14
                        note = AMIDATION
source                  1..14
                        mol_type = protein
                        organism = synthetic construct
SEQUENCE: 196
AICSRSXPPX XIPD                                                 14

SEQ ID NO: 197          moltype = AA  length = 12
FEATURE                 Location/Qualifiers
REGION                  1..12
                        note = Synthetic Construct
MOD_RES                 1
                        note = Xaa is
                         (2S)-2[(Amino)-2-(tetrahydro-2H-pyran-4-yl)]acetic acid
DISULFID                3..11
                        note = disulfide bond
MOD_RES                 9
                        note = Xaa is
                         2,3,3a,4,5,6,7,7a-Octahydroindole-2-carboxylic acid
source                  1..12
                        mol_type = protein
                        organism = synthetic construct
SEQUENCE: 197
XICSRSLPXI CI                                                   12

SEQ ID NO: 198          moltype = AA  length = 14
FEATURE                 Location/Qualifiers
REGION                  1..14
                        note = Synthetic Construct
DISULFID                3..11
```

```
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-N-Methylcysteine
MOD_RES                 14
                        note = AMIDATION
source                  1..14
                        mol_type = protein
                        organism = synthetic construct
SEQUENCE: 198
AICSRSLPXI XIPD                                                            14

SEQ ID NO: 199          moltype = AA  length = 12
FEATURE                 Location/Qualifiers
REGION                  1..12
                        note = Synthetic Construct
MOD_RES                 1
                        note = Orn
DISULFID                3..11
                        note = disulfide bond
MOD_RES                 7
                        note = Xaa is L-tert-Butylalanine
MOD_RES                 12
                        note = AMIDATION
source                  1..12
                        mol_type = protein
                        organism = synthetic construct
SEQUENCE: 199
XICSRSXPPI CI                                                              12

SEQ ID NO: 200          moltype = AA  length = 14
FEATURE                 Location/Qualifiers
REGION                  1..14
                        note = Synthetic Construct
MOD_RES                 1
                        note = Xaa is 4-(Aminomethyl)benzoic acid
DISULFID                3..11
                        note = disulfide bond
MOD_RES                 7
                        note = Xaa is L-tert-Butylalanine
MOD_RES                 11
                        note = Xaa is L-Penicillamine
MOD_RES                 14
                        note = AMIDATION
source                  1..14
                        mol_type = protein
                        organism = synthetic construct
SEQUENCE: 200
XICSRSXPPI XIPD                                                            14

SEQ ID NO: 201          moltype = AA  length = 12
FEATURE                 Location/Qualifiers
REGION                  1..12
                        note = Synthetic Construct
MOD_RES                 1
                        note = MeGly
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
source                  1..12
                        mol_type = protein
                        organism = synthetic construct
SEQUENCE: 201
XICSRSLPXI XI                                                              12

SEQ ID NO: 202          moltype = AA  length = 14
FEATURE                 Location/Qualifiers
REGION                  1..14
                        note = Synthetic Construct
SITE                    1
                        note = Xaa is D-Alanine
DISULFID                3..11
                        note = disulfide bond
```

```
MOD_RES                 9
                        note = Xaa is
                         2,3,3a,4,5,6,7,7a-Octahydroindole-2-carboxylic acid
MOD_RES                 11
                        note = Xaa is L-Penicillamine
source                  1..14
                        mol_type = protein
                        organism = synthetic construct
SEQUENCE: 202
XICSRSLPXI XIPQ                                                     14

SEQ ID NO: 203          moltype = AA  length = 13
FEATURE                 Location/Qualifiers
REGION                  1..13
                        note = Synthetic Construct
SITE                    1
                        note = Xaa is D-Alanine
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
source                  1..13
                        mol_type = protein
                        organism = synthetic construct
SEQUENCE: 203
XICSRSLPXI XIP                                                      13

SEQ ID NO: 204          moltype = AA  length = 14
FEATURE                 Location/Qualifiers
REGION                  1..14
                        note = Synthetic Construct
MOD_RES                 1
                        note = MeGly
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
MOD_RES                 14
                        note = AMIDATION
source                  1..14
                        mol_type = protein
                        organism = synthetic construct
SEQUENCE: 204
XICSRSLPXI XIPE                                                     14

SEQ ID NO: 205          moltype = AA  length = 14
FEATURE                 Location/Qualifiers
REGION                  1..14
                        note = Synthetic Construct
SITE                    1
                        note = Xaa is D-Alanine
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
MOD_RES                 14
                        note = AMIDATION
source                  1..14
                        mol_type = protein
                        organism = synthetic construct
SEQUENCE: 205
XICSRSLPXI XIPE                                                     14

SEQ ID NO: 206          moltype = AA  length = 14
FEATURE                 Location/Qualifiers
REGION                  1..14
                        note = Synthetic Construct
MOD_RES                 1
                        note = MeGly
DISULFID                3..11
```

```
                         note = disulfide bond
MOD_RES                  9
                         note = Xaa is
                          2,3,3a,4,5,6,7,7a-Octahydroindole-2-carboxylic acid
MOD_RES                  11
                         note = Xaa is L-Penicillamine
MOD_RES                  14
                         note = AMIDATION
MOD_RES                  14
                         note = Xaa is 3-Carboxyphenylalanine
source                   1..14
                         mol_type = protein
                         organism = synthetic construct
SEQUENCE: 206
XICSRSLPXI XIPX                                                  14

SEQ ID NO: 207           moltype = AA  length = 13
FEATURE                  Location/Qualifiers
REGION                   1..13
                         note = Synthetic Construct
MOD_RES                  1
                         note = MeGly
DISULFID                 3..11
                         note = disulfide bond
MOD_RES                  9
                         note = Xaa is
                          2,3,3a,4,5,6,7,7a-Octahydroindole-2-carboxylic acid
MOD_RES                  11
                         note = Xaa is L-Penicillamine
MOD_RES                  13
                         note = Xaa is 5-Azaspiro[2.4]heptane-1-carboxylic acid
source                   1..13
                         mol_type = protein
                         organism = synthetic construct
SEQUENCE: 207
XICSRSLPXI XIX                                                   13

SEQ ID NO: 208           moltype = AA  length = 12
FEATURE                  Location/Qualifiers
REGION                   1..12
                         note = Synthetic Construct
MOD_RES                  1
                         note = Dpr
DISULFID                 3..11
                         note = disulfide bond
MOD_RES                  7
                         note = Xaa is L-tert-Butylalanine
MOD_RES                  11
                         note = Xaa is L-Penicillamine
MOD_RES                  12
                         note = AMIDATION
source                   1..12
                         mol_type = protein
                         organism = synthetic construct
SEQUENCE: 208
XICSRSXPPI XI                                                    12

SEQ ID NO: 209           moltype = AA  length = 14
FEATURE                  Location/Qualifiers
REGION                   1..14
                         note = Synthetic Construct
MOD_RES                  1
                         note = MeGly
DISULFID                 3..11
                         note = disulfide bond
MOD_RES                  9
                         note = Xaa is
                          2,3,3a,4,5,6,7,7a-Octahydroindole-2-carboxylic acid
MOD_RES                  11
                         note = Xaa is L-Penicillamine
source                   1..14
                         mol_type = protein
                         organism = synthetic construct
SEQUENCE: 209
XICSRSLPXI XIPE                                                  14

SEQ ID NO: 210           moltype = AA  length = 13
FEATURE                  Location/Qualifiers
REGION                   1..13
```

```
                        note = Synthetic Construct
MOD_RES                 1
                        note = MeGly
DISULFID                3..11
                        note = disulfide bond
MOD_RES                 7
                        note = Xaa is (2S)-2-amino-3-(1-methylcyclopropyl)propanoic
                         acid
MOD_RES                 11
                        note = Xaa is L-Penicillamine
MOD_RES                 13
                        note = AMIDATION
source                  1..13
                        mol_type = protein
                        organism = synthetic construct
SEQUENCE: 210
XICSRSXPPI XIP                                                            13

SEQ ID NO: 211          moltype = AA  length = 12
FEATURE                 Location/Qualifiers
REGION                  1..12
                        note = Synthetic Construct
DISULFID                3..11
                        note = disulfide bond
MOD_RES                 7
                        note = Xaa is L-tert-Butylalanine
MOD_RES                 9
                        note = Xaa is
                         2,3,3a,4,5,6,7,7a-Octahydroindole-2-carboxylic acid
MOD_RES                 11
                        note = Xaa is L-N-Methylcysteine
MOD_RES                 12
                        note = AMIDATION
source                  1..12
                        mol_type = protein
                        organism = synthetic construct
SEQUENCE: 211
AICSRSXPXI XI                                                             12

SEQ ID NO: 212          moltype = AA  length = 14
FEATURE                 Location/Qualifiers
REGION                  1..14
                        note = Synthetic Construct
MOD_RES                 2
                        note = Nva
DISULFID                3..11
                        note = disulfide bond
MOD_RES                 7
                        note = Xaa is L-tert-Butylalanine
MOD_RES                 11
                        note = Xaa is L-Penicillamine
MOD_RES                 14
                        note = AMIDATION
source                  1..14
                        mol_type = protein
                        organism = synthetic construct
SEQUENCE: 212
AXCSRSXPPI XIPD                                                           14

SEQ ID NO: 213          moltype = AA  length = 14
FEATURE                 Location/Qualifiers
REGION                  1..14
                        note = Synthetic Construct
MOD_RES                 1
                        note = MeGly
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
MOD_RES                 14
                        note = AMIDATION
source                  1..14
                        mol_type = protein
                        organism = synthetic construct
SEQUENCE: 213
XICSRSLPXI XIPQ                                                           14
```

```
SEQ ID NO: 214          moltype = AA  length = 14
FEATURE                 Location/Qualifiers
REGION                  1..14
                        note = Synthetic Construct
SITE                    1
                        note = Xaa is D-Alanine
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
source                  1..14
                        mol_type = protein
                        organism = synthetic construct
SEQUENCE: 214
XICSRSLPXI XIPE                                                 14

SEQ ID NO: 215          moltype = AA  length = 14
FEATURE                 Location/Qualifiers
REGION                  1..14
                        note = Synthetic Construct
SITE                    1
                        note = Xaa is D-Alanine
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
MOD_RES                 14
                        note = AMIDATION
source                  1..14
                        mol_type = protein
                        organism = synthetic construct
SEQUENCE: 215
XICSRSLPXI XIPQ                                                 14

SEQ ID NO: 216          moltype = AA  length = 14
FEATURE                 Location/Qualifiers
REGION                  1..14
                        note = Synthetic Construct
MOD_RES                 1
                        note = MeGly
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
source                  1..14
                        mol_type = protein
                        organism = synthetic construct
SEQUENCE: 216
XICSRSLPXI XIPQ                                                 14

SEQ ID NO: 217          moltype = AA  length = 13
FEATURE                 Location/Qualifiers
REGION                  1..13
                        note = Synthetic Construct
MOD_RES                 1
                        note = Xaa is 3-(Aminomethyl)benzoic acid
DISULFID                3..11
                        note = disulfide bond
MOD_RES                 7
                        note = Xaa is L-tert-Butylalanine
MOD_RES                 11
                        note = Xaa is L-Penicillamine
MOD_RES                 13
                        note = AMIDATION
source                  1..13
                        mol_type = protein
                        organism = synthetic construct
SEQUENCE: 217
XICSRSXPPI XIP                                                  13
```

```
SEQ ID NO: 218          moltype = AA  length = 14
FEATURE                 Location/Qualifiers
REGION                  1..14
                        note = Synthetic Construct
MOD_RES                 2
                        note = MeIle
DISULFID                3..11
                        note = disulfide bond
MOD_RES                 14
                        note = AMIDATION
source                  1..14
                        mol_type = protein
                        organism = synthetic construct
SEQUENCE: 218
GXCSRSLPPI CIPD                                                     14

SEQ ID NO: 219          moltype = AA  length = 14
FEATURE                 Location/Qualifiers
REGION                  1..14
                        note = Synthetic Construct
DISULFID                3..11
                        note = disulfide bond
MOD_RES                 10
                        note = Xaa is L-Cyclohexylglycine
MOD_RES                 11
                        note = Xaa is L-Penicillamine
MOD_RES                 14
                        note = AMIDATION
source                  1..14
                        mol_type = protein
                        organism = synthetic construct
SEQUENCE: 219
AICSRSLPPX XIPD                                                     14

SEQ ID NO: 220          moltype = AA  length = 14
FEATURE                 Location/Qualifiers
REGION                  1..14
                        note = Synthetic Construct
MOD_RES                 1
                        note = MeGly
DISULFID                3..11
                        note = disulfide bond
MOD_RES                 7
                        note = Xaa is L-tert-Butylalanine
MOD_RES                 11
                        note = Xaa is L-Penicillamine
MOD_RES                 14
                        note = AMIDATION
MOD_RES                 14
                        note = Xaa is 9-Amino-4,7-dioxanonanoic acid
source                  1..14
                        mol_type = protein
                        organism = synthetic construct
SEQUENCE: 220
XICSRSXPPI XIPX                                                     14

SEQ ID NO: 221          moltype = AA  length = 12
FEATURE                 Location/Qualifiers
REGION                  1..12
                        note = Synthetic Construct
MOD_RES                 1
                        note = Xaa is 1-Aminocyclobutane-1-carboxylic acid
DISULFID                3..11
                        note = disulfide bond
MOD_RES                 7
                        note = Xaa is L-tert-Butylalanine
MOD_RES                 11
                        note = Xaa is L-Penicillamine
MOD_RES                 12
                        note = AMIDATION
source                  1..12
                        mol_type = protein
                        organism = synthetic construct
SEQUENCE: 221
XICSRSXPPI XI                                                       12

SEQ ID NO: 222          moltype = AA  length = 14
FEATURE                 Location/Qualifiers
```

-continued

```
REGION                  1..14
                        note = Synthetic Construct
DISULFID                3..11
                        note = disulfide bond
MOD_RES                 10
                        note = Xaa is (S)-2-Amino-3-ethyl-pentanoic acid
MOD_RES                 14
                        note = AMIDATION
source                  1..14
                        mol_type = protein
                        organism = synthetic construct
SEQUENCE: 222
AICSRSLPPX CIPD                                                  14

SEQ ID NO: 223          moltype = AA  length = 14
FEATURE                 Location/Qualifiers
REGION                  1..14
                        note = Synthetic Construct
DISULFID                3..11
                        note = disulfide bond
MOD_RES                 7
                        note = Xaa is L-tert-Butylalanine
source                  1..14
                        mol_type = protein
                        organism = synthetic construct
SEQUENCE: 223
AICSRSXPPI CIDD                                                  14

SEQ ID NO: 224          moltype = AA  length = 14
FEATURE                 Location/Qualifiers
REGION                  1..14
                        note = Synthetic Construct
DISULFID                3..11
                        note = disulfide bond
MOD_RES                 7
                        note = Xaa is L-tert-Butylalanine
MOD_RES                 11
                        note = Xaa is L-Penicillamine
MOD_RES                 14
                        note = AMIDATION
source                  1..14
                        mol_type = protein
                        organism = synthetic construct
SEQUENCE: 224
FICSRSXPPI XIPD                                                  14

SEQ ID NO: 225          moltype = AA  length = 14
FEATURE                 Location/Qualifiers
REGION                  1..14
                        note = Synthetic Construct
DISULFID                3..11
                        note = disulfide bond
MOD_RES                 7
                        note = Xaa is L-tert-Butylalanine
MOD_RES                 9
                        note = Xaa is
                         2,3,3a,4,5,6,7,7a-Octahydroindole-2-carboxylic acid
MOD_RES                 11
                        note = Xaa is L-N-Methylcysteine
MOD_RES                 14
                        note = AMIDATION
source                  1..14
                        mol_type = protein
                        organism = synthetic construct
SEQUENCE: 225
GICSRSXPXI XIPD                                                  14

SEQ ID NO: 226          moltype = AA  length = 15
FEATURE                 Location/Qualifiers
REGION                  1..15
                        note = Synthetic Construct
MOD_RES                 1
                        note = MeGly
DISULFID                4..12
                        note = disulfide bond
MOD_RES                 8
                        note = Xaa is L-tert-Butylalanine
MOD_RES                 12
                        note = Xaa is L-Penicillamine
```

-continued

```
MOD_RES                 15
                        note = AMIDATION
source                  1..15
                        mol_type = protein
                        organism = synthetic construct
SEQUENCE: 226
XGICSRSXPP IXIPD                                                   15

SEQ ID NO: 227          moltype = AA  length = 13
FEATURE                 Location/Qualifiers
REGION                  1..13
                        note = Synthetic Construct
MOD_RES                 1
                        note = MeGly
DISULFID                3..11
                        note = disulfide bond
MOD_RES                 7
                        note = Xaa is (S)-(trifluoromethyl)-L-cysteine
MOD_RES                 11
                        note = Xaa is L-Penicillamine
MOD_RES                 13
                        note = AMIDATION
source                  1..13
                        mol_type = protein
                        organism = synthetic construct
SEQUENCE: 227
XICSRSXPPI XIP                                                     13

SEQ ID NO: 228          moltype = AA  length = 14
FEATURE                 Location/Qualifiers
REGION                  1..14
                        note = Synthetic Construct
MOD_RES                 1
                        note = MeGly
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
source                  1..14
                        mol_type = protein
                        organism = synthetic construct
SEQUENCE: 228
XICSRSLPXI XIPE                                                    14

SEQ ID NO: 229          moltype = AA  length = 14
FEATURE                 Location/Qualifiers
REGION                  1..14
                        note = Synthetic Construct
MOD_RES                 1
                        note = Nva
DISULFID                3..11
                        note = disulfide bond
MOD_RES                 14
                        note = AMIDATION
source                  1..14
                        mol_type = protein
                        organism = synthetic construct
SEQUENCE: 229
XICSRSLPPI CIPD                                                    14

SEQ ID NO: 230          moltype = AA  length = 14
FEATURE                 Location/Qualifiers
REGION                  1..14
                        note = Synthetic Construct
SITE                    1
                        note = Xaa is D-Alanine
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
MOD_RES                 14
                        note = AMIDATION
source                  1..14
```

```
                        mol_type = protein
                        organism = synthetic construct
SEQUENCE: 230
XICSRSLPXI XIPD                                              14

SEQ ID NO: 231          moltype = AA  length = 14
FEATURE                 Location/Qualifiers
REGION                  1..14
                        note = Synthetic Construct
MOD_RES                 1
                        note = Xaa is L-4-Pyridylalanine
DISULFID                3..11
                        note = disulfide bond
MOD_RES                 7
                        note = Xaa is L-tert-Butylalanine
MOD_RES                 11
                        note = Xaa is L-Penicillamine
MOD_RES                 14
                        note = AMIDATION
source                  1..14
                        mol_type = protein
                        organism = synthetic construct
SEQUENCE: 231
XICSRSXPPI XIPD                                              14

SEQ ID NO: 232          moltype = AA  length = 12
FEATURE                 Location/Qualifiers
REGION                  1..12
                        note = Synthetic Construct
MOD_RES                 1
                        note = Xaa is 3-(Aminomethyl)benzoic acid
DISULFID                3..10
                        note = disulfide bond
MOD_RES                 7
                        note = Xaa is L-tert-Butylalanine
MOD_RES                 10
                        note = Xaa is L-Penicillamine
MOD_RES                 12
                        note = AMIDATION
source                  1..12
                        mol_type = protein
                        organism = synthetic construct
SEQUENCE: 232
XICSRSXPPX IP                                                12

SEQ ID NO: 233          moltype = AA  length = 14
FEATURE                 Location/Qualifiers
REGION                  1..14
                        note = Synthetic Construct
DISULFID                3..11
                        note = disulfide bond
MOD_RES                 12
                        note = Xaa is (S)-2-Amino-2-cyclobutylacetic acid
MOD_RES                 14
                        note = AMIDATION
source                  1..14
                        mol_type = protein
                        organism = synthetic construct
SEQUENCE: 233
AICSRSLPPI CXPD                                              14

SEQ ID NO: 234          moltype = AA  length = 14
FEATURE                 Location/Qualifiers
REGION                  1..14
                        note = Synthetic Construct
MOD_RES                 1
                        note = Xaa is Tranexamic acid
DISULFID                3..11
                        note = disulfide bond
MOD_RES                 7
                        note = Xaa is L-tert-Butylalanine
MOD_RES                 11
                        note = Xaa is L-Penicillamine
MOD_RES                 14
                        note = AMIDATION
MOD_RES                 14
                        note = Xaa is 9-Amino-4,7-dioxanonanoic acid
source                  1..14
                        mol_type = protein
```

```
                         organism = synthetic construct
SEQUENCE: 234
XICSRSXPPI XIPX                                                          14

SEQ ID NO: 235           moltype = AA  length = 14
FEATURE                  Location/Qualifiers
REGION                   1..14
                         note = Synthetic Construct
DISULFID                 3..11
                         note = disulfide bond
MOD_RES                  10
                         note = Xaa is L-Cyclohexylglycine
source                   1..14
                         mol_type = protein
                         organism = synthetic construct
SEQUENCE: 235
AICSRSLPPX CIPD                                                          14

SEQ ID NO: 236           moltype = AA  length = 12
FEATURE                  Location/Qualifiers
REGION                   1..12
                         note = Synthetic Construct
DISULFID                 3..11
                         note = disulfide bond
MOD_RES                  7
                         note = Xaa is L-tert-Butylalanine
MOD_RES                  11
                         note = Xaa is L-N-Methylcysteine
MOD_RES                  12
                         note = AMIDATION
source                   1..12
                         mol_type = protein
                         organism = synthetic construct
SEQUENCE: 236
WICSRSXPPI XI                                                            12

SEQ ID NO: 237           moltype = AA  length = 14
FEATURE                  Location/Qualifiers
REGION                   1..14
                         note = Synthetic Construct
DISULFID                 3..11
                         note = disulfide bond
MOD_RES                  9
                         note = Xaa is
                          2,3,3a,4,5,6,7,7a-Octahydroindole-2-carboxylic acid
MOD_RES                  14
                         note = AMIDATION
source                   1..14
                         mol_type = protein
                         organism = synthetic construct
SEQUENCE: 237
AICSRSLPXI CIPD                                                          14

SEQ ID NO: 238           moltype = AA  length = 14
FEATURE                  Location/Qualifiers
REGION                   1..14
                         note = Synthetic Construct
MOD_RES                  1
                         note = Orn
DISULFID                 3..11
                         note = disulfide bond
MOD_RES                  10
                         note = Xaa is L-Cyclohexylglycine
source                   1..14
                         mol_type = protein
                         organism = synthetic construct
SEQUENCE: 238
XICSRSLPPX CIPD                                                          14

SEQ ID NO: 239           moltype = AA  length = 13
FEATURE                  Location/Qualifiers
REGION                   1..13
                         note = Synthetic Construct
MOD_RES                  1
                         note = Xaa is 2-(3-Pyridyl)acetic acid
DISULFID                 3..11
                         note = disulfide bond
MOD_RES                  7
                         note = Xaa is L-tert-Butylalanine
```

```
MOD_RES                 11
                        note = Xaa is L-Penicillamine
MOD_RES                 13
                        note = AMIDATION
source                  1..13
                        mol_type = protein
                        organism = synthetic construct
SEQUENCE: 239
XICSRSXPPI XIP                                                            13

SEQ ID NO: 240          moltype = AA  length = 14
FEATURE                 Location/Qualifiers
REGION                  1..14
                        note = Synthetic Construct
SITE                    1
                        note = Xaa is D-Alanine
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
source                  1..14
                        mol_type = protein
                        organism = synthetic construct
SEQUENCE: 240
XICSRSLPXI XIPD                                                           14

SEQ ID NO: 241          moltype = AA  length = 14
FEATURE                 Location/Qualifiers
REGION                  1..14
                        note = Synthetic Construct
MOD_RES                 1
                        note = MeGly
DISULFID                3..11
                        note = disulfide bond
MOD_RES                 14
                        note = AMIDATION
source                  1..14
                        mol_type = protein
                        organism = synthetic construct
SEQUENCE: 241
XICSRSLPPI CIPD                                                           14

SEQ ID NO: 242          moltype = AA  length = 14
FEATURE                 Location/Qualifiers
REGION                  1..14
                        note = Synthetic Construct
MOD_RES                 1
                        note = Xaa is 2-(Cyclohexylamino)acetic acid
DISULFID                3..11
                        note = disulfide bond
MOD_RES                 7
                        note = Xaa is L-tert-Butylalanine
MOD_RES                 11
                        note = Xaa is L-Penicillamine
MOD_RES                 14
                        note = AMIDATION
source                  1..14
                        mol_type = protein
                        organism = synthetic construct
SEQUENCE: 242
XICSRSXPPI XIPD                                                           14

SEQ ID NO: 243          moltype = AA  length = 14
FEATURE                 Location/Qualifiers
REGION                  1..14
                        note = Synthetic Construct
MOD_RES                 1
                        note = Abu
DISULFID                3..11
                        note = disulfide bond
MOD_RES                 14
                        note = AMIDATION
source                  1..14
                        mol_type = protein
                        organism = synthetic construct
SEQUENCE: 243
```

```
XICSRSLPPI CIPD                                                   14

SEQ ID NO: 244          moltype = AA  length = 14
FEATURE                 Location/Qualifiers
REGION                  1..14
                        note = Synthetic Construct
DISULFID                3..11
                        note = disulfide bond
MOD_RES                 7
                        note = Xaa is L-tert-Butylalanine
MOD_RES                 9
                        note = Xaa is
                         2,3,3a,4,5,6,7,7a-Octahydroindole-2-carboxylic acid
MOD_RES                 11
                        note = Xaa is L-N-Methylcysteine
source                  1..14
                        mol_type = protein
                        organism = synthetic construct
SEQUENCE: 244
AICSRSXPXI XIPD                                                   14

SEQ ID NO: 245          moltype = AA  length = 14
FEATURE                 Location/Qualifiers
REGION                  1..14
                        note = Synthetic Construct
MOD_RES                 1
                        note = MeGly
DISULFID                3..11
                        note = disulfide bond
MOD_RES                 11
                        note = Xaa is L-N-Methylcysteine
source                  1..14
                        mol_type = protein
                        organism = synthetic construct
SEQUENCE: 245
XICSRSLPPI XIPD                                                   14

SEQ ID NO: 246          moltype = AA  length = 13
FEATURE                 Location/Qualifiers
REGION                  1..13
                        note = Synthetic Construct
SITE                    1
                        note = Xaa is D-Alanine
DISULFID                3..11
                        note = disulfide bond
MOD_RES                 7
                        note = Xaa is (S)-(trifluoromethyl)-L-cysteine
MOD_RES                 11
                        note = Xaa is L-Penicillamine
MOD_RES                 13
                        note = AMIDATION
source                  1..13
                        mol_type = protein
                        organism = synthetic construct
SEQUENCE: 246
XICSRSXPPI XIP                                                    13

SEQ ID NO: 247          moltype = AA  length = 14
FEATURE                 Location/Qualifiers
REGION                  1..14
                        note = Synthetic Construct
DISULFID                3..11
                        note = disulfide bond
MOD_RES                 7
                        note = Xaa is L-tert-Butylalanine
MOD_RES                 9
                        note = Xaa is
                         2,3,3a,4,5,6,7,7a-Octahydroindole-2-carboxylic acid
MOD_RES                 14
                        note = AMIDATION
source                  1..14
                        mol_type = protein
                        organism = synthetic construct
SEQUENCE: 247
AICSRSXPXI CIPD                                                   14

SEQ ID NO: 248          moltype = AA  length = 14
FEATURE                 Location/Qualifiers
REGION                  1..14
```

```
                        note = Synthetic Construct
DISULFID                3..11
                        note = disulfide bond
MOD_RES                 7
                        note = Xaa is 2,5-Difluoro-L-phenylalanine
MOD_RES                 11
                        note = Xaa is L-N-Methylcysteine
MOD_RES                 14
                        note = AMIDATION
source                  1..14
                        mol_type = protein
                        organism = synthetic construct
SEQUENCE: 248
AICSRSXPPI XIPD                                                             14

SEQ ID NO: 249          moltype = AA  length = 12
FEATURE                 Location/Qualifiers
REGION                  1..12
                        note = Synthetic Construct
MOD_RES                 1
                        note = Orn
DISULFID                3..11
                        note = disulfide bond
MOD_RES                 12
                        note = AMIDATION
source                  1..12
                        mol_type = protein
                        organism = synthetic construct
SEQUENCE: 249
XICSRSLPPI CI                                                               12

SEQ ID NO: 250          moltype = AA  length = 14
FEATURE                 Location/Qualifiers
REGION                  1..14
                        note = Synthetic Construct
DISULFID                3..11
                        note = disulfide bond
MOD_RES                 8
                        note = Xaa is L-dehydroproline
MOD_RES                 9
                        note = Xaa is
                         2,3,3a,4,5,6,7,7a-Octahydroindole-2-carboxylic acid
MOD_RES                 11
                        note = Xaa is L-Penicillamine
source                  1..14
                        mol_type = protein
                        organism = synthetic construct
SEQUENCE: 250
AICSRSLXXI XIPD                                                             14

SEQ ID NO: 251          moltype = AA  length = 14
FEATURE                 Location/Qualifiers
REGION                  1..14
                        note = Synthetic Construct
DISULFID                3..11
                        note = disulfide bond
MOD_RES                 7
                        note = Xaa is 2-Chloro-L-phenylalanine
MOD_RES                 11
                        note = Xaa is L-N-Methylcysteine
MOD_RES                 14
                        note = AMIDATION
source                  1..14
                        mol_type = protein
                        organism = synthetic construct
SEQUENCE: 251
AICSRSXPPI XIPD                                                             14

SEQ ID NO: 252          moltype = AA  length = 14
FEATURE                 Location/Qualifiers
REGION                  1..14
                        note = Synthetic Construct
MOD_RES                 1
                        note = Xaa is 4-(Aminomethyl)benzoic acid
DISULFID                3..11
                        note = disulfide bond
MOD_RES                 7
                        note = Xaa is L-tert-Butylalanine
MOD_RES                 11
```

-continued

```
                         note = Xaa is L-N-Methylcysteine
MOD_RES                  14
                         note = AMIDATION
source                   1..14
                         mol_type = protein
                         organism = synthetic construct
SEQUENCE: 252
XICSRSXPPI XIPD                                                     14

SEQ ID NO: 253           moltype = AA  length = 13
FEATURE                  Location/Qualifiers
REGION                   1..13
                         note = Synthetic Construct
MOD_RES                  1
                         note = Orn
DISULFID                 3..11
                         note = disulfide bond
MOD_RES                  7
                         note = Xaa is (S)-(trifluoromethyl)-L-cysteine
MOD_RES                  11
                         note = Xaa is L-Penicillamine
MOD_RES                  13
                         note = AMIDATION
source                   1..13
                         mol_type = protein
                         organism = synthetic construct
SEQUENCE: 253
XICSRSXPPI XIP                                                      13

SEQ ID NO: 254           moltype = AA  length = 13
FEATURE                  Location/Qualifiers
REGION                   1..13
                         note = Synthetic Construct
DISULFID                 3..10
                         note = disulfide bond
MOD_RES                  8
                         note = Xaa is
                          (4aR,6aR,9S,11aS)-11-Oxo-2,3,4,4a,6a,7,8,9,11,11a-decahydro
                          -1H-py rido[3,2-e]pyrrolo[1,2-a]azepine-9-carboxylic acid
MOD_RES                  13
                         note = AMIDATION
source                   1..13
                         mol_type = protein
                         organism = synthetic construct
SEQUENCE: 254
AICSRSLXIC IPD                                                      13

SEQ ID NO: 255           moltype = AA  length = 13
FEATURE                  Location/Qualifiers
REGION                   1..13
                         note = Synthetic Construct
MOD_RES                  1
                         note = Xaa is trans-2-(3-(Amino)cyclohexyl)acetic acid
DISULFID                 3..11
                         note = disulfide bond
MOD_RES                  7
                         note = Xaa is L-tert-Butylalanine
MOD_RES                  11
                         note = Xaa is L-Penicillamine
MOD_RES                  13
                         note = AMIDATION
source                   1..13
                         mol_type = protein
                         organism = synthetic construct
SEQUENCE: 255
XICSRSXPPI XIP                                                      13

SEQ ID NO: 256           moltype = AA  length = 14
FEATURE                  Location/Qualifiers
REGION                   1..14
                         note = Synthetic Construct
MOD_RES                  1
                         note = Xaa is L-N,N-Dimethylalanine
DISULFID                 3..11
                         note = disulfide bond
MOD_RES                  7
                         note = Xaa is L-tert-Butylalanine
MOD_RES                  14
                         note = AMIDATION
```

```
source                 1..14
                       mol_type = protein
                       organism = synthetic construct
SEQUENCE: 256
XICSRSXPPI CIPD                                                       14

SEQ ID NO: 257         moltype = AA  length = 12
FEATURE                Location/Qualifiers
REGION                 1..12
                       note = Synthetic Construct
MOD_RES                1
                       note = MeGly
DISULFID               3..11
                       note = disulfide bond
MOD_RES                9
                       note = Xaa is
                        2,3,3a,4,5,6,7,7a-Octahydroindole-2-carboxylic acid
MOD_RES                11
                       note = Xaa is L-Penicillamine
MOD_RES                12
                       note = AMIDATION
source                 1..12
                       mol_type = protein
                       organism = synthetic construct
SEQUENCE: 257
XICSRSLPXI XI                                                         12

SEQ ID NO: 258         moltype = AA  length = 14
FEATURE                Location/Qualifiers
REGION                 1..14
                       note = Synthetic Construct
DISULFID               3..11
                       note = disulfide bond
MOD_RES                9
                       note = Xaa is (6S)-5-Azaspiro[2.4]heptane-6-carboxylic acid
MOD_RES                14
                       note = AMIDATION
source                 1..14
                       mol_type = protein
                       organism = synthetic construct
SEQUENCE: 258
AICSRSLPXI CIPD                                                       14

SEQ ID NO: 259         moltype = AA  length = 14
FEATURE                Location/Qualifiers
REGION                 1..14
                       note = Synthetic Construct
MOD_RES                1
                       note = MeGly
DISULFID               3..11
                       note = disulfide bond
MOD_RES                7
                       note = Xaa is L-tert-Butylalanine
source                 1..14
                       mol_type = protein
                       organism = synthetic construct
SEQUENCE: 259
XICSRSXPPI CIPD                                                       14

SEQ ID NO: 260         moltype = AA  length = 12
FEATURE                Location/Qualifiers
REGION                 1..12
                       note = Synthetic Construct
DISULFID               3..11
                       note = disulfide bond
MOD_RES                10
                       note = Xaa is L-Cyclohexylglycine
MOD_RES                12
                       note = AMIDATION
source                 1..12
                       mol_type = protein
                       organism = synthetic construct
SEQUENCE: 260
AICSRSLPPX CI                                                         12

SEQ ID NO: 261         moltype = AA  length = 14
FEATURE                Location/Qualifiers
REGION                 1..14
                       note = Synthetic Construct
```

```
DISULFID              3..11
                      note = disulfide bond
MOD_RES               7
                      note = Xaa is 4-Fluoro-L-Leucine
MOD_RES               14
                      note = AMIDATION
source                1..14
                      mol_type = protein
                      organism = synthetic construct
SEQUENCE: 261
AICSRSXPPI CIPD                                                  14

SEQ ID NO: 262        moltype = AA  length = 13
FEATURE               Location/Qualifiers
REGION                1..13
                      note = Synthetic Construct
MOD_RES               1
                      note = MeGly
DISULFID              3..11
                      note = disulfide bond
MOD_RES               9
                      note = Xaa is
                       2,3,3a,4,5,6,7,7a-Octahydroindole-2-carboxylic acid
MOD_RES               11
                      note = Xaa is L-Penicillamine
MOD_RES               13
                      note = AMIDATION
source                1..13
                      mol_type = protein
                      organism = synthetic construct
SEQUENCE: 262
XICSRSLPXI XIP                                                   13

SEQ ID NO: 263        moltype = AA  length = 14
FEATURE               Location/Qualifiers
REGION                1..14
                      note = Synthetic Construct
MOD_RES               1
                      note = Xaa is N-Methyl-L-proline
DISULFID              3..11
                      note = disulfide bond
MOD_RES               7
                      note = Xaa is L-tert-Butylalanine
MOD_RES               14
                      note = AMIDATION
source                1..14
                      mol_type = protein
                      organism = synthetic construct
SEQUENCE: 263
XICSRSXPPI CIPD                                                  14

SEQ ID NO: 264        moltype = AA  length = 13
FEATURE               Location/Qualifiers
REGION                1..13
                      note = Synthetic Construct
MOD_RES               1
                      note = Xaa is trans-2-(3-(Amino)cyclohexyl)acetic acid
DISULFID              3..11
                      note = disulfide bond
MOD_RES               7
                      note = Xaa is L-tert-Butylalanine
MOD_RES               11
                      note = Xaa is L-Penicillamine
MOD_RES               13
                      note = AMIDATION
source                1..13
                      mol_type = protein
                      organism = synthetic construct
SEQUENCE: 264
XICSRSXPPI XIP                                                   13

SEQ ID NO: 265        moltype = AA  length = 14
FEATURE               Location/Qualifiers
REGION                1..14
                      note = Synthetic Construct
DISULFID              3..11
                      note = disulfide bond
MOD_RES               11
                      note = Xaa is L-Penicillamine
```

```
MOD_RES                 14
                        note = AMIDATION
source                  1..14
                        mol_type = protein
                        organism = synthetic construct
SEQUENCE: 265
AICSRSNPPI XIPD                                                            14

SEQ ID NO: 266          moltype = AA  length = 14
FEATURE                 Location/Qualifiers
REGION                  1..14
                        note = Synthetic Construct
MOD_RES                 1
                        note = Xaa is L-N-Methylalanine
DISULFID                3..11
                        note = disulfide bond
MOD_RES                 7
                        note = Xaa is L-tert-Butylalanine
MOD_RES                 14
                        note = AMIDATION
source                  1..14
                        mol_type = protein
                        organism = synthetic construct
SEQUENCE: 266
XICSRSXPPI CIPD                                                            14

SEQ ID NO: 267          moltype = AA  length = 14
FEATURE                 Location/Qualifiers
REGION                  1..14
                        note = Synthetic Construct
DISULFID                3..11
                        note = disulfide bond
MOD_RES                 10
                        note = Xaa is L-Cyclohexylglycine
MOD_RES                 14
                        note = AMIDATION
source                  1..14
                        mol_type = protein
                        organism = synthetic construct
SEQUENCE: 267
AICSRSLPPX CIPD                                                            14

SEQ ID NO: 268          moltype = AA  length = 13
FEATURE                 Location/Qualifiers
REGION                  1..13
                        note = Synthetic Construct
MOD_RES                 1
                        note = Acp
DISULFID                3..11
                        note = disulfide bond
MOD_RES                 7
                        note = Xaa is L-tert-Butylalanine
MOD_RES                 11
                        note = Xaa is L-Penicillamine
MOD_RES                 13
                        note = AMIDATION
source                  1..13
                        mol_type = protein
                        organism = synthetic construct
SEQUENCE: 268
XICSRSXPPI XIP                                                             13

SEQ ID NO: 269          moltype = AA  length = 13
FEATURE                 Location/Qualifiers
REGION                  1..13
                        note = Synthetic Construct
DISULFID                2..10
                        note = disulfide bond
MOD_RES                 6
                        note = Xaa is L-tert-Butylalanine
MOD_RES                 10
                        note = Xaa is L-N-Methylcysteine
MOD_RES                 13
                        note = AMIDATION
source                  1..13
                        mol_type = protein
                        organism = synthetic construct
SEQUENCE: 269
ICSRSXPPIX IPD                                                             13
```

```
SEQ ID NO: 270          moltype = AA  length = 12
FEATURE                 Location/Qualifiers
REGION                  1..12
                        note = Synthetic Construct
SITE                    1
                        note = Xaa is D-Lysine
DISULFID                3..11
                        note = disulfide bond
MOD_RES                 7
                        note = Xaa is L-tert-Butylalanine
MOD_RES                 11
                        note = Xaa is L-Penicillamine
MOD_RES                 12
                        note = AMIDATION
source                  1..12
                        mol_type = protein
                        organism = synthetic construct
SEQUENCE: 270
XICSRSXPPI XI                                                   12

SEQ ID NO: 271          moltype = AA  length = 12
FEATURE                 Location/Qualifiers
REGION                  1..12
                        note = Synthetic Construct
DISULFID                2..10
                        note = disulfide bond
MOD_RES                 6
                        note = Xaa is L-tert-Butylalanine
MOD_RES                 10
                        note = Xaa is L-Penicillamine
source                  1..12
                        mol_type = protein
                        organism = synthetic construct
SEQUENCE: 271
ICSRSXPPIX IP                                                   12

SEQ ID NO: 272          moltype = AA  length = 12
FEATURE                 Location/Qualifiers
REGION                  1..12
                        note = Synthetic Construct
MOD_RES                 1
                        note = Xaa is Piperidin-4-ylacetic acid
DISULFID                3..11
                        note = disulfide bond
MOD_RES                 7
                        note = Xaa is L-tert-Butylalanine
MOD_RES                 11
                        note = Xaa is L-N-Methylcysteine
MOD_RES                 12
                        note = AMIDATION
source                  1..12
                        mol_type = protein
                        organism = synthetic construct
SEQUENCE: 272
XICSRSXPPI XI                                                   12

SEQ ID NO: 273          moltype = AA  length = 14
FEATURE                 Location/Qualifiers
REGION                  1..14
                        note = Synthetic Construct
MOD_RES                 2
                        note = MeIle
DISULFID                3..11
                        note = disulfide bond
MOD_RES                 14
                        note = AMIDATION
source                  1..14
                        mol_type = protein
                        organism = synthetic construct
SEQUENCE: 273
AXCSRSLPPI CIPD                                                 14

SEQ ID NO: 274          moltype = AA  length = 14
FEATURE                 Location/Qualifiers
REGION                  1..14
                        note = Synthetic Construct
MOD_RES                 2
                        note = MeIle
```

```
DISULFID              3..11
                      note = disulfide bond
MOD_RES               14
                      note = AMIDATION
source                1..14
                      mol_type = protein
                      organism = synthetic construct
SEQUENCE: 274
GXCSRSLPPI CIPD                                                            14

SEQ ID NO: 275        moltype = AA  length = 14
FEATURE               Location/Qualifiers
REGION                1..14
                      note = Synthetic Construct
DISULFID              3..11
                      note = disulfide bond
MOD_RES               10
                      note = Xaa is L-Cyclopentylglycine
MOD_RES               14
                      note = AMIDATION
source                1..14
                      mol_type = protein
                      organism = synthetic construct
SEQUENCE: 275
AICSRSLPPX CIPD                                                            14

SEQ ID NO: 276        moltype = AA  length = 14
FEATURE               Location/Qualifiers
REGION                1..14
                      note = Synthetic Construct
MOD_RES               1
                      note = 4Abu
DISULFID              3..11
                      note = disulfide bond
MOD_RES               7
                      note = Xaa is L-tert-Butylalanine
MOD_RES               11
                      note = Xaa is L-N-Methylcysteine
MOD_RES               14
                      note = AMIDATION
source                1..14
                      mol_type = protein
                      organism = synthetic construct
SEQUENCE: 276
XICSRSXPPI XIPD                                                            14

SEQ ID NO: 277        moltype = AA  length = 13
FEATURE               Location/Qualifiers
REGION                1..13
                      note = Synthetic Construct
MOD_RES               1
                      note = MeGly
DISULFID              3..11
                      note = disulfide bond
MOD_RES               9
                      note = Xaa is
                       2,3,3a,4,5,6,7,7a-Octahydroindole-2-carboxylic acid
MOD_RES               11
                      note = Xaa is L-Penicillamine
MOD_RES               13
                      note = AMIDATION
source                1..13
                      mol_type = protein
                      organism = synthetic construct
SEQUENCE: 277
XICSRSLPXI XIP                                                             13

SEQ ID NO: 278        moltype = AA  length = 12
FEATURE               Location/Qualifiers
REGION                1..12
                      note = Synthetic Construct
DISULFID              2..10
                      note = disulfide bond
MOD_RES               8
                      note = Xaa is
                       2,3,3a,4,5,6,7,7a-Octahydroindole-2-carboxylic acid
MOD_RES               10
                      note = Xaa is L-Penicillamine
source                1..12
```

```
                         mol_type = protein
                         organism = synthetic construct
SEQUENCE: 278
ICSRSLPXIX IP                                                 12

SEQ ID NO: 279           moltype = AA  length = 17
FEATURE                  Location/Qualifiers
REGION                   1..17
                         note = Synthetic Construct
MOD_RES                  1
                         note = MeGly
MOD_RES                  2
                         note = MeGly
MOD_RES                  3
                         note = MeGly
MOD_RES                  4
                         note = MeGly
MOD_RES                  5
                         note = MeGly
DISULFID                 7..15
                         note = disulfide bond
MOD_RES                  11
                         note = Xaa is L-tert-Butylalanine
MOD_RES                  15
                         note = Xaa is L-Penicillamine
MOD_RES                  17
                         note = AMIDATION
source                   1..17
                         mol_type = protein
                         organism = synthetic construct
SEQUENCE: 279
XXXXXICSRS XPPIXIP                                            17

SEQ ID NO: 280           moltype = AA  length = 13
FEATURE                  Location/Qualifiers
REGION                   1..13
                         note = Synthetic Construct
MOD_RES                  1
                         note = MeGly
DISULFID                 3..11
                         note = disulfide bond
MOD_RES                  7
                         note = Xaa is (2S)-2-amino-3-(1-methylcyclopropyl)propanoic
                          acid
MOD_RES                  9
                         note = Xaa is
                          2,3,3a,4,5,6,7,7a-Octahydroindole-2-carboxylic acid
MOD_RES                  11
                         note = Xaa is L-Penicillamine
MOD_RES                  13
                         note = AMIDATION
source                   1..13
                         mol_type = protein
                         organism = synthetic construct
SEQUENCE: 280
XICSRSXPXI XIP                                                13

SEQ ID NO: 281           moltype = AA  length = 14
FEATURE                  Location/Qualifiers
REGION                   1..14
                         note = Synthetic Construct
DISULFID                 3..11
                         note = disulfide bond
MOD_RES                  7
                         note = Xaa is L-tert-Butylalanine
MOD_RES                  9
                         note = Xaa is
                          2,3,3a,4,5,6,7,7a-Octahydroindole-2-carboxylic acid
MOD_RES                  11
                         note = Xaa is L-N-Methylcysteine
MOD_RES                  14
                         note = AMIDATION
source                   1..14
                         mol_type = protein
                         organism = synthetic construct
SEQUENCE: 281
AICSRSXPXI XIPD                                               14

SEQ ID NO: 282           moltype = AA  length = 13
```

-continued

```
FEATURE                Location/Qualifiers
REGION                 1..13
                       note = Synthetic Construct
MOD_RES                1
                       note = Xaa is Tranexamic acid
DISULFID               3..11
                       note = disulfide bond
MOD_RES                7
                       note = Xaa is L-tert-Butylalanine
MOD_RES                11
                       note = Xaa is L-Penicillamine
MOD_RES                13
                       note = AMIDATION
source                 1..13
                       mol_type = protein
                       organism = synthetic construct
SEQUENCE: 282
XICSRSXPPI XIP                                                              13

SEQ ID NO: 283         moltype = AA  length = 14
FEATURE                Location/Qualifiers
REGION                 1..14
                       note = Synthetic Construct
DISULFID               3..11
                       note = disulfide bond
MOD_RES                9
                       note = Xaa is
                        2,3,3a,4,5,6,7,7a-Octahydroindole-2-carboxylic acid
MOD_RES                10
                       note = Xaa is L-Cyclohexylglycine
MOD_RES                14
                       note = AMIDATION
source                 1..14
                       mol_type = protein
                       organism = synthetic construct
SEQUENCE: 283
AICSRSLPXX CIPD                                                             14

SEQ ID NO: 284         moltype = AA  length = 14
FEATURE                Location/Qualifiers
REGION                 1..14
                       note = Synthetic Construct
MOD_RES                1
                       note = MeGly
DISULFID               3..11
                       note = disulfide bond
MOD_RES                14
                       note = AMIDATION
source                 1..14
                       mol_type = protein
                       organism = synthetic construct
SEQUENCE: 284
XICSRSLPPI CIPD                                                             14

SEQ ID NO: 285         moltype = AA  length = 14
FEATURE                Location/Qualifiers
REGION                 1..14
                       note = Synthetic Construct
MOD_RES                1
                       note = Xaa is (2-Thiomorpholine)acetyl
DISULFID               3..11
                       note = disulfide bond
MOD_RES                7
                       note = Xaa is L-tert-Butylalanine
MOD_RES                11
                       note = Xaa is L-Penicillamine
MOD_RES                14
                       note = AMIDATION
source                 1..14
                       mol_type = protein
                       organism = synthetic construct
SEQUENCE: 285
XICSRSXPPI XIPD                                                             14

SEQ ID NO: 286         moltype = AA  length = 14
FEATURE                Location/Qualifiers
REGION                 1..14
                       note = Synthetic Construct
MOD_RES                1
```

```
                        note = Xaa is Cyclopropylacetic acid
DISULFID                3..11
                        note = disulfide bond
MOD_RES                 7
                        note = Xaa is L-tert-Butylalanine
MOD_RES                 11
                        note = Xaa is L-Penicillamine
MOD_RES                 14
                        note = AMIDATION
source                  1..14
                        mol_type = protein
                        organism = synthetic construct
SEQUENCE: 286
XICSRSXPPI XIPD                                            14

SEQ ID NO: 287          moltype = AA  length = 12
FEATURE                 Location/Qualifiers
REGION                  1..12
                        note = Synthetic Construct
MOD_RES                 1
                        note = Xaa is Cyclopropylacetic acid
DISULFID                3..11
                        note = disulfide bond
MOD_RES                 7
                        note = Xaa is L-tert-Butylalanine
MOD_RES                 11
                        note = Xaa is L-N-Methylcysteine
MOD_RES                 12
                        note = AMIDATION
source                  1..12
                        mol_type = protein
                        organism = synthetic construct
SEQUENCE: 287
XICSRSXPPI XI                                              12

SEQ ID NO: 288          moltype = AA  length = 14
FEATURE                 Location/Qualifiers
REGION                  1..14
                        note = Synthetic Construct
MOD_RES                 2
                        note = MeIle
DISULFID                3..11
                        note = disulfide bond
source                  1..14
                        mol_type = protein
                        organism = synthetic construct
SEQUENCE: 288
GXCSRSLPPI CIPD                                            14

SEQ ID NO: 289          moltype = AA  length = 14
FEATURE                 Location/Qualifiers
REGION                  1..14
                        note = Synthetic Construct
MOD_RES                 2
                        note = MeIle
DISULFID                3..11
                        note = disulfide bond
SITE                    14
                        note = Xaa is D-Aspartic acid
source                  1..14
                        mol_type = protein
                        organism = synthetic construct
SEQUENCE: 289
GXCSRSLPPI CIPX                                            14

SEQ ID NO: 290          moltype = AA  length = 14
FEATURE                 Location/Qualifiers
REGION                  1..14
                        note = Synthetic Construct
MOD_RES                 1
                        note = MeGly
DISULFID                3..11
                        note = disulfide bond
MOD_RES                 12
                        note = aIle
MOD_RES                 14
                        note = AMIDATION
source                  1..14
                        mol_type = protein
```

-continued

```
                        organism = synthetic construct
SEQUENCE: 290
XICSRSLPPI CXPD                                                          14

SEQ ID NO: 291          moltype = AA  length = 14
FEATURE                 Location/Qualifiers
REGION                  1..14
                        note = Synthetic Construct
DISULFID                3..11
                        note = disulfide bond
MOD_RES                 6
                        note = Xaa is allo-L-Threonine
MOD_RES                 14
                        note = AMIDATION
source                  1..14
                        mol_type = protein
                        organism = synthetic construct
SEQUENCE: 291
AICSRXLPPI CIPD                                                          14

SEQ ID NO: 292          moltype = AA  length = 14
FEATURE                 Location/Qualifiers
REGION                  1..14
                        note = Synthetic Construct
DISULFID                3..11
                        note = disulfide bond
MOD_RES                 7
                        note = Xaa is 3-(Trimethylsilyl)-L-alanine
MOD_RES                 9
                        note = Xaa is
                         2,3,3a,4,5,6,7,7a-Octahydroindole-2-carboxylic acid
MOD_RES                 11
                        note = Xaa is L-N-Methylcysteine
MOD_RES                 14
                        note = AMIDATION
source                  1..14
                        mol_type = protein
                        organism = synthetic construct
SEQUENCE: 292
AICSRSXPXI XIPD                                                          14

SEQ ID NO: 293          moltype = AA  length = 11
FEATURE                 Location/Qualifiers
REGION                  1..11
                        note = Synthetic Construct
MOD_RES                 1
                        note = ACETYLATION
DISULFID                2..10
                        note = disulfide bond
MOD_RES                 6
                        note = Xaa is L-tert-Butylalanine
MOD_RES                 10
                        note = Xaa is L-N-Methylcysteine
MOD_RES                 11
                        note = AMIDATION
source                  1..11
                        mol_type = protein
                        organism = synthetic construct
SEQUENCE: 293
ICSRSXPPIX I                                                             11

SEQ ID NO: 294          moltype = AA  length = 14
FEATURE                 Location/Qualifiers
REGION                  1..14
                        note = Synthetic Construct
MOD_RES                 1
                        note = MeGly
DISULFID                3..11
                        note = disulfide bond
source                  1..14
                        mol_type = protein
                        organism = synthetic construct
SEQUENCE: 294
XICSRSLPPI CIPD                                                          14

SEQ ID NO: 295          moltype = AA  length = 14
FEATURE                 Location/Qualifiers
REGION                  1..14
                        note = Synthetic Construct
```

```
MOD_RES                 1
                        note = MeGly
DISULFID                3..11
                        note = disulfide bond
MOD_RES                 10
                        note = Xaa is L-Cyclohexylglycine
MOD_RES                 14
                        note = AMIDATION
source                  1..14
                        mol_type = protein
                        organism = synthetic construct
SEQUENCE: 295
XICSRSLPPX CIPD                                                  14

SEQ ID NO: 296          moltype = AA  length = 14
FEATURE                 Location/Qualifiers
REGION                  1..14
                        note = Synthetic Construct
MOD_RES                 1
                        note = Xaa is 2-(Morpholine)acetic acid
DISULFID                3..11
                        note = disulfide bond
MOD_RES                 7
                        note = Xaa is L-tert-Butylalanine
MOD_RES                 11
                        note = Xaa is L-Penicillamine
MOD_RES                 14
                        note = AMIDATION
source                  1..14
                        mol_type = protein
                        organism = synthetic construct
SEQUENCE: 296
XICSRSXPPI XIPD                                                  14

SEQ ID NO: 297          moltype = AA  length = 13
FEATURE                 Location/Qualifiers
REGION                  1..13
                        note = Synthetic Construct
MOD_RES                 1
                        note = Xaa is 2-(Cyclobutyl)acetic acid
DISULFID                3..11
                        note = disulfide bond
MOD_RES                 7
                        note = Xaa is L-tert-Butylalanine
MOD_RES                 11
                        note = Xaa is L-Penicillamine
MOD_RES                 13
                        note = AMIDATION
source                  1..13
                        mol_type = protein
                        organism = synthetic construct
SEQUENCE: 297
XICSRSXPPI XIP                                                   13

SEQ ID NO: 298          moltype = AA  length = 12
FEATURE                 Location/Qualifiers
REGION                  1..12
                        note = Synthetic Construct
MOD_RES                 1
                        note = Xaa is Tranexamic acid
DISULFID                3..11
                        note = disulfide bond
MOD_RES                 7
                        note = Xaa is L-tert-Butylalanine
MOD_RES                 11
                        note = Xaa is L-N-Methylcysteine
MOD_RES                 12
                        note = AMIDATION
source                  1..12
                        mol_type = protein
                        organism = synthetic construct
SEQUENCE: 298
XICSRSXPPI XI                                                    12

SEQ ID NO: 299          moltype = AA  length = 14
FEATURE                 Location/Qualifiers
REGION                  1..14
                        note = Synthetic Construct
DISULFID                3..11
```

-continued

```
                      note = disulfide bond
MOD_RES               13
                      note = Aib
source                1..14
                      mol_type = protein
                      organism = synthetic construct
SEQUENCE: 299
GICSRSLPPI CIXD                                                  14

SEQ ID NO: 300        moltype = AA  length = 14
FEATURE               Location/Qualifiers
REGION                1..14
                      note = Synthetic Construct
MOD_RES               1
                      note = MeGly
DISULFID              3..11
                      note = disulfide bond
MOD_RES               13
                      note = Xaa is trans-4-Fluoroproline
source                1..14
                      mol_type = protein
                      organism = synthetic construct
SEQUENCE: 300
XICSRSLPPI CIXD                                                  14

SEQ ID NO: 301        moltype = AA  length = 14
FEATURE               Location/Qualifiers
REGION                1..14
                      note = Synthetic Construct
MOD_RES               1
                      note = MeGly
DISULFID              3..11
                      note = disulfide bond
source                1..14
                      mol_type = protein
                      organism = synthetic construct
SEQUENCE: 301
XICTRSLPPI CIPD                                                  14

SEQ ID NO: 302        moltype = AA  length = 14
FEATURE               Location/Qualifiers
REGION                1..14
                      note = Synthetic Construct
MOD_RES               1
                      note = MeGly
DISULFID              3..11
                      note = disulfide bond
MOD_RES               13
                      note = Xaa is 2-Methyl-L-Proline
source                1..14
                      mol_type = protein
                      organism = synthetic construct
SEQUENCE: 302
XICSRSLPPI CIXD                                                  14

SEQ ID NO: 303        moltype = AA  length = 13
FEATURE               Location/Qualifiers
REGION                1..13
                      note = Synthetic Construct
MOD_RES               1
                      note = ACETYLATION
DISULFID              2..10
                      note = disulfide bond
MOD_RES               6
                      note = Xaa is L-tert-Butylalanine
MOD_RES               10
                      note = Xaa is L-Penicillamine
MOD_RES               13
                      note = AMIDATION
source                1..13
                      mol_type = protein
                      organism = synthetic construct
SEQUENCE: 303
ICSRSXPPIX IPD                                                   13

SEQ ID NO: 304        moltype = AA  length = 13
FEATURE               Location/Qualifiers
REGION                1..13
                      note = Synthetic Construct
```

-continued

```
DISULFID              3..11
                      note = disulfide bond
MOD_RES               9
                      note = Xaa is
                       2,3,3a,4,5,6,7,7a-Octahydroindole-2-carboxylic acid
MOD_RES               11
                      note = Xaa is L-Penicillamine
MOD_RES               13
                      note = AMIDATION
source                1..13
                      mol_type = protein
                      organism = synthetic construct
SEQUENCE: 304
FICSRSLPXI XIP                                                    13

SEQ ID NO: 305        moltype = AA  length = 12
FEATURE               Location/Qualifiers
REGION                1..12
                      note = Synthetic Construct
DISULFID              3..11
                      note = disulfide bond
MOD_RES               9
                      note = Xaa is
                       2,3,3a,4,5,6,7,7a-Octahydroindole-2-carboxylic acid
source                1..12
                      mol_type = protein
                      organism = synthetic construct
SEQUENCE: 305
AICSRSLPXI CI                                                     12

SEQ ID NO: 306        moltype = AA  length = 13
FEATURE               Location/Qualifiers
REGION                1..13
                      note = Synthetic Construct
DISULFID              2..10
                      note = disulfide bond
MOD_RES               8
                      note = Xaa is
                       2,3,3a,4,5,6,7,7a-Octahydroindole-2-carboxylic acid
MOD_RES               10
                      note = Xaa is L-Penicillamine
MOD_RES               13
                      note = AMIDATION
source                1..13
                      mol_type = protein
                      organism = synthetic construct
SEQUENCE: 306
ICSRSLPXIX IPD                                                    13

SEQ ID NO: 307        moltype = AA  length = 14
FEATURE               Location/Qualifiers
REGION                1..14
                      note = Synthetic Construct
MOD_RES               1
                      note = Xaa is Benzoic acid
DISULFID              3..11
                      note = disulfide bond
MOD_RES               7
                      note = Xaa is L-tert-Butylalanine
MOD_RES               11
                      note = Xaa is L-Penicillamine
MOD_RES               14
                      note = AMIDATION
source                1..14
                      mol_type = protein
                      organism = synthetic construct
SEQUENCE: 307
XICSRSXPPI XIPD                                                   14

SEQ ID NO: 308        moltype = AA  length = 14
FEATURE               Location/Qualifiers
REGION                1..14
                      note = Synthetic Construct
MOD_RES               1
                      note = Xaa is Phenylacetic acid
DISULFID              3..11
                      note = disulfide bond
MOD_RES               7
                      note = Xaa is L-tert-Butylalanine
```

-continued

```
MOD_RES                 11
                        note = Xaa is L-Penicillamine
MOD_RES                 14
                        note = AMIDATION
source                  1..14
                        mol_type = protein
                        organism = synthetic construct
SEQUENCE: 308
XICSRSXPPI XIPD                                                       14

SEQ ID NO: 309          moltype = AA  length = 13
FEATURE                 Location/Qualifiers
REGION                  1..13
                        note = Synthetic Construct
MOD_RES                 1
                        note = Xaa is Tetrahydro-2H-pyran-3-ylacetic acid
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
MOD_RES                 13
                        note = AMIDATION
source                  1..13
                        mol_type = protein
                        organism = synthetic construct
SEQUENCE: 309
XICSRSLPXI XIP                                                        13

SEQ ID NO: 310          moltype = AA  length = 14
FEATURE                 Location/Qualifiers
REGION                  1..14
                        note = Synthetic Construct
MOD_RES                 1
                        note = Xaa is L-N-Methylalanine
DISULFID                3..11
                        note = disulfide bond
MOD_RES                 14
                        note = AMIDATION
source                  1..14
                        mol_type = protein
                        organism = synthetic construct
SEQUENCE: 310
XICSRSLPPI CIPD                                                       14

SEQ ID NO: 311          moltype = AA  length = 12
FEATURE                 Location/Qualifiers
REGION                  1..12
                        note = Synthetic Construct
MOD_RES                 1
                        note = Xaa is N-Phenylglycine
DISULFID                3..11
                        note = disulfide bond
MOD_RES                 7
                        note = Xaa is L-tert-Butylalanine
MOD_RES                 11
                        note = Xaa is L-N-Methylcysteine
MOD_RES                 12
                        note = AMIDATION
source                  1..12
                        mol_type = protein
                        organism = synthetic construct
SEQUENCE: 311
XICSRSXPPI XI                                                         12

SEQ ID NO: 312          moltype = AA  length = 13
FEATURE                 Location/Qualifiers
REGION                  1..13
                        note = Synthetic Construct
MOD_RES                 1
                        note = Orn
DISULFID                3..11
                        note = disulfide bond
MOD_RES                 7
                        note = Xaa is L-tert-Butylalanine
MOD_RES                 11
                        note = Xaa is L-N-Methylcysteine
```

-continued

```
MOD_RES                 12
                        note = Xaa is
                         2-[(1S,2S)-1-(Amino)-2-methylbutyl]-1,3-oxazole-4-
                         carboxylic acid
MOD_RES                 13
                        note = AMIDATION
source                  1..13
                        mol_type = protein
                        organism = synthetic construct
SEQUENCE: 312
XICSRSXPPI XXD                                                            13

SEQ ID NO: 313          moltype = AA  length = 14
FEATURE                 Location/Qualifiers
REGION                  1..14
                        note = Synthetic Construct
MOD_RES                 1
                        note = Xaa is 2-Hydroxyacetic acid
DISULFID                3..11
                        note = disulfide bond
MOD_RES                 7
                        note = Xaa is L-tert-Butylalanine
MOD_RES                 11
                        note = Xaa is L-Penicillamine
MOD_RES                 14
                        note = AMIDATION
source                  1..14
                        mol_type = protein
                        organism = synthetic construct
SEQUENCE: 313
XICSRSXPPI XIPD                                                           14

SEQ ID NO: 314          moltype = AA  length = 12
FEATURE                 Location/Qualifiers
REGION                  1..12
                        note = Synthetic Construct
MOD_RES                 1
                        note = Xaa is Cyclobutanecarboxylic acid
DISULFID                3..11
                        note = disulfide bond
MOD_RES                 7
                        note = Xaa is L-tert-Butylalanine
MOD_RES                 11
                        note = Xaa is L-N-Methylcysteine
MOD_RES                 12
                        note = AMIDATION
source                  1..12
                        mol_type = protein
                        organism = synthetic construct
SEQUENCE: 314
XICSRSXPPI XI                                                             12

SEQ ID NO: 315          moltype = AA  length = 14
FEATURE                 Location/Qualifiers
REGION                  1..14
                        note = Synthetic Construct
DISULFID                3..11
                        note = disulfide bond
MOD_RES                 10
                        note = Xaa is 3-Chlorophenylglycine
MOD_RES                 14
                        note = AMIDATION
source                  1..14
                        mol_type = protein
                        organism = synthetic construct
SEQUENCE: 315
AICSRSLPPX CIPD                                                           14

SEQ ID NO: 316          moltype = AA  length = 13
FEATURE                 Location/Qualifiers
REGION                  1..13
                        note = Synthetic Construct
DISULFID                2..10
                        note = disulfide bond
MOD_RES                 6
                        note = Xaa is L-tert-Butylalanine
MOD_RES                 10
                        note = Xaa is L-Penicillamine
MOD_RES                 13
```

```
                        note = AMIDATION
source                  1..13
                        mol_type = protein
                        organism = synthetic construct
SEQUENCE: 316
ICSRSXPPIX IPP                                                             13

SEQ ID NO: 317          moltype = AA  length = 13
FEATURE                 Location/Qualifiers
REGION                  1..13
                        note = Synthetic Construct
MOD_RES                 1
                        note = Xaa is Tetrahydro-2H-pyran-3-ylacetic acid
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
MOD_RES                 13
                        note = AMIDATION
source                  1..13
                        mol_type = protein
                        organism = synthetic construct
SEQUENCE: 317
XICSRSLPXI XIP                                                             13

SEQ ID NO: 318          moltype = AA  length = 12
FEATURE                 Location/Qualifiers
REGION                  1..12
                        note = Synthetic Construct
MOD_RES                 1
                        note = Xaa is Tetrahydropyranyl-4-acetic acid
DISULFID                3..11
                        note = disulfide bond
MOD_RES                 7
                        note = Xaa is L-tert-Butylalanine
MOD_RES                 11
                        note = Xaa is L-N-Methylcysteine
MOD_RES                 12
                        note = AMIDATION
source                  1..12
                        mol_type = protein
                        organism = synthetic construct
SEQUENCE: 318
XICSRSXPPI XI                                                              12

SEQ ID NO: 319          moltype = AA  length = 14
FEATURE                 Location/Qualifiers
REGION                  1..14
                        note = Synthetic Construct
MOD_RES                 1
                        note = bAla
DISULFID                3..11
                        note = disulfide bond
source                  1..14
                        mol_type = protein
                        organism = synthetic construct
SEQUENCE: 319
XICSRSLPPI CIPD                                                            14

SEQ ID NO: 320          moltype = AA  length = 14
FEATURE                 Location/Qualifiers
REGION                  1..14
                        note = Synthetic Construct
MOD_RES                 1
                        note = Xaa is 2-(N-Methyl-N-cyclopropylamino)acetic acid
DISULFID                3..11
                        note = disulfide bond
MOD_RES                 7
                        note = Xaa is L-tert-Butylalanine
MOD_RES                 11
                        note = Xaa is L-Penicillamine
MOD_RES                 14
                        note = AMIDATION
source                  1..14
                        mol_type = protein
                        organism = synthetic construct
```

```
SEQUENCE: 320
XICSRSXPPI XIPD                                                    14

SEQ ID NO: 321          moltype = AA  length = 14
FEATURE                 Location/Qualifiers
REGION                  1..14
                        note = Synthetic Construct
MOD_RES                 1
                        note = Xaa is Cyclobutanecarboxylic acid
DISULFID                3..11
                        note = disulfide bond
MOD_RES                 7
                        note = Xaa is L-tert-Butylalanine
MOD_RES                 11
                        note = Xaa is L-Penicillamine
MOD_RES                 14
                        note = AMIDATION
source                  1..14
                        mol_type = protein
                        organism = synthetic construct
SEQUENCE: 321
XICSRSXPPI XIPD                                                    14

SEQ ID NO: 322          moltype = AA  length = 14
FEATURE                 Location/Qualifiers
REGION                  1..14
                        note = Synthetic Construct
MOD_RES                 1
                        note = Xaa is Isovaleric acid
DISULFID                3..11
                        note = disulfide bond
MOD_RES                 7
                        note = Xaa is L-tert-Butylalanine
MOD_RES                 11
                        note = Xaa is L-Penicillamine
MOD_RES                 14
                        note = AMIDATION
source                  1..14
                        mol_type = protein
                        organism = synthetic construct
SEQUENCE: 322
XICSRSXPPI XIPD                                                    14

SEQ ID NO: 323          moltype = AA  length = 13
FEATURE                 Location/Qualifiers
REGION                  1..13
                        note = Synthetic Construct
MOD_RES                 1
                        note = MeGly
DISULFID                3..11
                        note = disulfide bond
MOD_RES                 3
                        note = Xaa is L-Penicillamine
MOD_RES                 7
                        note = Xaa is L-tert-Butylalanine
MOD_RES                 13
                        note = AMIDATION
source                  1..13
                        mol_type = protein
                        organism = synthetic construct
SEQUENCE: 323
XIXSRSXPPI CIP                                                     13

SEQ ID NO: 324          moltype = AA  length = 13
FEATURE                 Location/Qualifiers
REGION                  1..13
                        note = Synthetic Construct
MOD_RES                 1
                        note = Xaa is N-Phenylglycine
DISULFID                3..11
                        note = disulfide bond
MOD_RES                 7
                        note = Xaa is L-tert-Butylalanine
MOD_RES                 11
                        note = Xaa is L-Penicillamine
MOD_RES                 13
                        note = AMIDATION
source                  1..13
                        mol_type = protein
```

```
                        organism = synthetic construct
SEQUENCE: 324
XICSRSXPPI XIP                                                      13

SEQ ID NO: 325          moltype = AA  length = 14
FEATURE                 Location/Qualifiers
REGION                  1..14
                        note = Synthetic Construct
MOD_RES                 1
                        note = Xaa is MeGly
DISULFID                3..11
                        note = disulfide bond
SITE                    14
                        note = Xaa is D-Aspartic acid
source                  1..14
                        mol_type = protein
                        organism = synthetic construct
SEQUENCE: 325
XICSRSLPPI CIPX                                                     14

SEQ ID NO: 326          moltype = AA  length = 14
FEATURE                 Location/Qualifiers
REGION                  1..14
                        note = Synthetic Construct
MOD_RES                 1
                        note = MeGly
DISULFID                3..11
                        note = disulfide bond
MOD_RES                 13
                        note = Abu
source                  1..14
                        mol_type = protein
                        organism = synthetic construct
SEQUENCE: 326
XICSRSLPPI CIXD                                                     14

SEQ ID NO: 327          moltype = AA  length = 14
FEATURE                 Location/Qualifiers
REGION                  1..14
                        note = Synthetic Construct
DISULFID                3..11
                        note = disulfide bond
MOD_RES                 7
                        note = Aad
MOD_RES                 11
                        note = Xaa is L-N-Methylcysteine
MOD_RES                 14
                        note = AMIDATION
source                  1..14
                        mol_type = protein
                        organism = synthetic construct
SEQUENCE: 327
AICSRSXPPI XIPD                                                     14

SEQ ID NO: 328          moltype = AA  length = 14
FEATURE                 Location/Qualifiers
REGION                  1..14
                        note = Synthetic Construct
MOD_RES                 1
                        note = Xaa is Cyclopropanecarboxylic acid
DISULFID                3..11
                        note = disulfide bond
MOD_RES                 7
                        note = Xaa is L-tert-Butylalanine
MOD_RES                 11
                        note = Xaa is L-Penicillamine
MOD_RES                 14
                        note = AMIDATION
source                  1..14
                        mol_type = protein
                        organism = synthetic construct
SEQUENCE: 328
XICSRSXPPI XIPD                                                     14

SEQ ID NO: 329          moltype = AA  length = 12
FEATURE                 Location/Qualifiers
REGION                  1..12
                        note = Synthetic Construct
DISULFID                2..10
```

```
                        note = disulfide bond
MOD_RES                 6
                        note = Xaa is L-tert-Butylalanine
MOD_RES                 10
                        note = Xaa is L-Penicillamine
MOD_RES                 12
                        note = AMIDATION
source                  1..12
                        mol_type = protein
                        organism = synthetic construct
SEQUENCE: 329
ICSRSXPPIX IP                                                       12

SEQ ID NO: 330          moltype = AA  length = 13
FEATURE                 Location/Qualifiers
REGION                  1..13
                        note = Synthetic Construct
MOD_RES                 1
                        note = MeGly
DISULFID                3..11
                        note = disulfide bond
MOD_RES                 13
                        note = AMIDATION
source                  1..13
                        mol_type = protein
                        organism = synthetic construct
SEQUENCE: 330
XICSRSLPPI CID                                                      13

SEQ ID NO: 331          moltype = AA  length = 14
FEATURE                 Location/Qualifiers
REGION                  1..14
                        note = Synthetic Construct
MOD_RES                 1
                        note = MeGly
DISULFID                3..11
                        note = disulfide bond
source                  1..14
                        mol_type = protein
                        organism = synthetic construct
SEQUENCE: 331
XICSRSLPPI CIPD                                                     14

SEQ ID NO: 332          moltype = AA  length = 14
FEATURE                 Location/Qualifiers
REGION                  1..14
                        note = Synthetic Construct
MOD_RES                 1
                        note = Xaa is Tranexamic acid
DISULFID                3..11
                        note = disulfide bond
MOD_RES                 7
                        note = Xaa is L-tert-Butylalanine
MOD_RES                 11
                        note = Xaa is L-N-Methylcysteine
MOD_RES                 14
                        note = AMIDATION
source                  1..14
                        mol_type = protein
                        organism = synthetic construct
SEQUENCE: 332
XICSRSXPPI XIPD                                                     14

SEQ ID NO: 333          moltype = AA  length = 15
FEATURE                 Location/Qualifiers
REGION                  1..15
                        note = Synthetic Construct
MOD_RES                 1
                        note = Xaa is 9-Amino-4,7-dioxanonanoic acid
DISULFID                4..12
                        note = disulfide bond
MOD_RES                 8
                        note = Xaa is L-tert-Butylalanine
MOD_RES                 12
                        note = Xaa is L-Penicillamine
MOD_RES                 15
                        note = AMIDATION
source                  1..15
                        mol_type = protein
```

```
                        organism = synthetic construct
SEQUENCE: 333
XAICSRSXPP IXIPD                                                   15

SEQ ID NO: 334          moltype = AA  length = 14
FEATURE                 Location/Qualifiers
REGION                  1..14
                        note = Synthetic Construct
MOD_RES                 1
                        note = MeGly
DISULFID                3..11
                        note = disulfide bond
MOD_RES                 7
                        note = Xaa is L-2-Amino-4-cyanobutyric acid
MOD_RES                 11
                        note = Xaa is L-Penicillamine
MOD_RES                 14
                        note = AMIDATION
source                  1..14
                        mol_type = protein
                        organism = synthetic construct
SEQUENCE: 334
XICSRSXPPI XIPD                                                    14

SEQ ID NO: 335          moltype = AA  length = 14
FEATURE                 Location/Qualifiers
REGION                  1..14
                        note = Synthetic Construct
MOD_RES                 1
                        note = Xaa is L-tert-Butylalanine
DISULFID                4..12
                        note = disulfide bond
MOD_RES                 10
                        note = Xaa is
                         2,3,3a,4,5,6,7,7a-Octahydroindole-2-carboxylic acid
MOD_RES                 12
                        note = Xaa is L-Penicillamine
MOD_RES                 14
                        note = AMIDATION
source                  1..14
                        mol_type = protein
                        organism = synthetic construct
SEQUENCE: 335
XGICSRSLPX IXIP                                                    14

SEQ ID NO: 336          moltype = AA  length = 14
FEATURE                 Location/Qualifiers
REGION                  1..14
                        note = Synthetic Construct
DISULFID                3..11
                        note = disulfide bond
MOD_RES                 9
                        note = Xaa is
                         2,3,3a,4,5,6,7,7a-Octahydroindole-2-carboxylic acid
source                  1..14
                        mol_type = protein
                        organism = synthetic construct
SEQUENCE: 336
GICSRSLPXI CIPD                                                    14

SEQ ID NO: 337          moltype = AA  length = 14
FEATURE                 Location/Qualifiers
REGION                  1..14
                        note = Synthetic Construct
MOD_RES                 1
                        note = MeGly
DISULFID                3..11
                        note = disulfide bond
MOD_RES                 9
                        note = Xaa is
                         (1R,3S,5R)-2-Azabicyclo[3.1.0]hexane-3-carboxylic acid
source                  1..14
                        mol_type = protein
                        organism = synthetic construct
SEQUENCE: 337
XICSRSLPXI CIPD                                                    14

SEQ ID NO: 338          moltype = AA  length = 14
FEATURE                 Location/Qualifiers
```

-continued

```
REGION                  1..14
                        note = Synthetic Construct
MOD_RES                 1
                        note = MeGly
DISULFID                3..11
                        note = disulfide bond
MOD_RES                 12
                        note = Xaa is L-Phenylglycine
source                  1..14
                        mol_type = protein
                        organism = synthetic construct
SEQUENCE: 338
XICSRSLPPI CXPD                                                     14

SEQ ID NO: 339          moltype = AA  length = 14
FEATURE                 Location/Qualifiers
REGION                  1..14
                        note = Synthetic Construct
DISULFID                3..11
                        note = disulfide bond
MOD_RES                 9
                        note = Xaa is 3,3-dimethyl-1,3-azasilolidine-5-carboxylic
                         acid
MOD_RES                 14
                        note = AMIDATION
source                  1..14
                        mol_type = protein
                        organism = synthetic construct
SEQUENCE: 339
AICSRSLPXI CIPD                                                     14

SEQ ID NO: 340          moltype = AA  length = 14
FEATURE                 Location/Qualifiers
REGION                  1..14
                        note = Synthetic Construct
MOD_RES                 1
                        note = Xaa is 3-Methoxypropionic acid
DISULFID                3..11
                        note = disulfide bond
MOD_RES                 7
                        note = Xaa is L-tert-Butylalanine
MOD_RES                 11
                        note = Xaa is L-Penicillamine
MOD_RES                 14
                        note = AMIDATION
source                  1..14
                        mol_type = protein
                        organism = synthetic construct
SEQUENCE: 340
XICSRSXPPI XIPD                                                     14

SEQ ID NO: 341          moltype = AA  length = 14
FEATURE                 Location/Qualifiers
REGION                  1..14
                        note = Synthetic Construct
MOD_RES                 1
                        note = Xaa is (1S,2S,4S)-Bicyclo[2.2.1]hept-5-en-2-ylacetic
                         acid
DISULFID                3..11
                        note = disulfide bond
MOD_RES                 7
                        note = Xaa is L-tert-Butylalanine
MOD_RES                 11
                        note = Xaa is L-Penicillamine
MOD_RES                 14
                        note = AMIDATION
source                  1..14
                        mol_type = protein
                        organism = synthetic construct
SEQUENCE: 341
XICSRSXPPI XIPD                                                     14

SEQ ID NO: 342          moltype = AA  length = 14
FEATURE                 Location/Qualifiers
REGION                  1..14
                        note = Synthetic Construct
MOD_RES                 1
                        note = MeGly
DISULFID                3..11
```

```
                        note = disulfide bond
MOD_RES                 13
                        note = MeGly
source                  1..14
                        mol_type = protein
                        organism = synthetic construct
SEQUENCE: 342
XICSRSLPPI CIXD                                                            14

SEQ ID NO: 343          moltype = AA  length = 14
FEATURE                 Location/Qualifiers
REGION                  1..14
                        note = Synthetic Construct
MOD_RES                 1
                        note = Xaa is L-3-Bromophenylalanine
DISULFID                3..11
                        note = disulfide bond
MOD_RES                 7
                        note = Xaa is L-tert-Butylalanine
MOD_RES                 11
                        note = Xaa is L-Penicillamine
MOD_RES                 14
                        note = AMIDATION
source                  1..14
                        mol_type = protein
                        organism = synthetic construct
SEQUENCE: 343
XICSRSXPPI XIPD                                                            14

SEQ ID NO: 344          moltype = AA  length = 14
FEATURE                 Location/Qualifiers
REGION                  1..14
                        note = Synthetic Construct
MOD_RES                 2
                        note = aIle
DISULFID                3..11
                        note = disulfide bond
MOD_RES                 14
                        note = AMIDATION
source                  1..14
                        mol_type = protein
                        organism = synthetic construct
SEQUENCE: 344
AXCSRSLPPI CIPD                                                            14

SEQ ID NO: 345          moltype = AA  length = 14
FEATURE                 Location/Qualifiers
REGION                  1..14
                        note = Synthetic Construct
MOD_RES                 1
                        note = Acp
DISULFID                3..11
                        note = disulfide bond
MOD_RES                 7
                        note = Xaa is L-tert-Butylalanine
MOD_RES                 11
                        note = Xaa is L-N-Methylcysteine
MOD_RES                 14
                        note = AMIDATION
source                  1..14
                        mol_type = protein
                        organism = synthetic construct
SEQUENCE: 345
XICSRSXPPI XIPD                                                            14

SEQ ID NO: 346          moltype = AA  length = 12
FEATURE                 Location/Qualifiers
REGION                  1..12
                        note = Synthetic Construct
MOD_RES                 1
                        note = Xaa is tert-Butylacetic acid
DISULFID                3..11
                        note = disulfide bond
MOD_RES                 7
                        note = Xaa is L-tert-Butylalanine
MOD_RES                 11
                        note = Xaa is L-N-Methylcysteine
MOD_RES                 12
                        note = AMIDATION
```

```
source                  1..12
                        mol_type = protein
                        organism = synthetic construct
SEQUENCE: 346
XICSRSXPPI XI                                                             12

SEQ ID NO: 347          moltype = AA  length = 14
FEATURE                 Location/Qualifiers
REGION                  1..14
                        note = Synthetic Construct
MOD_RES                 1
                        note = Xaa is Cyclopentanecarboxylic acid
DISULFID                3..11
                        note = disulfide bond
MOD_RES                 7
                        note = Xaa is L-tert-Butylalanine
MOD_RES                 11
                        note = Xaa is L-Penicillamine
MOD_RES                 14
                        note = AMIDATION
source                  1..14
                        mol_type = protein
                        organism = synthetic construct
SEQUENCE: 347
XICSRSXPPI XIPD                                                           14

SEQ ID NO: 348          moltype = AA  length = 13
FEATURE                 Location/Qualifiers
REGION                  1..13
                        note = Synthetic Construct
MOD_RES                 1
                        note = Xaa is L-tert-Butylalanine
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
source                  1..13
                        mol_type = protein
                        organism = synthetic construct
SEQUENCE: 348
XICSRSLPXI XIP                                                            13

SEQ ID NO: 349          moltype = AA  length = 12
FEATURE                 Location/Qualifiers
REGION                  1..12
                        note = Synthetic Construct
DISULFID                2..10
                        note = disulfide bond
MOD_RES                 8
                        note = Xaa is
                         2,3,3a,4,5,6,7,7a-Octahydroindole-2-carboxylic acid
MOD_RES                 10
                        note = Xaa is L-Penicillamine
MOD_RES                 12
                        note = AMIDATION
source                  1..12
                        mol_type = protein
                        organism = synthetic construct
SEQUENCE: 349
ICSRSLPXIX IP                                                             12

SEQ ID NO: 350          moltype = AA  length = 14
FEATURE                 Location/Qualifiers
REGION                  1..14
                        note = Synthetic Construct
DISULFID                3..11
                        note = disulfide bond
MOD_RES                 7
                        note = Xaa is (2S)-2-Amino-4,4,4-trifluorobutanoic acid
MOD_RES                 11
                        note = Xaa is L-N-Methylcysteine
MOD_RES                 14
                        note = AMIDATION
source                  1..14
                        mol_type = protein
                        organism = synthetic construct
```

-continued

```
SEQUENCE: 350
AICSRSXPPI XIPD                                                   14

SEQ ID NO: 351          moltype = AA  length = 13
FEATURE                 Location/Qualifiers
REGION                  1..13
                        note = Synthetic Construct
MOD_RES                 1
                        note = Xaa is
                         (2S,3S)-2-[(3R)-3-Amino-2-oxopyrrolidin-1-yl]-3-
                         methylpentanoic acid
DISULFID                2..10
                        note = disulfide bond
source                  1..13
                        mol_type = protein
                        organism = synthetic construct
SEQUENCE: 351
XCSRSLPPIC IAD                                                    13

SEQ ID NO: 352          moltype = AA  length = 14
FEATURE                 Location/Qualifiers
REGION                  1..14
                        note = Synthetic Construct
MOD_RES                 1
                        note = MeGly
DISULFID                3..11
                        note = disulfide bond
source                  1..14
                        mol_type = protein
                        organism = synthetic construct
SEQUENCE: 352
XICSRSLPPI CIPE                                                   14

SEQ ID NO: 353          moltype = AA  length = 14
FEATURE                 Location/Qualifiers
REGION                  1..14
                        note = Synthetic Construct
MOD_RES                 1
                        note = MeGly
MOD_RES                 2
                        note = MeIle
DISULFID                3..11
                        note = disulfide bond
MOD_RES                 14
                        note = AMIDATION
source                  1..14
                        mol_type = protein
                        organism = synthetic construct
SEQUENCE: 353
XXCSRSLPPI CIPD                                                   14

SEQ ID NO: 354          moltype = AA  length = 11
FEATURE                 Location/Qualifiers
REGION                  1..11
                        note = Synthetic Construct
DISULFID                2..10
                        note = disulfide bond
MOD_RES                 8
                        note = Xaa is
                         2,3,3a,4,5,6,7,7a-Octahydroindole-2-carboxylic acid
MOD_RES                 10
                        note = Xaa is L-Penicillamine
MOD_RES                 11
                        note = AMIDATION
source                  1..11
                        mol_type = protein
                        organism = synthetic construct
SEQUENCE: 354
ICSRSLPXIX I                                                      11

SEQ ID NO: 355          moltype = AA  length = 14
FEATURE                 Location/Qualifiers
REGION                  1..14
                        note = Synthetic Construct
MOD_RES                 1
                        note = Xaa is Tetrahydropyranyl-4-acetic acid
DISULFID                3..11
                        note = disulfide bond
MOD_RES                 7
```

```
                          note = Xaa is L-tert-Butylalanine
MOD_RES                   14
                          note = AMIDATION
source                    1..14
                          mol_type = protein
                          organism = synthetic construct
SEQUENCE: 355
XICSRSXPPI CIPD                                                    14

SEQ ID NO: 356            moltype = AA  length = 14
FEATURE                   Location/Qualifiers
REGION                    1..14
                          note = Synthetic Construct
MOD_RES                   1
                          note = Xaa is Cyclopentylacetic acid
DISULFID                  3..11
                          note = disulfide bond
MOD_RES                   7
                          note = Xaa is L-tert-Butylalanine
MOD_RES                   11
                          note = Xaa is L-Penicillamine
MOD_RES                   14
                          note = AMIDATION
source                    1..14
                          mol_type = protein
                          organism = synthetic construct
SEQUENCE: 356
XICSRSXPPI XIPD                                                    14

SEQ ID NO: 357            moltype = AA  length = 14
FEATURE                   Location/Qualifiers
REGION                    1..14
                          note = Synthetic Construct
DISULFID                  3..11
                          note = disulfide bond
MOD_RES                   7
                          note = Xaa is 2-Amino-7-(tert-butoxy)-7-oxoheptanoic acid
MOD_RES                   11
                          note = Xaa is L-Penicillamine
MOD_RES                   14
                          note = AMIDATION
source                    1..14
                          mol_type = protein
                          organism = synthetic construct
SEQUENCE: 357
AICSRSXPPI XIPD                                                    14

SEQ ID NO: 358            moltype = AA  length = 11
FEATURE                   Location/Qualifiers
REGION                    1..11
                          note = Synthetic Construct
DISULFID                  2..10
                          note = disulfide bond
MOD_RES                   6
                          note = Xaa is L-tert-Butylalanine
MOD_RES                   10
                          note = Xaa is L-Penicillamine
MOD_RES                   11
                          note = AMIDATION
source                    1..11
                          mol_type = protein
                          organism = synthetic construct
SEQUENCE: 358
ICSRSXPPIX I                                                       11

SEQ ID NO: 359            moltype = AA  length = 14
FEATURE                   Location/Qualifiers
REGION                    1..14
                          note = Synthetic Construct
DISULFID                  3..11
                          note = disulfide bond
MOD_RES                   10
                          note = aIle
MOD_RES                   14
                          note = AMIDATION
source                    1..14
                          mol_type = protein
                          organism = synthetic construct
SEQUENCE: 359
```

```
AICSRSLPPX CIPD                                                      14

SEQ ID NO: 360          moltype = AA  length = 13
FEATURE                 Location/Qualifiers
REGION                  1..13
                        note = Synthetic Construct
DISULFID                2..10
                        note = disulfide bond
MOD_RES                 8
                        note = Xaa is
                         2,3,3a,4,5,6,7,7a-Octahydroindole-2-carboxylic acid
MOD_RES                 10
                        note = Xaa is L-Penicillamine
source                  1..13
                        mol_type = protein
                        organism = synthetic construct
SEQUENCE: 360
ICSRSLPXIX IPD                                                       13

SEQ ID NO: 361          moltype = AA  length = 14
FEATURE                 Location/Qualifiers
REGION                  1..14
                        note = Synthetic Construct
DISULFID                3..11
                        note = disulfide bond
MOD_RES                 13
                        note = Xaa is Hydroxyproline
source                  1..14
                        mol_type = protein
                        organism = synthetic construct
SEQUENCE: 361
GICSRSLPPI CIXD                                                      14

SEQ ID NO: 362          moltype = AA  length = 14
FEATURE                 Location/Qualifiers
REGION                  1..14
                        note = Synthetic Construct
MOD_RES                 1
                        note = MeGly
DISULFID                3..11
                        note = disulfide bond
MOD_RES                 9
                        note = Xaa is
                         2,3,3a,4,5,6,7,7a-Octahydroindole-2-carboxylic acid
source                  1..14
                        mol_type = protein
                        organism = synthetic construct
SEQUENCE: 362
XICSRSLPXI CIPD                                                      14

SEQ ID NO: 363          moltype = AA  length = 14
FEATURE                 Location/Qualifiers
REGION                  1..14
                        note = Synthetic Construct
MOD_RES                 1
                        note = Xaa is N,N-Dimethylglycine
DISULFID                3..11
                        note = disulfide bond
MOD_RES                 14
                        note = AMIDATION
source                  1..14
                        mol_type = protein
                        organism = synthetic construct
SEQUENCE: 363
XICSRSLPPI CIPD                                                      14

SEQ ID NO: 364          moltype = AA  length = 14
FEATURE                 Location/Qualifiers
REGION                  1..14
                        note = Synthetic Construct
MOD_RES                 1
                        note = Xaa is 2-(Cyclobutyl)acetic acid
DISULFID                3..11
                        note = disulfide bond
MOD_RES                 7
                        note = Xaa is L-tert-Butylalanine
MOD_RES                 11
                        note = Xaa is L-Penicillamine
MOD_RES                 14
```

-continued

```
                        note = AMIDATION
source                  1..14
                        mol_type = protein
                        organism = synthetic construct
SEQUENCE: 364
XICSRSXPPI XIPD                                                           14

SEQ ID NO: 365          moltype = AA  length = 15
FEATURE                 Location/Qualifiers
REGION                  1..15
                        note = Synthetic Construct
MOD_RES                 1
                        note = Xaa is Acp
SITE                    1
                        note = Modified by D-(+)Biotin
DISULFID                4..12
                        note = disulfide bond
MOD_RES                 8
                        note = Xaa is L-tert-Butylalanine
MOD_RES                 12
                        note = Xaa is L-Penicillamine
source                  1..15
                        mol_type = protein
                        organism = synthetic construct
SEQUENCE: 365
XAICSRSXPP IXIPD                                                          15

SEQ ID NO: 366          moltype = AA  length = 12
FEATURE                 Location/Qualifiers
REGION                  1..12
                        note = Synthetic Construct
MOD_RES                 1
                        note = Xaa is Cyclopropanecarboxylic acid
DISULFID                3..11
                        note = disulfide bond
MOD_RES                 7
                        note = Xaa is L-tert-Butylalanine
MOD_RES                 11
                        note = Xaa is L-N-Methylcysteine
MOD_RES                 12
                        note = AMIDATION
source                  1..12
                        mol_type = protein
                        organism = synthetic construct
SEQUENCE: 366
XICSRSXPPI XI                                                             12

SEQ ID NO: 367          moltype = AA  length = 14
FEATURE                 Location/Qualifiers
REGION                  1..14
                        note = Synthetic Construct
MOD_RES                 1
                        note = MeGly
DISULFID                3..11
                        note = disulfide bond
MOD_RES                 8
                        note = Xaa is trans-4-Fluoroproline
source                  1..14
                        mol_type = protein
                        organism = synthetic construct
SEQUENCE: 367
XICSRSLXPI CIPD                                                           14

SEQ ID NO: 368          moltype = AA  length = 14
FEATURE                 Location/Qualifiers
REGION                  1..14
                        note = Synthetic Construct
DISULFID                3..11
                        note = disulfide bond
MOD_RES                 9
                        note = Xaa is L-trans-3-Hydroxyproline
MOD_RES                 14
                        note = AMIDATION
source                  1..14
                        mol_type = protein
                        organism = synthetic construct
SEQUENCE: 368
AICSRSLPXI CIPD                                                           14
```

```
SEQ ID NO: 369          moltype = AA  length = 14
FEATURE                 Location/Qualifiers
REGION                  1..14
                        note = Synthetic Construct
MOD_RES                 1
                        note = Xaa is (S)-3-Methylvaleric Acid
DISULFID                3..11
                        note = disulfide bond
MOD_RES                 7
                        note = Xaa is L-tert-Butylalanine
MOD_RES                 11
                        note = Xaa is L-Penicillamine
MOD_RES                 14
                        note = AMIDATION
source                  1..14
                        mol_type = protein
                        organism = synthetic construct
SEQUENCE: 369
XICSRSXPPI XIPD                                                 14

SEQ ID NO: 370          moltype = AA  length = 14
FEATURE                 Location/Qualifiers
REGION                  1..14
                        note = Synthetic Construct
DISULFID                3..11
                        note = disulfide bond
MOD_RES                 8
                        note = Xaa is (3S)-Morpholine-3-carboxylic acid
source                  1..14
                        mol_type = protein
                        organism = synthetic construct
SEQUENCE: 370
GICSRSLXPI CIPD                                                 14

SEQ ID NO: 371          moltype = AA  length = 12
FEATURE                 Location/Qualifiers
REGION                  1..12
                        note = Synthetic Construct
MOD_RES                 1
                        note = Xaa is Isovaleric acid
DISULFID                3..11
                        note = disulfide bond
MOD_RES                 7
                        note = Xaa is L-tert-Butylalanine
MOD_RES                 11
                        note = Xaa is L-N-Methylcysteine
MOD_RES                 12
                        note = AMIDATION
source                  1..12
                        mol_type = protein
                        organism = synthetic construct
SEQUENCE: 371
XICSRSXPPI XI                                                   12

SEQ ID NO: 372          moltype = AA  length = 13
FEATURE                 Location/Qualifiers
REGION                  1..13
                        note = Synthetic Construct
MOD_RES                 1
                        note = Xaa is tert-Butylacetic acid
DISULFID                3..11
                        note = disulfide bond
MOD_RES                 7
                        note = Xaa is L-tert-Butylalanine
MOD_RES                 11
                        note = Xaa is L-Penicillamine
MOD_RES                 13
                        note = AMIDATION
source                  1..13
                        mol_type = protein
                        organism = synthetic construct
SEQUENCE: 372
XICSRSXPPI XIP                                                  13

SEQ ID NO: 373          moltype = AA  length = 13
FEATURE                 Location/Qualifiers
REGION                  1..13
                        note = Synthetic Construct
MOD_RES                 1
```

```
                        note = Xaa is
                         4-(3,5-Dimethyl-1,2-oxazol-4-yl)-L-phenylalanine
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
MOD_RES                 13
                        note = AMIDATION
source                  1..13
                        mol_type = protein
                        organism = synthetic construct
SEQUENCE: 373
XICSRSLPXI XIP                                                  13

SEQ ID NO: 374          moltype = AA  length = 14
FEATURE                 Location/Qualifiers
REGION                  1..14
                        note = Synthetic Construct
MOD_RES                 1
                        note = MeGly
DISULFID                4..12
                        note = disulfide bond
MOD_RES                 8
                        note = Xaa is L-tert-Butylalanine
MOD_RES                 12
                        note = Xaa is L-Penicillamine
MOD_RES                 14
                        note = AMIDATION
source                  1..14
                        mol_type = protein
                        organism = synthetic construct
SEQUENCE: 374
XPICSRSXPP IXIP                                                 14

SEQ ID NO: 375          moltype = AA  length = 14
FEATURE                 Location/Qualifiers
REGION                  1..14
                        note = Synthetic Construct
MOD_RES                 1
                        note = Xaa is 4-(Aminomethyl)benzoic acid
DISULFID                3..11
                        note = disulfide bond
MOD_RES                 11
                        note = Xaa is L-N-Methylcysteine
MOD_RES                 14
                        note = AMIDATION
source                  1..14
                        mol_type = protein
                        organism = synthetic construct
SEQUENCE: 375
XICSRSLPPI XIPD                                                 14

SEQ ID NO: 376          moltype = AA  length = 15
FEATURE                 Location/Qualifiers
REGION                  1..15
                        note = Synthetic Construct
MOD_RES                 1
                        note = Xaa is Acp
SITE                    1
                        note = Modified by D-(+)Biotin
DISULFID                4..12
                        note = disulfide bond
MOD_RES                 8
                        note = Xaa is L-tert-Butylalanine
MOD_RES                 12
                        note = Xaa is L-Penicillamine
MOD_RES                 15
                        note = AMIDATION
source                  1..15
                        mol_type = protein
                        organism = synthetic construct
SEQUENCE: 376
XAICSRSXPP IXIPD                                                15

SEQ ID NO: 377          moltype = AA  length = 14
FEATURE                 Location/Qualifiers
```

```
REGION                  1..14
                        note = Synthetic Construct
MOD_RES                 1
                        note = Xaa is Tranexamic acid
DISULFID                3..11
                        note = disulfide bond
MOD_RES                 11
                        note = Xaa is L-N-Methylcysteine
MOD_RES                 14
                        note = AMIDATION
source                  1..14
                        mol_type = protein
                        organism = synthetic construct
SEQUENCE: 377
XICSRSLPPI XIPD                                                        14

SEQ ID NO: 378          moltype = AA  length = 14
FEATURE                 Location/Qualifiers
REGION                  1..14
                        note = Synthetic Construct
MOD_RES                 1
                        note = Xaa is 4-Methylpentanoic acid
DISULFID                3..11
                        note = disulfide bond
MOD_RES                 7
                        note = Xaa is L-tert-Butylalanine
MOD_RES                 11
                        note = Xaa is L-Penicillamine
MOD_RES                 14
                        note = AMIDATION
source                  1..14
                        mol_type = protein
                        organism = synthetic construct
SEQUENCE: 378
XICSRSXPPI XIPD                                                        14

SEQ ID NO: 379          moltype = AA  length = 14
FEATURE                 Location/Qualifiers
REGION                  1..14
                        note = Synthetic Construct
MOD_RES                 1
                        note = Xaa is 5-Chlorothiophene-2-carboxylic acid
DISULFID                3..11
                        note = disulfide bond
MOD_RES                 7
                        note = Xaa is L-tert-Butylalanine
MOD_RES                 11
                        note = Xaa is L-Penicillamine
MOD_RES                 14
                        note = AMIDATION
source                  1..14
                        mol_type = protein
                        organism = synthetic construct
SEQUENCE: 379
XICSRSXPPI XIPD                                                        14

SEQ ID NO: 380          moltype = AA  length = 14
FEATURE                 Location/Qualifiers
REGION                  1..14
                        note = Synthetic Construct
MOD_RES                 1
                        note = MeGly
DISULFID                3..11
                        note = disulfide bond
MOD_RES                 13
                        note = Xaa is
                         2,3,3a,4,5,6,7,7a-Octahydroindole-2-carboxylic acid
source                  1..14
                        mol_type = protein
                        organism = synthetic construct
SEQUENCE: 380
XICSRSLPPI CIXD                                                        14

SEQ ID NO: 381          moltype = AA  length = 11
FEATURE                 Location/Qualifiers
REGION                  1..11
                        note = Synthetic Construct
DISULFID                2..10
                        note = disulfide bond
```

```
MOD_RES                 8
                        note = Xaa is
                         2,3,3a,4,5,6,7,7a-Octahydroindole-2-carboxylic acid
MOD_RES                 10
                        note = Xaa is L-Penicillamine
source                  1..11
                        mol_type = protein
                        organism = synthetic construct
SEQUENCE: 381
ICSRSLPXIX I                                                             11

SEQ ID NO: 382          moltype = AA  length = 13
FEATURE                 Location/Qualifiers
REGION                  1..13
                        note = Synthetic Construct
DISULFID                2..10
                        note = disulfide bond
MOD_RES                 8
                        note = Xaa is
                         2,3,3a,4,5,6,7,7a-Octahydroindole-2-carboxylic acid
MOD_RES                 10
                        note = Xaa is L-Penicillamine
source                  1..13
                        mol_type = protein
                        organism = synthetic construct
SEQUENCE: 382
ICSRSLPXIX IPE                                                           13

SEQ ID NO: 383          moltype = AA  length = 13
FEATURE                 Location/Qualifiers
REGION                  1..13
                        note = Synthetic Construct
SITE                    1
                        note = Xaa is D-Phenylalanine
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
MOD_RES                 13
                        note = AMIDATION
source                  1..13
                        mol_type = protein
                        organism = synthetic construct
SEQUENCE: 383
XICSRSLPXI XIP                                                           13

SEQ ID NO: 384          moltype = AA  length = 13
FEATURE                 Location/Qualifiers
REGION                  1..13
                        note = Synthetic Construct
DISULFID                4..12
                        note = disulfide bond
MOD_RES                 8
                        note = Xaa is L-tert-Butylalanine
MOD_RES                 12
                        note = Xaa is L-Penicillamine
MOD_RES                 13
                        note = AMIDATION
source                  1..13
                        mol_type = protein
                        organism = synthetic construct
SEQUENCE: 384
PPICSRSXPP IXI                                                           13

SEQ ID NO: 385          moltype = AA  length = 13
FEATURE                 Location/Qualifiers
REGION                  1..13
                        note = Synthetic Construct
DISULFID                2..10
                        note = disulfide bond
MOD_RES                 8
                        note = Xaa is
                         2,3,3a,4,5,6,7,7a-Octahydroindole-2-carboxylic acid
MOD_RES                 10
                        note = Xaa is L-Penicillamine
MOD_RES                 13
```

```
                     note = AMIDATION
source               1..13
                     mol_type = protein
                     organism = synthetic construct
SEQUENCE: 385
ICSRSLPXIX IPE                                                          13

SEQ ID NO: 386       moltype = AA  length = 14
FEATURE              Location/Qualifiers
REGION               1..14
                     note = Synthetic Construct
MOD_RES              1
                     note = Aib
DISULFID             3..11
                     note = disulfide bond
MOD_RES              14
                     note = AMIDATION
source               1..14
                     mol_type = protein
                     organism = synthetic construct
SEQUENCE: 386
XICSRSLPPI CIPD                                                         14

SEQ ID NO: 387       moltype = AA  length = 14
FEATURE              Location/Qualifiers
REGION               1..14
                     note = Synthetic Construct
DISULFID             3..11
                     note = disulfide bond
MOD_RES              12
                     note = Xaa is 2-Methyl-D-alloisoleucine
MOD_RES              14
                     note = AMIDATION
source               1..14
                     mol_type = protein
                     organism = synthetic construct
SEQUENCE: 387
AICSRSLPPI CXPD                                                         14

SEQ ID NO: 388       moltype = AA  length = 14
FEATURE              Location/Qualifiers
REGION               1..14
                     note = Synthetic Construct
MOD_RES              1
                     note = Xaa is 4-Methylpentanoic acid
DISULFID             3..11
                     note = disulfide bond
MOD_RES              7
                     note = Xaa is L-tert-Butylalanine
MOD_RES              11
                     note = Xaa is L-Penicillamine
source               1..14
                     mol_type = protein
                     organism = synthetic construct
SEQUENCE: 388
XICSRSXPPI XIPD                                                         14

SEQ ID NO: 389       moltype = AA  length = 13
FEATURE              Location/Qualifiers
REGION               1..13
                     note = Synthetic Construct
MOD_RES              1
                     note = MeGly
DISULFID             3..11
                     note = disulfide bond
MOD_RES              9
                     note = Xaa is
                      2,3,3a,4,5,6,7,7a-Octahydroindole-2-carboxylic acid
MOD_RES              11
                     note = Xaa is L-Penicillamine
MOD_RES              13
                     note = AMIDATION
source               1..13
                     mol_type = protein
                     organism = synthetic construct
SEQUENCE: 389
XICSRSLPXI XIP                                                          13

SEQ ID NO: 390       moltype = AA  length = 13
```

```
FEATURE                Location/Qualifiers
REGION                 1..13
                       note = Synthetic Construct
DISULFID               2..10
                       note = disulfide bond
MOD_RES                8
                       note = Xaa is
                        2,3,3a,4,5,6,7,7a-Octahydroindole-2-carboxylic acid
MOD_RES                10
                       note = Xaa is L-Penicillamine
MOD_RES                13
                       note = AMIDATION
source                 1..13
                       mol_type = protein
                       organism = synthetic construct
SEQUENCE: 390
ICSRSLPXIX IPQ                                                     13

SEQ ID NO: 391         moltype = AA  length = 14
FEATURE                Location/Qualifiers
REGION                 1..14
                       note = Synthetic Construct
DISULFID               4..12
                       note = disulfide bond
MOD_RES                8
                       note = Xaa is L-tert-Butylalanine
MOD_RES                12
                       note = Xaa is L-Penicillamine
MOD_RES                14
                       note = AMIDATION
source                 1..14
                       mol_type = protein
                       organism = synthetic construct
SEQUENCE: 391
PPICSRSXPP IXIP                                                    14

SEQ ID NO: 392         moltype = AA  length = 12
FEATURE                Location/Qualifiers
REGION                 1..12
                       note = Synthetic Construct
MOD_RES                1
                       note = MeIle
DISULFID               2..10
                       note = disulfide bond
MOD_RES                6
                       note = Xaa is L-tert-Butylalanine
MOD_RES                10
                       note = Xaa is L-Penicillamine
MOD_RES                12
                       note = AMIDATION
source                 1..12
                       mol_type = protein
                       organism = synthetic construct
SEQUENCE: 392
XCSRSXPPIX IP                                                      12

SEQ ID NO: 393         moltype = AA  length = 14
FEATURE                Location/Qualifiers
REGION                 1..14
                       note = Synthetic Construct
DISULFID               3..11
                       note = disulfide bond
MOD_RES                8
                       note = Xaa is Hydroxyproline
source                 1..14
                       mol_type = protein
                       organism = synthetic construct
SEQUENCE: 393
GICSRSLXPI CIPD                                                    14

SEQ ID NO: 394         moltype = AA  length = 16
FEATURE                Location/Qualifiers
REGION                 1..16
                       note = Synthetic Construct
MOD_RES                1
                       note = MeGly
MOD_RES                2
                       note = Orn
MOD_RES                3
```

```
                         note = Orn
MOD_RES                  4
                         note = Orn
DISULFID                 6..14
                         note = disulfide bond
MOD_RES                  10
                         note = Xaa is L-tert-Butylalanine
MOD_RES                  14
                         note = Xaa is L-Penicillamine
MOD_RES                  16
                         note = AMIDATION
source                   1..16
                         mol_type = protein
                         organism = synthetic construct
SEQUENCE: 394
XXXXICSRSX PPIXIP                                                          16

SEQ ID NO: 395           moltype = AA  length = 12
FEATURE                  Location/Qualifiers
REGION                   1..12
                         note = Synthetic Construct
MOD_RES                  1
                         note = Xaa is 2-(Cyclobutyl)acetic acid
DISULFID                 3..11
                         note = disulfide bond
MOD_RES                  7
                         note = Xaa is L-tert-Butylalanine
MOD_RES                  11
                         note = Xaa is L-N-Methylcysteine
MOD_RES                  12
                         note = AMIDATION
source                   1..12
                         mol_type = protein
                         organism = synthetic construct
SEQUENCE: 395
XICSRSXPPI XI                                                              12

SEQ ID NO: 396           moltype = AA  length = 12
FEATURE                  Location/Qualifiers
REGION                   1..12
                         note = Synthetic Construct
MOD_RES                  1
                         note = Acp
DISULFID                 3..11
                         note = disulfide bond
MOD_RES                  9
                         note = Xaa is
                          2,3,3a,4,5,6,7,7a-Octahydroindole-2-carboxylic acid
source                   1..12
                         mol_type = protein
                         organism = synthetic construct
SEQUENCE: 396
XICSRSLPXI CI                                                              12

SEQ ID NO: 397           moltype = AA  length = 14
FEATURE                  Location/Qualifiers
REGION                   1..14
                         note = Synthetic Construct
DISULFID                 3..11
                         note = disulfide bond
MOD_RES                  7
                         note = Xaa is 5,5,5-Trifluoro-DL-leucine
source                   1..14
                         mol_type = protein
                         organism = synthetic construct
SEQUENCE: 397
GICSRSXPPI CIPD                                                            14

SEQ ID NO: 398           moltype = AA  length = 14
FEATURE                  Location/Qualifiers
REGION                   1..14
                         note = Synthetic Construct
MOD_RES                  1
                         note = Xaa is 3-Phenylpropanoic acid
DISULFID                 3..11
                         note = disulfide bond
MOD_RES                  7
                         note = Xaa is L-tert-Butylalanine
MOD_RES                  11
```

```
                        note = Xaa is L-Penicillamine
MOD_RES                 14
                        note = AMIDATION
source                  1..14
                        mol_type = protein
                        organism = synthetic construct
SEQUENCE: 398
XICSRSXPPI XIPD                                                             14

SEQ ID NO: 399          moltype = AA  length = 14
FEATURE                 Location/Qualifiers
REGION                  1..14
                        note = Synthetic Construct
MOD_RES                 1
                        note = MeGly
DISULFID                3..11
                        note = disulfide bond
SITE                    13
                        note = Xaa is D-Proline
source                  1..14
                        mol_type = protein
                        organism = synthetic construct
SEQUENCE: 399
XICSRSLPPI CIXD                                                             14

SEQ ID NO: 400          moltype = AA  length = 14
FEATURE                 Location/Qualifiers
REGION                  1..14
                        note = Synthetic Construct
MOD_RES                 1
                        note = Xaa is L-(+)-Lactic acid
DISULFID                3..11
                        note = disulfide bond
MOD_RES                 7
                        note = Xaa is L-tert-Butylalanine
MOD_RES                 14
                        note = AMIDATION
source                  1..14
                        mol_type = protein
                        organism = synthetic construct
SEQUENCE: 400
XICSRSXPPI CIPD                                                             14

SEQ ID NO: 401          moltype = AA  length = 13
FEATURE                 Location/Qualifiers
REGION                  1..13
                        note = Synthetic Construct
DISULFID                2..10
                        note = disulfide bond
MOD_RES                 8
                        note = Xaa is
                         2,3,3a,4,5,6,7,7a-Octahydroindole-2-carboxylic acid
MOD_RES                 10
                        note = Xaa is L-Penicillamine
source                  1..13
                        mol_type = protein
                        organism = synthetic construct
SEQUENCE: 401
ICSRSLPXIX IPQ                                                              13

SEQ ID NO: 402          moltype = AA  length = 14
FEATURE                 Location/Qualifiers
REGION                  1..14
                        note = Synthetic Construct
DISULFID                3..11
                        note = disulfide bond
MOD_RES                 10
                        note = Xaa is L-Cyclobutylglycine
MOD_RES                 14
                        note = AMIDATION
source                  1..14
                        mol_type = protein
                        organism = synthetic construct
SEQUENCE: 402
AICSRSLPPX CIPD                                                             14

SEQ ID NO: 403          moltype = AA  length = 14
FEATURE                 Location/Qualifiers
REGION                  1..14
```

```
                        note = Synthetic Construct
MOD_RES                 1
                        note = MeGly
DISULFID                3..11
                        note = disulfide bond
MOD_RES                 9
                        note = Xaa is trans-4-Fluoroproline
source                  1..14
                        mol_type = protein
                        organism = synthetic construct
SEQUENCE: 403
XICSRSLPXI CIPD                                                       14

SEQ ID NO: 404          moltype = AA  length = 14
FEATURE                 Location/Qualifiers
REGION                  1..14
                        note = Synthetic Construct
MOD_RES                 1
                        note = Xaa is Cyclohexanecarboxylic acid
DISULFID                3..11
                        note = disulfide bond
MOD_RES                 7
                        note = Xaa is L-tert-Butylalanine
MOD_RES                 11
                        note = Xaa is L-N-Methylcysteine
MOD_RES                 14
                        note = AMIDATION
source                  1..14
                        mol_type = protein
                        organism = synthetic construct
SEQUENCE: 404
XICSRSXPPI XIPD                                                       14

SEQ ID NO: 405          moltype = AA  length = 14
FEATURE                 Location/Qualifiers
REGION                  1..14
                        note = Synthetic Construct
MOD_RES                 1
                        note = Xaa is 2-Hydroxyisobutyric acid
DISULFID                3..11
                        note = disulfide bond
MOD_RES                 7
                        note = Xaa is L-tert-Butylalanine
MOD_RES                 14
                        note = AMIDATION
source                  1..14
                        mol_type = protein
                        organism = synthetic construct
SEQUENCE: 405
XICSRSXPPI CIPD                                                       14

SEQ ID NO: 406          moltype = AA  length = 13
FEATURE                 Location/Qualifiers
REGION                  1..13
                        note = Synthetic Construct
MOD_RES                 1
                        note = Xaa is
                         (2S,3S)-2-[(3S)-2-oxopiperazin-1-yl]-3-methylpentanoic acid
DISULFID                2..10
                        note = disulfide bond
source                  1..13
                        mol_type = protein
                        organism = synthetic construct
SEQUENCE: 406
XCSRSLPPIC IAD                                                        13

SEQ ID NO: 407          moltype = AA  length = 14
FEATURE                 Location/Qualifiers
REGION                  1..14
                        note = Synthetic Construct
MOD_RES                 1
                        note = MeGly
DISULFID                3..11
                        note = disulfide bond
source                  1..14
                        mol_type = protein
                        organism = synthetic construct
SEQUENCE: 407
XICSRSLPPI CIPN                                                       14
```

```
SEQ ID NO: 408          moltype = AA  length = 14
FEATURE                 Location/Qualifiers
REGION                  1..14
                        note = Synthetic Construct
MOD_RES                 1
                        note = Xaa is Adipic acid
DISULFID                3..11
                        note = disulfide bond
MOD_RES                 7
                        note = Xaa is L-tert-Butylalanine
MOD_RES                 11
                        note = Xaa is L-Penicillamine
MOD_RES                 14
                        note = AMIDATION
source                  1..14
                        mol_type = protein
                        organism = synthetic construct
SEQUENCE: 408
XICSRSXPPI XIPD                                                             14

SEQ ID NO: 409          moltype = AA  length = 12
FEATURE                 Location/Qualifiers
REGION                  1..12
                        note = Synthetic Construct
MOD_RES                 1
                        note = Xaa is tert-Butylacetic acid
DISULFID                3..11
                        note = disulfide bond
MOD_RES                 7
                        note = Xaa is L-tert-Butylalanine
MOD_RES                 11
                        note = Xaa is L-Penicillamine
MOD_RES                 12
                        note = AMIDATION
source                  1..12
                        mol_type = protein
                        organism = synthetic construct
SEQUENCE: 409
XICSRSXPPI XI                                                               12

SEQ ID NO: 410          moltype = AA  length = 13
FEATURE                 Location/Qualifiers
REGION                  1..13
                        note = Synthetic Construct
MOD_RES                 1
                        note = Xaa is
                         (2S,3S)-2-[2-Oxopiperazin-1-yl]-3-methylpentanoic acid
DISULFID                2..10
                        note = disulfide bond
source                  1..13
                        mol_type = protein
                        organism = synthetic construct
SEQUENCE: 410
XCSRSLPPIC IPD                                                              13

SEQ ID NO: 411          moltype = AA  length = 12
FEATURE                 Location/Qualifiers
REGION                  1..12
                        note = Synthetic Construct
MOD_RES                 1
                        note = Xaa is Pivalic acid
DISULFID                3..11
                        note = disulfide bond
MOD_RES                 7
                        note = Xaa is L-tert-Butylalanine
MOD_RES                 11
                        note = Xaa is L-N-Methylcysteine
MOD_RES                 12
                        note = AMIDATION
source                  1..12
                        mol_type = protein
                        organism = synthetic construct
SEQUENCE: 411
XICSRSXPPI XI                                                               12

SEQ ID NO: 412          moltype = AA  length = 15
FEATURE                 Location/Qualifiers
REGION                  1..15
```

-continued

```
                       note = Synthetic Construct
MOD_RES                1
                       note = Orn
DISULFID               4..12
                       note = disulfide bond
MOD_RES                8
                       note = Xaa is L-tert-Butylalanine
MOD_RES                12
                       note = Xaa is L-N-Methylcysteine
MOD_RES                15
                       note = AMIDATION
source                 1..15
                       mol_type = protein
                       organism = synthetic construct
SEQUENCE: 412
XAICSRSXPP IXIPD                                                15

SEQ ID NO: 413         moltype = AA  length = 14
FEATURE                Location/Qualifiers
REGION                 1..14
                       note = Synthetic Construct
MOD_RES                1
                       note = Xaa is Fumaric acid
DISULFID               3..11
                       note = disulfide bond
MOD_RES                7
                       note = Xaa is L-tert-Butylalanine
MOD_RES                11
                       note = Xaa is L-Penicillamine
MOD_RES                14
                       note = AMIDATION
source                 1..14
                       mol_type = protein
                       organism = synthetic construct
SEQUENCE: 413
XICSRSXPPI XIPD                                                 14

SEQ ID NO: 414         moltype = AA  length = 13
FEATURE                Location/Qualifiers
REGION                 1..13
                       note = Synthetic Construct
DISULFID               3..11
                       note = disulfide bond
MOD_RES                8
                       note = Xaa is L-Pipecolic acid
source                 1..13
                       mol_type = protein
                       organism = synthetic construct
SEQUENCE: 414
GICSRSLXPI CID                                                  13

SEQ ID NO: 415         moltype = AA  length = 14
FEATURE                Location/Qualifiers
REGION                 1..14
                       note = Synthetic Construct
MOD_RES                1
                       note = MeGly
DISULFID               3..11
                       note = disulfide bond
MOD_RES                3
                       note = Xaa is L-Penicillamine
source                 1..14
                       mol_type = protein
                       organism = synthetic construct
SEQUENCE: 415
XIXSRSLPPI CIPD                                                 14

SEQ ID NO: 416         moltype = AA  length = 14
FEATURE                Location/Qualifiers
REGION                 1..14
                       note = Synthetic Construct
DISULFID               3..11
                       note = disulfide bond
MOD_RES                5
                       note = Xaa is N(5)-methyl-L-arginine
MOD_RES                7
                       note = Xaa is L-tert-Butylalanine
MOD_RES                11
                       note = Xaa is L-Penicillamine
```

```
MOD_RES                 14
                        note = AMIDATION
source                  1..14
                        mol_type = protein
                        organism = synthetic construct
SEQUENCE: 416
AICSXSXPPI XIPD                                                           14

SEQ ID NO: 417          moltype = AA  length = 14
FEATURE                 Location/Qualifiers
REGION                  1..14
                        note = Synthetic Construct
MOD_RES                 1
                        note = Xaa is Isobutyric acid
DISULFID                3..11
                        note = disulfide bond
MOD_RES                 7
                        note = Xaa is L-tert-Butylalanine
MOD_RES                 11
                        note = Xaa is L-N-Methylcysteine
MOD_RES                 14
                        note = AMIDATION
source                  1..14
                        mol_type = protein
                        organism = synthetic construct
SEQUENCE: 417
XICSRSXPPI XIPD                                                           14

SEQ ID NO: 418          moltype = AA  length = 16
FEATURE                 Location/Qualifiers
REGION                  1..16
                        note = Synthetic Construct
MOD_RES                 1
                        note = MeGly
MOD_RES                 2
                        note = Orn
MOD_RES                 3
                        note = Orn
MOD_RES                 4
                        note = Orn
DISULFID                6..14
                        note = disulfide bond
MOD_RES                 12
                        note = Xaa is
                         2,3,3a,4,5,6,7,7a-Octahydroindole-2-carboxylic acid
MOD_RES                 14
                        note = Xaa is L-Penicillamine
MOD_RES                 16
                        note = AMIDATION
source                  1..16
                        mol_type = protein
                        organism = synthetic construct
SEQUENCE: 418
XXXXICSRSL PXIXIP                                                         16

SEQ ID NO: 419          moltype = AA  length = 14
FEATURE                 Location/Qualifiers
REGION                  1..14
                        note = Synthetic Construct
MOD_RES                 1
                        note = Xaa is 3-Phenylpropanoic acid
DISULFID                3..11
                        note = disulfide bond
MOD_RES                 7
                        note = Xaa is L-tert-Butylalanine
MOD_RES                 11
                        note = Xaa is L-Penicillamine
source                  1..14
                        mol_type = protein
                        organism = synthetic construct
SEQUENCE: 419
XICSRSXPPI XIPD                                                           14

SEQ ID NO: 420          moltype = AA  length = 14
FEATURE                 Location/Qualifiers
REGION                  1..14
                        note = Synthetic Construct
MOD_RES                 1
                        note = Xaa is Suberic acid
```

```
DISULFID              3..11
                      note = disulfide bond
MOD_RES               7
                      note = Xaa is L-tert-Butylalanine
MOD_RES               11
                      note = Xaa is L-Penicillamine
MOD_RES               14
                      note = AMIDATION
source                1..14
                      mol_type = protein
                      organism = synthetic construct
SEQUENCE: 420
XICSRSXPPI XIPD                                                 14

SEQ ID NO: 421        moltype = AA  length = 12
FEATURE               Location/Qualifiers
REGION                1..12
                      note = Synthetic Construct
MOD_RES               1
                      note = Xaa is Cyclopentanecarboxylic acid
DISULFID              3..11
                      note = disulfide bond
MOD_RES               7
                      note = Xaa is L-tert-Butylalanine
MOD_RES               11
                      note = Xaa is L-N-Methylcysteine
MOD_RES               12
                      note = AMIDATION
source                1..12
                      mol_type = protein
                      organism = synthetic construct
SEQUENCE: 421
XICSRSXPPI XI                                                   12

SEQ ID NO: 422        moltype = AA  length = 15
FEATURE               Location/Qualifiers
REGION                1..15
                      note = Synthetic Construct
MOD_RES               1
                      note = Xaa is 9-Amino-4,7-dioxanonanoic acid
DISULFID              4..12
                      note = disulfide bond
source                1..15
                      mol_type = protein
                      organism = synthetic construct
SEQUENCE: 422
XGICSRSLPP ICIPD                                                15

SEQ ID NO: 423        moltype = AA  length = 14
FEATURE               Location/Qualifiers
REGION                1..14
                      note = Synthetic Construct
DISULFID              3..11
                      note = disulfide bond
MOD_RES               9
                      note = Xaa is Hydroxyproline
source                1..14
                      mol_type = protein
                      organism = synthetic construct
SEQUENCE: 423
GICSRSLPXI CIPD                                                 14

SEQ ID NO: 424        moltype = AA  length = 14
FEATURE               Location/Qualifiers
REGION                1..14
                      note = Synthetic Construct
DISULFID              3..11
                      note = disulfide bond
MOD_RES               7
                      note = Xaa is L-tert-Butylglycine
MOD_RES               14
                      note = AMIDATION
source                1..14
                      mol_type = protein
                      organism = synthetic construct
SEQUENCE: 424
AICSRSXPPI CIPD                                                 14

SEQ ID NO: 425        moltype = AA  length = 13
```

-continued

```
FEATURE                Location/Qualifiers
REGION                 1..13
                       note = Synthetic Construct
MOD_RES                1
                       note = MeGly
DISULFID               3..11
                       note = disulfide bond
MOD_RES                7
                       note = Xaa is L-tert-Butylalanine
MOD_RES                11
                       note = Xaa is L-Penicillamine
MOD_RES                13
                       note = AMIDATION
source                 1..13
                       mol_type = protein
                       organism = synthetic construct
SEQUENCE: 425
XICKRSXPPI XIP                                                                13

SEQ ID NO: 426         moltype = AA  length = 14
FEATURE                Location/Qualifiers
REGION                 1..14
                       note = Synthetic Construct
MOD_RES                1
                       note = MeGly
DISULFID               3..11
                       note = disulfide bond
MOD_RES                6
                       note = Dpr
source                 1..14
                       mol_type = protein
                       organism = synthetic construct
SEQUENCE: 426
XICSRXLPPI CIPD                                                               14

SEQ ID NO: 427         moltype = AA  length = 14
FEATURE                Location/Qualifiers
REGION                 1..14
                       note = Synthetic Construct
DISULFID               3..11
                       note = disulfide bond
MOD_RES                9
                       note = Xaa is (2S,4S)-4-Fluoroproline
source                 1..14
                       mol_type = protein
                       organism = synthetic construct
SEQUENCE: 427
GICSRSLPXI CIPD                                                               14

SEQ ID NO: 428         moltype = AA  length = 14
FEATURE                Location/Qualifiers
REGION                 1..14
                       note = Synthetic Construct
MOD_RES                1
                       note = Xaa is Cyclohexylacetic acid
DISULFID               3..11
                       note = disulfide bond
MOD_RES                7
                       note = Xaa is L-tert-Butylalanine
MOD_RES                11
                       note = Xaa is L-Penicillamine
MOD_RES                14
                       note = AMIDATION
source                 1..14
                       mol_type = protein
                       organism = synthetic construct
SEQUENCE: 428
XICSRSXPPI XIPD                                                               14

SEQ ID NO: 429         moltype = AA  length = 14
FEATURE                Location/Qualifiers
REGION                 1..14
                       note = Synthetic Construct
DISULFID               3..11
                       note = disulfide bond
MOD_RES                7
                       note = Xaa is L-4-Bromophenylalanine
source                 1..14
                       mol_type = protein
```

```
                        organism = synthetic construct
SEQUENCE: 429
GICSRSXPPI CIPD                                                            14

SEQ ID NO: 430          moltype = AA  length = 14
FEATURE                 Location/Qualifiers
REGION                  1..14
                        note = Synthetic Construct
DISULFID                3..11
                        note = disulfide bond
MOD_RES                 12
                        note = Xaa is (2S,3S)-2-((Amino)methyl)-3-methylpentanoic
                         acid
MOD_RES                 14
                        note = AMIDATION
source                  1..14
                        mol_type = protein
                        organism = synthetic construct
SEQUENCE: 430
AICSRSLPPI CXPD                                                            14

SEQ ID NO: 431          moltype = AA  length = 14
FEATURE                 Location/Qualifiers
REGION                  1..14
                        note = Synthetic Construct
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
source                  1..14
                        mol_type = protein
                        organism = synthetic construct
SEQUENCE: 431
AICSRSLPXI XIPN                                                            14

SEQ ID NO: 432          moltype = AA  length = 13
FEATURE                 Location/Qualifiers
REGION                  1..13
                        note = Synthetic Construct
MOD_RES                 1
                        note = MeGly
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
MOD_RES                 13
                        note = Xaa is 5-Azaspiro[2.4]heptane-1-carboxylic acid
source                  1..13
                        mol_type = protein
                        organism = synthetic construct
SEQUENCE: 432
XICSRSLPXI XIX                                                             13

SEQ ID NO: 433          moltype = AA  length = 14
FEATURE                 Location/Qualifiers
REGION                  1..14
                        note = Synthetic Construct
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
MOD_RES                 14
                        note = AMIDATION
source                  1..14
                        mol_type = protein
                        organism = synthetic construct
SEQUENCE: 433
AICSRSLPXI XIPD                                                            14

SEQ ID NO: 434          moltype = AA  length = 14
```

```
FEATURE                 Location/Qualifiers
REGION                  1..14
                        note = Synthetic Construct
MOD_RES                 1
                        note = Xaa is Tranexamic acid
DISULFID                3..11
                        note = disulfide bond
MOD_RES                 7
                        note = Xaa is L-tert-Butylalanine
MOD_RES                 11
                        note = Xaa is L-Penicillamine
MOD_RES                 14
                        note = AMIDATION
MOD_RES                 14
                        note = Xaa is 12-Amino-4,7,10-trioxadodecanoic acid
source                  1..14
                        mol_type = protein
                        organism = synthetic construct
SEQUENCE: 434
XICSRSXPPI XIPX                                                   14

SEQ ID NO: 435          moltype = AA  length = 14
FEATURE                 Location/Qualifiers
REGION                  1..14
                        note = Synthetic Construct
MOD_RES                 1
                        note = Xaa is Tranexamic acid
DISULFID                3..11
                        note = disulfide bond
MOD_RES                 7
                        note = Xaa is L-tert-Butylalanine
MOD_RES                 11
                        note = Xaa is L-Penicillamine
MOD_RES                 14
                        note = AMIDATION
MOD_RES                 14
                        note = Xaa is 14-Amino-3,6,9,12-tetraoxatetradecanoic acid
source                  1..14
                        mol_type = protein
                        organism = synthetic construct
SEQUENCE: 435
XICSRSXPPI XIPX                                                   14

SEQ ID NO: 436          moltype = AA  length = 14
FEATURE                 Location/Qualifiers
REGION                  1..14
                        note = Synthetic Construct
MOD_RES                 1
                        note = Xaa is Tranexamic acid
DISULFID                3..11
                        note = disulfide bond
MOD_RES                 7
                        note = Xaa is L-tert-Butylalanine
MOD_RES                 11
                        note = Xaa is L-Penicillamine
MOD_RES                 14
                        note = AMIDATION
MOD_RES                 14
                        note = Xaa is 15-Amino-4,7,10,13-tetraoxa(Pen)tadecanoic
                         acid
source                  1..14
                        mol_type = protein
                        organism = synthetic construct
SEQUENCE: 436
XICSRSXPPI XIPX                                                   14

SEQ ID NO: 437          moltype = AA  length = 14
FEATURE                 Location/Qualifiers
REGION                  1..14
                        note = Synthetic Construct
MOD_RES                 1
                        note = Xaa is Tranexamic acid
DISULFID                3..11
                        note = disulfide bond
MOD_RES                 7
                        note = Xaa is L-tert-Butylalanine
MOD_RES                 11
                        note = Xaa is L-Penicillamine
MOD_RES                 14
```

```
                        note = AMIDATION
MOD_RES                 14
                        note = Xaa is 17-Amino-3,6,9,12,15-(Pen)taoxaheptadecanoic
                         acid
source                  1..14
                        mol_type = protein
                        organism = synthetic construct
SEQUENCE: 437
XICSRSXPPI XIPX                                                            14

SEQ ID NO: 438          moltype = AA  length = 14
FEATURE                 Location/Qualifiers
REGION                  1..14
                        note = Synthetic Construct
MOD_RES                 1
                        note = Xaa is Tranexamic acid
DISULFID                3..11
                        note = disulfide bond
MOD_RES                 7
                        note = Xaa is L-tert-Butylalanine
MOD_RES                 11
                        note = Xaa is L-Penicillamine
MOD_RES                 14
                        note = AMIDATION
MOD_RES                 14
                        note = Xaa is
                         1-Amino-3,6,9,12,15,18-hexaoxahenicosan-21-oic acid
source                  1..14
                        mol_type = protein
                        organism = synthetic construct
SEQUENCE: 438
XICSRSXPPI XIPX                                                            14

SEQ ID NO: 439          moltype = AA  length = 14
FEATURE                 Location/Qualifiers
REGION                  1..14
                        note = Synthetic Construct
MOD_RES                 1
                        note = Xaa is Tranexamic acid
DISULFID                3..11
                        note = disulfide bond
MOD_RES                 7
                        note = Xaa is L-tert-Butylalanine
MOD_RES                 11
                        note = Xaa is L-Penicillamine
MOD_RES                 14
                        note = AMIDATION
MOD_RES                 14
                        note = Xaa is
                         1-Amino-3,6,9,12,15,18,21-heptaoxatetracosan-24-oic acid
source                  1..14
                        mol_type = protein
                        organism = synthetic construct
SEQUENCE: 439
XICSRSXPPI XIPX                                                            14

SEQ ID NO: 440          moltype = AA  length = 14
FEATURE                 Location/Qualifiers
REGION                  1..14
                        note = Synthetic Construct
MOD_RES                 1
                        note = Xaa is Tranexamic acid
DISULFID                3..11
                        note = disulfide bond
MOD_RES                 7
                        note = Xaa is L-tert-Butylalanine
MOD_RES                 11
                        note = Xaa is L-Penicillamine
MOD_RES                 14
                        note = AMIDATION
MOD_RES                 14
                        note = Xaa is
                         1-Amino-3,6,9,12,15,18,21,24-octaoxaheptacosan-27-oic acid
source                  1..14
                        mol_type = protein
                        organism = synthetic construct
SEQUENCE: 440
XICSRSXPPI XIPX                                                            14
```

-continued

```
SEQ ID NO: 441          moltype = AA  length = 15
FEATURE                 Location/Qualifiers
REGION                  1..15
                        note = Synthetic Construct
MOD_RES                 1
                        note = MeGly
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
MOD_RES                 15
                        note = AMIDATION
MOD_RES                 15
                        note = Xaa is
                         1-Amino-3,6,9,12,15,18,21,24,27-nonaoxatriacontan-30-oic
                         acid
source                  1..15
                        mol_type = protein
                        organism = synthetic construct
SEQUENCE: 441
XICSRSLPXI XIPDX                                                            15

SEQ ID NO: 442          moltype = AA  length = 14
FEATURE                 Location/Qualifiers
REGION                  1..14
                        note = Synthetic Construct
MOD_RES                 1
                        note = Xaa is Tranexamic acid
DISULFID                3..11
                        note = disulfide bond
MOD_RES                 7
                        note = Xaa is L-tert-Butylalanine
MOD_RES                 11
                        note = Xaa is L-Penicillamine
MOD_RES                 14
                        note = AMIDATION
MOD_RES                 14
                        note = Xaa is 1,13-Diamino-4,7,10-trioxatridecan-succinamic
                         acid
source                  1..14
                        mol_type = protein
                        organism = synthetic construct
SEQUENCE: 442
XICSRSXPPI XIPX                                                             14

SEQ ID NO: 443          moltype = AA  length = 16
FEATURE                 Location/Qualifiers
REGION                  1..16
                        note = Synthetic Construct
MOD_RES                 1
                        note = MeGly
DISULFID                3..11
                        note = disulfide bond
MOD_RES                 7
                        note = Xaa is L-tert-Butylalanine
MOD_RES                 11
                        note = Xaa is L-Penicillamine
MOD_RES                 14
                        note = Orn
MOD_RES                 15
                        note = Orn
MOD_RES                 16
                        note = AMIDATION
MOD_RES                 16
                        note = Orn
source                  1..16
                        mol_type = protein
                        organism = synthetic construct
SEQUENCE: 443
XICSRSXPPI XIPXXX                                                           16

SEQ ID NO: 444          moltype = AA  length = 14
FEATURE                 Location/Qualifiers
REGION                  1..14
                        note = Synthetic Construct
DISULFID                3..11
```

```
                      note = disulfide bond
MOD_RES               9
                      note = Xaa is
                       2,3,3a,4,5,6,7,7a-Octahydroindole-2-carboxylic acid
MOD_RES               11
                      note = Xaa is L-Penicillamine
source                1..14
                      mol_type = protein
                      organism = synthetic construct
SEQUENCE: 444
AICSRSLPXI XIPD                                               14

SEQ ID NO: 445        moltype = AA  length = 14
FEATURE               Location/Qualifiers
REGION                1..14
                      note = Synthetic Construct
DISULFID              3..11
                      note = disulfide bond
MOD_RES               9
                      note = Xaa is
                       2,3,3a,4,5,6,7,7a-Octahydroindole-2-carboxylic acid
MOD_RES               11
                      note = Xaa is L-Penicillamine
source                1..14
                      mol_type = protein
                      organism = synthetic construct
SEQUENCE: 445
AICSRSLPXI XIPD                                               14

SEQ ID NO: 446        moltype = AA  length = 17
FEATURE               Location/Qualifiers
REGION                1..17
                      note = Synthetic Construct
MOD_RES               1
                      note = MeGly
DISULFID              3..11
                      note = disulfide bond
MOD_RES               7
                      note = Xaa is L-tert-Butylalanine
MOD_RES               11
                      note = Xaa is L-Penicillamine
MOD_RES               15
                      note = MeGly
MOD_RES               16
                      note = MeGly
MOD_RES               17
                      note = AMIDATION
MOD_RES               17
                      note = MeGly
source                1..17
                      mol_type = protein
                      organism = synthetic construct
SEQUENCE: 446
XICSRSXPPI XIPDXXX                                            17

SEQ ID NO: 447        moltype = AA  length = 15
FEATURE               Location/Qualifiers
REGION                1..15
                      note = Synthetic Construct
MOD_RES               1
                      note = Xaa is 1,18-Octadecanedioic acid
DISULFID              4..12
                      note = disulfide bond
MOD_RES               10
                      note = Xaa is
                       2,3,3a,4,5,6,7,7a-Octahydroindole-2-carboxylic acid
MOD_RES               12
                      note = Xaa is L-Penicillamine
source                1..15
                      mol_type = protein
                      organism = synthetic construct
SEQUENCE: 447
XAICSRSLPX IXIPD                                              15

SEQ ID NO: 448        moltype = AA  length = 14
FEATURE               Location/Qualifiers
REGION                1..14
                      note = Synthetic Construct
MOD_RES               1
```

```
                        note = Xaa is Tranexamic acid
DISULFID                3..11
                        note = disulfide bond
MOD_RES                 7
                        note = Xaa is L-tert-Butylalanine
MOD_RES                 11
                        note = Xaa is L-Penicillamine
MOD_RES                 14
                        note = AMIDATION
MOD_RES                 14
                        note = Xaa is 18-Amino-4,7,10,13,16-(Pen)taoxaoctadecanoic
                         acid
source                  1..14
                        mol_type = protein
                        organism = synthetic construct
SEQUENCE: 448
XICSRSXPPI XIPX                                                     14

SEQ ID NO: 449          moltype = AA  length = 15
FEATURE                 Location/Qualifiers
REGION                  1..15
                        note = Synthetic Construct
MOD_RES                 1
                        note = MeGly
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
MOD_RES                 15
                        note = AMIDATION
MOD_RES                 15
                        note = Xaa is (2S)-3-(Triazol-1-yl)-2-(amino)propanoic acid
source                  1..15
                        mol_type = protein
                        organism = synthetic construct
SEQUENCE: 449
XICSRSLPXI XIPPX                                                    15

SEQ ID NO: 450          moltype = AA  length = 14
FEATURE                 Location/Qualifiers
REGION                  1..14
                        note = Synthetic Construct
MOD_RES                 1
                        note = MeGly
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
MOD_RES                 14
                        note = AMIDATION
MOD_RES                 14
                        note = Xaa is (2S)-3-(Triazol-1-yl)-2-(amino)propanoic acid
source                  1..14
                        mol_type = protein
                        organism = synthetic construct
SEQUENCE: 450
XICSRSLPXI XIPX                                                     14

SEQ ID NO: 451          moltype = AA  length = 14
FEATURE                 Location/Qualifiers
REGION                  1..14
                        note = Synthetic Construct
MOD_RES                 1
                        note = MeGly
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
MOD_RES                 14
                        note = Xaa is 5-Azaspiro[2.4]heptane-1-carboxylic acid
```

```
source                 1..14
                       mol_type = protein
                       organism = synthetic construct
SEQUENCE: 451
XICSRSLPXI XIPX                                                            14

SEQ ID NO: 452         moltype = AA  length = 13
FEATURE                Location/Qualifiers
REGION                 1..13
                       note = Synthetic Construct
MOD_RES                1
                       note = MeGly
DISULFID               3..11
                       note = disulfide bond
MOD_RES                7
                       note = Xaa is L-tert-Butylalanine
MOD_RES                9
                       note = Xaa is (6S)-5-Azaspiro[2.4]heptane-6-carboxylic acid
MOD_RES                11
                       note = Xaa is L-Penicillamine
MOD_RES                13
                       note = AMIDATION
source                 1..13
                       mol_type = protein
                       organism = synthetic construct
SEQUENCE: 452
XICSRSXPXI XIP                                                             13

SEQ ID NO: 453         moltype = AA  length = 13
FEATURE                Location/Qualifiers
REGION                 1..13
                       note = Synthetic Construct
MOD_RES                1
                       note = MeGly
DISULFID               3..11
                       note = disulfide bond
MOD_RES                7
                       note = Xaa is (2S)-3-(2,3-difluorophenyl)-2-aminopropanoic
                        acid
MOD_RES                11
                       note = Xaa is L-Penicillamine
MOD_RES                13
                       note = AMIDATION
source                 1..13
                       mol_type = protein
                       organism = synthetic construct
SEQUENCE: 453
XICSRSXPPI XIP                                                             13

SEQ ID NO: 454         moltype = AA  length = 13
FEATURE                Location/Qualifiers
REGION                 1..13
                       note = Synthetic Construct
MOD_RES                1
                       note = MeGly
DISULFID               3..11
                       note = disulfide bond
MOD_RES                7
                       note = Xaa is (2S)-3-(2,3-difluorophenyl)-2-aminopropanoic
                        acid
MOD_RES                9
                       note = Xaa is
                        2,3,3a,4,5,6,7,7a-Octahydroindole-2-carboxylic acid
MOD_RES                11
                       note = Xaa is L-Penicillamine
MOD_RES                13
                       note = AMIDATION
source                 1..13
                       mol_type = protein
                       organism = synthetic construct
SEQUENCE: 454
XICSRSXPXI XIP                                                             13

SEQ ID NO: 455         moltype = AA  length = 14
FEATURE                Location/Qualifiers
REGION                 1..14
                       note = Synthetic Construct
MOD_RES                1
                       note = MeGly
```

```
DISULFID              3..11
                      note = disulfide bond
MOD_RES               7
                      note = Xaa is L-tert-Butylalanine
MOD_RES               9
                      note = Xaa is
                       (1S,2S,5R)-3-azabicyclo[3.1.0]hexane-2-carboxylic acid
MOD_RES               11
                      note = Xaa is L-Penicillamine
source                1..14
                      mol_type = protein
                      organism = synthetic construct
SEQUENCE: 455
XICSRSXPXI XIPD                                                    14

SEQ ID NO: 456        moltype = AA  length = 13
FEATURE               Location/Qualifiers
REGION                1..13
                      note = Synthetic Construct
MOD_RES               1
                      note = Xaa is L-N-Methylalanine
DISULFID              3..11
                      note = disulfide bond
MOD_RES               7
                      note = Xaa is L-tert-Butylalanine
MOD_RES               9
                      note = Xaa is
                       (3R,6R)-1,1-Difluoro-5-azaspiro[2.4]heptane-6-carboxylic
                       acid (enantiomer 1)
MOD_RES               11
                      note = Xaa is L-Penicillamine
MOD_RES               13
                      note = AMIDATION
source                1..13
                      mol_type = protein
                      organism = synthetic construct
SEQUENCE: 456
XICSRSXPXI XIP                                                     13

SEQ ID NO: 457        moltype = AA  length = 13
FEATURE               Location/Qualifiers
REGION                1..13
                      note = Synthetic Construct
MOD_RES               1
                      note = Xaa is L-3-Methylhistidine
DISULFID              3..11
                      note = disulfide bond
MOD_RES               9
                      note = Xaa is
                       2,3,3a,4,5,6,7,7a-Octahydroindole-2-carboxylic acid
MOD_RES               11
                      note = Xaa is L-Penicillamine
MOD_RES               13
                      note = AMIDATION
source                1..13
                      mol_type = protein
                      organism = synthetic construct
SEQUENCE: 457
XICSRSLPXI XIP                                                     13

SEQ ID NO: 458        moltype = AA  length = 13
FEATURE               Location/Qualifiers
REGION                1..13
                      note = Synthetic Construct
MOD_RES               1
                      note = Xaa is L-N-Methylalanine
DISULFID              3..11
                      note = disulfide bond
MOD_RES               7
                      note = Xaa is L-tert-Butylalanine
MOD_RES               9
                      note = Xaa is
                       (3R,6R)-1,1-Difluoro-5-azaspiro[2.4]heptane-6-carboxylic
                       acid (enantiomer 2)
MOD_RES               11
                      note = Xaa is L-Penicillamine
MOD_RES               13
                      note = AMIDATION
source                1..13
```

```
                        mol_type = protein
                        organism = synthetic construct
SEQUENCE: 458
XICSRSXPXI XIP                                                    13

SEQ ID NO: 459          moltype = AA  length = 14
FEATURE                 Location/Qualifiers
REGION                  1..14
                        note = Synthetic Construct
MOD_RES                 1
                        note = MeGly
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
MOD_RES                 14
                        note = Xaa is Iminodiacetic acid
source                  1..14
                        mol_type = protein
                        organism = synthetic construct
SEQUENCE: 459
XICSRSLPXI XIPX                                                   14

SEQ ID NO: 460          moltype = AA  length = 14
FEATURE                 Location/Qualifiers
REGION                  1..14
                        note = Synthetic Construct
MOD_RES                 1
                        note = MeGly
DISULFID                3..11
                        note = disulfide bond
MOD_RES                 7
                        note = Xaa is L-tert-Butylalanine
MOD_RES                 11
                        note = Xaa is L-Penicillamine
MOD_RES                 14
                        note = Xaa is 1-Benzyl-L-histidine
source                  1..14
                        mol_type = protein
                        organism = synthetic construct
SEQUENCE: 460
XICSRSXPPI XIPX                                                   14

SEQ ID NO: 461          moltype = AA  length = 13
FEATURE                 Location/Qualifiers
REGION                  1..13
                        note = Synthetic Construct
MOD_RES                 1
                        note = MeGly
DISULFID                3..11
                        note = disulfide bond
MOD_RES                 7
                        note = Xaa is L-tert-Butylalanine
MOD_RES                 10
                        note = Nva
MOD_RES                 11
                        note = Xaa is L-Penicillamine
MOD_RES                 13
                        note = AMIDATION
source                  1..13
                        mol_type = protein
                        organism = synthetic construct
SEQUENCE: 461
XICRRSXPPX XIP                                                    13

SEQ ID NO: 462          moltype = AA  length = 14
FEATURE                 Location/Qualifiers
REGION                  1..14
                        note = Synthetic Construct
MOD_RES                 1
                        note = MeGly
DISULFID                3..11
                        note = disulfide bond
MOD_RES                 9
                        note = Xaa is
                         2,3,3a,4,5,6,7,7a-Octahydroindole-2-carboxylic acid
```

-continued

```
MOD_RES                 11
                        note = Xaa is L-Penicillamine
MOD_RES                 14
                        note = Xaa is (1R,3S)-3-(Amino)cyclopentanecarboxylic acid
source                  1..14
                        mol_type = protein
                        organism = synthetic construct
SEQUENCE: 462
XICSRSLPXI XIPX                                                           14

SEQ ID NO: 463          moltype = AA  length = 14
FEATURE                 Location/Qualifiers
REGION                  1..14
                        note = Synthetic Construct
MOD_RES                 1
                        note = MeGly
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
MOD_RES                 14
                        note = Xaa is (R)-4-Amino-6-methylheptanoic acid
source                  1..14
                        mol_type = protein
                        organism = synthetic construct
SEQUENCE: 463
XICSRSLPXI XIPX                                                           14

SEQ ID NO: 464          moltype = AA  length = 14
FEATURE                 Location/Qualifiers
REGION                  1..14
                        note = Synthetic Construct
MOD_RES                 1
                        note = MeGly
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
MOD_RES                 14
                        note = Xaa is (S)-(1-Piperidin-3-yl)-acetic acid
source                  1..14
                        mol_type = protein
                        organism = synthetic construct
SEQUENCE: 464
XICSRSLPXI XIPX                                                           14

SEQ ID NO: 465          moltype = AA  length = 14
FEATURE                 Location/Qualifiers
REGION                  1..14
                        note = Synthetic Construct
MOD_RES                 1
                        note = MeGly
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
MOD_RES                 14
                        note = Xaa is (1S,3R)-3-(Amino)cyclopentanecarboxylic acid
source                  1..14
                        mol_type = protein
                        organism = synthetic construct
SEQUENCE: 465
XICSRSLPXI XIPX                                                           14

SEQ ID NO: 466          moltype = AA  length = 14
FEATURE                 Location/Qualifiers
REGION                  1..14
                        note = Synthetic Construct
MOD_RES                 1
                        note = MeGly
```

```
DISULFID              3..11
                      note = disulfide bond
MOD_RES               9
                      note = Xaa is
                       2,3,3a,4,5,6,7,7a-Octahydroindole-2-carboxylic acid
MOD_RES               11
                      note = Xaa is L-Penicillamine
MOD_RES               14
                      note = Xaa is (S)-3-(1-Pyrrolidine-2-yl)-propionic acid
source                1..14
                      mol_type = protein
                      organism = synthetic construct
SEQUENCE: 466
XICSRSLPXI XIPX                                                14

SEQ ID NO: 467        moltype = AA  length = 14
FEATURE               Location/Qualifiers
REGION                1..14
                      note = Synthetic Construct
MOD_RES               1
                      note = MeGly
DISULFID              3..11
                      note = disulfide bond
MOD_RES               9
                      note = Xaa is
                       2,3,3a,4,5,6,7,7a-Octahydroindole-2-carboxylic acid
MOD_RES               11
                      note = Xaa is L-Penicillamine
source                1..14
                      mol_type = protein
                      organism = synthetic construct
SEQUENCE: 467
XICSRSLPXI XIPN                                                14

SEQ ID NO: 468        moltype = AA  length = 14
FEATURE               Location/Qualifiers
REGION                1..14
                      note = Synthetic Construct
MOD_RES               1
                      note = MeGly
DISULFID              3..11
                      note = disulfide bond
MOD_RES               9
                      note = Xaa is
                       2,3,3a,4,5,6,7,7a-Octahydroindole-2-carboxylic acid
MOD_RES               11
                      note = Xaa is L-Penicillamine
MOD_RES               14
                      note = Xaa is (2S)-Pyrrolidin-2-ylacetic acid
source                1..14
                      mol_type = protein
                      organism = synthetic construct
SEQUENCE: 468
XICSRSLPXI XIPX                                                14

SEQ ID NO: 469        moltype = AA  length = 14
FEATURE               Location/Qualifiers
REGION                1..14
                      note = Synthetic Construct
MOD_RES               1
                      note = MeGly
DISULFID              3..11
                      note = disulfide bond
MOD_RES               9
                      note = Xaa is
                       2,3,3a,4,5,6,7,7a-Octahydroindole-2-carboxylic acid
MOD_RES               11
                      note = Xaa is L-Penicillamine
MOD_RES               14
                      note = Xaa is (S)-Pyrrolidine-3-carboxylic acid
source                1..14
                      mol_type = protein
                      organism = synthetic construct
SEQUENCE: 469
XICSRSLPXI XIPX                                                14

SEQ ID NO: 470        moltype = AA  length = 14
FEATURE               Location/Qualifiers
REGION                1..14
```

```
                        note = Synthetic Construct
MOD_RES                 1
                        note = Xaa is (2,4-Dioxoimidazolidin-1-yl)acetic acid
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
source                  1..14
                        mol_type = protein
                        organism = synthetic construct
SEQUENCE: 470
XICSRSLPXI XIPD                                                            14

SEQ ID NO: 471          moltype = AA  length = 14
FEATURE                 Location/Qualifiers
REGION                  1..14
                        note = Synthetic Construct
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
MOD_RES                 14
                        note = Xaa is Dpr (peptide bond via amino group at position
                         3)
source                  1..14
                        mol_type = protein
                        organism = synthetic construct
SEQUENCE: 471
AICSRSLPXI XIPX                                                            14

SEQ ID NO: 472          moltype = AA  length = 12
FEATURE                 Location/Qualifiers
REGION                  1..12
                        note = Synthetic Construct
MOD_RES                 1
                        note = Xaa is (R)-Piperidine-3-Carboxylic Acid
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
source                  1..12
                        mol_type = protein
                        organism = synthetic construct
SEQUENCE: 472
XICSRSLPXI XI                                                              12

SEQ ID NO: 473          moltype = AA  length = 12
FEATURE                 Location/Qualifiers
REGION                  1..12
                        note = Synthetic Construct
MOD_RES                 1
                        note = Xaa is (S)-Piperidine-3-carboxylic acid
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
source                  1..12
                        mol_type = protein
                        organism = synthetic construct
SEQUENCE: 473
XICSRSLPXI XI                                                              12

SEQ ID NO: 474          moltype = AA  length = 14
FEATURE                 Location/Qualifiers
REGION                  1..14
                        note = Synthetic Construct
MOD_RES                 1
```

```
                        note = Xaa is 8-Aminocubane-1-carboxylic acid
DISULFID                3..11
                        note = disulfide bond
MOD_RES                 7
                        note = Xaa is L-tert-Butylalanine
MOD_RES                 11
                        note = Xaa is L-Penicillamine
source                  1..14
                        mol_type = protein
                        organism = synthetic construct
SEQUENCE: 474
XICSRSXPPI XIPD                                                14

SEQ ID NO: 475          moltype = AA  length = 14
FEATURE                 Location/Qualifiers
REGION                  1..14
                        note = Synthetic Construct
MOD_RES                 1
                        note = Xaa is L-N-Methylalanine
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
MOD_RES                 14
                        note = AMIDATION
MOD_RES                 14
                        note = Xaa is
                         (2S)-2-Amino-4-(benzylamino)-4-oxobutanecarboxylic acid
source                  1..14
                        mol_type = protein
                        organism = synthetic construct
SEQUENCE: 475
XICSRSLPXI XIPX                                                14

SEQ ID NO: 476          moltype = AA  length = 15
FEATURE                 Location/Qualifiers
REGION                  1..15
                        note = Synthetic Construct
MOD_RES                 1
                        note = MeGly
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
source                  1..15
                        mol_type = protein
                        organism = synthetic construct
SEQUENCE: 476
XICSRSLPXI XIPDK                                               15

SEQ ID NO: 477          moltype = AA  length = 15
FEATURE                 Location/Qualifiers
REGION                  1..15
                        note = Synthetic Construct
MOD_RES                 1
                        note = MeGly
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
source                  1..15
                        mol_type = protein
                        organism = synthetic construct
SEQUENCE: 477
XICSRSLPXI XIPGD                                               15

SEQ ID NO: 478          moltype = AA  length = 15
FEATURE                 Location/Qualifiers
REGION                  1..15
                        note = Synthetic Construct
```

```
MOD_RES                 1
                        note = MeGly
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
MOD_RES                 15
                        note = Acp
source                  1..15
                        mol_type = protein
                        organism = synthetic construct
SEQUENCE: 478
XICSRSLPXI XIPDX                                                     15

SEQ ID NO: 479          moltype = AA  length = 15
FEATURE                 Location/Qualifiers
REGION                  1..15
                        note = Synthetic Construct
MOD_RES                 1
                        note = MeGly
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
source                  1..15
                        mol_type = protein
                        organism = synthetic construct
SEQUENCE: 479
XICSRSLPXI XIPDD                                                     15

SEQ ID NO: 480          moltype = AA  length = 14
FEATURE                 Location/Qualifiers
REGION                  1..14
                        note = Synthetic Construct
MOD_RES                 1
                        note = MeGly
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
MOD_RES                 14
                        note = Xaa is Dpr (peptide bond via amino group at position
                         3)
source                  1..14
                        mol_type = protein
                        organism = synthetic construct
SEQUENCE: 480
XICSRSLPXI XIPX                                                      14

SEQ ID NO: 481          moltype = AA  length = 14
FEATURE                 Location/Qualifiers
REGION                  1..14
                        note = Synthetic Construct
MOD_RES                 1
                        note = MeGly
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
MOD_RES                 14
                        note = Xaa is 12-Amino-4,7,10-trioxadodecanoic acid
source                  1..14
                        mol_type = protein
                        organism = synthetic construct
SEQUENCE: 481
XICSRSLPXI XIPX                                                      14
```

-continued

```
SEQ ID NO: 482          moltype = AA  length = 14
FEATURE                 Location/Qualifiers
REGION                  1..14
                        note = Synthetic Construct
MOD_RES                 1
                        note = Orn
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
source                  1..14
                        mol_type = protein
                        organism = synthetic construct
SEQUENCE: 482
XICSRSLPXI XIPD                                                              14

SEQ ID NO: 483          moltype = AA  length = 14
FEATURE                 Location/Qualifiers
REGION                  1..14
                        note = Synthetic Construct
MOD_RES                 1
                        note = MeGly
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
MOD_RES                 14
                        note = Xaa is 14-Amino-3,6,9,12-tetraoxatetradecanoic acid
source                  1..14
                        mol_type = protein
                        organism = synthetic construct
SEQUENCE: 483
XICSRSLPXI XIPX                                                              14

SEQ ID NO: 484          moltype = AA  length = 15
FEATURE                 Location/Qualifiers
REGION                  1..15
                        note = Synthetic Construct
MOD_RES                 1
                        note = MeGly
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
MOD_RES                 15
                        note = Xaa is 14-Amino-3,6,9,12-tetraoxatetradecanoic acid
source                  1..15
                        mol_type = protein
                        organism = synthetic construct
SEQUENCE: 484
XICSRSLPXI XIPDX                                                             15

SEQ ID NO: 485          moltype = AA  length = 14
FEATURE                 Location/Qualifiers
REGION                  1..14
                        note = Synthetic Construct
MOD_RES                 1
                        note = MeGly
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
MOD_RES                 14
                        note = Xaa is
                         1-Amino-3,6,9,12,15,18-hexaoxahenicosan-21-oic acid
source                  1..14
                        mol_type = protein
```

```
                         organism = synthetic construct
SEQUENCE: 485
XICSRSLPXI XIPX                                                    14

SEQ ID NO: 486           moltype = AA  length = 14
FEATURE                  Location/Qualifiers
REGION                   1..14
                         note = Synthetic Construct
DISULFID                 3..11
                         note = disulfide bond
MOD_RES                  9
                         note = Xaa is
                          2,3,3a,4,5,6,7,7a-Octahydroindole-2-carboxylic acid
MOD_RES                  11
                         note = Xaa is L-Penicillamine
source                   1..14
                         mol_type = protein
                         organism = synthetic construct
SEQUENCE: 486
AICSRSLPXI XIPD                                                    14

SEQ ID NO: 487           moltype = AA  length = 13
FEATURE                  Location/Qualifiers
REGION                   1..13
                         note = Synthetic Construct
MOD_RES                  1
                         note = MeGly
DISULFID                 3..11
                         note = disulfide bond
MOD_RES                  9
                         note = Xaa is
                          2,3,3a,4,5,6,7,7a-Octahydroindole-2-carboxylic acid
MOD_RES                  11
                         note = Xaa is L-Penicillamine
MOD_RES                  13
                         note = Xaa is (S)-4-Piperazine-2-carboxylic acid
source                   1..13
                         mol_type = protein
                         organism = synthetic construct
SEQUENCE: 487
XICSRSLPXI XIX                                                     13

SEQ ID NO: 488           moltype = AA  length = 14
FEATURE                  Location/Qualifiers
REGION                   1..14
                         note = Synthetic Construct
MOD_RES                  1
                         note = Xaa is Piperidin-4-ylacetic acid
DISULFID                 3..11
                         note = disulfide bond
MOD_RES                  7
                         note = Xaa is L-tert-Butylalanine
source                   1..14
                         mol_type = protein
                         organism = synthetic construct
SEQUENCE: 488
XICSRSXPPI CIPD                                                    14

SEQ ID NO: 489           moltype = AA  length = 14
FEATURE                  Location/Qualifiers
REGION                   1..14
                         note = Synthetic Construct
MOD_RES                  1
                         note = MeGly
DISULFID                 3..11
                         note = disulfide bond
MOD_RES                  9
                         note = Xaa is
                          2,3,3a,4,5,6,7,7a-Octahydroindole-2-carboxylic acid
MOD_RES                  11
                         note = Xaa is L-Penicillamine
MOD_RES                  14
                         note = Xaa is 4-Aminomethylphenylacetic acid
source                   1..14
                         mol_type = protein
                         organism = synthetic construct
SEQUENCE: 489
XICSRSLPXI XIPX                                                    14
```

-continued

```
SEQ ID NO: 490          moltype = AA  length = 14
FEATURE                 Location/Qualifiers
REGION                  1..14
                        note = Synthetic Construct
MOD_RES                 1
                        note = MeGly
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
MOD_RES                 14
                        note = Xaa is 3-Aminomethylphenylacetic acid
source                  1..14
                        mol_type = protein
                        organism = synthetic construct
SEQUENCE: 490
XICSRSLPXI XIPX                                                        14

SEQ ID NO: 491          moltype = AA  length = 14
FEATURE                 Location/Qualifiers
REGION                  1..14
                        note = Synthetic Construct
SITE                    1
                        note = Xaa is D-Alanine
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
MOD_RES                 14
                        note = Xaa is 3-Aminomethylphenylacetic acid
source                  1..14
                        mol_type = protein
                        organism = synthetic construct
SEQUENCE: 491
XICSRSLPXI XIPX                                                        14

SEQ ID NO: 492          moltype = AA  length = 14
FEATURE                 Location/Qualifiers
REGION                  1..14
                        note = Synthetic Construct
MOD_RES                 1
                        note = Orn
DISULFID                3..11
                        note = disulfide bond
MOD_RES                 7
                        note = Xaa is L-tert-Butylalanine
MOD_RES                 11
                        note = Xaa is L-N-Methylcysteine
source                  1..14
                        mol_type = protein
                        organism = synthetic construct
SEQUENCE: 492
XICSRSXPPI XIPD                                                        14

SEQ ID NO: 493          moltype = AA  length = 14
FEATURE                 Location/Qualifiers
REGION                  1..14
                        note = Synthetic Construct
MOD_RES                 1
                        note = Xaa is (S)-Pyrrolidine-2-carboxylic acid
DISULFID                3..11
                        note = disulfide bond
MOD_RES                 7
                        note = Xaa is L-tert-Butylalanine
MOD_RES                 11
                        note = Xaa is L-Penicillamine
source                  1..14
                        mol_type = protein
                        organism = synthetic construct
SEQUENCE: 493
XICSRSXPPI XIPD                                                        14

SEQ ID NO: 494          moltype = AA  length = 14
```

-continued

```
FEATURE                Location/Qualifiers
REGION                 1..14
                       note = Synthetic Construct
SITE                   1
                       note = Xaa is D-beta-Proline
DISULFID               3..11
                       note = disulfide bond
MOD_RES                7
                       note = Xaa is L-tert-Butylalanine
MOD_RES                11
                       note = Xaa is L-Penicillamine
source                 1..14
                       mol_type = protein
                       organism = synthetic construct
SEQUENCE: 494
XICSRSXPPI XIPD                                                    14

SEQ ID NO: 495         moltype = AA  length = 14
FEATURE                Location/Qualifiers
REGION                 1..14
                       note = Synthetic Construct
MOD_RES                1
                       note = MeGly
DISULFID               3..11
                       note = disulfide bond
MOD_RES                7
                       note = Xaa is L-tert-Butylalanine
MOD_RES                11
                       note = Xaa is L-Penicillamine
MOD_RES                14
                       note = Xaa is 3-Carboxyphenylalanine
source                 1..14
                       mol_type = protein
                       organism = synthetic construct
SEQUENCE: 495
XICSRSXPPI XIPX                                                    14

SEQ ID NO: 496         moltype = AA  length = 14
FEATURE                Location/Qualifiers
REGION                 1..14
                       note = Synthetic Construct
MOD_RES                1
                       note = MeGly
DISULFID               3..11
                       note = disulfide bond
MOD_RES                9
                       note = Xaa is
                        2,3,3a,4,5,6,7,7a-Octahydroindole-2-carboxylic acid
MOD_RES                11
                       note = Xaa is L-Penicillamine
MOD_RES                14
                       note = Xaa is 3-Carboxyphenylalanine
source                 1..14
                       mol_type = protein
                       organism = synthetic construct
SEQUENCE: 496
XICSRSLPXI XIPX                                                    14

SEQ ID NO: 497         moltype = AA  length = 15
FEATURE                Location/Qualifiers
REGION                 1..15
                       note = Synthetic Construct
MOD_RES                1
                       note = MeGly
DISULFID               3..11
                       note = disulfide bond
MOD_RES                9
                       note = Xaa is
                        2,3,3a,4,5,6,7,7a-Octahydroindole-2-carboxylic acid
MOD_RES                11
                       note = Xaa is L-Penicillamine
MOD_RES                15
                       note = Xaa is 12-Amino-4,7,10-trioxadodecanoic acid
source                 1..15
                       mol_type = protein
                       organism = synthetic construct
SEQUENCE: 497
XICSRSLPXI XIPDX                                                   15
```

-continued

```
SEQ ID NO: 498          moltype = AA  length = 14
FEATURE                 Location/Qualifiers
REGION                  1..14
                        note = Synthetic Construct
MOD_RES                 1
                        note = MeGly
DISULFID                3..11
                        note = disulfide bond
MOD_RES                 7
                        note = Xaa is L-tert-Butylalanine
MOD_RES                 11
                        note = Xaa is L-Penicillamine
MOD_RES                 14
                        note = Xaa is 15-Amino-4, 7, 10, 13-tetraoxapentadecanoic
                         acid
source                  1..14
                        mol_type = protein
                        organism = synthetic construct
SEQUENCE: 498
XICSRSXPPI XIPX                                                            14

SEQ ID NO: 499          moltype = AA  length = 15
FEATURE                 Location/Qualifiers
REGION                  1..15
                        note = Synthetic Construct
MOD_RES                 1
                        note = MeGly
DISULFID                3..11
                        note = disulfide bond
MOD_RES                 7
                        note = Xaa is L-tert-Butylalanine
MOD_RES                 11
                        note = Xaa is L-Penicillamine
MOD_RES                 14
                        note = Orn
source                  1..15
                        mol_type = protein
                        organism = synthetic construct
SEQUENCE: 499
XICSRSXPPI XIPXD                                                           15

SEQ ID NO: 500          moltype = AA  length = 14
FEATURE                 Location/Qualifiers
REGION                  1..14
                        note = Synthetic Construct
MOD_RES                 1
                        note = MeGly
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
source                  1..14
                        mol_type = protein
                        organism = synthetic construct
SEQUENCE: 500
XICSRSLPXI XIPR                                                            14

SEQ ID NO: 501          moltype = AA  length = 14
FEATURE                 Location/Qualifiers
REGION                  1..14
                        note = Synthetic Construct
MOD_RES                 1
                        note = Xaa is (R)-Piperidine-3-carboxylic acid
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
source                  1..14
                        mol_type = protein
                        organism = synthetic construct
SEQUENCE: 501
XICSRSLPXI XIPD                                                            14
```

```
SEQ ID NO: 502          moltype = AA  length = 14
FEATURE                 Location/Qualifiers
REGION                  1..14
                        note = Synthetic Construct
MOD_RES                 1
                        note = Xaa is (S)-Piperidine-3-carboxylic acid
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
source                  1..14
                        mol_type = protein
                        organism = synthetic construct
SEQUENCE: 502
XICSRSLPXI XIPD                                                             14

SEQ ID NO: 503          moltype = AA  length = 15
FEATURE                 Location/Qualifiers
REGION                  1..15
                        note = Synthetic Construct
MOD_RES                 1
                        note = Xaa is 4-Carboxybenzoic acid
DISULFID                4..12
                        note = disulfide bond
MOD_RES                 10
                        note = Xaa is
                         2,3,3a,4,5,6,7,7a-Octahydroindole-2-carboxylic acid
MOD_RES                 12
                        note = Xaa is L-Penicillamine
source                  1..15
                        mol_type = protein
                        organism = synthetic construct
SEQUENCE: 503
XGICSRSLPX IXIPD                                                            15

SEQ ID NO: 504          moltype = AA  length = 15
FEATURE                 Location/Qualifiers
REGION                  1..15
                        note = Synthetic Construct
MOD_RES                 1
                        note = Xaa is 3-Carboxybenzoic acid
DISULFID                4..12
                        note = disulfide bond
MOD_RES                 10
                        note = Xaa is
                         2,3,3a,4,5,6,7,7a-Octahydroindole-2-carboxylic acid
MOD_RES                 12
                        note = Xaa is L-Penicillamine
source                  1..15
                        mol_type = protein
                        organism = synthetic construct
SEQUENCE: 504
XGICSRSLPX IXIPD                                                            15

SEQ ID NO: 505          moltype = AA  length = 14
FEATURE                 Location/Qualifiers
REGION                  1..14
                        note = Synthetic Construct
MOD_RES                 1
                        note = MeGly
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
source                  1..14
                        mol_type = protein
                        organism = synthetic construct
SEQUENCE: 505
XICSRSLPXI XIPT                                                             14

SEQ ID NO: 506          moltype = AA  length = 14
FEATURE                 Location/Qualifiers
REGION                  1..14
```

-continued

```
                        note = Synthetic Construct
MOD_RES                 1
                        note = MeGly
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
source                  1..14
                        mol_type = protein
                        organism = synthetic construct
SEQUENCE: 506
XICSRSLPXI XIPY                                                   14

SEQ ID NO: 507          moltype = AA  length = 15
FEATURE                 Location/Qualifiers
REGION                  1..15
                        note = Synthetic Construct
MOD_RES                 1
                        note = MeGly
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
source                  1..15
                        mol_type = protein
                        organism = synthetic construct
SEQUENCE: 507
XICSRSLPXI XIPDA                                                  15

SEQ ID NO: 508          moltype = AA  length = 15
FEATURE                 Location/Qualifiers
REGION                  1..15
                        note = Synthetic Construct
MOD_RES                 1
                        note = MeGly
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
SITE                    15
                        note = Xaa is D-aspartic acid
source                  1..15
                        mol_type = protein
                        organism = synthetic construct
SEQUENCE: 508
XICSRSLPXI XIPGX                                                  15

SEQ ID NO: 509          moltype = AA  length = 14
FEATURE                 Location/Qualifiers
REGION                  1..14
                        note = Synthetic Construct
MOD_RES                 1
                        note = MeGly
DISULFID                3..11
                        note = disulfide bond
MOD_RES                 7
                        note = Xaa is L-tert-Butylalanine
MOD_RES                 11
                        note = Xaa is L-Penicillamine
MOD_RES                 14
                        note = Xaa is 17-Amino-3,6,9,12,15-pentaoxaheptadecanoic
                         acid
source                  1..14
                        mol_type = protein
                        organism = synthetic construct
SEQUENCE: 509
XICSRSXPPI XIPX                                                   14

SEQ ID NO: 510          moltype = AA  length = 16
FEATURE                 Location/Qualifiers
```

-continued

```
REGION                  1..16
                        note = Synthetic Construct
MOD_RES                 1
                        note = MeGly
DISULFID                3..11
                        note = disulfide bond
MOD_RES                 7
                        note = Xaa is L-tert-Butylalanine
MOD_RES                 11
                        note = Xaa is L-Penicillamine
MOD_RES                 14
                        note = MeGly
MOD_RES                 15
                        note = MeGly
MOD_RES                 16
                        note = MeGly
source                  1..16
                        mol_type = protein
                        organism = synthetic construct
SEQUENCE: 510
XICSRSXPPI XIPXXX                                                           16

SEQ ID NO: 511          moltype = AA  length = 14
FEATURE                 Location/Qualifiers
REGION                  1..14
                        note = Synthetic Construct
MOD_RES                 1
                        note = MeGly
DISULFID                3..11
                        note = disulfide bond
MOD_RES                 7
                        note = Xaa is L-tert-Butylalanine
MOD_RES                 11
                        note = Xaa is L-Penicillamine
MOD_RES                 14
                        note = Xaa is 9-Amino-4,7-dioxanonanoic acid
source                  1..14
                        mol_type = protein
                        organism = synthetic construct
SEQUENCE: 511
XICSRSXPPI XIPX                                                             14

SEQ ID NO: 512          moltype = AA  length = 14
FEATURE                 Location/Qualifiers
REGION                  1..14
                        note = Synthetic Construct
DISULFID                3..11
                        note = disulfide bond
MOD_RES                 5
                        note = Xaa is L-Arginine-N-Fmoc, Pbf-OH (13C6, 15N4)
MOD_RES                 9
                        note = Xaa is
                         2,3,3a,4,5,6,7,7a-Octahydroindole-2-carboxylic acid
MOD_RES                 11
                        note = Xaa is L-Penicillamine
source                  1..14
                        mol_type = protein
                        organism = synthetic construct
SEQUENCE: 512
AICSXSLPXI XIPD                                                             14

SEQ ID NO: 513          moltype = AA  length = 15
FEATURE                 Location/Qualifiers
REGION                  1..15
                        note = Synthetic Construct
MOD_RES                 1
                        note = MeGly
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
MOD_RES                 15
                        note = Xaa is 9-Amino-4, 7-dioxanonanoic acid
source                  1..15
                        mol_type = protein
                        organism = synthetic construct
```

```
SEQUENCE: 513
XICSRSLPXI XIPDX                                                   15

SEQ ID NO: 514          moltype = AA  length = 15
FEATURE                 Location/Qualifiers
REGION                  1..15
                        note = Synthetic Construct
MOD_RES                 1
                        note = MeGly
DISULFID                3..11
                        note = disulfide bond
MOD_RES                 7
                        note = Xaa is L-tert-Butylalanine
MOD_RES                 11
                        note = Xaa is L-Penicillamine
MOD_RES                 15
                        note = Xaa is 15-Amino-4,7,10,13-tetraoxapentadecanoic acid
source                  1..15
                        mol_type = protein
                        organism = synthetic construct
SEQUENCE: 514
XICSRSXPPI XIPDX                                                   15

SEQ ID NO: 515          moltype = AA  length = 14
FEATURE                 Location/Qualifiers
REGION                  1..14
                        note = Synthetic Construct
MOD_RES                 1
                        note = Xaa is 2-(Pyrrolidin-1-yl)acetic acid
DISULFID                3..11
                        note = disulfide bond
MOD_RES                 7
                        note = Xaa is L-tert-Butylalanine
MOD_RES                 11
                        note = Xaa is L-Penicillamine
source                  1..14
                        mol_type = protein
                        organism = synthetic construct
SEQUENCE: 515
XICSRSXPPI XIPD                                                    14

SEQ ID NO: 516          moltype = AA  length = 14
FEATURE                 Location/Qualifiers
REGION                  1..14
                        note = Synthetic Construct
MOD_RES                 1
                        note = MeGly
DISULFID                3..11
                        note = disulfide bond
MOD_RES                 7
                        note = Xaa is L-tert-Butylalanine
MOD_RES                 11
                        note = Xaa is L-Penicillamine
MOD_RES                 14
                        note = Xaa is
                         1-Amino-3,6,9,12,15,18,21,24,27-nonaoxatriacontan-30-oic
                         acid
source                  1..14
                        mol_type = protein
                        organism = synthetic construct
SEQUENCE: 516
XICSRSXPPI XIPX                                                    14

SEQ ID NO: 517          moltype = AA  length = 15
FEATURE                 Location/Qualifiers
REGION                  1..15
                        note = Synthetic Construct
MOD_RES                 1
                        note = MeGly
DISULFID                3..11
                        note = disulfide bond
MOD_RES                 7
                        note = Xaa is L-tert-Butylalanine
MOD_RES                 11
                        note = Xaa is L-Penicillamine
MOD_RES                 15
                        note = Xaa is
                         1-Amino-3,6,9,12,15,18,21,24,27-nonaoxatriacontan-30-oic
                         acid
```

```
source                  1..15
                        mol_type = protein
                        organism = synthetic construct
SEQUENCE: 517
XICSRSXPPI XIPDX                                                    15

SEQ ID NO: 518          moltype = AA  length = 14
FEATURE                 Location/Qualifiers
REGION                  1..14
                        note = Synthetic Construct
MOD_RES                 1
                        note = MeGly
DISULFID                3..11
                        note = disulfide bond
MOD_RES                 7
                        note = Xaa is L-tert-Butylalanine
MOD_RES                 11
                        note = Xaa is L-Penicillamine
MOD_RES                 14
                        note = Xaa is
                         1-Amino-3,6,9,12,15,18,21,24-octaoxaheptacosan-27-oic acid
source                  1..14
                        mol_type = protein
                        organism = synthetic construct
SEQUENCE: 518
XICSRSXPPI XIPX                                                     14

SEQ ID NO: 519          moltype = AA  length = 14
FEATURE                 Location/Qualifiers
REGION                  1..14
                        note = Synthetic Construct
MOD_RES                 1
                        note = MeGly
DISULFID                3..11
                        note = disulfide bond
MOD_RES                 7
                        note = Xaa is L-tert-Butylalanine
MOD_RES                 11
                        note = Xaa is L-Penicillamine
MOD_RES                 14
                        note = Xaa is 14-Amino-3,6,9,12-tetraoxatetradecanoic acid
source                  1..14
                        mol_type = protein
                        organism = synthetic construct
SEQUENCE: 519
XICSRSXPPI XIPX                                                     14

SEQ ID NO: 520          moltype = AA  length = 14
FEATURE                 Location/Qualifiers
REGION                  1..14
                        note = Synthetic Construct
DISULFID                3..11
                        note = disulfide bond
MOD_RES                 8
                        note = Xaa is
                         (1S,2S,5R)-3-Azabicyclo[3.1.0]hexane-2-carboxylic acid
MOD_RES                 11
                        note = Xaa is L-Penicillamine
source                  1..14
                        mol_type = protein
                        organism = synthetic construct
SEQUENCE: 520
AICSRSLXPI XIPD                                                     14

SEQ ID NO: 521          moltype = AA  length = 14
FEATURE                 Location/Qualifiers
REGION                  1..14
                        note = Synthetic Construct
MOD_RES                 1
                        note = MeGly
DISULFID                3..11
                        note = disulfide bond
MOD_RES                 7
                        note = Xaa is 2-Amino-5,5,5-trifluoro-4-methyl-pentanoic
                         acid
MOD_RES                 11
                        note = Xaa is L-Penicillamine
source                  1..14
                        mol_type = protein
```

```
                        organism = synthetic construct
SEQUENCE: 521
XICSRSXPPI XIPD                                                    14

SEQ ID NO: 522          moltype = AA  length = 14
FEATURE                 Location/Qualifiers
REGION                  1..14
                        note = Synthetic Construct
MOD_RES                 1
                        note = MeGly
DISULFID                3..11
                        note = disulfide bond
MOD_RES                 7
                        note = Xaa is (2S)-2-Amino-5-methyl-hexanoic acid
MOD_RES                 11
                        note = Xaa is L-Penicillamine
source                  1..14
                        mol_type = protein
                        organism = synthetic construct
SEQUENCE: 522
XICSRSXPPI XIPD                                                    14

SEQ ID NO: 523          moltype = AA  length = 14
FEATURE                 Location/Qualifiers
REGION                  1..14
                        note = Synthetic Construct
MOD_RES                 1
                        note = Xaa is (2S)-2-(morpholin-4-yl)propanoic acid)
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
source                  1..14
                        mol_type = protein
                        organism = synthetic construct
SEQUENCE: 523
XICSRSLPXI XIPD                                                    14

SEQ ID NO: 524          moltype = AA  length = 14
FEATURE                 Location/Qualifiers
REGION                  1..14
                        note = Synthetic Construct
DISULFID                3..11
                        note = disulfide bond
MOD_RES                 10
                        note = Xaa is 3-Chlorophenylglycine
source                  1..14
                        mol_type = protein
                        organism = synthetic construct
SEQUENCE: 524
AICSRSLPPX CIPD                                                    14

SEQ ID NO: 525          moltype = AA  length = 16
FEATURE                 Location/Qualifiers
REGION                  1..16
                        note = Synthetic Construct
MOD_RES                 1
                        note = Xaa is 1,18-Octadecanedioic acid
DISULFID                4..12
                        note = disulfide bond
MOD_RES                 10
                        note = Xaa is
                         2,3,3a,4,5,6,7,7a-Octahydroindole-2-carboxylic acid
MOD_RES                 12
                        note = Xaa is L-Penicillamine
MOD_RES                 16
                        note = Orn
source                  1..16
                        mol_type = protein
                        organism = synthetic construct
SEQUENCE: 525
XAICSRSLPX IXIPDX                                                  16

SEQ ID NO: 526          moltype = AA  length = 15
FEATURE                 Location/Qualifiers
REGION                  1..15
```

```
                          note = Synthetic Construct
MOD_RES                   1
                          note = Xaa is 1,18-Octadecanedioic acid
MOD_RES                   2
                          note = Orn
DISULFID                  4..12
                          note = disulfide bond
MOD_RES                   10
                          note = Xaa is
                           2,3,3a,4,5,6,7,7a-Octahydroindole-2-carboxylic acid
MOD_RES                   12
                          note = Xaa is L-Penicillamine
source                    1..15
                          mol_type = protein
                          organism = synthetic construct
SEQUENCE: 526
XXICSRSLPX IXIPD                                                15

SEQ ID NO: 527            moltype = AA  length = 14
FEATURE                   Location/Qualifiers
REGION                    1..14
                          note = Synthetic Construct
MOD_RES                   1
                          note = MeGly
DISULFID                  3..11
                          note = disulfide bond
MOD_RES                   7
                          note = Xaa is L-tert-Butylalanine
MOD_RES                   11
                          note = Xaa is L-Penicillamine
MOD_RES                   14
                          note = Xaa is 12-Amino-4,7,10-trioxadodecanoic acid
source                    1..14
                          mol_type = protein
                          organism = synthetic construct
SEQUENCE: 527
XICSRSXPPI XIPX                                                 14

SEQ ID NO: 528            moltype = AA  length = 14
FEATURE                   Location/Qualifiers
REGION                    1..14
                          note = Synthetic Construct
MOD_RES                   1
                          note = MeGly
DISULFID                  3..11
                          note = disulfide bond
MOD_RES                   9
                          note = Xaa is
                           2,3,3a,4,5,6,7,7a-Octahydroindole-2-carboxylic acid
MOD_RES                   11
                          note = Xaa is L-Penicillamine
MOD_RES                   14
                          note = Xaa is (S)-2-(Amino )-1,6-hexanedioic acid
source                    1..14
                          mol_type = protein
                          organism = synthetic construct
SEQUENCE: 528
XICSRSLPXI XIPX                                                 14

SEQ ID NO: 529            moltype = AA  length = 14
FEATURE                   Location/Qualifiers
REGION                    1..14
                          note = Synthetic Construct
DISULFID                  3..11
                          note = disulfide bond
MOD_RES                   9
                          note = Xaa is
                           (2S,4S)-4-Trifluoromethyl-pyrrolidine-2-carboxylic acid
source                    1..14
                          mol_type = protein
                          organism = synthetic construct
SEQUENCE: 529
AICSRSLPXI CIPD                                                 14

SEQ ID NO: 530            moltype = AA  length = 14
FEATURE                   Location/Qualifiers
REGION                    1..14
                          note = Synthetic Construct
DISULFID                  3..11
```

```
                          note = disulfide bond
MOD_RES                   7
                          note = Xaa is L-tert-Butylalanine
MOD_RES                   9
                          note = Xaa is
                           (2S,4S)-4-Trifluoromethyl-pyrrolidine-2-carboxylic acid
MOD_RES                   11
                          note = Xaa is L-Penicillamine
source                    1..14
                          mol_type = protein
                          organism = synthetic construct
SEQUENCE: 530
AICSRSXPXI XIPD                                                14

SEQ ID NO: 531            moltype = AA  length = 11
FEATURE                   Location/Qualifiers
REGION                    1..11
                          note = Synthetic Construct
MOD_RES                   1
                          note = MeGly
DISULFID                  3..8
                          note = disulfide bond
MOD_RES                   7
                          note = Xaa is L-tert-Butylalanine
MOD_RES                   8
                          note = Xaa is L-Penicillamine
source                    1..11
                          mol_type = protein
                          organism = synthetic construct
SEQUENCE: 531
XFCTRKXXYP D                                                   11

SEQ ID NO: 532            moltype = AA  length = 14
FEATURE                   Location/Qualifiers
REGION                    1..14
                          note = Synthetic Construct
MOD_RES                   1
                          note = MeGly
DISULFID                  3..11
                          note = disulfide bond
MOD_RES                   7
                          note = Xaa is 2,5-Difluoro-L-phenylalanine
MOD_RES                   11
                          note = Xaa is L-Penicillamine
source                    1..14
                          mol_type = protein
                          organism = synthetic construct
SEQUENCE: 532
XICSRSXPPI XIPD                                                14

SEQ ID NO: 533            moltype = AA  length = 14
FEATURE                   Location/Qualifiers
REGION                    1..14
                          note = Synthetic Construct
MOD_RES                   1
                          note = MeGly
DISULFID                  3..11
                          note = disulfide bond
MOD_RES                   7
                          note = Xaa is 2,5-Difluoro-L-phenylalanine
MOD_RES                   11
                          note = Xaa is L-Penicillamine
SITE                      14
                          note = Xaa is D-Glutamic acid
source                    1..14
                          mol_type = protein
                          organism = synthetic construct
SEQUENCE: 533
XICSRSXPPI XIPX                                                14

SEQ ID NO: 534            moltype = AA  length = 15
FEATURE                   Location/Qualifiers
REGION                    1..15
                          note = Synthetic Construct
MOD_RES                   1
                          note = MeGly
DISULFID                  3..11
                          note = disulfide bond
MOD_RES                   7
```

```
                          note = Xaa is 2,5-Difluoro-L-phenylalanine
MOD_RES                   11
                          note = Xaa is L-Penicillamine
SITE                      15
                          note = Xaa is D-Aspartic acid
source                    1..15
                          mol_type = protein
                          organism = synthetic construct
SEQUENCE: 534
XICSRSXPPI XIPDX                                                      15

SEQ ID NO: 535            moltype = AA  length = 14
FEATURE                   Location/Qualifiers
REGION                    1..14
                          note = Synthetic Construct
SITE                      1
                          note = Xaa is D-Alanine
DISULFID                  3..11
                          note = disulfide bond
MOD_RES                   7
                          note = Xaa is L-tert-Butylalanine
MOD_RES                   9
                          note = Xaa is (6S)-5-Azaspiro[2.4]heptane-6-carboxylic acid
MOD_RES                   11
                          note = Xaa is L-Penicillamine
source                    1..14
                          mol_type = protein
                          organism = synthetic construct
SEQUENCE: 535
XICSRSXPXI XIPD                                                       14

SEQ ID NO: 536            moltype = AA  length = 14
FEATURE                   Location/Qualifiers
REGION                    1..14
                          note = Synthetic Construct
SITE                      1
                          note = Xaa is D-Alanine
DISULFID                  3..11
                          note = disulfide bond
MOD_RES                   7
                          note = Xaa is L-tert-Butylalanine
MOD_RES                   9
                          note = Xaa is (6S)-5-Azaspiro[2.4]heptane-6-carboxylic acid
MOD_RES                   11
                          note = Xaa is L-Penicillamine
SITE                      14
                          note = Xaa is D-Glutamic acid
source                    1..14
                          mol_type = protein
                          organism = synthetic construct
SEQUENCE: 536
XICSRSXPXI XIPX                                                       14

SEQ ID NO: 537            moltype = AA  length = 14
FEATURE                   Location/Qualifiers
REGION                    1..14
                          note = Synthetic Construct
DISULFID                  3..11
                          note = disulfide bond
MOD_RES                   7
                          note = Xaa is L-tert-Butylalanine
MOD_RES                   9
                          note = Xaa is
                           (2S,4S)-4-Trifluoromethyl-pyrrolidine-2-carboxylic acid
source                    1..14
                          mol_type = protein
                          organism = synthetic construct
SEQUENCE: 537
AICSRSXPXI CIPD                                                       14

SEQ ID NO: 538            moltype = AA  length = 14
FEATURE                   Location/Qualifiers
REGION                    1..14
                          note = Synthetic Construct
MOD_RES                   1
                          note = MeGly
DISULFID                  3..11
                          note = disulfide bond
MOD_RES                   7
```

```
                        note = Xaa is (2S)-2-amino-3-(1-methylcyclopropyl)propanoic
                         acid
MOD_RES                 9
                        note = Xaa is
                         2,3,3a,4,5,6,7,7a-Octahydroindole-2-carboxylic acid
MOD_RES                 11
                        note = Xaa is L-Penicillamine
source                  1..14
                        mol_type = protein
                        organism = synthetic construct
SEQUENCE: 538
XICSRSXPXI XIPD                                                             14

SEQ ID NO: 539          moltype = AA  length = 14
FEATURE                 Location/Qualifiers
REGION                  1..14
                        note = Synthetic Construct
MOD_RES                 1
                        note = MeGly
DISULFID                3..11
                        note = disulfide bond
MOD_RES                 7
                        note = Xaa is L-tert-Butylalanine
MOD_RES                 9
                        note = Xaa is
                         (1S,2S,5R)-3-azabicyclo[3.1.0]hexane-2-carboxylic acid
MOD_RES                 11
                        note = Xaa is L-Penicillamine
source                  1..14
                        mol_type = protein
                        organism = synthetic construct
SEQUENCE: 539
XICSRSXPXI XIPD                                                             14

SEQ ID NO: 540          moltype = AA  length = 14
FEATURE                 Location/Qualifiers
REGION                  1..14
                        note = Synthetic Construct
MOD_RES                 1
                        note = MeGly
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
MOD_RES                 14
                        note = Xaa is
                         (2S)-2-[(3R)-3-Amino-2-oxopyrrolidin-1-yl]-4-methylpentanoi
                         c acid
source                  1..14
                        mol_type = protein
                        organism = synthetic construct
SEQUENCE: 540
XICSRSLPXI XIPX                                                             14

SEQ ID NO: 541          moltype = AA  length = 14
FEATURE                 Location/Qualifiers
REGION                  1..14
                        note = Synthetic Construct
SITE                    1
                        note = Xaa is D-Proline
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is
                         2,3,3a,4,5,6,7,7a-Octahydroindole-2-carboxylic acid
MOD_RES                 14
                        note = Xaa is Iminodiacetic acid
source                  1..14
                        mol_type = protein
                        organism = synthetic construct
SEQUENCE: 541
XICSRSLPXI XIPX                                                             14
```

-continued

```
SEQ ID NO: 542          moltype = AA  length = 14
FEATURE                 Location/Qualifiers
REGION                  1..14
                        note = Synthetic Construct
MOD_RES                 1
                        note = Orn
DISULFID                3..11
                        note = disulfide bond
MOD_RES                 7
                        note = Xaa is
                         (2R)-2-amino-3-(trifluoromethylsulfanyl)propanoic acid)
MOD_RES                 11
                        note = Xaa is L-Penicillamine
source                  1..14
                        mol_type = protein
                        organism = synthetic construct
SEQUENCE: 542
XICSRSXPPI XIPD                                                    14

SEQ ID NO: 543          moltype = AA  length = 14
FEATURE                 Location/Qualifiers
REGION                  1..14
                        note = Synthetic Construct
MOD_RES                 1
                        note = MeGly
DISULFID                3..11
                        note = disulfide bond
MOD_RES                 9
                        note = Xaa is
                         2,3,3a,4,5,6,7,7a-Octahydroindole-2-carboxylic acid
MOD_RES                 11
                        note = Xaa is L-Penicillamine
MOD_RES                 14
                        note = Xaa is (R)-Pyrrolidine-3-acetic acid
source                  1..14
                        mol_type = protein
                        organism = synthetic construct
SEQUENCE: 543
XICSRSLPXI XIPX                                                    14

SEQ ID NO: 544          moltype = AA  length = 14
FEATURE                 Location/Qualifiers
REGION                  1..14
                        note = Synthetic Construct
MOD_RES                 1
                        note = MeGly
DISULFID                3..11
                        note = disulfide bond
MOD_RES                 7
                        note = Xaa is L-tert-Butylalanine
MOD_RES                 9
                        note = Xaa is (3S)-2-azaspiro[4.4]nonane-3-carboxylic acid
MOD_RES                 11
                        note = Xaa is L-Penicillamine
source                  1..14
                        mol_type = protein
                        organism = synthetic construct
SEQUENCE: 544
XICSRSXPXI XIPD                                                    14

SEQ ID NO: 545          moltype = AA  length = 14
FEATURE                 Location/Qualifiers
REGION                  1..14
                        note = Synthetic Construct
MOD_RES                 1
                        note = MeGly
DISULFID                3..11
                        note = disulfide bond
MOD_RES                 9
                        note = Xaa is
                         2,3,3a,4,5,6,7,7a-Octahydroindole-2-carboxylic acid
```

-continued

| | | |
|---|---|---|
| MOD_RES | 11<br>note = Xaa is L-Penicillamine | |
| MOD_RES | 14<br>note = Xaa is (R)-Pyrrolidine-3-carboxylic acid | |
| source | 1..14<br>mol_type = protein<br>organism = synthetic construct | |
| SEQUENCE: 545 | | |
| XICSRSLPXI XIPX | | 14 |